United States Patent
Cullen et al.

(10) Patent No.: US 11,560,385 B2
(45) Date of Patent: Jan. 24, 2023

(54) PROTEASOME ACTIVITY ENHANCING COMPOUNDS

(71) Applicant: Proteostasis Therapeutics, Inc., Boston, MA (US)

(72) Inventors: Matthew Cullen, Braintree, MA (US); Cecilia M. Bastos, South Grafton, MA (US); Daniel Parks, Pepperell, MA (US); Benito Munoz, Newtonville, MA (US)

(73) Assignee: Proteostasis Therapeutics, Inc., Boston, MA (US)

( * ) Notice: Subject to any disclaimer, the term of this patent is extended or adjusted under 35 U.S.C. 154(b) by 0 days.

(21) Appl. No.: 17/133,372

(22) Filed: Dec. 23, 2020

(65) Prior Publication Data
US 2021/0115057 A1     Apr. 22, 2021

Related U.S. Application Data

(63) Continuation of application No. PCT/US2019/039600, filed on Jun. 27, 2019.

(60) Provisional application No. 62/690,565, filed on Jun. 27, 2018, provisional application No. 62/690,563, filed on Jun. 27, 2018.

(51) Int. Cl.
| | | |
|---|---|---|
| *C07D 487/08* | (2006.01) | |
| *C07D 451/06* | (2006.01) | |
| *C07D 491/22* | (2006.01) | |
| *C07F 7/08* | (2006.01) | |

(52) U.S. Cl.
CPC ......... *C07D 487/08* (2013.01); *C07D 451/06* (2013.01); *C07D 491/22* (2013.01); *C07F 7/0812* (2013.01)

(58) Field of Classification Search
CPC .................................................. C07D 487/08
See application file for complete search history.

(56) References Cited

U.S. PATENT DOCUMENTS 3,706,750 A    12/1972   Teotino et al.
9,850,262 B2 *  12/2017  Cullen .................. C07D 209/12

FOREIGN PATENT DOCUMENTS

| GB | 1142508 A | 2/1969 |
| WO | 2011094545 A2 | 8/2011 |
| WO | 2012154967 A1 | 11/2012 |
| WO | 2014116228 A1 | 7/2014 |
| WO | 2015073528 A1 | 5/2015 |

OTHER PUBLICATIONS

Banker, G.S. et al, "Modern Pharmaceutics, 3ed.", Marcel Dekker, New York, 1996, pp. 451 and 596.*
Rautio et. al. "Prodrugs: design and clinical Applications" Nature Reviews Drug Discovery 2008, 7, 255-270.*
Beaumont "Design of Ester Prodrugs to Enhance Oral Absorption of Poorly Permeable Compounds: Challenges to the Discovery Scientist" Current Drug Metabolism, 2003, 4, 461-485.*
Malmborg "Predicting human exposure of active drug after oral prodrug administration, using a joined in vitro/in silico-in vivo extrapolation and physiologically-based pharmacokinetic modeling approach" Journal of Pharmacological and Toxicological Methods 67 (2013) 203-213.*
Wolff, Manfred E. "Burger's Medicinal Chemistry, 5ed, Part I", John Wiley & Sons, 1995, pp. 975-977.*
Boselli et al, "An inhibitor of the proteasomal deubiquitinating enzyme USP14 induces tau elimination in cultured neurons", J. Biol. Chem., 2017, vol. 292, No. 47, pp. 19209-19225.
Carson et al., "Aroyl(aminoacyl)pyrroles, a New Class of Anticonvulsant Agents", J. Med. Chem., 1997, vol. 40, No. 11, pp. 1578-1584.
Di Santo et al, "Design, Synthesis, and Biological Activities of Pyrrolylethanoneamine Derivatives, a Novel Class of Monoamine Oxidases Inhibitors", J. Med. Chem. 2005, vol. 48 No. 13, pp. 4220-4223.
Hesabi et al., "Light-Induced Reactions of Heteroaryl N-Methylanilinomethyl Ketones: Formation of 3-Heteroaryl-1-phenylazetidin-3-ols", J. Chem. Society, Perkin Transactions 1, Royal Society of Chemistry, GB, Jan. 1980, vol. 11, pp. 2371-2373.
Database Registry [Online] Chemical Abstracts Service, Jun. 4, 2008, XP-002793777, retrieved from STN Database accession No. 1025216-77-6, 1 page.
Database Registry [Online] Chemical Abstracts Service, Jun. 3, 2008, XP-002793778, retrieved from STN Database accession No. 1025028-84-5, 1 page.
Database Registry [Online] Chemical Abstracts Service, Feb. 16, 2017, XP-002793590, retrieved from STN Database accession No. 2071559-65-2, 2 pages.
Database Registry [Online] Chemical Abstracts Service, Sep. 7, 2011, XP-002793591, retrieved from STN Database accession No. 1329566-19-9, 3 pages.

(Continued)

*Primary Examiner* — David K O'Dell
(74) *Attorney, Agent, or Firm* — Armstrong Teasdale LLP

(57) ABSTRACT

The present invention is directed to compounds having the Formulae (Ia), (Ib), (Ic), or (Id); or the Formulae (II), (IIa), (IIb), or (IIc); or the Formulae (III), (IIIa), (IIIb), (IIIc), (IIId), or (IIIe), and pharmaceutically acceptable salts, solvates, clathrates and prodrugs of any Formula thereof, compositions thereof, and methods for the treatment of a condition associated with a dysfunction in proteostasis.

21 Claims, No Drawings

(56) References Cited

OTHER PUBLICATIONS

Database Registry [Online] Chemical Abstracts Service, Sep. 6, 2011, XP-002793592, retrieved from STN Database accession No. 1328692-07-4, 1 page.
Database Registry [Online] Chemical Abstracts Service, Sep. 2, 2011, XP-002793593, retrieved from STN Database accession No. 1327009-43-7, 1 page.
Database Registry [Online] Chemical Abstracts Service, Sep. 1, 2011, XP-002793594, retrieved from STN Database accession No. 1326694-91-0, 1 page.
International Search Report and Written Opinion for PCT/US2019/039600, dated Sep. 9, 2019, 19 pages.

* cited by examiner

PROTEASOME ACTIVITY ENHANCING COMPOUNDS

CROSS REFERENCE TO RELATED APPLICATIONS

This application is a continuation of International Application No. PCT/US2019/039600, which was filed Jun. 27, 2019 and published as WO 2020/006296, the disclosure of which is hereby incorporated by reference as if set forth in its entirety. International Application No. PCT/US2019/039600 U.S. provisional application Ser. No. 62/690,563, filed Jun. 27, 2018, the disclosure of which is hereby incorporated by reference as if set forth in its entirety. International Application No. PCT/US2019/039600 claims the benefit of priority to U.S. provisional application Ser. No. 62/690,565, filed Jun. 27, 2018, the disclosure of which is hereby incorporated by reference as if set forth in its entirety.

BACKGROUND OF THE INVENTION

Cells normally maintain a balance between protein synthesis, folding, trafficking, aggregation, and degradation, referred to as protein homeostasis, utilizing sensors and networks of pathways [Sitia et al., *Nature* 426: 891-894, 2003; Ron et al., *Nat Rev Mol Cell Biol* 8: 519-529, 2007]. The cellular maintenance of protein homeostasis, or proteostasis, refers to controlling the conformation, binding interactions, location and concentration of individual proteins making up the proteome. Protein folding in vivo is accomplished through interactions between the folding polypeptide chain and macromolecular cellular components, including multiple classes of chaperones and folding enzymes, which minimize aggregation [Wiseman et al., *Cell* 131: 809-821, 2007]. Whether a given protein folds in a certain cell type depends on the distribution, concentration, and subcellular localization of chaperones, folding enzymes, metabolites and the like [Wiseman et al.]. Human loss of function diseases are often the result of a disruption of normal protein homeostasis, typically caused by a mutation in a given protein that compromises its cellular folding, leading to efficient degradation [Cohen et al., *Nature* 426: 905-909, 2003]. Human gain of function diseases are similarly frequently the result of a disruption in protein homeostasis, such as the accumulation of misfolded proteins, leading to protein aggregation [Balch et al. (2008), *Science* 319: 916-919].

The proteasome is a large protein complex of multiple subunits which acts as a protease to degrade misfolded proteins. Most proteasome substrates are targeted for degradation by the covalent attachment of ubiquitin moieties which are recognized by the proteasome [Lee et al. (2010), *Nature* 467(7312): 179-184]. Proteins with longer ubiquitin chains tend to have a stronger association with the proteasome than those with smaller chains [Lee et al. (2010); Proctor et al. (2007), BMC Systems Biology 1: 17]. The length of the ubiquitin chains is modulated, in part, by proteasome-associated deubiquitinating enzymes. One such mammalian deubiquitinating enzyme is Usp14 which has been shown to act as an inhibitor of the proteasome [Lee et al. (2010)].

Both proteasome dysfunction and dysfunction in proteostasis have been implicated in a diverse range of diseases including, for example, neurodegenerative disease, metabolic diseases, inflammatory diseases, and cancer. In many such diseases and conditions, the proteasome has decreased ability to degrade misfolded or abnormal proteins, leading to the presence of toxic protein aggregates. In addition, the enhancement of proteasome activity can be therapeutic for any disease characterized by deficient proteasome activity, or deficient activity of other components of the ubiquitin-proteasome pathway including, but not limited to, von Hippel-Lindau disease, spinocerebellar ataxia 1, Angelman syndrome, giant axon neuropathy, inclusion body myopathy with Paget disease of bone and frontotemporal dementia (IBMPFD), and others [Lehman, N. L., (2009), Acta Neuropathologica, 118(3), 329-347; Weihl et al., (2007), Neuromuscular Disorders, 17, 87-87]. Enhancing proteasome activity is also therapeutic for diseases in which proteasome substrates are involved and contribute to pathology, but which do not satisfy a strict definition of proteinopathies. For example, numerous oncoproteins are proteasome substrates and their ability to promote cancer can potentially be attenuated by enhancing proteasome activity.

Therefore, there is a need for compounds and pharmaceutical compositions to treat conditions associated with proteostasis dysfunction and/or that provide therapies based on enhancing proteasome activity.

SUMMARY OF THE INVENTION

The present invention is based, in part, on the discovery that compounds of the invention inhibit Usp14. The present invention is directed to compounds encompassed by any of the Formulae (Ia), (Ib), (Ic), (Id), (II), (IIa), (IIb), (IIc), (III), (IIIa), (IIIb), (IIIc), (IIId), and (IIIe), and pharmaceutically acceptable salts, solvates, clathrates and prodrugs of any of thereof, compositions thereof, methods for the treatment of a condition associated with a dysfunction in proteostasis, methods for enhancing proteasome activity and methods for treating cancer or tumor.

In some embodiments, the invention is directed to a compound having the Formula (Ia):

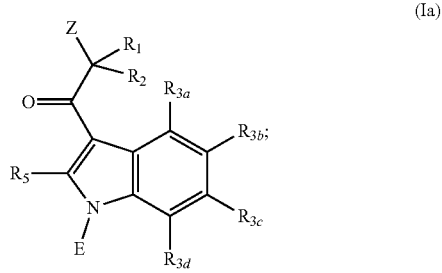

or a pharmaceutically acceptable salt, solvate, clathrate or prodrug thereof; wherein:

E is selected from the group consisting of optionally substituted aryl or optionally substituted heteroaryl;

each of $R_1$ and $R_2$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl;

Z is an optionally substituted, 6- to 12-membered bridged N-heterocyclic;

each of $R_{3a}$, $R_{3b}$, $R_{3c}$ and $R_{3d}$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C=NR_d)R_c$, $OC(O)R_c$, optionally substituted heterocyclic and optionally substituted heteroaryl;

$R_5$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C=NR_d)R_c$, $OC(O)R_c$, optionally substituted heterocyclic, and optionally substituted heteroaryl;

wherein substituents of optionally substituted E, Z, $R_1$, $R_2$, $R_{3a}$, $R_{3b}$, $R_{3c}$, $R_{3d}$, and $R_5$ are each independently selected from the group consisting of $C_1$-$C_{10}$ alkyl, $C_2$-$C_{10}$ alkenyl, $C_2$-$C_{10}$ alkynyl, $C_3$-$C_{12}$ cycloalkyl, $C_3$-$C_{12}$ cycloalkenyl, aryl, halo, $N_3$, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C=NR_d)R_c$, $OC(O)R_c$, heterocyclic, and heteroaryl;

each $R_c$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl;

each $R_d$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl; or two geminal $R_d$ groups are taken together with the nitrogen atom to which they are attached to form an optionally substituted heterocyclic or an optionally substituted heteroaryl; and each n is independently 0, 1 or 2.

In yet an additional embodiment, the invention is directed to a compound having the Formula (Ib):

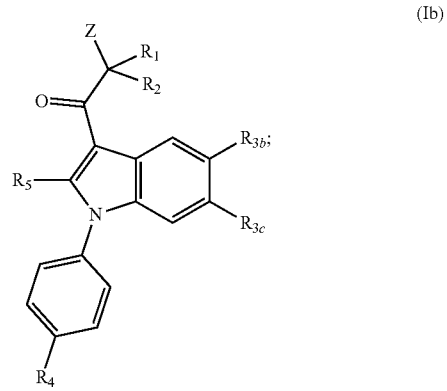

(Ib)

or a pharmaceutically acceptable salt, solvate, clathrate or prodrug thereof; wherein:

Z is an optionally substituted, 6- to 12-membered bridged N-heterocyclic;

each of $R_1$ and $R_2$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl;

each of $R_{3b}$ and $R_{3c}$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C=NR_d)R_c$, $OC(O)R_c$, optionally substituted heterocyclic and optionally substituted heteroaryl;

$R_4$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C=NR_d)R_c$, $OC(O)R_c$, optionally substituted heterocyclic and optionally substituted heteroaryl;

$R_5$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C=NR_d)R_c$, $OC(O)R_c$, optionally substituted heterocyclic, and optionally substituted heteroaryl;

wherein substituents of optionally substituted Z, $R_1$, $R_2$, $R_{3b}$, $R_{3c}$, $R_4$, and $R_5$ are each independently selected from the group consisting of $C_1$-$C_{10}$ alkyl, $C_2$-$C_{10}$ alkenyl, $C_2$-$C_{10}$ alkynyl, $C_3$-$C_{12}$ cycloalkyl, $C_3$-$C_{12}$ cycloalkenyl, aryl, halo, $N_3$, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C=NR_d)R_c$, $OC(O)R_c$, heterocyclic, and heteroaryl;

each $R_c$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl;

each $R_d$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl; or two geminal $R_d$ groups are taken together with the nitrogen atom to which they are attached to form an optionally substituted heterocyclic or an optionally substituted heteroaryl;

each n is independently 0, 1 or 2.

In yet another embodiment, the invention is directed to a compound having the Formula (II):

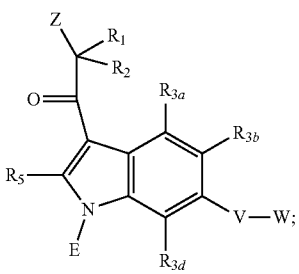

(II)

or a pharmaceutically acceptable salt, solvate, clathrate or prodrug thereof; wherein:

E is selected from the group consisting of optionally substituted aryl or optionally substituted heteroaryl;

each of $R_1$ and $R_2$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl;

$Z_1$ is an optionally substituted N-heterocyclic;

each of $R_{3a}$, $R_{3b}$, and $R_{3d}$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C=NR_d)R_c$, $OC(O)R_c$, optionally substituted heterocyclic and optionally substituted heteroaryl;

$R_5$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C=NR_d)R_c$, $OC(O)R_c$, optionally substituted heterocyclic, and optionally substituted heteroaryl;

V is selected from the group consisting of $C_1$-$C_6$ alkylene, $C_2$-$C_6$ alkenylene, $C_2$-$C_6$ alkynylene, each optionally substituted;

W is selected from the group consisting of $S(O)_pR_m$, CN, optionally substituted heteroaryl and optionally substituted heterocyclic;

wherein substituents of optionally substituted E, Z, V, W, $R_{3a}$, $R_{3b}$, $R_{3d}$, and $R_5$ are each independently selected from the group consisting of $C_1$-$C_{10}$ alkyl, $C_2$-$C_{10}$ alkenyl, $C_2$-$C_{10}$ alkynyl, $C_3$-$C_{12}$ cycloalkyl, $C_3$-$C_{12}$ cycloalkenyl, aryl, halo, $N_3$, $OR_c$, $NR_dR_d$, $C(O)OR_c$, $NO_2$, CN, $C(O)R_c$, $C(O)C(O)R_c$, $C(O)NR_dR_d$, $NR_dC(O)R_d$, $NR_dS(O)_nR_c$, $N(R_d)(COOR_c)$, $NR_dC(O)C(O)R_c$, $NR_dC(O)NR_dR_d$, $NR_dS(O)_n NR_dR_d$, $NR_dS(O)_nR_c$, $S(O)_nR_c$, $S(O)_nNR_dR_d$, $OC(O)OR_c$, $(C=NR_d)R_c$, $OC(O)R_c$, heterocyclic, and heteroaryl;

each $R_c$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl;

each $R_d$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl; or two geminal $R_d$ groups are taken together with the nitrogen atom to which they are attached to form an optionally substituted heterocyclic or an optionally substituted heteroaryl; and each n is independently 0, 1 or 2; and p is 0, 1 or 2.

In certain aspects, the present invention is directed to compounds encompassed by the Formula (III):

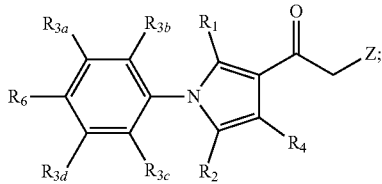

(III)

or a pharmaceutically acceptable salt, solvate, clathrate or prodrug thereof; wherein:

$R_1$ is selected from the group consisting of hydrogen, optionally substituted $C_1$-$C_4$ alkyl, and halo;

$R_2$ is selected from the group consisting of optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted 4- to 12-membered heterocyclic, optionally substituted aryl, optionally substituted 4- to 12-membered heteroaryl, halo, and CN;

$R_{3a}$, $R_{3b}$, $R_{3c}$ and $R_{3d}$ are each independently selected from the group consisting of hydrogen, optionally substituted $C_1$-$C_6$ alkyl, CN, and halo;

$R_4$ is selected from the group consisting of hydrogen, optionally substituted $C_1$-$C_{10}$ alkyl, halo, and CN;

$R_6$ is selected from the group consisting of hydrogen, optionally substituted $C_1$-$C_6$ alkyl, CN, and halo; and Z is an optionally substituted, 6- to 12-membered bridged N-heterocyclic;

wherein substituents of optionally substituted Z, $R_1$, $R_2$, $R_{3a}$, $R_{3b}$, $R_{3c}$, $R_{3d}$, $R_4$, and $R_6$ are each independently selected from the group consisting of $C_1$-$C_{10}$ alkyl, $C_2$-$C_{10}$ alkenyl, $C_2$-$C_{10}$ alkynyl, $C_3$-$C_{12}$ cycloalkyl, $C_3$-$C_{12}$ cycloalkenyl, aryl, halo, $N_3$, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_n$-$NR_dR_d$, $OC(O)OR_c$, $(C=NR_d)R_c$, $OC(O)R_c$, $Si(R_c)_3$, heterocyclic, and heteroaryl;

each $R_c$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl;

each $R_d$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl; or two geminal $R_d$ groups are taken together with the nitrogen atom to which they are attached to form an optionally substituted heterocyclic or an optionally substituted heteroaryl; and each n is independently 0, 1 or 2.

In additional embodiments, the invention is directed to a pharmaceutical composition comprising a pharmaceutically acceptable carrier or excipient and a compound of any of the Formulae (Ia), (Ib), (Ic), (Id), (II), (IIa), (IIb), (IIc), (III), (IIIa), (IIIb), (IIIc), (IIId), and (IIIe), or a pharmaceutically acceptable salt, solvate, clathrate or prodrug thereof.

In an additional aspect, the invention is directed to a method of inhibiting deubiquitination activity of a Usp14 protein comprising contacting the Usp14 protein with an effective amount of a compound of any of the Formulae (Ia), (Ib), (Ic), (Id), (II), (IIa), (IIb), (IIc), (III), (IIIa), (IIIb), (IIIc), (IIId), and (IIIe), or a pharmaceutically acceptable salt, solvate, clathrate or prodrug thereof, in an amount sufficient to inhibit deubiquitination activity of the Usp14 protein.

In yet another embodiment, the invention is directed to a method of enhancing protein degradation by a proteasome in a cell comprising contacting the cell with an effective amount of a compound of any of the Formulae (Ia), (Ib), (Ic), (Id), (II), (IIa), (IIb), (IIc), (III), (IIIa), (IIIb), (IIIc), (IIId), and (IIIe), or a pharmaceutically acceptable salt, solvate, clathrate or prodrug thereof, in an amount sufficient to enhance protein degradation by the proteasome.

In additional embodiments, the invention encompasses a method of treating a patient suffering from a condition associated with a dysfunction in proteostasis comprising administering to said patient an effective amount of a compound of any of the Formulae (Ia), (Ib), (Ic), (Id), (II), (IIa), (IIb), (IIc), (III), (IIIa), (IIIb), (IIIc), (IIId), and (IIIe), or a pharmaceutically acceptable salt, solvate, clathrate or prodrug thereof.

In another aspect, the invention is directed to a method of enhancing proteasome function in a subject in need thereof comprising administering to said subject an effective amount of a compound of any of the Formulae (Ia), (Ib), (Ic), (Id), (II), (IIa), (IIb), (IIc), (III), (IIIa), (IIIb), (IIIc), (IIId), and (IIIe), or a pharmaceutically acceptable salt, solvate, clathrate or prodrug thereof.

In a further embodiment, the invention is directed to a method for treating a condition characterized by deficient proteasome activity or deficiency of other components of the ubiquitin-proteasome pathway in a subject comprising administering to said subject an effective amount of a compound of any of the Formulae (Ia), (Ib), (Ic), (Id), (II), (IIa), (IIb), (IIc), (III), (IIIa), (IIIb), (IIIc), (IIId), and (IIIe), or a pharmaceutically acceptable salt, solvate, clathrate or prodrug thereof.

In yet another embodiment, the invention encompasses a method of treating cancer or a tumor in a subject in need thereof comprising administering to said subject an effective amount of a compound of any of the Formulae (Ia), (Ib), (Ic), (Id), (II), (IIa), (IIb), (IIc), (III), (IIIa), (IIIb), (IIIc), (IIId), and (IIIe), a pharmaceutically acceptable salt, solvate, clathrate or prodrug thereof.

In a further aspect, the invention is a pharmaceutical composition comprising:

a pharmaceutically acceptable carrier or excipient;

an agent selected from the group consisting of a proteostasis regulator and a pharmacologic chaperone; and a compound of any of the Formulae (Ia), (Ib), (Ic), (Id), (II), (IIa), (IIb), (IIc), (III), (IIIa), (IIIb), (IIIc), (IIId), and (IIIe), or a pharmaceutically acceptable salt, solvate, clathrate or prodrug thereof.

DETAILED DESCRIPTION OF THE INVENTION

A description of preferred embodiments of the invention follows.

As used herein, the words "a" and "an" are meant to include one or more unless otherwise specified. For example, the term "a cell" encompasses both a single cell and a combination of two or more cells.

Compounds of Formula (Ia), (Ib), (Ic), (Id)

In some embodiments, the present invention encompasses compounds of (Ia), (Ib), (Ic), or (Id), or pharmaceutically acceptable salts, solvates, clathrates or prodrugs thereof, pharmaceutical compositions thereof, methods of use thereof in the treatment of conditions associated with a dysfunction in proteostasis, methods of enhancing proteasome activity and methods for treating cancer or a tumor.

In some embodiments, the invention is directed to a compound having the Formula (Ia):

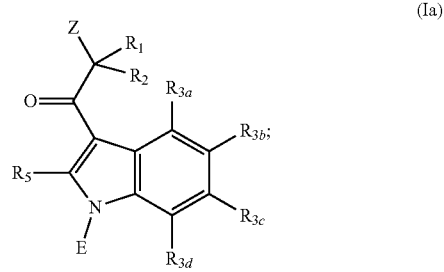

or a pharmaceutically acceptable salt, solvate, clathrate or prodrug thereof; wherein:

E is selected from the group consisting of optionally substituted aryl or optionally substituted heteroaryl;

each of $R_1$ and $R_2$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl;

Z is an optionally substituted, 6- to 12-membered bridged N-heterocyclic;

each of $R_{3a}$, $R_{3b}$, $R_{3c}$ and $R_{3d}$ is independently selected from the group consisting of hydrogen, optionally substituted $C_1$-$C_{10}$ alkyl, optionally substituted $C_2$-$C_{10}$ alkenyl, optionally substituted $C_2$-$C_0$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C=NR_d)R_c$, $OC(O)R_c$, optionally substituted heterocyclic and optionally substituted heteroaryl;

$R_5$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C=NR_d)R_c$, $OC(O)R_c$, optionally substituted heterocyclic, and optionally substituted heteroaryl;

wherein substituents of optionally substituted E, Z, $R_1$, $R_2$, $R_{3a}$, $R_{3b}$, $R_{3c}$, $R_{3d}$, and $R_5$ are each independently selected from the group consisting of $C_1$-$C_{10}$ alkyl, $C_2$-$C_{10}$ alkenyl, $C_2$-$C_{10}$ alkynyl, $C_3$-$C_{12}$ cycloalkyl, $C_3$-$C_{12}$ cycloalkenyl, aryl, halo, $N_3$, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C=NR_d)R_c$, $OC(O)R_c$, heterocyclic, and heteroaryl;

each $R_c$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl;

each $R_d$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl; or two geminal $R_d$ groups are taken together with the nitrogen atom to which they are attached to form an optionally substituted heterocyclic or an optionally substituted heteroaryl; and each n is independently 0, 1 or 2.

In certain aspects, the compound has the Formula (Ia), or a pharmaceutically acceptable salt, solvate, clathrate or prodrug thereof, wherein $R_5$ is an optionally substituted $C_1$-$C_4$ alkyl. In additional embodiments, $R_5$ is methyl or ethyl. In yet additional embodiments, $R_5$ is methyl.

In additional embodiments, the compound has the Formula (Ia), or a pharmaceutically acceptable salt, solvate, clathrate or prodrug thereof, wherein $R_1$ and $R_2$ are each independently selected from hydrogen and optionally substituted $C_1$-$C_{10}$ alkyl. In some embodiments, $R_1$ and $R_2$ are each hydrogen.

In yet additional embodiments, the compound has the Formula (Ia), or a pharmaceutically acceptable salt, solvate, clathrate or prodrug thereof, wherein E is an optionally substituted heteroaryl.

In further embodiments, the compound has the Formula (Ia), or a pharmaceutically acceptable salt, solvate, clathrate or prodrug thereof, wherein E is an optionally substituted aryl. In some embodiments, E is an optionally substituted phenyl. In yet further embodiments, E is a para-substituted phenyl, wherein the phenyl is optionally further substituted. In additional aspects, E is unsubstituted phenyl. In some embodiments, E is phenyl, substituted with one or more $R_4$, wherein each $R_4$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C=NR_d)R_c$, $OC(O)R_c$, optionally substituted heterocyclic, and optionally substituted heteroaryl. In additional aspects, $R_4$ is selected from the group consisting of hydrogen, halo, $N_3$, $C(O)OR_c$, CN, $C(O)R_c$, $C(O)C(O)R_c$, $C(O)NR_dR_d$, $NO_2$ and $NR_dR_d$. In yet additional embodiments, $R_4$ is selected from the group consisting of halo, $N_3$, $C(O)OR_c$, CN, $C(O)R_c$, $C(O)C(O)R_c$, $C(O)NR_dR_d$, $NO_2$ and $NR_dR_d$. In yet additional embodiments, E is phenyl, substituted at the para-position with $R_4$, wherein $R_4$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C=NR_d)R_c$, $OC(O)R_c$, optionally substituted heterocyclic, and optionally substituted heteroaryl. In additional aspects, $R_4$ is selected from the group consisting of hydrogen, halo, $N_3$, $C(O)OR_c$, CN, $C(O)R_c$, $C(O)C(O)R_c$, $C(O)NR_dR_d$, $NO_2$ and $NR_dR_d$. In yet additional embodiments, $R_4$ is selected from the group consisting of halo, $N_3$, $C(O)OR_c$, CN, $C(O)R_c$, $C(O)C(O)R_c$, $C(O)NR_dR_d$, $NO_2$ and $NR_dR_d$.

In additional embodiments, the compound has the Formula (Ia), or a pharmaceutically acceptable salt, solvate, clathrate or prodrug thereof, wherein each of $R_{3a}$, $R_{3b}$, $R_{3c}$ and $R_{3d}$ is independently selected from the group consisting of hydrogen, halo, $NR_dR_d$, $NO_2$, CN, optionally substituted $C_1$-$C_{10}$ alkyl, optionally substituted $C_2$-$C_{10}$ alkenyl, optionally substituted $C_2$-$C_{10}$ alkynyl, $C(O)OR_c$, $C(O)R_cNR_dC(O)R_c$, $OC(O)R_c$ and $OR_c$. In some aspects, $R_{3a}$ and $R_{3d}$ are each hydrogen.

In additional aspects, the compound has the Formula (Ia), wherein $R_{3c}$ is:

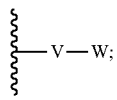

wherein V is selected from the group consisting of $C_1$-$C_6$ alkylene, $C_2$-$C_6$ alkenylene, $C_2$-$C_6$ alkynylene, each optionally substituted; W is selected from the group consisting of $S(O)_p R_m$, CN, optionally substituted heteroaryl and optionally substituted heterocyclic; $R_m$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl; and p is 0, 1 or 2. In some embodiments, V is an optionally substituted $C_1$-$C_6$ alkylene. In yet other aspects, V is an optionally substituted $C_2$-$C_4$ alkylene. In further aspects of the invention, W is selected from the group consisting of $S(O)_p R_m$, CN,

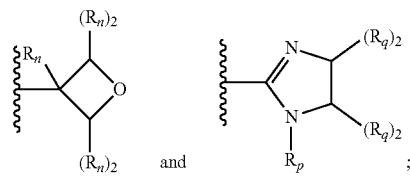

wherein each $R_n$, $R_p$, and $R_q$ are each independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, $OR_c$, $NR_d R_d$, $C(O)OR_c$, CN, $C(O)R_c$, $C(O)C(O)R_c$, $C(O)NR_d R_d$, $NR_d C(O)R_c$, $NR_d S(O)_n R_c$, $N(R_d)(COOR_c)$, $NR_d C(O)C(O)R_c$, $NR_d C(O)NR_d R_d$, $NR_d S(O)_n NR_d R_d$, $NR_d S(O)_n R_c$, $S(O)_n R_c$, $S(O)_n NR_d R_d$, $OC(O)OR_c$, $OC(O)R_c$, optionally substituted heterocyclic and optionally substituted heteroaryl. In some embodiments, $R_p$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl.

In some aspects, the compound has the Formula (Ia), or a pharmaceutically acceptable salt, solvate, clathrate or prodrug thereof, wherein $R_{3c}$ is:

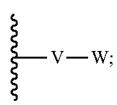

wherein W is $S(O)_p R_m$. In certain embodiments, W is $S(O)_2 R_m$ or $SR_m$, wherein $R_m$ is an optionally substituted $C_1$-$C_6$ alkyl or an optionally substituted $C_3$-$C_6$ cycloalkyl.

In yet additional aspects, W is CN. In certain embodiments, W is CN and V is $C_1$-$C_6$ alkylene or $C_2$-$C_6$ alkenylene. In additional embodiments, W is CN and V is $C_2$-$C_6$ alkylene or $C_2$-$C_6$ alkenylene. In yet further embodiments, W is CN and V is $C_2$-$C_4$ alkylene.

In further embodiments, the compound has the Formula (Ia), or a pharmaceutically acceptable salt, solvate, clathrate or prodrug thereof, wherein $R_{3c}$ is:

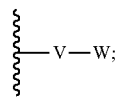

wherein W is optionally substituted heteroaryl. In certain embodiments, W is an optionally substituted heteroaryl and V is $C_1$-$C_6$ alkylene or $C_2$-$C_6$ alkenylene. In additional embodiments, W is an optionally substituted heteroaryl and V is $C_2$-$C_6$ alkylene or $C_2$-$C_6$ alkenylene. In yet further embodiments, W is an optionally substituted heteroaryl and V is $C_2$-$C_4$ alkylene.

In additional aspects, the compound has the Formula (Ia), or a pharmaceutically acceptable salt, solvate, clathrate or prodrug thereof, wherein $R_{3c}$ is:

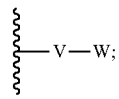

wherein W is optionally substituted heterocyclic.

In additional embodiments, W is selected from the group consisting of:

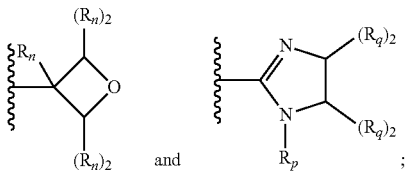

wherein each $R_n$, $R_p$, and $R_q$ are each independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, $OR_c$, $NR_d R_d$, $C(O)OR_c$, CN, $C(O)R_c$, $C(O)C(O)R_c$, $C(O)NR_d R_d$, $NR_d C(O)R_c$, $NR_d S(O)_n R_c$, $N(R_d)(COOR_c)$, $NR_d C(O)C(O)R_c$, $NR_d C(O)NR_d R_d$, $NR_d S(O)_n NR_d R_d$, $NR_d S(O)_n R_c$, $S(O)_n R_c$, $S(O)_n NR_d R_d$, $OC(O)OR_c$, $OC(O)R_c$, optionally substituted heterocyclic and optionally substituted heteroaryl. In additional embodiments, each $R_n$, $R_p$, and $R_q$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, $C(O)OR_c$, $C(O)R_c$, $C(O)C(O)R_c$, $C(O)NR_d R_d$, optionally substituted heterocyclic and optionally substituted heteroaryl. In some embodiments, $R_p$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl. In certain embodiments, V is $C_1$-$C_6$ alkylene or $C_2$-$C_6$ alkenylene. In additional embodiments, V is $C_2$-$C_6$ alkylene or $C_2$-$C_6$ alkenylene. In yet further embodiments, V is $C_2$-$C_4$ alkylene.

In additional embodiments, the compound has the Formula (Ia), or a pharmaceutically acceptable salt, solvate, clathrate or prodrug thereof, wherein Z is an optionally substituted, 6- to 10-membered bridged N-heterocyclic. In additional aspects, Z is an optionally substituted, 6- to 9-membered bridged N-heterocyclic. In yet further embodiments, Z is an optionally substituted, 6- to 8-membered bridged N-heterocyclic. In yet additional aspects, Z is an optionally substituted, 7-membered bridged N-heterocyclic or an optionally substituted, 8-membered bridged N-heterocyclic. In certain embodiments, Z is:

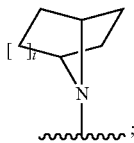

wherein the bridged heterocyclic is optionally substituted and wherein t is 0, 1, 2, 3, 4, 5 or 6.

In some embodiments, Z is:

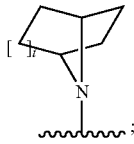

wherein the bridged heterocyclic is optionally substituted with one or more $R_6$, wherein each $R_6$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C=NR_d)R_c$, $OC(O)R_c$, optionally substituted heterocyclic and optionally substituted heteroaryl, and wherein t is 0, 1, 2, 3, 4, 5 or 6. In some additional embodiments, t is 1, 2, 3 or 4. In yet further embodiments, t is 1, 2 or 3.

In some embodiments, Z is selected from the group consisting of:

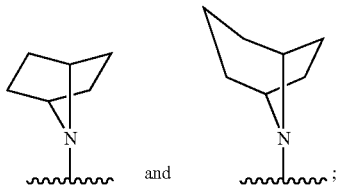 [SMILES: *N1C2CCC1CC2 ; *N1C2CCCC1CC2]

each optionally substituted.

In some embodiments Z is selected from the group consisting of:

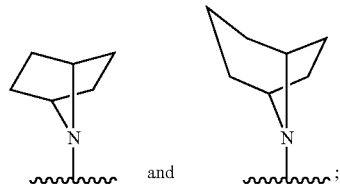 [SMILES: *N1C2CCC1CC2 ; *N1C2CCCC1CC2]

wherein each bridged heterocyclic is optionally substituted with one or more $R_6$, wherein each $R_6$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C=NR_d)R_c$, $OC(O)R_c$, optionally substituted heterocyclic and optionally substituted heteroaryl.

In further embodiments, Z is selected from the group consisting of:

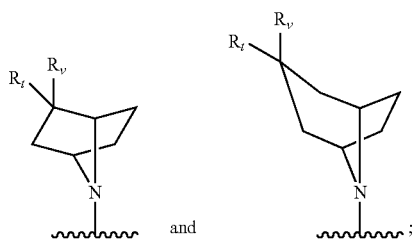

wherein $R_t$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C=NR_d)R_c$, $OC(O)R_c$, optionally substituted heterocyclic and optionally substituted heteroaryl; and $R_v$ is selected from the group consisting of hydrogen and optionally substituted $C_1$-$C_{10}$ alkyl. In yet additional aspects, $R_t$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, $OR_c$, $NR_dR_d$, $C(O)OR_c$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C=NR_d)R_c$, $OC(O)R_c$, optionally substituted heterocyclic and optionally substituted heteroaryl; and $R_v$ is selected from the group consisting of hydrogen, $OR_c$ and optionally substituted $C_1$-$C_{10}$ alkyl. In yet further embodiments, $R_v$ is an optionally substituted $C_1$-$C_4$ alkyl, $OR_c$ or hydrogen. In further embodiments, $R_t$ is selected from the group consisting of hydrogen, optionally substituted $C_1$-$C_{10}$ alkyl and $OR_c$; and $R_v$ is an optionally substituted $C_1$-$C_4$ alkyl, $OR_c$ or hydrogen. In additional embodiments, $R_t$ is selected from the group consisting of hydrogen, optionally substituted $C_1$-$C_{10}$ alkyl and OH and $R_v$ is an optionally substituted $C_1$-$C_4$ alkyl, OH, or hydrogen.

In additional embodiments, the compound has the Formula (Ia), or a pharmaceutically acceptable salt, solvate, clathrate or prodrug thereof, wherein substituents of optionally substituted E, Z, $R_1$, $R_2$, $R_{3a}$, $R_{3b}$, $R_{3c}$, $R_{3d}$, and $R_5$ are each independently selected from the group consisting of $C_1$-$C_4$ alkyl, halo, $OR_c$, CN, $S(O)_nR_c$, heterocyclyl, and heteroaryl.

In some embodiments, the invention is directed to a compound having the Formula (Ib):

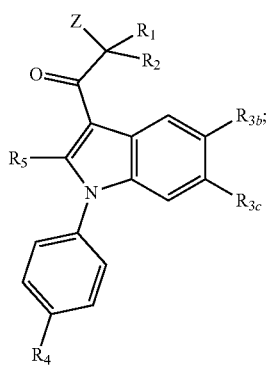

(Ib)

or a pharmaceutically acceptable salt, solvate, clathrate or prodrug thereof; wherein:

Z is an optionally substituted, 6- to 12-membered bridged N-heterocyclic;

each of $R_1$ and $R_2$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl;

each of $R_{3b}$ and $R_{3c}$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C=NR_d)R_c$, $OC(O)R_c$, optionally substituted heterocyclic and optionally substituted heteroaryl;

$R_4$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_n NR_dR_d$, $NR_dS(O)_nR_c$, $S(O)_nR_c$, $S(O)_nNR_dR_d$, $OC(O)OR_c$, $(C=NR_d)R_c$, $OC(O)R_c$, optionally substituted heterocyclic and optionally substituted heteroaryl;

$R_5$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_n NR_dR_d$, $NR_dS(O)_nR_c$, $S(O)_nR_c$, $S(O)_nNR_dR_d$, $OC(O)OR_c$, $(C=NR_d)R_c$, $OC(O)R_c$, optionally substituted heterocyclic, and optionally substituted heteroaryl;

wherein substituents of optionally substituted Z, $R_1$, $R_2$, $R_{3b}$, $R_{3c}$, $R_4$, and $R_5$ are each independently selected from the group consisting of $C_1$-$C_{10}$ alkyl, $C_2$-$C_{10}$ alkenyl, $C_2$-$C_{10}$ alkynyl, $C_3$-$C_{12}$ cycloalkyl, $C_3$-$C_{12}$ cycloalkenyl, aryl, halo, $N_3$, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_n NR_dR_d$, $NR_dS(O)_nR_c$, $S(O)_nR_c$, $S(O)_nNR_dR_d$, $OC(O)OR_c$, $(C=NR_d)R_c$, $OC(O)R_c$, heterocyclic, and heteroaryl;

each $R_c$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl;

each $R_d$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl; or two geminal $R_d$ groups are taken together with the nitrogen atom to which they are attached to form an optionally substituted heterocyclic or an optionally substituted heteroaryl;

each n is independently 0, 1 or 2.

In additional embodiments, the compound has the Formula (Ib), or a pharmaceutically acceptable salt, solvate, clathrate or prodrug thereof, wherein substituents of optionally substituted E, Z, $R_1$, $R_2$, $R_{3c}$, $R_{3d}$, $R_4$, and $R_5$ are each independently selected from the group consisting of $C_1$-$C_{10}$ alkyl, $C_2$-$C_{10}$ alkenyl, $C_2$-$C_{10}$ alkynyl, $C_3$-$C_{12}$ cycloalkyl, $C_3$-$C_{12}$ cycloalkenyl, aryl, halo, $N_3$, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C=NR_d)R_c$, $OC(O)R_c$, heterocyclic, and heteroaryl;

each $R_c$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl;

each $R_d$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl; or two geminal $R_d$ groups are taken together with the nitrogen atom to which they are attached to form an optionally substituted heterocyclic or an optionally substituted heteroaryl; and each n is independently 0, 1 or 2.

In additional embodiments, the compound has the Formula (Ia), or a pharmaceutically acceptable salt, solvate, clathrate or prodrug thereof, wherein $R_1$ and $R_2$ are each independently selected from hydrogen and optionally substituted $C_1$-$C_{10}$ alkyl. In some embodiments, $R_1$ and $R_2$ are each hydrogen.

In additional aspects, $R_4$ is selected from the group consisting of hydrogen, halo, $N_3$, C(O)O$R_c$, CN, C(O)$R_c$, C(O)C(O)$R_c$, C(O)NR$_d$R$_d$, NO$_2$ and NR$_d$R$_d$. In yet additional embodiments, $R_4$ is selected from the group consisting of halo, $N_3$, C(O)O$R_c$, CN, C(O)$R_c$, C(O)C(O)$R_c$, C(O)NR$_d$R$_d$, NO$_2$ and NR$_d$R$_d$. In some embodiments, $R_4$ is halo, such as Cl.

In certain embodiments, the compound has the Formula (Ib), or a pharmaceutically acceptable salt, solvate, clathrate or prodrug thereof, wherein $R_5$ is an optionally substituted $C_1$-$C_4$ alkyl. In additional embodiments, $R_5$ is methyl or ethyl. In yet additional embodiments, $R_5$ is methyl.

In additional embodiments, the compound has the Formula (Ib), or a pharmaceutically acceptable salt, solvate, clathrate or prodrug thereof, wherein $R_{3b}$ is hydrogen.

In yet additional embodiments, the compound has the Formula (Ib), wherein $R_{3c}$ is selected from the group consisting of hydrogen, halo, NR$_d$R$_d$, NO$_2$, CN, optionally substituted $C_1$-$C_{10}$ alkyl, optionally substituted $C_2$-$C_{10}$ alkenyl, optionally substituted $C_2$-$C_{10}$ alkynyl, C(O)OR$_c$, C(O)R$_c$, NR$_d$C(O)R$_c$, OC(O)R$_c$ and OR$_c$. In yet additional embodiments, $R_{3c}$ is selected from the group consisting of optionally substituted $C_1$-$C_{10}$ alkyl, optionally substituted $C_2$-$C_{10}$ alkenyl, and optionally substituted $C_2$-$C_{10}$ alkynyl.

In yet further embodiments, the compound has the Formula (Ib), or a pharmaceutically acceptable salt, solvate, clathrate or prodrug thereof, wherein $R_{3c}$ is:

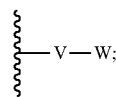

wherein V is selected from the group consisting of $C_1$-$C_6$ alkylene, $C_2$-$C_6$ alkenylene, $C_2$-$C_6$ alkynylene, each optionally substituted; W is selected from the group consisting of S(O)$_p$R$_m$, CN, optionally substituted heteroaryl and optionally substituted heterocyclic; $R_m$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl; and p is 0, 1 or 2. In some embodiments, V is an optionally substituted $C_1$-$C_6$ alkylene. In yet other aspects, V is an optionally substituted $C_2$-$C_4$ alkylene.

In further aspects of the invention, W is selected from the group consisting of S(O)$_p$R$_m$, CN,

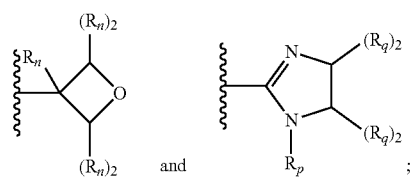

wherein each of $R_n$, $R_p$, and $R_q$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, OR$_c$, NR$_d$R$_d$, C(O)OR$_c$, CN, C(O)R$_c$, C(O)C(O)R$_c$, C(O)NR$_d$R$_d$, NR$_d$C(O)R$_c$, NR$_d$S(O)$_n$R$_c$, N(R$_d$)(COOR$_c$), NR$_d$C(O)C(O)R$_c$, NR$_d$C(O)NR$_d$R$_d$, NR$_d$S(O)$_n$NR$_d$R$_d$, NR$_d$S(O)$_n$R$_c$, S(O)$_n$R$_c$, S(O)$_n$NR$_d$R$_d$, OC(O)OR$_c$, OC(O)R$_c$, optionally substituted heterocyclic and optionally substituted heteroaryl. In some embodiments, $R_p$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl.

In some aspects, the compound has the Formula (Ib), or a pharmaceutically acceptable salt, solvate, clathrate or prodrug thereof, wherein $R_{3c}$ is:

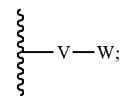

wherein W is S(O)$_p$R$_m$. In additional aspects, W is S(O)$_2$R$_m$ or SR$_m$, wherein $R_m$ is an optionally substituted $C_1$-$C_6$ alkyl or an optionally substituted $C_3$-$C_6$ cycloalkyl.

In yet additional aspects, W is CN. In certain embodiments, W is CN and V is $C_1$-$C_6$ alkylene or $C_2$-$C_6$ alkenylene. In additional embodiments, W is CN and V is $C_2$-$C_6$ alkylene or $C_2$-$C_6$ alkenylene. In yet further embodiments, W is CN and V is $C_2$-$C_4$ alkylene.

In further embodiments, the compound has the Formula (Ib), or a pharmaceutically acceptable salt, solvate, clathrate or prodrug thereof, wherein $R_{3c}$ is

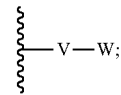

wherein W is optionally substituted heteroaryl. In certain embodiments, W is an optionally substituted heteroaryl and V is $C_1$-$C_6$ alkylene or $C_2$-$C_6$ alkenylene. In additional embodiments, V is $C_2$-$C_6$ alkylene or $C_2$-$C_6$ alkenylene. In yet further embodiments, V is $C_2$-$C_4$ alkylene.

In additional aspects, the compound has the Formula (Ib), or a pharmaceutically acceptable salt, solvate, clathrate or prodrug thereof, wherein $R_{3c}$ is:

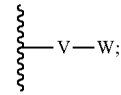

wherein W is optionally substituted heterocyclic.

In additional embodiments, W is selected from the group consisting of:

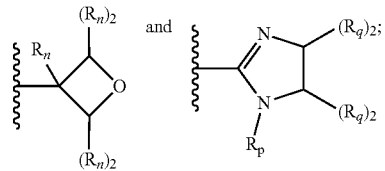

wherein each of $R_n$, $R_p$, and $R_y$ are each independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, $OR_c$, $NR_dR_d$, $C(O)OR_c$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $OC(O)R_c$, optionally substituted heterocyclic and optionally substituted heteroaryl. In additional embodiments, each $R_n$, $R_p$, and $R_q$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, $C(O)OR_c$, $C(O)R_c$, $C(O)C(O)R_c$, $C(O)NR_dR_d$, optionally substituted heterocyclic and optionally substituted heteroaryl. In some embodiments, $R_p$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl. In certain embodiments, V is $C_1$-$C_6$ alkylene or $C_2$-$C_6$ alkenylene. In additional embodiments, V is $C_2$-$C_6$ alkylene or $C_2$-$C_6$ alkenylene. In yet further embodiments, V is $C_2$-$C_4$ alkylene.

In further embodiments, the compound has the Formula (Ib), or a pharmaceutically acceptable salt, solvate, clathrate or prodrug thereof, wherein $R_4$ is selected from the group consisting of hydrogen, halo, $N_3$, $C(O)OR_c$, CN, $C(O)R_c$, $C(O)C(O)R_c$, $C(O)NR_dR_d$, $NO_2$ and $NR_dR_d$. In additional aspects, $R_4$ is selected from the group consisting of halo, $N_3$, $C(O)OR_c$, CN, $C(O)R_c$, $C(O)C(O)R_c$, $C(O)NR_dR_d$, $NO_2$ and $NR_dR_d$. In additional aspects, $R_4$ is chloro.

In yet additional embodiments, the compound has the Formula (Ib), or a pharmaceutically acceptable salt, solvate, clathrate or prodrug thereof, wherein Z is an optionally substituted, 6- to 10-membered bridged N-heterocyclic. In some aspects, Z is optionally substituted, 6- to 9-membered bridged N-heterocyclic. In additional embodiments, Z is an optionally substituted, 6- to 8-membered bridged N-heterocyclic. In further embodiments, Z is an optionally substituted, 7-membered bridged N-heterocyclic or an optionally substituted 8-membered bridged N-heterocyclic.

In certain embodiments, Z is:

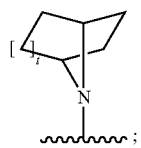

wherein the bridged heterocyclic is optionally substituted and wherein t is 0, 1, 2, 3, 4, 5 or 6.

In some embodiments, Z is:

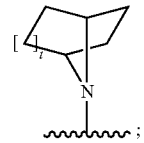

wherein the bridged heterocyclic is optionally substituted with one or more $R_6$, wherein each $R_6$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C=NR_d)R_c$, $OC(O)R_c$, optionally substituted heterocyclic and optionally substituted heteroaryl, and wherein t is 0, 1, 2, 3, 4, 5 or 6. In some additional embodiments, t is 1, 2, 3 or 4. In yet further embodiments, t is 1, 2 or 3.

In some embodiments, Z is selected from the group consisting of:

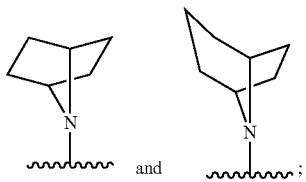 [SMILES: *N1C2CCC1CC2 ; *N1C2CCCC1CC2]

each optionally substituted.

In some embodiments, Z is selected from the group consisting of:

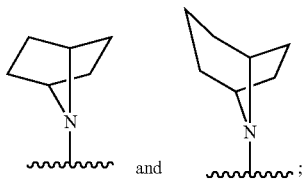 [SMILES: *N1C2CCC1CC2 ; *N1C2CCCC1CC2]

wherein each bridged heterocyclic is optionally substituted with one or more $R_6$, wherein each $R_6$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C=NR_d)R_c$, $OC(O)R_c$, optionally substituted heterocyclic and optionally substituted heteroaryl.

In further embodiments, Z is selected from the group consisting of:

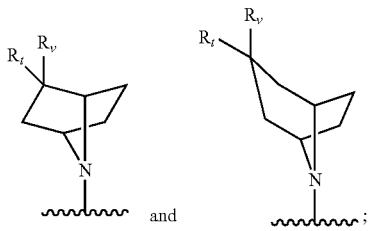

and wherein $R_t$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(CO-OR_c)$, $NR_dC(O)C(O)R_c$, $NR_dC(O)NR_dR_d$, $NR_dS(O)_n NR_dR_d$, $NR_dS(O)_nR_c$, $S(O)_nR_c$, $S(O)_nNR_dR_d$, $OC(O)OR_c$, $(C=NR_d)R_c$, $OC(O)R_c$, optionally substituted heterocyclic and optionally substituted heteroaryl; and $R_v$ is selected from the group consisting of hydrogen and optionally substituted $C_1$-$C_{10}$ alkyl. In yet additional aspects, $R_t$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, $OR_c$, $NR_dR_d$, $C(O)OR_c$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C=NR_d)R_c$, $OC(O)R_c$, optionally substituted heterocyclic and optionally substituted heteroaryl; and $R_v$ is selected from the group consisting of hydrogen, $OR_c$ and optionally substituted $C_1$-$C_{10}$ alkyl. In yet further embodiments, $R_v$ is an optionally substituted $C_1$-$C_4$ alkyl, $OR_c$ or hydrogen. In further embodiments, $R_t$ is selected from the group consisting of hydrogen, optionally substituted $C_1$-$C_{10}$ alkyl and $OR_c$; and $R_v$ is an optionally substituted $C_1$-$C_4$ alkyl, $OR_c$ or hydrogen. In additional embodiments, $R_t$ is selected from the group consisting of hydrogen, optionally substituted $C_1$-$C_{10}$ alkyl and OH and $R_v$ is an optionally substituted $C_1$-$C_4$ alkyl, OH, or hydrogen.

In additional embodiments, the compound has the Formula (Ib), or a pharmaceutically acceptable salt, solvate, clathrate or prodrug thereof, wherein substituents of optionally substituted E, Z, $R_1$, $R_2$, $R_{3c}$, $R_{3d}$, $R_4$, and $R_5$ are each independently selected from the group consisting of $C_1$-$C_4$ alkyl, halo, $OR_c$, CN, $S(O)_nR_c$, heterocyclyl, and heteroaryl.

In some embodiments, the invention is directed to a compound having the Formula (Ic) or Formula (Id):

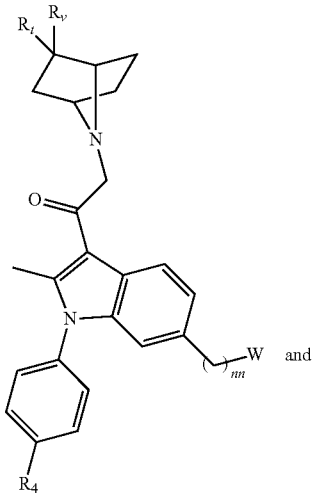

(Ic)

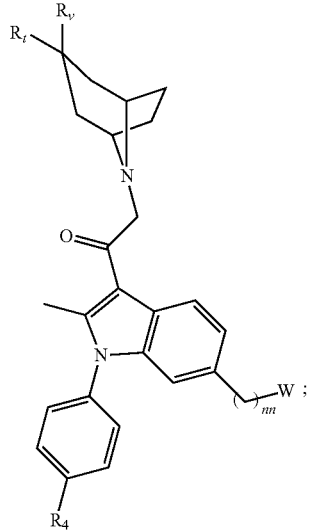

(Id)

or a pharmaceutically acceptable salt, solvate, clathrate or prodrug thereof;

wherein:

$R_t$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(CO-OR_c)$, $NR_dC(O)C(O)R_c$, $NR_dC(O)NR_dR_d$, $NR_dS(O)_n NR_dR_d$, $NR_dS(O)_nR_c$, $S(O)_nR_c$, $S(O)_nNR_dR_d$, $OC(O)OR_c$, $(C=NR_d)R_c$, $OC(O)R_c$, optionally substituted heterocyclic and optionally substituted heteroaryl;

$R_v$ is selected from the group consisting of hydrogen and optionally substituted $C_1$-$C_{10}$ alkyl;

$R_4$ is selected from the group consisting of halo, $N_3$, $C(O)OR_c$, CN, $C(O)R_c$, $C(O)C(O)R_c$, $C(O)NR_dR_d$, $NO_2$ and $NR_dR_d$;

W is selected from the group consisting of $S(O)_pR_m$, CN, optionally substituted heteroaryl and optionally substituted heterocyclic;

nn is 1, 2, or 3; and p is 0, 1, or 2.

In some embodiments, the invention is directed to a compound having the Formula (Ic) or Formula (Id), or a pharmaceutically acceptable salt, solvate, clathrate or prodrug thereof, wherein $R_t$ and $R_v$ are independently selected from the group consisting of hydrogen, hydroxyl, —OCH$_3$, and —C(CH$_3$)$_3$.

In some embodiments, the invention is directed to a compound having the Formula (Ic) or Formula (Id), or a pharmaceutically acceptable salt, solvate, clathrate or prodrug thereof, wherein $R_4$ is chloro.

In some embodiments, the invention is directed to a compound having the Formula (Ic) or Formula (Id), or a pharmaceutically acceptable salt, solvate, clathrate or prodrug thereof, wherein W is selected from the group consisting of —SO$_2$CH$_3$, —CN,

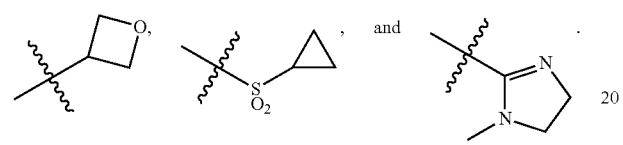

and

In some embodiments the compound, or a pharmaceutically acceptable salt, solvate, clathrate or prodrug thereof, is selected from the group shown in the following Table 1:

TABLE 1

| Compound No. | Structure |
|---|---|
| 1A | 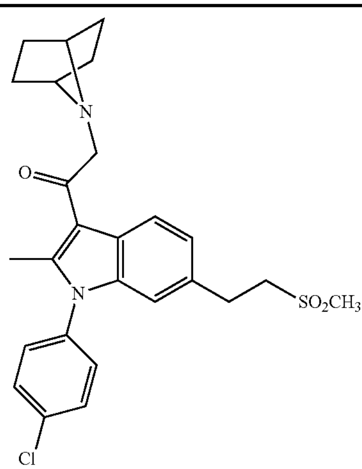 |
| 2A | 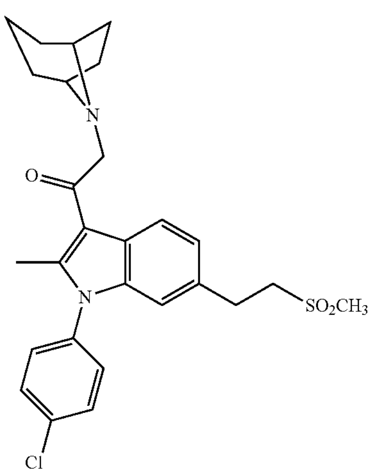 [SMILES: Cc1c(C(=O)CN2C3CCCC2CC3)c2ccc(CCS(C)(=O)=O)cc2n1-c1ccc(Cl)cc1] |

TABLE 1-continued

| Compound No. | Structure |
|---|---|
| 3A | 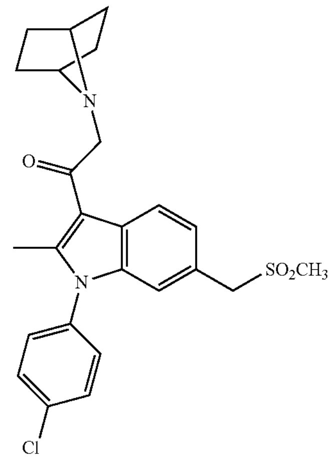 [SMILES: Cc1c(C(=O)CN2C3CCC2CC3)c2ccc(CS(C)(=O)=O)cc2n1-c1ccc(Cl)cc1] |
| 4A | 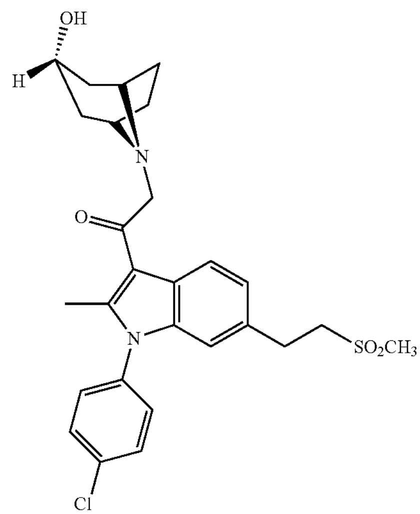 |
| 5A | 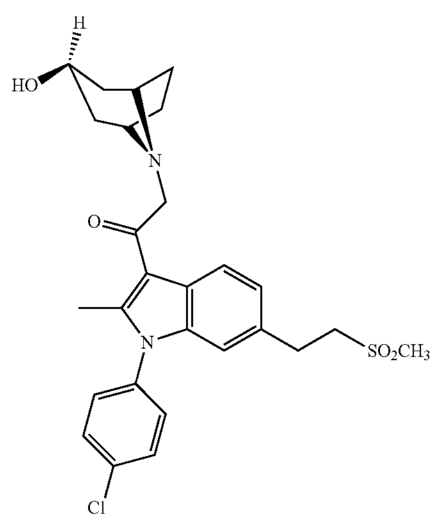 |

TABLE 1-continued
| Compound No. | Structure |
|---|---|
| 6A | 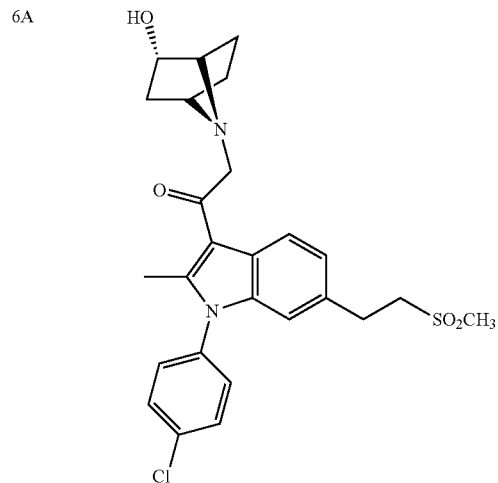 |
| 8A | 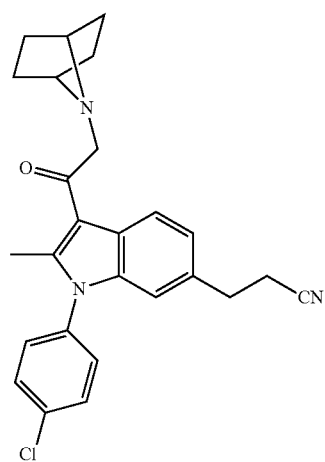 [SMILES: Cc1c(C(=O)CN2C3CCC2CC3)c2ccc(CCC#N)cc2n1-c1ccc(Cl)cc1] |
| 10A | 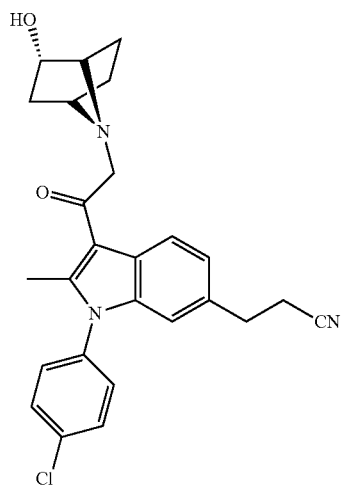 |
| 11A | 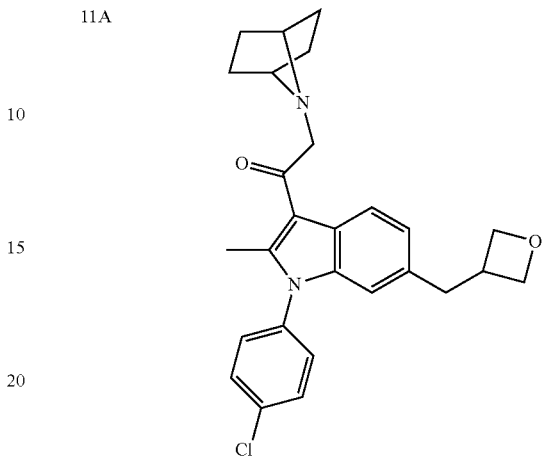 |
| 12A | 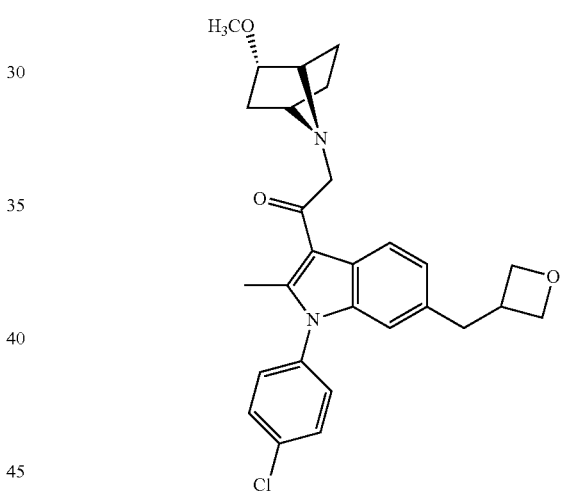 |
| 13A | 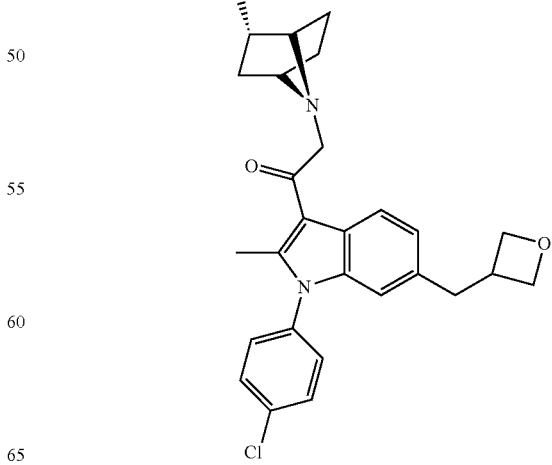 |

TABLE 1-continued
| Compound No. | Structure |
|---|---|
| 15A | 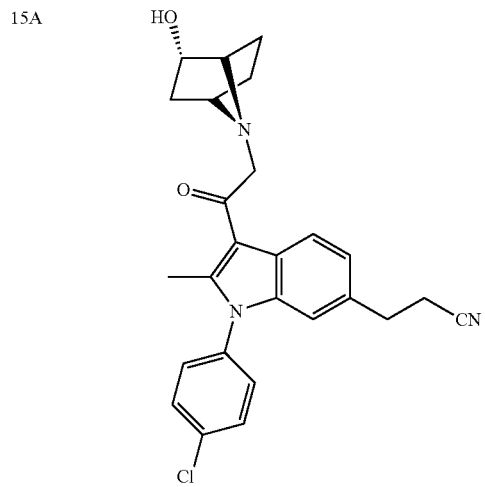 |
| 16A | 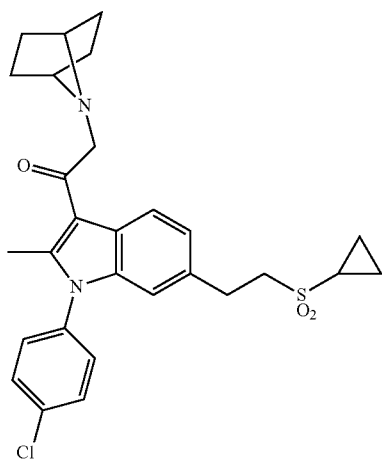 [SMILES: Cc1c(C(=O)CN2C3CCC2CC3)c2ccc(CCS(=O)(=O)C3CC3)cc2n1-c1ccc(Cl)cc1] |
| 17A | 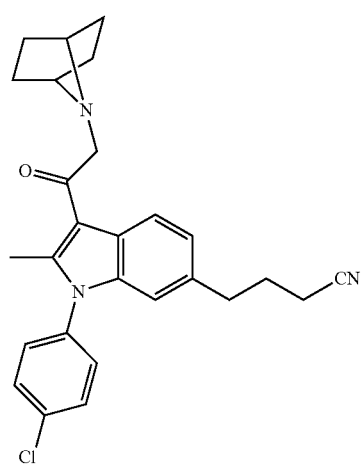 [SMILES: Cc1c(C(=O)CN2C3CCC2CC3)c2ccc(CCCC#N)cc2n1-c1ccc(Cl)cc1] |
| 18A | 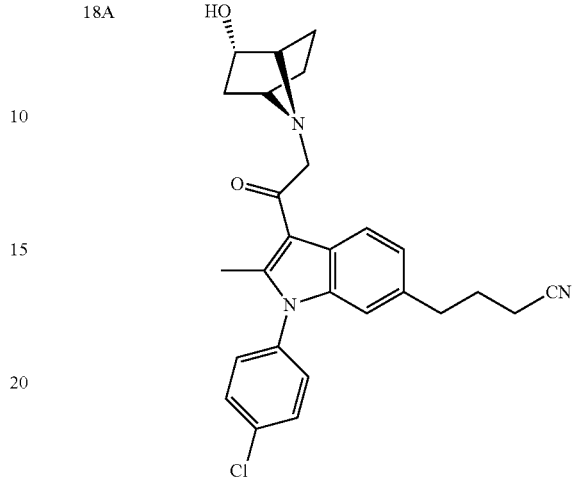 |
| 19A | 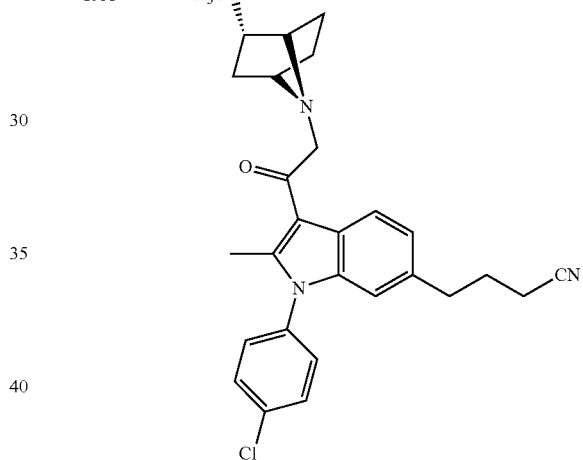 |
| 20A | 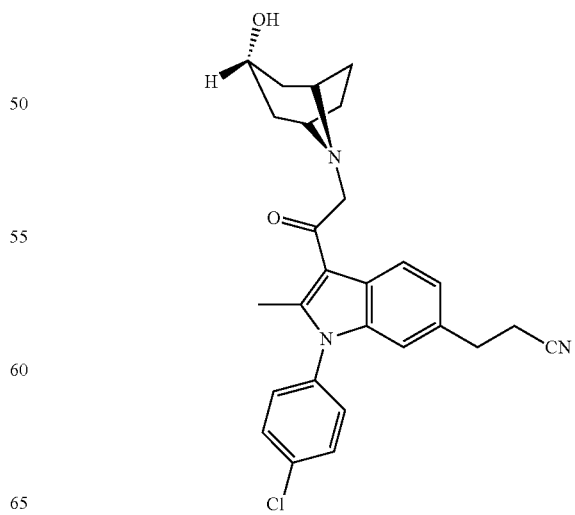 |

TABLE 1-continued
| Compound No. | Structure |
|---|---|
| 21A | 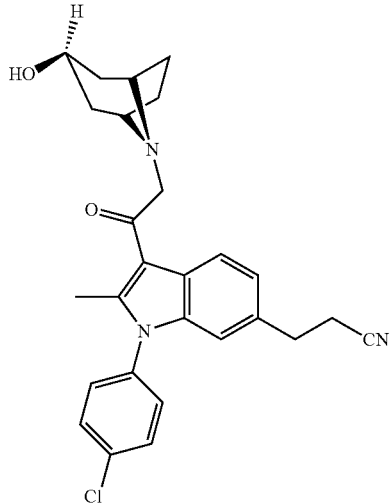 |
| 22A | 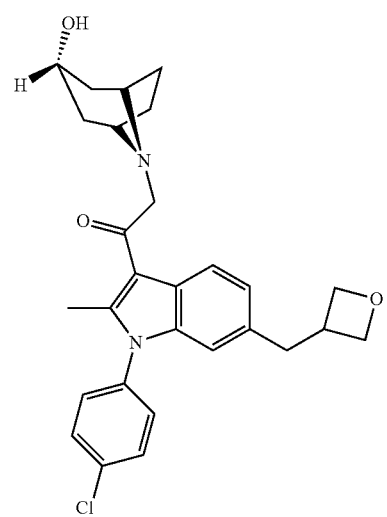 |
| 23A | 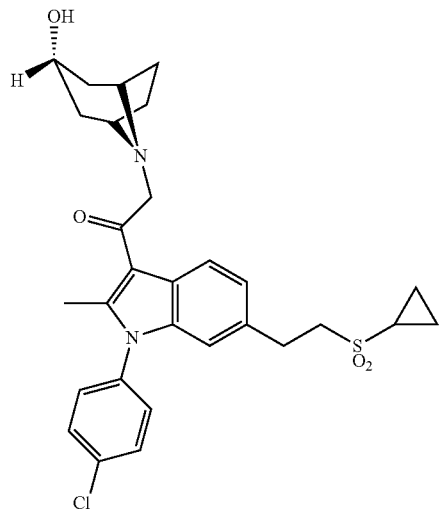 |
| 24A | 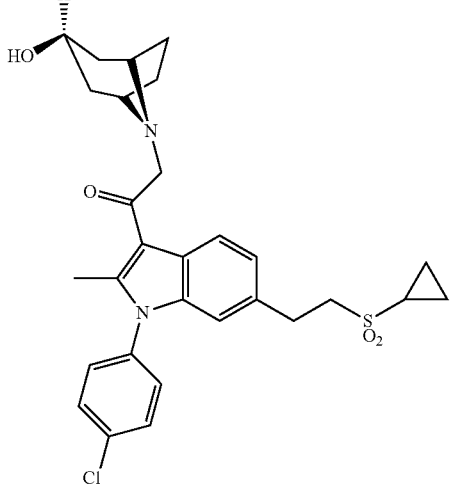 |
| 25A | 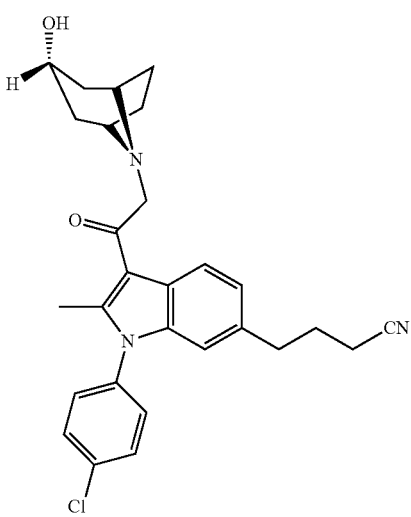 |
| 26A | 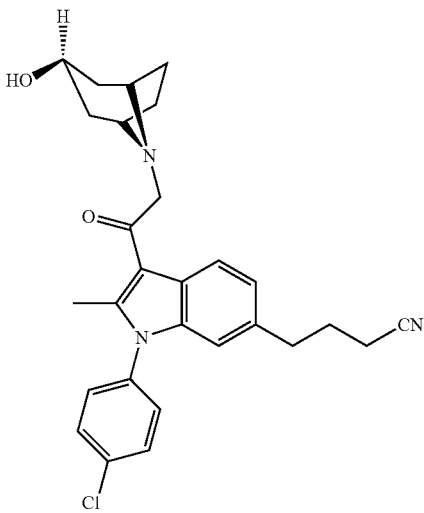 |

TABLE 1-continued

| Compound No. | Structure |
|---|---|
| 27A | (structure) |
| 28A | (structure) |
| 29A | (structure) |
| 30A | (structure) |
| 31A | (structure) |
| 32A | (structure) |

TABLE 1-continued

| Compound No. | Structure |
|---|---|
| 33A | 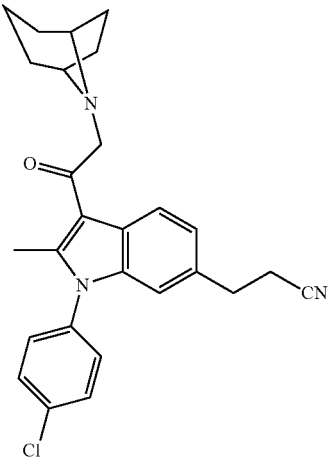 [SMILES: Cc1c(C(=O)CN2C3CCCC2CC3)c2ccc(CCC#N)cc2n1-c1ccc(Cl)cc1] |

Compounds of Formula (II), (IIa), (IIb), and (IIc)

In further embodiments of the invention, the compound has the Formula (II):

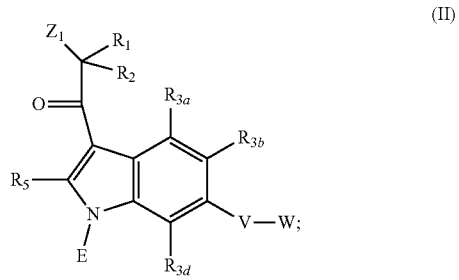

(II)

or a pharmaceutically acceptable salt, solvate, clathrate or prodrug thereof; wherein:

E is selected from the group consisting of optionally substituted aryl or optionally substituted heteroaryl;

each of $R_1$ and $R_2$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl;

$Z_1$ is an optionally substituted N-heterocyclic;

each of $R_{3a}$, $R_{3b}$, and $R_{3d}$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C=NR_d)R_c$, $OC(O)R_c$, optionally substituted heterocyclic and optionally substituted heteroaryl;

$R_5$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C=NR_d)R_c$, $OC(O)R_c$, optionally substituted heterocyclic, and optionally substituted heteroaryl;

V is selected from the group consisting of $C_1$-$C_6$ alkylene, $C_2$-$C_6$ alkenylene, $C_2$-$C_6$ alkynylene, each optionally substituted;

W is selected from the group consisting of $S(O)_pR_m$, CN, optionally substituted heteroaryl and optionally substituted heterocyclic;

wherein substituents of optionally substituted E, Z, V, W, $R_1$, $R_2$, $R_{3a}$, $R_{3b}$, $R_{3d}$, and $R_5$ are each independently selected from the group consisting of $C_1$-$C_{10}$ alkyl, $C_2$-$C_{10}$ alkenyl, $C_2$-$C_{10}$ alkynyl, $C_3$-$C_{12}$ cycloalkyl, $C_3$-$C_{12}$ cycloalkenyl, aryl, halo, $N_3$, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C=NR_d)R_c$, $OC(O)R_c$, heterocyclic, and heteroaryl;

each $R_c$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl;

each $R_d$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl; or two geminal $R_d$ groups are taken together with the nitrogen atom to which they are attached to form an optionally substituted heterocyclic or an optionally substituted heteroaryl;

$R_m$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl;

each n is independently 0, 1 or 2; and p is 0, 1 or 2.

In additional embodiments, the compound has the Formula (II), or a pharmaceutically acceptable salt, solvate, clathrate or prodrug thereof, wherein $R_1$ and $R_2$ are each independently selected from hydrogen and optionally substituted $C_1$-$C_{10}$ alkyl. In yet additional embodiments, $R_1$ and $R_2$ are each hydrogen.

In further embodiments, the compound has the Formula (II), or a pharmaceutically acceptable salt, solvate, clathrate or prodrug thereof, wherein $R_5$ is an optionally substituted $C_1$-$C_4$ alkyl. In additional embodiments, $R_5$ is methyl or ethyl. In yet additional embodiments, $R_5$ is methyl.

In additional aspects, the compound has the Formula (II), or a pharmaceutically acceptable salt, solvate, clathrate or prodrug thereof, wherein E is an optionally substituted phenyl. In some embodiments, E is a para-substituted phenyl, wherein the phenyl is optionally further substituted. In additional embodiments, E is a para-substituted phenyl, wherein the phenyl is not further substituted. In additional aspects, E is unsubstituted phenyl.

In some embodiments, E is phenyl, substituted with one or more $R_4$, wherein each $R_4$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C=NR_d)R_c$, $OC(O)R_c$, optionally substituted heterocyclic, and optionally substituted heteroaryl.

In additional aspects, $R_4$ is selected from the group consisting of hydrogen, halo, $N_3$, $C(O)OR_c$, CN, $C(O)R_c$, $C(O)C(O)R_c$, $C(O)NR_dR_d$, $NO_2$ and $NR_dR_d$. In yet additional embodiments, $R_4$ is selected from the group consisting of halo, $N_3$, $C(O)OR_c$, CN, $C(O)R_c$, $C(O)C(O)R_c$, $C(O)NR_dR_d$, $NO_2$ and $NR_dR_d$.

In yet additional embodiments, E is phenyl, substituted at the para-position with $R_4$, wherein $R_4$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_n$-$NR_dR_d$, $OC(O)OR_c$, $(C=NR_d)R_c$, $OC(O)R_c$, optionally substituted heterocyclic, and optionally substituted heteroaryl.

In additional aspects, $R_4$ is selected from the group consisting of hydrogen, halo, $N_3$, $C(O)OR_c$, CN, $C(O)R_c$, $C(O)C(O)R_c$, $C(O)NR_dR_d$, $NO_2$ and $NR_dR_d$. In yet additional embodiments, $R_4$ is selected from the group consisting of halo, $N_3$, $C(O)OR_c$, CN, $C(O)R_c$, $C(O)C(O)R_c$, $C(O)NR_dR_d$, $NO_2$ and $NR_dR_d$.

In additional embodiments, the compound has the Formula (II), wherein $Z_1$ is an optionally substituted 5- to 12-membered N-heterocyclic. In yet additional embodiments, $Z_1$ is an optionally substituted 5- to 7-membered N-heterocyclic. In further embodiments, $Z_1$ is selected from the group consisting of optionally substituted 1-pyrrolidinyl and optionally substituted 1-piperidinyl.

In further embodiments, the compound has the Formula (II), or a pharmaceutically acceptable salt, solvate, clathrate or prodrug thereof, wherein $Z_1$ is an optionally substituted, 6- to 12-membered bridged N-heterocyclic. In yet further embodiments, $Z_1$ is an optionally substituted, 6- to 10-membered bridged N-heterocyclic. In further embodiments, $Z_1$ is an optionally substituted, 6- to 8-membered bridged N-heterocyclic.

In certain embodiments, $Z_1$ is:

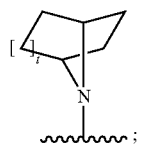

wherein the bridged heterocyclic is optionally substituted and wherein t is 0, 1, 2, 3, 4, 5 or 6.

In some embodiments, $Z_1$ is:

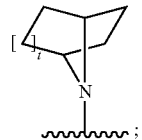

wherein the bridged heterocyclic is optionally substituted with one or more $R_6$, wherein each $R_6$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C=NR_d)R_c$, $OC(O)R_c$, optionally substituted heterocyclic and optionally substituted heteroaryl, and wherein t is 0, 1, 2, 3, 4, 5 or 6. In some additional embodiments, t is 1, 2, 3 or 4. In yet further embodiments, t is 1, 2 or 3.

In some embodiments, $Z_1$ is selected from the group consisting of:

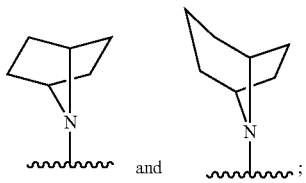 [SMILES: *N1C2CCC1CC2 ; *N1C2CCCC1CC2]

each optionally substituted.

In some embodiments, Z is selected from the group consisting of:

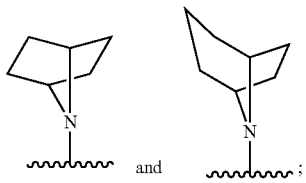 [SMILES: *N1C2CCC1CC2 ; *N1C2CCCC1CC2]

wherein each bridged heterocyclic is optionally substituted with one or more $R_6$, wherein each $R_6$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NRS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C=NR_d)R_c$, $OC(O)R_c$, optionally substituted heterocyclic and optionally substituted heteroaryl.

In further embodiments, $Z_1$ is selected from the group consisting of:

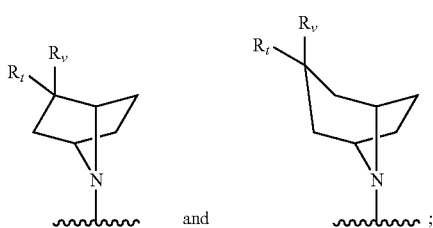

wherein $R_t$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C=NR_d)R_c$, $OC(O)R_c$, optionally substituted heterocyclic and optionally substituted heteroaryl; and $R_v$ is selected from the group consisting of hydrogen and optionally substituted $C_1$-$C_{10}$ alkyl. In yet additional aspects, $R_t$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, $OR_c$, $NR_dR_d$, $C(O)OR_c$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C=NR_d)R_c$, $OC(O)R_c$, optionally substituted heterocyclic and optionally substituted heteroaryl; and $R_v$ is selected from the group consisting of hydrogen, $OR_c$ and optionally substituted $C_1$-$C_{10}$ alkyl. In yet further embodiments, $R_v$ is an optionally substituted $C_1$-$C_4$ alkyl, $OR_c$ or hydrogen. In further embodiments, $R_t$ is selected from the group consisting of hydrogen, optionally substituted $C_1$-$C_{10}$ alkyl and $OR_c$; and $R_v$ is an optionally substituted $C_1$-$C_4$ alkyl, $OR_c$ or hydrogen. In additional embodiments, $R_t$ is selected from the group consisting of hydrogen, optionally substituted $C_1$-$C_{10}$ alkyl and OH and $R_v$ is an optionally substituted $C_1$-$C_4$ alkyl, OH, or hydrogen.

In some embodiments, the compound has the Formula (II), or a pharmaceutically acceptable salt, solvate, clathrate or prodrug thereof, wherein V is an optionally substituted $C_1$-$C_6$ alkylene. In yet other aspects, V is an optionally substituted $C_2$-$C_4$ alkylene. In further aspects of the invention, W is selected from the group consisting of $S(O)_pR_m$, CN,

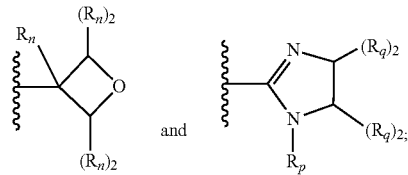

wherein each of $R_n$, $R_p$, and $R_q$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, $OR_c$, $NR_dR_d$, $C(O)OR_c$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $OC(O)R_c$, optionally substituted heterocyclic and optionally substituted heteroaryl. In some embodiments, $R_p$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl.

In some aspects, the compound has the Formula (II), or a pharmaceutically acceptable salt, solvate, clathrate or prodrug thereof, wherein W is $S(O)_pR_m$, for example, W is $S(O)_2R_m$ or $SR_m$, wherein $R_m$ is an optionally substituted $C_1$-$C_6$ alkyl or an optionally substituted $C_3$-$C_6$ cycloalkyl.

In yet additional aspects, W is CN. In certain embodiments, W is CN and V is $C_1$-$C_6$ alkylene or $C_2$-$C_6$ alkenylene. In additional embodiments, W is CN and V is $C_2$-$C_6$ alkylene or $C_2$-$C_6$ alkenylene. In yet further embodiments, W is CN and V is $C_2$-$C_4$ alkylene.

In further embodiments, the compound has the Formula (II), or a pharmaceutically acceptable salt, solvate, clathrate or prodrug thereof, wherein W is optionally substituted heteroaryl. In certain embodiments, V is $C_1$-$C_6$ alkylene or $C_2$-$C_6$ alkenylene.

In additional aspects, the compound has the Formula (II), or a pharmaceutically acceptable salt, solvate, clathrate or prodrug thereof, wherein W is optionally substituted heterocyclic. In additional embodiments, W is selected from the group consisting of:

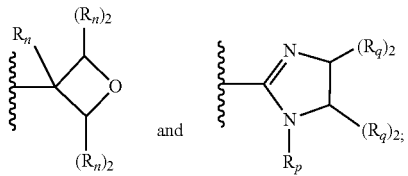

wherein each of $R_n$, $R_p$ and $R_q$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, $OR_c$, $NR_dR_d$, $C(O)OR_c$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $OC(O)R_c$, optionally substituted heterocyclic and optionally substituted heteroaryl. In additional embodiments, each $R_n$, $R_p$ and $R_q$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, $C(O)OR_c$, $C(O)R_c$, $C(O)C(O)R_c$, $C(O)NR_dR_d$, optionally substituted heterocyclic and optionally substituted heteroaryl. In some embodiments, $R_p$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl. In certain embodiments, W is heterocyclic and V is $C_1$-$C_6$ alkylene or $C_2$-$C_6$ alkenylene. In additional embodiments, W is heterocyclic and V is $C_2$-$C_6$ alkylene or $C_2$-$C_6$ alkenylene. In yet further embodiments, W is heterocyclic and V is $C_2$-$C_4$ alkylene.

It is to be understood that the specific embodiments described herein can be taken in combination with other specific embodiments delineated herein. For example, for compounds of Formula (Ia), Z was described as an optionally substituted, 7-membered bridged N-heterocyclic in certain embodiments, E was described as optionally substituted phenyl in some embodiments, and $R_5$ was described as methyl in some embodiments. It is thus to be understood that the invention specifically encompasses compounds of Formula (Ia), wherein Z is an optionally substituted, 7-membered bridged N-heterocyclic, E is optionally substituted phenyl, and $R_5$ is methyl.

In additional embodiments, the compound has the Formula (II), or a pharmaceutically acceptable salt, solvate, clathrate or prodrug thereof, wherein substituents of optionally substituted E, Z, V, W, $R_1$, $R_2$, $R_{3a}$, $R_{3b}$, $R_{3d}$, and $R_5$ are each independently selected from the group consisting of $C_1$-$C_4$ alkyl, halo, $OR_c$, CN, $S(O)_nR_c$, heterocyclyl, and heteroaryl.

In some embodiments, the invention is directed to a compound having the Formula (IIa), Formula (IIb), or Formula (IIc):

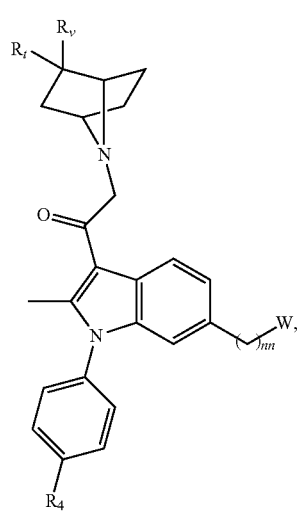
(IIa)

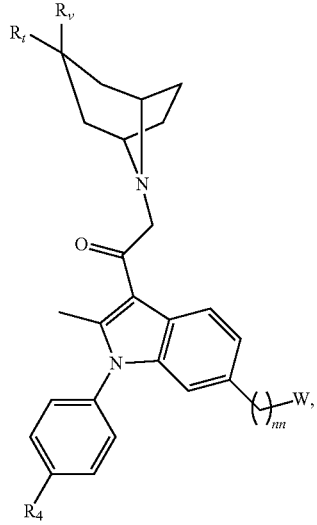
(IIb)

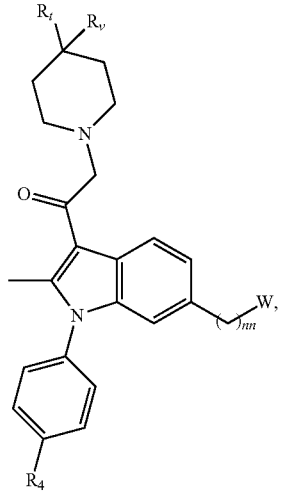
(IIc)

or a pharmaceutically acceptable salt, solvate, clathrate or prodrug thereof, wherein:

$R_t$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(CO-OR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C=NR_d)R_c$, $OC(O)R_c$, optionally substituted heterocyclic and optionally substituted heteroaryl;

$R_v$ is selected from the group consisting of hydrogen and optionally substituted $C_1$-$C_{10}$ alkyl;

$R_4$ is selected from the group consisting of halo, $N_3$, $C(O)OR_c$, CN, $C(O)R_c$, $C(O)C(O)R_c$, $C(O)NR_dR_d$, $NO_2$ and $NR_dR_d$;

W is selected from the group consisting of $S(O)_pR_m$, CN, optionally substituted heteroaryl and optionally substituted heterocyclic;

nn is 1, 2, or 3; and p is 0, 1, or 2.

In some embodiments, the invention is directed to a compound having the Formula (IIa), Formula (IIb), or Formula (IIc), or a pharmaceutically acceptable salt, solvate, clathrate or prodrug thereof, wherein $R_t$ and $R_v$ are independently selected from the group consisting of hydrogen, hydroxyl, —OCH$_3$, and —C(CH$_3$)$_3$.

In some embodiments, the invention is directed to a compound having the Formula (IIa), Formula (IIb), or Formula (IIc), or a pharmaceutically acceptable salt, solvate, clathrate or prodrug thereof, wherein $R_4$ is chloro.

In some embodiments, the invention is directed to a compound having the Formula (IIa), Formula (IIb), or Formula (IIc), or a pharmaceutically acceptable salt, solvate, clathrate or prodrug thereof, wherein W is selected from the group consisting of —SO$_2$CH$_3$, —CN,

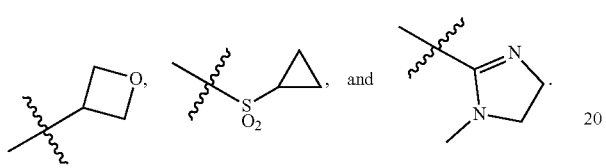

and

The present invention additionally encompasses the compounds shown below in Table 2:

TABLE 2

| Compound No. | Structure |
|---|---|
| 1A | |
| 2A | |
| 3A | 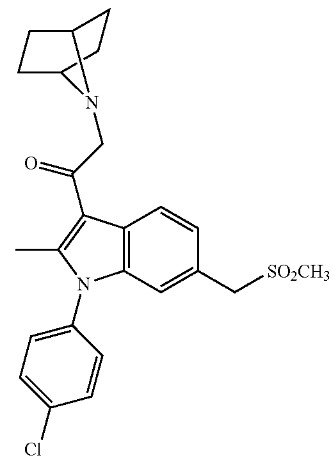 [SMILES: Cc1c(C(=O)CN2C3CCC2CC3)c2ccc(CS(C)(=O)=O)cc2n1-c1ccc(Cl)cc1] |
| 4A | 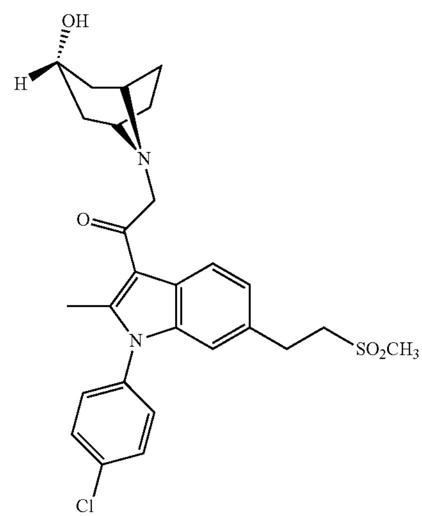 |
| 5A | 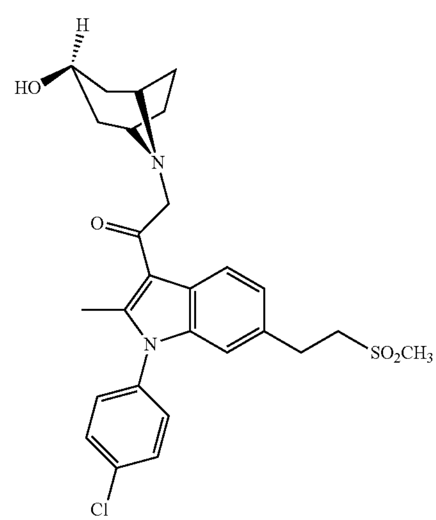 |

TABLE 2-continued
| Compound No. | Structure |
|---|---|
| 6A | 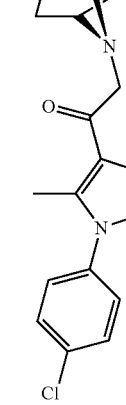 |
| 7A | 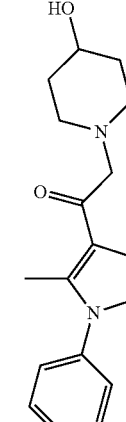 |
| 8A | 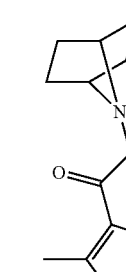 |
| 9A | 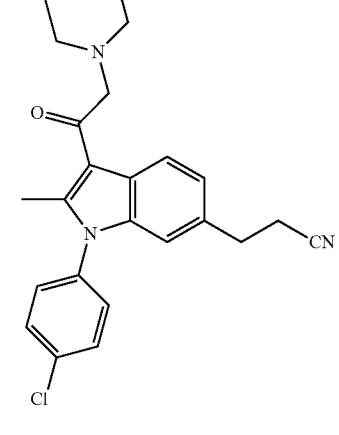 |
| 10A | 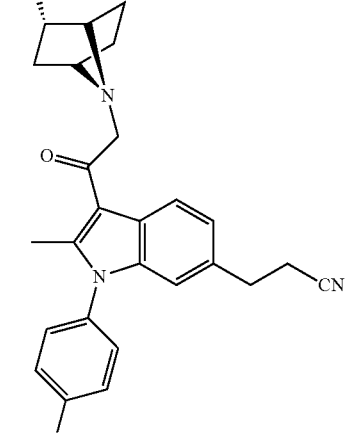 |
| 11A | 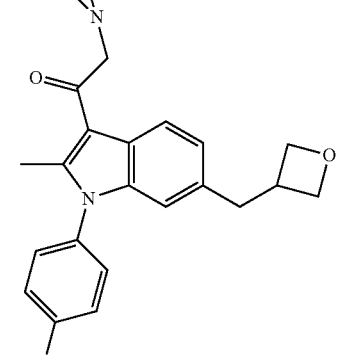 |

TABLE 2-continued
| Compound No. | Structure |
|---|---|
| 12A | 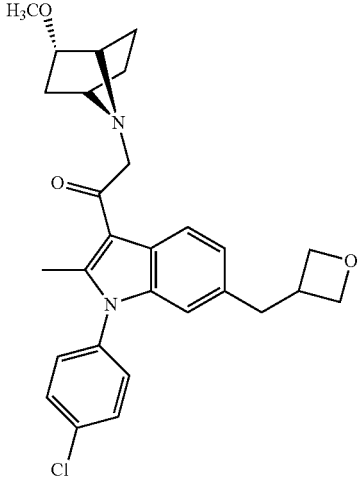 |
| 13A | 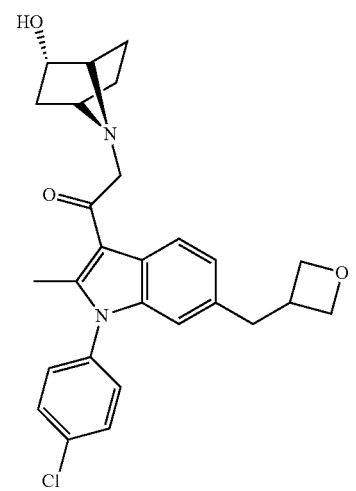 |
| 14A | 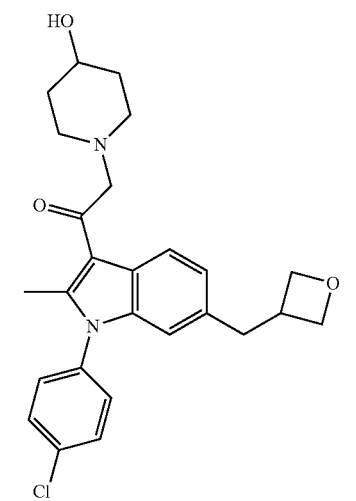 [SMILES: Cc1c(C(=O)CN2CCC(O)CC2)c2ccc(CC3COC3)cc2n1-c1ccc(Cl)cc1] |
| 15A | 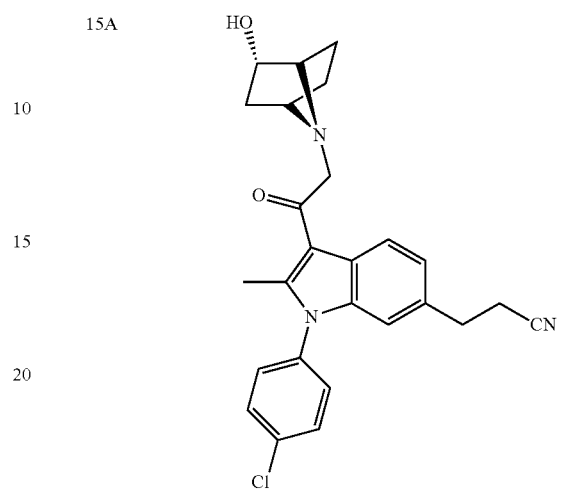 |
| 16A | 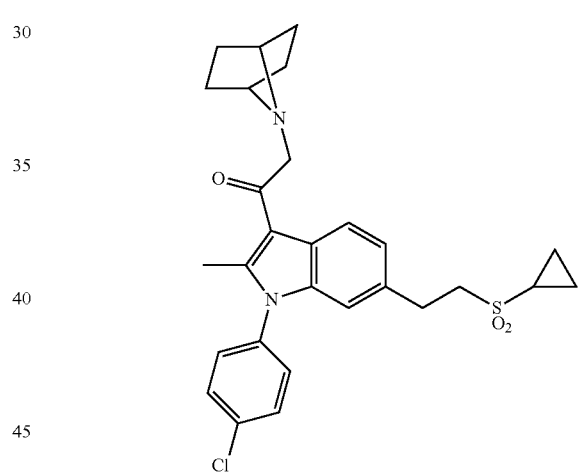 |
| 17A | 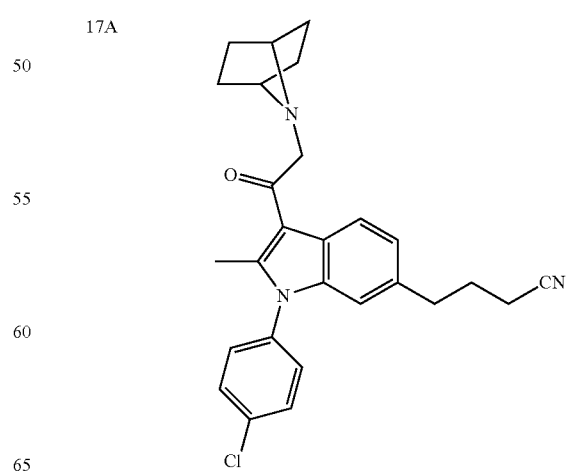 |

TABLE 2-continued
| Compound No. | Structure |
|---|---|
| 18A | 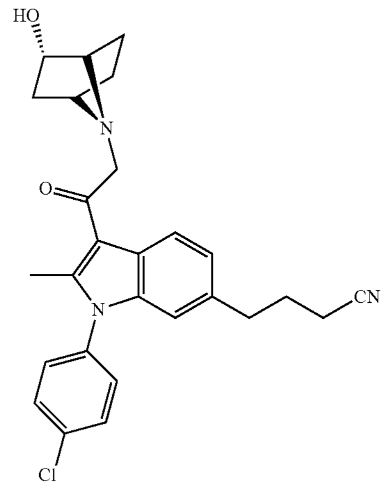 |
| 19A | 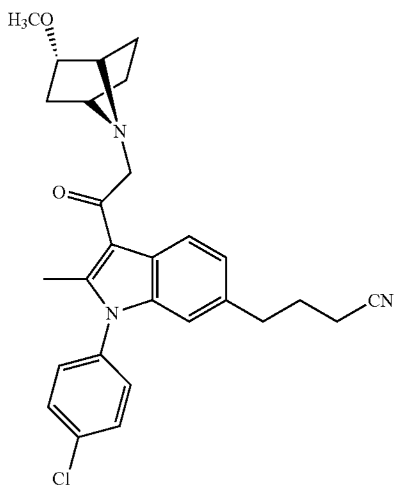 |
| 20A | 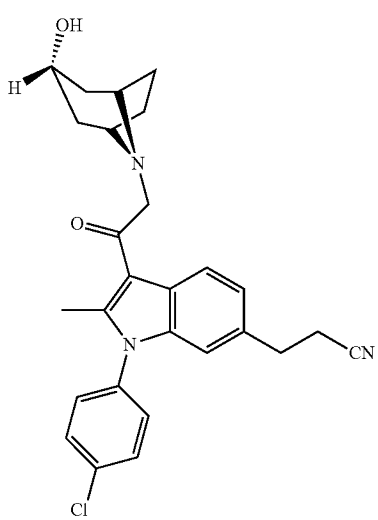 |
| 21A | |
| 22A | |
| 23A | |
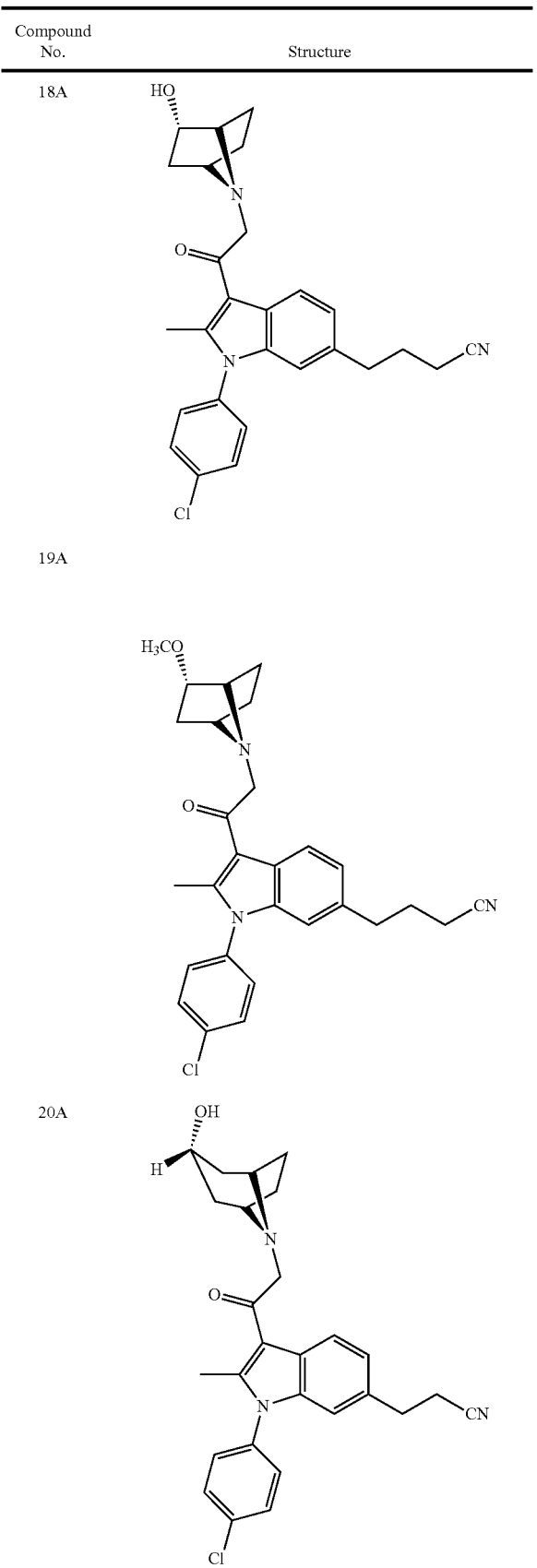
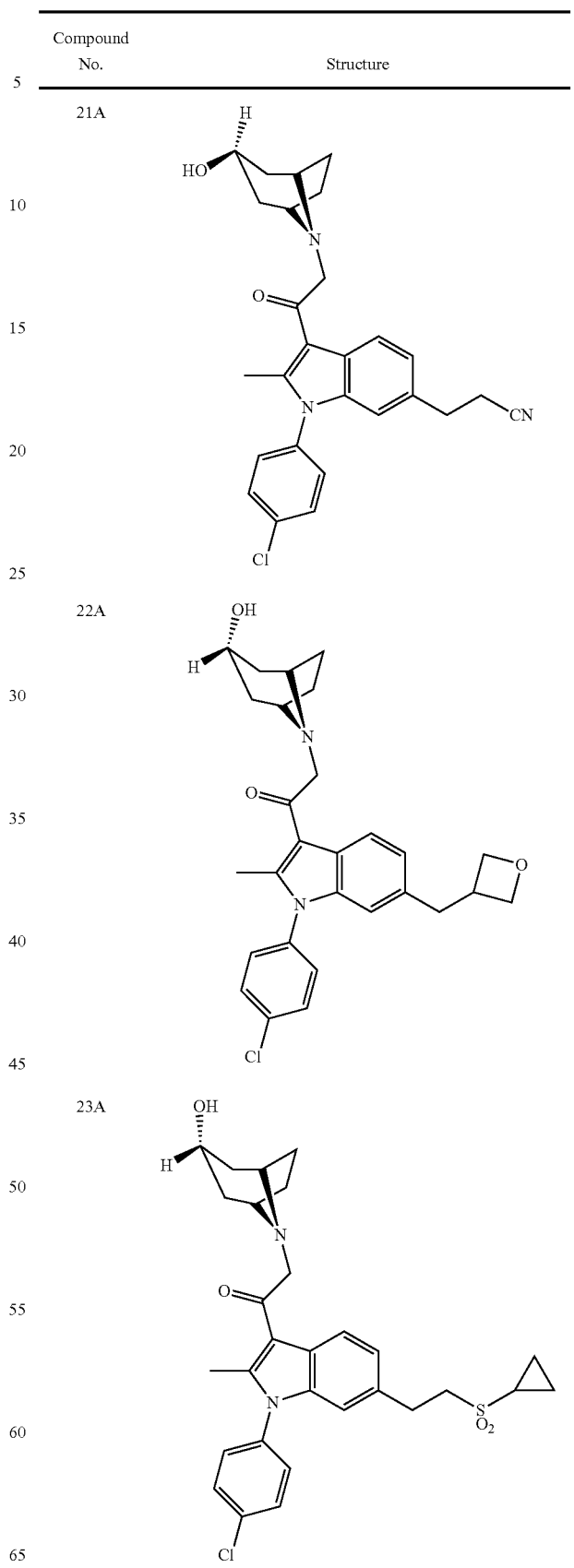

TABLE 2-continued
| Compound No. | Structure |
|---|---|
| 24A | 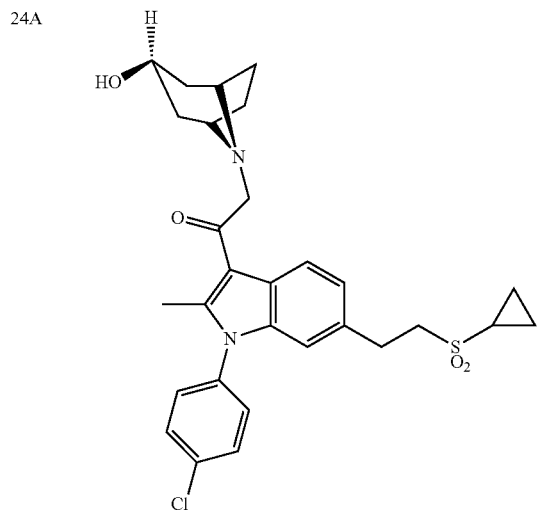 |
| 25A | 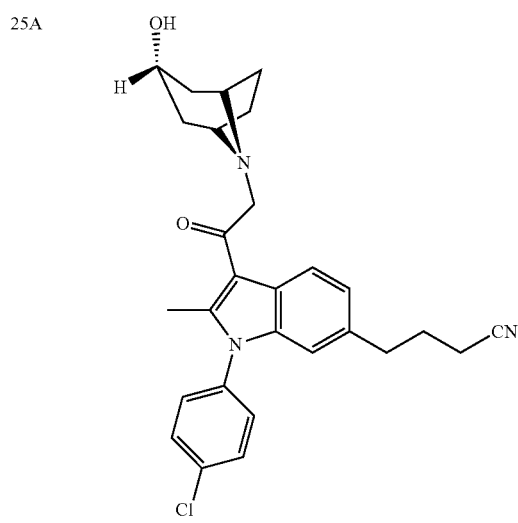 |
| 26A | 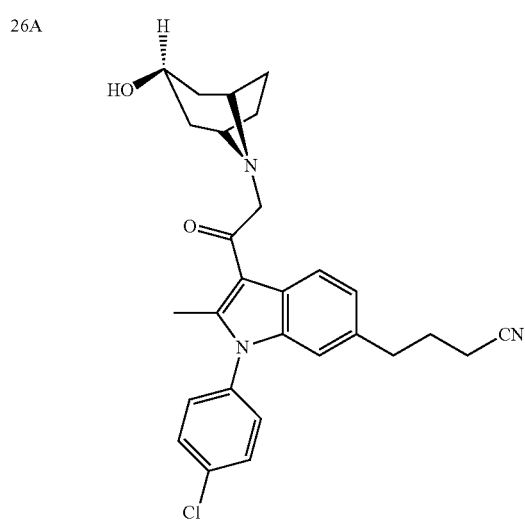 |
| 27A | 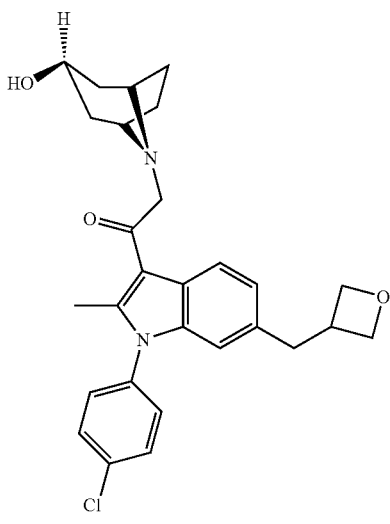 |
| 28A | 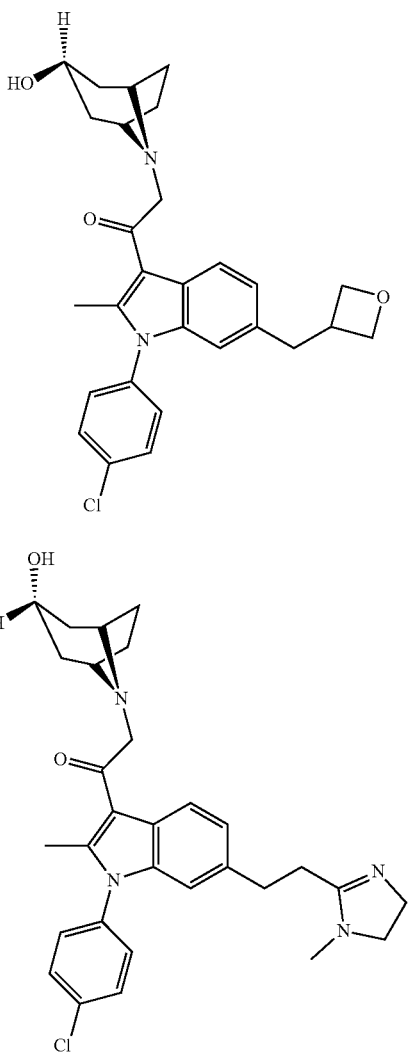 |
| 29A | 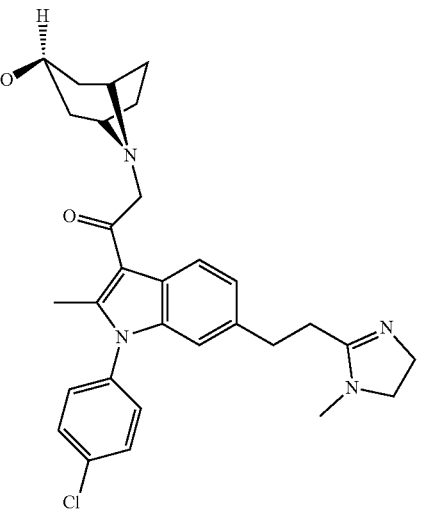 |

TABLE 2-continued

| Compound No. | Structure |
|---|---|
| 30A | 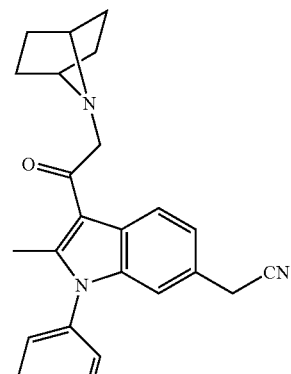 |
| 31A | 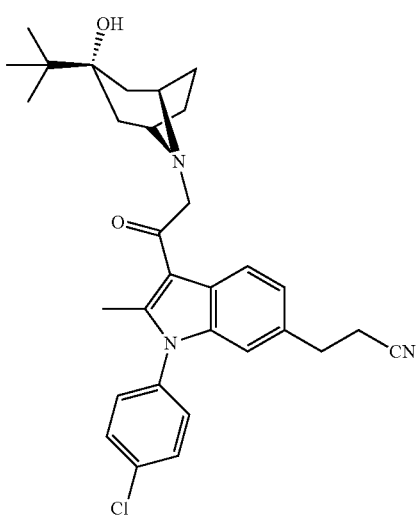 |
| 32A | 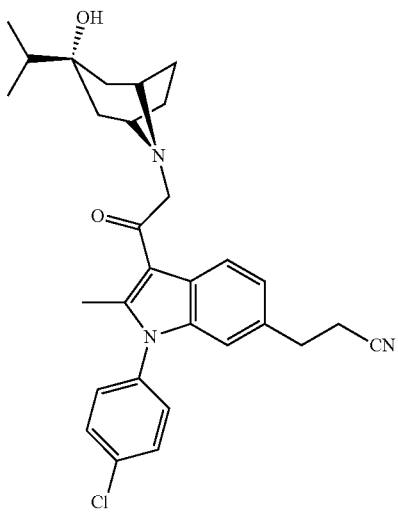 |
| 33A | |

TABLE 2-continued

| Compound No. | Structure |
|---|---|
| 33A | (See above) |

Method of Preparation

In some embodiments, methods that can be used for the synthesis of the compounds of Formulae (Ia), (Ib), (Ic), or (Id) or the compounds of Formulae (II), (IIa), (IIb), or (IIc) described herein have been reported in the literature, for example in: 1) Zhu, L. et al. "Simple Copper Salt-Catalyzed N-Arylation of Nitrogen-Containing Heterocycles with Aryl and Heteroaryl Halides" *J. Org. Chem.* 2007, 72, 8535; 2) Zhang, H. et al. "Amino Acid Promoted CuI-Catalyzed C—N Bond Formation between Aryl Halides and Amines or N-Containing Heterocycles" *J. Org. Chem.* 2005, 70, 5164; 3) Murakami, Y. et al. "Chemical confirmation of the structure of a mutagenic aminophenylnorharman, 9-(4'-aminophenyl)-9H-pyrido[3,4-b]indole: an authentic synthesis of 9-(4'-nitrophenyl)-9H-pyrido[3,4-b]indole as its relay compound" *Heterocycles*, 2010, 80, 455; 4) Wang, L. et al. "Gold-Catalyzed Deacylative Cycloisomerization Reactions of 3-Acylindole/ynes: A New Approach for Carbazole Synthesis" *Org. Lett.* 2011, 13, 3786; 5) Golubeva, G. A. et al. "Electrophilic substitution in alkylated 2-aminoindoles" *Khimiya Geterotsiklicheskikh Soedinenii* 1985, 7, 946; 6) Sawada, Y. et al. "Eight-Membered Oxygen Hetercycles by Brook Rearrangement-mediated [3+4] Annulation" *Org. Lett.* 2004, 6, 2277; 7) Aubé, J. et al. "Synthetic Aspects of an Asymmetric Nitrogen-Insertion Process: Preparation of Chiral, Non-Racemic Caprolactams and Valerolactams. Total Synthesis of (−)-Alloyohimbane" *J. Am. Chem. Soc.* 1990, 112, 4879; 8) Antila, J. C. et al. "The Copper-Catalyzed N-Arylation of Indoles" *J. Am. Chem. Soc.* 2002, 124, 11684; 9) Larock, R. C. et al. "Synthesis of 2,3-Disubstituted Indoles via Palladium-Catalyzed Annulation of Internal Alkynes" *J. Org. Chem.* 1998, 63, 7652; 10) Harcken, C. et al. "A general and efficient synthesis of azaindoles and diazaindoles" *Synlett.* 2005, 20, 3121; 10) Wei, Y. et al. "Palladium-Catalyzed Aerobic Oxidative Cyclization of N-Aryl Imines: Indole Synthesis from Anilines and Ketones" *J. Am. Chem. Soc.* 2012, 134, 9098; 11) Kaila, N. et al. "Diazine Indole Acetic Acids as Potent, Selective, and Orally Bioavailable Antagonists of Chemoattractant Receptor Homologous Molecule Expressed on Th2 Cells (CRTH2) for the Treatment of Allergic Inflammatory Diseases". *J. Med Chem.* 2012, 55, 5088; 12) Carpita, A. et al. "Microwave-assisted synthesis of indole- and azaindole-derivatives in water via cycloisomerization of 2-alkynylanilines and alkynylpyridinamines promoted by amines or catalytic amounts of neutral or basic salts" *Tetrahedron*. 2010, 66, 7169.

Exemplary synthetic routes for the preparation of compounds of Formulae (Ia), (Ib), (Ic), or (Id) or the compounds of Formulae (II), (IIa), (IIb), or (IIc) of the invention are shown in the Schemes I to III below. As will be understood by the skilled artisan, diastereomers can be separated from the reaction mixture using column chromatography.

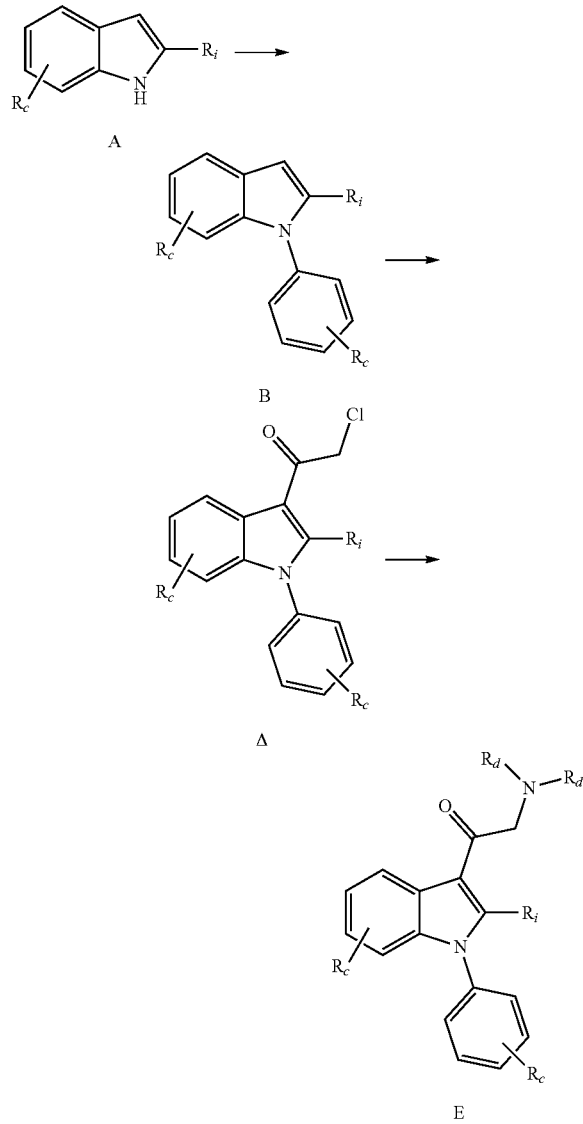

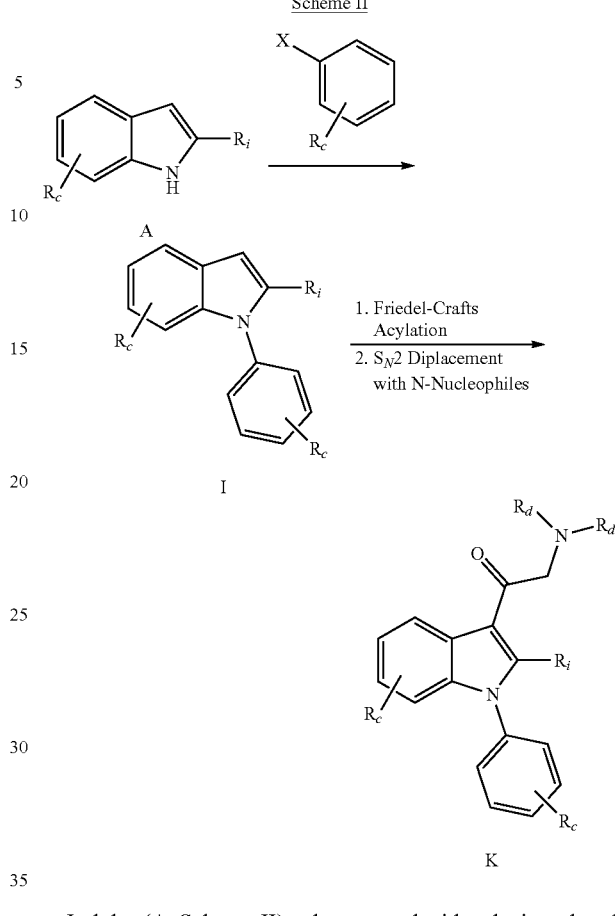

A copper-catalyzed arylation of substituted indole of type A with substituted halobenzenes affords intermediate B (Scheme I).[1,2] Additionally, nucleophilic-aromatic substitution of electron poor benzenes with indole A affords product B.[3] A Friedel-Crafts acylation with an acyl chloride or chloro acetyl chloride, in conjunction with an aluminum-based Lewis acid and/or pyridine provides compounds Δ.[4,5] In intermediate Δ the chloride is easily displaced with a variety of O[6] and N[7]-based nucleophiles, followed in some instances by further modifications, to provide desired compounds of type E.

Indoles (A, Scheme II), when treated with substituted aryl and heteroaryl compounds in the presence of copper (I) reagents, affords intermediates I.[8] Intermediates like I can be further modified through processes analogous to those described above (Scheme 1) to afford compounds of type K.

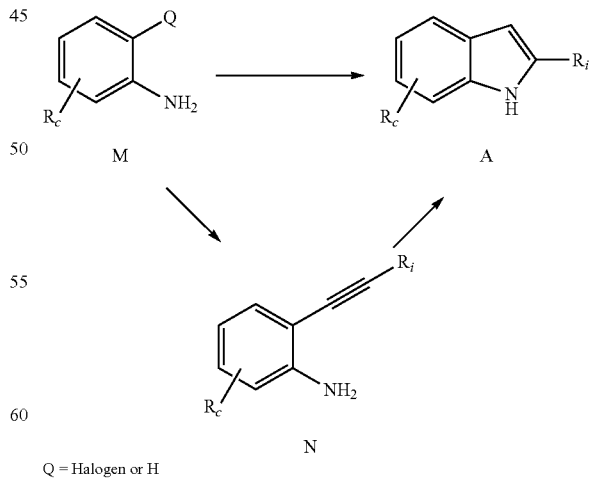

Substituted indoles of type A (Scheme III) are prepared via a Larock indole synthesis from substituted alkynes and halogenated anilines of type M.[9,10] Compounds of type A are also prepared directly from compounds of type M by treating with ketones, copper (II) salts, and palladium (II) salts.[10] Alternatively, compounds of type A are also prepared in a step-wise fashion from compounds of type M through Sonogoshira couplings with terminal alkynes to afford compounds of type N,[11,12] which are then cyclized by treating with a base to compounds of type A.[12]

Compounds of Formula (III)

In some embodiments, the present invention encompasses compounds of (III), or pharmaceutically acceptable salts, solvates, clathrates or prodrugs thereof, pharmaceutical compositions thereof, methods of use thereof in the treatment of conditions associated with a dysfunction in proteostasis, methods of enhancing proteasome activity and methods for treating cancer or a tumor.

In some embodiments, the invention is directed to a compound having the Formula (III):

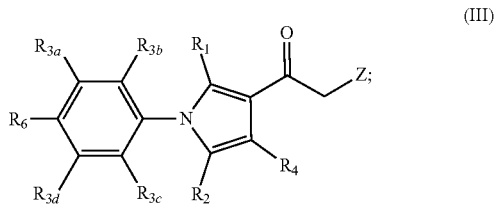

(III)

or a pharmaceutically acceptable salt, solvate, clathrate or prodrug thereof; wherein:

$R_1$ is selected from the group consisting of optionally substituted $C_1$-$C_4$ alkyl, and halo;

$R_2$ is selected from the group consisting optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted 4- to 12-membered heterocyclic, optionally substituted aryl, optionally substituted 4- to 12-membered heteroaryl, halo, and CN;

$R_{3a}$, $R_{3b}$, $R_{3c}$ and $R_{3d}$ are each independently selected from the group consisting of hydrogen, optionally substituted $C_1$-$C_6$ alkyl, CN and halo;

$R_6$ is independently selected from the group consisting of hydrogen, optionally substituted $C_1$-$C_6$ alkyl, CN and halo;

$R_4$ is selected from the group consisting of hydrogen, optionally substituted $C_1$-$C_{10}$ alkyl, halo, and CN; and Z is an optionally substituted, 6- to 12-membered bridged N-heterocyclic;

wherein substituents of optionally substituted Z, $R_1$, $R_2$, $R_{3a}$, $R_{3b}$, $R_{3c}$, $R_{3d}$, $R_4$, and $R_6$ are each independently selected from the group consisting of $C_1$-$C_{10}$ alkyl, $C_2$-$C_{10}$ alkenyl, $C_2$-$C_{10}$ alkynyl, $C_3$-$C_{12}$ cycloalkyl, $C_3$-$C_{12}$ cycloalkenyl, aryl, halo, $N_3$, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NRAS(O)_nR_c$, $S(O)_nR_c$, $S(O)_n$-$NR_dR_d$, $OC(O)OR_c$, $(C=NR_d)R_c$, $OC(O)R_c$, $Si(R_c)_3$, heterocyclic, and heteroaryl;

each $R_c$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl;

each $R_d$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl; or two geminal $R_d$ groups are taken together with the nitrogen atom to which they are attached to form an optionally substituted heterocyclic or an optionally substituted heteroaryl; and each n is independently 0, 1 or 2.

In some embodiments, the invention is directed to a compound having the Formula (III), or a pharmaceutically acceptable salt, solvate, clathrate or prodrug thereof, wherein $R_1$ is selected from the group consisting of optionally substituted $C_1$-$C_4$ alkyl, and halo. In additional aspects, $R_1$ is an optionally substituted $C_1$-$C_4$ alkyl. In yet additional embodiments, $R_1$ is methyl or ethyl. In yet further aspects, $R_1$ is methyl.

In certain embodiments, the compound has the Formula (III), or a pharmaceutically acceptable salt, solvate, clathrate or prodrug thereof, wherein at least two of $R_{3a}$, $R_{3b}$, $R_{3c}$ and $R_{3d}$ are hydrogen. In yet additional aspects, $R_{3a}$, $R_{3b}$, $R_{3c}$ and $R_{3d}$ are each hydrogen. In yet further aspects, $R_{3a}$, and $R_{3d}$ are each independently selected from the group consisting of hydrogen, optionally substituted $C_1$-$C_6$ alkyl, CN and halo, and $R_{3b}$ and $R_{3c}$ are each hydrogen.

In yet additional aspects, the compound has the Formula (III), or a pharmaceutically acceptable salt, solvate, clathrate or prodrug thereof, wherein $R_1$ is selected from the group consisting of optionally substituted $C_1$-$C_4$ alkyl, and halo, at least two of $R_{3a}$, $R_{3b}$, $R_{3c}$ and $R_{3d}$ are hydrogen.

The invention also encompasses compounds having the Formula (III), or a pharmaceutically acceptable salt, solvate, clathrate or prodrug thereof, wherein $R_6$ is selected from the group consisting of CN and halo. In certain aspects, $R_6$ is CN. In certain additional aspects, $R_6$ is halo. In yet additional aspects, $R_{3a}$, $R_{3b}$, $R_{3c}$ and $R_{3d}$ are each hydrogen, and $R_6$ is CN. In yet additional aspects, $R_{3a}$, $R_{3b}$, $R_{3c}$ and $R_{3d}$ are each hydrogen, and $R_6$ is halo. In yet further aspects, $R_{3a}$, and $R_{3d}$ are each independently selected from the group consisting of hydrogen, optionally substituted $C_1$-$C_6$ alkyl, CN and halo; $R_{3b}$ and $R_{3c}$ are each hydrogen; and $R_6$ is CN. In additional aspects, $R_{3a}$, and $R_{3d}$ are each independently selected from the group consisting of hydrogen, optionally substituted $C_1$-$C_6$ alkyl, CN and halo; $R_{3b}$ and $R_{3c}$ are each hydrogen; and $R_6$ is halo.

In additional embodiments, the compound has the Formula (III), or a pharmaceutically acceptable salt, solvate, clathrate or prodrug thereof, wherein $R_2$ is selected from the group consisting of optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, and optionally substituted $C_3$-$C_{12}$ cycloalkenyl.

In yet additional aspects, $R_2$ is selected from the group consisting of optionally substituted $C_1$-$C_6$ alkyl, optionally substituted $C_2$-$C_6$ alkenyl, and optionally substituted $C_2$-$C_6$ alkynyl.

In further aspects, the compound has the Formula (III), or a pharmaceutically acceptable salt, solvate, clathrate or prodrug thereof, wherein $R_2$ is $C_1$-$C_6$ alkyl, $C_2$-$C_6$ alkenyl, or $C_2$-$C_6$ alkynyl, each optionally substituted with one or more substituents independently selected from the group consisting of optionally substituted $C_3$-$C_{12}$ cycloalkyl, optionally substituted $C_3$-$C_{12}$ cycloalkenyl, optionally substituted, aryl, halo, $N_3$, $OR_{c1}$, $NR_{d1}R_{d1}$, $C(O)OR_{e1}$, $NO_2$, CN, C(O)$R_{e1}$, C(O)C(O)$R_{e1}$, C(O)N$R_{d1}R_{d1}$, N$R_{d1}$C(O)$R_{e1}$, N$R_{d1}$S(O)$_n R_{e1}$, N($R_{d1}$)(COO$R_{e1}$), N$R_{d1}$C(O)C(O)$R_{e1}$, N$R_{d1}$C(O)N$R_{d1}R_{d1}$, N$R_{d1}$S(O)$_n$N$R_{d1}R_{d1}$, N$R_{d1}$S(O)$_n R_{c1}$, S(O)$_n R_{e1}$, S(O)$_n$N$R_{d1}R_{d1}$, OC(O)O$R_{e1}$, (C=N$R_d$)$R_{e1}$, OC(O)$R_{e1}$, tri($C_1$-$C_4$ alkyl)silyl, optionally substituted 4- to 12-membered heterocyclic, and optionally substituted 4- to 12-membered heteroaryl;

wherein each $R_{c1}$ and $R_{e1}$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted 4- to 12-membered heterocyclic, optionally substituted aryl, and optionally substituted 4- to 12-membered heteroaryl;

wherein each $R_{d1}$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted 4- to 12-membered heterocyclic, optionally substituted aryl, and optionally substituted 4- to 12-membered heteroaryl; or two geminal $R_d$, groups are taken together with the nitrogen atom to which they are attached to form an optionally substituted 4- to 12-membered heterocyclic or an optionally substituted 4- to 12-membered heteroaryl; and each n is independently 0, 1 or 2; or a pharmaceutically acceptable salt, solvate, clathrate or prodrug thereof.

In further aspects, the compound has the Formula (III), or a pharmaceutically acceptable salt, solvate, clathrate or prodrug thereof, wherein $R_2$ is $C_1$-$C_6$ alkyl, $C_2$-$C_6$ alkenyl, or $C_2$-$C_6$ alkynyl, each optionally substituted with one or more substituents independently selected from the group consisting of $C_3$-$C_{12}$ cycloalkyl, $C_3$-$C_{12}$ cycloalkenyl, aryl, halo, $N_3$, O$R_{c1}$, N$R_{d1}R_{d1}$, C(O)O$R_{e1}$, $NO_2$, CN, C(O)$R_{e1}$, C(O)C(O)$R_{e1}$, C(O)N$R_{d1}R_{d1}$, N$R_{d1}$C(O)$R_{e1}$, N$R_{d1}$S(O)$_n R_{e1}$, N($R_{d1}$)(COO$R_{e1}$), N$R_{d1}$C(O)C(O)$R_{e1}$, N$R_{d1}$C(O)N$R_{d1}R_{d1}$, N$R_{d1}$S(O)$_n$N$R_{d1}R_{d1}$, N$R_{d1}$S(O)$_n R_{c1}$, S(O)$_n R_{e1}$, S(O)$_n$N$R_{d1}R_{d1}$, OC(O)O$R_{e1}$, (C=N$R_{d1}$)$R_{e1}$, OC(O)$R_{e1}$, tri($C_1$-$C_4$ alkyl)silyl, 4- to 12-membered heterocyclic, and 4- to 12-membered heteroaryl, wherein the $C_3$-$C_{12}$ cycloalkyl, the $C_3$-$C_{12}$ cycloalkenyl, the aryl, the 4- to 12-membered heterocyclic and the 4- to 12-membered heteroaryl are each optionally substituted with one or more R';

each $R_{c1}$ and $R_{e1}$ is independently selected from the group consisting of hydrogen, $C_1$-$C_{10}$ alkyl, $C_2$-$C_{10}$ alkenyl, $C_2$-$C_{10}$ alkynyl, $C_3$-$C_{12}$ cycloalkyl, $C_3$-$C_{12}$ cycloalkenyl, 4- to 12-membered heterocyclic, aryl, and 4- to 12-membered heteroaryl; wherein the $C_1$-$C_{10}$ alkyl, the $C_2$-$C_{10}$ alkenyl, and the $C_2$-$C_{10}$ alkynyl are each optionally substituted with one or more R'', and the $C_3$-$C_{12}$ cycloalkyl, the $C_3$-$C_{12}$ cycloalkenyl, the 4- to 12-membered heterocyclic, the aryl, and the 4- to 12-membered heteroaryl are each optionally substituted with one or more R'; and each $R_{d1}$ is independently selected from the group consisting of hydrogen, $C_1$-$C_{10}$ alkyl, $C_2$-$C_{10}$ alkenyl, $C_2$-$C_{10}$ alkynyl, $C_1$-$C_{10}$ alkoxy, $C_3$-$C_{12}$ cycloalkyl, $C_3$-$C_{12}$ cycloalkenyl, 4- to 12-membered heterocyclic, aryl, and 4- to 12-membered heteroaryl; or two geminal $R_d$, groups are taken together with the nitrogen atom to which they are attached to form a 4- to 12-membered heterocyclic or a 4- to 12-membered heteroaryl; wherein the $C_1$-$C_{10}$ alkyl, the $C_2$-$C_{10}$ alkenyl, the $C_2$-$C_{10}$ alkynyl, and the $C_1$-$C_{10}$ alkoxy are each optionally substituted with one or more R''; and the $C_3$-$C_{12}$ cycloalkyl, the $C_3$-$C_{12}$ cycloalkenyl, the 4- to 12-membered heterocyclic, the aryl, and the 4- to 12-membered heteroaryl are each optionally substituted with one or more R';

each n is independently 0, 1 or 2;

wherein each R' is independently selected from the group consisting of $C_1$-$C_4$ alkyl, $C_1$-$C_4$ haloalkyl, CN, halo, and oxo; and wherein each R'' is selected from the group consisting CN and halo.

In yet additional aspects, the compound has the Formula (III), or a pharmaceutically acceptable salt, solvate, clathrate or prodrug thereof, wherein $R_2$ is $C_1$-$C_6$ alkyl, $C_2$-$C_6$ alkenyl, or $C_2$-$C_6$ alkynyl, optionally substituted with one or more substituents independently selected from the group consisting of optionally substituted $C_3$-$C_{12}$ cycloalkyl, optionally substituted $C_3$-$C_{12}$ cycloalkenyl, halo, O$R_{c1}$, S(O)$_n R_{e1}$, optionally substituted 4- to 12-membered heteroaryl, optionally substituted aryl, optionally substituted 4- to 12-membered heterocyclic, CN, and tri($C_1$-$C_4$ alkyl)silyl, wherein $R_{e1}$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted 4- to 12-membered heterocyclic, optionally substituted aryl, and optionally substituted 4- to 12-membered heteroaryl; in certain aspects, $R_{e1}$ is independently selected from the group consisting of hydrogen, $C_1$-$C_{10}$ alkyl, $C_2$-$C_{10}$ alkenyl, $C_2$-$C_{10}$ alkynyl, $C_3$-$C_{12}$ cycloalkyl, $C_3$-$C_{12}$ cycloalkenyl, 4- to 12-membered heterocyclic, aryl, and 4- to 12-membered heteroaryl; wherein the $C_1$-$C_{10}$ alkyl, the $C_2$-$C_{10}$ alkenyl, and the $C_2$-$C_{10}$ alkynyl are each optionally substituted with one or more R'', and the $C_3$-$C_{12}$ cycloalkyl, the $C_3$-$C_{12}$ cycloalkenyl, the 4- to 12-membered heterocyclic, the aryl, and the 4- to 12-membered heteroaryl are each optionally substituted with one or more R'; and wherein R' and R'' are each as defined above.

In yet an additional aspect, the compound has the Formula (III), or a pharmaceutically acceptable salt, solvate, clathrate or prodrug thereof, wherein $R_2$ is $C_1$-$C_6$ alkyl, $C_2$-$C_6$ alkenyl, or $C_2$-$C_6$ alkynyl, optionally substituted with one or more substituents independently selected from the group consisting of $C_3$-$C_{12}$ cycloalkyl, $C_3$-$C_{12}$ cycloalkenyl, halo, O$R_{c1}$, S(O)$_n R_{e1}$, 4- to 12-membered heteroaryl, aryl, 4- to 12-membered heterocyclic, CN, and tri($C_1$-$C_4$ alkyl)silyl, wherein the $C_3$-$C_{12}$ cycloalkyl, the $C_3$-$C_{12}$ cycloalkyenyl, the 4- to 12-membered heteroaryl, the aryl, and the 4- to 12-membered are each optionally substituted with one or more R'; and wherein Rei and Rei are each independently selected from the group consisting of hydrogen and $C_1$-$C_6$ alkyl optionally substituted with one or more R''; and wherein R' and R'' are each as defined above.

In a further aspect, $R_2$ is $C_1$-$C_6$ alkyl, $C_2$-$C_6$ alkenyl, or $C_2$-$C_6$ alkynyl, optionally substituted with one or more substituents selected from the group consisting of the following:

Halo;
SH;
S—$C_1$-$C_4$ alkyl;
S(O)$_2$H;
S(O)$_2$—$C_1$-$C_4$ alkyl;
$C_3$-$C_6$ cycloalkyl, optionally substituted with one or more R';
4- to 6-membered heterocyclic, optionally substituted with one or more R' (for example, 4- to 6-membered heterocyclic containing at least one ring oxygen atom, optionally substituted with one or more R'; more specific examples include tetrahydropyranyl, optionally substituted with one or more R'; oxetanyl, optionally substituted with one or more R'; and furanyl, optionally substituted with one or more R';

CN;
OH;
O—$C_1$-$C_4$ alkyl, wherein the $C_1$-$C_4$ alkyl is optionally substituted with one or more R";
$NH_2$;
4- to 6-membered heteroaryl, optionally substituted by one or more R' (for example, 4- to 6-membered heteroaryl containing at least one ring nitrogen atom, optionally substituted by one or more R'; more specific examples include imidazolyl, optionally substituted with one or more R'; pyrazolyl, optionally substituted with one or more R'; and thiazolyl, optionally substituted with one or more R'); and
tri($C_1$-$C_4$ alkyl)silyl;
wherein R' and R" are each as defined above.

In yet an additional aspect, $R_2$ is selected from the group consisting of $C_3$-$C_{12}$ cycloalkyl or $C_3$-$C_{12}$ cycloalkenyl, optionally substituted with one or more substituents independently selected from the group consisting of optionally substituted $C_1$-$C_{10}$ alkyl, optionally substituted $C_2$-$C_{10}$ alkenyl, optionally substituted $C_2$-$C_{10}$ alkynyl, halo, $OR_{e1}$, $S(O)_nR_{e1}$, optionally substituted 4- to 12-membered heteroaryl, optionally substituted aryl, optionally substituted 4- to 12-membered heterocyclic, CN, and tri($C_1$-$C_4$ alkyl)silyl;
wherein $R_{e1}$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted 4- to 12-membered heterocyclic, optionally substituted aryl, and optionally substituted 4- to 12-membered heteroaryl; and n is as defined above.

In a further aspect, $R_2$ is $C_3$-$C_{12}$ cycloalkyl or $C_3$-$C_{12}$ cycloalkenyl optionally substituted with one or more substituents independently selected from the group consisting of $C_1$-$C_{10}$ alkyl, $C_2$-$C_{10}$ alkenyl, $C_2$-$C_{10}$ alkynyl, halo, $OR_1$, $S(O)_nR_{e1}$, 4- to 12-membered heteroaryl, 4- to 12-membered heterocyclic, aryl, CN, and tri($C_1$-$C_4$ alkyl)silyl; wherein the $C_1$-$C_{10}$ alkyl, the $C_2$-$C_{10}$ alkenyl, and the $C_2$-$C_{10}$ alkynyl are each optionally substituted with one or more R", and wherein the 4- to 12-membered heteroaryl, the aryl and the 4- to 12-membered heterocyclic are each optionally substituted with one or more R'; and wherein $R_{e1}$ is selected from the group consisting of hydrogen and $C_1$-$C_6$ alkyl optionally substituted with one or more R"; and wherein R' and R" are each as defined above.

In further embodiments, $R_2$ is $C_3$-$C_{12}$ cycloalkyl or $C_3$-$C_{12}$ cycloalkenyl, optionally substituted with one or more substituents independently selected from halo and $C_1$-$C_4$ alkyl optionally substituted with one or more R".

In yet additional aspects, $R_2$ is an optionally substituted $C_3$-$C_6$ cycloalkyl.

In yet further aspects, $R_2$ is an $C_3$-$C_6$ cycloalkyl, optionally substituted with one or more substituents independently selected from the group consisting of optionally substituted $C_1$-$C_{10}$ alkyl, optionally substituted $C_2$-$C_{10}$ alkenyl, optionally substituted $C_2$-$C_{10}$ alkynyl, halo, $OR_c$, $S(O)_nR_{e1}$, optionally substituted 4- to 12-membered heteroaryl, optionally substituted aryl, optionally substituted 4- to 12-membered heterocyclic, CN, and tri($C_1$-$C_4$ alkyl)silyl;
wherein $R_{e1}$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted 4- to 12-membered heterocyclic, optionally substituted aryl, and optionally substituted 4- to 12-membered heteroaryl; and n is as defined above.

In a further aspect, $R_2$ is $C_3$-$C_6$ cycloalkyl optionally substituted with one or more substituents independently selected from the group consisting of $C_1$-$C_{10}$ alkyl, $C_2$-$C_{10}$ alkenyl, $C_2$-$C_{10}$ alkynyl, halo, $OR_{e1}$, $S(O)_nR_{e1}$, 4- to 12-membered heteroaryl, 4- to 12-membered heterocyclic, aryl, CN, and tri($C_1$-$C_4$ alkyl)silyl; wherein the $C_1$-$C_{10}$ alkyl, the $C_2$-$C_{10}$ alkenyl, and the $C_2$-$C_{10}$ alkynyl are each optionally substituted with one or more R", and wherein the 4- to 12-membered heteroaryl, the aryl and the 4- to 12-membered heterocyclic are each optionally substituted with one or more R'; and wherein Rei is selected from the group consisting of hydrogen and $C_1$-$C_6$ alkyl optionally substituted with one or more R"; and wherein R' and R" are each as defined above.

In further embodiments, $R_2$ is $C_3$-$C_6$ cycloalkyl, optionally substituted with one or more substituents independently selected from halo and $C_1$-$C_4$ alkyl optionally substituted with one or more R".

In additional aspects, $R^2$ is selected from the group consisting of optionally substituted phenyl and optionally substituted 4- to 8-membered heteroaryl. In additional aspects, $R^2$ is selected from the group consisting of optionally substituted phenyl and optionally substituted thiazolyl. In yet additional aspects, $R^2$ is selected from the group consisting of substituted phenyl and thiazolyl, wherein the phenyl and thiazolyl are each optionally substituted with one or more R'.

In yet additional embodiments, $R_2$ is $C_1$-$C_6$ haloalkyl, halo, or CN.

In further aspects, $R_1$ is methyl and $R_2$ is $C_1$-$C_6$ alkyl. In certain aspects, $R_1$ is methyl and $R_2$ is methyl.

In yet additional aspects, $R_1$ is methyl and $R_2$ is a $C_1$-$C_6$ haloalkyl, halo or CN.

In additional embodiments, the compound has the Formula (III), or a pharmaceutically acceptable salt, solvate, clathrate or prodrug thereof, wherein substituents of optionally substituted E, Z, $R_1$, $R_2$, $R_{3a}$, $R_{3b}$, $R_{3c}$, $R_{3d}$, and $R_5$ are each independently selected from the group consisting of $C_1$-$C_4$ alkyl, halo, $OR_c$, CN, $S(O)_nR_c$, $Si(R_c)_3$, heterocyclyl, and heteroaryl.

In certain embodiments, the compound has the Formula (III), or a pharmaceutically acceptable salt, solvate, clathrate or prodrug thereof, wherein $R_2$ is selected from the group consisting of —Cl, —Br, —$CH_3$, —$CH(CH_3)_2$, —$CH(CH_3)CH_2CH_3$, —$C(CH_3)_3$, —$CF_3$, —$CH_2CF_3$, —CN, —$CH_2CH_2Si(CH_3)_3$, —$CH_2CH_2CH_2OCH_3$, —$CH_2CH_2CH_2OCF_3$, —$CH_2CH_2CH_2CH_2SCH_3$, —$CH_2CH_2CH_2SO_2CH_3$, —CH=$CHCH_2NH_2$, —CH=$CHCH_2SO_2CH_3$, —$CH(CH_3)CH_2CH_2SO_2CH_3$, —$CH_2CH_2CH_2CN$, —$CH_2CH_2CH_2CH_2CN$, —$CH_2OCH_2CH_2CN$,

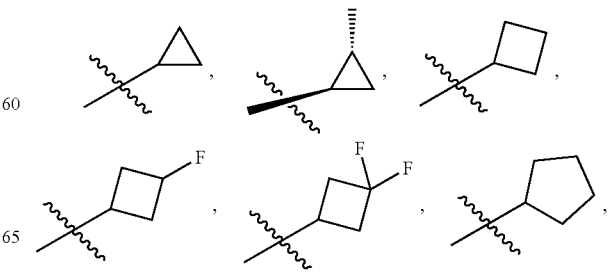

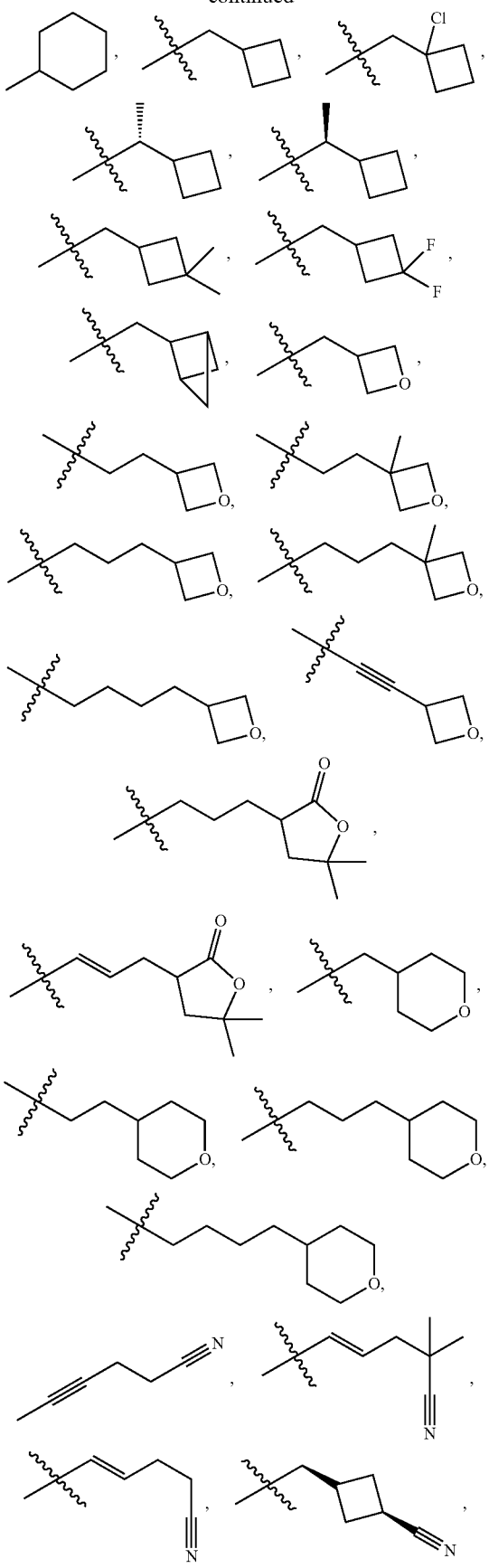
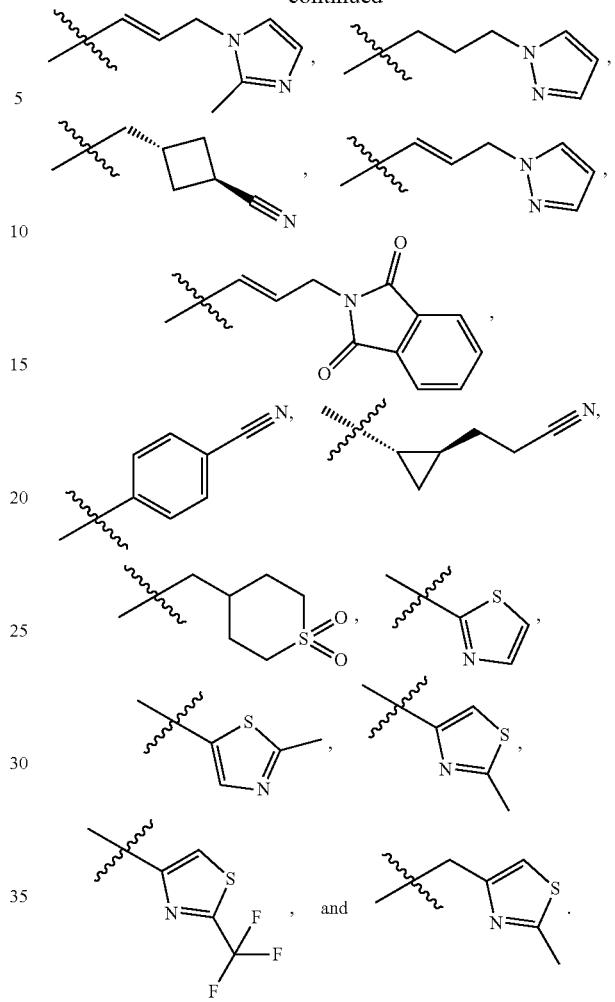

In certain embodiments, the compound has the Formula (III), or a pharmaceutically acceptable salt, solvate, clathrate or prodrug thereof, wherein $R_4$ is selected from the group consisting of hydrogen, optionally substituted $C_1$-$C_4$ alkyl, halo, and CN. In yet additional aspects, $R_4$ is hydrogen. In further aspects, $R_4$ is halo. In yet additional aspects, $R_1$ is methyl and $R_4$ is hydrogen. In yet additional aspects, $R_1$ is methyl and $R_4$ is halo. In some embodiments, $R_4$ is methyl or ethyl. In further aspects, $R_4$ is $C_1$-$C_4$ haloalkyl. In additional embodiments, $R_4$ is CN. In additional embodiments, $R_4$ is —Cl, —F, —Br, —CN, methyl, ethyl, —CF$_3$, or —CH$_2$CH$_2$CH$_2$SO$_2$CH$_3$. In additional embodiments, $R_4$ is selected from the group consisting of hydrogen, methyl, chloro, and CN.

In certain aspects, the compound has the Formula (III), or a pharmaceutically acceptable salt, solvate, clathrate or prodrug thereof, wherein Z is an optionally substituted, 6- to 10-membered bridged N-heterocyclic. In yet an additional aspect, Z is a 6- to 10-membered bridged N-heterocyclic, optionally substituted with one or more substituents independently selected from the group consisting of optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_{e2}$, $NR_{d2}R_{d2}$, $C(O)OR_{e2}$, $NO_2$, CN, $C(O)R_{e2}$, $C(O)C(O)R_{e2}$, $C(O)NR_{d2}R_{d2}$, $NR_{d2}C(O)R_{e2}$, $NR_{d2}S(O)_nR_{e2}$, $N(R_{d2})(CO$-

OR$_{e2}$), NR$_d$C(O)C(O)R$_{e2}$, NR$_{d2}$C(O)NR$_{d2}$R$_{d2}$, NR$_{d2}$S(O)$_n$ NR$_{d2}$R$_{d2}$, NR$_{d2}$S(O)$_n$R$_{e2}$, S(O)$_n$R$_{e2}$, S(O)$_n$NR$_{d2}$R$_{d2}$, OC(O) OR$_{e2}$, (C=NR$_{d2}$)R$_{e2}$, OC(O)R$_{e2}$, optionally substituted 4- to 12-membered heterocyclic, and optionally substituted 4- to 12-membered heteroaryl;

each R$_{c2}$ and R$_{e2}$ is independently selected from the group consisting of hydrogen, optionally substituted C$_1$-C$_{10}$ alkyl, optionally substituted C$_2$-C$_{10}$ alkenyl, optionally substituted C$_2$-C$_{10}$ alkynyl, optionally substituted C$_3$-C$_{12}$ cycloalkyl, optionally substituted C$_3$-C$_{12}$ cycloalkenyl, optionally substituted 4- to 12-membered heterocyclic, optionally substituted aryl, and optionally substituted 4- to 12-membered heteroaryl; and each R$_{d2}$ is independently selected from the group consisting of hydrogen, optionally substituted C$_1$-C$_{10}$ alkyl, optionally substituted C$_2$-C$_{10}$ alkenyl, optionally substituted C$_2$-C$_{10}$ alkynyl, optionally substituted C$_1$-C$_{10}$ alkoxy, optionally substituted C$_3$-C$_{12}$ cycloalkyl, optionally substituted C$_3$-C$_{12}$ cycloalkenyl, optionally substituted 4- to 12-membered heterocyclic, optionally substituted aryl, and optionally substituted 4- to 12-membered heteroaryl; or two geminal R$_d$ groups are taken together with the nitrogen atom to which they are attached to form an optionally substituted 4- to 12-membered heterocyclic or an optionally substituted 4- to 12-membered heteroaryl;

and each n is independently 0, 1 or 2.

In yet additional embodiments, the compound has the Formula (III), or a pharmaceutically acceptable salt, solvate, clathrate or prodrug thereof, wherein Z is a 6- to 10-membered bridged N-heterocyclic, optionally substituted with one or more substituents independently selected from optionally substituted C$_1$-C$_4$ alkyl, optionally substituted C$_2$-C$_4$ alkenyl, OR$_{c2}$, and C(O)OR$_{e2}$. In yet additional aspects, Z is a 6- to 10-membered bridged N-heterocyclic, optionally substituted with one or more substituents independently selected from C$_1$-C$_4$ alkyl, OH, OCH$_3$, OCF$_3$, C(O)OH, C(O)OCH$_3$, CF$_3$, and C$_1$-C$_4$ alkyl substituted with OH or OCH$_3$. In additional aspects, Z is a 6- to 10-membered bridged N-heterocyclic, optionally substituted with one or more substituents independently selected from optionally substituted C$_1$-C$_4$ alkyl, OH and haloalkyl. In yet additional aspects, Z is an unsubstituted 6- to 10-membered bridged N-heterocyclic.

In some embodiments, the compound has the Formula (III), or a pharmaceutically acceptable salt, solvate, clathrate or prodrug thereof, wherein Z is an optionally substituted, 6- to 9-membered bridged N-heterocyclic. In yet additional aspects, the compound has the Formula (III), wherein Z is a 6- to 9-membered bridged N-heterocyclic, optionally substituted with one or more substituents independently selected from optionally substituted C$_1$-C$_4$ alkyl, optionally substituted C$_2$-C$_4$ alkenyl, OR$_{c2}$, and C(O)OR$_{e2}$. In yet additional aspects, Z is a 6- to 9-membered bridged N-heterocyclic, optionally substituted with one or more substituents independently selected from C$_1$-C$_4$ alkyl, OH, OCH$_3$, OCF$_3$, C(O)OH, C(O)OCH$_3$, CF$_3$, and C$_1$-C$_4$ alkyl substituted with OH or OCH$_3$. In additional aspects, Z is a 6- to 9-membered bridged N-heterocyclic, optionally substituted with one or more substituents independently selected from optionally substituted C$_1$-C$_4$ alkyl, OH and haloalkyl. In yet additional aspects, Z is an unsubstituted 6- to 9-membered bridged N-heterocyclic.

In additional embodiments, Z is an optionally substituted, 6- to 8-membered bridged N-heterocyclic.

In yet additional aspects, the compound has the Formula (III), or a pharmaceutically acceptable salt, solvate, clathrate or prodrug thereof, wherein Z is a 6- to 8-membered bridged N-heterocyclic, optionally substituted with one or more substituents independently selected from optionally substituted C$_1$-C$_4$ alkyl, optionally substituted C$_2$-C$_4$ alkenyl, OR$_{c2}$, and C(O)OR$_{e2}$. In yet additional aspects, Z is a 6- to 8-membered bridged N-heterocyclic, optionally substituted with one or more substituents independently selected from C$_1$-C$_4$ alkyl, OH, OCH$_3$, OCF$_3$, C(O)OH, C(O)OCH$_3$, CF$_3$, and C$_1$-C$_4$ alkyl substituted with OH or OCH$_3$. In additional aspects, Z is a 6- to 8-membered bridged N-heterocyclic, optionally substituted with one or more substituents independently selected from optionally substituted C$_1$-C$_4$ alkyl, OH and haloalkyl.

In yet additional aspects, Z is an unsubstituted 6- to 8-membered bridged N-heterocyclic.

In further aspects, Z is an optionally substituted, 7-membered bridged N-heterocyclic. In another aspect Z is an optionally substituted, 8-membered bridged N-heterocyclic.

In certain other embodiments, Z is a 9-membered bridged N-heterocyclic. In further Z is a 9-membered bridged heterocyclic, wherein the bridged N-heterocyclic includes a ring oxygen atom.

In yet additional aspects, Z is a 10-membered bridged N-heterocyclic. In further aspects, Z is a 10-membered bridged heterocyclic, wherein the bridged N-heterocyclic includes a ring oxygen atom.

In certain embodiments, Z is selected from the group consisting of:

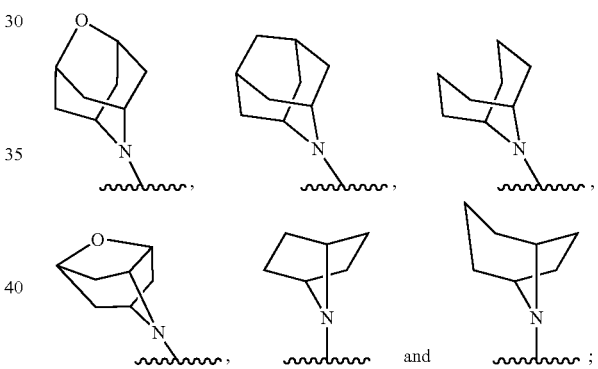

each optionally substituted.

In further aspects, Z is selected from the group consisting of:

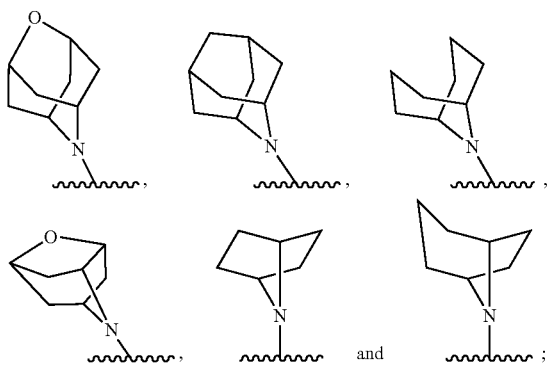

optionally substituted with one or more substituents independently selected from optionally substituted C$_1$-C$_4$ alkyl, optionally substituted C$_2$-C$_4$ alkenyl, OR$_{c2}$, and C(O)OR$_{e2}$.

In yet additional aspects, the one or more substituents are independently selected from $C_1$-$C_4$ alkyl, OH, $OCH_3$, $OCF_3$, C(O)OH, C(O)$OCH_3$, $CF_3$, and $C_1$-$C_4$ alkyl substituted with OH or OCH. In additional aspects, the one or more substituents are independently selected from optionally substituted $C_1$-$C_4$ alkyl, OH and haloalkyl.

In certain aspects, Z is selected from the group consisting of:

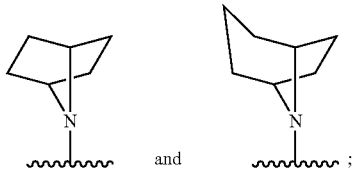 [SMILES: *N1C2CCC1CC2 ; *N1C2CCCC1CC2]

each optionally substituted.

In yet additional aspects, Z is selected from the group consisting of:

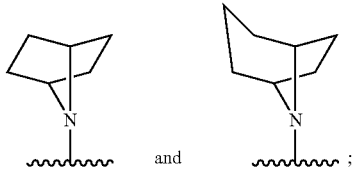 [SMILES: *N1C2CCC1CC2 ; *N1C2CCCC1CC2]

each optionally substituted with one or more substituents independently selected from optionally substituted $C_1$-$C_4$ alkyl, optionally substituted $C_2$-$C_4$ alkenyl, $OR_{c2}$, and C(O)$OR_{e2}$; wherein $R_{c2}$ and $R_{e2}$ are each as defined above. In yet additional aspects, the one or more substituents are independently selected from $C_1$-$C_4$ alkyl, OH, $OCH_3$, $OCF_3$, C(O)OH, C(O)$OCH_3$, $CF_3$, and $C_1$-$C_4$ alkyl substituted with OH or OCH. In additional aspects, the one or more substituents are independently selected from optionally substituted $C_1$-$C_4$ alkyl, OH and haloalkyl.

In yet additional embodiments, Z is selected from the group consisting of:

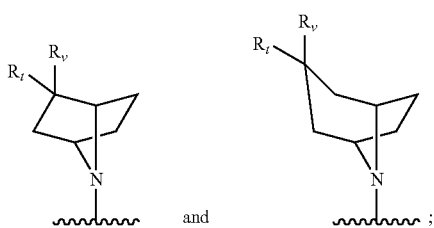

wherein:

$R_t$ is selected from the group consisting of hydrogen, optionally substituted $C_1$-$C_4$ alkyl, optionally substituted $C_2$-$C_4$ alkenyl, $OR_{c2}$, and C(O)$OR_{e2}$; in certain aspects, $R_t$ is optionally substituted $C_1$-$C_4$ alkyl, optionally substituted $C_2$-$C_4$ alkenyl, $OR_{c2}$, and C(O)$OR_{e2}$;

$R_v$ is selected from the group consisting of hydrogen and optionally substituted $C_1$-$C_{10}$ alkyl; and each $R_{c2}$ and $R_{e2}$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted 4- to 12-membered heterocyclic, optionally substituted aryl, and optionally substituted 4- to 12-membered heteroaryl.

In some embodiments, $R_t$ is selected from the group consisting of optionally substituted $C_1$-$C_{10}$ alkyl and $OR_{c2}$. In additional aspects, $R_t$ is selected from the group consisting of $C_1$-$C_4$ alkyl, OH, $OCH_3$, $OCF_3$, C(O)OH, C(O)$OCH_3$, $CF_3$, and $C_1$-$C_4$ alkyl substituted with OH or $OCH_3$. In additional aspects, $R_t$ is selected from the group consisting of $C_1$-$C_4$ alkyl, OH, $OCH_3$, $OCF_3$, C(O)OH, C(O)$OCH_3$, $CF_3$, and $C_1$-$C_4$ alkyl substituted with OH or $OCH_3$; and $R_v$ is hydrogen. In yet additional aspects, $R_t$ is OH. In yet further aspects, $R_t$ is OH and $R_v$ is hydrogen.

In some embodiments, the invention is directed to a compound having the Formula (III) wherein Z is an optionally substituted, 6- to 10-membered bridged N-heterocyclic; $R_1$ is methyl; $R_2$ is methyl; $R_4$ is halo; and $R_6$ is CN. In yet additional aspects, Z is an optionally substituted, 6- to 10-membered bridged N-heterocyclic; $R_1$ is methyl; $R_2$ is methyl; $R_6$ is CN; and $R_4$ is fluoro. In additional aspects, Z is an optionally substituted, 6- to 10-membered bridged N-heterocyclic; $R_1$ is methyl; $R_2$ is methyl; $R_4$ is halo; $R_6$ is CN, and $R_{3a}$, $R_{3b}$, $R_{3c}$ and $R_{3d}$ are each hydrogen. In yet additional aspects, Z is an optionally substituted, 6- to 10-membered bridged N-heterocyclic; R is methyl; $R_2$ is methyl; $R_4$ is fluoro; $R_6$ is CN, and $R_{3a}$, $R_{3b}$, $R_{3c}$ and $R_{3d}$ are each hydrogen. In further aspects, Z is an optionally substituted, 7-membered or 8-membered bridged N-heterocyclic; $R_1$ is methyl; $R_2$ is methyl; $R_4$ is halo; $R_6$ is CN, and $R_{3a}$, $R_{3b}$, $R_{3c}$ and $R_{3d}$ are each hydrogen. In further aspects, Z is an optionally substituted, 7-membered or 8-membered bridged N-heterocyclic; $R_1$ is methyl; $R_2$ is methyl; $R_4$ is fluoro; $R_6$ is CN, and $R_{3a}$, $R_{3b}$, $R_{3c}$ and $R_{3d}$ are each hydrogen. In certain aspects, Z is an optionally substituted 7-membered bridged N-heterocyclic; $R_1$ is methyl; $R_2$ is methyl; $R_4$ is halo; $R_6$ is CN, and $R_{3a}$, $R_{3b}$, $R_{3c}$ and $R_{3d}$ are each hydrogen. In certain aspects, Z is an optionally substituted 7-membered bridged N-heterocyclic; $R_1$ is methyl; $R_2$ is methyl; $R_4$ is fluoro; $R_6$ is CN, and $R_{3a}$, $R_{3b}$, $R_{3c}$ and $R_{3d}$ are each hydrogen.

In yet additional aspects, the compound has the Formula (III), or a pharmaceutically acceptable salt, solvate, clathrate or prodrug thereof, wherein Z is an optionally substituted, 6- to 10-membered bridged N-heterocyclic; $R_1$ is methyl; $R_2$ is methyl; $R_4$ is hydrogen; and $R_6$ is CN.

In further aspects, the compound has the Formula (III), or a pharmaceutically acceptable salt, solvate, clathrate or prodrug thereof, wherein Z is an optionally substituted, 6- to 10-membered bridged N-heterocyclic; $R_1$ is methyl; $R_4$ is hydrogen; $R_6$ is CN; and $R_2$ is selected from the group consisting of $C_1$-$C_6$ alkyl, $C_2$-$C_6$ alkenyl, and $C_2$-$C_6$ alkynyl, each optionally substituted with one or more substituents independently selected from the group consisting of optionally substituted $C_3$-$C_{12}$ cycloalkyl, optionally substituted $C_3$-$C_{12}$ cycloalkenyl, halo, $OR_c$, $S(O)_nR_e$, optionally substituted 4- to 12-membered heteroaryl, optionally substituted aryl, optionally substituted 4- to 12-membered heterocyclic, CN, and tri($C_1$-$C_4$ alkyl)silyl. In further aspects, Z is an optionally substituted, 6- to 10-membered bridged N-heterocyclic; $R_1$ is methyl; $R_4$ is hydrogen; $R_6$ is CN; and $R_2$ is $C_1$-$C_6$ alkyl, $C_2$-$C_6$ alkenyl, or $C_2$-$C_6$ alkynyl, optionally substituted with one or more substituents independently selected from the group consisting of $C_3$-$C_{12}$ cycloalkyl, $C_3$-$C_{12}$ cycloalkenyl, halo, $OR_{c1}$, $S(O)_nR_{e1}$, 4- to 12-membered heteroaryl, aryl 4- to 12-membered heterocyclic, CN, and tri($C_1$-$C_4$ alkyl)silyl, wherein the $C_3$-$C_{12}$ cycloalkyl, the $C_3$-$C_{12}$ cycloalkenyl, the 4- to 12-membered heteroaryl, the aryl, and the 4- to 12-membered are each optionally substituted with one or more R'; and wherein $R_{c1}$ and $R_{e1}$ are each independently selected from the group consisting of hydrogen and $C_1$-$C_6$ alkyl optionally substituted with one or more R''; and wherein R' and R'' are each as defined above.

It is to be understood that the specific embodiments described herein can be taken in combination with other specific embodiments delineated herein. For example, Z is described as an optionally substituted, 7-membered bridged N-heterocyclic in certain embodiments, $R_4$ is described as halo in some embodiments, and $R_1$ is described as methyl in some embodiments. It is thus to be understood that the invention specifically encompasses compounds of Formula (III), or a pharmaceutically acceptable salt, solvate, clathrate or prodrug thereof, wherein Z is an optionally substituted, 7-membered bridged N-heterocyclic, R4 is halo, and $R_1$ is methyl.

In some embodiments, the invention is directed to a compounding having the Formula (IIIa), Formula (IIIb), Formula (IIIc), Formula (IIId), or Formula (IIIe):

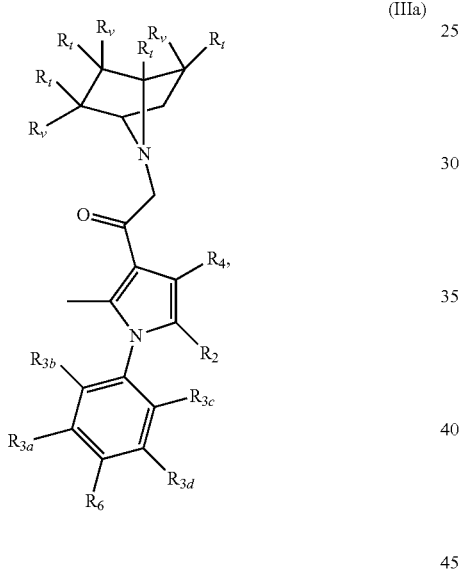

(IIIa)

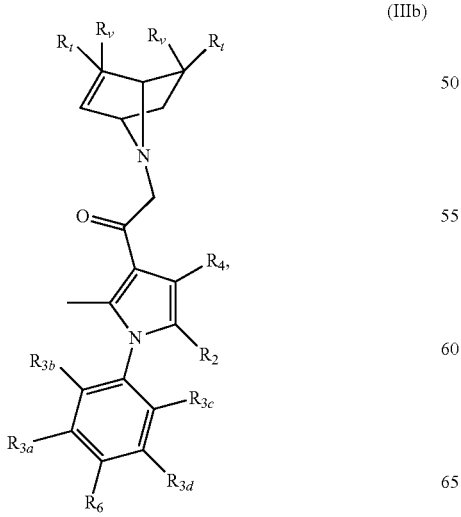

(IIIb)

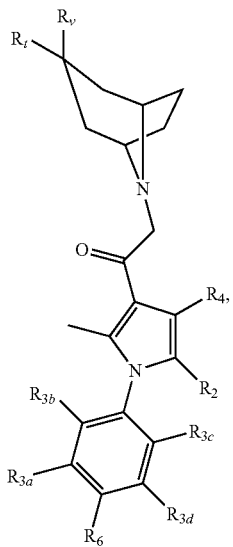

(IIIc)

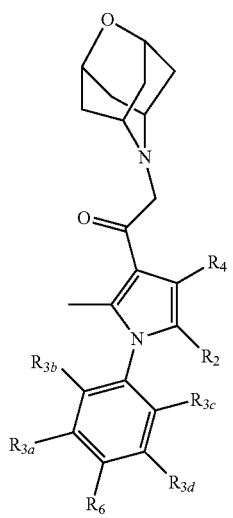

(IIId)

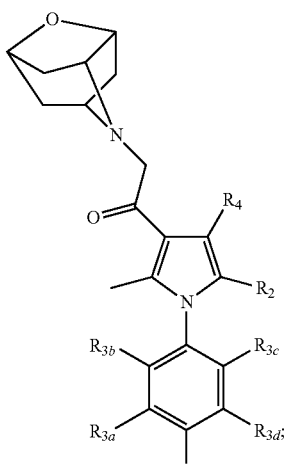

(IIIe)

wherein:

$R_t$ is selected from the group consisting of optionally substituted $C_1$-$C_4$ alkyl, optionally substituted $C_2$-$C_4$ alkenyl, $OR_{c2}$, and $C(O)OR_{e2}$, or any two $R_t$ together form a 5-membered or 6-membered heterocyclic;

$R_v$ is selected from the group consisting of hydrogen and optionally substituted $C_1$-$C_{10}$ alkyl; and each $R_{c2}$ and $R_{e2}$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted 4- to 12-membered heterocyclic, optionally substituted aryl, and optionally substituted 4- to 12-membered heteroaryl;

$R_2$ is selected from the group consisting optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted 4- to 12-membered heterocyclic, optionally substituted aryl, optionally substituted 4- to 12-membered heteroaryl, halo, and CN;

$R_{3a}$, $R_{3b}$, $R_{3c}$, and $R_{3d}$ are each independently hydrogen or fluoro;

$R_4$ is —H, —Cl, —F, —Br, —CN, —$CH_3$, —$CH_2CH_3$, —$CF_3$ or —$CH_2CH_2CH_2SO_2CH_3$; and $R_6$ is CN or Cl.

In some embodiments, $R_t$ and $R_v$ are independently selected from the group consisting of hydrogen, hydroxyl, —$CH_3$, —$CF_3$, —$CH_2OH$, —$CH(CH_3)OH$, —$CH_2C(CH_3)_2OH$, —COOH, —$OCH_3$, —$OCF_3$, —$C(CH_3)_3$, and —$C(CF_3)_3$, or any two $R_t$ together form —$CH_2OCH_2$— or —$CH_2CH_2O$—.

In some embodiments, $R_2$ is selected from the group consisting of —Cl, —Br, —$CH_3$, —$CH(CH_3)_2$, —$CH(CH_3)CH_2CH_3$, —$C(CH_3)_3$, —$CF_3$, —$CH_2CF_3$, —CN, —$CH_2CH_2Si(CH_3)_3$, —$CH_2CH_2CH_2OCH_3$, —$CH_2CH_2CH_2OCF_3$, —$CH_2CH_2CH_2CH_2SCH_3$, —$CH_2CH_2CH_2SO_2CH_3$, —CH=$CHCH_2NH_2$, —CH=$CHCH_2SO_2CH_3$, —$CH(CH_3)CH_2CH_2SO_2CH_3$, —$CH_2CH_2CH_2CN$, —$CH_2CH_2CH_2CN$, —$CH_2OCH_2CH_2CN$,

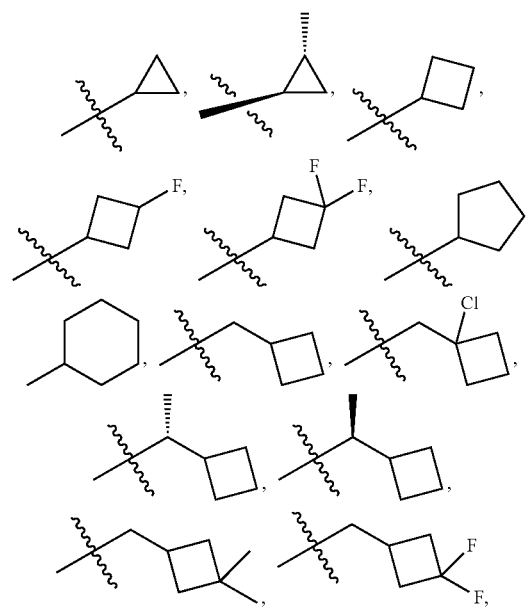

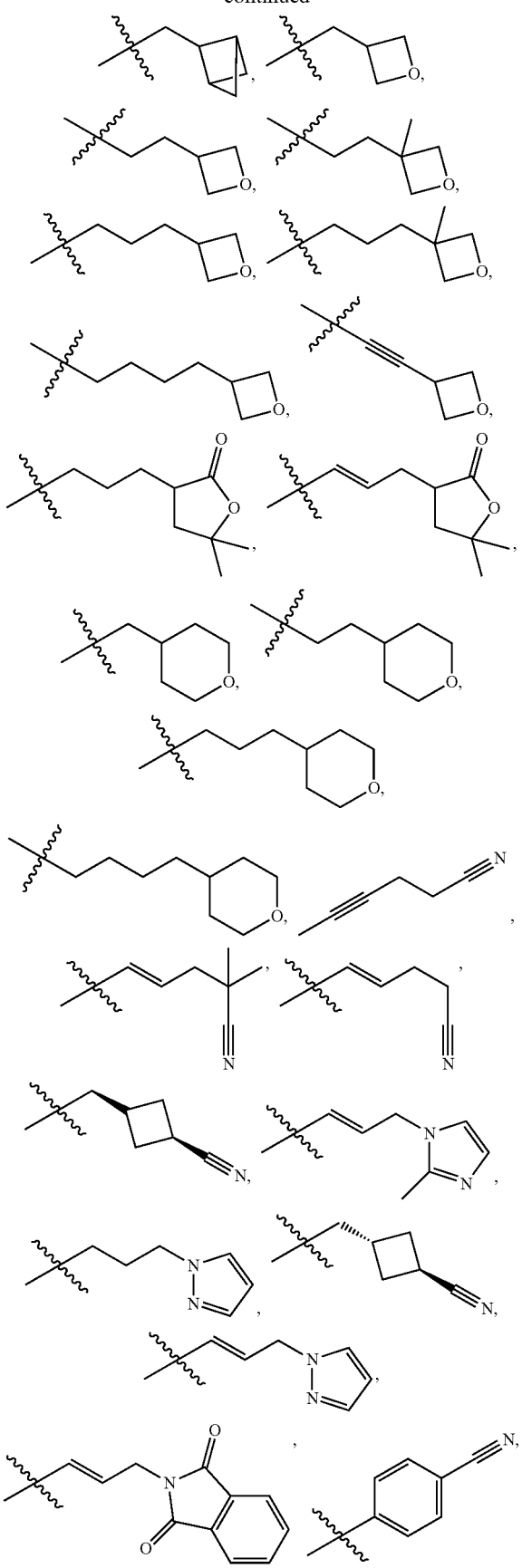

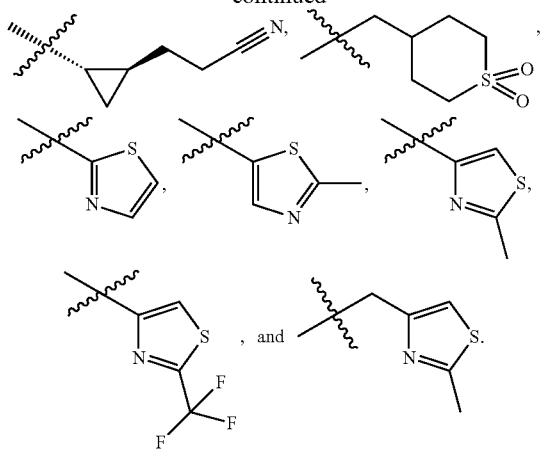
Non-limiting examples of compounds of Formula (III) are shown below in Table 3:
TABLE 3
| Compound No. | Structure |
|---|---|
| 1B | 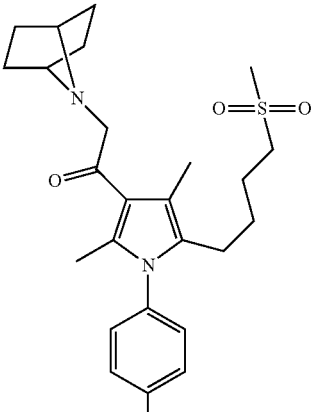 |
| 2B | 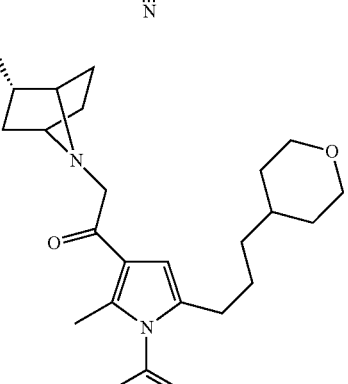 |
TABLE 3-continued
| Compound No. | Structure |
|---|---|
| 3B | 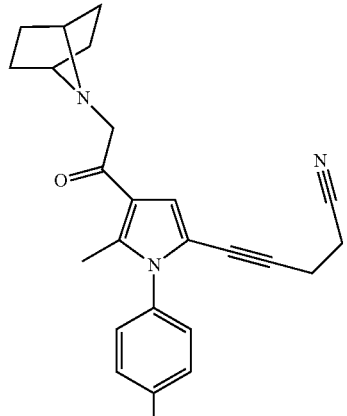 |
| 4B | 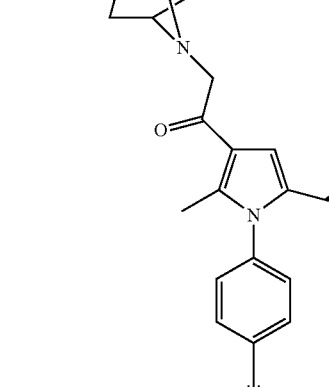 |
| 5B | 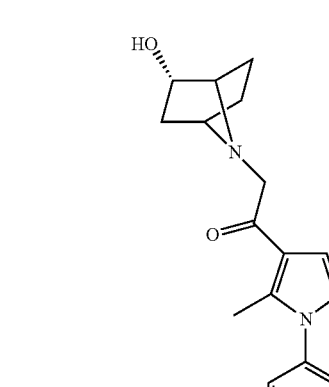 |

TABLE 3-continued
| Compound No. | Structure |
|---|---|
| 6B | 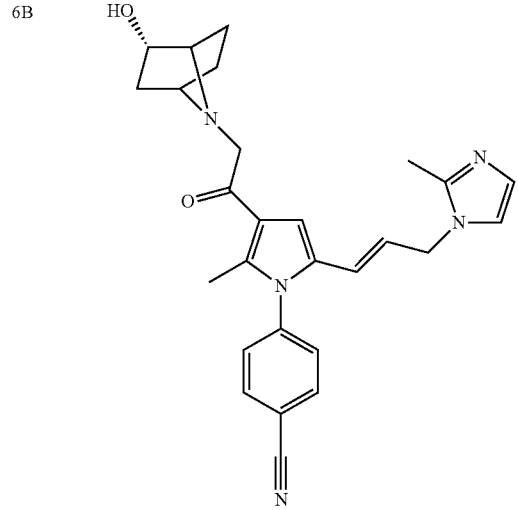 |
| 7B | 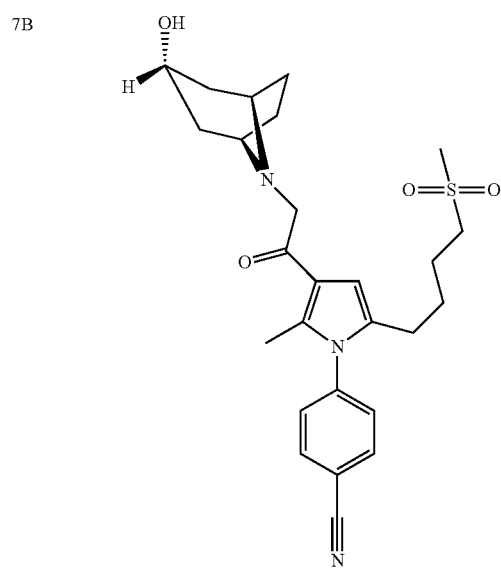 |
| 8B | 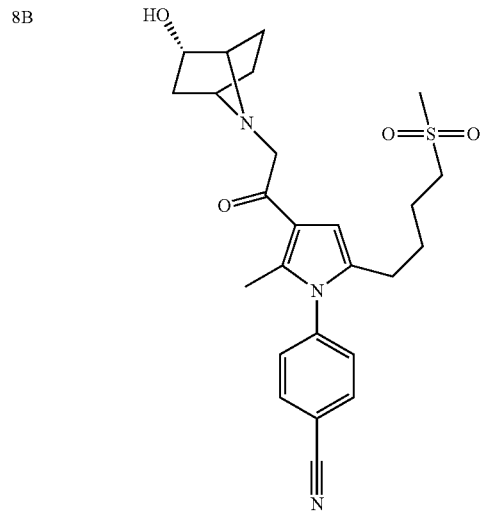 |
| 9B | 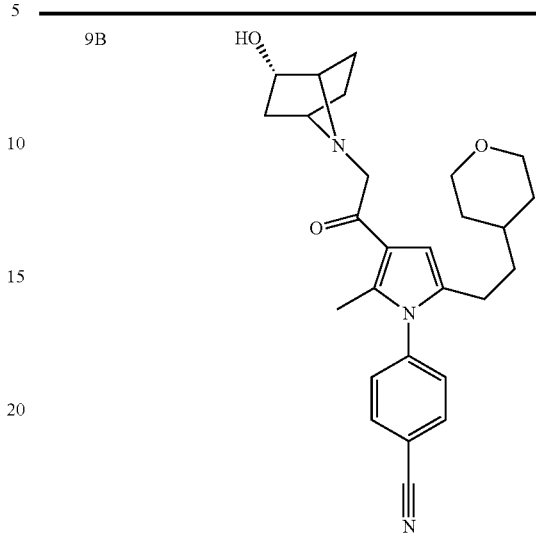 |
| 10B | 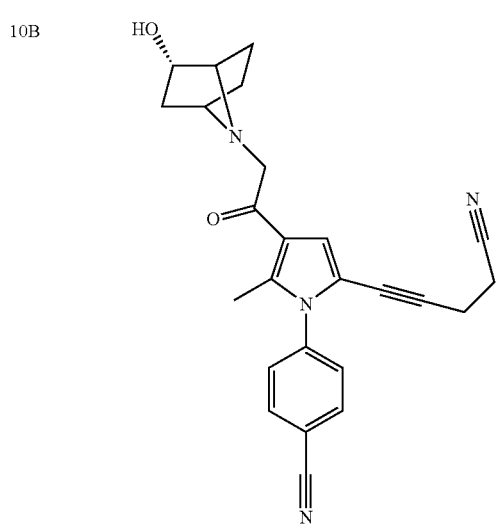 |
| 11B | 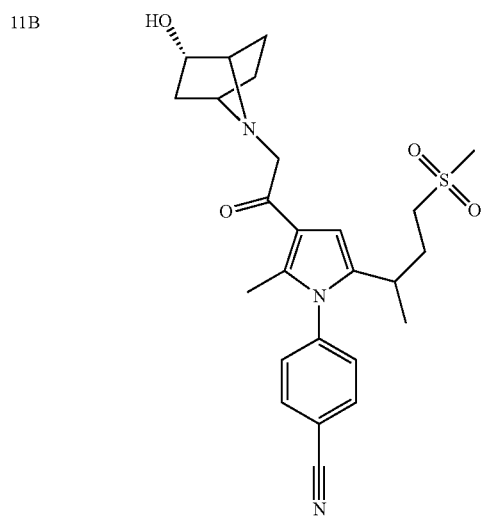 |

TABLE 3-continued
| Compound No. | Structure |
|---|---|
| 12B | 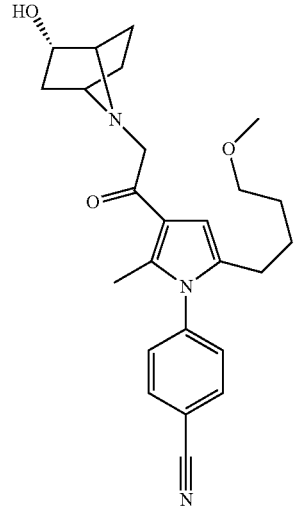 [SMILES: COCCCCc1cc(C(=O)CN2C3CCC2[C@@H](O)C3)c(C)n1-c1ccc(C#N)cc1] |
| 13B | 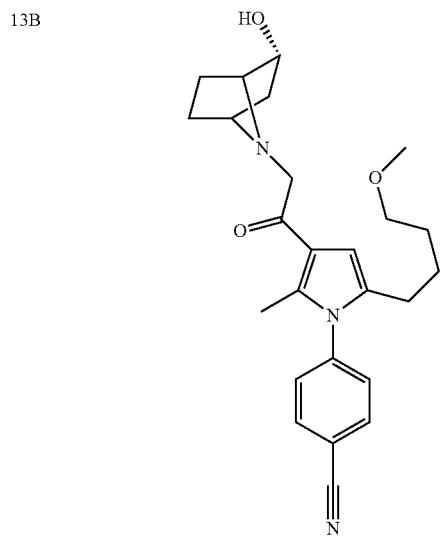 |
| 14B | 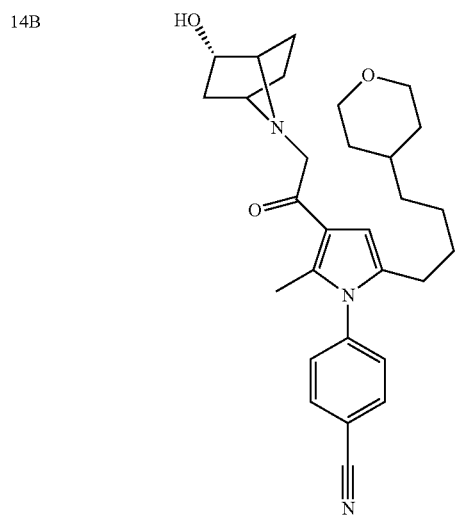 |
| 15B | 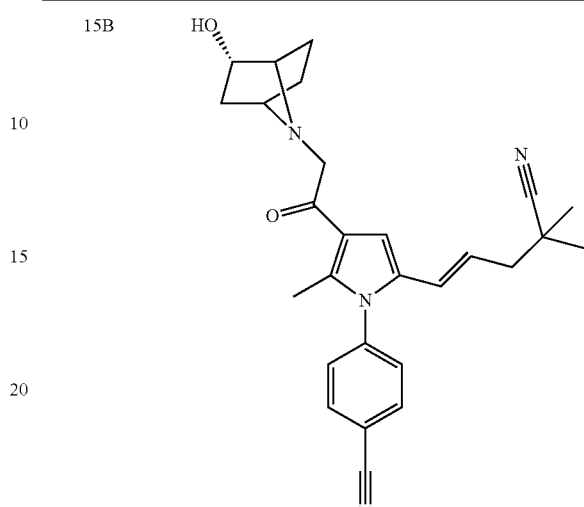 |
| 16B | 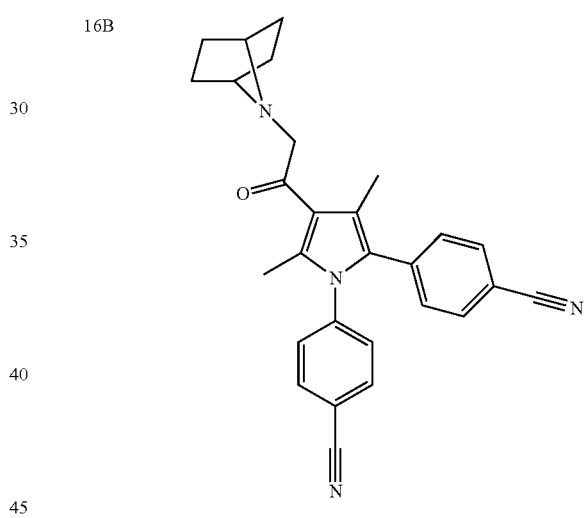 |
| 17B | 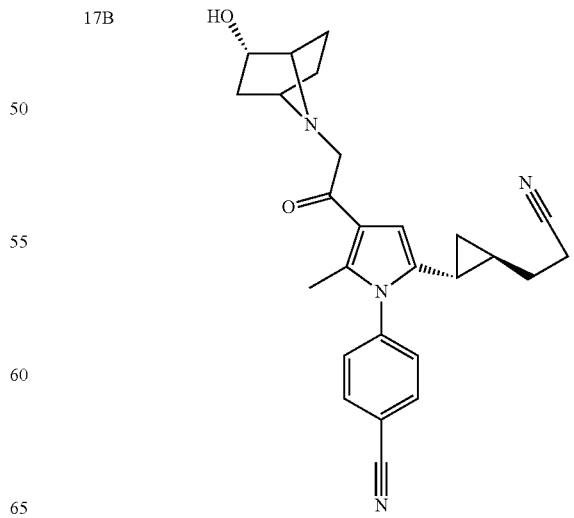 |

TABLE 3-continued
| Compound No. | Structure |
|---|---|
| 18B | 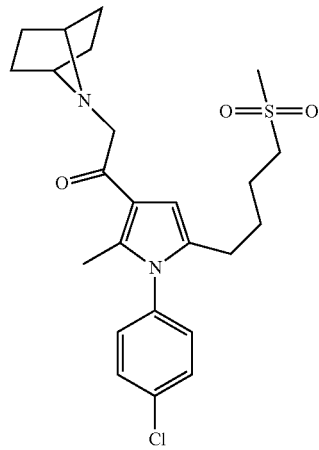 [SMILES: Cc1c(C(=O)CN2C3CCC2CC3)cc(CCCCS(C)(=O)=O)n1-c1ccc(Cl)cc1] |
| 19B | 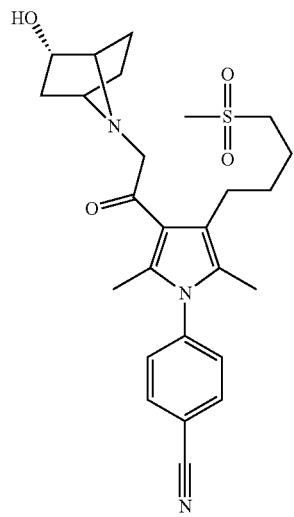 [SMILES: Cc1c(CCCCS(C)(=O)=O)c(C(=O)CN2C3CCC2[C@@H](O)C3)c(C)n1-c1ccc(C#N)cc1] |
| 20B | 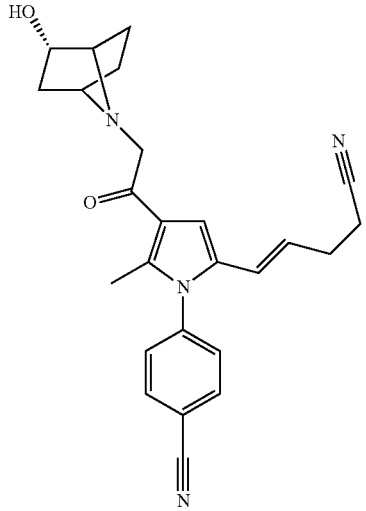 [SMILES: Cc1c(C(=O)CN2C3CCC2[C@@H](O)C3)cc(/C=C/CCC#N)n1-c1ccc(C#N)cc1] |
| 21B | 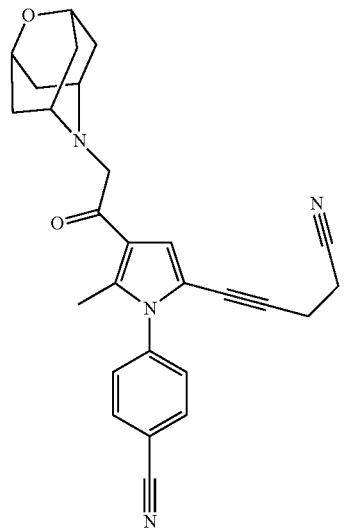 [SMILES: Cc1c(C(=O)CN2C3CC4CC2CC(C3)O4)cc(C#CCCC#N)n1-c1ccc(C#N)cc1] |
| 22B | 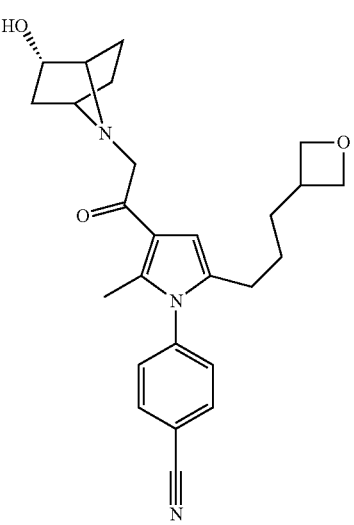 [SMILES: Cc1c(C(=O)CN2C3CCC2[C@@H](O)C3)cc(CCCC2COC2)n1-c1ccc(C#N)cc1] |
| 23B | 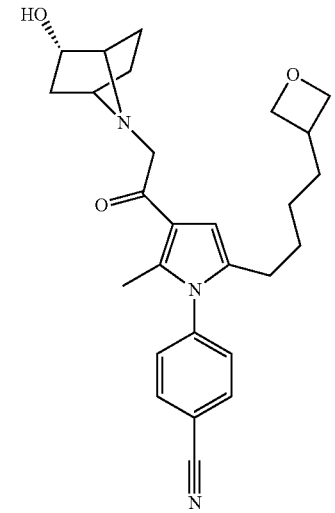 [SMILES: Cc1c(C(=O)CN2C3CCC2[C@@H](O)C3)cc(CCCCC2COC2)n1-c1ccc(C#N)cc1] |

TABLE 3-continued
| Compound No. | Structure |
|---|---|
| 24B | 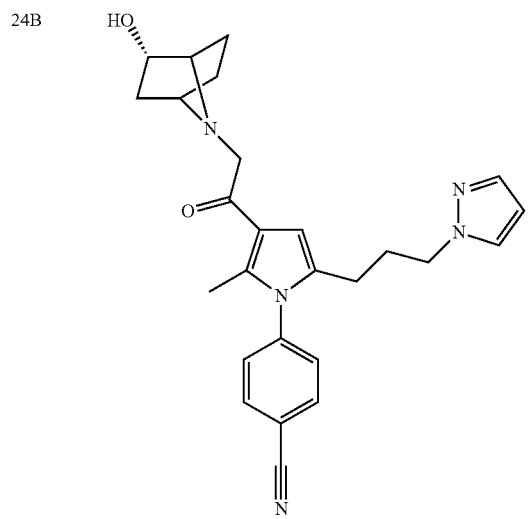 |
| 25B | 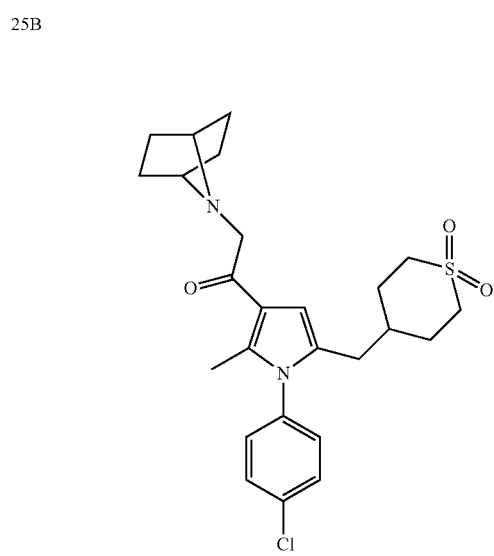 |
| 26B | 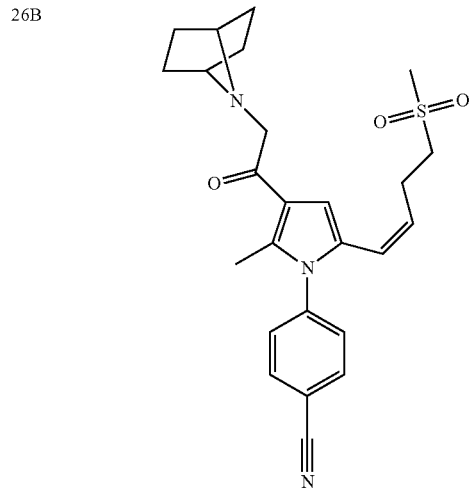 |
| 27B | 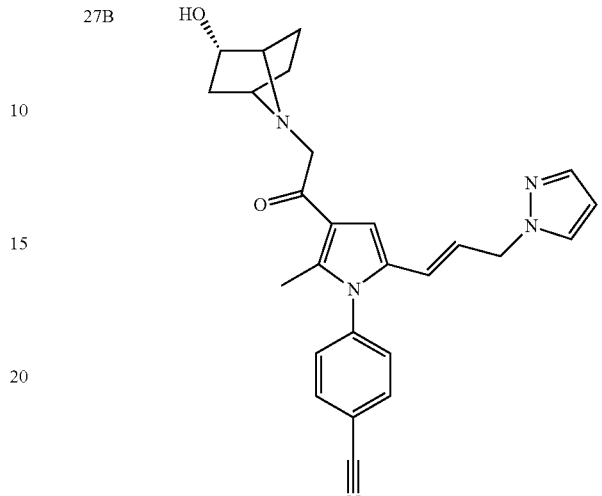 |
| 28B | 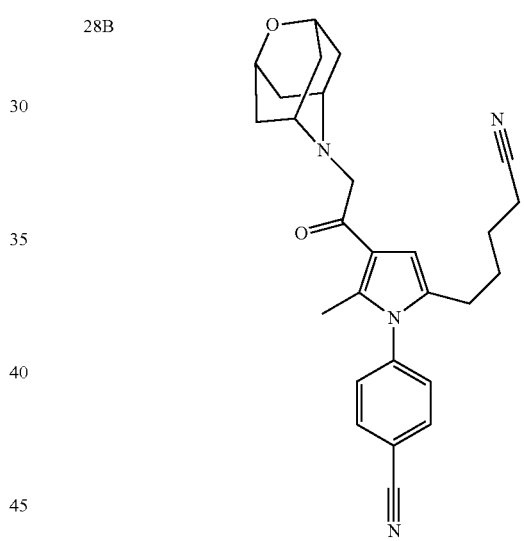 |
| 29B | 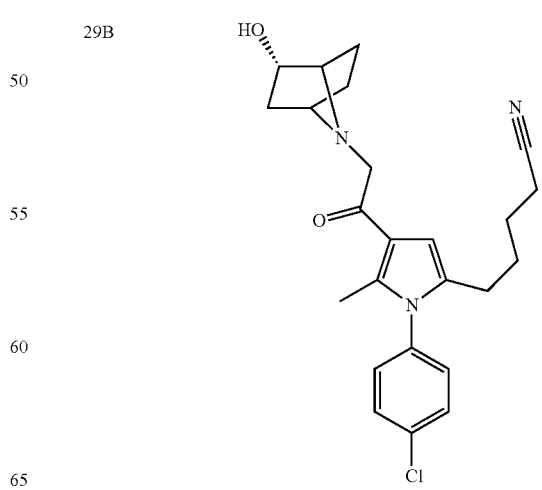 |

TABLE 3-continued
| Compound No. | Structure |
|---|---|
| 30B | 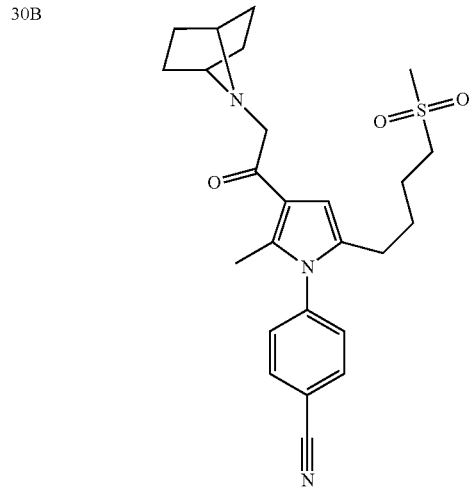 |
| 31B | 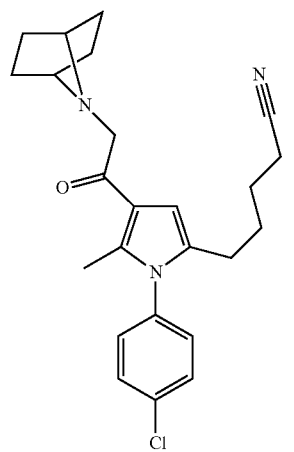 [SMILES: Cc1c(C(=O)CN2C3CCC2CC3)cc(CCCCC#N)n1-c1ccc(Cl)cc1] |
| 32B | 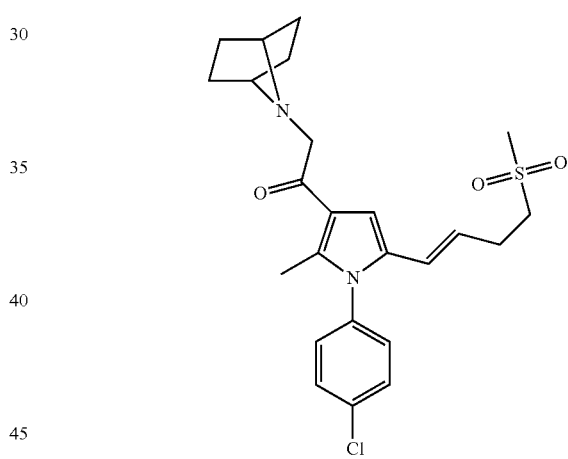 |
TABLE 3-continued
| Compound No. | Structure |
|---|---|
| 33B | 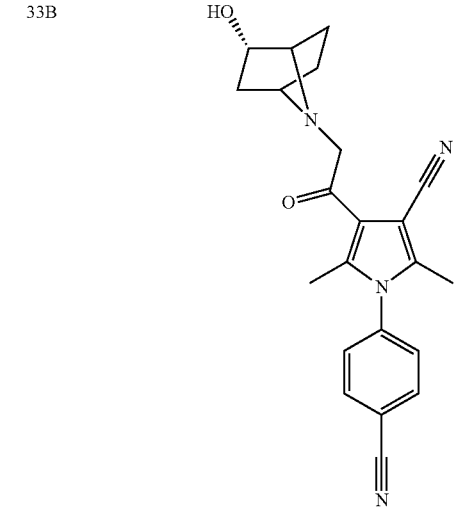 |
| 34B | |
| 35B | 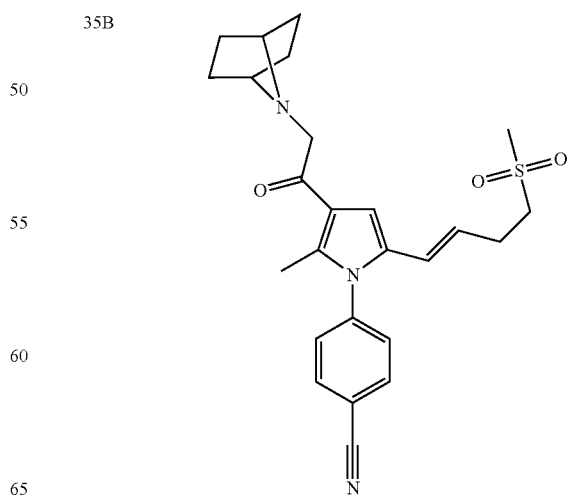 |

TABLE 3-continued

| Compound No. | Structure |
|---|---|
| 36B | (structure) |
| 37B | (structure) |
| 38B | (structure) |
| 39B | (structure) |
| 40B | (structure) |
| 41B | (structure) |

TABLE 3-continued
| Compound No. | Structure |
|---|---|
| 42B | 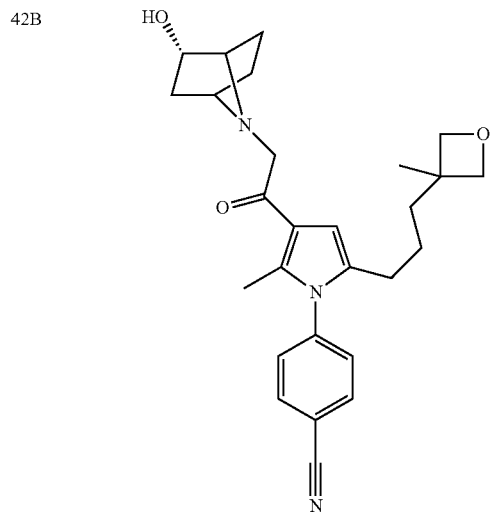 |
| 43B | 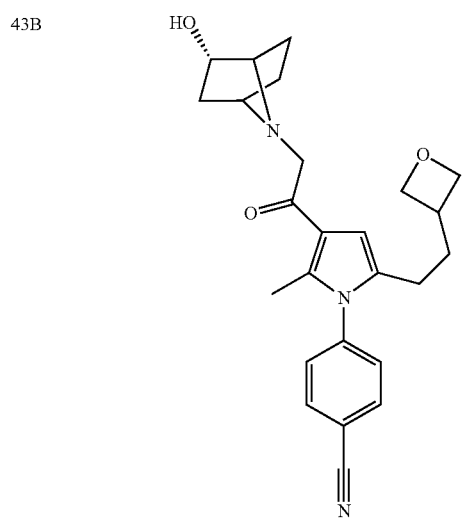 |
| 44B | 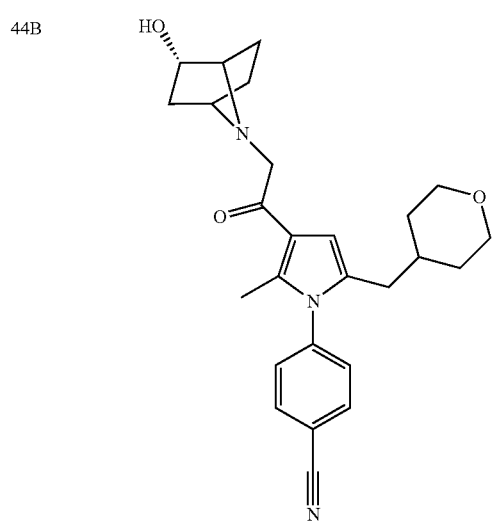 |
| 45B | 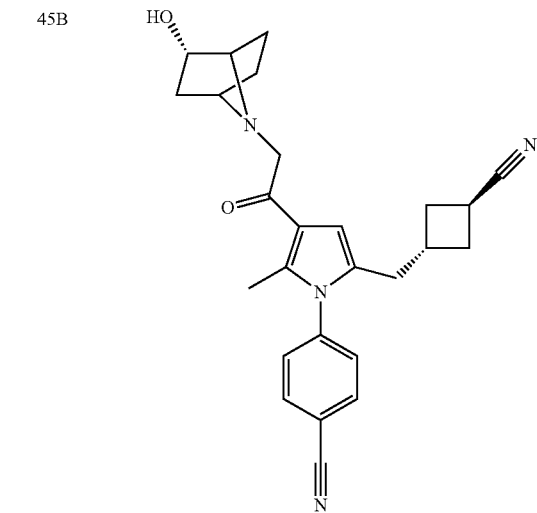 |
| 46B | 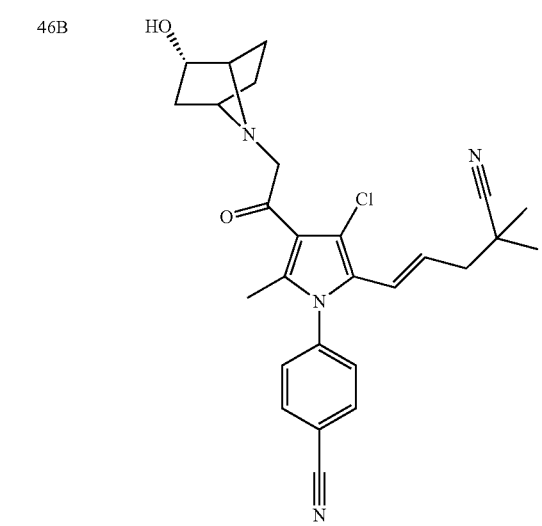 |
| 47B | 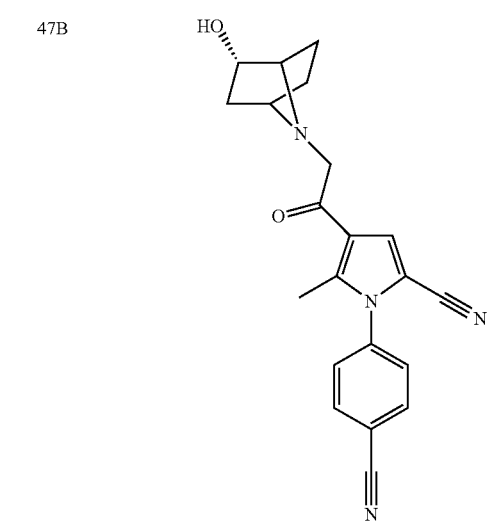 |

TABLE 3-continued
| Compound No. | Structure |
|---|---|
| 50B | 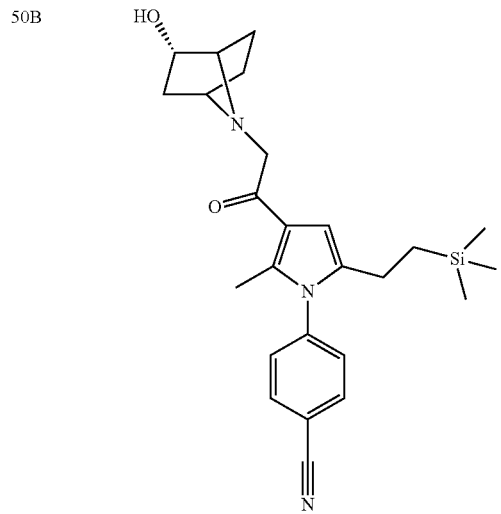 |
| 51B | 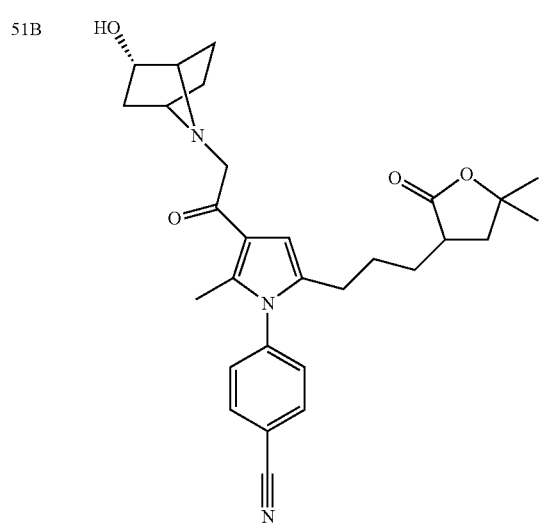 |
| 52B | 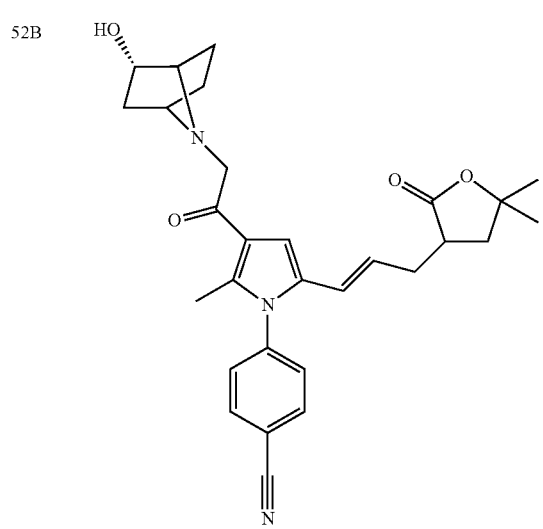 |
| 53B | 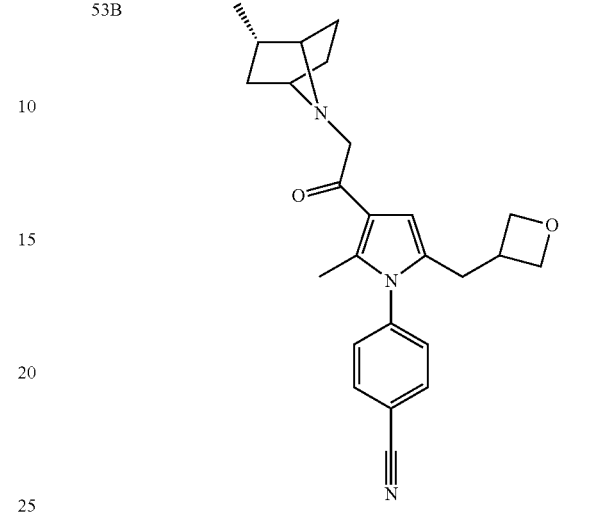 |
| 54B | 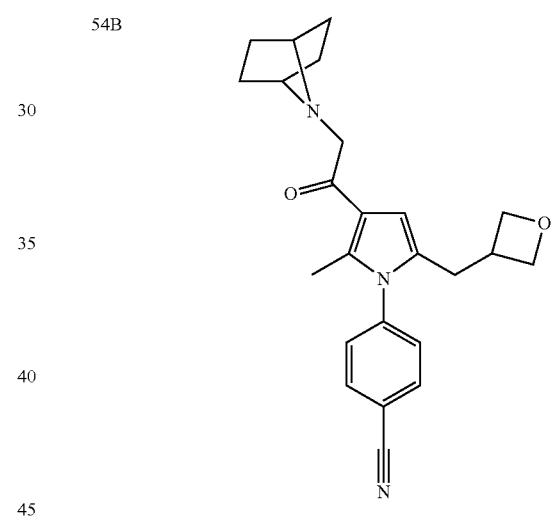 |
| 55B | 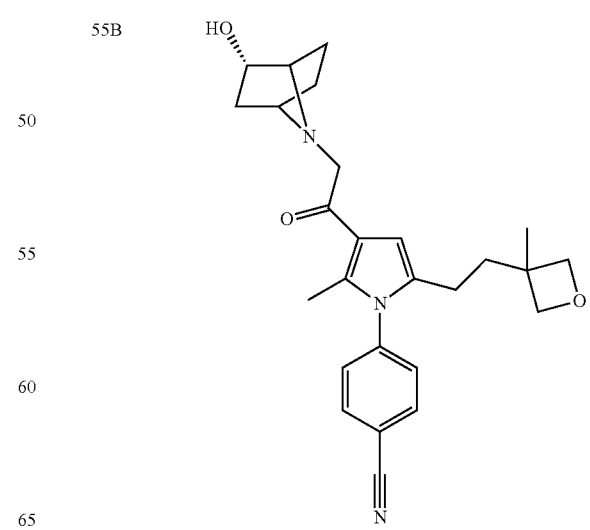 |

TABLE 3-continued

| Compound No. | Structure |
|---|---|
| 56B | 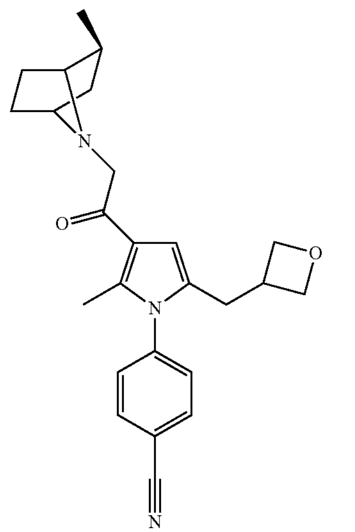 [SMILES: Cc1c(C(=O)CN2C3CCC2[C@@H](C)C3)cc(CC2COC2)n1-c1ccc(C#N)cc1] |
| 57B | 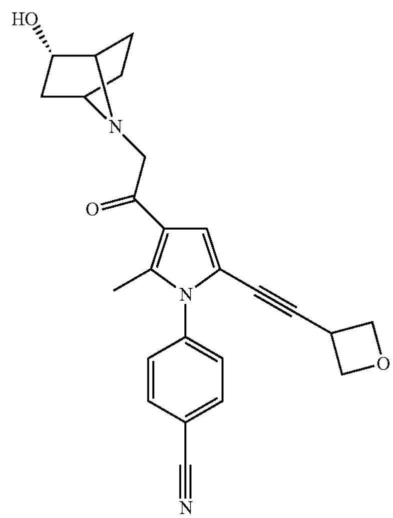 [SMILES: Cc1c(C(=O)CN2C3CCC2[C@@H](O)C3)cc(C#CC2COC2)n1-c1ccc(C#N)cc1] |
| 63B | 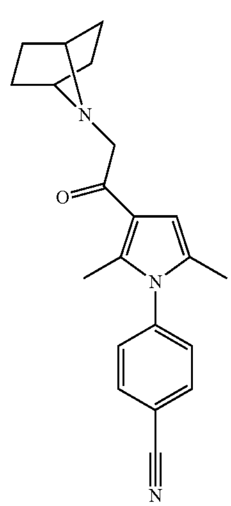 [SMILES: Cc1cc(C(=O)CN2C3CCC2CC3)c(C)n1-c1ccc(C#N)cc1] |
| 64B | 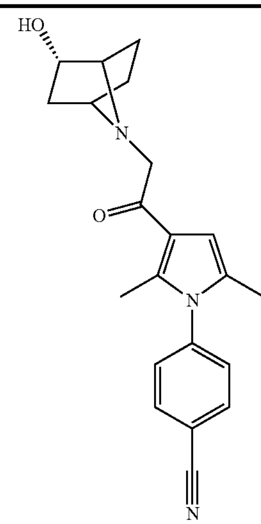 |
| 66B | 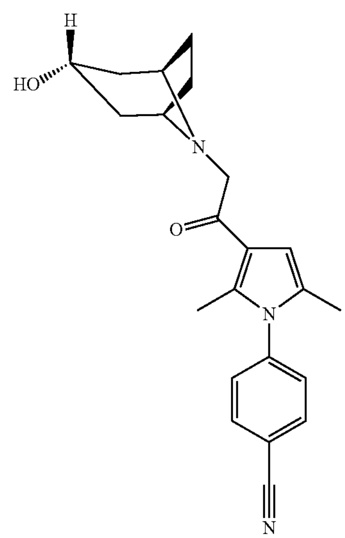 |
| 67B | 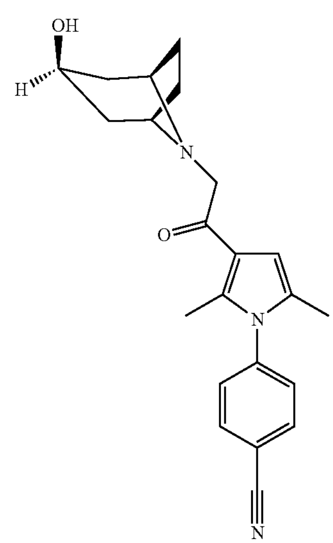 |

TABLE 3-continued

| Compound No. | Structure |
|---|---|
| 68B | (structure) |
| 69B | (structure) |
| 70B | (structure) |
| 71B | (structure) |
| 72B | (structure) |
| 73B | (structure) |

TABLE 3-continued
| Compound No. | Structure |
|---|---|
| 74B | 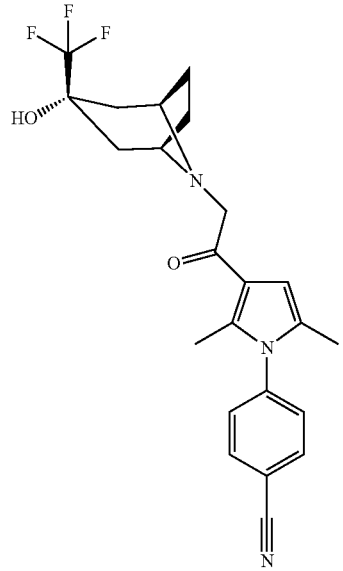 |
| 75B | 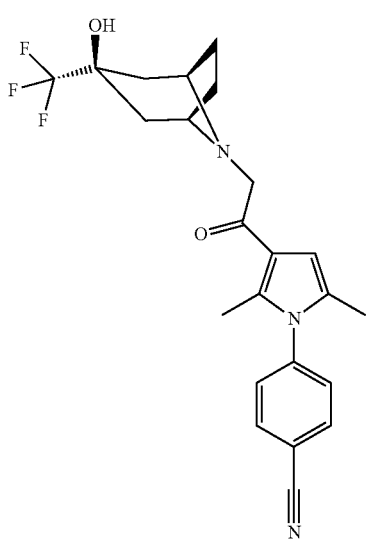 |
| 76B | 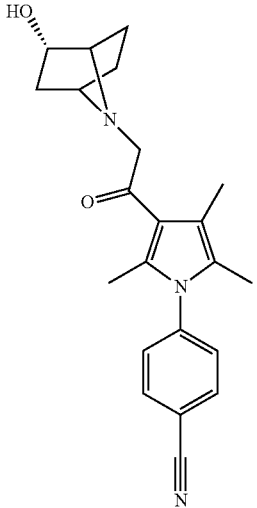 [SMILES: Cc1c(C(=O)CN2C3CCC2[C@@H](O)C3)c(C)n(-c2ccc(C#N)cc2)c1C] |
| 77B | 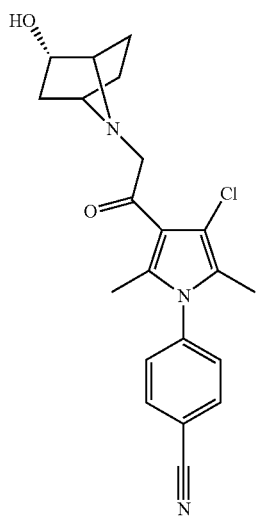 [SMILES: Cc1c(Cl)c(C(=O)CN2C3CCC2[C@@H](O)C3)c(C)n1-c1ccc(C#N)cc1] |
| 78B | 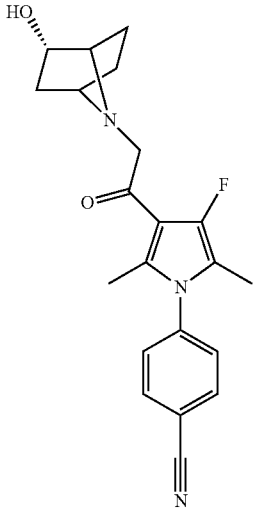 [SMILES: Cc1c(F)c(C(=O)CN2C3CCC2[C@@H](O)C3)c(C)n1-c1ccc(C#N)cc1] |

TABLE 3-continued
| Compound No. | Structure |
|---|---|
| 79B | 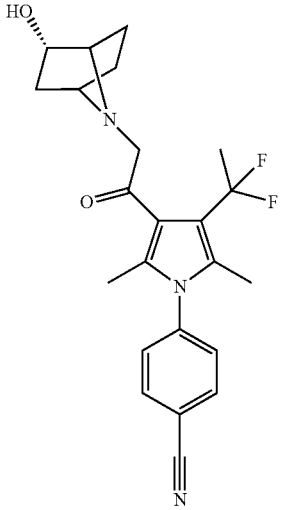 [SMILES: Cc1c(C(=O)CN2C3CCC2[C@@H](O)C3)c(C(C)(F)F)c(C)n1-c1ccc(C#N)cc1] |
| 80B | 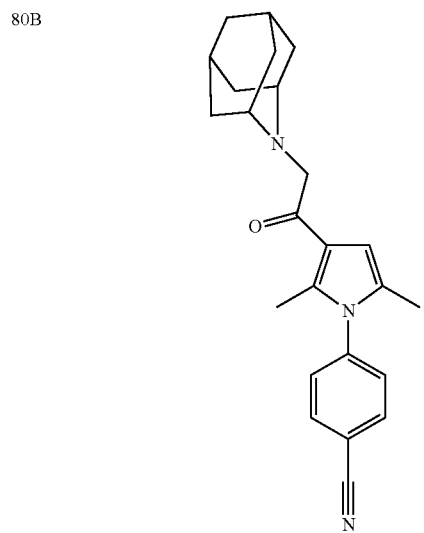 |
| 81B | 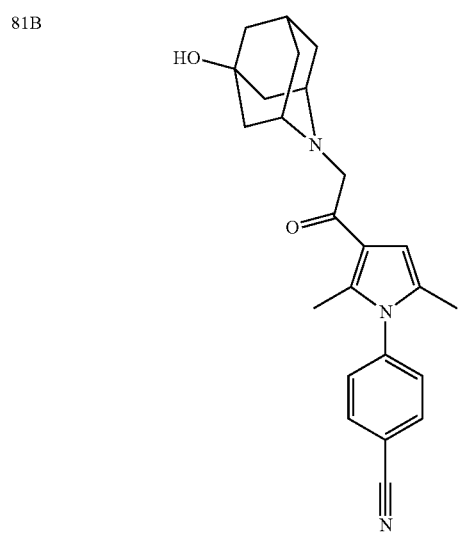 |
| 82B | 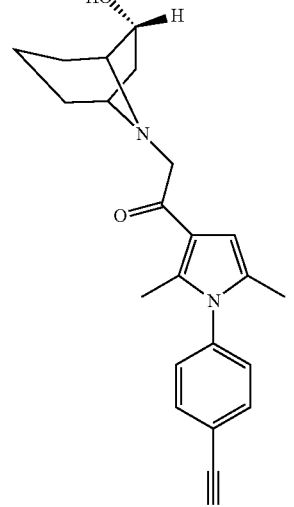 |
| 83B | 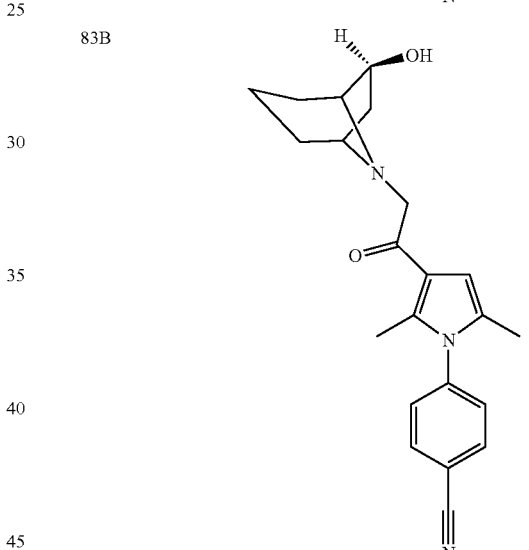 |
| 84B | 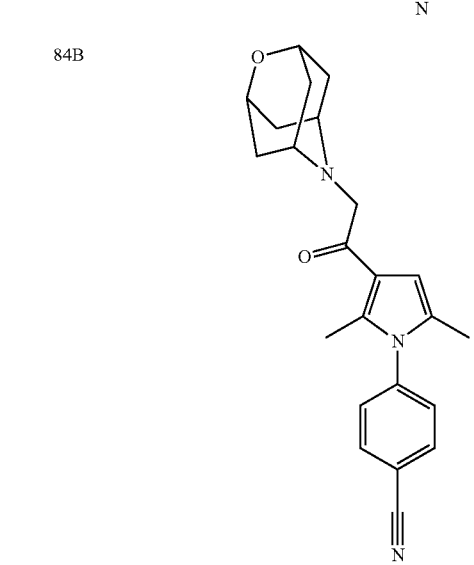 |

TABLE 3-continued
| Compound No. | Structure |
|---|---|
| 85B | 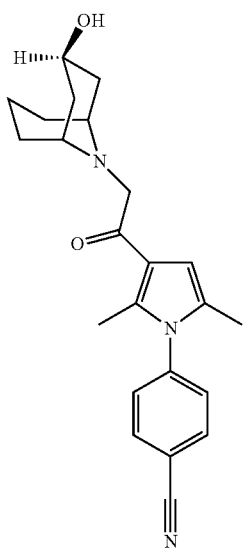 |
| 86B | 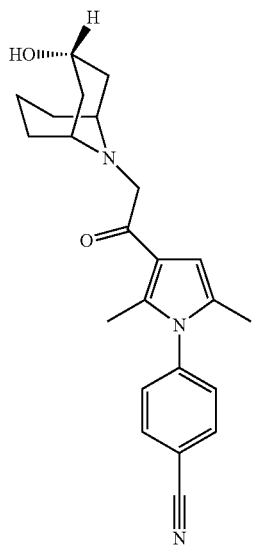 |
| 87B | 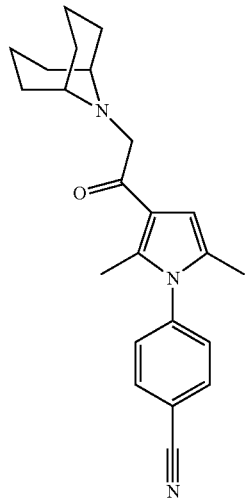 [SMILES: Cc1cc(C(=O)CN2C3CCCC2CCC3)c(C)n1-c1ccc(C#N)cc1] |
| 88B | 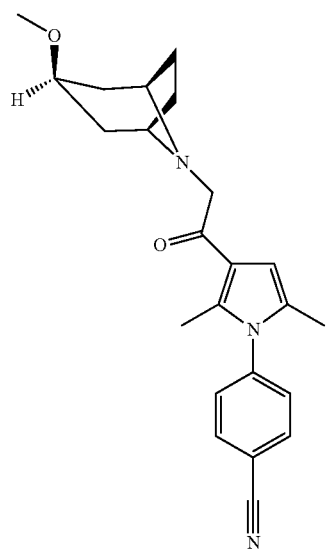 |
| 89B | 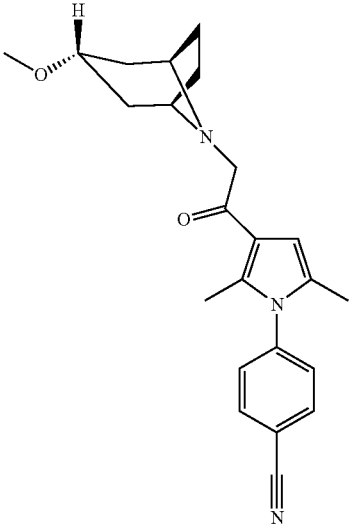 |

TABLE 3-continued
| Compound No. | Structure |
|---|---|
| 90B | 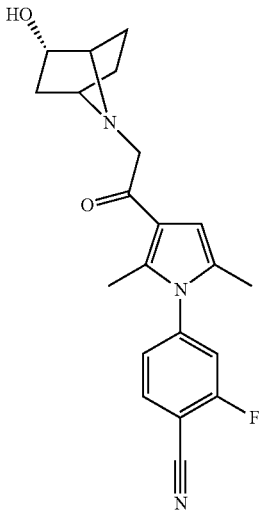 |
| 91B | 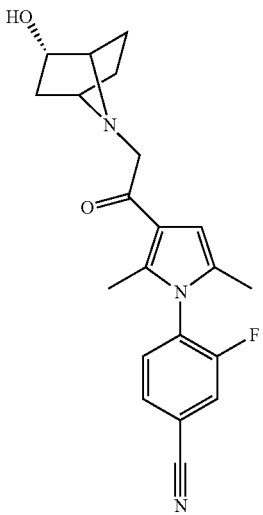 [SMILES: Cc1cc(C(=O)CN2C3CCC2[C@@H](O)C3)c(C)n1-c1ccc(C#N)cc1F] |
| 92B | 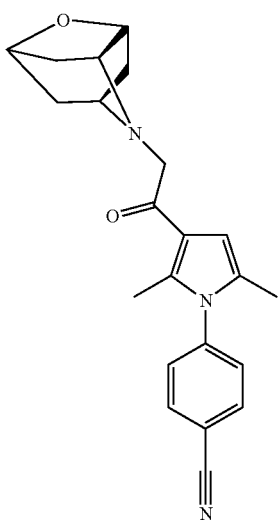 [SMILES: Cc1cc(C(=O)CN2[C@H]3CC4C[C@H]2C(C3)O4)c(C)n1-c1ccc(C#N)cc1] |
| 94B | 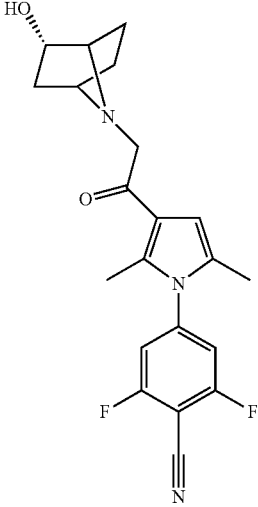 [SMILES: Cc1cc(C(=O)CN2C3CCC2[C@@H](O)C3)c(C)n1-c1cc(F)c(C#N)c(F)c1] |
| 95B | 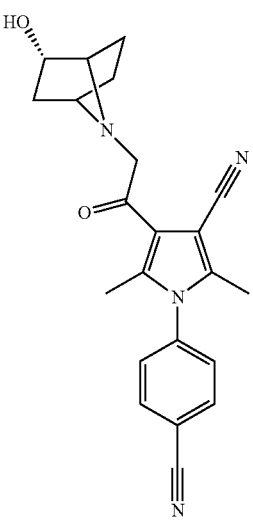 [SMILES: Cc1c(C#N)c(C(=O)CN2C3CCC2[C@@H](O)C3)c(C)n1-c1ccc(C#N)cc1] |
| 96B | 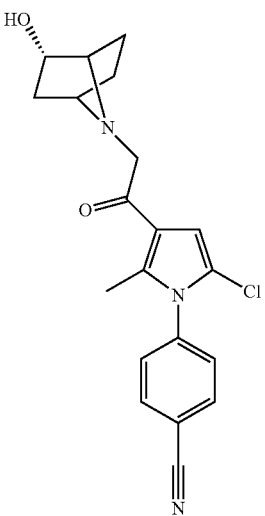 [SMILES: Cc1c(C(=O)CN2C3CCC2[C@@H](O)C3)cc(Cl)n1-c1ccc(C#N)cc1] |

TABLE 3-continued
| Compound No. | Structure |
|---|---|
| 97B | 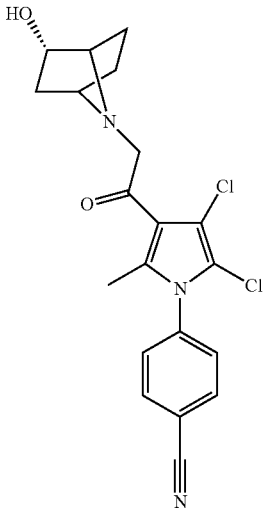 [SMILES: Cc1c(C(=O)CN2C3CCC2[C@@H](O)C3)c(Cl)c(Cl)n1-c1ccc(C#N)cc1] |
| 98B | 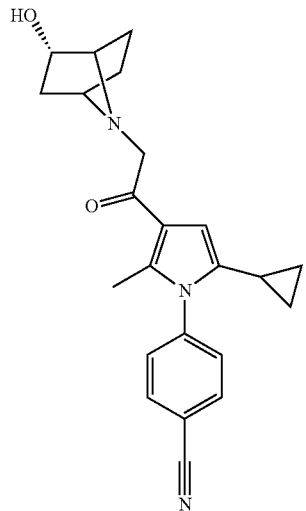 [SMILES: Cc1c(C(=O)CN2C3CCC2[C@@H](O)C3)cc(C2CC2)n1-c1ccc(C#N)cc1] |
| 99B | 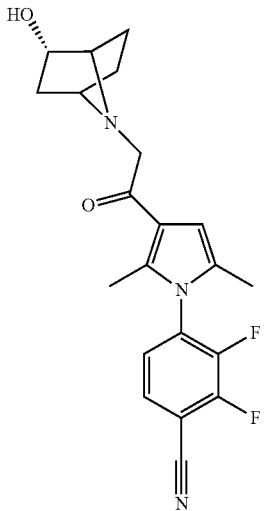 [SMILES: Cc1cc(C(=O)CN2C3CCC2[C@@H](O)C3)c(C)n1-c1ccc(C#N)c(F)c1F] |
| 100B | 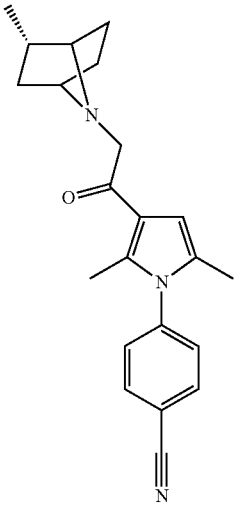 |
| 101B | 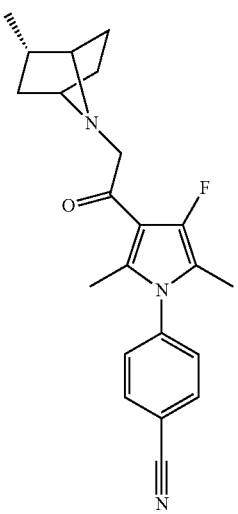 |
| 102B | 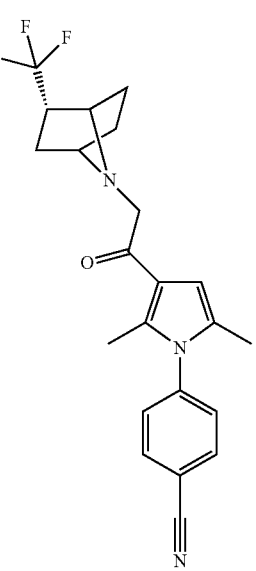 |

TABLE 3-continued
| Compound No. | Structure |
|---|---|
| 103B | 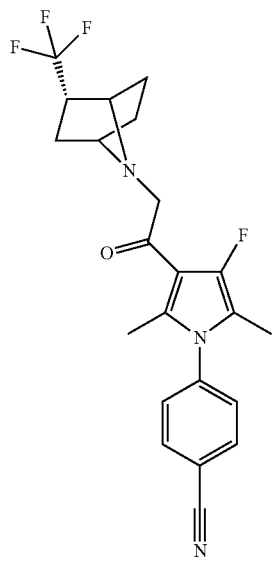 [SMILES: Cc1c(F)c(C(=O)CN2C3CCC2[C@@H](C(F)(F)F)C3)c(C)n1-c1ccc(C#N)cc1] |
| 104B | 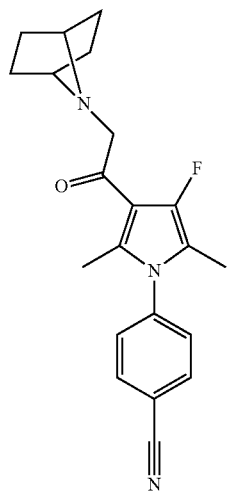 [SMILES: Cc1c(F)c(C(=O)CN2C3CCC2CC3)c(C)n1-c1ccc(C#N)cc1] |
TABLE 3-continued
| Compound No. | Structure |
|---|---|
| 105B | 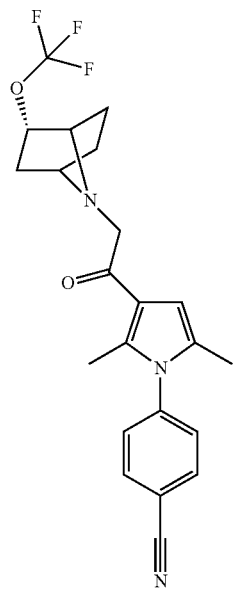 [SMILES: Cc1cc(C(=O)CN2C3CCC2[C@@H](OC(F)(F)F)C3)c(C)n1-c1ccc(C#N)cc1] |
| 106B | 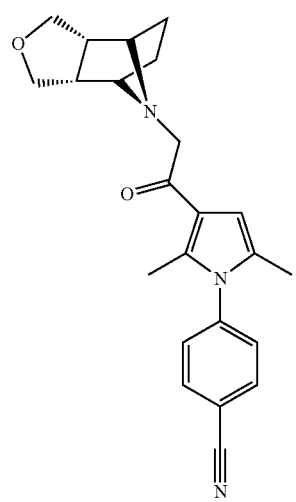 |
| 107B | 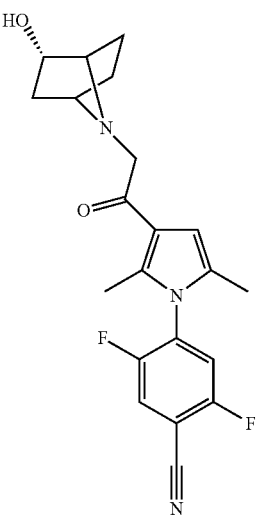 [SMILES: Cc1cc(C(=O)CN2C3CCC2[C@@H](O)C3)c(C)n1-c1cc(F)c(C#N)cc1F] |

TABLE 3-continued
| Compound No. | Structure |
|---|---|
| 108B | 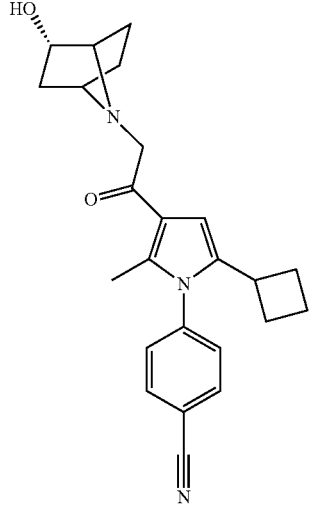 [SMILES: Cc1c(C(=O)CN2C3CCC2[C@@H](O)C3)cc(C2CCC2)n1-c1ccc(C#N)cc1] |
| 109B | 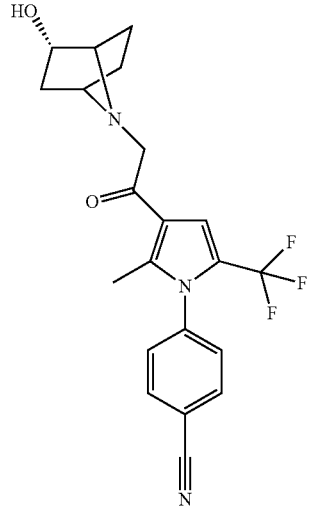 [SMILES: Cc1c(C(=O)CN2C3CCC2[C@@H](O)C3)cc(C(F)(F)F)n1-c1ccc(C#N)cc1] |
| 110B | 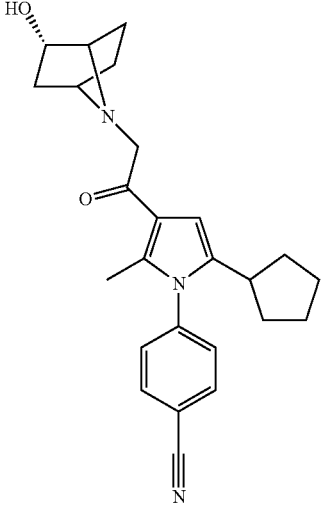 [SMILES: Cc1c(C(=O)CN2C3CCC2[C@@H](O)C3)cc(C2CCCC2)n1-c1ccc(C#N)cc1] |
| 111B | 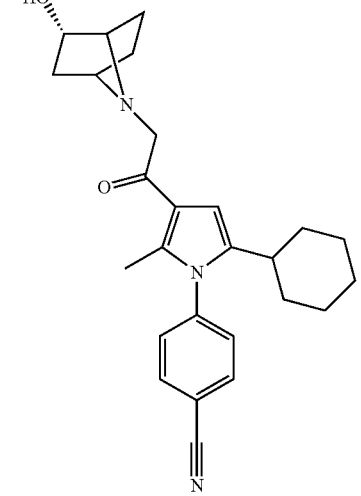 |
| 112B | 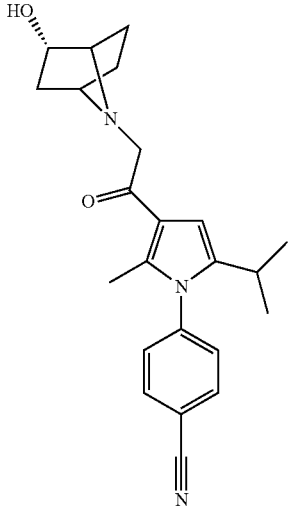 [SMILES: Cc1c(C(=O)CN2C3CCC2[C@@H](O)C3)cc(C(C)C)n1-c1ccc(C#N)cc1] |
| 113B | 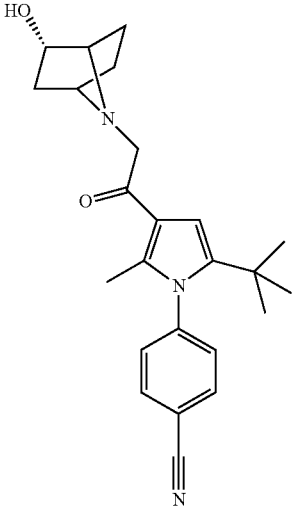 [SMILES: Cc1c(C(=O)CN2C3CCC2[C@@H](O)C3)cc(C(C)(C)C)n1-c1ccc(C#N)cc1] |

TABLE 3-continued
| Compound No. | Structure |
|---|---|
| 114B | 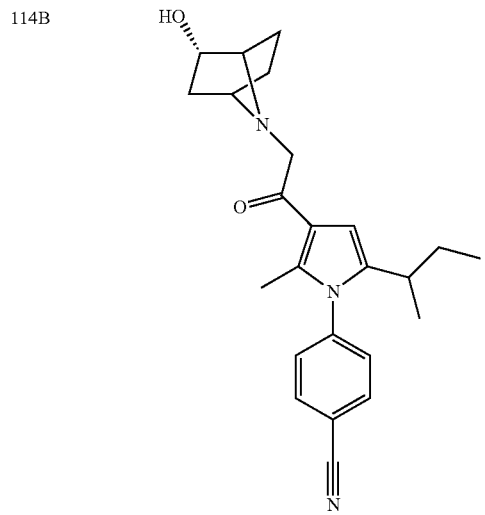 |
| 115B | 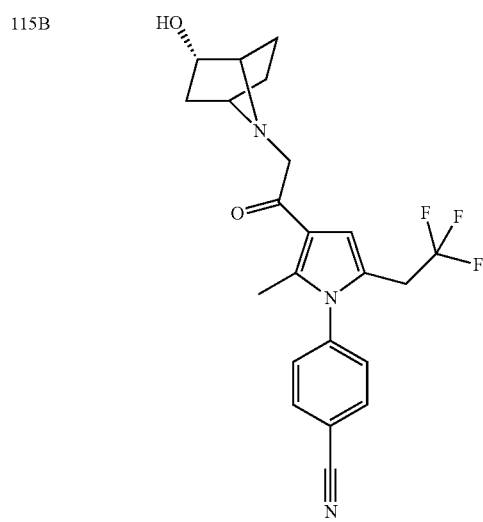 |
| 116B | 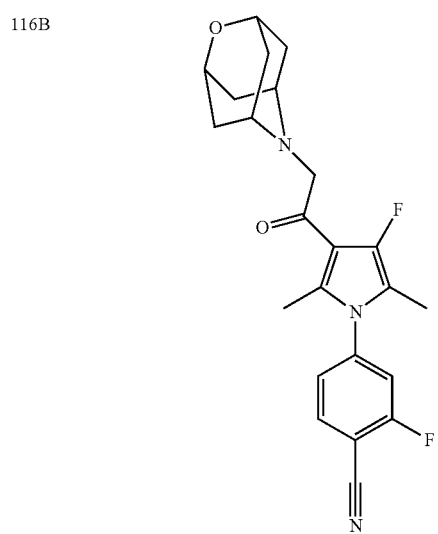 |
| 117B | 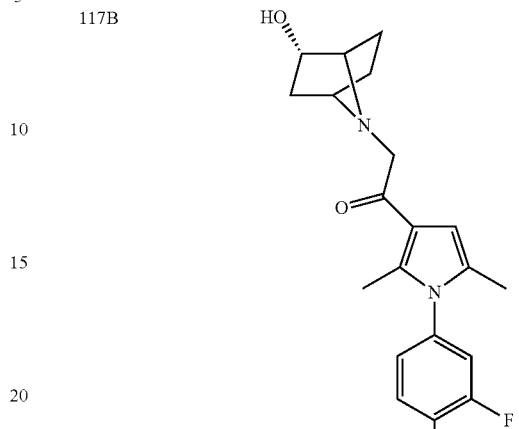 |
| 118B | 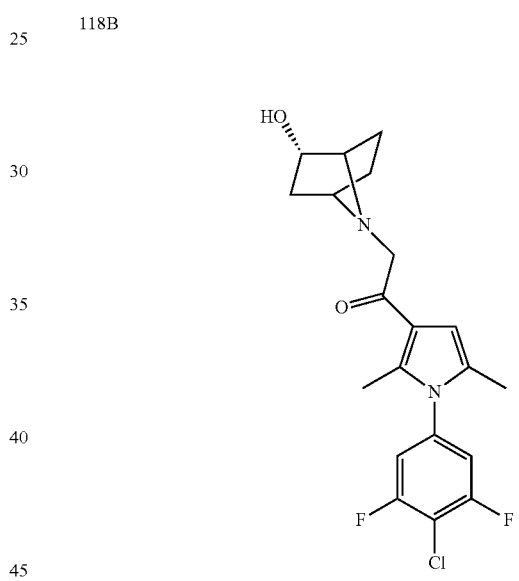 |
| 119B | 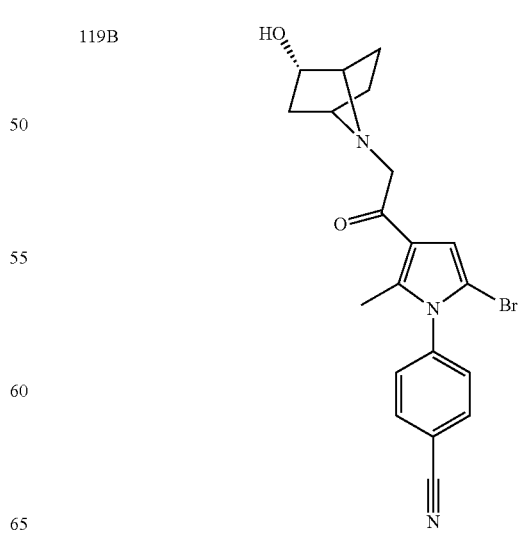 |

TABLE 3-continued
| Compound No. | Structure |
|---|---|
| 120B | 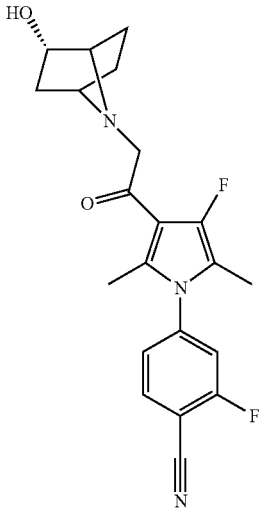 [SMILES: Cc1c(F)c(C(=O)CN2C3CCC2[C@@H](O)C3)c(C)n1-c1ccc(C#N)c(F)c1] |
| 121B | 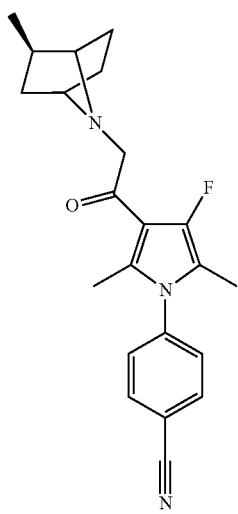 |
| 122B | 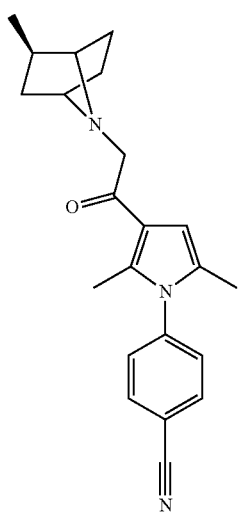 |
TABLE 3-continued
| Compound No. | Structure |
|---|---|
| 124B | 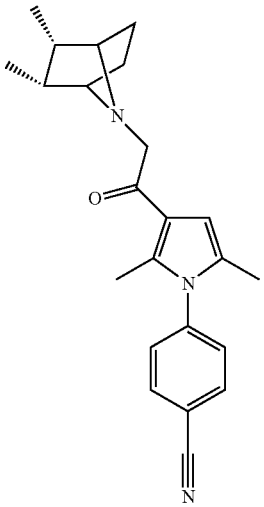 |
| 125B | 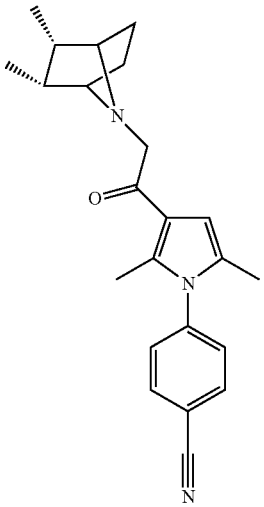 |
| 126B | 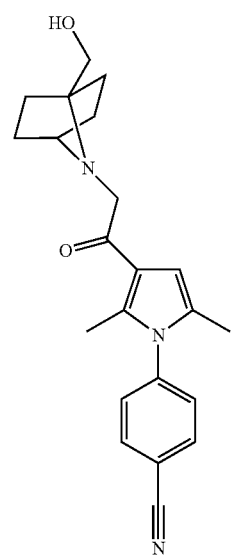 [SMILES: Cc1cc(C(=O)CN2C3CCC2(CO)CC3)c(C)n1-c1ccc(C#N)cc1] |

TABLE 3-continued

| Compound No. | Structure |
|---|---|
| 127B | (structure) |
| 128B | (structure) |
| 129B | (structure) |
| 130B | (structure) |
| 131B | (structure) |
| 132B | (structure) |

TABLE 3-continued
| Compound No. | Structure |
|---|---|
| 133B | 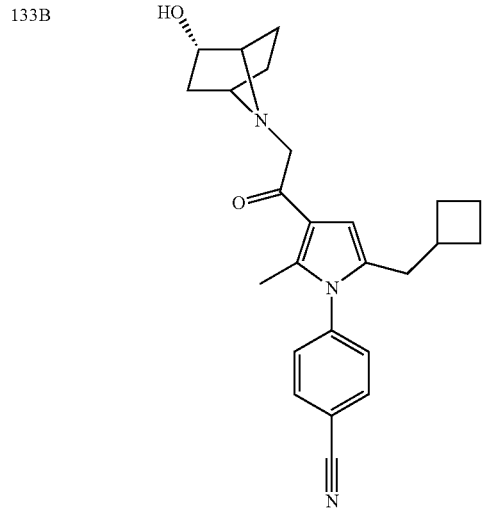 |
| 134B | 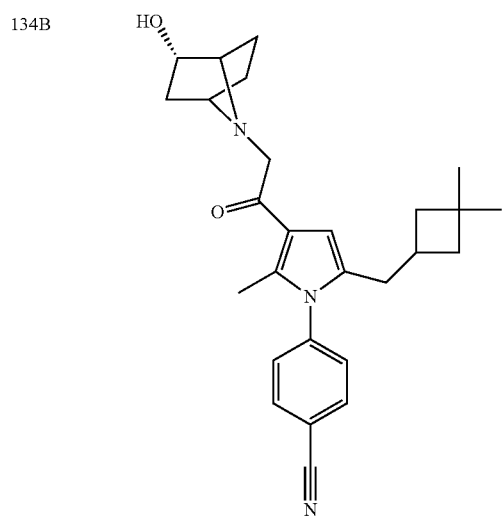 |
| 135B | 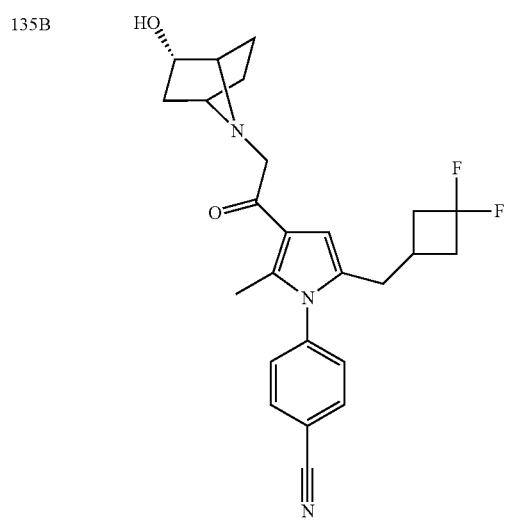 |
| 136B | 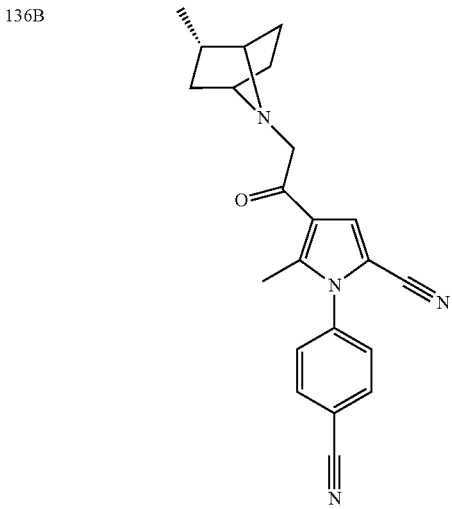 |
| 137B | 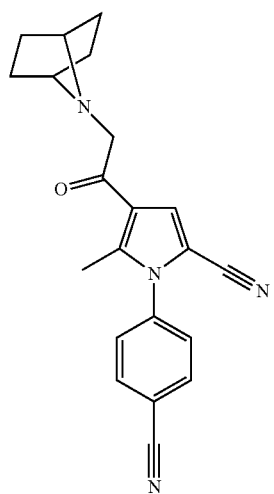 [SMILES: Cc1c(C(=O)CN2C3CCC2CC3)cc(C#N)n1-c1ccc(C#N)cc1] |
| 138B | 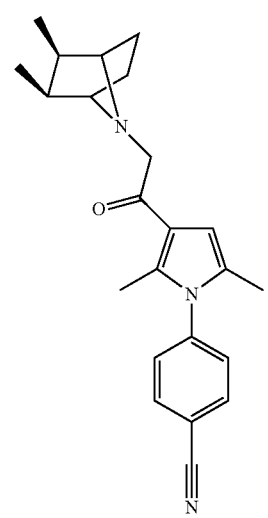 |

TABLE 3-continued

| Compound No. | Structure |
|---|---|
| 139B | 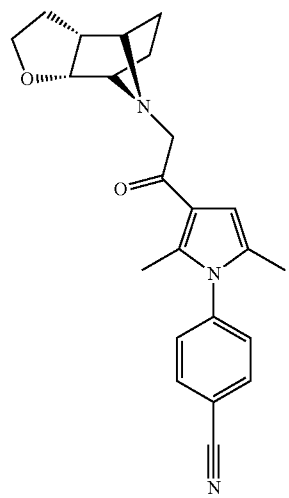 |
| 140B | 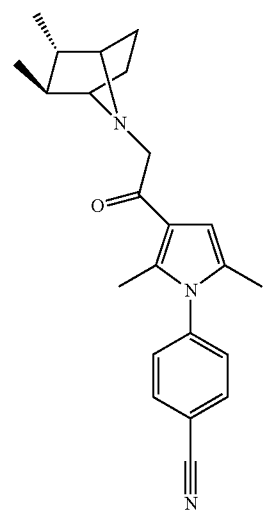 |
| 141B | 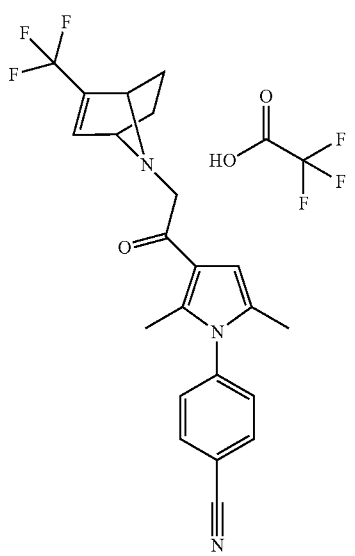 [SMILES: Cc1cc(C(=O)CN2C3C=C(C(F)(F)F)C2CC3)c(C)n1-c1ccc(C#N)cc1 ; O=C(O)C(F)(F)F] |
| 142B | |
| 143B | |
| 144B | |

TABLE 3-continued
| Compound No. | Structure |
|---|---|
| 145B | 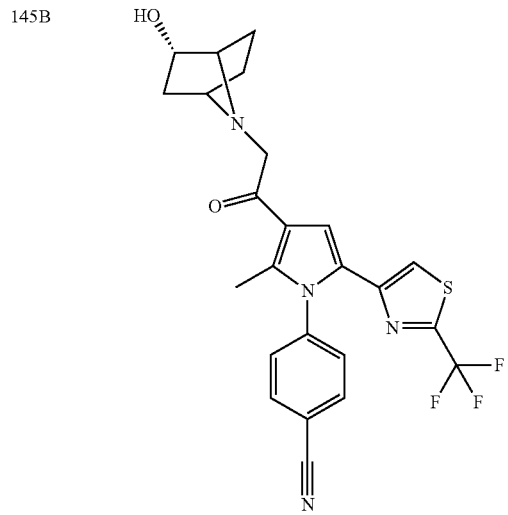 |
| 146B | 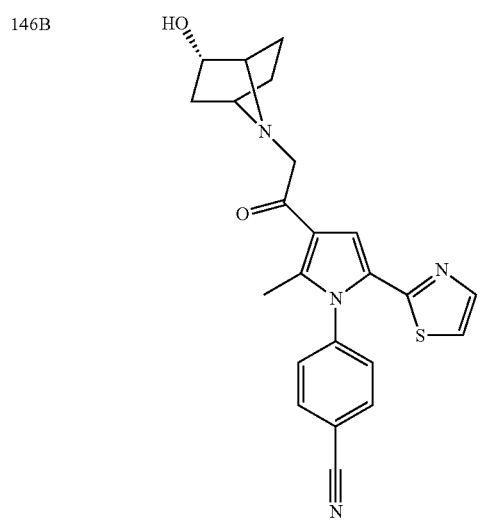 |
| 147B | 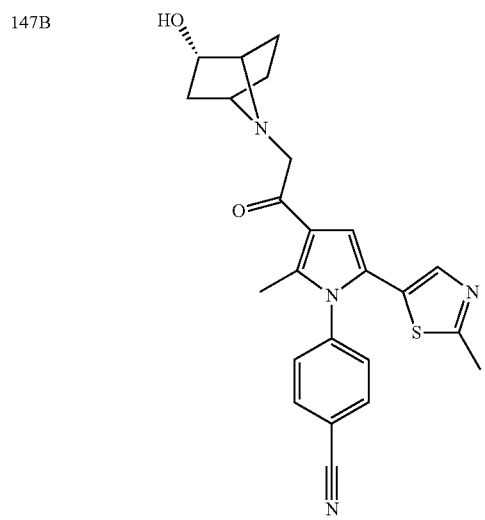 |
| 148B | 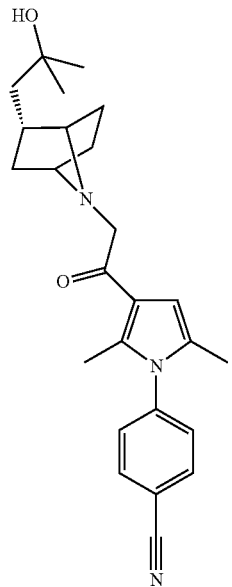 [SMILES: Cc1cc(C(=O)CN2C3CCC2[C@@H](CC(C)(C)O)C3)c(C)n1-c1ccc(C#N)cc1] |
| 149B | 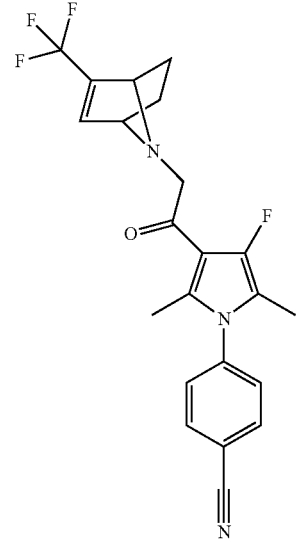 [SMILES: Cc1c(F)c(C(=O)CN2C3C=C(C(F)(F)F)C2CC3)c(C)n1-c1ccc(C#N)cc1] |

TABLE 3-continued

| Compound No. | Structure |
|---|---|
| 150B | (structure) |
| 151B | (structure) |
| 153B | (structure) |
| 155B | (structure) |
| 156B | (structure) |
| 157B | (structure) |

TABLE 3-continued

| Compound No. | Structure |
|---|---|
| 158B | 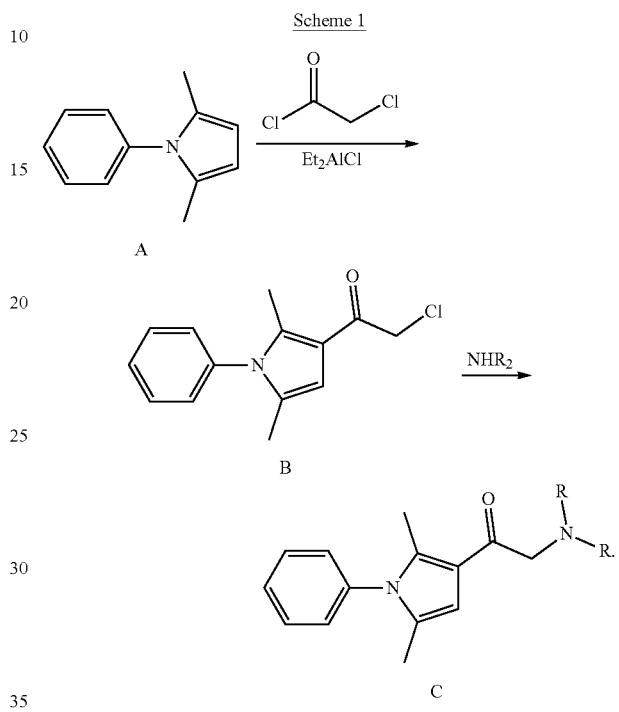 |

Methods of Preparation

In some embodiments, methods that can be used for the synthesis of the compounds of Formulae (III), (IIIa), (IIIb), (IIIc), (IIId), and (IIIe) described herein have been reported in the literature, for example in: 1) Banik, B. et al. "Simple Synthesis of Substituted Pyrroles" J. Org. Chem, 2004, 69, 213; 2) Sawada, Y. et al. "Eight-Membered Oxygen Heterocycles by Brook Rearrangement-mediated [3+4] Annulation" Org. Let. 2004, 6, 2277; 3) Aubé, J. et al. "Synthetic Aspects of an Asymmetric Nitrogen-Insertion Process: Preparation of Chiral, Non-Racemic Caprolactams and Valerolactams. Total Synthesis of (−)-Alloyohimbane" J. Am. Chem. Soc. 1990, 112, 4879; 4) Antilla, J. C. et al. "Copper-diamine-catalyzed N-arylation of pyrroles, pyrazoles, indazoles, imidazoles, and triazoles" J. Org. Chem. 2004, 69, 5578; 5) Huang, K. H. et al. "Benzene, pyridine, and pyridazine derivatives as HSP-90 inhibitors and their preparation, pharmaceutical compositions and use in the treatment of proliferative diseases" WO 2008024978; 6) Taylor, J. et al. "Friedel-Crafts Acylation of Pyrroles and Indoles using 1,5-Diazabicyclo[4.3.0]non-5-ene (DBN) as a Nucleophilic Catalyst" Org. Lett. 2010, 12, 5740; 7) Sinha, N. et al. "Preparation of pyrrole derivatives as alpha 7 nAChR modulators for treatment of neurological disorders and other diseases" WO 2014203150; 8) Greenhouse, R. et al. "Synthesis of alkylpyrroles by the sodium borohydride reduction of acylpyrroles" J. Org. Chem. 1995, 50, 2961; 9) Stevens, R. W. et al. "Preparation of 3-aminoindole compounds as cyclooxygenase (COX-2) inhibitors" WO 1999005104; 10) Davidson, J. E. P. et al. "New isoindoline or isoquinoline derivatives, their preparation as pro-apoptotic and antitumor agents and their pharmaceutical compositions containing them" WO 2015011164; 11) Pfaff, U. et al. "Electronically Strongly Coupled Divinylheterocyclic-Bridged Diruthenium Complexes" Chemistry—A European J. 2016, 22, 783; 12) Toguem, S.-M. T. et al. "2,5,6-Trisubstituted N-methylindoles from site-selective Suzuki-Miyaura cross-coupling, twofold Heck and 6π-electrocyclization-dehydrogenation reactions of 2,3,5-tribromo-N-methylpyrrole" Synlett, 2011, 4, 513; the contents of each of which are expressly incorporated by reference herein.

Exemplary synthetic routes for the preparation of compounds of Formulae (III), (IIIa), (IIIb), (IIIc), (IIId), and (IIIe) of the invention are shown in the Schemes 1 through 3 below. As will be understood by the skilled artisan, diastereomers can be separated from the reaction mixture using column chromatography.

Scheme 1

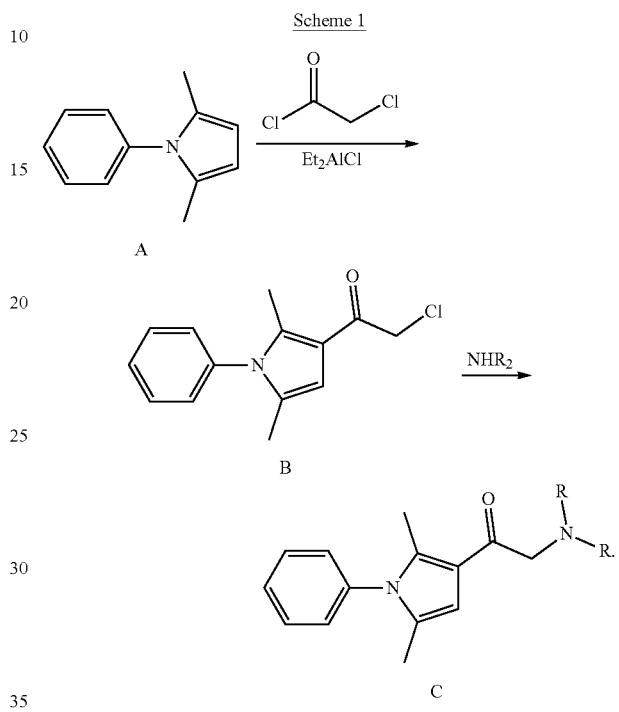

As depicted in Scheme 1, a Paal-Knorr pyrrole synthesis utilizing an aniline and an appropriate diketone affords pyrrole A.[1] A Friedel-Crafts acylation with chloroacetyl chloride and an aluminum-based Lewis acid (ex. $AlCl_3$ or diethylaluminum chloride) provides intermediate B. The chlorine can be easily displaced with a variety of $O^2$, $N^3$, S and C based nucleophiles to provide the desired compounds, such as scaffold C.

Scheme 2

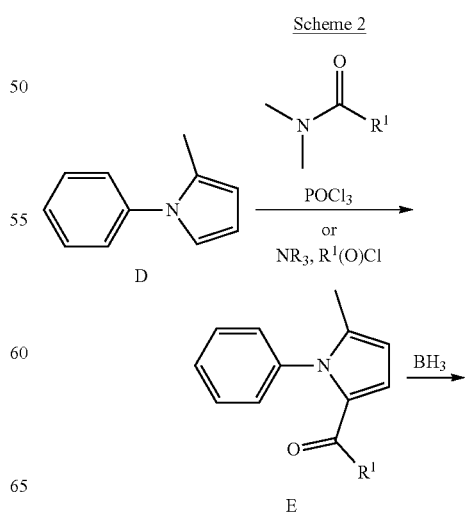

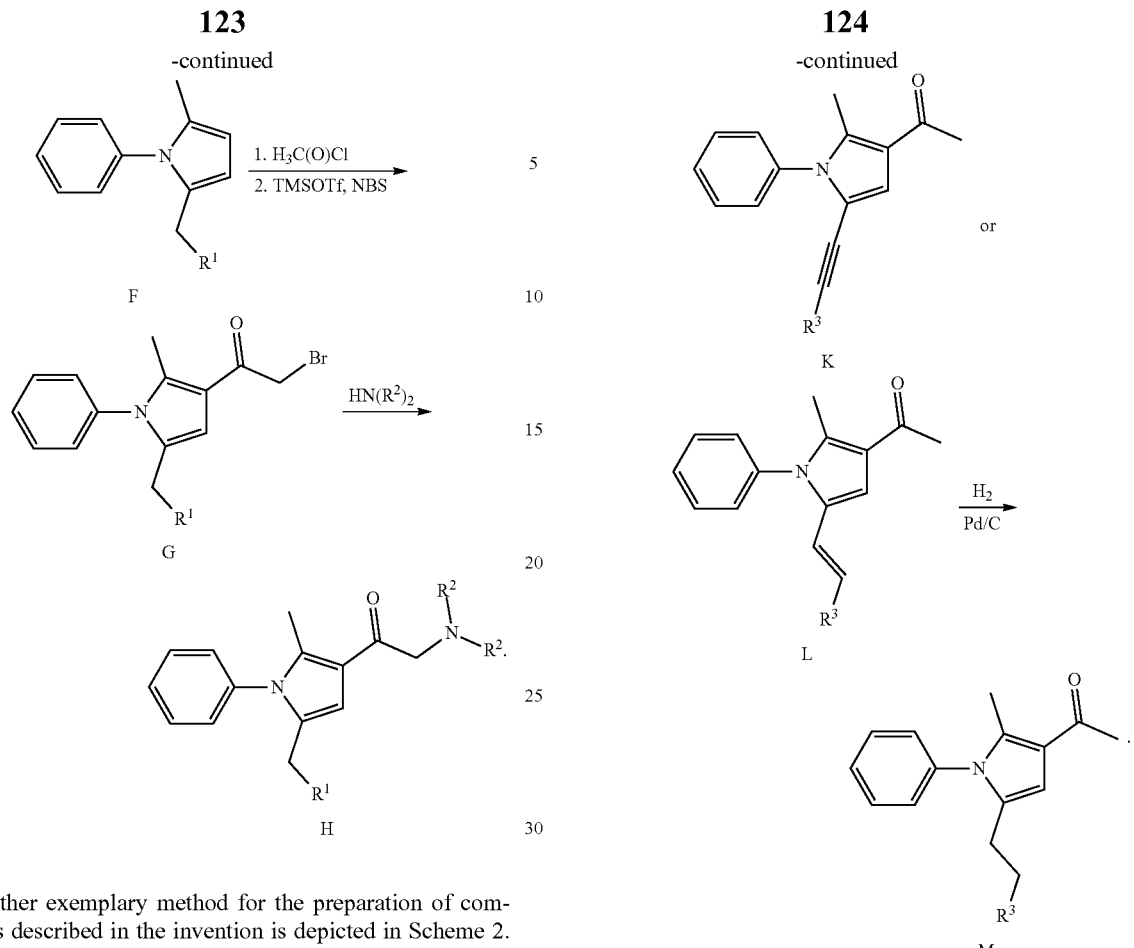

Another exemplary method for the preparation of compounds described in the invention is depicted in Scheme 2. Aryl pyrrole D, which is prepared through metal-catalyzed coupling[4] or nucleophilic aromatic substitution[5] between a pyrrole and suitably substituted aryl group, is acylated with an acyl chloride[6] or amide of similar structure via Vilsmeir chemistry to yield ketone E.[7] Complete reduction of ketone E to pyrrole F can be achieved with borane or related-borohydride reagents, where the pyrrole product F can be processed further, as shown in Scheme 1, to obtain compounds of the invention. Alternatively, pyrrole F is transformed in a two step procedure to obtain bromo-ketone G,[9] which is further processed to obtain compounds of the invention.

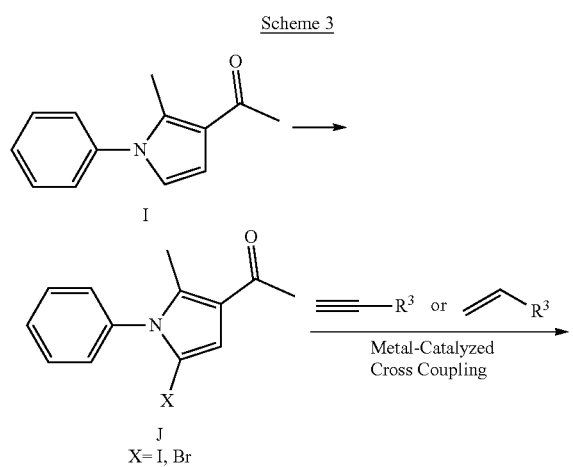

Scheme 3 depicts yet another method of preparing compound described by the invention. Pyrrole I, which is prepared via methods analogues to those presented for pyrrole D (Scheme 2), is halogenated at the 5-position to generate pyrrole J.[10] Sonagoshira[11] or Heck[12] chemistries are used to couple pyrrole J with substituted alkynes or alkenes, respectively, to obtain pyrroles K and L, which can be directly processed as shown in Schemes 1 and 2 to generate compounds relevant to the invention. Alternatively, pyrroles K and L can be reduced via common hydrogenation methods and further processed, as described above, to further obtain compounds relevant to the invention.

Definitions

The term "alkyl", as used herein, unless otherwise indicated, refers to both branched and straight-chain saturated aliphatic hydrocarbon groups having the specified number of carbon atoms; for example, "$C_1$-$C_{10}$ alkyl" denotes alkyl having 1 to 10 carbon atoms. Examples of alkyl include, but are not limited to, methyl, ethyl, n-propyl, i-propyl, n-butyl, i-butyl, sec-butyl, t-butyl, n-pentyl, n-hexyl, 2-methylbutyl, 2-methylpentyl, 2-ethylbutyl, 3-methylpentyl, and 4-methylpentyl.

The term, "alkenyl", as used herein, refers to both straight and branched-chain moieties having the specified number of carbon atoms and having at least one carbon-carbon double bond.

The term, "alkynyl", as used herein, refers to both straight and branched-chain moieties having the specified number or carbon atoms and having at least one carbon-carbon triple bond.

The term "alkylene" means a divalent alkyl radical, for example, —CH$_2$— or —CH$_2$CH$_2$CH$_2$—.

The term "alkenylene" means a divalent alkenyl radical, for example, —CH=CH—.

The term "alkynylene" means a divalent alkynyl radical.

The term "cycloalkyl," as used herein, refers to cyclic alkyl moieties having 3 or more carbon atoms (for example, 3 to 12, or 3 to 10, or 3 to 8, or 3 to 7, or 3 to 6 carbon atoms). Examples of cycloalkyl include, but are not limited to, cyclopropyl, cyclobutyl, cyclopentyl, cyclohexyl, cycloheptyl and adamantyl.

The term "cycloalkenyl," as used herein, refers to cyclic alkenyl moieties having 3 or more carbon atoms (for example, 3 to 12, or 3 to 10, or 3 to 8, or 3 to 7, or 3 to 6 carbon atoms).

The term "cycloalkynyl," as used herein, refers to cyclic alkynyl moieties having 5 or more carbon atoms (for example, 5 to 12, or 5 to 10, or 5 to 8 carbon atoms).

The term "heterocyclic" refers to a ring system in which one or more ring atoms is a heteroatom and which is not aromatic. The term "heterocyclic" encompasses heterocycloalkyl, heterocycloalkenyl, heterobicycloalkyl, heterobicycloalkenyl, heteropolycycloalkyl, heteropolycycloalkenyl, and the like. The term "heterocyclic" includes fused, spiro, or bridged heterocyclic ring systems. In certain aspects, the heterocyclic is a bi-, tri-, or tetracyclic ring system. Heterocycloalkyl refers to cycloalkyl groups containing one or more heteroatoms (O, S, or N) within the ring. Heterocycloalkenyl as used herein refers to cycloalkenyl groups containing one or more heteroatoms (O, S or N) within the ring. Heterobicycloalkyl refers to bicycloalkyl groups containing one or more heteroatoms (O, S or N) within a ring. Heterobicycloalkenyl as used herein refers to bicycloalkenyl groups containing one or more heteroatoms (O, S or N) within a ring. A heterocyclic can have 3 or more atoms. For example, a heterocyclic can be 3- to 15-membered heterocyclic. In some embodiments, the heterocyclic is 3- to 12-membered heterocyclic. In yet additional aspects, the heterocyclic is a 4- to 12-membered heterocyclic, or a 4- to 10-membered heterocyclic. The foregoing heterocyclic groups may be C-attached or heteroatom-attached (where such is possible). As used herein, the term N-heterocyclic denotes that the heterocyclic group is N-attached (nitrogen-attached).

Cycloalkyl, cycloalkenyl, heterocyclic, groups also include groups similar to those described above for each of these respective categories, but which are substituted with one or more oxo moieties.

The term "aryl", as used herein, refers to mono- or polycyclic aromatic carbocyclic ring systems. A polycyclic aryl is a polycyclic ring system that comprises at least one aromatic ring. Polycyclic aryls can comprise fused rings, covalently attached rings or a combination thereof. The term "aryl" embraces aromatic radicals, such as, phenyl, naphthyl, indenyl, tetrahydronaphthyl, and indanyl. An aryl group may be substituted or unsubstituted. In some embodiments, the aryl is a $C_4$-$C_{10}$ aryl. In some embodiments, the aryl is a phenyl.

The term "heteroaryl", as used herein, refers to aromatic carbocyclic groups containing one or more heteroatoms (O, S, or N) within a ring. A heteroaryl group can be monocyclic or polycyclic. A heteroaryl group may additionally be substituted or unsubstituted. The heteroaryl groups of this invention can also include ring systems substituted with one or more oxo moieties. A polycyclic heteroaryl can comprise fused rings, covalently attached rings or a combination thereof. A polycyclic heteroaryl is a polycyclic ring system that comprises at least one aromatic ring containing one or more heteroatoms within a ring. In certain aspects, the heteroaryl is a bi-, tri-, or tetracyclic ring system. Polycyclic aryls can comprise fused rings, covalently attached rings or a combination thereof. Examples of heteroaryl groups include, but are not limited to, pyridinyl, pyridazinyl, imidazolyl, pyrimidinyl, pyrazolyl, triazolyl, pyrazinyl, quinolyl, isoquinolyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, triazinyl, isoindolyl, purinyl, oxadiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl, thiazolopyridinyl, oxazolopyridinyl and azaindolyl. The foregoing heteroaryl groups may be C-attached or heteroatom-attached (where such is possible). For instance, a group derived from pyrrole may be pyrrol-1-yl (N-attached) or pyrrol-3-yl (C-attached). In some embodiments, the heteroaryl is 4- to 12-membered heteroaryl. In additional embodiments, the heteroaryl is 4- to 10-membered heteroaryl.

A "bridged N-heterocyclic" refers to a polycyclic (such as a bicyclic) heterocyclic ring system comprising at least one ring nitrogen atom and having at least one bridge; said bridged N-heterocyclic can be saturated or partially unsaturated. Preferably, the bridged N-heterocyclic is a bi-, tri-, or tetracyclic ring system. A "bridge" is an unbranched chain of atoms or an atom connecting two bridgeheads, where a "bridgehead" is any skeletal atom of the ring system which is bonded to three or more skeletal atoms (excluding hydrogen). In some embodiments, a bridged N-heterocyclic has 6 to 12 ring members including at least one ring nitrogen atom and can contain one or more additional ring heteroatoms. Bridged N-heterocyclic groups are well known in the art and include those described herein, including those in the specific example compounds as described herein, for example those shown in the Tables and in the Examples below. In some embodiments, the bridged N-heterocyclic of the substituent "Z" is N-attached (by a ring nitrogen atom) to the methylene group in Formula (I).

The term "substituted" refers to substitution by independent replacement of one, two, or three, or more of the hydrogen atoms with substituents including, but not limited to, —$C_1$-$C_{12}$ alkyl, —$C_2$-$C_{12}$ alkenyl, —$C_2$-$C_{12}$ alkynyl, —$C_3$-$C_{12}$ cycloalkyl, —$C_3$-$C_{12}$ cycloalkenyl, $C_3$-$C_{12}$ cycloalkynyl, -heterocyclic, —F, —Cl, —Br, —I, —OH, —NO$_2$, —N$_3$, —CN, —NH$_2$, oxo, thioxo, —NHR$_x$, —NR$_x$R$_x$, dialkylamino, -diarylamino, -diheteroarylamino, —OR$_x$, —C(O)R$_y$, —C(O)OR$_x$, —C(O)N(R$_x$)$_2$, —C(O)C(O)R$_y$, —OCO$_2$R$_y$, —OC(O)R$_y$, OC(O)C(O)R$_y$, —NHC(O)R$_y$, —NHCO$_2$R$_y$, —NHC(O)C(O)R$_y$, NHC(S)NH$_2$, —NHC(S)NHR$_x$, —NHC(NH)NH$_2$, —NHC(NH)NHR$_x$, —NHC(NH)R$_x$, —C(NH)NHR$_x$, (C=NR$_x$)R$_x$; —NR$_x$C(O)R$_x$, —NR$_x$C(O)N(R$_x$)$_2$, —NR$_x$CO$_2$R$_y$, —NRxC(O)C(O)R$_y$, —NR$_x$C(S)NH$_2$, —NR$_x$C(S)NHR$_x$, —NR$_x$C(NH)NH$_2$, —NR$_x$C(NH)NHR$_x$, —NRxC(NH)R$_x$, —C(NR$_x$)NHR$_x$, —S(O)$_2$R$_x$, —S(O)$_2$R$_y$, —S(O)R$_y$, —NHSO$_2$R$_x$, —SO$_2$N(R$_x$)$_2$, —CH$_2$NH$_2$, —CH$_2$SO$_2$CH$_3$, -aryl, -arylalkyl, -heteroaryl, -heteroarylalkyl, -heterocycloalkyl, -heterocyclic, —$C_3$-$C_{12}$-cycloalkyl, —$C_3$-$C_{12}$ cycloalkenyl, —$C_1$-$C_{12}$ haloalkyl, —O—$C_1$-$C_{12}$ haloalkyl, -polyalkoxyalkyl, -polyalkoxy, -methoxymethoxy, -methoxyethoxy, —SH, —S—R$_x$, —methylthiomethyl, or silyl, wherein R$_x$ is selected from the group consisting of hydrogen, —$C_1$-$C_{12}$ alkyl, —$C_2$-$C_{12}$ alkenyl, —$C_2$-$C_{12}$ alkynyl, —$C_3$-$C_{12}$ cycloalkyl, -aryl, -heteroaryl and -heterocyclic and —$R_y$ is selected from the group consisting of hydrogen, —$C_1$-$C_{12}$ alkyl, —$C_2$-$C_{12}$ alkenyl, —$C_2$-$C_{12}$ alkynyl, —$C_3$-$C_{12}$ cycloalkyl, -aryl, -heteroaryl, -heterocyclic, —$NH_2$, —NH—$C_1$-$C_{12}$ alkyl, —NH—$C_2$-$C_{12}$ alkenyl, —NH—$C_2$-$C_{12}$-alkynyl, —NH—$C_3$-$C_{12}$ cycloalkyl, —NH-aryl, —NH— heteroaryl and —NH-heterocyclic. It is understood that the aryls, heteroaryls, alkyls, and the like can be further substituted.

The term "haloalkyl" as used herein refers to an alkyl group having 1 to (2n+1) substituent(s) independently selected from F, Cl, Br or I, where n is the maximum number of carbon atoms in the alkyl group.

As will be understood by the skilled artisan, "H" is the symbol for hydrogen, "N" is the symbol for nitrogen, "S" is the symbol for sulfur, and "O" is the symbol for oxygen. "Me" is an abbreviation for methyl.

Non-limiting examples of optionally substituted aryl are phenyl, substituted phenyl, napthyl and substituted naphthyl.

Certain of the compounds described herein contain one or more asymmetric centers and may thus give rise to enantiomers, diastereomers, and other stereoisomeric forms that may be defined, in terms of absolute stereochemistry, as (R)- or (S)—. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. "Isomers" are different compounds that have the same molecular formula. "Stereoisomers" are isomers that differ only in the way the atoms are arranged in space. "Enantiomers" are a pair of stereoisomers that are non-superimposable mirror images of each other. A 1:1 mixture of a pair of enantiomers is a "racemic" mixture. The term "(±)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R—S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. When the compounds described herein contain olefinic double bonds or other centers of geometric asymmetry, and unless specified otherwise, it is intended that the compounds include both E and Z geometric isomers. Likewise, all tautomeric forms are also intended to be included.

The term "enantiomerically pure" means a stereomerically pure composition of a compound. For example, a stereochemically pure composition is a composition that is free or substantially free of other stereoisomers of that compound. In another example, for a compound having one chiral center, an enantiomerically pure composition of the compound is free or substantially free of the other enantiomer. In yet another example, for a compound having two chiral centers, an enantiomerically pure composition is free or substantially free of the other diastereomers.

Where a particular stereochemistry is described or depicted it is intended to mean that a particular enantiomer is present in excess relative to the other enantiomer. A compound has an R-configuration at a specific position when it is present in excess compared to the compound having an S-configuration at that position. A compound has an S-configuration at a specific position when it is present in excess compared to the compound having an R-configuration at that position.

Likewise, all tautomeric forms are also intended to be included. Where a particular compound is described or depicted, it is intended to encompass that chemical structure as well as tautomers of that structure.

It is to be understood that atoms making up the compounds of the present invention are intended to include isotopic forms of such atoms. Isotopes, as used herein, include those atoms having the same atomic number but different mass numbers. Isotopes of hydrogen include, for example, tritium and deuterium, and isotopes of carbon include, for example, $^{13}C$ and $^{14}C$. The invention therefore encompasses embodiments in which one or more of the hydrogen atoms in any compound of Formulae (Ia), (Ib), (Ic), or (Id); or any compound of Formulae (II), (IIa), (IIb), or (IIc); or any compound of Formulae (III), (IIIa), (IIIb), (IIIc), (IIId), or (IIIe) or any compound described herein, are replaced with deuterium. The invention also encompasses embodiments wherein one or more of the carbon atoms in any compound of Formulae (Ia), (Ib), (Ic), or (Id); or any compound of Formulae (II), (IIa), (IIb), or (IIc); or any compound of Formulae (III), (IIIa), (IIIb), (IIIc), (IIId), or (IIIe) or any compound described herein is replaced with silicon atoms.

The invention additionally encompasses embodiment wherein one or more of the nitrogen atoms in any compound of Formulae (Ia), (Ib), (Ic), or (Id); or any compound of Formulae (II), (IIa), (IIb), or (IIc); or any compound of Formulae (III), (IIIa), (IIIb), (IIIc), (IIId), or (IIIe) or any compound described herein are oxidized to N-oxide.

The invention encompasses pharmaceutically acceptable salts of the compounds described herein. Thus, in certain aspects, the invention is directed to pharmaceutically acceptable salts of compounds of the invention and pharmaceutical compositions thereof. A "pharmaceutically acceptable salt" includes an ionic bond-containing product of the reaction between the disclosed compound with either an acid or a base, suitable for administering to a subject. Pharmaceutically acceptable salts are well known in the art and are described, for example, in Berge et al. (1977), Pharmaceutical Salts. Journal of Pharmaceutical Sciences, 69(1): 1-19, the contents of which are herein incorporated by reference. A non-limiting example of a pharmaceutically acceptable salt is an acid salt of a compound containing an amine or other basic group which can be obtained by reacting the compound with a suitable organic or inorganic acid. Examples of pharmaceutically acceptable salts also can be metallic salts including, but not limited to, sodium, magnesium, calcium, lithium and aluminum salts. Further examples of pharmaceutically acceptable salts include hydrochlorides, hydrobromides, sulfates, methanesulfonates, nitrates, maleates, acetates, citrates, fumarates, tartrates (e.g. (+)-tartrates, (−)-tartrates or mixtures thereof including racemic mixtures), succinates, trifluoroacetates, benzoates and salts with amino acids such as glutamic acid. In some aspects, the invention is directed to a trifluoroacetate, hydrochloride, hydrobromides, hydroiodide, or acetate salt of a compound of Formula (I). Salts can also be formed with suitable organic bases when the compound comprises an acid functional group such as —C(O)OH or —$SO_3H$. Such bases suitable for the formation of a pharmaceutically acceptable base addition salts with compounds of the present invention include organic bases that are nontoxic and strong enough to react with the acid functional group. Such organic bases are well known in the art and include amino acids such as arginine and lysine, mono-, di-, and triethanolamine, choline, mono-, di-, and trialkylamine, such as methylamine, dimethylamine, and trimethylamine, guanidine, N-benzylphenethylamine, N-methylglucosamine, N-methylpiperazine, morpholine, ethylendiamine, tris(hydroxymethyl) aminomethane and the like.

The invention also includes hydrates of the compounds described herein, including, for example, solvates of the compounds described herein, pharmaceutical compositions comprising the solvates and methods of use of the solvates. In some embodiments, the invention is a solvate of any compound of Formulae (Ia), (Ib), (Ic), or (Id); or any compound of Formulae (II), (IIa), (IIb), or (IIc); or any compound of Formulae (III), (IIIa), (IIIb), (IIIc), (IIId), or (IIIe) or any compound described herein, or a pharmaceutical composition thereof.

Also included in the present invention are prodrugs of the compounds described herein, for example, prodrugs of any compound of Formulae (Ia), (Ib), (Ic), or (Id); or any compound of Formulae (II), (IIa), (IIb), or (IIc); or any compound of Formulae (III), (IIIa), (IIIb), (IIIc), (IIId), or (IIIe) or any compound described herein, or a pharmaceutical composition of any of thereof or method of use of the prodrug.

The invention additionally includes clathrates of the compounds described herein, pharmaceutical compositions comprising the clathrates, and methods of use of the clathrates. In some embodiments, the invention is directed to clathrates of any compound of Formulae (Ia), (Ib), (Ic), or (Id); or any compound of Formulae (II), (IIa), (IIb), or (IIc); or any compound of Formulae (III), (IIIa), (IIIb), (IIIc), (IIId), or (IIIe) or any compound described herein, or a pharmaceutical composition thereof.

Methods of Treatment

The invention encompasses a method of inhibiting deubiquitination activity of a Usp14 protein comprising contacting the Usp14 protein with a compound described herein, or a pharmaceutically acceptable salt, solvate, clathrate or prodrug thereof, in an amount sufficient to inhibit deubiquitination activity of the Usp14 protein. In certain embodiments, a cell is contacted with the compound described herein or a pharmaceutically acceptable salt, solvate, clathrate or prodrug thereof, in an amount sufficient to inhibit deubiquitination activity of the Usp14 protein.

In yet an additional aspect, the invention is directed to a method of treating a subject for a condition that can be ameliorated by the inhibition of Usp14 comprising administering to said subject an effective amount of a compound of any of the formula described herein, or a pharmaceutically acceptable salt, solvate, clathrate or prodrug thereof.

The invention also encompasses a method of enhancing protein degradation by a proteasome in a cell comprising contacting the cell with a compound of a compound described herein, or a pharmaceutically acceptable salt, solvate, clathrate or prodrug thereof, in an amount sufficient to enhance protein degradation by the proteasome.

In some embodiments, the invention includes pharmaceutical compositions comprising a pharmaceutically acceptable carrier or excipient and a compound described herein. Any compound of Formulae (Ia), (Ib), (Ic), or (Id); or any compound of Formulae (II), (IIa), (IIb), or (IIc); or any compound of Formulae (III), (IIIa), (IIIb), (IIIc), (IIId), or (IIIe) or any compound described herein, or a pharmaceutically acceptable salt, solvate, clathrate or prodrug, or a compound described herein, can be administered in pharmaceutical compositions comprising a pharmaceutically acceptable carrier or excipient. The excipient can be chosen based on the expected route of administration of the composition in therapeutic applications. The route of administration of the composition depends on the condition to be treated. For example, intravenous injection may be preferred for treatment of a systemic disorder and oral administration may be preferred to treat a gastrointestinal disorder. The route of administration and the dosage of the composition to be administered can be determined by the skilled artisan without undue experimentation in conjunction with standard dose-response studies. Relevant circumstances to be considered in making those determinations include the condition or conditions to be treated, the choice of composition to be administered, the age, weight, and response of the individual patient, and the severity of the patient's symptoms.

Pharmaceutical compositions comprising any compound of Formulae (Ia), (Ib), (Ic), or (Id); or any compound of Formulae (II), (IIa), (IIb), or (IIc); or any compound of Formulae (III), (IIIa), (IIIb), (IIIc), (IIId), or (IIIe) or any compound described herein, or a pharmaceutically acceptable salt, solvate, clathrate or prodrug, or a compound described herein, can be administered by a variety of routes including, but not limited to, parenteral, oral, pulmonary, ophthalmic, nasal, rectal, vaginal, aural, topical, buccal, transdermal, intravenous, intramuscular, subcutaneous, intradermal, intraocular, intracerebral, intralymphatic, intraarticular, intrathecal and intraperitoneal.

Formulations

The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the pharmacologic agent or composition. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like. Pharmaceutical compositions can also include large, slowly metabolized macromolecules such as proteins, polysaccharides such as chitosan, polylactic acids, polyglycolic acids and copolymers (such as latex functionalized SEPHAROSE™, agarose, cellulose, and the like), polymeric amino acids, amino acid copolymers, and lipid aggregates (such as oil droplets or liposomes).

The compositions can be administered parenterally such as, for example, by intravenous, intramuscular, intrathecal or subcutaneous injection. Parenteral administration can be accomplished by incorporating a composition into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as, for example, benzyl alcohol or methyl parabens, antioxidants such as, for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions.

Injectable formulations can be prepared either as liquid solutions or suspensions; solid forms suitable for solution in, or suspension in, liquid vehicles prior to injection can also be prepared. The preparation also can also be emulsified or encapsulated in liposomes or micro particles such as polylactide, polyglycolide, or copolymer for enhanced adjuvant effect [Langer, *Science* 249: 1527, 1990 and Hanes, *Advanced Drug Delivery Reviews* 28: 97-119, 1997]. The compositions and pharmacologic agents described herein can be administered in the form of a depot injection or implant preparation which can be formulated in such a manner as to permit a sustained or pulsatile release of the active ingredient.

Additional formulations suitable for other modes of administration include oral, intranasal, and pulmonary formulations, suppositories, transdermal applications and ocular delivery. For suppositories, binders and carriers include, for example, polyalkylene glycols or triglycerides; such suppositories can be formed from mixtures containing the active ingredient in the range of about 0.5% to about 10%, preferably about 1% to about 2%. Oral formulations include excipients, such as pharmaceutical grades of mannitol, lactose, starch, magnesium stearate, sodium saccharine, cellulose, and magnesium carbonate. Topical application can result in transdermal or intradermal delivery. Transdermal delivery can be achieved using a skin patch or using transferosomes. [Paul et al., Eur. J. Immunol. 25: 3521-24, 1995; Cevc et al., *Biochem. Biophys. Acta* 1368: 201-15, 1998].

For the purpose of oral therapeutic administration, the pharmaceutical compositions can be incorporated with excipients and used in the form of tablets, troches, capsules, elixirs, suspensions, syrups, wafers, chewing gums and the like. Tablets, pills, capsules, troches and the like may also contain binders, excipients, disintegrating agent, lubricants, glidants, sweetening agents, and flavoring agents. Some examples of binders include microcrystalline cellulose, gum tragacanth or gelatin. Examples of excipients include starch or lactose. Some examples of disintegrating agents include alginic acid, corn starch and the like. Examples of lubricants include magnesium stearate or potassium stearate. An example of a glidant is colloidal silicon dioxide. Some examples of sweetening agents include sucrose, saccharin and the like. Examples of flavoring agents include peppermint, methyl salicylate, orange flavoring and the like. Materials used in preparing these various compositions should be pharmaceutically pure and non-toxic in the amounts used. In another embodiment, the composition is administered as a tablet or a capsule.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor, and the like. For vaginal administration, a pharmaceutical composition may be presented as pessaries, tampons, creams, gels, pastes, foams or spray.

The pharmaceutical composition can also be administered by nasal administration. As used herein, nasally administering or nasal administration includes administering the composition to the mucus membranes of the nasal passage or nasal cavity of the patient. As used herein, pharmaceutical compositions for nasal administration of a composition include therapeutically effective amounts of the compounds prepared by well-known methods to be administered, for example, as a nasal spray, nasal drop, suspension, gel, ointment, cream or powder. Administration of the composition may also take place using a nasal tampon or nasal sponge.

For topical administration, suitable formulations may include biocompatible oil, wax, gel, powder, polymer, or other liquid or solid carriers. Such formulations may be administered by applying directly to affected tissues, for example, a liquid formulation to treat infection of conjunctival tissue can be administered dropwise to the subject's eye, or a cream formulation can be administered to the skin.

Rectal administration includes administering the pharmaceutical compositions into the rectum or large intestine. This can be accomplished using suppositories or enemas. Suppository formulations can easily be made by methods known in the art. For example, suppository formulations can be prepared by heating glycerin to about 120° C., dissolving the pharmaceutical composition in the glycerin, mixing the heated glycerin after which purified water may be added, and pouring the hot mixture into a suppository mold.

Transdermal administration includes percutaneous absorption of the composition through the skin. Transdermal formulations include patches, ointments, creams, gels, salves and the like.

In addition to the usual meaning of administering the formulations described herein to any part, tissue or organ whose primary function is gas exchange with the external environment, for purposes of the present invention, "pulmonary" will also mean to include a tissue or cavity that is contingent to the respiratory tract, in particular, the sinuses. For pulmonary administration, an aerosol formulation containing the active agent, a manual pump spray, nebulizer or pressurized metered-dose inhaler as well as dry powder formulations are contemplated. Suitable formulations of this type can also include other agents, such as antistatic agents, to maintain the disclosed compounds as effective aerosols.

A drug delivery device for delivering aerosols comprises a suitable aerosol canister with a metering valve containing a pharmaceutical aerosol formulation as described and an actuator housing adapted to hold the canister and allow for drug delivery. The canister in the drug delivery device has a head space representing greater than about 15% of the total volume of the canister. Often, the compound intended for pulmonary administration is dissolved, suspended or emulsified in a mixture of a solvent, surfactant and propellant. The mixture is maintained under pressure in a canister that has been sealed with a metering valve.

The invention also encompasses a method of treating a patient suffering from a condition associated with a dysfunction in protein homeostasis comprising administering to said patient a therapeutically effective amount of a compound described herein.

"Treating" or "treatment" includes preventing or delaying the onset of the symptoms, complications, or biochemical indicia of a disease, alleviating or ameliorating the symptoms or arresting or inhibiting further development of the disease, condition, or disorder. A "subject" is an animal to be treated or in need of treatment. A "patient" is a human subject in need of treatment.

An "effective amount" refers to that amount of an agent that is sufficient to achieve a desired and/or recited effect. In the context of a therapeutic agent, an "effective amount" of the therapeutic agent that is sufficient to ameliorate of one or more symptoms of a disorder and/or prevent advancement of a disorder, cause regression of the disorder and/or to achieve a desired effect.

As used herein, the term "inhibiting" or "decreasing" encompasses causing a net decrease by either direct or indirect means. The term "increasing" or "enhancing" means to cause a net gain by either direct or indirect means.

The invention encompasses the treatment of a condition associated with a dysfunction in proteostasis. Proteostasis refers to protein homeostasis. Dysfunction in protein homeostasis is a result of protein misfolding, protein aggregation, defective protein trafficking or protein degradation. Exemplary proteins of which there can be a dysfunction in proteostasis, for example that can exist in a misfolded state, include, but are not limited to, glucocerebrosidase, hexosamine A, cystic fibrosis transmembrane conductance regulator, aspartylglucosaminidase, α-galactosidase A, cysteine transporter, acid ceramidase, acid a-L-fucosidase, protective protein, cathepsin A, acid β-glucosidase, acid β-galactosidase, iduronate 2-sulfatase, α-L-iduronidase, galactocerebrosidase, acid α-mannosidase, acid β-mannosidase, arylsulfatase B, arylsulfatase A, N-acetylgalactosamine-6-sulfate sulfatase, acid β-galactosidase, N-acetylglucosamine-1-phosphotransferase, acid sphingomyelinase, NPC-1, acid α-glucosidase, β-hexosamine B, heparin N-sulfatase, α-N-acetylglucosaminidase, islet amyloid polypeptide (IAPP or amylin), α-glucosaminide N-acetyltransferase, N-acetylglucosamine-6-sulfate sulfatase, al anti-trypsin, α-N-acetylgalactosaminidase, α-neuramidase, β-glucuronidase, β-hexosamine A and acid lipase, polyglutamine, α-synuclein, Aβ peptide, tau protein, hERG potassium channel, islet amyloid polypeptide, transthyretin, Huntingtin, superoxide dismutase, TAR DNA-binding protein 43 (TDP-43), ataxin-3, superoxide dismutase (SOD) and rhodopsin.

In certain embodiments, the protein is selected from the group consisting of huntingtin, tau, alpha-synuclein, α1 anti-trypsin and superoxide dismutase.

Protein conformational diseases encompass gain of function disorders and loss of function disorders. In one embodiment, the protein conformational disease is a gain of function disorder. The terms "gain of function disorder," "gain of function disease," "gain of toxic function disorder" and "gain of toxic function disease" are used interchangeably herein. A gain of function disorder is a disease characterized by increased aggregation-associated proteotoxicity. In these diseases, aggregation exceeds clearance inside and/or outside of the cell. Gain of function diseases include, but are not limited to neurodegenerative diseases associated with aggregation of polyglutamine, Lewy body diseases, amyotrophic lateral sclerosis, transthyretin-associated aggregation diseases, Alzheimer's disease, Machado-Joseph disease, cerebral B-amyloid angiopathy, retinal ganglion cell degeneration, tautopathies (progressive supranuclear palsy, corticobasal degeration, frontotemporal lobar degeneration), cerebral hemorrhage with amyloidosis, Alexander disease, Serpinopathies, familial amyloidotic neuropathy, senile systemic amyloidosis, ApoAI amyloidosis, ApoAII amyloidosis, ApoAIV amyloidosis, familial amyloidosis of the Finnish type, lysoyzme amyloidosis, fibrinogen amyloidosis, dialysis amyloidosis, inclusion body myositis/myopathy, cataracts, medullary thyroid carcinoma, cardiac atrial amyloidosis, pituitary prolactinoma, hereditary lattice corneal dystrophy, cutaneous lichen amyloidosis, corneal lactoferrin amyloidosis, corneal lactoferrin amyloidosis, pulmonary alveolar proteinosis, odontogenic tumor amyloid, seminal vesical amyloid, sickle cell disease, critical illness myopathy, von Hippel-Lindau disease, spinocerebellar ataxia 1, Angelman syndrome, giant axon neuropathy, inclusion body myopathy with Paget disease of bone, frontotemporal dementia (IBMPFD) and prion diseases. Neurodegenerative diseases associated with aggregation of polyglutamine include, but are not limited to, Huntington's disease, dentatorubral and pallidoluysian atrophy, several forms of spino-cerebellar ataxia, and spinal and bulbar muscular atrophy. Alzheimer's disease is characterized by the formation of two types of aggregates: extracellular aggregates of Aα peptide and intracellular aggregates of the microtubule associated protein tau. Transthyretin-associated aggregation diseases include, for example, senile systemic amyloidoses and familial amyloidotic neuropathy. Lewy body diseases are characterized by an aggregation of α-synuclein protein and include, for example, Parkinson's disease. Prion diseases (also known as transmissible spongiform encephalopathies or TSEs) are characterized by aggregation of prion proteins. Exemplary human prion diseases are Creutzfeldt-Jakob Disease (CJD), Variant Creutzfeldt-Jakob Disease, Gerstmann-Straussler-Scheinker Syndrome, Fatal Familial Insomnia and Kuru. Additional neurodegenerative diseases include tauopathies, Frontal Lobe Dementia (FLD), Dementias (including, but not limited to, Dementia with Lewy bodies (DLB), familial dementia, Serpinopathies, Down's Syndrome dementia), Multiple Sclerosis, and Neuropathic pain.

In a further embodiment, the protein conformation disease is a loss of function disorder.

The terms "loss of function disease" and "loss of function disorder" are used interchangeably herein. Loss of function diseases are a group of diseases characterized by inefficient folding of a protein resulting in excessive degradation of the protein. Loss of function diseases include, for example, lysosomal storage diseases. Lysosomal storage diseases are a group of diseases characterized by a specific lysosomal enzyme deficiency which may occur in a variety of tissues, resulting in the build-up of molecules normally degraded by the deficient enzyme. The lysosomal enzyme deficiency can be in a lysosomal hydrolase or a protein involved in the lysosomal trafficking. Lysosomal storage diseases include, but are not limited to, aspartylglucosaminuria, Fabry's disease, Batten disease, Cystinosis, Farber, Fucosidosis, Galactasidosialidosis, Gaucher's disease (including Types 1, 2 and 3), Gm1 gangliosidosis, Hunter's disease, Hurler-Scheie's disease, Krabbe's disease, α-Mannosidosis, β-Mannosidosis, Maroteaux-Lamy's disease, Metachromatic Leukodystrophy, Morquio A syndrome, Morquio B syndrome, Mucolipidosis II, Mucolipidosis III, Neimann-Pick Disease (including Types A, B and C), Pompe's disease, Sandhoff disease, Sanfilippo syndrome (including Types A, B, C and D), Schindler disease, Schindler-Kanzaki disease, Sialidosis, Sly syndrome, Tay-Sach's disease and Wolman disease.

In yet an additional embodiment, the disease associated with a dysfunction in proteostasis is a myopathy. In some embodiments, the myopathy is selected from the group consisting of Duchenne muscular dystrophy (DMD), Becker's muscular dystrophy (BMD), Spinal muscular atrophy (SMA), Spinal-Bulbar Muscular Atrophy (SBMA), Inclusion body myositis, Freidreich's Ataxia, multiple systems atrophy, spinocerebellar ataxias and seipinopathies.

In another embodiment, the disease associated with a dysfunction in proteostasis is a cardiovascular disease. Cardiovascular diseases include, but are not limited to, coronary artery disease, myocardial infarction, stroke, restenosis and arteriosclerosis. Conditions associated with a dysfunction of proteostasis also include ischemic conditions, such as, ischemia/reperfusion injury, myocardial ischemia, stable angina, unstable angina, stroke, ischemic heart disease and cerebral ischemia.

In yet another embodiment, the disease associated with a dysfunction in proteostasis is diabetes and/or complications of diabetes, including, but not limited to, diabetic retinopathy, cardiomyopathy, neuropathy, nephropathy, and impaired wound healing.

In a further embodiment, the disease associated with a dysfunction in proteostasis is an ocular disease including, but not limited to, age-related macular degeneration (AMD), diabetic macular edema (DME), diabetic retinopathy, glaucoma, cataracts, retinitis pigmentosa (RP) and dry macular degeneration.

In some embodiments, the condition associated with a dysfunction in proteostasis is selected from the group consisting of Huntington's disease, Alzheimer's disease, Parkinson's disease, amyotrophic lateral sclerosis, diabetes and complications thereof, ocular diseases and cancer or tumor.

Additional conditions associated with a dysfunction of proteostasis include hemoglobinopathies, inflammatory diseases, intermediate filament diseases, drug-induced lung damage and hearing loss. The invention also encompasses methods for the treatment of hemoglobinopathies (such as sickle cell anemia), an inflammatory disease (such as inflammatory bowel disease, colitis, ankylosing spondylitis), intermediate filament diseases (such as non-alcoholic and alcoholic fatty liver disease) and drug induced lung damage (such as methotrexate-induced lung damage). The invention additionally encompasses methods for treating hearing loss, such as noise-induced hearing loss, aminoglycoside-induced hearing loss, and cisplatin-induced hearing loss.

In addition to conditions associated with a dysfunction in proteostasis, the compound of the present invention can be used to treat a disease or condition characterized by deficient proteasome activity or deficient activity of other components of the ubiquitin-proteasome pathway. Such conditions include, for example, Hippel-Lindau disease, spino-cerebellar ataxia 1, Angelman syndrome, giant axon neuropathy, inclusion body myopathy with Paget disease, and fronto-temporal dementia.

In certain embodiments, the invention encompasses a method for the treatment of a condition selected from the group consisting of Parkinson's disease, Alzheimer's disease, Frontotemporal lobar dementia (FTLD), Progressive Supranuclear Palsy (PSP), Amyotrophic lateral sclerosis (ALS), Spinocerebellar ataxia (SCA), Retinitis pigmentosum, prion diseases and autism.

In certain embodiments, the invention includes methods for the treatment of a condition associated with a dysfunction in proteostasis comprising administering to a patient in need thereof an effective amount of any compound of Formulae (Ia), (Ib), (Ic), or (Id); or any compound of Formulae (II), (IIa), (IIb), or (IIc); or any compound of Formulae (III), (IIIa), (IIIb), (IIIc), (IIId), or (IIIe) or any compound described herein, or a pharmaceutically acceptable salt, solvate, clathrate or prodrug of any compound of any formula thereof and a second agent (e.g., a second therapeutic agent). Co-administered agents, compounds, or therapeutics need not be administered at exactly the same time. In certain embodiments, however, any compound of Formulae (Ia), (Ib), (Ic), or (Id); or any compound of Formulae (II), (IIa), (IIb), or (IIc); or any compound of Formulae (III), (IIIa), (IIIb), (IIIc), (IIId), or (IIIe) or any compound described herein, or a pharmaceutically acceptable salt, solvate, clathrate or prodrug of any compound of any formula thereof is administered substantially simultaneously as the second agent. By "substantially simultaneously," it is meant that any compound of Formulae (Ia), (Ib), (Ic), or (Id); or any compound of Formulae (II), (IIa), (IIb), or (IIc); or any compound of Formulae (III), (IIIa), (IIIb), (IIIc), (IIId), or (IIIe) or any compound described herein, or a pharmaceutically acceptable salt, solvate, clathrate or prodrug of any compound of any formula thereof is administered before, at the same time, and/or after the administration of the second agent, and encompasses, for example, administration within the same treatment session or as part of the same treatment regimen. Exemplary second agents include pharmacologic chaperones and proteostasis regulators (such as, those described below).

In yet additional aspects, the invention encompasses a method for treating a condition characterized by deficient proteasome activity or deficiency of other components of the ubiquitin-proteasome pathway in a subject comprising administering to said subject an effective amount of a compound of the invention, or a pharmaceutically acceptable salt, solvate, clathrate or prodrug thereof.

In an additional embodiment, the invention is directed to a pharmaceutical composition comprising any compound of Formulae (Ia), (Ib), (Ic), or (Id); or any compound of Formulae (II), (IIa), (IIb), or (IIc); or any compound of Formulae (III), (IIIa), (IIIb), (IIIc), (IIId), or (IIIe) or any compound described herein, or a pharmaceutically acceptable salt, solvate, clathrate or prodrug of any compound of any formula thereof and a second agent, wherein the second agent is selected from the group consisting of a pharmacologic chaperone and a proteostasis regulator. The invention also encompasses a method of treating a patient suffering from a condition associated with a dysfunction in proteostasis comprising administering a therapeutically effective amount of a compound of the invention and a second agent, wherein the second agent is a pharmacologic chaperone. Pharmacologic chaperones or kinetic stabilizers refer to compounds that bind an existing steady state level of the folded mutant protein and chemically enhance the folding equilibrium by stabilizing the fold [Bouvier, *Chem Biol* 14: 241-242, 2007; Fan et al., *Nat Med* 5: 112-115, 1999; Sawkar et al., *Proc Natl Acad Sci USA* 99:15428-15433, 2002; Johnson and Kelly, *Accounts of Chemical Research* 38: 911-921, 2005]. The pharmacologic chaperone is administered in amount that in combination with a compound described herein in an amount that is sufficient to treat a patient suffering from a condition associated with a dysfunction in proteostasis. Exemplary pharmacologic chaperones are described in U.S. Patent Application Publication No's. 20080056994, 20080009516, 20070281975, 20050130972, 20050137223, 20050203019, 20060264467 and 20060287358, the contents of each of which are incorporated by reference herein.

In another embodiment, the invention is a method of treating a patient suffering from a condition associated with a dysfunction in proteostasis comprising administering to said patient an effective amount of a compound described herein or a pharmaceutically acceptable salt, solvate, clathrate or prodrug, of any of thereof, and a second agent, wherein the second agent is a proteostasis regulator. The term "proteostasis regulator" refers to small molecules, siRNA and biologicals (including, for example, proteins) that enhance cellular protein homeostasis. For example, proteostasis regulators can be agents that influence protein synthesis, folding, trafficking and degradation pathways. Proteostasis regulators encompass pharmacologic agents that stimulate the heat shock response (HSR) signaling activity. Proteostasis regulators function by manipulating signaling pathways, including, but not limited to, the heat shock response or the unfolded protein response, or both, resulting in transcription and translation of proteostasis network components. Proteostasis regulators can enhance the folding, trafficking and function of proteins (for example, mutated proteins). Proteostasis regulators can also regulate protein chaperones by upregulating transcription or translation of the protein chaperone, or inhibiting degradation of the protein chaperone. Proteostasis regulators can influence the biology of folding, often by the coordinated increase in chaperone and folding enzyme levels and macromolecules that bind to partially folded conformational ensembles, thus enabling their progression to intermediates with more native structure and ultimately increasing the concentration of folded mutant protein for export. In one aspect, the proteostasis regulator is distinct from a chaperone in that the proteostasis regulator can enhance the homeostasis of a mutated protein but does not bind the mutated protein. In addition, proteostasis regulators can upregulate an aggregation pathway or a disaggregase activity. Exemplary proteostasis regulators are the celastrols, MG-132 and L-type $Ca^{2+}$ channel blockers (e.g., dilitiazem and verapamil). The term "celastrols" refers to celastrol and derivatives or analogs thereof, including, but not limited to, those celastrol derivatives described in Westerheide et al., J Biol Chem, 2004. 279(53): p. 56053-60, the contents of which are expressly incorporated by reference herein. Celastrol derivatives include, for example, celastrol methyl ester, dihydrocelastrol diacetate, celastrol butyl ether, dihydrocelastrol, celastrol benzyl ester, primesterol, primesterol diacetate and triacetate of celastrol. In certain aspects, the proteostasis regulator is a heat shock response activator. A heat shock response activator is an agent that indirectly or directly activates the heat shock response, for example, by directly or indirectly activating heat shock transcription factor 1 (HSF1), inhibiting Hsp90, and/or activating chaperone expression (Westerheide et al., J Biol Chem, 2004. 279(53): p. 56053-60, the contents of which are expressly incorporated by reference herein). The terms "heat shock response activator," "heat shock activator," "heat shock response inducer," and "heat shock inducer" are used interchangeably herein. Non-limiting examples of heat shock response activators are celastrols, non-steroidal anti-inflammatory drugs, ansamycin, geldenamycin, radiciol, glucuronic acid, and tributylin. Heat shock response activators have also been described, for example, in U.S. Patent Application Publication No's. 20070259820, 20070207992, 20070179087, 20060148767, the contents of each of which are expressly incorporated by reference herein. In some embodiments, the heat shock response activator is a small molecule heat shock response activator.

The invention also encompasses a method of treating cancer or a tumor in a patient in need thereof comprising administering to said patient an effective amount of any compound of Formulae (Ia), (Ib), (Ic), or (Id); or any compound of Formulae (II), (IIa), (IIb), or (IIc); or any compound of Formulae (III), (IIIa), (IIIb), (IIIc), (IIId), or (IIIe) or any compound described herein, or a pharmaceutically acceptable salt, solvate, clathrate or prodrug of any compound of any formula thereof. The invention additionally encompasses a method of treating cancer or a tumor in a patient in need thereof comprising administering to said patient an effective amount of a compound described herein. Cancers that can be treated according to methods of the present invention include, but are not limited to, breast cancer, colon cancer, pancreatic cancer, prostate cancer, lung cancer, ovarian cancer, cervical cancer, multiple myeloma, basal cell carcinoma, neuroblastoma, hematologic cancer, rhabdomyosarcoma, liver cancer, skin cancer, leukemia, basal cell carcinoma, bladder cancer, endometrial cancer, glioma, lymphoma, and gastrointestinal cancer.

In another embodiment, the invention is a method of treating cancer or a tumor comprising administering any compound of Formulae (Ia), (Ib), (Ic), or (Id); or any compound of Formulae (II), (IIa), (IIb), or (IIc); or any compound of Formulae (III), (IIIa), (IIIb), (IIIc), (IIId), or (IIIe) or any compound described herein, or a pharmaceutically acceptable salt, solvate, clathrate or prodrug of any compound of any formula thereof in combination with the administration of a chemotherapeutic agent. Chemotherapeutic agents that can be utilized include, but are not limited to, alkylating agents such as cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL®, Bristol-Myers Squibb Oncology, Princeton, N.J.) and docetaxel (TAXOTERE®; Aventis Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; and pharmaceutically acceptable salts, acids or derivatives of any of the above.

In a further embodiment, the invention is a method of treating cancer or a tumor comprising administering to a patient in need thereof an effective amount of any compound of Formulae (Ia), (Ib), (Ic), or (Id); or any compound of Formulae (II), (IIa), (IIb), or (IIc); or any compound of Formulae (III), (IIIa), (IIIb), (IIIc), (IIId), or (IIIe) or any compound described herein, or a pharmaceutically acceptable salt, solvate, clathrate or prodrug of any compound of any formula thereof in combination with radiation therapy.

In yet an additional embodiment, the invention is a method of treating a viral infection comprising administering to a subject in need thereof an effective amount of any compound of Formulae (Ia), (Ib), (Ic), or (Id); or any compound of Formulae (II), (IIa), (IIb), or (IIc); or any compound of Formulae (III), (IIIa), (IIIb), (IIIc), (IIId), or (IIIe) or any compound described herein, or a pharmaceutically acceptable salt, solvate, clathrate or prodrug of any compound of any formula thereof. In certain embodiments, the viral infection is an infection from a virus of the flavivirus family. Examples of viruses in the flavivirus family include, for example, Dengue virus, West Nile virus, Japanese encephalitis virus, yellow fever virus and tick-borne encephalitis viruses. In an additional embodiment, the virus is the La Crosse virus. In another embodiment, the virus is Dengue virus or West Nile virus.

EMBODIMENTS OF THE INVENTION

Further embodiments are provided herein.

Embodiment 1: A compound having the Formula (IA):

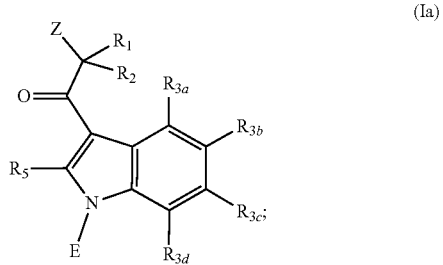

(Ia)

or a pharmaceutically acceptable salt, solvate, clathrate or prodrug thereof; wherein:

E is selected from the group consisting of optionally substituted aryl or optionally substituted heteroaryl;

each of $R_1$ and $R_2$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl;

Z is an optionally substituted, 6- to 12-membered bridged N-heterocyclic;

each of $R_{3a}$, $R_{3b}$, $R_{3c}$ and $R_{3d}$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NRS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C=NR_d)R_c$, $OC(O)R_c$, optionally substituted heterocyclic and optionally substituted heteroaryl;

$R_5$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C=NR_d)R_c$, $OC(O)R_c$, optionally substituted heterocyclic, and optionally substituted heteroaryl;

wherein substituents of optionally substituted E, Z, $R_1$, $R_2$, $R_{3a}$, $R_{3b}$, $R_{3c}$, $R_{3d}$, and $R_5$ are each independently selected from the group consisting of $C_1$-$C_{10}$ alkyl, $C_2$-$C_{10}$ alkenyl, $C_2$-$C_{10}$ alkynyl, $C_3$-$C_{12}$ cycloalkyl, $C_3$-$C_{12}$ cycloalkenyl, aryl, halo, $N_3$, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C=NR_d)R_c$, $OC(O)R_c$, heterocyclic, and heteroaryl;

each $R_c$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl;

each $R_d$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl; or two geminal $R_d$ groups are taken together with the nitrogen atom to which they are attached to form an optionally substituted heterocyclic or an optionally substituted heteroaryl; and each n is independently 0, 1 or 2.

Embodiment 2: The compound of Embodiment 1, or a pharmaceutically acceptable salt, solvate, clathrate or prodrug thereof, wherein $R_5$ is an optionally substituted $C_1$-$C_4$ alkyl.

Embodiment 3: The compound of Embodiment 1, or a pharmaceutically acceptable salt, solvate, clathrate or prodrug thereof, wherein $R_5$ is methyl.

Embodiment 4: The compound of any one of embodiments 1 to 3, or a pharmaceutically acceptable salt, solvate, clathrate or prodrug thereof, wherein $R_1$ and $R_2$ are each independently selected from hydrogen and optionally substituted $C_1$-$C_{10}$ alkyl.

Embodiment 5: The compound of any one of embodiments 1 to 3, or a pharmaceutically acceptable salt, solvate, clathrate or prodrug thereof, wherein $R_1$ and $R_2$ are each hydrogen.

Embodiment 6: The compound of any one of embodiments 1 to 5, or a pharmaceutically acceptable salt, solvate, clathrate or prodrug thereof, wherein E is an optionally substituted heteroaryl.

Embodiment 7: The compound of any one of embodiments 1 to 5, or a pharmaceutically acceptable salt, solvate, clathrate or prodrug thereof, wherein E is an optionally substituted aryl.

Embodiment 8: The compound of any one of embodiments 1 to 5, or a pharmaceutically acceptable salt, solvate, clathrate or prodrug thereof, wherein E is an optionally substituted phenyl.

Embodiment 9: The compound of any one of embodiments 1 to 5, or a pharmaceutically acceptable salt, solvate, clathrate or prodrug thereof, wherein E is a para-substituted phenyl, wherein the phenyl is optionally further substituted.

Embodiment 10: The compound of any one of embodiments 1 to 9, or a pharmaceutically acceptable salt, solvate, clathrate or prodrug thereof, wherein each of $R_{3a}$, $R_{3b}$, $R_{3c}$ and $R_{3d}$ is independently selected from the group consisting of hydrogen, halo, $NR_dR_d$, $NO_2$, CN, optionally substituted $C_1$-$C_{10}$ alkyl, optionally substituted $C_2$-$C_{10}$ alkenyl, optionally substituted $C_2$-$C_{10}$ alkynyl, $C(O)OR_c$, $C(O)R_c$, $NR_dC(O)R_c$, $OC(O)R_c$ and $OR_c$.

Embodiment 11: The compound of any one of embodiments 1 to 10, or a pharmaceutically acceptable salt, solvate, clathrate or prodrug thereof, wherein $R_{3a}$ and $R_{3d}$ are each hydrogen.

Embodiment 12: The compound of any one of embodiments 1 to 11, or a pharmaceutically acceptable salt, solvate clathrate or prodrug thereof, wherein $R_{3c}$ is:

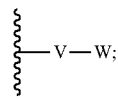

wherein V is selected from the group consisting of $C_1$-$C_6$ alkylene, $C_2$-$C_6$ alkenylene, $C_2$-$C_6$ alkynylene, each optionally substituted;

W is selected from the group consisting of $S(O)_pR_m$, CN, optionally substituted heteroaryl and optionally substituted heterocyclic;

$R_m$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl; and p is 0, 1 or 2.

Embodiment 13: The compound of embodiment 12, or a pharmaceutically acceptable salt, solvate, clathrate or prodrug thereof, wherein V is an optionally substituted $C_1$-$C_6$ alkylene.

Embodiment 14: The compound of embodiment 12, or a pharmaceutically acceptable salt, solvate, clathrate or prodrug thereof, wherein V is an optionally substituted $C_2$-$C_4$ alkylene.

Embodiment 15: The compound of any one of embodiments 12 to 14, or a pharmaceutically acceptable salt, solvate, clathrate or prodrug thereof, wherein W is selected from the group consisting of:

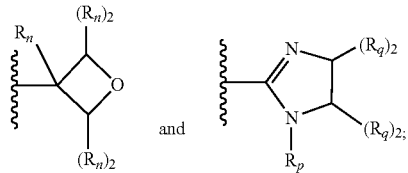

wherein each $R_n$, and $R_q$ are independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, $OR_c$, $NR_dR_d$, $C(O)OR_c$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_n NR_dR_d$, $OC(O)OR_c$, $OC(O)R_c$, optionally substituted heterocyclic and optionally substituted heteroaryl; and $R_p$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl.

Embodiment 16 The compound of any one of embodiments 12 to 14, or a pharmaceutically acceptable salt, solvate, clathrate or prodrug thereof, wherein W is $S(O)_pR_m$.

Embodiment 17: The compound of any one of embodiments 12 to 14, or a pharmaceutically acceptable salt, solvate, clathrate or prodrug thereof, wherein W is $S(O)_2R_m$, wherein $R_m$ is an optionally substituted $C_1$-$C_6$ alkyl or an optionally substituted $C_3$-$C_6$ cycloalkyl.

Embodiment 18: The compound of any one of embodiments 12 to 14, or a pharmaceutically acceptable salt, solvate, clathrate or prodrug thereof, wherein W is $SR_m$, wherein $R_m$ is an optionally substituted $C_1$-$C_6$ alkyl or an optionally substituted $C_3$-$C_6$ cycloalkyl.

Embodiment 19: The compound of any one of embodiments 12 to 14, or a pharmaceutically acceptable salt, solvate, clathrate or prodrug thereof, wherein W is CN.

Embodiment 20: The compound of any one of embodiments 12 to 14, or a pharmaceutically acceptable salt, solvate, clathrate or prodrug thereof, wherein W is optionally substituted heteroaryl.

Embodiment 21: The compound of any one of embodiments 12 to 14, or a pharmaceutically acceptable salt, solvate, clathrate or prodrug thereof, wherein W is optionally substituted heterocyclic.

Embodiment 22: The compound of any one of embodiments 12 to 14, or a pharmaceutically acceptable salt, solvate, clathrate or prodrug thereof, wherein W is selected from the group consisting of:

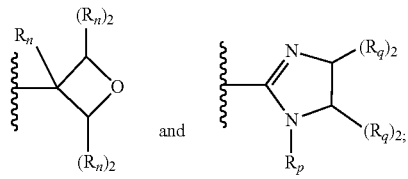

wherein each $R_n$ and $R_q$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, $OR_c$, $NR_dR_d$, $C(O)OR_c$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_n$-$NR_dR_d$, $OC(O)OR_c$, $OC(O)R_c$, optionally substituted heterocyclic and optionally substituted heteroaryl; and $R_p$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl.

Embodiment 23: The compound of any one of embodiments 1 to 22, or a pharmaceutically acceptable salt, solvate, clathrate or prodrug thereof, wherein Z is an optionally substituted, 6- to 10-membered bridged N-heterocyclic.

Embodiment 24: The compound of any one of embodiments 1 to 22, or a pharmaceutically acceptable salt, solvate, clathrate or prodrug thereof, wherein Z is an optionally substituted, 6- to 9-membered bridged N-heterocyclic.

Embodiment 25: The compound of any one of embodiments 1 to 22, or a pharmaceutically acceptable salt, solvate, clathrate or prodrug thereof, wherein Z is an optionally substituted, 6- to 8-membered bridged N-heterocyclic.

Embodiment 26: The compound of any one of embodiments 1 to 22, or a pharmaceutically acceptable salt, solvate, clathrate or prodrug thereof, wherein Z is an optionally substituted, 7-membered bridged N-heterocyclic.

Embodiment 27: The compound of any one of embodiments 1 to 22, or a pharmaceutically acceptable salt, solvate, clathrate or prodrug thereof, wherein Z is an optionally substituted, 8-membered bridged N-heterocyclic.

Embodiment 28: The compound of any one of embodiments 1 to 22, or a pharmaceutically acceptable salt, solvate, clathrate or prodrug thereof, wherein Z is selected from the group consisting of:

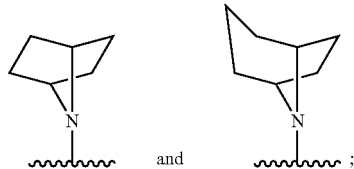 [SMILES: *N1C2CCC1CC2 ; *N1C2CCCC1CC2]

each optionally substituted.

Embodiment 29: The compound of any one of embodiments 1 to 22, or a pharmaceutically acceptable salt, solvate, clathrate or prodrug thereof, wherein Z is selected from the group consisting of:

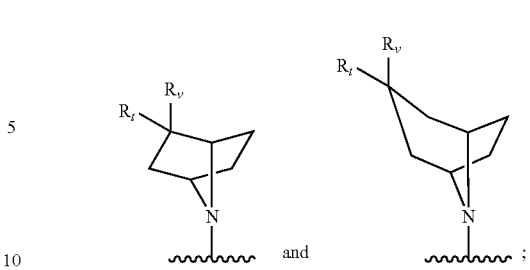

wherein:

$R_t$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_n$ $NR_dR_d$, $NR_dS(O)_nR_c$, $S(O)_nR_c$, $S(O)_nNR_dR_d$, $OC(O)OR_c$, $(C=NR_d)R_c$, $OC(O)R_c$, optionally substituted heterocyclic and optionally substituted heteroaryl; and $R_v$ is selected from the group consisting of hydrogen and optionally substituted $C_1$-$C_{10}$ alkyl.

Embodiment 30: The compound of embodiment 29, or a pharmaceutically acceptable salt, solvate, clathrate or prodrug thereof, wherein $R_t$ is selected from the group consisting of optionally substituted $C_1$-$C_{10}$ alkyl and $OR_c$.

Embodiment 31: The compound of embodiment 1, or a pharmaceutically acceptable salt, solvate, clathrate or prodrug thereof, wherein the compound has the Formula (Ib):

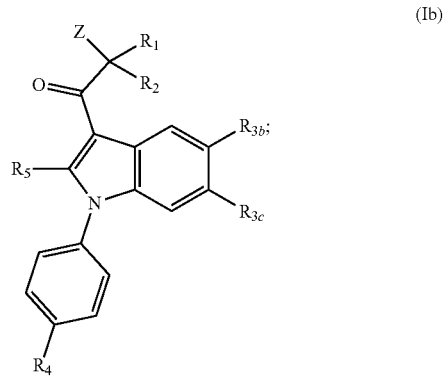

(Ib)

wherein $R_4$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, CN, $C(O)R_c$, $C(O)C(O)R_c$, $C(O)NR_dR^d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_n$-$NR_dR_d$, $NR_dS(O)_nR_c$, $S(O)_nR_c$, $S(O)_nNR_dR_d$, $OC(O)OR_c$, $(C=NR_d)R_c$, $OC(O)R_c$, optionally substituted heterocyclic and optionally substituted heteroaryl;

wherein substituents of optionally substituted Z, $R_1$, $R_2$, $R_{3b}$, $R_{3c}$, $R_4$, and $R_5$ are each independently selected from the group consisting of $C_1$-$C_{10}$ alkyl, $C_2$-$C_{10}$ alkenyl, $C_2$-$C_{10}$ alkynyl, $C_3$-$C_{12}$ cycloalkyl, $C_3$-$C_{12}$ cycloalkenyl, aryl, halo, $N_3$, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(CO-$ $OR_c$), $NR_dC(O)C(O)R_c$, $NR_dC(O)NR_dR_d$, $NR_dS(O)_n$ $NR_dR_d$, $NR_dS(O)_nR_c$, $S(O)_nR_c$, $S(O)_nNR_dR_d$, $OC(O)OR_c$, $(C=NR_d)R_c$, $OC(O)R_c$, heterocyclic, and heteroaryl;

each $R_c$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl;

each $R_d$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl; or two geminal $R_d$ groups are taken together with the nitrogen atom to which they are attached to form an optionally substituted heterocyclic or an optionally substituted heteroaryl; and each n is independently 0, 1 or 2.

Embodiment 32: The compound of embodiment 31, or a pharmaceutically acceptable salt, solvate, clathrate or prodrug thereof, wherein $R_{3b}$ is hydrogen.

Embodiment 33: The compound of embodiment 31 or 32, or a pharmaceutically acceptable salt, solvate, clathrate or prodrug thereof, wherein $R_4$ is selected from the group consisting of hydrogen, halo, $N_3$, $C(O)OR_c$, CN, $C(O)R_c$, $C(O)C(O)R_c$, $C(O)NR_dR_d$, $NO_2$ and $NR_dR_d$.

Embodiment 34: The compound of embodiment 31 or 32, or a pharmaceutically acceptable salt, solvate, clathrate or prodrug thereof, wherein $R_4$ is selected from the group consisting of halo, $N_3$, $C(O)OR_c$, CN, $C(O)R_c$, $C(O)C(O)R_c$, $C(O)NR_dR_d$, $NO_2$ and $NR_dR_d$.

Embodiment 35: The compound of embodiment 31 or 32, or a pharmaceutically acceptable salt, solvate, clathrate or prodrug thereof, wherein $R_4$ is Cl.

Embodiment 36: The compound of any one of embodiments 31 to 35, or a pharmaceutically acceptable salt, solvate, clathrate or prodrug thereof, wherein $R_{3c}$ is selected from the group consisting of hydrogen, halo, $NR_dR_d$, $NO_2$, CN, optionally substituted $C_1$-$C_{10}$ alkyl, optionally substituted $C_2$-$C_{10}$ alkenyl, optionally substituted $C_2$-$C_{10}$ alkynyl, $C(O)OR_c$, $C(O)R_c$, $NR_dC(O)R_c$, $OC(O)R_c$ and $OR_c$.

Embodiment 37: The compound of any one of embodiments 31 to 35, or a pharmaceutically acceptable salt, solvate, clathrate or prodrug thereof, wherein $R_{3c}$ is selected from the group consisting of optionally substituted $C_1$-$C_{10}$ alkyl, optionally substituted $C_2$-$C_{10}$ alkenyl, and optionally substituted $C_2$-$C_{10}$ alkynyl.

Embodiment 38: The compound of any one of embodiments 31 to 35, or a pharmaceutically acceptable salt, solvate, clathrate or prodrug thereof, wherein $R_{3c}$ is:

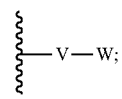

wherein V is selected from the group consisting of $C_1$-$C_6$ alkylene, $C_2$-$C_6$ alkenylene, $C_2$-$C_6$ alkynylene, each optionally substituted;

W is selected from the group consisting of $S(O)_pR_m$, CN, optionally substituted heteroaryl and optionally substituted heterocyclic;

$R_m$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl; and p is 0, 1 or 2.

Embodiment 39: The compound of embodiment 38, or a pharmaceutically acceptable salt, solvate, clathrate or prodrug thereof, wherein V is an optionally substituted $C_1$-$C_6$ alkylene.

Embodiment 40: The compound of embodiment 38, or a pharmaceutically acceptable salt, solvate, clathrate or prodrug thereof, wherein V is an optionally substituted $C_2$-$C_4$ alkylene.

Embodiment 41: The compound of any one of embodiments 38 to 40, or a pharmaceutically acceptable salt, solvate, clathrate or prodrug thereof, wherein W is selected from the group consisting of $S(O)_pR_m$, CN,

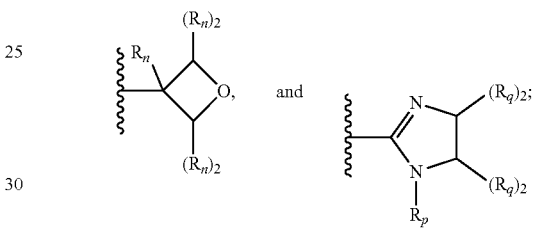

wherein each $R_n$ and $R_q$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, $OR_c$, $NR_dR_d$, $C(O)OR_c$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $OC(O)R_c$, optionally substituted heterocyclic and optionally substituted heteroaryl; and $R_p$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl.

Embodiment 42: The compound of any one of embodiments 38 to 40, or a pharmaceutically acceptable salt, solvate, clathrate or prodrug thereof, wherein W is $S(O)_pR_m$.

Embodiment 43: The compound of any one of embodiments 38 to 40, or a pharmaceutically acceptable salt, solvate, clathrate or prodrug thereof, wherein W is $S(O)_2R_m$, wherein $R_m$ is an optionally substituted $C_1$-$C_6$ Embodiment 44: The compound of any one of claims 38 to 40, or a pharmaceutically acceptable salt, solvate, clathrate or prodrug thereof, wherein W is $SR_m$, wherein $R_m$ is an optionally substituted $C_1$-$C_6$ alkyl or an optionally substituted $C_3$-$C_6$ cycloalkyl.

Embodiment 45: The compound of any one of embodiments 38 to 40, or a pharmaceutically acceptable salt, solvate, clathrate or prodrug thereof, wherein W is CN.

Embodiment 46: The compound of any one of embodiments 38 to 40, or a pharmaceutically acceptable salt, solvate, clathrate or prodrug thereof, wherein W is optionally substituted heteroaryl.

Embodiment 47: The compound of any one of embodiments 38 to 40, or a pharmaceutically acceptable salt, solvate, clathrate or prodrug thereof, wherein W is optionally substituted heterocyclic.

Embodiment 48: The compound of any one of embodiments 38 to 40, or a pharmaceutically acceptable salt, solvate, clathrate or prodrug thereof, wherein W is selected from the group consisting of:

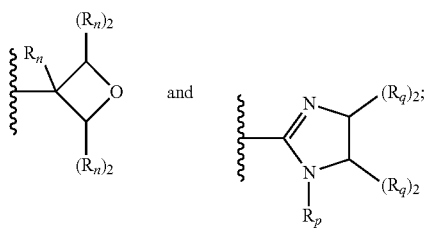

wherein each of $R_n$ and $R_q$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, $OR_c$, $NR_dR_d$, $C(O)OR_c$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_n$-$NR_dR_d$, $OC(O)OR_c$, $OC(O)R_c$, optionally substituted heterocyclic and optionally substituted heteroaryl; and $R_p$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl.

Embodiment 49: The compound of any one of embodiments 31 to 48, or a pharmaceutically acceptable salt, solvate, clathrate or prodrug thereof, wherein Z is an optionally substituted, 6- to 10-membered bridged N-heterocyclic.

Embodiment 50: The compound of any one of embodiments 31 to 48, or a pharmaceutically acceptable salt, solvate, clathrate or prodrug thereof, wherein Z is optionally substituted, 6- to 9-membered bridged N-heterocyclic.

Embodiment 51: The compound of any one of embodiments 31 to 48, or a pharmaceutically acceptable salt, solvate, clathrate or prodrug thereof, wherein Z is an optionally substituted, 6- to 8-membered bridged N-heterocyclic.

Embodiment 52: The compound of any one of embodiments 31 to 48, or a pharmaceutically acceptable salt, solvate, clathrate or prodrug thereof, wherein Z is an optionally substituted, 7-membered bridged N-heterocyclic.

Embodiment 53: The compound of any one of embodiments 31 to 48, or a pharmaceutically acceptable salt, solvate, clathrate or prodrug thereof, wherein Z is an optionally substituted 8-membered bridged N-heterocyclic.

Embodiment 54: The compound of any one of embodiments 31 to 48, or a pharmaceutically acceptable salt, solvate, clathrate or prodrug thereof, wherein Z is selected from the group consisting of:

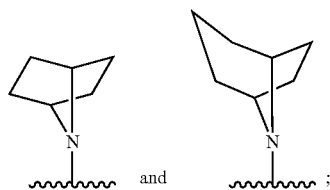

each optionally substituted.

Embodiment 55: The compound of any one of embodiments 31 to 48, or a pharmaceutically acceptable salt, solvate, clathrate or prodrug thereof, wherein Z is selected from the group consisting of:

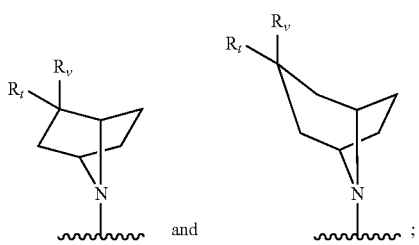

wherein:

$R_t$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_n$ $NR_dR_d$, $NR_dS(O)_nR_c$, $S(O)_nR_c$, $S(O)_nNR_dR_d$, $OC(O)OR_c$, $(C=NR_d)R_c$, $OC(O)R_c$, optionally substituted heterocyclic and optionally substituted heteroaryl; and $R_v$ is selected from the group consisting of hydrogen and optionally substituted $C_1$-$C_{10}$ alkyl.

Embodiment 56: The compound of embodiment 55, or a pharmaceutically acceptable salt, solvate, clathrate or prodrug thereof, wherein $R_t$ is selected from the group consisting of optionally substituted $C_1$-$C_{10}$ alkyl and $OR_c$.

Embodiment 57: The compound of embodiment 1, or a pharmaceutically acceptable salt, solvate, clathrate or prodrug thereof, wherein the compound has the Formula (Ic) or Formula (Id):

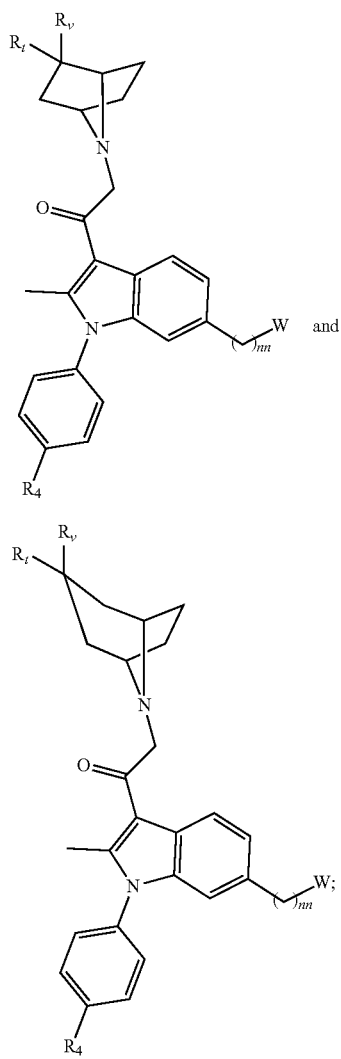

wherein:

$R_t$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, $CN$, $C(O)R_c$, $C(O)C(O)R_c$, $C(O)NR_dR_d$, $NR_dC(O)R_c$, $NR_dS(O)_nR_c$, $N(R_d)(CO-OR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C=NR_d)R_c$, $OC(O)R_c$, optionally substituted heterocyclic and optionally substituted heteroaryl;

$R_v$ is selected from the group consisting of hydrogen and optionally substituted $C_1$-$C_{10}$ alkyl;

$R_4$ is selected from the group consisting of halo, $N_3$, $C(O)OR_c$, $CN$, $C(O)R_c$, $C(O)C(O)R_c$, $C(O)NR_dR_d$, $NO_2$ and $NR_dR_d$;

W is selected from the group consisting of $S(O)_pR_m$, $CN$, optionally substituted heteroaryl and optionally substituted heterocyclic;

nn is 1, 2, or 3; and p is 0, 1, or 2.

Embodiment 58: The compound of embodiment 57, or a pharmaceutically acceptable salt, solvate, clathrate or prodrug thereof, wherein $R_t$ and $R_v$ are independently selected from the group consisting of hydrogen, hydroxyl, —$OCH_3$, and —$C(CH_3)_3$.

Embodiment 59: The compound of embodiment 57 or claim 58, or a pharmaceutically acceptable salt, solvate, clathrate or prodrug thereof, wherein $R_4$ is chloro.

Embodiment 60: The compound of any one of embodiments 57 to 59, or a pharmaceutically acceptable salt, solvate, clathrate or prodrug thereof, wherein W is selected from the group consisting of —$SO_2CH_3$, —$CN$,

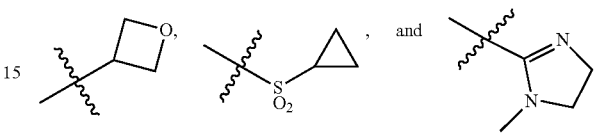

Embodiment 61: The compound of embodiment 1, or a pharmaceutically acceptable salt, solvate, clathrate or prodrug thereof, wherein the compound is selected from the group consisting of 1A, 2A, 3A, 4A, 5A, 6A, 8A, 10A, 11A, 12A, 13A, 15A, 16A, 17A, 18A, 19A, 20A, 21A, 22A, 23A, 24A, 25A, 26A, 27A, 28A, 29A, 30A, 31A, 32A, and 33A.

Embodiment 62: A compound having the Formula (II):

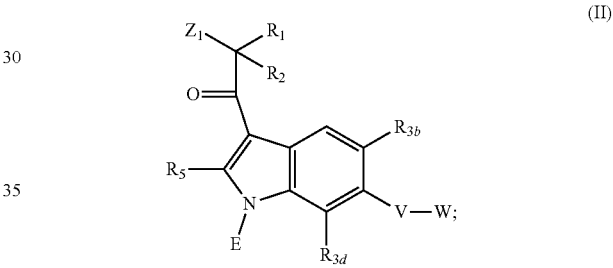

or a pharmaceutically acceptable salt, solvate, clathrate or prodrug thereof; wherein:

E is selected from the group consisting of optionally substituted aryl or optionally substituted heteroaryl;

each of $R_1$ and $R_2$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl;

$Z_1$ is an optionally substituted N-heterocyclic;

each of $R_{3a}$, $R_{3b}$, and $R_{3d}$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, $CN$, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C=NR_d)R_c$, $OC(O)R_c$, optionally substituted heterocyclic and optionally substituted heteroaryl;

$R_5$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, $CN$, $C(O)R_c$, $C(O)$ C(O)R$_c$, C(O)NR$_d$R$_d$, NR$_d$C(O)R$_c$, NR$_d$S(O)$_n$R$_c$, N(R$_d$)(COOR$_c$), NR$_d$C(O)C(O)R$_c$, NR$_d$C(O)NR$_d$R$_d$, NR$_d$S(O)$_n$NR$_d$R$_d$, NR$_d$S(O)$_n$R$_c$, S(O)$_n$R$_c$, S(O)$_n$NR$_d$R$_d$, OC(O)OR$_c$, (C=NR$_d$)R$_c$, OC(O)R$_c$, optionally substituted heterocyclic, and optionally substituted heteroaryl;

V is selected from the group consisting of C$_1$-C$_6$ alkylene, C$_2$-C$_6$ alkenylene, C$_2$-C$_6$ alkynylene, each optionally substituted;

W is selected from the group consisting of S(O)$_p$R$_m$, CN, optionally substituted heteroaryl and optionally substituted heterocyclic;

wherein substituents of optionally substituted E, Z, V, W, R$_1$, R$_2$, R$_{3a}$, R$_{3b}$, R$_{3d}$, and R$_5$ are each independently selected from the group consisting of C$_1$-C$_{10}$ alkyl, C$_2$-C$_{10}$ alkenyl, C$_2$-C$_{10}$ alkynyl, C$_3$-C$_{12}$ cycloalkyl, C$_3$-C$_{12}$ cycloalkenyl, aryl, halo, N$_3$, OR$_c$, NR$_d$R$_d$, C(O)OR$_c$, NO$_2$, CN, C(O)R$_c$, C(O)C(O)R$_c$, C(O)NR$_d$R$_d$, NR$_d$C(O)R$_c$, NR$_d$S(O)$_n$R$_c$, N(R$_d$)(COOR$_c$), NR$_d$C(O)C(O)R$_c$, NR$_d$C(O)NR$_d$R$_d$, NR$_d$S(O)$_n$NR$_d$R$_d$, NR$_d$S(O)$_n$R$_c$, S(O)$_n$R$_c$, S(O)$_n$NR$_d$R$_d$, OC(O)OR$_c$, (C=NR$_d$)R$_c$, OC(O)R$_c$, heterocyclic, and heteroaryl;

each R$_c$ is independently selected from the group consisting of hydrogen, optionally substituted C$_1$-C$_{10}$ alkyl, optionally substituted C$_2$-C$_{10}$ alkenyl, optionally substituted C$_2$-C$_{10}$ alkynyl, optionally substituted C$_3$-C$_{12}$ cycloalkyl, optionally substituted C$_3$-C$_{12}$ cycloalkenyl, optionally substituted heterocyclic, optionally substituted aryl, and optionally substituted heteroaryl;

each R$_d$ is independently selected from the group consisting of hydrogen, optionally substituted C$_1$-C$_{10}$ alkyl, optionally substituted C$_2$-C$_{10}$ alkenyl, optionally substituted C$_2$-C$_{10}$ alkynyl, optionally substituted C$_1$-C$_{10}$ alkoxy, optionally substituted C$_3$-C$_{12}$ cycloalkyl, optionally substituted C$_3$-C$_{12}$ cycloalkenyl, optionally substituted heterocyclic, optionally substituted aryl, and optionally substituted heteroaryl; or two geminal R$_d$ groups are taken together with the nitrogen atom to which they are attached to form an optionally substituted heterocyclic or an optionally substituted heteroaryl;

R$_m$ is selected from the group consisting of hydrogen, optionally substituted C$_1$-C$_{10}$ alkyl, optionally substituted C$_2$-C$_{10}$ alkenyl, optionally substituted C$_2$-C$_{10}$ alkynyl, optionally substituted C$_3$-C$_{12}$ cycloalkyl, optionally substituted C$_3$-C$_{12}$ cycloalkenyl, optionally substituted heterocyclic, optionally substituted aryl, and optionally substituted heteroaryl;

each n is independently 0, 1 or 2; and p is 0, 1 or 2.

Embodiment 63: The compound of embodiment 62, or a pharmaceutically acceptable salt, solvate, clathrate or prodrug thereof, wherein R$_1$ and R$_2$ are each independently selected from hydrogen and optionally substituted C$_1$-C$_{10}$ alkyl.

Embodiment 64: The compound of embodiment 62, or a pharmaceutically acceptable salt, solvate, clathrate or prodrug thereof, wherein R$_1$ and R$_2$ are each hydrogen.

Embodiment 65: The compound of any one of embodiments 62 to 64, or a pharmaceutically acceptable salt, solvate, clathrate or prodrug thereof, wherein R$_5$ is an optionally substituted C$_1$-C$_4$ alkyl.

Embodiment 66: The compound of any one of embodiments 62 to 64, or a pharmaceutically acceptable salt, solvate, clathrate or prodrug thereof, wherein R$_5$ is methyl.

Embodiment 67: The compound of any one of embodiments 62 to 66, or a pharmaceutically acceptable salt, solvate, clathrate or prodrug thereof, wherein E is an optionally substituted phenyl.

Embodiment 68: The compound of any one of embodiments 62 to 66, or a pharmaceutically acceptable salt, solvate, clathrate or prodrug thereof, wherein E is a para-substituted phenyl, wherein the phenyl is optionally further substituted.

Embodiment 69: The compound of any one of embodiments 62 to 66, or a pharmaceutically acceptable salt, solvate, clathrate or prodrug thereof, wherein E is phenyl, substituted at the para-position with R$_4$, wherein R$_4$ is selected from the group consisting of hydrogen, optionally substituted C$_1$-C$_{10}$ alkyl, optionally substituted C$_2$-C$_{10}$ alkenyl, optionally substituted C$_2$-C$_{10}$ alkynyl, optionally substituted C$_3$-C$_{12}$ cycloalkyl, optionally substituted C$_3$-C$_{12}$ cycloalkenyl, optionally substituted aryl, halo, N$_3$, OR$_c$, NR$_d$R$_d$, C(O)OR$_c$, NO$_2$, CN, C(O)R$_c$, C(O)C(O)R$_c$, C(O)NR$_d$R$_d$, NR$_d$C(O)R$_c$, NR$_d$S(O)$_n$R$_c$, N(R$_d$)(COOR$_c$), NR$_d$C(O)C(O)R$_c$, NR$_d$C(O)NR$_d$R$_d$, NR$_d$S(O)$_n$NR$_d$R$_d$, NR$_d$S(O)$_n$R$_c$, S(O)$_n$R$_c$, S(O)$_n$NR$_d$R$_d$, OC(O)OR$_c$, (C=NR$_d$)R$_c$, OC(O)R$_c$, optionally substituted heterocyclic, and optionally substituted heteroaryl.

Embodiment 70: The compound of embodiment 69, or a pharmaceutically acceptable salt, solvate, clathrate or prodrug thereof, wherein R$_4$ is selected from the group consisting of hydrogen, halo, N$_3$, C(O)OR$_c$, CN, C(O)R$_c$, C(O)C(O)R$_c$, C(O)NR$_d$R$_d$, NO$_2$ and NR$_d$R$_d$.

Embodiment 71: The compound of embodiment 69, or a pharmaceutically acceptable salt, solvate, clathrate or prodrug thereof, wherein R$_4$ is selected from the group consisting of halo, N$_3$, C(O)OR$_c$, CN, C(O)R$_c$, C(O)C(O)R$_c$, C(O)NR$_d$R$_d$, NO$_2$ and NR$_d$R$_d$.

Embodiment 72: The compound of embodiment 69, or a pharmaceutically acceptable salt, solvate, clathrate or prodrug thereof, wherein R$_4$ is Cl.

Embodiment 73: The compound of any one of embodiments 62 to 72, or a pharmaceutically acceptable salt, solvate, clathrate or prodrug thereof, wherein Z$_1$ is an optionally substituted 5- to 12-membered N-heterocyclic.

Embodiment 74: The compound of any one of embodiments 62 to 72, or a pharmaceutically acceptable salt, solvate, clathrate or prodrug thereof, wherein Z$_1$ is an optionally substituted 5- to 7-membered N-heterocyclic.

Embodiment 75: The compound of any one of embodiments 62 to 72, or a pharmaceutically acceptable salt, solvate, clathrate or prodrug thereof, wherein Z$_1$ is selected from the group consisting of optionally substituted 1-pyrrolidinyl and optionally substituted 1-piperidinyl.

Embodiment 76: The compound of any one of embodiments 62 to 72, or a pharmaceutically acceptable salt, solvate, clathrate or prodrug thereof, wherein Z$_1$ is an optionally substituted, 6- to 12-membered, bridged N-heterocyclic.

Embodiment 77: The compound of any one of embodiments 62 to 72, or a pharmaceutically acceptable salt, solvate, clathrate or prodrug thereof, wherein Z$_1$ is an optionally substituted, 6- to 10-membered bridged N-heterocyclic.

Embodiment 78: The compound of any one of embodiments 62 to 72, or a pharmaceutically acceptable salt, solvate, clathrate or prodrug thereof, wherein Z$_1$ is an optionally substituted, 6- to 8-membered bridged N-heterocyclic.

Embodiment 79: The compound of any one of embodiments 62 to 78, or a pharmaceutically acceptable salt, solvate, clathrate or prodrug thereof, wherein V is an optionally substituted C$_1$-C$_6$ alkylene.

Embodiment 80: The compound of any one of embodiments 62 to 78, or a pharmaceutically acceptable salt, solvate, clathrate or prodrug thereof, wherein V is an optionally substituted $C_2$-$C_4$ alkylene.

Embodiment 81: The compound of any one of embodiments 62 to 80, or a pharmaceutically acceptable salt, solvate, clathrate or prodrug thereof, wherein W is selected from the group consisting of $S(O)_p R_m$, CN,

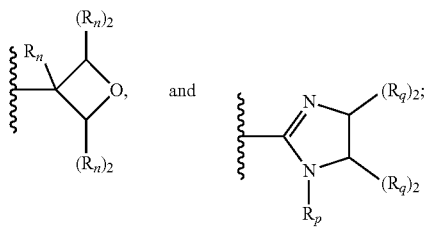

wherein each $R_n$ and $R_q$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, $OR_c$, $NR_dR_d$, $C(O)OR_c$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_n$-$NR_dR_d$, $OC(O)OR_c$, $OC(O)R_c$, optionally substituted heterocyclic and optionally substituted heteroaryl; and $R_p$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl.

Embodiment 82: The compound of any one of embodiments 62 to 80, or a pharmaceutically acceptable salt, solvate, clathrate or prodrug thereof, wherein W is $S(O)_p R_m$.

Embodiment 83: The compound of embodiment 81, or a pharmaceutically acceptable salt, solvate, clathrate or prodrug thereof, wherein $R_m$ is an optionally substituted $C_1$-$C_6$ alkyl or an optionally substituted $C_3$-$C_6$ cycloalkyl.

Embodiment 84: The compound of any one of embodiments 62 to 80, or a pharmaceutically acceptable salt, solvate, clathrate or prodrug thereof, wherein W is $SR_m$, wherein $R_m$ is an optionally substituted $C_1$-$C_6$ alkyl or an optionally substituted $C_3$-$C_6$ cycloalkyl.

Embodiment 85: The compound of any one of embodiments 62 to 80, or a pharmaceutically acceptable salt, solvate, clathrate or prodrug thereof, wherein W is CN.

Embodiment 86: The compound of any one of embodiments 62 to 80, or a pharmaceutically acceptable salt, solvate, clathrate or prodrug thereof, wherein W is an optionally substituted heteroaryl.

Embodiment 87: The compound of any one of embodiments 62 to 80, or a pharmaceutically acceptable salt, solvate, clathrate or prodrug thereof, wherein W is an optionally substituted heterocyclic.

Embodiment 88: The compound of any one of embodiments 62 to 80, or a pharmaceutically acceptable salt, solvate, clathrate or prodrug thereof, wherein W is selected from the group consisting of:

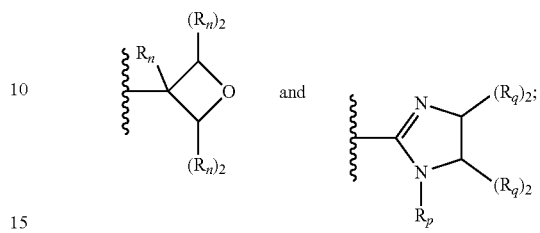

wherein each $R_n$ and $R_q$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, $OR_c$, $NR_dR_d$, $C(O)OR_c$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_n$-$NR_dR_d$, $OC(O)OR_c$, $OC(O)R_c$, optionally substituted heterocyclic and optionally substituted heteroaryl; and $R_p$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl.

Embodiment 89: The compound of embodiment 62, or a pharmaceutically acceptable salt, solvate, clathrate or prodrug thereof, wherein the compound has the Formula (IIa), Formula (IIb), or Formula (IIc):

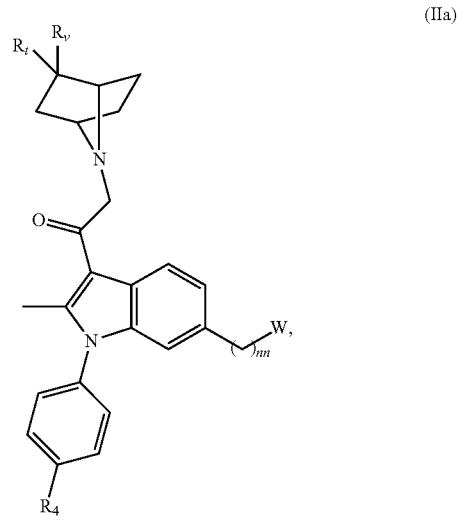

(IIa)

-continued

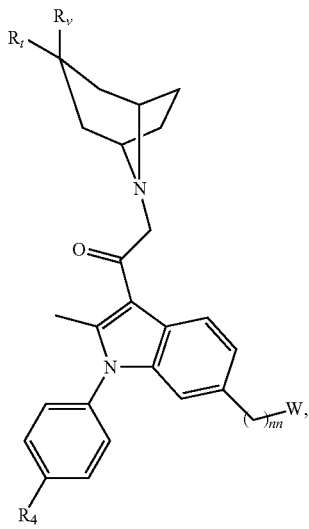

(IIb)

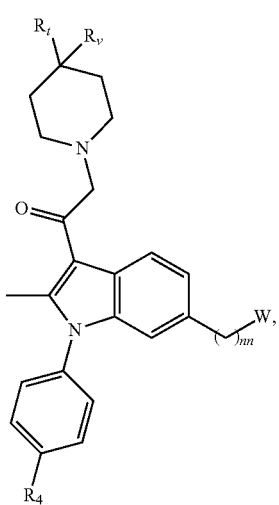

(IIc)

wherein:

$R_t$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, $CN$, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_n NR_dR_d$, $NR_dS(O)_nR_c$, $S(O)_nR_c$, $S(O)_nNR_dR_d$, $OC(O)OR_c$, $(C=NR_d)R_c$, $OC(O)R_c$, optionally substituted heterocyclic and optionally substituted heteroaryl;

$R_v$ is selected from the group consisting of hydrogen and optionally substituted $C_1$-$C_{10}$ alkyl;

$R_4$ is selected from the group consisting of halo, $N_3$, $C(O)OR_c$, $CN$, $C(O)R_c$, $C(O)C(O)R_c$, $C(O)NR_dR_d$, $NO_2$ and $NR_dR_d$;

W is selected from the group consisting of $S(O)_pR_m$, $CN$, optionally substituted heteroaryl and optionally substituted heterocyclic;

nn is 1, 2, or 3; and p is 0, 1, or 2.

Embodiment 90: The compound of embodiment 89, or a pharmaceutically acceptable salt, solvate, clathrate or prodrug thereof, wherein $R_t$ and $R_v$ are independently selected from the group consisting of hydrogen, hydroxyl, —$OCH_3$, and —$C(CH_3)_3$.

Embodiment 91: The compound of embodiment 89 or embodiment 90, or a pharmaceutically acceptable salt, solvate, clathrate or prodrug thereof, wherein $R_4$ is chloro.

Embodiment 92: The compound of any one of embodiment 89 to 91, or a pharmaceutically acceptable salt, solvate, clathrate or prodrug thereof, wherein W is selected from the group consisting of —$SO_2CH_3$, —CN,

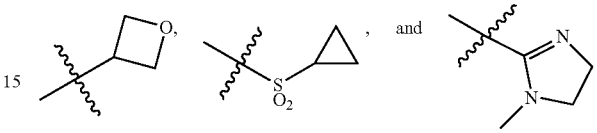

and

Embodiment 93: The compound of embodiment 62, or a pharmaceutically acceptable salt, solvate, clathrate or prodrug thereof, wherein the compound is selected from the group consisting of 1A, 2A, 3A, 4A, 5A, 6A, 7A 8A, 9A, 10A, 11A, 12A, 13A, 14A, 15A, 16A, 17A, 18A, 19A, 20A, 21A, 22A, 23A, 24A, 25A, 26A, 27A, 28A, 29A, 30A, 31A, 32A, and 33A.

Embodiment 94: A compound having the Formula (III):

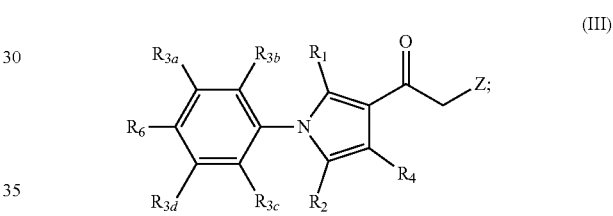

(III)

or a pharmaceutically acceptable salt, solvate, clathrate or prodrug thereof; wherein:

$R_1$ is selected from the group consisting of optionally substituted $C_1$-$C_4$ alkyl, and halo;

$R_2$ is selected from the group consisting optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted 4- to 12-membered heterocyclic, optionally substituted aryl, optionally substituted 4- to 12-membered heteroaryl, halo, and CN;

$R_{3a}$, $R_{3b}$, $R_{3c}$ and $R_{3d}$ are each independently selected from the group consisting of hydrogen, optionally substituted $C_1$-$C_6$ alkyl, CN and halo;

$R_6$ is independently selected from the group consisting of hydrogen, optionally substituted $C_1$-$C_6$ alkyl, CN and halo;

$R_4$ is selected from the group consisting of hydrogen, optionally substituted $C_1$-$C_{10}$ alkyl, halo, and CN; and Z is an optionally substituted, 6- to 12-membered bridged N-heterocyclic; and wherein substituents of optionally substituted Z, $R_1$, $R_2$, $R_{3a}$, $R_{3b}$, $R_{3c}$, $R_{3d}$, $R_4$, and $R_6$ are each independently selected from the group consisting of $C_1$-$C_{10}$ alkyl, $C_2$-$C_{10}$ alkenyl, $C_2$-$C_{10}$ alkynyl, $C_3$-$C_{12}$ cycloalkyl, $C_3$-$C_{12}$ cycloalkenyl, aryl, halo, $N_3$, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C=NR_d)R_c$, $OC(O)R_c$, $Si(R_c)_3$, heterocyclic, and heteroaryl;

each $R_c$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl;

each $R_d$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl; or two geminal $R_d$ groups are taken together with the nitrogen atom to which they are attached to form an optionally substituted heterocyclic or an optionally substituted heteroaryl; and each n is independently 0, 1 or 2.

Embodiment 95: The compound of embodiment 94, or a pharmaceutically acceptable salt, solvate, clathrate or prodrug thereof, wherein $R_1$ is an optionally substituted $C_1$-$C_4$ alkyl.

Embodiment 96: The compound of embodiment 94, or a pharmaceutically acceptable salt, solvate, clathrate or prodrug thereof, wherein $R_1$ is methyl.

Embodiment 97: The compound of any one of embodiments 94 to 96, or a pharmaceutically acceptable salt, solvate, clathrate or prodrug thereof, wherein $R_2$ is selected from the group consisting of optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, and optionally substituted $C_3$-$C_{12}$ cycloalkenyl.

Embodiment 98: The compound of any one of embodiments 94 to 96, or a pharmaceutically acceptable salt, solvate, clathrate or prodrug thereof, wherein $R_2$ is selected from the group consisting of optionally substituted $C_1$-$C_6$ alkyl, optionally substituted $C_2$-$C_6$ alkenyl, and optionally substituted $C_2$-$C_6$ alkynyl.

Embodiment 99: The compound of any one of embodiments 94 to 96, or a pharmaceutically acceptable salt, solvate, clathrate or prodrug thereof, wherein $R_2$ is $C_1$-$C_6$ alkyl, $C_2$-$C_6$ alkenyl, or $C_2$-$C_6$ alkynyl, each optionally substituted with one or more substituents independently selected from optionally substituted $C_3$-$C_{12}$ cycloalkyl, optionally substituted $C_3$-$C_{12}$ cycloalkenyl, optionally substituted aryl, halo, $N_3$, $OR_{c1}$, $NR_{d1}R_{d1}$, $C(O)OR_{e1}$, $NO_2$, CN, $C(O)R_{e1}$, $C(O)C(O)R_{e1}$, $C(O)NR_{d1}R_{d1}$, $NR_dC(O)R_c$, $NR_dS(O)_nR_{e1}$, $N(R_{d1})(COOR_{e1})$, $NR_{d1}C(O)C(O)R_{e1}$, $NR_{d1}C(O)NR_{d1}R_{d1}$, $NR_{d1}S(O)_nNR_{d1}R_{d1}$, $NR_{d1}S(O)_nR_{c1}$, $S(O)_nR_{e1}$, $S(O)_nNR_{d1}R_{d1}$, $OC(O)OR_{e1}$, $(C=NR_{d1})R_{e1}$, $OC(O)R_{e1}$, tri($C_1$-$C_4$ alkyl)silyl, optionally substituted 4- to 12-membered heterocyclic, and optionally substituted 4- to 12-membered heteroaryl;

each $R_{c1}$ and $R_{e1}$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted 4- to 12-membered heterocyclic, optionally substituted aryl, and optionally substituted 4- to 12-membered heteroaryl; and each $R_{d1}$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted 4- to 12-membered heterocyclic, optionally substituted aryl, and optionally substituted 4- to 12-membered heteroaryl; or two geminal $R_{d1}$ groups are taken together with the nitrogen atom to which they are attached to form an optionally substituted 4- to 12-membered heterocyclic or an optionally substituted 4- to 12-membered heteroaryl; and each n is independently 0, 1 or 2.

Embodiment 100: The compound of any one of embodiments 94 to 96, or a pharmaceutically acceptable salt, solvate, clathrate or prodrug thereof, wherein $R_2$ is $C_1$-$C_6$ alkyl, $C_2$-$C_6$ alkenyl, or $C_2$-$C_6$ alkynyl, substituted with one or more substituents independently selected from the group consisting of optionally substituted $C_3$-$C_{12}$ cycloalkyl, optionally substituted $C_3$-$C_{12}$ cycloalkenyl, halo, $OR_{c1}$, $S(O)_nR_{e1}$, optionally substituted 4- to 12-membered heteroaryl, optionally substituted 4- to 12-membered heterocyclic, CN, and tri($C_1$-$C_4$ alkyl)silyl.

Embodiment 101: The compound of any one of embodiments 94 to 96, or a pharmaceutically acceptable salt, solvate, clathrate or prodrug thereof, wherein $R_2$ is $C_3$-$C_{12}$ cycloalkyl or $C_3$-$C_{12}$ cycloalkenyl optionally substituted with one or more substituents independently selected from the group consisting of optionally substituted $C_1$-$C_{10}$ alkyl, optionally substituted $C_2$-$C_{10}$ alkenyl, optionally substituted $C_2$-$C_{10}$ alkynyl, halo, $OR_c$, $S(O)_nR_{e1}$, optionally substituted 4- to 12-membered heteroaryl, optionally substituted 4- to 12-membered heterocyclic, CN, and tri($C_1$-$C_4$ alkyl)silyl;

$R_{e1}$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted 4- to 12-membered heterocyclic, optionally substituted aryl, and optionally substituted 4- to 12-membered heteroaryl.

Embodiment 102: The compound of any one of embodiments 94 to 96, or a pharmaceutically acceptable salt, solvate, clathrate or prodrug thereof, wherein $R_2$ is optionally substituted $C_3$-$C_6$ cycloalkyl.

Embodiment 103: The compound of any one of embodiments 94 to 96, or a pharmaceutically acceptable salt, solvate, clathrate or prodrug thereof, wherein $R_2$ is $C_1$-$C_6$ alkyl.

Embodiment 104: The compound of any one of embodiments 94 to 96, or a pharmaceutically acceptable salt, solvate, clathrate or prodrug thereof, wherein $R_2$ is methyl.

Embodiment 105: The compound of any one of embodiments 94 to 96, or a pharmaceutically acceptable salt, solvate, clathrate or prodrug thereof, wherein $R_2$ is a $C_1$-$C_6$ haloalkyl.

Embodiment 106: The compound of any one of embodiments 94 to 96, or a pharmaceutically acceptable salt, solvate, clathrate or prodrug thereof, wherein $R_2$ is halo.

Embodiment 107: The compound of any one of embodiments 94 to 96, or a pharmaceutically acceptable salt, solvate, clathrate or prodrug thereof, wherein $R_2$ is Br, Cl or F.

Embodiment 108: The compound of any one of embodiments 94 to 96, or a pharmaceutically acceptable salt, solvate, clathrate or prodrug thereof, wherein $R_2$ is CN.

Embodiment 109: The compound of any one of embodiments 94 to 96, or a pharmaceutically acceptable salt, solvate, clathrate or prodrug thereof, wherein $R_2$ is selected from the group consisting of —Cl, —Br, —$CH_3$, —CH($CH_3$)$_2$, —CH($CH_3$)$CH_2CH_3$, —C($CH_3$)$_3$, —$CF_3$, —$CH_2CF_3$, —CN, —$CH_2CH_2Si(CH_3)_3$, —$CH_2CH_2CH_2OCH_3$, —$CH_2CH_2CH_2OCF_3$, —CH₂CH₂CH₂CH₂SCH₃,   —CH₂CH₂CH₂SO₂CH₃,
—CH=CHCH₂NH₂,   —CH=CHCH₂SO₂CH₃,   —CH(CH₃)CH₂CH₂SO₂CH₃,   —CH₂CH₂CH₂CN,
—CH₂CH₂CH₂CH₂CN, —CH₂OCH₂CH₂CN,

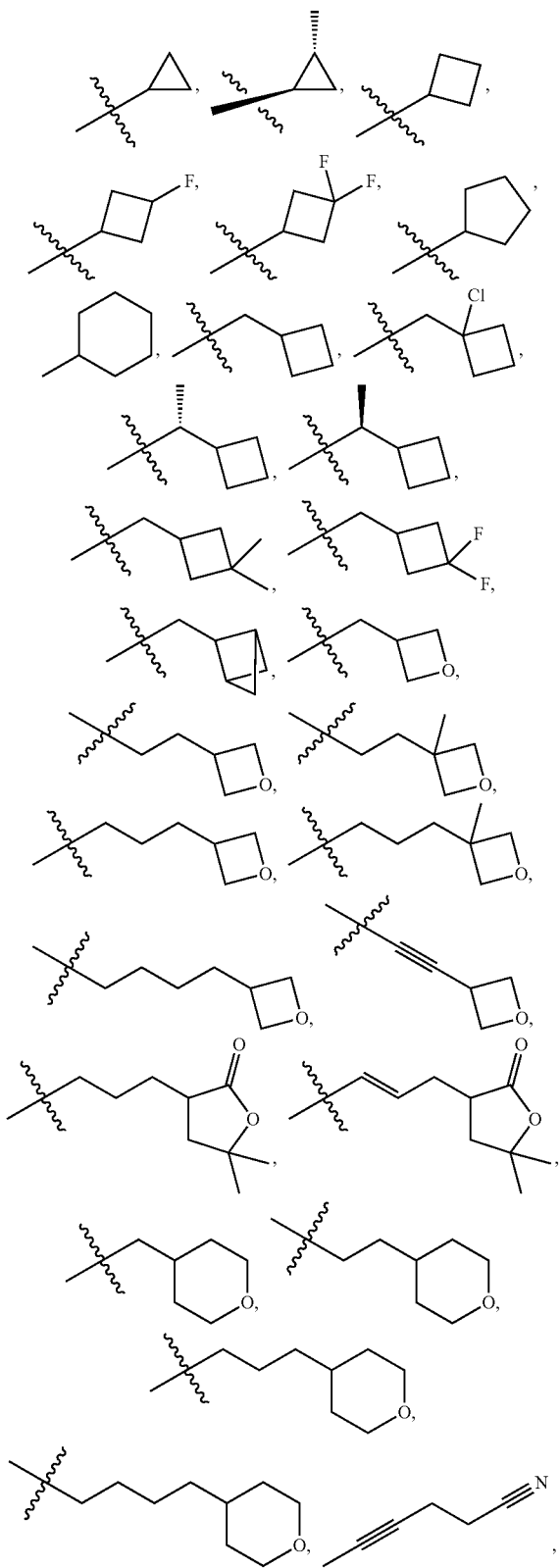

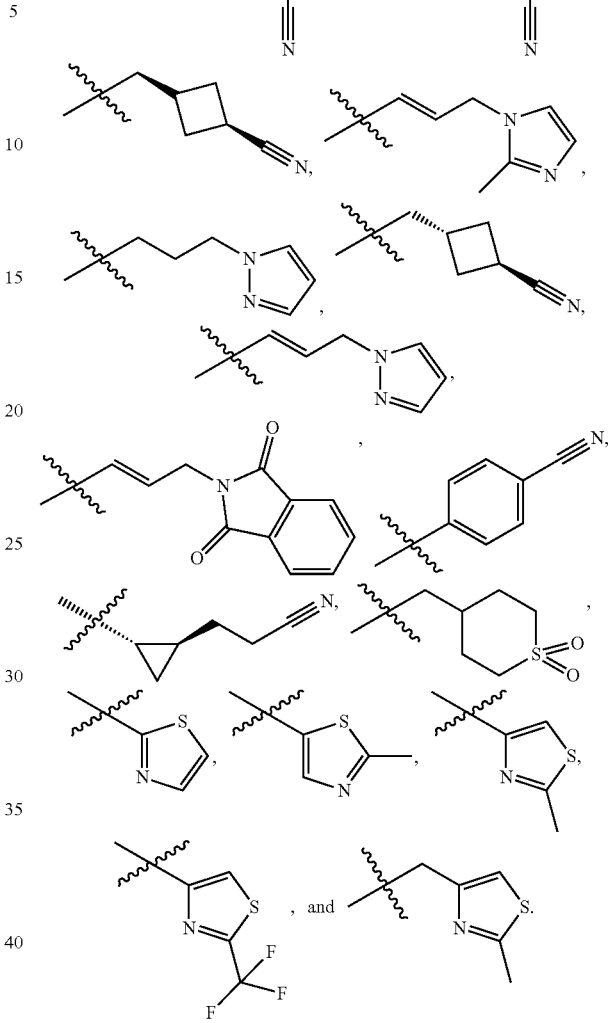

Embodiment 110: The compound of any one of embodiments 94 to 109, or a pharmaceutically acceptable salt, solvate, clathrate or prodrug thereof, wherein $R_6$ is selected from the group consisting of CN and halo.

Embodiment 111: The compound of any one of embodiments 94 to 109, or a pharmaceutically acceptable salt, solvate, clathrate or prodrug thereof, wherein $R_6$ is selected from the group consisting of CN and Cl.

Embodiment 112: The compound of any one of embodiments 94 to 109, or a pharmaceutically acceptable salt, solvate, clathrate or prodrug thereof, wherein $R_6$ is CN.

Embodiment 113: The compound of any one of embodiments 94 to 112, or a pharmaceutically acceptable salt, solvate, clathrate or prodrug thereof, wherein $R_{3a}$, $R_{3b}$, $R_{3c}$ and $R_{3d}$ are each hydrogen.

Embodiment 114: The compound of any one of embodiments 94 to 112, or a pharmaceutically acceptable salt, solvate, clathrate or prodrug thereof, wherein $R_{3a}$ and $R_{3d}$ are each independently selected from the group consisting of hydrogen, optionally substituted $C_1$-$C_6$ alkyl, CN and halo, and $R_{3b}$ and $R_{3c}$ are each hydrogen.

Embodiment 115: The compound of any one of embodiments 94 to 112, or a pharmaceutically acceptable salt, solvate, clathrate or prodrug thereof, wherein $R_4$ is selected from the group consisting of hydrogen, optionally substituted $C_1$-$C_4$ alkyl, halo, and CN.

Embodiment 116: The compound of any one of embodiments 94 to 112, or a pharmaceutically acceptable salt, solvate, clathrate or prodrug thereof, wherein $R_4$ is hydrogen.

Embodiment 117: The compound of any one of embodiments 94 to 112, or a pharmaceutically acceptable salt, solvate, clathrate or prodrug thereof, wherein $R_4$ is F, Cl or Br.

Embodiment 118: The compound of any one of embodiments 94 to 112, or a pharmaceutically acceptable salt, solvate, clathrate or prodrug thereof, wherein $R_4$ is F.

Embodiment 119: The compound of any one of embodiments 94 to 112, or a pharmaceutically acceptable salt, solvate, clathrate or prodrug thereof, wherein $R_4$ is methyl or ethyl.

Embodiment 120: The compound of any one of embodiments 94 to 112, or a pharmaceutically acceptable salt, solvate, clathrate or prodrug thereof, wherein $R_4$ is methyl.

Embodiment 121: The compound of any one of embodiments 94 to 112, or a pharmaceutically acceptable salt, solvate, clathrate or prodrug thereof, wherein $R_4$ is a $C_1$-$C_4$ haloalkyl.

Embodiment 122: The compound of any one of embodiments 94 to 112, or a pharmaceutically acceptable salt, solvate, clathrate or prodrug thereof, wherein $R_4$ is —Cl, —F, —Br, —CN, methyl, ethyl, —CF$_3$, or —CH$_2$CH$_2$CH$_2$SO$_2$CH$_3$.

Embodiment 123: The compound of any one of embodiments 94 to 122, or a pharmaceutically acceptable salt, solvate, clathrate or prodrug thereof, wherein Z is an optionally substituted, 6- to 10-membered bridged N-heterocyclic.

Embodiment 124: The compound of any one of embodiments 94 to 122, or a pharmaceutically acceptable salt, solvate, clathrate or prodrug thereof, wherein Z is a 6- to 10-membered bridged N-heterocyclic, optionally substituted with one or more substituents independently selected from the group consisting of optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, N$_3$, OR$_{c2}$, NR$_{d2}$R$_{d2}$, C(O)OR$_2$, NO$_2$, CN, C(O)R$_{e2}$, C(O)C(O)R$_{e2}$, C(O)NR$_{d2}$R$_{d2}$, NR$_{d2}$C(O)R$_{e2}$, NR$_{2d}$S(O)$_n$R$_{e2}$, N(R$_{d2}$)(COOR$_{e2}$), NR$_d$C(O)C(O)R$_{e2}$, NRC(O)NR$_{d2}$R$_{d2}$, NR$_{d2}$S(O)$_n$NR$_{d2}$R$_{d2}$, NR$_{d2}$S(O)$_n$R$_{e2}$, S(O)$_n$R$_{e2}$, S(O)$_n$NR$_{d2}$R$_{d2}$, OC(O)OR$_{e2}$, (C=NR$_{d2}$)R$_{e2}$, OC(O)R$_c$, optionally substituted 4- to 12-membered heterocyclic and optionally substituted 4- to 12-membered heteroaryl;

each R$_{c2}$ and R$_{e2}$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted 4- to 12-membered heterocyclic, optionally substituted aryl, and optionally substituted 4- to 12-membered heteroaryl;

each R$_{d2}$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted 4- to 12-membered heterocyclic, optionally substituted aryl, and optionally substituted 4- to 12-membered heteroaryl; or two geminal R$_d$ groups are taken together with the nitrogen atom to which they are attached to form an optionally substituted 4- to 12-membered heterocyclic or an optionally substituted 4- to 12-membered heteroaryl;

n is 0, 1 or 2.

Embodiment 125: The compound of any one of embodiments 94 to 122, or a pharmaceutically acceptable salt, solvate, clathrate or prodrug thereof, wherein Z is a 6- to 10-membered bridged N-heterocyclic, optionally substituted with one or more substituents independently selected from optionally substituted $C_1$-$C_4$ alkyl, optionally substituted $C_2$-$C_4$ alkenyl, OR$_{c2}$, and C(O)OR$_{e2}$.

Embodiment 126: The compound of any one of embodiments 94 to 122, or a pharmaceutically acceptable salt, solvate, clathrate or prodrug thereof, wherein Z is a 6- to 10-membered bridged N-heterocyclic, optionally substituted with one or more substituents independently selected from $C_1$-$C_4$ alkyl, OH, OCH$_3$, OCF$_3$, C(O)OH, C(O)OCH$_3$, CF$_3$, and $C_1$-$C_4$ alkyl substituted with OH or OCH$_3$.

Embodiment 127: The compound of any one of embodiments 94 to 122, or a pharmaceutically acceptable salt, solvate, clathrate or prodrug thereof, wherein Z is a 6- to 10-membered bridged N-heterocyclic, optionally substituted with one or more substituents independently selected from optionally substituted $C_1$-$C_4$ alkyl, OH and haloalkyl.

Embodiment 128: The compound of any one of embodiments 94 to 122, or a pharmaceutically acceptable salt, solvate, clathrate or prodrug thereof, wherein Z is an unsubstituted 6- to 10-membered bridged N-heterocyclic.

Embodiment 129: The compound of any one of embodiments 94 to 122, or a pharmaceutically acceptable salt, solvate, clathrate or prodrug thereof, wherein Z is an optionally substituted, 6- to 9-membered bridged N-heterocyclic.

Embodiment 130: The compound of any one of embodiments 94 to 122, or a pharmaceutically acceptable salt, solvate, clathrate or prodrug thereof, wherein Z is an optionally substituted, 6- to 8-membered bridged N-heterocyclic.

Embodiment 131: The compound of any one of embodiments 94 to 122, or a pharmaceutically acceptable salt, solvate, clathrate or prodrug thereof, wherein Z is an optionally substituted, 7-membered bridged N-heterocyclic.

Embodiment 132: The compound of any one of embodiments 94 to 122, or a pharmaceutically acceptable salt, solvate, clathrate or prodrug thereof, wherein Z is an optionally substituted, 8-membered bridged N-heterocyclic.

Embodiment 133: The compound of any one of embodiments 94 to 122, or a pharmaceutically acceptable salt, solvate, clathrate or prodrug thereof, wherein Z is selected from the group consisting of:

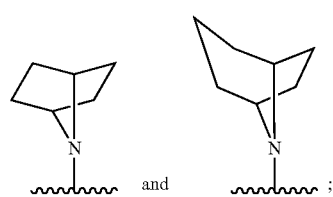 [SMILES: *N1C2CCC1CC2 ; *N1C2CCCC1CC2]

each optionally substituted.

Embodiment 134: The compound of any one of embodiments 94 to 122, or a pharmaceutically acceptable salt, solvate, clathrate or prodrug thereof, wherein Z is selected from the group consisting of:

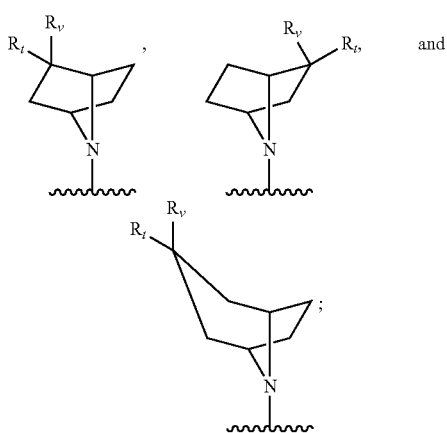

wherein:

$R_t$ is selected from the group consisting of optionally substituted $C_1$-$C_4$ alkyl, optionally substituted $C_2$-$C_4$ alkenyl, $OR_{c2}$, and $C(O)OR_{e2}$;

$R_v$ is selected from the group consisting of hydrogen and optionally substituted $C_1$-$C_{10}$ alkyl; and each $R_{c2}$ and $R_{e2}$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted 4- to 12-membered heterocyclic, optionally substituted aryl, and optionally substituted 4- to 12-membered heteroaryl.

Embodiment 135: The compound of embodiment 134, or a pharmaceutically acceptable salt, solvate, clathrate or prodrug thereof, wherein $R_t$ is selected from the group consisting of optionally substituted $C_1$-$C_{10}$ alkyl and $OR_{c2}$.

Embodiment 136: The compound of embodiment 134, or a pharmaceutically acceptable salt, solvate, clathrate or prodrug thereof, wherein R is selected from the group consisting of $C_1$-$C_4$ alkyl, OH, $OCH_3$, $OCF_3$, $C(O)OH$, $C(O)OCH_3$, $CF_3$, and $C_1$-$C_4$ alkyl substituted with OH or $OCH_3$.

Embodiment 137: The compound of any one of embodiments 94 to 122, or a pharmaceutically acceptable salt, solvate, clathrate or prodrug thereof, wherein Z is an optionally substituted, 6- to 10-membered bridged N-heterocyclic; $R_1$ is methyl; $R_2$ is methyl; $R_4$ is halo; and $R_6$ is CN.

Embodiment 138: The compound of embodiment 137, or a pharmaceutically acceptable salt, solvate, clathrate or prodrug thereof, wherein $R_{3a}$, $R_{3b}$, $R_{3c}$ and $R_{3d}$ are each hydrogen.

Embodiment 139: The compound of any one of embodiments 94 to 122, or a pharmaceutically acceptable salt, solvate, clathrate or prodrug thereof, wherein Z is an optionally substituted, 7-membered or 8-membered bridged N-heterocyclic.

Embodiment 140: The compound of any one of embodiments claims 94 to 122, or a pharmaceutically acceptable salt, solvate, clathrate or prodrug thereof, wherein Z is an optionally substituted 7-membered bridged N-heterocyclic.

Embodiment 141: The compound of embodiment 140, or a pharmaceutically acceptable salt, solvate, clathrate or prodrug thereof, wherein $R_4$ is F.

Embodiment 142: The compound of any one of embodiments 94 to 122, or a pharmaceutically acceptable salt, solvate, clathrate or prodrug thereof, wherein Z is an optionally substituted, 6- to 10-membered bridged N-heterocyclic; $R_1$ is methyl; $R_2$ is methyl; $R_4$ is hydrogen; and $R_6$ is CN.

Embodiment 143: The compound of embodiment 94, or a pharmaceutically acceptable salt, solvate, clathrate or prodrug thereof, wherein:

Z is an optionally substituted, 6- to 10-membered bridged N-heterocyclic;

$R_1$ is methyl;

$R_4$ is hydrogen;

$R_6$ is CN; and $R_2$ is selected from the group consisting of $C_1$-$C_6$ alkyl, $C_2$-$C_6$ alkenyl, and $C_2$-$C_6$ alkynyl, each substituted with one or more substituents independently selected from the group consisting of optionally substituted $C_3$-$C_{12}$ cycloalkyl, optionally substituted $C_3$-$C_{12}$ cycloalkenyl, halo, $OR_c$, $S(O)_n R_e$, optionally substituted aryl, optionally substituted 4- to 12-membered heteroaryl, optionally substituted 4- to 12-membered heterocyclic, CN, and tri($C_1$-$C_4$ alkyl)silyl.

Embodiment 144: The compound of embodiment 94, or a pharmaceutically acceptable salt, solvate, clathrate or prodrug thereof, wherein the compound has the Formula (IIIa), Formula (IIIb), Formula (IIIc), Formula (IIId), or Formula (IIIe):

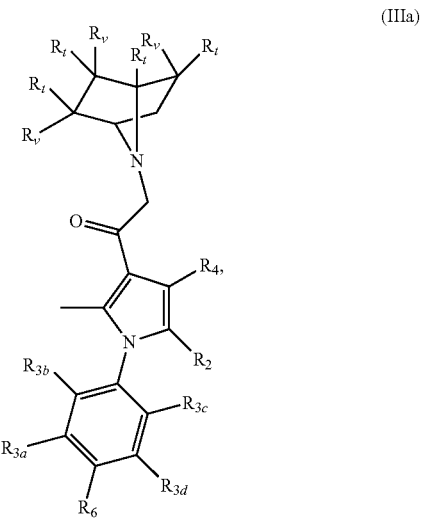

(IIIa)

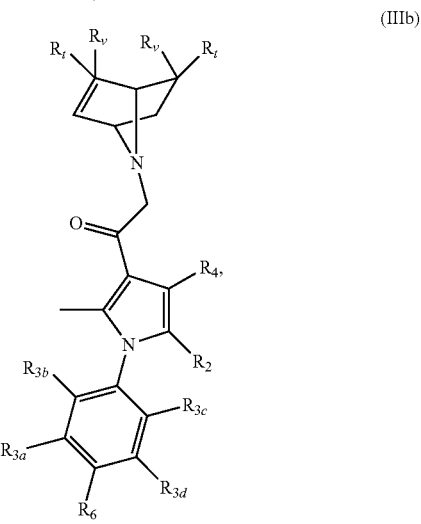

(IIIb)

-continued

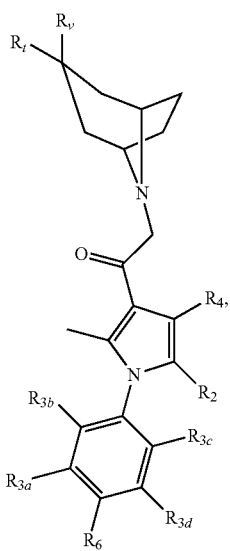

(IIIc)

(IIId)

(IIIe)

wherein:

R_t is selected from the group consisting of optionally substituted C_1-C_4 alkyl, optionally substituted C_2-C_4 alkenyl, $OR_{c2}$, and $C(O)OR_{e2}$, or any two $R_t$ together form a 5-membered or 6-membered heterocyclic;

$R_v$ is selected from the group consisting of hydrogen and optionally substituted $C_1$-$C_{10}$ alkyl; and each $R_{c2}$ and $R_{e2}$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted 4- to 12-membered heterocyclic, optionally substituted aryl, and optionally substituted 4- to 12-membered heteroaryl;

$R_2$ is selected from the group consisting optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted 4- to 12-membered heterocyclic, optionally substituted aryl, optionally substituted 4- to 12-membered heteroaryl, halo, and CN;

$R_{3a}$, $R_{3b}$, $R_{3c}$, and $R_{3d}$ are each independently hydrogen or fluoro;

$R_4$ is —H, —Cl, —F, —Br, —CN, —CH_3, —CH_2CH_3, —CF_3, or —CH_2CH_2CH_2SO_2CH_3; and $R_6$ is CN or Cl.

Embodiment 145: The compound of embodiment 144, or a pharmaceutically acceptable salt, solvate, clathrate or prodrug thereof, wherein $R_t$ and $R_v$ are independently selected from the group consisting of hydrogen, hydroxyl, —CH_3, —CF_3, —CH_2OH, —CH(CH_3)OH, —CH_2C(CH_3)_2OH, —COOH, —OCH_3, —OCF_3, —C(CH_3)_3, and —C(CF_3)_3, or any two $R_t$ together form —CH_2OCH_2— or —CH_2CH_2O—.

Embodiment 146: The compound of embodiment 144 or embodiment 145, or a pharmaceutically acceptable salt, solvate, clathrate or prodrug thereof, wherein $R_2$ is selected from the group consisting of —Cl, —Br, —CH_3, —CH(CH_3)_2, —CH(CH_3)CH_2CH_3, —C(CH_3)_3, —CF_3, —CH_2CF_3, —CN, —CH_2CH_2Si(CH_3)_3, —CH_2CH_2CH_2OCH_3, —CH_2CH_2CH_2OCF_3, —CH_2CH_2CH_2CH_2SCH_3, —CH_2CH_2CH_2SO_2CH_3, —CH=CHCH_2NH_2, —CH=CHCH_2SO_2CH_3, —CH(CH_3)CH_2CH_2SO_2CH_3, —CH_2CH_2CH_2CN, —CH_2CH_2CH_2CH_2CN, —CH_2OCH_2CH_2CN,

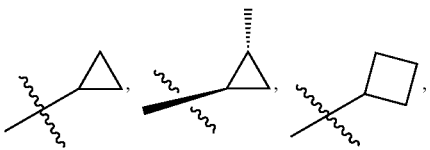

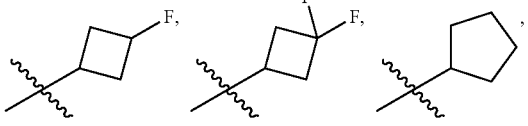

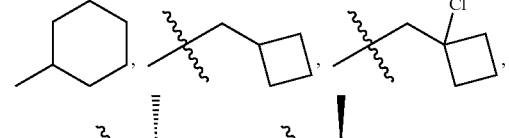

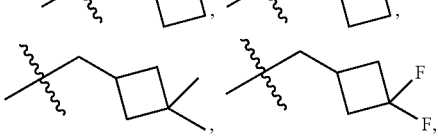

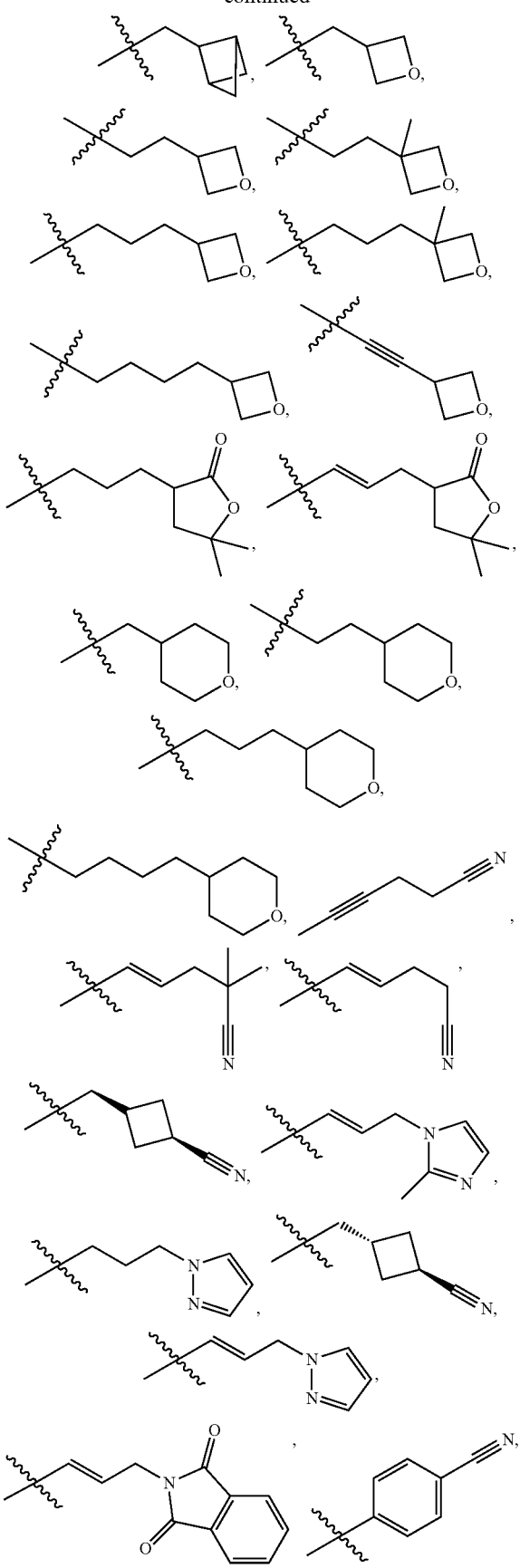

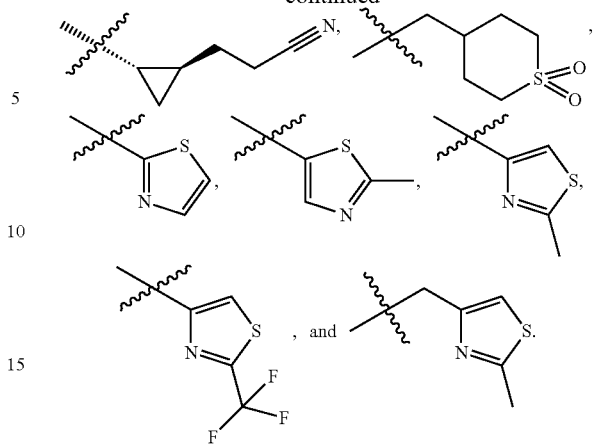

Embodiment 147: The compound of embodiment 94, or a pharmaceutically acceptable salt, solvate, clathrate or prodrug thereof, wherein the compound is selected from the group consisting 1B, 2B, 3B, 4B, 5B, 6B, 7B, 8B, 9B, 10B, 11B, 12B, 14B, 15B, 16B, 17B, 18B, 19B, 20B, 21B, 22B, 23B, 24B, 25B, 26B, 27B, 28B, 29B, 30B, 31B, 32B, 33B, 34B, 35B, 36B, 37B, 38B, 39B, 40B, 41B, 42B, 43B, 44B, 45B, 46B, 47B, 50B, 51B, 52B, 53B, 54B, 55B, 56B, 57B, 63B, 64B, 66B, 67B, 68B, 69B, 70B, 71B, 72B, 73B, 74B, 75B, 76B, 77B, 78B, 79B, 80B, 81B, 82B, 83B, 84B, 85B, 86B, 87B, 88B, 89B 90B, 91B, 92B, 94B, 95B, 96B, 97B, 98B, 99B, 100B, 101B, 102B, 103B, 104B, 105B, 106B, 107B, 108B, 109B, 110B, 111B, 112B, 113, 114B, 115B, 116B, 117B, 118B, 119B, 120B, 121B, 122B, 124B, 125B, 126B, 127B, 128B, 129B, 130B, 131B, 132B, 133B, 134B, 135B, 136B, 137B, 138B, 139B, 140B, 141B, 142B, 143B, 144B, 145B, 146B, 147B, 148B, 149B, 150B, 151B, 153B, 155B, 156B, 157B, and 158B.

Embodiment 148: A pharmaceutical composition comprising a pharmaceutically acceptable carrier or excipient and a compound of any one of embodiments 1 to 147, or a pharmaceutically acceptable salt, solvate, clathrate or prodrug thereof.

Embodiment 149: A method of inhibiting deubiquitination activity of a Usp14 protein comprising contacting the Usp14 protein with an effective amount of a compound of any one of embodiments 1 to 147, or a pharmaceutically acceptable salt, solvate, clathrate or prodrug thereof, in an amount sufficient to inhibit deubiquitination activity of the Usp14 protein.

Embodiment 150: A method of enhancing protein degradation by a proteasome in a cell comprising contacting the cell with an effective amount of a compound of any one of embodiments 1 to 147, or a pharmaceutically acceptable salt, solvate, clathrate or prodrug thereof, in an amount sufficient to enhance protein degradation by the proteasome.

Embodiment 151: A method of treating a patient suffering from a condition associated with a dysfunction in proteostasis comprising administering to said patient an effective amount of a compound of any one of embodiments 1 to 147.

Embodiment 152: The method of embodiment 151, wherein the condition associated with a dysfunction of proteostasis is a gain of function condition.

Embodiment 153: The method of embodiment 151, wherein the condition associated with a dysfunction of protein homeostasis is a loss of function condition.

Embodiment 154: The method of embodiment 151, wherein the condition is associated with a dysfunction in the proteostasis of a protein selected from the group consisting of hexosamine A, cystic fibrosis transmembrane conductance regulator, aspartylglucosaminidase, α-galactosidase A, cysteine transporter, acid ceramidase, acid α-L-fucosidase, protective protein, cathepsin A, acid β-glucosidase, acid β-galactosidase, iduronate 2-sulfatase, α-L-iduronidase, galactocerebrosidase, acid α-mannosidase, acid β-mannosidase, arylsulfatase B, arylsulfatase A, N-acetylgalactosamine-6-sulfate sulfatase, acid β-galactosidase, N-acetylglucosamine-1-phosphotransferase, acid sphingomyelinase, NPC-1, acid α-glucosidase, β-hexosamine B, heparin N-sulfatase, α-N-acetylglucosaminidase, islet amyloid polypeptide (IAPP or amylin), α-glucosaminide N-acetyltransferase, N-acetylglucosamine-6-sulfate sulfatase, a1 anti-trypsin, α-N-acetylgalactosaminidase, α-neuramidase, β-glucuronidase, β-hexosamine A and acid lipase, polyglutamine, α-synuclein, A peptide, tau protein, hERG potassium channel, islet amyloid polypeptide, transthyretin, Huntingtin, superoxide dismutase, TAR DNA-binding protein 43 (TDP-43), ataxin-3, superoxide dismutase (SOD) and rhodopsin.

Embodiment 155: The method of embodiment 151, wherein the condition is associated with a dysfunction in the proteostasis of a protein selected from the group consisting of Huntingtin, tau, alpha-synuclein, a1 anti-trypsin and superoxide dismutase.

Embodiment 156: The method of embodiment 151, wherein the condition is selected from the group consisting of Huntington's disease, Alzheimer's disease, Parkinson's disease, amyotrophic lateral sclerosis, diabetes and complications of diabetes.

Embodiment 157: The method of embodiment 151, wherein the condition is selected from the group consisting of Parkinson's disease, Alzheimer's disease, Frontotemporal lobar dementia (FTLD), Progressive Supranuclear Palsy (PSP), Amyotrophic lateral sclerosis (ALS), Spinocerebellar ataxia (SCA), Retinitis pigmentosum, Prion diseases and autism.

Embodiment 158: The method of embodiment 151, further comprising administering a second agent selected from the group consisting of a proteostasis regulator and a pharmacologic chaperone.

Embodiment 159: A method of enhancing proteasome function in a subject comprising administering to said subject an effective amount of a compound of any one of embodiments 1 to 147, or a pharmaceutically acceptable salt, solvate, clathrate or prodrug thereof.

Embodiment 160: A method for treating a condition characterized by deficient proteasome activity or deficiency of other components of the ubiquitin-proteasome pathway in a subject comprising administering to said subject an effective amount of a compound of any one of embodiments 1 to 147, or a pharmaceutically acceptable salt, solvate, clathrate or prodrug thereof.

Embodiment 161: A method of treating cancer or a tumor in a subject in need thereof comprising administering to said subject an effective amount of a compound of any one of embodiments 1 to 147, or a pharmaceutically acceptable salt, solvate, clathrate or prodrug thereof.

EXEMPLARY EMBODIMENTS

The invention is illustrated by the following examples which are not meant to be limiting in any way.

Exemplification of Compounds of Formulae (Ia), (Ib), (Ic), or (Id) and of Formulae (II), (IIa), (IIb), or (IIc)

| List of Abbreviations | |
|---|---|
| Abbreviation | Meaning |
| THF | tetrahydrofuran |
| EtOAc | ethyl acetate |
| MeOH | methanol |
| DMF | N,N-dimethylformamide |
| DCM | dichloromethane |
| rt | room temperature |
| DIPEA | diisopropylethylamine |
| TEA | triethylamine |
| DMAP | 4-dimethylaminopyridine |
| H | hour(s) |
| Min | minute(s) |
| Pd/C | palladium on carbon |
| Dioxane | 1,4-dioxane |
| DMP | Dess-Martin Periodinane |
| DIBAL-H | diisobutylaluminum hydride |
| Cpd | Compound |
| Satd | saturated |
| Aq | aqueous |
| TsCl | 4-methylbenzenesulfonyl chloride |
| MsCl | methanesulfonyl chloride |
| Boc$_2$O | di-tert-butyl dicarbonate |
| ACN | Acetonitrile |
| Et$_2$AlCl | Diethylaluminum chloride |
| n-BuLi | n-Butyllithium |

Example A. Preparation of Intermediates IA Through IVA

Preparation of Intermediate IA: (Ethenesulfonyl)cyclopropane

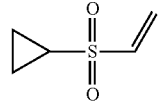

To a 250 mL 3-necked round-bottom flask, was placed a solution of cyclopropanesulfonyl chloride (7.05 g, 50.2 mmol) in THF (50 mL). To this solution was added vinylmagnesium bromide (6.55 g, 49.9 mmol) under nitrogen. The reaction was stirred overnight at 60° C., then the mixture was cooled to rt and quenched with 100 mL of cooled brine. The resulting solution was extracted with EtOAc (3×100 mL). The combined organic layers was washed with brine (2×80 mL), dried over anhydrous Na$_2$SO$_4$ and concentrated under vacuum. The crude product was purified by column chromatography using EtOAc/petroleum ether (1:3) as eluent affording 798 mg (12%) of the title compound as light yellow oil. $^1$H NMR (400 MHz, CDCl$_3$): δ 6.74-6.78 (m, 1H), 6.42-6.38 (d, 1H, J=13.8 Hz), 6.11-6.09 (d, 1H, J=10.0 Hz), 2.41-2.35 (m, 1H), 1.34-1.22 (m, 2H), 1.14-1.05 (m, 2H).

171

Preparation of Intermediate IIA: (1R,3R,5S)-3-(tert-Butyl)-8-azabicyclo[3.2.1]octan-3-ol

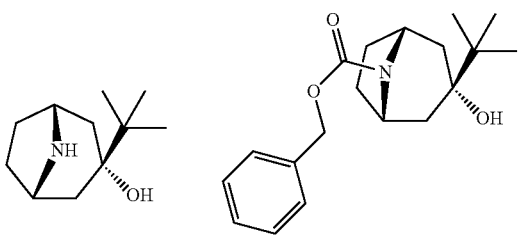 [SMILES: CC(C)(C)[C@]1(O)C[C@H]2CC[C@@H](C1)N2 ; CC(C)(C)[C@]1(O)C[C@H]2CC[C@@H](C1)N2C(=O)OCc1ccccc1]

A. Benzyl (1R,3R,5S)-3-(tert-Butyl)-3-hydroxy-8-azabicyclo[3.2.1]octane-8-carboxylate To a 250 mL 3-necked round-bottom flask purged with $N_2$, was placed a solution of LaCl$_3$ (23 mL, 13.9 mmol) and benzyl (1R,5S)-3-oxo-8-azabicyclo[3.2.1]octane-8-carboxylate (3.00 g, 11.6 mmol) in THF (15 mL). The resulting solution was stirred for 1 h at room temperature, then the solution was cooled to 0° C. and a solution of tert-butylmagnesium chloride (14 mL) was added drop-wise. The reaction was allowed to warm to rt and then stirred for 1 h. The reaction was quenched with water, then extracted with EtOAc. The organic layers were combined, washed with brine, dried over anhydrous Na$_2$SO$_4$, and concentrated under reduced pressure. The crude product was purified by column chromatography using a silica gel column eluting with EtOAc/petroleum ether (1:6) affording 2.64 g (72%) of the title compound as a white solid. Mass Spectrum (LCMS, ESI pos.): Calcd. for $C_{19}H_{28}NO_3$: 318 (M+H); found: 318. $^1$H NMR (300 MHz, CDCl$_3$): δ 7.39-7.30 (m, 5H), 5.13-5.16 (m, 2H), 4.33 (3, 2H), 2.18-2.12 (m, 4H), 1.93-1.90 (m, 2H), 1.44-1.49 (m, 2H), 1.27 (brs, 2H), 0.82 (s, 9H).

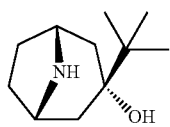

B. (1R,3R,5S)-3-(tert-Butyl)-8-azabicyclo[3.2.1]octan-3-ol

To a 100 mL round-bottom flask, was placed a solution of benzyl 3-tert-butyl-3-hydroxy-8-azabicyclo[3.2.1]octane-8-carboxylate (1.20 g, 3.78 mmol, as prepared in the previous step) in MeOH (45 mL). To this mixture was added Pd/C (200 mg) then the solution was degassed and back-flushed with H$_2$. The reaction was stirred at rt for 140 min, then the suspension was filtered and the filtrate was concentrated under reduced pressure affording 800 mg (quantitative) of the crude title compound as a yellow liquid. Mass Spectrum (LCMS, ESI pos.): Calcd. for $C_{11}H_{22}NO$: 184 (M+H); found: 184.

172

Preparation of Intermediate IIIA: (1R,3R,5S)-3-isopropyl-8-azabicyclo[3.2.1]octan-3-ol

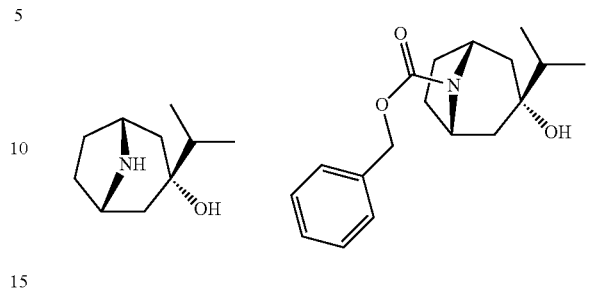

A. Benzyl (1R,3R,5S)-3-hydroxy-3-isopropyl-8-azabicyclo[3.2.1]octane-8-carboxylate To a 250 mL 3-necked round-bottom flask purged with $N_2$ was placed a solution of benzyl (1R,5S)-3-oxo-8-azabicyclo [3.2.1]octane-8-carboxylate (4.078 g, 15.73 mmol) in THF (40 mL), then LaCl$_3$(LiCl)$_2$ (0.6N) (31.5 mL, 18.88 mmol) was added. The solution was stirred at rt for 1 h, then the reaction was cooled to 0° C. and isopropylmagnesium bromide (19 mL, 18.88 mmol) was added drop-wise. The reaction was stirred for 1 h at 0° C., then quenched by the addition of water, and extracted with EtOAc. The organic extracts were combined, washed with brine, dried over anhydrous Na$_2$SO$_4$, and concentrated under reduced pressure. The crude product was purified by column chromatography using silica gel eluting with EtOAc/petroleum ether (1:10) affording 3.8 g (80%) of the title compound as a white solid. $^1$H NMR (300 MHz, CDCl$_3$): δ 7.38-7.30 (m, 5H), 5.14 (s, 2H), 4.33 (s, 2H), 2.19-2.12 (m, 2H), 1.93-1.85 (m, 4H),

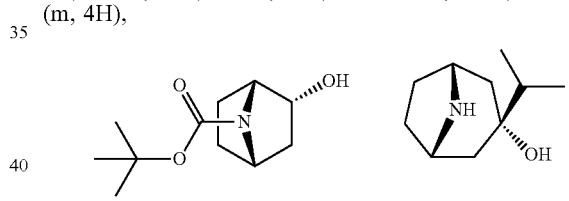

1.64-1.59 (d, 2H, J=9.0 Hz), 1.41-1.32 (m, 1H), 1.08-1.01 (m, 1H), 0.83-0.81 (d, 6H, J=6.6 Hz), 1.76-1.73 (m, 4H).

B. (1R,3R,5S)-3-isopropyl-8-azabicyclo[3.2.1]octan-3-ol

To a 250 mL round-bottom flask, was placed a solution of benzyl (1R,3R,5S)-3-hydroxy-3-isopropyl-8-azabicyclo [3.2.1]octane-8-carboxylate (1.80 g, 5.93 mmol, as prepared in the previous step) in MeOH (50 mL). To this mixture was added Pd/C (200 mg) then the solution was degassed and back-flushed with H$_2$. The reaction was stirred at rt for 2 h, then the suspension was filtered and the filtrate was concentrated under reduced pressure affording 1.00 g (quantitative) of the crude title compound as a white solid. Mass Spectrum (LCMS, ESI pos.):

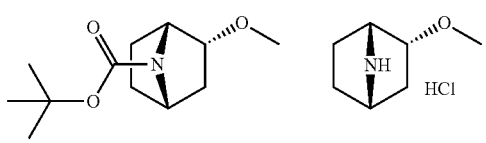

Calcd. for $C_{10}H_{20}NO$: 170 (M+H); found: 170.

Preparation of Intermediate IVA: (±)-(1R,2R,4S)-2-Methoxy-7-azabicyclo[2.2.1]heptane Hydrochloride A. tert-Butyl (1R,2R,4S)-2-Hydroxy-7-azabicyclo[2.2.1]heptane-7-carboxylate To a 100 mL round-bottom flask purged with $N_2$ was placed a solution of tert-butyl 2-oxo-7-azabicyclo[2.2.1]heptane-7-carboxylate (900 mg, 4.26 mmol) in MeOH (15 mL) then $NaBH_4$ (243 mg, 6.4 mmol) was added. The resulting solution was stirred at rt overnight. The reaction was quenched by the addition of 100 mL of water, then the mixture was extracted with EtOAc (3×100 mL). The organic extracts were combined, washed with brine (3×100 mL), dried over anhydrous $Na_2SO_4$, and concentrated under reduced pressure. The residue was purified by column chromatography using a silica gel column eluting with EtOAc/petroleum ether (1:4) affording 550 mg (61%) of the title compound as a colorless oil. Mass Spectrum (LCMS, ESI pos.): Calcd. for $C_{11}H_{20}NO_3$: 214 (M+H); found: 214.

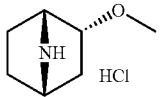

B. tert-Butyl (1R,2R,4S)-2-Methoxy-7-azabicyclo[2.2.1]heptane-7-carboxylate

To a 100 mL round-bottom flask purged with $N_2$ was placed a solution of tert-butyl (1R,2S,4S)-2-hydroxy-7-azabicyclo[2.2.1]heptane-7-carboxylate (358 mg, 1.68 mmol, as prepared in the previous step) and NaH (81 mg, 3.38 mmol) in DMF (5 mL). This was followed by the addition of iodomethane (477 mg, 3.36 mmol) then the reaction was stirred at rt overnight. The reaction was quenched by the addition of 100 mL of water and the resulting mixture was extracted with EtOAc (3×100 mL). The organic extracts were combined, washed with brine (3×100 mL), dried over anhydrous $Na_2SO_4$, and concentrated under reduced pressure. The crude product was purified by column chromatography using a silica gel column eluting with EtOAc/petroleum ether (1:4) affording 281 mg (74%) of the title compound as a colorless oil. Mass Spectrum (LCMS, ESI pos.): Calcd. for $C_{12}H_{22}NO_3$: 228 (M+H); found: 228. $^1$H NMR (400 MHz, $CDCl_3$): δ 4.29-4.26 (m, 1H), 4.14-4.11 (m, 1H), 3.84-3.81 (m, 1H), 3.28 (s, 3H), 2.17-2.14 (m, 1H), 2.03-1.99 (m, 1H), 1.80-1.76 (m, 1H), 1.61-1.58 (m, 1H), 1.49-1.46 (m, 1H), 1.45 (s, 9H), 1.11-1.08 (m, 1H).

C. (±)-(1R,2R,4S)-2-Methoxy-7-azabicyclo[2.2.1]heptane Hydrochloride

To a 50 mL round-bottom flask purged with $N_2$ was placed tert-butyl (1R,2S,4S)-2-methoxy-7-azabicyclo[2.2.1]heptane-7-carboxylate (280 mg, 1.23 mmol, as prepared in the previous step) and a solution of HCl in dioxane (3 mL). The resulting solution was stirred at rt for 2 h then the reaction was concentrated under reduced pressure affording 140 mg of the title compound as white solid. Mass Spectrum (LCMS, ESI pos.): Calcd. for $C_7H_{14}NO$: 128 (M+H); found: 128.

Example 1A. 2-(7-Azabicyclo[2.2.1]heptan-7-yl)-1-(1-(4-chlorophenyl)-2-methyl-6-(2-(methylsulfonyl)ethyl)-1H-indol-3-yl)ethan-1-one-(1A)

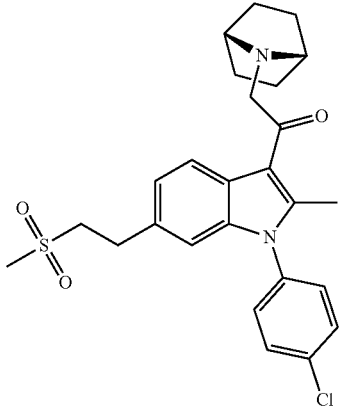

A. tert-Butyl 6-Bromo-2-methyl-1H-indole-1-carboxylate

To a 100 mL round-bottom flask purged with $N_2$ was placed a solution of 6-bromo-2-methyl-1H-indole (1.00 g, 4.76 mmol) and DMAP (58 mg, 0.47 mmol) in THF (15 mL), followed by the addition of $Boc_2O$ (1.565 g, 7.17 mmol). The resulting solution was stirred at rt for 2 h then the solvent was removed under reduced pressure. The crude product was purified by column chromatography affording 1.32 g (89%) of the title compound as a yellow solid. Mass Spectrum (LCMS, ESI pos.): Calcd. for $C_{14}H_{17}BrNO_2$: 310; found: 310 [M+H].

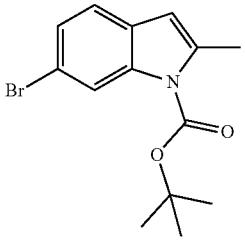

B. (E)-2-Methyl-6-(2-(methylsulfonyl)vinyl)-1H-indole

To a 20 mL microwave tube purged with $N_2$ was placed a solution of tert-butyl 6-bromo-2-methyl-1H-indole-1-carboxylate (1.27 g, 4.08 mmol, as prepared in the previous step), DIPEA (1.58 g, 12.3 mmol) and vinylmethylsulfone (651 mg, 6.13 mmol) in DMF (15 mL). To the stirred solution was added $Pd(OAc)_2$ (46.0 mg, 0.200 mmol) and $P(o\text{-Tolyl})_3$ (125 mg, 0.41 mmol). The reaction was heated to 160° C. for 2.5 h in the microwave, then the reaction was filtered and the filtrate was concentrated under reduced pressure. The crude product was purified by Prep-HPLC ((IntelFlash-1): Column, C18; mobile phase, ACN:H₂O=5:95 to 50:50 over 20 min, then ACN:H₂O=50:50 to 95:5 over 10 min) affording 437 mg (46%) of the title compound as a yellow solid. Mass Spectrum (LCMS, ESI pos.): Calcd. for $C_{12}H_{14}NO_2S$: 236 (M+H); found: 236.

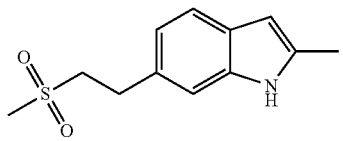

C. 2-Methyl-6-(2-(methylsulfonyl)ethyl)-1H-indole

To a 100 mL round-bottom flask purged with N₂ was placed a solution of 6-[(E)-2-methanesulfonylethenyl]-2-methyl-1H-indole (337 mg, 1.43 mmol, as prepared in the previous step) in EtOAc (20 mL), followed by the addition of Pd/C (65 mg). The resulting solution was degassed and back-flushed with H₂ then the mixture was stirred at rt for 3 h under an atmosphere of H₂. The H₂ was vented from the flask then the reaction was filtered, and the filtrate was concentrated under reduced pressure affording 290 mg (85%) of the title compound as a yellow solid. Mass Spectrum (LCMS, ESI pos.): Calcd. for $C_{12}H_{16}NO_2S$: 238 (M+H); found: 238.

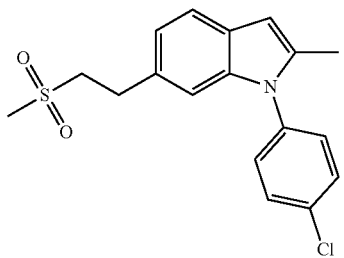 [SMILES: Cc1cc2ccc(CCS(C)(=O)=O)cc2n1-c1ccc(Cl)cc1]

D. 1-(4-Chlorophenyl)-2-methyl-6-(2-(methylsulfonyl)ethyl)-1H-indole

To a 20 mL microwave tube purged with N₂ was placed a solution of 6-(2-methanesulfonylethyl)-2-methyl-1H-indole (340 mg, 1.43 mmol, as prepared in the previous step), 1-chloro-4-iodobenzene (512 mg, 2.15 mmol), and K₃PO₄ (608 mg, 2.86 mmol) in dioxane (10 mL). Then (1R,2R)-cyclohexane-1,2-diamine (33 mg, 0.29 mmol) and CuI (27 mg, 0.14 mmol) were added. The reaction was heated to 130° C. for 3 h in the microwave. The reaction was filtered and the filtrate was diluted with 100 mL of brine. The mixture was extracted with DCM (3×150 mL) and the extracts were combined, dried over anhydrous MgSO₄, and concentrated under reduced pressure. The crude product was purified by Flash-Prep-HPLC ((IntelFlash-1): Column, C18; mobile phase, ACN:H₂O=5:95 to 60:40 over 15 min, then ACN:H₂O=60:40 for 10 min) affording 220 mg (44%) of the title compound as a yellow solid. Mass Spectrum (LCMS, ESI pos.): Calcd. for $C_{18}H_{19}ClNO_2S$: 348 (M+H); found: 348.

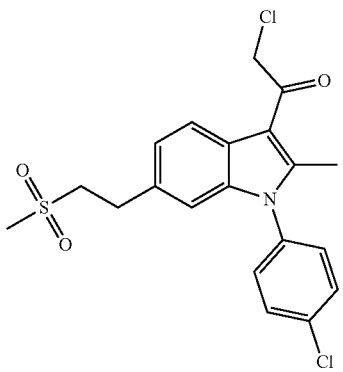 [SMILES: Cc1c(C(=O)CCl)c2ccc(CCS(C)(=O)=O)cc2n1-c1ccc(Cl)cc1]

E. 2-Chloro-1-(1-(4-chlorophenyl)-2-methyl-6-(2-(methylsulfonyl)ethyl)-1H-indol-3-yl)ethan-1-one To a 50 mL 3-necked round-bottom flask purged with N₂ was placed a solution of 1-(4-chlorophenyl)-6-(2-methanesulfonylethyl)-2-methyl-1H-indole (100 mg, 0.290 mmol, as prepared in the previous step) in DCM (2 mL). The solution was cooled to 0° C., then a solution of Et₂AlCl in (0.55 mL, 0.493 mmol) was added drop-wise with stirring. The solution was stirred for 30 min at 0° C., then 2-chloroacetyl chloride (40.0 µL, 0.503 mmol) was added drop-wise to the stirred reaction. The solution was stirred for 30 min at 0° C., then warmed to rt and stirred for 1 h. The reaction mixture was diluted with 10 mL of brine and then the pH was adjusted to 8 with saturated aqueous NaHCO₃. The mixture was extracted with DCM (2×30 mL), the organic extracts were combined, washed with brine (3×10 mL), and dried over anhydrous Na₂SO₄. The solvent was removed under reduced pressure affording 120 mg (98%) of the title compound as a crude yellow oil. Mass Spectrum (LCMS, ESI pos.): Calcd. for $C_{20}H_{20}Cl_2NO_3S$: 424 (M+H); found: 424.

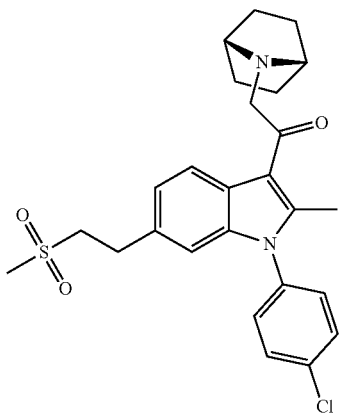 [SMILES: Cc1c(C(=O)CN2[C@H]3CC[C@@H]2CC3)c2ccc(CCS(C)(=O)=O)cc2n1-c1ccc(Cl)cc1]

F. 2-((1S,4S)-7-Azabicyclo[2.2.1]heptan-7-yl)-1-(1-(4-chlorophenyl)-2-methyl-6-(2-(methylsulfonyl)ethyl)-1H-indol-3-yl)ethan-1-one (1A)

To a 50-mL round-bottom flask purged with N₂ was placed a solution of 2-chloro-1-[1-(4-chlorophenyl)-6-(2-methanesulfonylethyl)-2-methyl-1H-indol-3-yl]ethan-1-one (120 mg, 0.28 mmol, as prepared in the previous step) in DMF (2 mL). Then 7-azabicyclo[2.2.1]heptane (194 mg, 2.00 mmol) and K$_2$CO$_3$ (160 mg, 1.16 mmol) were added. The resulting solution was stirred overnight at room temperature. The crude product was purified by Flash-Prep-HPLC ((IntelFlash-1): Column, C18; mobile phase, ACN: H$_2$O (with 0.05% NH$_3$.H$_2$O)=0:100 to 95:5 over 15 min, then MeOH (with 0.05% NH$_3$.H$_2$O):H$_2$O (with 0.05% NH$_3$.H$_2$O)=95:5 for 10 min) affording 47.5 mg (35%) of the title compound as a yellow solid. Mass Spectrum (LCMS, ESI pos.): Calcd. for C$_{26}$H$_{30}$ClN$_2$O$_3$S: 485.2 (M+H); found: 485.3. $^1$H NMR (400 MHz, DMSO-d$_6$): δ 8.04 (d, J=8.4 Hz, 1H), 7.73 (d, J=8.8 Hz, 2H), 7.52 (d, J=8.8 Hz, 2H), 7.19 (d, J=8.0 Hz, 1H), 6.94 (s, 1H), 3.71 (s, 2H), 3.43-3.35 (m, 4H), 3.05-3.00 (m, 2H), 2.94 (s, 3H), 1.73-1.67 (m, 4H), 1.30-1.23 (m, 4H).

Using the procedures described in Example 1A, and reagents, starting materials, and conditions known to those skilled in the art, the following compounds representative of the present invention were prepared:

| Cpd | Data |
|---|---|
| 2A | 2-((1R,5S)-8-Azabicyclo[3.2.1]octan-8-yl)-1-(1-(4-chlorophenyl)-2-methyl-6-(2-(methylsulfonyl)ethyl)-1H-indol-3-yl)ethan-1-one<br>Mass Spectrum (LCMS, ESI pos.): Calcd. for C$_{27}$H$_{32}$ClN$_2$O$_3$S: 499 (M + H); found: 499. $^1$H NMR (300 MHz, DMSO-d$_6$): δ 8.06 (d, J = 8.1 Hz, 1H), 7.72 (d, J = 8.7 Hz, 2H), 7.52 (d, J = 8.7 Hz, 2H), 7.18 (d, J = 8.1 Hz, 1H), 6.94 (s, 1H), 3.63 (s, 2H), 3.41-3.37 (m, 2H), 3.25-3.21 (m, 2H), 3.05-3.02 (m, 2H), 2.93 (s, 3H), 2.56 (s, 3H), 1.99-1.92 (m, 2H), 1.66-1.53 (m, 6H), 1.32-1.22 (m, 4H). |
| 4A | 1-(1-(4-Chlorophenyl)-2-methyl-6-(2-(methylsulfonyl)ethyl)-1H-indol-3-yl)-2-((1R,3R,5S)-3-hydroxy-8-azabicyclo[3.2.1]octan-8-yl)ethan-1-one<br>Mass Spectrum (LCMS, ESI pos.): Calcd. for C$_{27}$H$_{32}$ClN$_2$O$_4$S: 515 (M + H); found: 515. $^1$H NMR (400 MHz, DMSO-d$_6$): δ 8.05 (d, J = 8.0 Hz, 1H), 7.73 (d, J = 8.4 Hz, 2H), 7.52 (d, J = 8.4 Hz, 2H), 7.18 (d, J = 8.4 Hz, 1H), 6.94 (s, 1H), 4.30 (s, 1H), 3.82 (s, 1H), 3.64 (s, 2H), 3.37 (m, 2H), 3.21 (s, 2H), 3.03 (m, 2H), 2.94 (s, 3H), 2.55 (s, 3H), 2.10-2.09 (m, 2H), 1.93-1.89 (m, 4H), 1.58-1.55 (m, 2H). |
| 5A | 1-(1-(4-Chlorophenyl)-2-methyl-6-(2-(methylsulfonyl)ethyl)-1H-indol-3-yl)-2-((1R,3S,5S)-3-hydroxy-8-azabicyclo[3.2.1]octan-8-yl)ethan-1-one<br>Mass Spectrum (LCMS, ESI pos.): Calcd. for C$_{27}$H$_{32}$ClN$_2$O$_4$S: 515 (M + H); found: 515. $^1$H NMR (400 MHz, DMSO-d$_6$): δ 8.05 (d, J = 8.0 Hz, 1H), 7.73 (d, J = 8.8 Hz, 2H), 7.52 (d, J = 8.8 Hz, 2H), 7.19 (d, J = 8.4 Hz, 1H), 6.95 (s, 1H), 4.38-4.37 (m, 1H), 3.74 (s, 3H), 3.39-3.35 (m, 2H), 3.32 (s, 2H), 3.05-3.01 (m, 2H), 2.94 (s, 3H), 2.55 (s, 3H), 1.92-1.90 (m, 2H), 1.64 (s, 2H), 1.54-1.48 (m, 4H). |
| 6A | 1-(1-(4-Chlorophenyl)-2-methyl-6-(2-(methylsulfonyl)ethyl)-1H-indol-3-yl)-2-((1R,2S,4S)-2-hydroxy-7-azabicyclo[2.2.1]heptan-7-yl)ethan-1-one<br>Mass Spectrum (LCMS, ESI pos.): Calcd. for C$_{26}$H$_{30}$ClN$_2$O$_4$S: 501 (M + H); found: 501. $^1$H NMR (400 MHz, DMSO-d$_6$): δ 8.03 (d, J = 8.4 Hz, 1H), 7.73 (d, J = 8.4 Hz, 2H), 7.52 (d, J = 8.4 Hz, 2H), 7.19 (d, J = 8.4 Hz, 1H), 6.94 (s, 1H), 4.69 (m, 1H), 4.06-4.04 (m, 1H), 3.75-3.66 (m, 2H), 3.39-3.35 (m, 2H), 3.32 (s, 2H), 3.05-3.01 (m, 2H), 2.94 (s, 3H), 2.54 (s, 3H), 2.06-1.97 (m, 2H), 1.82-1.79 (m, 1H), 1.60-1.54 (m, 1H), 1.39-1.38 (m, 1H), 0.83-0.79 (m, 1H). |
| 7A | 1-(1-(4-Chlorophenyl)-2-methyl-6-(2-(methylsulfonyl)ethyl)-1H-indol-3-yl)-2-(4-hydroxypiperidin-1-yl)ethan-1-one<br>Mass Spectrum (LCMS, ESI pos.): Calcd. for C$_{25}$H$_{30}$ClN$_2$O$_4$S: 489 (M + H); found: 489. $^1$H NMR (400 MHz, DMSO-d$_6$): δ 8.02 (d, J = 8.0 Hz, 1H), 7.74 (d, J = 8.8 Hz, 2H), 7.53 (d, J = 8.8 Hz, 2H), 7.20 (d, J = 8.0 Hz, 1H), 6.95 (s, 1H), 4.56 (m, 1H), 3.66 (s, 2H), 3.37-3.35 (m, 1H), 3.32 (s, 2H), 3.05-3.01 (m, 2H), 2.94 (s, 3H), 2.82-2.80 (m, 2H), 2.53 (s, 3H), 2.31-2.18 (m, 2H), 1.73-1.71 (m, 2H), 1.42-1.39 (m, 2H). |
| 16A | 2-(7-Azabicyclo[2.2.1]heptan-7-yl)-1-(1-(4-chlorophenyl)-6-(2-(cyclopropylsulfonyl)ethyl)-2-methyl-1H-indol-3-yl)ethan-1-one<br>Mass Spectrum (LCMS, ESI pos.): Calcd. for C$_{28}$H$_{32}$ClN$_2$O$_3$S: 511 (M + H); found 511. $^1$H NMR (400 MHz, DMSO-d$_6$): δ 8.05-8.03 (d, 1H, J = 8.0 Hz), 7.74-7.72 (d, 2H, J = 8.8 Hz), 7.53-7.51 (d, 2H, J = 8.8 Hz), 7.21-7.19 (d, 1H, J = 7.6 Hz), 6.95 (s, 1H), 3.67 (s, 2H), 3.44-3.40 (m, 4H), 3.08-3.04 (m, 2H), 2.69-2.64 (m, 1H), 2.54 (s, 3H), 1.71-1.69 (m, 4H), 1.28-1.26 (m, 4H), 0.98-0.96 (m, 4H). |
| 23A | 1-(1-(4-Chlorophenyl)-6-(2-(cyclopropylsulfonyl)ethyl)-2-methyl-1H-indol-3-yl)-2-((1R,3R,5S)-3-hydroxy-8-azabicyclo[3.2.1]octan-8-yl)ethan-1-one<br>Mass Spectrum (LCMS, ESI pos.): Calcd. for C$_{29}$H$_{34}$ClN$_2$O$_4$S: 541 (M + H); found: 541. $^1$H NMR (400 MHz, DMSO-d$_6$): δ 8.06-8.04 (d, 1H, J = 8.4 Hz), 7.74-7.72 (d, 2H, J = 8.4 Hz), 7.54-7.51 (d, 2H, J = 8.4 Hz), 7.21-7.19 (d, 1H, J = 7.6 Hz), 6.95 (s, 1H), 4.24 (s, 1H), 3.83 (s, 1H), 3.66 (s, 2H), 3.44-3.40 (m, 2H), 3.29-3.23 (m, 2H), 3.08-3.06 (m, 2H), 2.70-2.63 (m, 2H), 2.55 (s, 3H), 2.11-2.09 (m, 2H), 1.94-1.91 (m, 4H), 1.60-1.56 (m, 2H), 0.98-0.96 (m, 4H). |
| 24A | 1-(1-(4-Chlorophenyl)-6-(2-(cyclopropylsulfonyl)ethyl)-2-methyl-1H-indol-3-yl)-2-((1R,3s,5S)-3-hydroxy-8-azabicyclo[3.2.1]octan-8-yl)ethan-1-one<br>Mass Spectrum (LCMS, ESI pos.): Calcd. for C$_{29}$H$_{34}$ClN$_2$O$_4$S: 541 (M + H); found: 541. $^1$H NMR (400 MHz, DMSO-d$_6$): δ 8.07-8.05 (d, 1H, J = 8.4 Hz), 7.75-7.73 (d, 2H, J = 8.8 Hz), 7.54-7.52 (d, 2H, J = 8.4 Hz), 7.22-7.20 (d, 1H, J = 8.4 Hz), 6.96 (s, 1H), 4.37-4.34 (m, 1H), 3.73 (brs, 3H), 3.45-3.41 (m, 2H), 3.33 (brs, 2H), 3.09-3.05 (m, 2H), 2.70-2.64 (m, 1H), 2.56 (s, 3H), 1.91 (brs, 2H), 1.64-1.49 (m, 6H), 0.98-0.93 (m, 4H). |
| 8A | 3-(3-(2-(7-Azabicyclo[2.2.1]heptan-7-yl)acetyl)-1-(4-chlorophenyl)-2-methyl-1H-indol-6-yl)propanenitrile<br>Mass Spectrum (LCMS, ESI pos.) Calcd. for C$_{26}$H$_{27}$ClN$_3$O: 432 (M + H); found: |

| Cpd | Data |
|---|---|
| | 432. ¹H NMR (300 MHz, d₆-DMSO): δ 8.05 (d, J = 8.4 Hz, 1H), 7.73 (d, J = 8.7 Hz, 2H), 7.52 (d, J = 8.7 Hz, 2H), 7.21 (d, J = 8.4 Hz, 1H), 6.94 (s, 1H), 3.71 (s, 2H), 3.37 (brs, 2H), 2.93-2.90 (m, 2H), 2.78-2.76 (m, 2H), 2.55 (s, 3H), 1.73-1.70 (m, 4H), 1.29-1.27 (m, 4H). |
| 17A | 4-(3-(2-(7-Azabicyclo[2.2.1]heptan-7-yl)acetyl)-1-(4-chlorophenyl)-2-methyl-1H-indol-6-yl)butanenitrile<br>Mass Spectrum (LCMS, ESI pos.) Calcd. for C27H29ClN3O: 446 (M + H); found: 446. ¹H NMR (400 MHz, DMSO-d₆): δ 8.03 (d, J = 8.0 Hz, 1H), 7.72 (d, J = 8.4 Hz, 2H), 7.53 (d, J = 8.4 Hz, 2H), 7.12 (d, J = 8.4 Hz, 1H), 6.82 (s, 1H), 3.67 (s, 2H), 3.39 (s, 2H), 2.68 (m, 2H), 2.54 (s, 3H), 2.43 (t, J = 6.8 Hz, 2H), 1.85-1.78 (m, 2H), 1.71-1.69 (m, 4H), 1.28-1.26 (m, 4H). |
| 10A | (±)-3-(1-(4-Chlorophenyl)-3-(2-((2S)-2-hydroxy-7-azabicyclo[2.2.1]heptan-7-yl)acetyl)-2-methyl-1H-indol-6-yl)propanenitrile<br>Mass Spectrum (LCMS, ESI pos.): Calcd. for C₂₆H₂₇ClN₃O₂: 448 (M + H); found: 448. ¹H NMR (400 MHz, CD₃OD): δ 8.03 (d, J = 8.4 Hz, 1H), 7.69 (d, J = 8.4 Hz, 2H), 7.44 (d, J = 8.4 Hz, 2H), 7.24 (d, J = 8.4 Hz, 1H), 6.96 (s, 1H), 3.91-3.94 (m, 1H), 3.71-3.72 (m, 1H), 3.33-3.37 (m, 1H), 3.04-3.06 (m, 2H), 2.96-3.00 (m, 2H), 2.72-2.77 (m, 2H), 2.65 (s, 3H), 2.53-2.61 (m, 2H), 1.93-1.95 (m, 2H), 1.67-1.69 (m, 2H). |
| 15A | (±)-3-(1-(4-Chlorophenyl)-3-(2-((2S)-2-methoxy-7-azabicyclo[2.2.1]heptan-7-yl)acetyl)-2-methyl-1H-indol-6-yl)propanenitrile<br>Mass Spectrum (LCMS, ESI pos.): Calcd. for C₂₇H₂₉ClN₃O₂: 462 (M + H); found: 462. ¹H NMR (300 MHz, DMSO-d₆): δ 8.03 (d, J = 8.1 Hz, 1H), 7.71-7.75 (m, 2H), 7.50-7.53 (m, 2H), 7.18-7.21 (m, 1H), 6.94 (s, 1H), 3.76 (brs, 3H), 3.60 (s, 1H), 3.38 (s, 1H), 3.16 (s, 3H), 2.88-2.92 (m, 2H), 2.73-2.78 (m, 2H), 2.54 (s, 3H), 1.96-2.04 (m, 1H), 1.80-1.84 (m, 2H), 1.63-1.67 (m, 1H), 1.33-1.39 (m, 1H). |
| 20A | 3-(1-(4-Chlorophenyl)-3-(2-((1R,3R,5S)-3-hydroxy-8-azabicyclo[3.2.1]octan-8-yl)acetyl)-2-methyl-1H-indol-6-yl)propanenitrile<br>Mass Spectrum (LCMS, ESI pos.): Calcd. for C₂₇H₂₉ClN₃O₂: 462 (M + H); found: 462. ¹H NMR (400 MHz, DMSO-d₆): δ 8.05 (d, J = 8.0 Hz, 1H), 7.74-7.72 (m, 2H), 7.53-7.51 (m, 2H), 7.18 (d, J = 6.8 Hz, 1H), 6.93 (s, 1H), 4.34 (s, 1H), 3.82 (s, 1H), 3.64 (s, 2H), 3.21 (brs, 2H), 2.90 (t, J = 7.2 Hz, 2H), 2.75 (t, J = 7.2 Hz, 2H), 2.55 (s, 3H), 2.10-2.08 (m, 2H), 1.95-1.85 (m, 4H) 1.59-1.55 (m, 2H). |
| 21A | 3-(1-(4-Chlorophenyl)-3-(2-((1R,3S,5S)-3-hydroxy-8-azabicyclo[3.2.1]octan-8-yl)acetyl)-2-methyl-1H-indol-6-yl)propanenitrile<br>Mass Spectrum (LCMS, ESI pos.): Calcd. for C₂₇H₂₉ClN₃O₂: 462 (M + H); found: 462. ¹H NMR (400 MHz, DMSO-d₆): δ 8.06 (d, J = 8.4 Hz, 1H), 7.75-7.72 (m, 2H), 7.54-7.51 (m, 2H), 7.19 (d, J = 7.6 Hz, 1H), 6.94 (s, 1H), 4.38 (s, 1H), 3.73 (brs, 3H), 3.32 (brs, 2H), 2.90 (t, J = 7.2 Hz, 2H), 2.76 (t, J = 6.8 Hz, 2H), 2.56 (s, 3H), 1.91-1.85 (m, 2H), 1.64-1.53 (m, 6H). |
| 31A | 3-(3-(2-(3-(tert-Butyl)-3-hydroxy-8-azabicyclo[3.2.1]octan-8-yl)acetyl)-1-(4-chlorophenyl)-2-methyl-1H-indol-6-yl)propanenitrile<br>Mass Spectrum (LCMS, ESI pos.): Calcd. for C₃₁H₃₇ClN₃O₂: 518 (M + H); found: 518. ¹H NMR (300 MHz, DMSO-d₆): δ 8.07 (d, J = 8.1 Hz, 1H), 7.72 (d, J = 8.7 Hz, 1H), 7.49 (d, J = 8.7 Hz, 1H), 7.16 (d, J = 7.2 Hz, 1H), 6.92 (s, 1H), 3.65 (s, 2H), 3.58 (s, 1H), 3.24 (brs, 2H), 2.91-2.86 (m, 2H), 2.76-2.72 (m, 2H), 2.55 (s, 3H), 2.08-2.11 (m, 2H), 1.96? 1.75 (m, 4H), 1.34 (d, J = 13.6 Hz, 2H), 0.77 (s, 9H). |
| 32A | 3-(1-(4-Chlorophenyl)-3-(2-(3-hydroxy-3-isopropyl-8-azabicyclo[3.2.1]octan-8-yl)acetyl)-2-methyl-1H-indol-6-yl)propanenitrile<br>Mass Spectrum (LCMS, ESI pos.): Calcd. for C₃₀H₃₅ClN₃O₂: 504 (M + H); found: 504. ¹H NMR (400 MHz, DMSO-d₆): δ 8.05 (d, J = 8.4Hz, 1H), 7.72 (d, J = 8.7Hz, 2H), 7.51 (d, J = 8.4Hz, 2H), 7.18 (d, J = 8.4Hz, 1H), 6.93 (s, 1H), 3.66 (s, 2H), 3.55 (s, 1H), 3.25 (brs, 2H), 2.91-2.87 (m, 2H), 2.77-2.72 (m, 2H), 2.54 (s, 3H), 2.10-2.08 (m, 2H), 1.83-1.82 (m, 2H), 1.71-1.67 (m, 2H), 1.50-1.45 (m, 2H), 1.26-1.23 (m, 1H), 0.85-0.83 (m, 6H). |
| 33A | 3-(3-(2-(8-Azabicyclo[3.2.1]octan-8-yl)acetyl)-1-(4-chlorophenyl)-2-methyl-1H-indol-6-yl)propanenitrile<br>Mass Spectrum (LCMS, ESI pos.): Calcd. for C₂₇H₂₉ClN₃O: 446 (M + H); found: 446. ¹H NMR (400 MHz, DMSO-d₆): δ 7.22 (d, J = 8.0 Hz, 1H), 6.88 (d, J = 8.4 Hz, 2H), 6.63 (d, J = 8.8 Hz, 2H), 6.43 (d, J = 8.0 Hz, 1H), 6.15 (s, 1H), 2.68 (s, 2H), 2.53-2.51 (m, 2H), 2.19-2.15 (m, 2H), 1.93-1.89 (m, 2H), 1.81 (s, 3H), 1.34-1.32 (m, 2H), 1.15-1.13 (m, 2H), 0.97-0.95 (m, 3H), 0.90-0.71 (m, 3H). |
| 18A | (±)-4-(1-(4-Chlorophenyl)-3-(2-((2S)-2-hydroxy-7-azabicyclo[2.2.1]heptan-7-yl)acetyl)-2-methyl-1H-indol-6-yl)butanenitrile<br>Mass Spectrum (LCMS, ESI pos.): Calcd. for C₂₇H₂₉ClN₃O₂: 462 (M + H); found: 462. ¹H NMR (400 MHz, DMSO-d₆): δ 8.01(d, J = 8.0 Hz, 1H), 7.72 (d, J = 8.8 Hz, 2H), 7.53 (d, J = 8.8 Hz, 2H), 7.12 (d, J = 8.0 Hz, 1H), 6.82 (s, 1H), 4.70 (s, 1H), 4.09-4.02 (m, 2H), 3.76 (s, 2H), 3.17(d, J = 5.2 Hz, 1H), 2.69-2.67 (m, 2H), 2.53 (s, 3H), 2.43 (t, J = 7.2 Hz, 2H), 2.01-1.92 (m, 2H), 1.83-1.79 (m, 3H), 1.60-1.52 (m, 1H), 1.41-1.33 (m, 1H), 0.85-0.82 (m, 1H). |
| 19A | (±)-4-(1-(4-Chlorophenyl)-3-(2-((2S)-2-methoxy-7-azabicyclo[2.2.1]heptan-7-yl)acetyl)-2-methyl-1H-indol-6-yl)butanenitrile<br>Mass Spectrum (LCMS, ESI pos.): Calcd. for C₂₈H₃₁ClN₃O₂: 476 (M + H); |

-continued

| Cpd | Data |
|---|---|
| | found: 476. $^1$H NMR (400 MHz, DMSO-$d_6$): δ 8.01 (d, J = 8.4 Hz, 1H), 7.73 (d, J = 8.4 Hz, 2H), 7.53 (d, J = 8.4 Hz, 2H), 7.12 (d, J = 7.2 Hz, 1H), 6.82 (s, 1H), 3.74-3.71 (m, 3H), 3.58 (t, J = 4.4 Hz, 1H), 3.37-3.35 (m, 1H), 3.32 (s, 3H), 2.68 (t, J = 4.8 Hz, 2H), 2.53 (s, 3H), 2.43 (t, J = 7.2 Hz, 2H), 1.99-1.98 (m, 1H), 1.85-1.77 (m, 4H), 1.65-1.62 (m, 1H), 1.37-1.33 (m, 1H), 0.95-0.90 (m, 1H). |
| 25A | 4-(1-(4-Chlorophenyl)-3-(2-(3-hydroxy-8-azabicyclo[3.2.1]octan-8-yl)acetyl)-2-methyl-1H-indol-6-yl)butanenitrile<br>Mass Spectrum (LCMS, ESI pos.): Calcd. for $C_{28}H_{31}ClN_3O_2$: 476 (M + H); found: 476. $^1$H NMR (400 MHz, DMSO-$d_6$): δ 8.03 (d, J = 8.0 Hz, 1H), 7.73-7.71 (m, 2H), 7.54-7.53 (m, 2H), 7.11 (d, J = 8.4 Hz, 1H), 6.81 (s, 1H), 4.30 (s, 1H), 3.82 (brs, 1H), 3.63 (s, 2H), 3.20 (brs, 2H), 2.70-2.67 (m, 2H), 2.55 (s, 3H), 2.45-2.41 (m, 2H), 2.10-2.08 (m, 2H), 1.83-1.79 (m, 6H), 1.58-1.55 (m, 2H). |
| 26A | 4-(1-(4-Chlorophenyl)-3-(2-(3-hydroxy-8-azabicyclo[3.2.1]octan-8-yl)acetyl)-2-methyl-1H-indol-6-yl)butanenitrile<br>Mass Spectrum (LCMS, ESI pos.): Calcd. for $C_{28}H_{31}ClN_3O_2$: 476 (M + H); found: 476. $^1$H NMR (400 MHz, DMSO-$d_6$): δ 8.03 (d, J = 8.1 Hz, 1H), 7.73 (d, J = 8.7 Hz, 2H), 7.52 (d, J = 8.7 Hz, 2H), 7.12 (d, J = 7.5 Hz, 1H), 6.82 (s, 1H), 4.36 (s, 1H), 3.82-3.70 (m, 3H), 3.30-3.25 (m, 2H), 2.71-2.65 (m, 2H), 2.55 (s, 3H), 2.42 (t, J = 7.2 Hz, 2H), 1.90-1.52 (m, 10H). |

Example 2A. 2-(7-Azabicyclo[2.2.1]heptan-7-yl)-1-(1-(4-chlorophenyl)-2-methyl-6-((methylsulfonyl)methyl)-1H-indol-3-yl)ethan-1-one (3A)

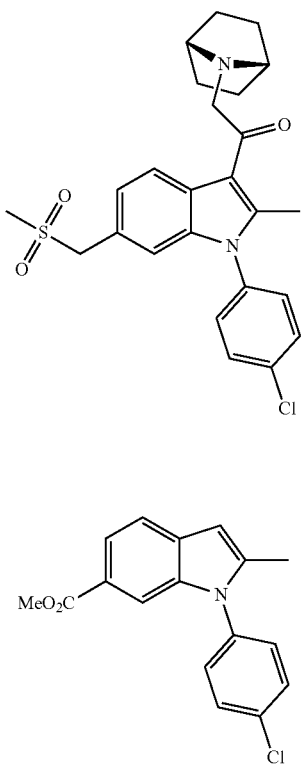

A. Methyl 1-(4-Chlorophenyl)-2-methyl-1H-indole-6-carboxylate

To a 25 mL sealed tube purged with $N_2$ was placed a solution of methyl 2-methyl-1H-indole-6-carboxylate (1.5 g, 7.93 mmol), 1-chloro-4-iodobenzene (3.8 g, 15.94 mmol) and $K_3PO_4$ (5.3 g, 24.97 mmol) in dioxane (10 mL). To this stirred solution were added CuI (310 mg, 1.63 mmol) and (1S,2S)-cyclohexane-1,2-diamine (390 mg, 3.42 mmol). The resulting solution was stirred for 8 h at 120° C. The reaction was cooled to, quenched with 100 mL of water, and then the mixture was extracted with EtOAc (2×500 mL). The organic extracts were combined, washed with brine (2×50 mL), and then concentrated under reduced pressure affording 2.3 g (97%) of the title compound as a brown solid. Mass Spectrum (LCMS, ESI pos.): Calcd. for $C_{17}H_{15}ClNO_2$: 300 (M+H); found: 300.

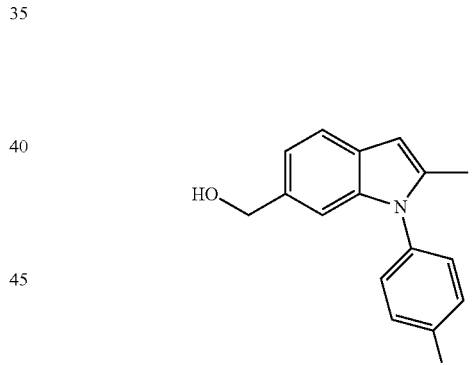

B. (1-(4-Chlorophenyl)-2-methyl-1H-indol-6-yl)methanol

To a 500 mL round-bottom flask purged with $N_2$ was placed a solution of methyl 1-(4-chlorophenyl)-2-methyl-1H-indole-6-carboxylate (2.3 g, 7.67 mmol, as prepared in the previous step) in THF (200 mL). The solution was cooled to 0° C., then $LiAlH_4$ (585 mg, 17.24 mmol) was added in portions. The reaction was stirred for 1 h at rt, then quenched by the addition of 10 mL of water. The solids were removed by filtration, then the filtrate was concentrated under reduced pressure affording 1.6 g (77%) of the title compound as a white solid. Mass Spectrum (LCMS, ESI pos.): Calcd. for $C_{16}H_{15}ClNO$: 272 (M+H); found 272.

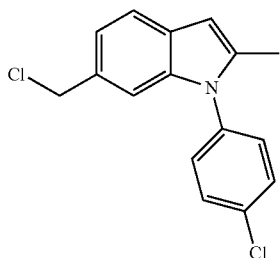 [SMILES: Cc1cc2ccc(CCl)cc2n1-c1ccc(Cl)cc1]

C. 6-(Chloromethyl)-1-(4-chlorophenyl)-2-methyl-1H-indole

To a 250 mL round-bottom flask purged with $N_2$ was placed a solution of [1-(4-chlorophenyl)-2-methyl-1H-indol-6-yl]methanol (1.0 g, 3.68 mmol, as prepared in the previous step) in DCM (20 mL). To this solution was added TEA (900 mg, 8.89 mmol) and MsCl (600 mg, 5.24 mmol) and then the reaction was stirred at rt for 16 h. The reaction was quenched by the addition of 100 mL of water and the mixture was extracted with EtOAc (2×200 mL). The organic extracts were combined, washed with brine (2×100 mL), and concentrated under reduced pressure affording 100 mg (9%) of the title compound as a white solid. Mass Spectrum (LCMS, ESI pos.): Calcd. for $C_{16}H_{14}Cl_2N$: 290 (M+H); found: 290.

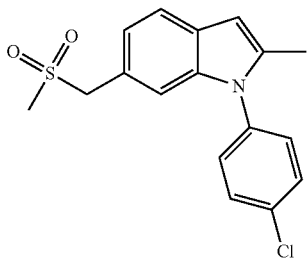 [SMILES: Cc1cc2ccc(CS(C)(=O)=O)cc2n1-c1ccc(Cl)cc1]

D. 1-(4-Chlorophenyl)-2-methyl-6-((methylsulfonyl)methyl)-1H-indole

To a 50 mL round-bottom flask purged with $N_2$ was placed a solution of 6-(chloromethyl)-1-(4-chlorophenyl)-2-methyl-1H-indole (200 mg, 0.69 mmol, as prepared in the previous step) in DMF (5 mL). To this solution was added sodium methanesulfinate (351 mg, 3.44 mmol) and the reaction was stirred at 120° C. for 1 h. The reaction was quenched by the addition of 10 mL of water and extracted with EtOAc (2×50 mL). The organic layers were combined, washed with brine (2×10 mL), and concentrated under reduced pressure affording 118 mg (51%) of the title compound as a yellow solid. $^1$H NMR (400 MHz, DMSO-$d_6$): δ 7.69-7.66 (m, 2H), 7.53-7.48 (m, 3H), 7.12-7.08 (m, 2H), 6.46 (s, 1H), 4.45 (s, 1H), 2.82 (s, 3H), 2.78 (s, 3H).

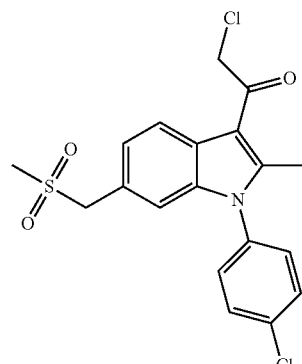

E. 2-Chloro-1-(1-(4-chlorophenyl)-2-methyl-6-((methylsulfonyl)methyl)-1H-indol-3-yl)ethan-1-one To a 50 mL 3-necked round-bottom flask purged with $N_2$ was placed a solution of 1-(4-chlorophenyl)-6-(methanesulfonylmethyl)-2-methyl-1H-indole (200 mg, 0.60 mmol, as prepared in the previous step) in DCM (5 mL). To this solution were added $Et_2AlCl$ (1 mL, 0.89 mmol) and 2-chloroacetyl chloride (100 mg, 0.89 mmol). The resulting solution was stirred at rt for 5 h then the reaction was quenched with water (10 mL) and extracted with EtOAc (2×50 mL). The organic extracts were combined, washed with brine (2×10 mL), and concentrated under reduced pressure affording 140 mg of the crude title compound as a brown solid. Mass Spectrum (LCMS, ESI pos.): Calcd. for $C_{19}H_{18}Cl_2NO_3S$: 410 (M+H); found: 410.

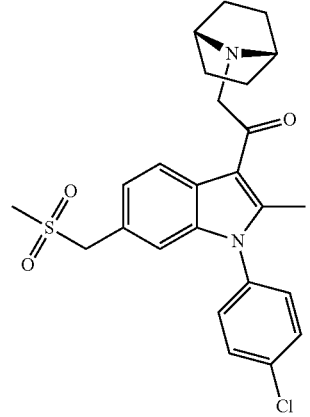

F. 2-(7-Azabicyclo[2.2.1]heptan-7-yl)-1-(1-(4-chlorophenyl)-2-methyl-6-((methylsulfonyl) methyl)-1H-indol-3-yl)ethan-1-one (3A)

To a 50 mL round-bottom flask purged with $N_2$ was placed a solution of 2-chloro-1-[1-(4-chlorophenyl)-6-(methanesulfonylmethyl)-2-methyl-1H-indol-3-yl]ethan-1-one (144 mg, 0.35 mmol, as prepared in the previous step) in DMF (3 mL), then $K_2CO_3$ (242 mg, 1.74 mmol) and 4-chlorocyclohexan-1-amine (233 mg, 1.74 mmol) were added. The resulting solution was stirred at rt for 5 h. The crude product was purified by Flash-Prep-HPLC ((IntelFlash-1): Column, C18; mobile phase, $H_2O$/ACN=100:1 to 45:55 over 30 min)

affording 29 mg (18%) of the title compound as a yellow solid. Mass Spectrum (LCMS, ESI pos.): Calcd. for $C_{25}H_{28}ClN_2O_3S$: 471 (M+H); found: 471. $^1$H NMR (400 MHz, DMSO-$d_6$): δ 8.13-8.11 (d, J=8.4 Hz, 1H), S 7.76-7.74 (d, J=8.8 Hz, 2H), 7.56-7.54 (d, J=8.4 Hz, 2H), 7.30-7.28 (d, J=8.4 Hz, 1H), 7.08 (s, 1H), 4.49 (s, 2H), 3.69 (s, 2H), 3.40 (s, 2H), 2.83 (s, 3H), 2.57 (s, 3H), 1.72-1.70 (m, 4H), 1.29-1.27 (m, 4H).

Example 3A. 2-(7-Azabicyclo[2.2.1]heptan-7-yl)-1-(1-(4-chlorophenyl)-2-methyl-6-(oxetan-3-ylmethyl)-1H-indol-3-yl)ethan-1-one (11A)

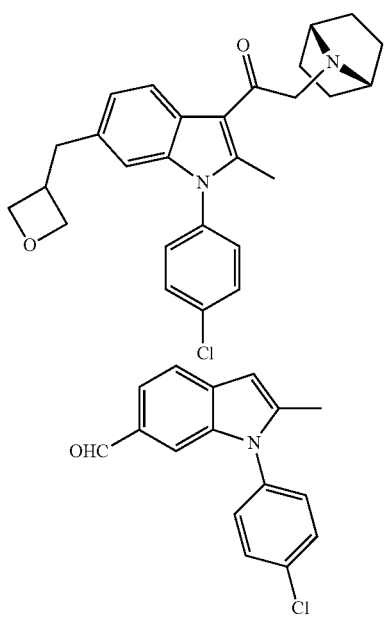

A. 1-(4-Chlorophenyl)-2-methyl-1H-indole-6-carbaldehyde

To a 50 mL round-bottom flask purged with $N_2$ was placed a solution of [1-(4-chlorophenyl)-2-methyl-1H-indol-6-yl]methanol (770 mg, 2.84 mmol, as prepared in Step B of Example 2A) in DCM (30 mL). To this solution was added DMP (1.33 g, 3.11 mmol) and the resulting solution was stirred at rt for 2 h. The crude reaction mixture was purified by column chromatography using a silica gel column eluting with EtOAc/petroleum ether (1/10) affording 577 mg (75%) of the title compound as light yellow oil. Mass Spectrum (LCMS, ESI pos.): Calcd. for $C_{16}H_{13}ClNO$: 270 (M+H); found: 270.

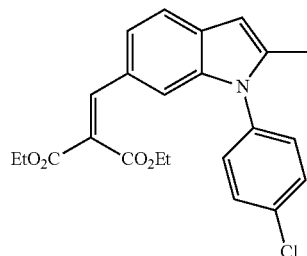

B. Diethyl 2-((1-(4-Chlorophenyl)-2-methyl-1H-indol-6-yl)methylene)malonate

To a 100 mL round-bottom flask with $N_2$ was placed a solution of 1-(4-chlorophenyl)-2-methyl-1H-indole-6-carbaldehyde (1.377 g, 5.12 mmol, as prepared in the previous step), diethyl malonate (3.9 mL, 25.6 mmol), piperidine (0.48 mL, 4.86 mmol), and benzoic acid (384 mg, 3.14 mmol) in toluene (50 mL), then the reaction was stirred overnight at 110° C. in an oil bath. The reaction mixture was cooled to, diluted with 50 mL of EtOAc, washed with brine (3×15 mL), dried, and concentrated under reduced pressure. The crude product was purified by column chromatography on a silica gel column eluting with EtOAc/petroleum ether (1/10) affording 1.781 g (85%) of the title compound as light yellow oil. Mass Spectrum (LCMS, ESI pos.): Calcd. for $C_{23}H_{23}ClNO_4$: 412 (M+H); found: 412.

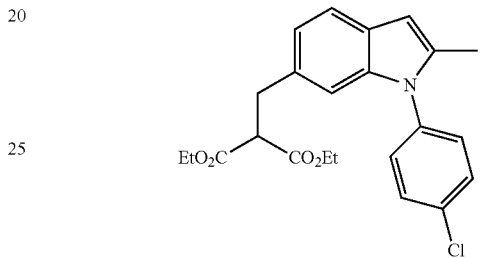

C. Diethyl 2-((1-(4-Chlorophenyl)-2-methyl-1H-indol-6-yl)methyl)malonate

To a 100 mL round-bottom flask, was placed a solution of 1,3-diethyl 2-[[1-(4-chlorophenyl)-2-methyl-1H-indol-6-yl]methylidene]propanedioate (1.781 g, 4.33 mmol, as prepared in the previous step) and Pd/C (178 mg) in EtOAc (50 mL). The resulting solution degassed and back-flushed with $H_2$ and then stirred at rt under $H_2$ overnight. The suspension was filtered and the filtrate was concentrated under reduced pressure. The crude product was purified by column chromatographed on a silica gel column eluting with EtOAc/petroleum ether (1/10) affording 1.58 g (88%) of the title compound as a yellow oil. Mass Spectrum (LCMS, ESI pos.): Calcd. for $C_{23}H_{24}ClNO_4$: 414 (M+H); found: 414.

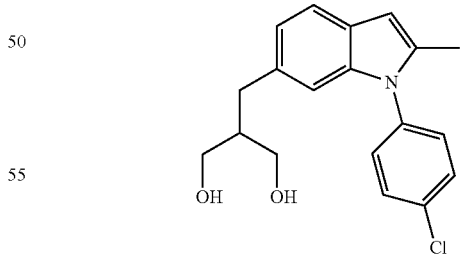

D. 2-((1-(4-Chlorophenyl)-2-methyl-1H-indol-6-yl)methyl)propane-1,3-diol

To a 100 mL round-bottom flask purged with $N_2$ was placed a solution of 1,3-diethyl 2-[[1-(4-chlorophenyl)-2-methyl-1H-indol-6-yl]methyl]propanedioate (1.580 g, 3.82 mmol, as prepared in the previous step) in THF (50 mL)

followed by the addition of DIBAL-H (30.6 mL, 30.6 mmol) drop-wise with stirring. The resulting solution was stirred at rt for 3 h then the reaction was quenched by the addition of 30 mL of methanol/satd aq Rochelle salt. The mixture was filtered, then the filtrate was washed with brine (2×20 mL), dried, and concentrated under reduced pressure. The crude product was purified by column chromatography on a silica gel column eluting with EtOAc/petroleum ether (1/1) affording 731 mg (58%) of the title compound as light yellow oil. Mass Spectrum (LCMS, ESI pos.): Calcd. for $C_{19}H_{21}ClNO_2$: 330 (M+H); found: 330.

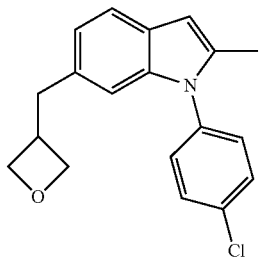 [SMILES: Cc1cc2ccc(CC3COC3)cc2n1-c1ccc(Cl)cc1]

E. 1-(4-Chlorophenyl)-2-methyl-6-(oxetan-3-ylmethyl)-1H-indole

To a 100 mL round-bottom flask purged with $N_2$ was placed a solution of 2-[[1-(4-chlorophenyl)-2-methyl-1H-indol-6-yl]methyl]propane-1,3-diol (1.20 g, 3.64 mmol, as prepared in the previous step) in THF (50 mL), then the solution was cooled to 0° C. and n-BuLi (1.46 mL, 3.64 mmol) was added drop-wise. After 30 min, TsCl (693 mg, 3.63 mmol) was added and the mixture was stirred at 0° C. for 1 h. n-BuLi (1.57 mL, 4.00 mmol) was added drop-wise to the stirred reaction mixture at 0° C., then the reaction was heated to 60° C. and stirred for 3 h. The reaction was cooled to rt, quenched by the addition of 30 mL of brine, and extracted with EtOAc (3×30 mL). The organic extracts were combined, washed with brine (1×30 mL), dried over anhydrous $Na_2SO_4$, and concentrated under reduced pressure. The crude product was purified by column chromatography on a silica gel column eluting with EtOAc/petroleum ether (1/10) affording 795 mg (70%) of the title compound as light yellow oil. Mass Spectrum (LCMS, ESI pos.): Calcd. for $C_{19}H_{19}ClNO$: 312 (M+H); found: 312.

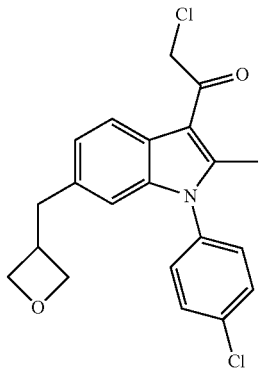 [SMILES: Cc1c(C(=O)CCl)c2ccc(CC3COC3)cc2n1-c1ccc(Cl)cc1]

F. 2-Chloro-1-(1-(4-chlorophenyl)-2-methyl-6-(oxetan-3-ylmethyl)-1H-indol-3-yl)ethan-1-one To a 25 mL round-bottom flask purged with $N_2$ was placed a solution of 1-(4-chlorophenyl)-2-methyl-6-(oxetan-3-ylmethyl)-1H-indole (110 mg, 0.35 mmol, as prepared in the previous step) in DCM (10 mL), followed by the addition of 2-chloroacetyl chloride (80.0 µL, 1.01 mmol) and $Et_2AlCl$ (0.78 mL, 0.70 mmol). The resulting solution was stirred at 0° C. for 40 min then the mixture was concentrated under reduced pressure affording 142 mg (crude) of the title compound as a yellow oil. Mass Spectrum (LCMS, ESI pos.): Calcd. for $C_{21}H_{20}Cl_2NO_2$: 388 (M+H); found: 388.

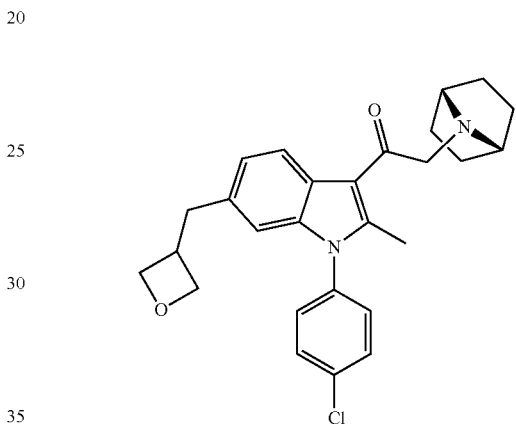

G. 2-(7-Azabicyclo[2.2.1]heptan-7-yl)-1-(1-(4-chlorophenyl)-2-methyl-6-(oxetan-3-ylmethyl)-1H-indol-3-yl)ethan-1-one (11A)

To a 25 mL round-bottom flask purged with $N_2$ was placed a solution of 2-chloro-1-[1-(4-chlorophenyl)-2-methyl-6-(oxetan-3-ylmethyl)-1H-indol-3-yl]ethan-1-one (111 mg, 0.286 mmol, as prepared in the previous step) in DMF (5 mL) then 7-aza-bicyclo[2.2.1]heptane hydrochloride (77 mg, 0.572 mmol) and $K_2CO_3$ (59.0 mg, 0.427 mmol) were added. The reaction was stirred at rt overnight then the crude product was purified by Prep-HPLC (Column, X-bridge RP18, 19×150 mm; mobile phase: Water (0.05% $NH_4HCO_3$)/ACN 85:15 to 40:60 over 10 min) affording 42.8 mg (33%) of the title compound as a white solid. Mass Spectrum (LCMS, ESI pos.): Calcd. for $C_{27}H_{30}ClN_2O_2$: 449 (M+H); found 449. $^1$H NMR (300 MHz, $CDCl_3$): δ 7.87 (d, J=8.4 Hz, 1H), 7.59-7.55 (m, 2H), 7.28-7.23 (m, 2H), 0.07-7.04 (m, 1H), 6.74 (s, 1H), 4.75-4.71 (m, 2H), 4.45-4.41 (m, 2H), 3.89 (s, 2H), 3.58 (s, 2H), 3.31-3.21 (m, 1H), 3.04 (d, J=7.8 Hz, 2H), 2.59 (s, 3H), 1.90-1.88 (m, 4H, H), 1.39-1.36 (m, 4H).

Using the procedures described in Example 3A, and reagents, starting materials, and conditions known to those skilled in the art, the following compounds representative of the present invention were prepared:

| Cpd | Data |
|---|---|
| 12A | 1-(1-(4-Chlorophenyl)-2-methyl-6-(oxetan-3-ylmethyl)-1H-indol-3-yl)-2-((1R,2S,4S)-2-methoxy-7-azabicyclo[2.2.1]heptan-7-yl)ethan-1-one<br>Mass Spectrum (LCMS, ESI pos.): Calcd. for $C_{28}H_{32}ClN_2O_3$: 479 (M + H); found 479. $^1$H NMR (400 MHz, CDCl$_3$): δ 7.86 (d, J = 8.0 Hz, 1H), 7.60 (d, J = 8.4 Hz, 2H), 7.28 (d, J = 7.2 Hz, 2H), 7.09 (d, J = 8.0 Hz, 1H), 6.77 (s, 1H), 4.77-4.75 (m, 2H), 4.46-4.43 (m, 2H), 4.02-3.96 (m, 3H), 3.81 (brs, 1H), 3.56 (brs, 1H), 3.31-3.25 (m, 4H), 3.06 (d, J = 7.6 Hz, 2H), 2.61 (s, 3H), 2.32-2.31 (m, 1H), 2.05-1.96 (m, 2H), 1.77-1.72 (m, 1H), 1.59-1.57 (m, 1H), 1.10-1.07 (m, 1H). |
| 13A | 1-(1-(4-Chlorophenyl)-2-methyl-6-(oxetan-3-ylmethyl)-1H-indol-3-yl)-2-((1R,2R,4S)-2-hydroxy-7-azabicyclo[2.2.1]heptan-7-yl)ethan-1-one<br>Mass Spectrum (LCMS, ESI pos.): Calcd. for $C_{27}H_{30}ClN_2O_3$: 465 (M + H); found: 465. $^1$H NMR (300 MHz, DMSO-d$_6$): δ 7.98 (d, J = 8.1 Hz, 1H), 7.73 (d, J = 8.7 Hz, 2H), 7.51 (d, J = 8.1 Hz, 2H), 7.07 (d, J = 7.2 Hz, 1H), 6.79 (s, 1H), 4.70 (d, J = 3.6 Hz, 1H), 4.56-4.52 (m, 2H), 4.30-4.27 (m, 2H), 4.06 (d, J = 5.1 Hz, 1H), 3.76-3.65 (m, 2H), 3.24-3.12 (m, 1H), 2.96 (d, J = 7.8 Hz, 2H), 2.52 (s, 3H), 2.06-1.98 (m, 2H), 1.81 (m, 1H), 1.60-1.57 (m, 1H), 1.40-1.30 (m, 1H), 1.39-1.36 (m, 1H). |
| 14A | 1-(1-(4-Chlorophenyl)-2-methyl-6-(oxetan-3-ylmethyl)-1H-indol-3-yl)-2-(4-hydroxypiperidin-1-yl)ethan-1-one<br>Mass Spectrum (LCMS, ESI pos.): Calcd. for $C_{26}H_{30}ClN_2O_3$: 453 (M + H); found: 453. $^1$H NMR (400 MHz, CDCl$_3$): δ 7.92 (d, J = 8.0 Hz, 1H), 7.61 (d, J = 8.4 Hz, 2H), 7.27 (d, J = 8.0 Hz, 1H), 7.09 (d, J = 8.0 Hz, 1H), 6.76 (s, 1H), 4.77-4.73 (m, 2H), 4.46-4.43 (m, 2H), 3.90-3.83 (m, 3H), 3.12-3.25 (m, 1H), 3.07-3.05 (m, 4H), 2.60-2.55 (m, 5H), 2.03 (m, 2H), 1.79-1.73 (m, 3H). |
| 22A | 1-(1-(4-Chlorophenyl)-2-methyl-6-(oxetan-3-ylmethyl)-1H-indol-3-yl)-2-((1R,3r,5S)-3-hydroxy-8-azabicyclo[3.2.1]octan-8-yl)ethan-1-one<br>Mass Spectrum (LCMS, ESI pos.): Calcd. for $C_{28}H_{32}ClN_2O_3$: 479 (M + H); found 479. $^1$H NMR (300 MHz, DMSO-d$_6$): δ 7.93 (d, J = 8.1 Hz, 1H), 7.66 (d, J = 8.7 Hz, 2H), 7.44 (d, J = 8.7 Hz, 2H), 7.00 (d, J = 7.8 Hz, 1H), 6.72 (s, 1H), 4.49-4.45 (m, 2H), 4.22-4.19 (m, 3H), 3.75 (brs, 1H), 3.56 (s, 2H), 3.12 (brs, 3H), 2.90-2.87 (m, 2H), 2.47 (s, 3H), 2.03-2.01 (m, 2H), 1.93-1.81 (m, 4H), 1.51-1.46 (m, 2H). |
| 27A | 1-(1-(4-Chlorophenyl)-2-methyl-6-(oxetan-3-ylmethyl)-1H-indol-3-yl)-2-((1R,3S,5S)-3-hydroxy-8-azabicyclo[3.2.1]octan-8-yl)ethan-1-one<br>Mass Spectrum (LCMS, ESI pos.): Calcd. for $C_{28}H_{32}ClN_2O_3$: 479 (M + H); found 479. $^1$H NMR (400 MHz, DMSO-d$_6$): δ 8.00 (d, J = 8.0 Hz, 1H), 7.73 (d, J = 8.8 Hz, 2H), 7.52 (d, J = 8.4 Hz, 2H), 7.08 (d, J = 8.4 Hz, 1H), 6.79 (s, 1H), 4.55-4.53 (m, 2H), 4.37-4.36 (m, 2H), 4.30-4.27 (m, 2H), 3.72-3.66 (m, 3H), 3.23-3.16 (m, 3H), 2.97-2.95 (m, 2H), 2.55 (s, 3H), 1.91-1.88 (m, 2H), 1.63-1.62 (m, 2H), 1.53-1.51 (m, 4H). |

Example 4A. 1-(1-(4-Chlorophenyl)-2-methyl-6-(2-(1-methyl-4,5-dihydro-1H-imidazol-2-yl)ethyl)-1H-indol-3-yl)-2-((1R,3S,5S)-3-hydroxy-8-azabicyclo[3.2.1]octan-8-yl)ethan-1-one (28A)

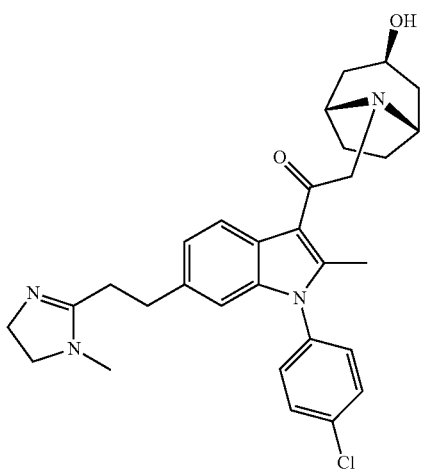 [SMILES: Cc1c(C(=O)CN2[C@@H]3CC[C@H]2C[C@H](O)C3)c2ccc(CCC3=NCCN3C)cc2n1-c1ccc(Cl)cc1]

1-(1-(4-Chlorophenyl)-2-methyl-6-(2-(1-methyl-4,5-dihydro-1H-imidazol-2-yl)ethyl)-1H-indol-3-yl)-2-((1R,3S,5S)-3-hydroxy-8-azabicyclo[3.2.1]octan-8-yl)ethan-1-one (28A)

To a 25 mL round-bottom flask was placed a solution of 3-(1-(4-chlorophenyl)-3-(2-((1R,3S,5S)-3-hydroxy-8-azabicyclo[3.2.1]octan-8-yl)acetyl)-2-methyl-1H-indol-6-yl)propanenitrile (212 mg, 0.46 mmol, as prepared in Example 1A) in a mixture of MeOH and DCM (10 mL). Hydrogen chloride gas was introduced into the flask, followed by addition of TEA (252 mg, 2.49 mmol) and (2-aminoethyl)(methyl)amine (68 mg, 0.92 mmol). The resulting mixture was stirred for 0.5 h at 0° C., then warmed to rt and stirred for 24 h. The crude reaction mixture (6 mL) was purified by Flash-Prep-HPLC ((CombiFlash-1) Column, C18 silica gel; mobile phase, water/MeOH=95:5 to 50:50 over 35 min) affording 19 mg (8%) of the title compound as a white solid. Mass Spectrum (LCMS, ESI pos.): Calcd. for $C_{30}H_{36}ClN_4O_2$: 519 (M+H); found: 519. $^1$H NMR (400 MHz, CDCl$_3$): δ 7.92-7.93 (m, 1H), 7.57-7.59 (m, 2H), 7.26-7.28 (m, 2H), 7.15-7.18 (m, 1H), 6.86 (s, 1H), 3.95-3.99 (m, 1H), 3.92 (s, 2H), 3.66-3.71 (m, 2H), 3.51 (brs, 2H), 3.31-3.36 (m, 2H), 3.01-3.05 (m, 2H), 2.71 (s, 3H), 2.60 (s, 3H), 2.54-2.58 (m, 2H), 2.07-2.09 (m, 2H), 1.87-1.88 (m, 2H), 1.74-1.79 (m, 2H), 1.61-1.66 (m, 2H).

Using the procedures described in Example 4A, and reagents, starting materials, and conditions known to those skilled in the art, the following compounds representative of the present invention were prepared:

| Cpd | Data |
|---|---|
| 29A | 1-(1-(4-Chlorophenyl)-2-methyl-6-(2-(1-methyl-4,5-dihydro-1H-bimidazol-2-yl)ethyl)-1H-indol-3-yl)-2-((1R,3R,5S)-3-hydroxy-8-azabicyclo[3.2.1]octan-8-yl)ethan-1-one<br>Mass Spectrum (LCMS, ESI pos.): Calcd. for $C_{30}H_{36}ClN_4O_2$: 519/521 (M + H); found: 519. $^1H$ NMR (400 MHz, $CD_3OD$): δ 8.07 (d, J = 8.0 Hz, 1H), 7.71 (d, J = 8.4 Hz, 2H), 7.44 (d, J = 8.4 Hz, 2H), 7.22 (d, J = 8.4 Hz, 1H), 6.91 (s, 1H), 4.03-4.08 (m, 1H), 3.73-3.85 (m, 4H), 3.55 (s, 2H), 3.01-3.05 (m, 2H), 2.95 (s, 3H), 2.82-2.86 (m, 2H), 2.62 (s, 3H), 2.24-2.36 (m, 4H), 2.11-2.15 (m, 2H), 1.80-1.85 (m, 2H). |
General Schemes
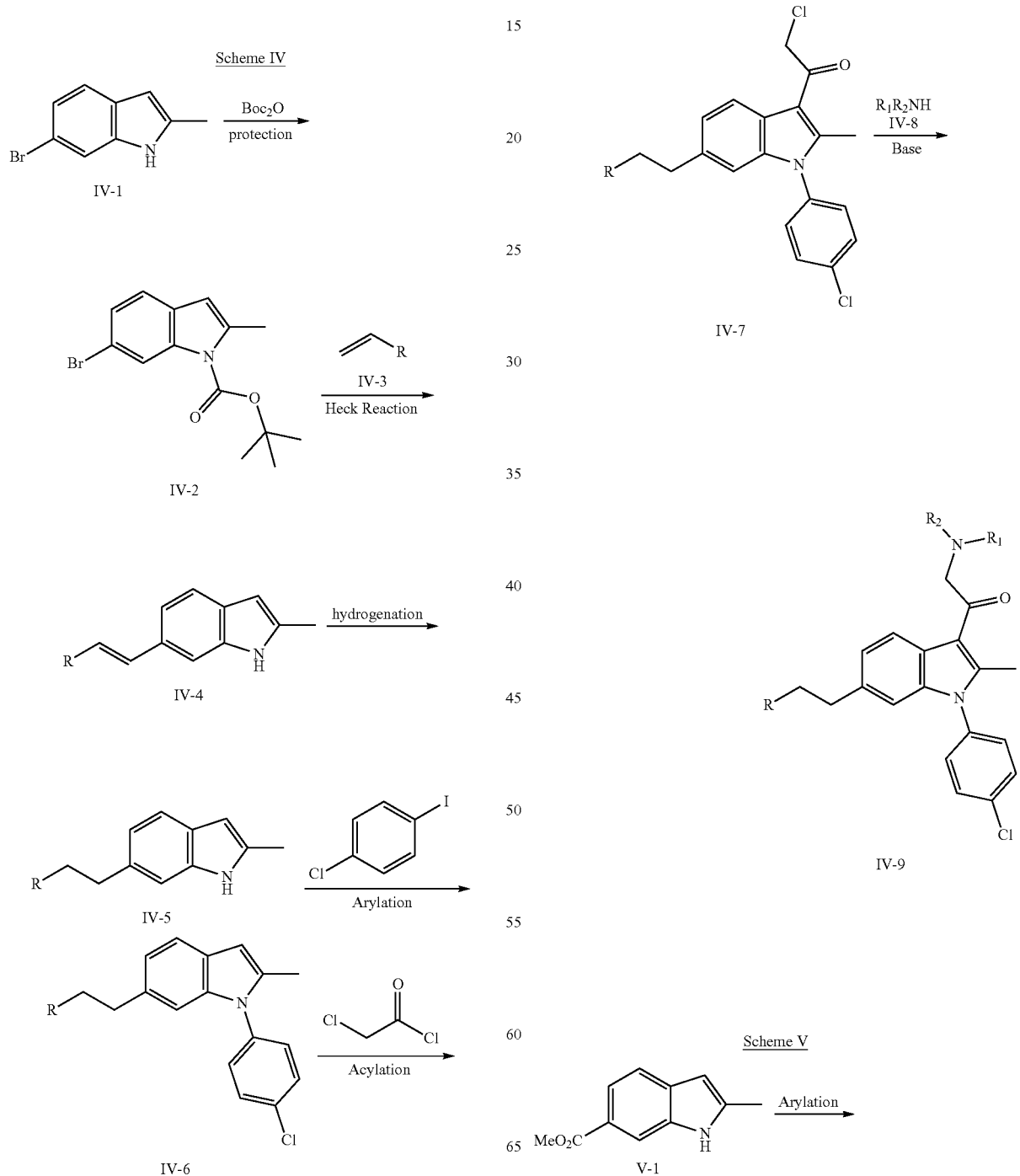

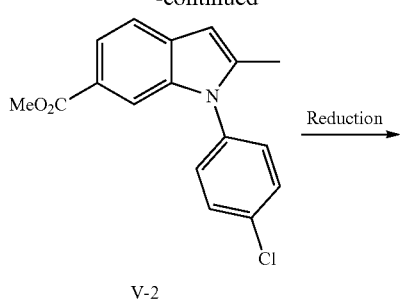
V-2
Reduction →
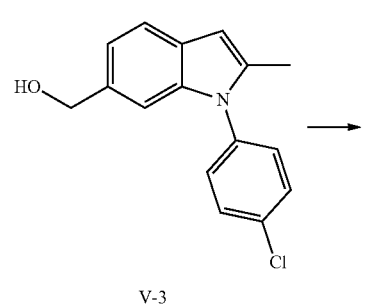
V-3
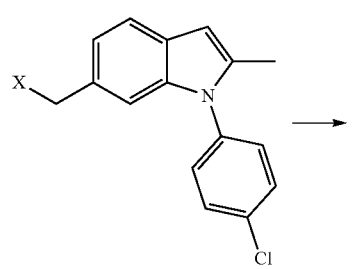
V-4
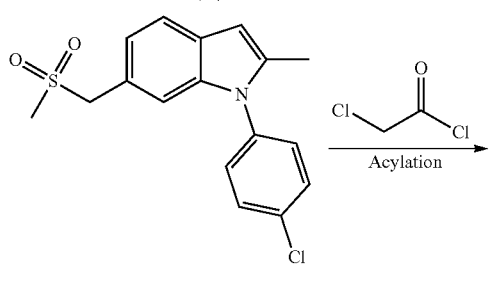
V-5
Cl—CH₂—C(=O)—Cl
Acylation →
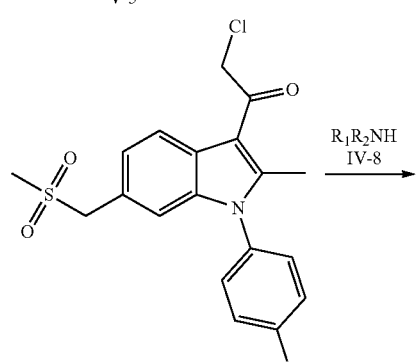
V-6
R₁R₂NH
IV-8 →
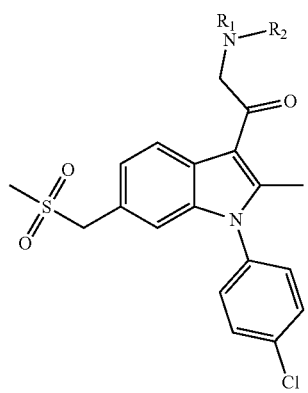
V-7
Scheme VI
V-3 →
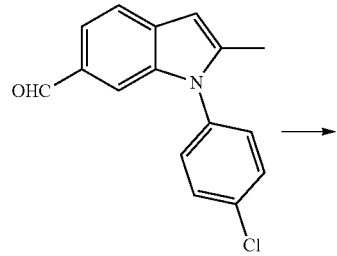
VI-1
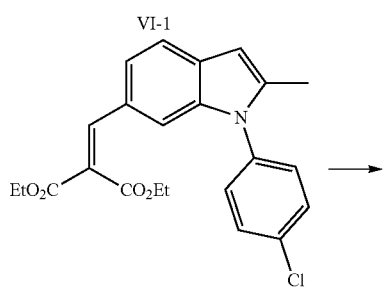
VI-2
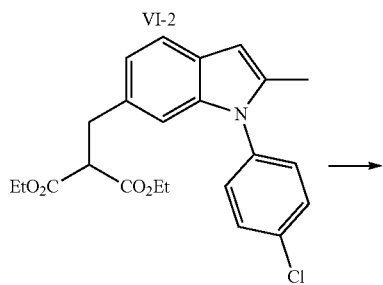
VI-3
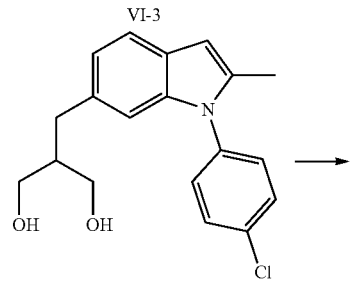
VI-4

195
-continued
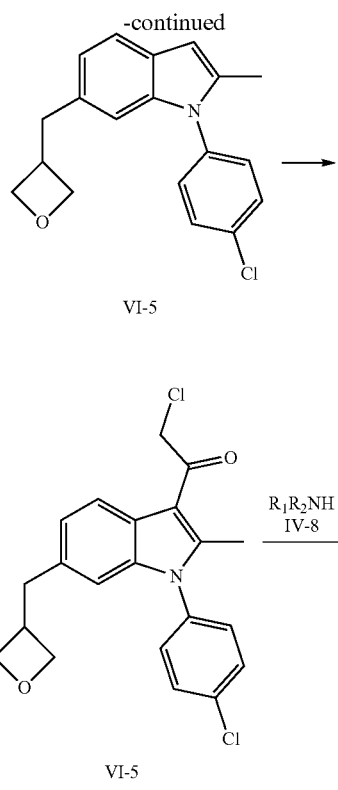
VI-5
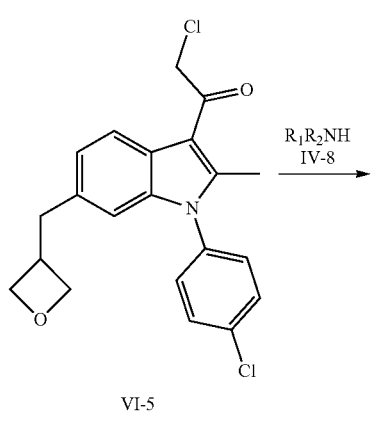
VI-5
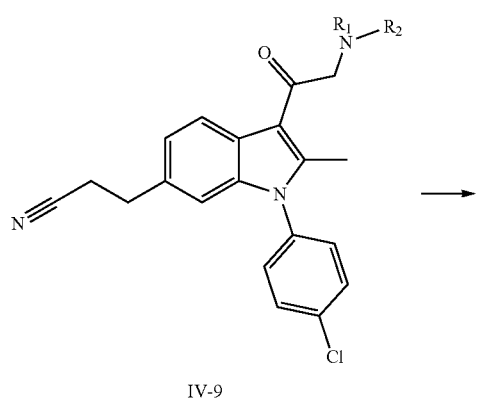
VI-7
Scheme VII
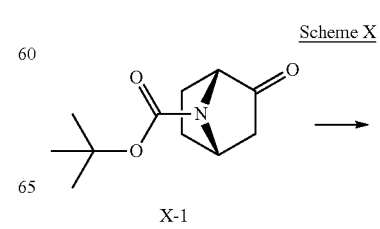
IV-9
196
-continued
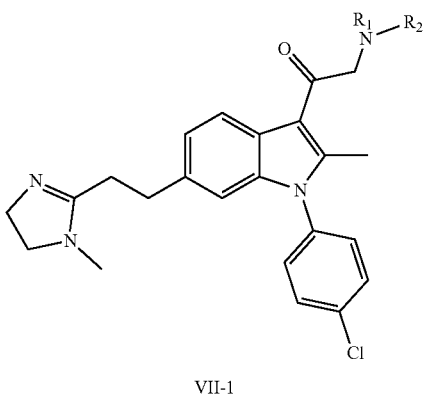
VII-1
Scheme VII
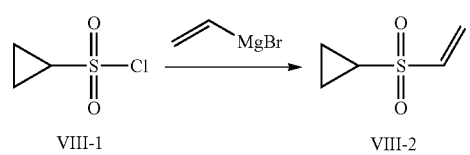
VIII-1    VIII-2
Scheme IX
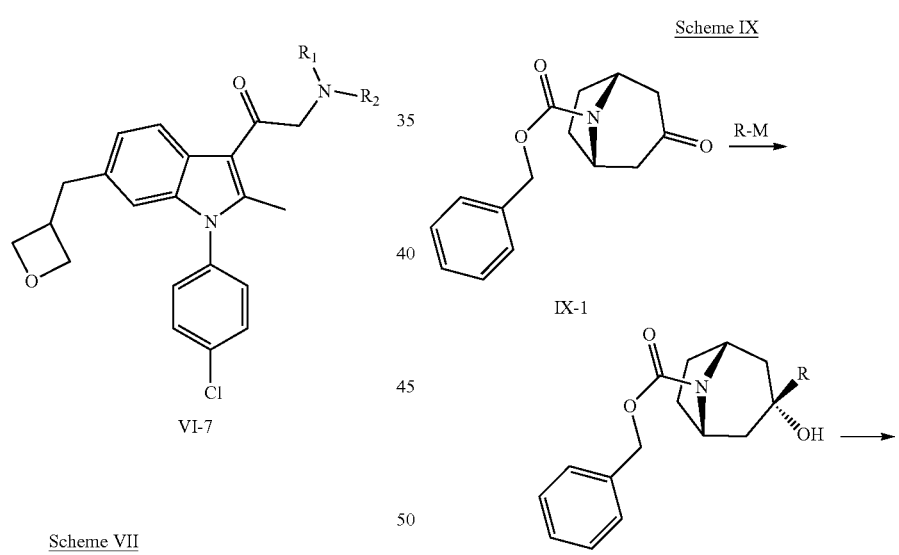
IX-1
IX-2
IX-3
Scheme X
X-1

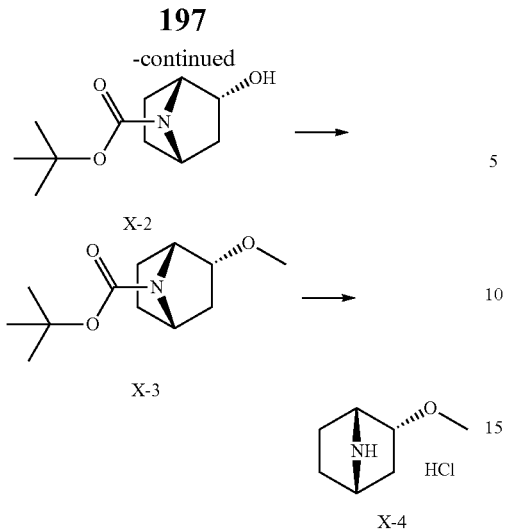

Example 5A: Usp14 Inhibition Assay

Using previously described methodology [B. H. Lee et al. Nature 2010, 467 (9), 179, the contents of which are expressly incorporated by reference herein], select compounds described herein were found to inhibit USP14 as delineated in Table 4. "I" in the Table below designates an $IC_{50}$ of >0.1 μM, "II" in the Table below designates and $IC_{50}$ between 0.05 and 0.1 μM, and "III" designates an $IC_{50}$<0.05 μM. The $IC_{50}$ values in the Table below represent the average value from a minimum of two experimental determinations.

TABLE 4

| Compound No. | Usp14 $IC_{50}$ Category |
| --- | --- |
| 1A | III |
| 2A | III |
| 3A | II |
| 4A | III |
| 5A | III |
| 6A | III |
| 7A | III |
| 8A | III |
| 9A | I |
| 10A | III |
| 11A | III |
| 12A | II |
| 13A | III |
| 14A | II |
| 15A | III |
| 16A | III |
| 17A | III |
| 18A | III |
| 19A | III |
| 20A | I |
| 21A | II |
| 22A | II |
| 23A | III |
| 24A | II |
| 25A | I |
| 26A | I |
| 27A | I |
| 28A | III |
| 29A | III |
| 30A | II |
| 31A | I |
| 32A | II |
| 33A | III |

Exemplification of Compounds of Formula (III), (IIIa), (IIIb), (IIIc), (IIId), or (IIIe)

| List of Abbreviations | |
| --- | --- |
| Abbreviation | Meaning |
| THF | Tetrahydrofuran |
| EtOAc | Ethyl acetate |
| MeOH | Methanol |
| Ethanol | Ethanol |
| DMF | N,N-Dimethylformamide |
| DCM | Dichloromethane |
| DMSO | Dimethylsulfoxide |
| rt | Room temperature |
| DIPEA | Diisopropylethylamine |
| dppf | 1,1'-Ferrocenediyl-bis(diphenylphosphine) |
| TEA | Triethylamine |
| DMAP | 4-dimethylaminopyridine |
| h | Hour(s) |
| min | Minute(s) |
| Pd/C | Palladium on carbon |
| Dioxane | 1,4-dioxane |
| DMP | Dess-Martin Periodinane |
| DIBAL-H | Diisobutylaluminum hydride |
| Cpd | Compound |
| Satd | Saturated |
| Aq | Aqueous |
| TsCl | 4-Methylbenzenesulfonyl chloride |
| MsCl | Methanesulfonyl chloride |
| $Boc_2O$ | Di-tert-butyl dicarbonate |
| ACN | Acetonitrile |
| MeCN | Acetonitrile |
| $Et_2AlCl$ | Diethylaluminum chloride |
| n-BuLi | n-Butyllithium |
| HPLC | High performance liquid chromatography |
| TLC | Thin layer chromatography |

Example B. Preparation of Intermediates IB to XXXIB

Preparation of Intermediate IB: 4-(3-Acetyl-5-iodo-2-methyl-1H-pyrrol-1-yl)benzonitrile

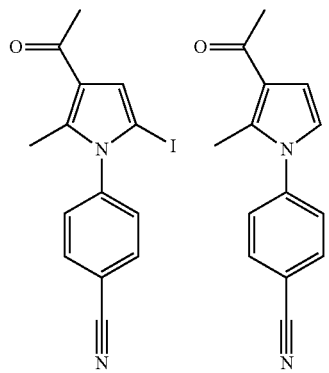

A. 4-(3-Acetyl-2-methyl-1H-pyrrol-1-yl)benzonitrile

Into a 2 L, 3-necked round-bottom flask was placed a mixture of 1-(2-methyl-1H-pyrrol-3-yl)ethan-1-one (30.0 g, 244 mmol), 4-fluorobenzonitrile (44.0 g, 363 mmol), $Cs_2CO_3$ (156 g, 479 mmol) and N,N-dimethylformamide (400 mL). The resulting mixture was heated at 130° C. for 16 h and then allowed to cool to room temperature. The mixture was diluted with water (1.2 L) and then extracted with ethyl acetate (3×600 mL). The combined organic extracts were washed with brine (2×200 mL) and then concentrated under vacuum. The remaining residue was purified by column chromatography on silica gel using ethyl acetate/petroleum ether (1:8) as the eluant to afford 45 g (82%) of 4-(3-acetyl-2-methyl-1H-pyrrol-1-yl)benzonitrile as a white solid. Mass Spectrum (LCMS, ESI pos.): Calcd. for $C_{14}H_{12}N_2O$: 225 (M+H); found 225. $^1$H-NMR (300 MHz, $CDCl_3$) δ 7.83-7.81 (m, 2H), 7.45-7.43 (m, 2H), 6.72 (d, J=3.2 Hz, 1H), 6.68 (d, J=3.2 Hz, 1H), 2.51 (s, 3H), 2.47 (s, 3H).

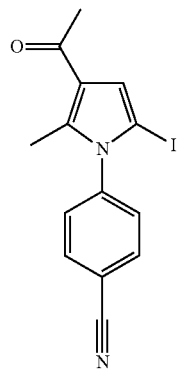 [SMILES: CC(=O)c1cc(I)n(-c2ccc(C#N)cc2)c1C]

B. 4-(3-Acetyl-5-iodo-2-methyl-1H-pyrrol-1-yl)benzonitrile

Into a 2 L, 3-necked round-bottom flask, being maintained under an atmosphere of nitrogen, was placed a solution of 4-(3-acetyl-2-methyl-1H-pyrrol-1-yl)benzonitrile (20.0 g, 89.2 mmol) in dichloromethane (1 L). To the solution was added solid N-iodosuccinimide (40.0 g, 178 mmol) and the resulting mixture was heated at 40° C. for 16 h. After cooling to room temperature the reaction mixture was washed with an aqueous, saturated solution of $Na_2S_2O_3$ (3×400 mL) and then concentrated under vacuum. The remaining residue was purified by column chromatography on silica gel using ethyl acetate/petroleum ether (1:8) as the eluant to afford 30 g (96%) of 4-(3-acetyl-5-iodo-2-methyl-1H-pyrrol-1-yl)benzonitrile as an off-white solid. Mass Spectrum (LCMS, ESI pos.): Calcd. for $C_{14}H_{11}IN_2O$: 350 (M+H); found 350. $^1$H-NMR (400 MHz, $CDCl_3$) δ 7.86-7.84 (m, 2H), 7.36-7.34 (m, 2H), 6.89 (s, 1H), 2.44 (s, 3H), 2.40 (s, 3H).

Preparation of Intermediate IB: 1-(5-Bromo-1-(4-chlorophenyl)-2-methyl-1H-pyrrol-3-yl)ethan-1-one

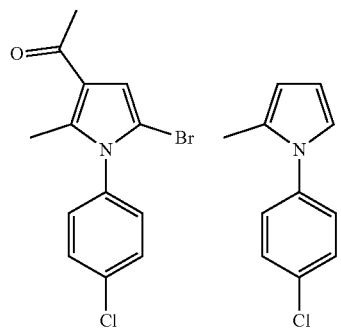

A. 1-(4-Chlorophenyl)-2-methyl-1H-pyrrole

A mixture of 4-oxo-pentanal (5.00 g, 50.00 mmol) and 4-chloroaniline (6.35 g, 50.00 mmol) in acetic acid (50 mL) was heated at 120° C. for 3 hours. After cooling to room temperature the reaction mixture was poured into ice-cold water (100 mL) and the resulting mixture was extracted with ethyl acetate (3×100 mL). The combined organic extracts were dried over sodium sulfate and concentrated under vacuum. The remaining crude product was purified by column chromatography on 60-120 mesh silica gel and eluted with hexane to afford 1-(4-chlorophenyl)-2-methyl-1H-pyrrole (3.0 g, 31%) as a colorless liquid. $^1$H NMR (400 MHz, $CDCl_3$): δ 7.39 (d, J=8.6 Hz, 2H), 7.23 (d, J=8.7 Hz, 2H), 6.72 (brt, J=2.1 Hz 1H), 6.18 (brt, J=3.1 Hz, 1H), 6.03 (brs, 1H), 2.19 (s, 3H).

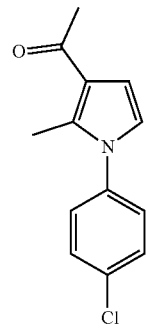 [SMILES: CC(=O)c1ccn(-c2ccc(Cl)cc2)c1C]

B. 1-(1-(4-Chlorophenyl)-2-methyl-1H-pyrrol-3-yl)ethan-1-one

Into a 250 mL 3-necked, round-bottom flask was placed a solution of 1-(4-chlorophenyl)-2-methyl-1H-pyrrole (4.0 g, 20.87 mmol) in dichloromethane (40 mL). The solution was cooled to 0° C., after which acetyl chloride (2.46 g, 31.34 mmol) and a solution of diethylaluminum chloride (25% wt in toluene, 35 mL) were added. The resulting mixture was allowed to stir for 2 h at 0° C. before it was diluted with ice-cold water (100 mL). The mixture was extracted with dichloromethane (3×100 mL) and the combined organic extracts were washed with a 5% aqueous solution of sodium bicarbonate (3×100 mL), dried over anhydrous sodium sulfate and concentrated under vacuum. The remaining residue was purified by column chromatography on silica gel, using ethyl acetate/hexanes (1:20) as the eluant, to afford 1.7 g (35%) of 1-(1-(4-chlorophenyl)-2-methyl-1H-pyrrol-3-yl)ethan-1-one as a white solid. Mass Spectrum (LCMS, ESI pos.): Calcd. for $C_{13}H_{12}ClNO$: 234 (M+H); found 234. $^1$H-NMR (300 MHz, DMSO-$d_6$) δ 7.71 (d, J=1.5 Hz, 1H), 7.59 (d, J=8.4 Hz, 2H), 7.50 (d, J=8.7 Hz, 2H), 6.36 (s, 1H), 2.31 (s, 3H), 3.10 (s, 3H).

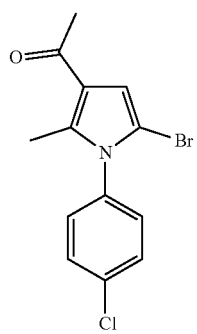 [SMILES: CC(=O)c1cc(Br)n(-c2ccc(Cl)cc2)c1C]

C. 1-(5-Bromo-1-(4-chlorophenyl)-2-methyl-1H-pyrrol-3-yl)ethan-1-one

Into a 100 mL 3-necked round-bottom flask, being maintained under an inert atmosphere of nitrogen, was placed a solution of 1-(1-(4-chlorophenyl)-2-methyl-1H-pyrrol-3-yl)ethan-1-one (1.10 g, 4.71 mmol) in tetrahydrofuran (30 mL). The solution was cooled to −10° C. and then solid NBS (838 mg, 4.71 mmol) was added to the flask. The resulting mixture was allowed to stir at −10° C. for 2 h before it was diluted with ice-cold water (30 mL). The mixture was extracted with dichloromethane (2×20 mL) and the combined organic extracts were concentrated under vacuum. The remaining residue was purified by column chromatography on silica gel, using ethyl acetate/hexanes (20:1) as the eluant, to afford 1.45 g (99%) of 1-(5-bromo-1-(4-chlorophenyl)-2-methyl-1H-pyrrol-3-yl)ethan-1-one as a yellow solid. Mass Spectrum (LCMS, ESI pos.): Calcd. for $C_{13}H_{11}BrClNO$: 312 (M+H); found 312. $^1$H-NMR (300 MHz, DMSO-$d_6$) δ 7.63-7.68 (m, 2H), 7.38-7.42 (m, 2H), 6.89 (s, 1H), 2.36 (s, 3H), 2.25 (s, 3H).

Preparation of Intermediate IIIB: 4-(But-3-yn-1-yl)tetrahydro-2H-pyran

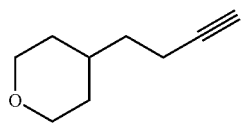

Into a 100 mL round-bottom flask was placed a solution of dimethyl (1-diazo-2-oxopropyl)phosphonate (1.5 g, 7.81 mmol) in methanol (30 mL). To the solution were added potassium carbonate (2.2 g, 15.92 mmol) and 3-(oxan-4-yl)propanal (560 mg, 3.94 mmol). The resulting mixture was allowed to stir for 16 h at room temperature before it was diluted with water. The biphasic mixture was extracted with ethyl acetate and the combined organic extracts were washed with brine, dried over anhydrous sodium sulfate and concentrated under vacuum. The remaining residue was purified by column chromatography on silica gel using ethyl acetate/petroleum ether (1:6) as the eluant. This procedure afforded in 100 mg (18%) of partially pure 4-(but-3-yn-1-yl)oxane as colorless oil.

Preparation of Intermediate IVB: 3-(But-3-yn-1-yl)oxetane

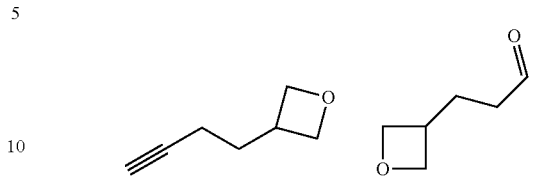

A. 3-(Oxetan-3-yl)propanal

Into a 100 mL round-bottom flask was placed a solution of 3-(oxetan-3-yl)propan-1-ol (700 mg, 6.03 mmol) in dichloromethane (30 mL). To the solution was added Dess-Martin reagent (2.68 g, 6.32 mmol) and the resulting mixture was allowed to stir at room temperature for 2 h. The heterogeneous mixture was concentrated and remaining residue was treated with 30 mL of petroleum ether/ethyl acetate (5:1). The mixture was allowed to stir for 10 min before it was filtered. The filtrate was concentrated to afford 0.7 g (crude) of 3-(oxetan-3-yl)propanal as light yellow oil.

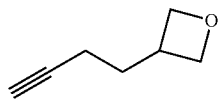

B. 3-(But-3-yn-1-yl)oxetane

Into a 100 mL round-bottom flask was placed a solution of dimethyl(1-diazo-2-oxopropyl)phosphonate (1.2 g) in methanol (20 mL). To the solution was added potassium carbonate (1.45 g, 10.42 mmol) and the resulting mixture was allowed to stir at room temperature for 10 min. The heterogeneous mixture was then treated with a solution of 3-(oxetan-3-yl)propanal (600 mg, 5.26 mmol) in methanol (2 mL) in a dropwise fashion. The resulting mixture was allowed to stir for at room temperature for 2 h before it was diluted with water (50 mL). The mixture was extracted with dichloromethane (2×30 mL) and the combined organic extracts were concentrated under vacuum to afford 600 mg (crude) of 3-(but-3-yn-1-yl)oxetane as light yellow oil.

Preparation of Intermediate VB: 3-(Prop-2-yn-1-yl)oxetane

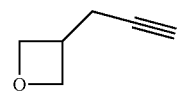

Into a 250 mL round-bottom flask, being maintained under an inert atmosphere of nitrogen, was placed a mixture of potassium carbonate (4.14 g, 29.95 mmol) and methanol (75 mL). The flask was cooled to 0° C. and then dimethyl (1-diazo-2-oxopropyl)phosphonate (3.45 g, 17.96 mmol) was then added to the flask in a dropwise fashion. The resulting mixture was allowed to stir for 1 h at 0° C. and then 2-(oxetan-3-yl)acetaldehyde (1.5 g, 14.98 mmol) was added.

The reaction mixture was allowed to warm to room temperature and stir for 3 h before it was diluted with water (75 mL). The mixture was extracted with dichloromethane (3×70 mL) and the combined organic extracts were dried over anhydrous sodium sulfate and concentrated under vacuum to afford 1.44 g (crude) of 3-(prop-2-yn-1-yl)oxetane as colorless oil.

Preparation of Intermediate VIB: (E)-1-(3-(4,4,5,5-Tetramethyl-1,3,2-dioxaborolan-2-yl)allyl)-1H-pyrazole

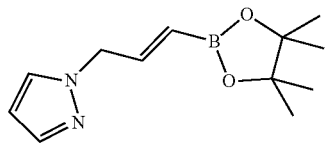 [SMILES: CC1(C)OB(/C=C/Cn2cccn2)OC1(C)C]

Into a 100 mL round-bottom flask, being maintained under an inert atmosphere of nitrogen, was placed a mixture of 1-(prop-2-yn-1-yl)-1H-pyrazole (330 mg, 3.11 mmol) and 4,4,4',4',5,5,5',5'-octamethyl-2,2'-bi(1,3,2-dioxaborolane) (1.19 g, 4.67 mmol) in ethanol (10 mL). Then copper sand (20 mg) and sodium methoxide (34 mg) were added to the flask. The resulting mixture was allowed to stir overnight at room temperature. The reaction mixture was diluted with ethyl acetate (150 mL) and then the organic phase was washed with brine (3×100 mL), dried over sodium sulfate and concentrated under vacuum to afford 1.2 g (crude) of (E)-1-(3-(4,4,5,5-tetramethyl-1,3,2-dioxaborolan-2-yl)allyl)-1H-pyrazole as a yellow oil. Mass Spectrum (LCMS, ESI pos.): Calcd. for $C_{12}H_{19}BN_2O_2$: 235 (M+H); found 235.

Preparation of Intermediate VIIB: (E)-2,2-Dimethyl-5-(4,4,5,5-tetramethyl-1,3,2-dioxaborolan-2-yl)pent-4-enenitrile

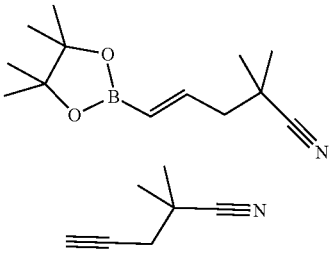

A. 2,2-Dimethylpent-4-ynenitrile

Into a 250 mL 3-necked, round-bottom flask was placed a solution of 2-methylpropanenitrile (750 mg, 10.85 mmol) in tetrahydrofuran (50 mL). The system was cooled to −78° C. and then a solution of LDA in tetrahydrofuran (2.0 M, 8.25 mL) was added in a dropwise fashion over 15 min. The resulting mixture was allowed to stir for 30 min at −78° C. and then 3-bromoprop-1-yne (2.6 g, 21.86 mmol) was added in a dropwise fashion over 5 min. The reaction mixture was allowed to slowly warm to room temperature and then stir for an additional 2 h. The reaction mixture was with diluted with aqueous ammonium chloride (100 mL) and then extracted with ethyl acetate (2×100 mL). The combined organic extracts were washed with brine (2×100 mL), dried over anhydrous sodium sulfate and then concentrated under vacuum to afford 1.0 g (crude) of 2,2-dimethylpent-4-ynenitrile as a yellow oil.

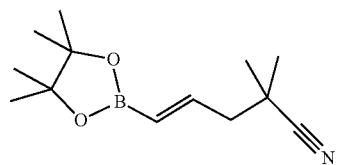 [SMILES: CC(C)(C#N)C/C=C/B1OC(C)(C)C(C)(C)O1]

B. (E)-2,2-Dimethyl-5-(4,4,5,5-tetramethyl-1,3,2-dioxaborolan-2-yl)pent-4-enenitrile Into a 100 mL round-bottom flask was placed a solution of 2,2-dimethylpent-4-ynenitrile (1.0 g, 9.33 mmol) in ethanol (30 mL). Copper sand (64 mg, 1.01 mmol), 4,4,4',4',5,5,5',5'-octamethyl-2,2'-bi(1,3,2-dioxaborolane) (5.08 g, 20.00 mmol) and sodium methoxide (540 mg, 3.00 mmol, 0.30 equiv) were then added to the flask. The resulting mixture was allowed to stir at room temperature for 16 h before it was diluted with water (100 mL). The mixture was extracted with ethyl acetate (2×100 mL) and the combined organic extracts were washed with brine (2×100 mL), dried over anhydrous sodium sulfate and concentrated under vacuum. The remaining residue was purified by column chromatography on silica gel, using petroleum ether/ethyl acetate (10:1) as the eluant, to afford 1.1 g (50%) of (E)-2,2-dimethyl-5-(4,4,5,5-tetramethyl-1,3,2-dioxaborolan-2-yl)pent-4-enenitrile as a white solid. Mass Spectrum (LCMS, ESI pos.): Calcd. for $C_{13}H_{22}BNO_2$: 236 (M+H); found 236.

Preparation of Intermediate VIIIB: 3-Ethynyloxetane

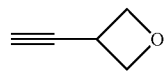

Into a 100 mL round-bottom flask was placed a mixture of dimethyl 1-diazo-2-oxopropylphosphonate (3.74 g, 19.48 mmol), $K_2CO_3$ (4.42 g, 31.75 mmol), and methanol (75 mL). The mixture as cooled to 0° C. and then oxetane-3-carbaldehyde (1.17 g, 13.59 mmol) was added. The resulting mixture was allowed to warm to room temperature and stir for 2 h. The reaction mixture was diluted with water (150 mL) and then extracted with dichloromethane (2×30 mL). The combined organic extracts were dried over sodium sulfate and then concentrated to afford 1.37 g (crude) of 3-ethynyloxetane as light yellow oil.

Preparation of Intermediate IXB: 3-Methyl-3-(prop-2-yn-1-yl)oxetane

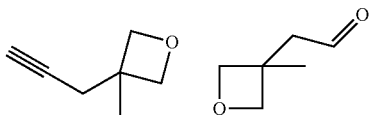

A. 2-(3-Methyloxetan-3-yl)acetaldehyde

Into a 100 mL round-bottom flask, being maintained under an inert atmosphere of nitrogen, was placed a solution of 2-(3-methyloxetan-3-yl)ethan-1-ol (1.1 g, 9.47 mmol) in dichloromethane (5 mL). The solution was cooled to 0° C. and then DessMartin periodinane (4.8 g, 11.3 mmol) was added in portions. The reaction mixture was allowed to warm to room temperature and stir overnight. The reaction mixture was concentrated under vacuum and the remaining residue was re-dissolved in ethyl acetate. The organic mixture was washed with an aqueous, saturated solution of sodium bicarbonate (1×30 mL), dried over sodium sulfate, and then concentrated under vacuum to afford 1.0 g (93%) of crude 2-(3-methyloxetan-3-yl)acetaldehyde as yellow oil.

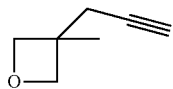

B. 3-Methyl-3-(prop-2-yn-1-yl)oxetane

Into a 100 mL round-bottom flask, being maintained under an inert atmosphere of nitrogen, was placed a solution of 2-(3-methyloxetan-3-yl)acetaldehyde (800 mg, 7.01 mmol) in methanol (20 mL). After cooling to 0° C., the solution was treated with solid potassium carbonate (1.90 g, 13.8 mmol), followed by a solution of dimethyl (1-diazo-2-oxopropyl)phosphonate (1.62 g, 8.37 mmol) in methanol (3 mL). The reaction mixture was allowed to stir at room temperature for 3 h, before it was concentrated under vacuum. The remaining materials were re-dissolved in ethyl acetate (200 mL). The organic mixture was washed with brine (3×100 mL), dried over anhydrous sodium sulfate and concentrated under vacuum to afford 770 mg (crude) of 3-methyl-3-(prop-2-yn-1-yl)oxetane as yellow crude oil.

Preparation of Intermediate XB: 4-(3-(2-Chloroacetyl)-2,5-dimethyl-1H-pyrrol-1-yl)benzonitrile

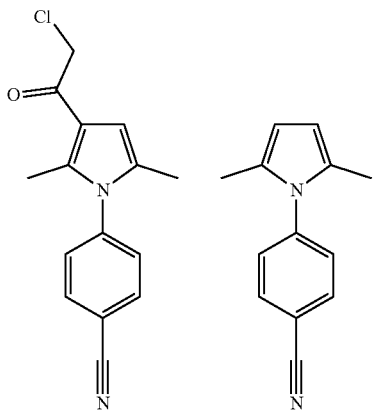

A. 4-(2,5-Dimethyl-1H-pyrrol-1-yl)benzonitrile

A mixture of p-aminobenzonitrile (2.0 g, 0.01 mol) and hexane-2,5-dione (5.7 g, 0.05 mol) in acetic acid (30 mL) was heated at reflux for 2 h. After cooling to room temperature the excess acetic acid was removed under vacuum and the remaining material was diluted with water. The aqueous mixture was extracted with ethyl acetate (3×100 mL) and the combined organic extracts were washed with water and brine. The organic layer was dried over anhydrous sodium sulfate and then concentrated in vacuo. The crude product was purified by column chromatography on 100-200 mesh silica gel using 2% ethyl acetate in hexanes as the eluant to afford 4-(2,5-dimethyl-1H-pyrrol-1-yl)benzonitrile (3.0 g, 97%) as white solid. ¹H NMR (400 MHz, CDCl₃): δ 7.76 (d, J=8.4 Hz, 2H), 7.33 (d, J=8.4 Hz, 2H), 5.92 (s, 2H), 2.03 (s, 6H).

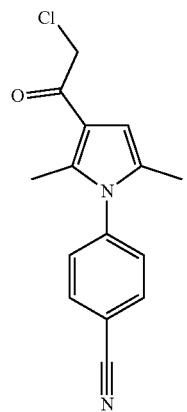 [SMILES: Cc1cc(C(=O)CCl)c(C)n1-c1ccc(C#N)cc1]

B. 4-(3-(2-Chloroacetyl)-2,5-dimethyl-1H-pyrrol-1-yl)benzonitrile

To a cold suspension of anhydrous aluminum trichloride (2.6 g, 0.019 mol) in dry dichloromethane (50 mL) was added chloro acetyl chloride (2.2 g, 0.019 mol). The reaction mixture was allowed to stir for 0.5 h at 0° C. and then a solution of 4-(2,5-dimethyl-1H-pyrrol-1-yl)benzonitrile (3.3 g, 0.018 mol) in dichloromethane (30 mL) was added in single portion. The reaction mixture was allowed to warm to room temperature and stir for 2 h before it was poured into ice water. The biphasic mixture was extracted with dichloromethane (3×100 mL) and the combined organic extracts were dried over sodium sulfate. The organic phases was concentrated under vacuum and the remaining residue was purified by column chromatography on 100-200 mesh silica gel, using 30% ethyl acetate in hexanes as the eluant, to afford 4-(3-(2-chloroacetyl)-2,5-dimethyl-1H-pyrrol-1-yl)benzonitrile (1.4 g, 31%) as black solid. ¹H NMR (400 MHz, CDCl₃): δ 7.85 (d, 2H), 7.35 (d, 2H), 6.35 (s, 1H), 4.46 (s, 2H), 2.33 (s, 3H), 2.01 (s, 3H).

Preparation of Intermediate XIB: (±)-(1R,2R,4S)-2-Methoxy-7-azabicyclo[2.2.1]heptane Hydrochloride

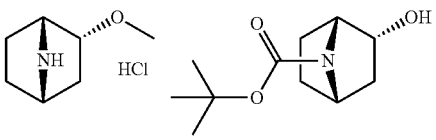

A. tert-Butyl (1R,2R,4S)-2-Hydroxy-7-azabicyclo[2.2.1]heptane-7-carboxylate

To a 100 mL round-bottom flask purged with $N_2$ was placed a solution of tert-butyl 2-oxo-7-azabicyclo[2.2.1]heptane-7-carboxylate (900 mg, 4.26 mmol) in MeOH (15 mL) then $NaBH_4$ (243 mg, 6.4 mmol) was added. The resulting solution was stirred at rt overnight. The reaction was quenched by the addition of 100 mL of water, then the mixture was extracted with EtOAc (3×100 mL). The organic extracts were combined, washed with brine (3×100 mL), dried over anhydrous $Na_2SO_4$, and concentrated under reduced pressure. The residue was purified by column chromatography using a silica gel column eluting with EtOAc/petroleum ether (1:4) affording 550 mg (61%) of the title compound as a colorless oil. Mass Spectrum (LCMS, ESI pos.): Calcd. for $C_{11}H_{20}NO_3$: 214 (M+H); found: 214.

B. tert-Butyl (1R,2R,4S)-2-Methoxy-7-azabicyclo[2.2.1]heptane-7-carboxylate

To a 100 mL round-bottom flask purged with $N_2$ was placed a solution of tert-butyl (1R,2S,4S)-2-hydroxy-7-azabicyclo[2.2.1]heptane-7-carboxylate (358 mg, 1.68 mmol, as prepared in the previous step) and NaH (81 mg, 3.38 mmol) in DMF (5 mL). This was followed by the addition of iodomethane (477 mg, 3.36 mmol) then the reaction was stirred at rt overnight. The reaction was quenched by the addition of 100 mL of water and the resulting mixture was extracted with EtOAc (3×100 mL). The organic extracts were combined, washed with brine (3×100 mL), dried over anhydrous $Na_2SO_4$, and concentrated under reduced pressure. The crude product was purified by column chromatography using a silica gel column eluting with EtOAc/petroleum ether (1:4) affording 281 mg (74%) of the title compound as a colorless oil. Mass Spectrum (LCMS, ESI pos.): Calcd. for $C_{12}H_{22}NO_3$: 228 (M+H); found: 228. $^1$H NMR (400 MHz, $CDCl_3$): δ 4.29-4.26 (m, 1H), 4.14-4.11 (m, 1H), 3.84-3.81 (m, 1H), 3.28 (s, 3H), 2.17-2.14 (m, 1H), 2.03-1.99 (m, 1H), 1.80-1.76 (m, 1H), 1.61-1.58 (m, 1H), 1.49-1.46 (m, 1H), 1.45 (s, 9H), 1.11-1.08 (m, 1H).

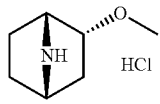

C. (±)-(1R,2R,4S)-2-Methoxy-7-azabicyclo[2.2.1]heptane Hydrochloride

To a 50 mL round-bottom flask purged with $N_2$ was placed tert-butyl (1R,2S,4S)-2-methoxy-7-azabicyclo[2.2.1]heptane-7-carboxylate (280 mg, 1.23 mmol, as prepared in the previous step) and a solution of HCl in dioxane (3 mL). The resulting solution was stirred at rt for 2 h then the reaction was concentrated under reduced pressure affording 140 mg of the title compound as white solid. Mass Spectrum (LCMS, ESI pos.): Calcd. for $C_7H_{14}NO$: 128 (M+H); found: 128.

Preparation of Intermediate XIIB: (±)-(1R,2R,4S)-2-Methyl-7-azabicyclo[2.2.1]heptan-2-ol Hydrochloride

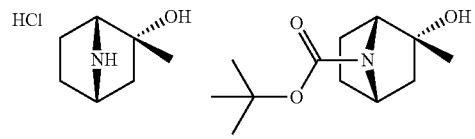

A. tert-Butyl (1R,2R,4S)-2-Hydroxy-2-methyl-7-azabicyclo[2.2.1]heptane-7-carboxylate Into a 100 mL 3-necked round-bottom flask, being maintained under an inert atmosphere of nitrogen, was placed a solution of racemic tert-butyl 2-oxo-7-azabicyclo[2.2.1]heptane-7-carboxylate (1.5 g, 7.10 mmol) in tetrahydrofuran (40 mL). The solution was cooled to −10° C. and then methylmagnesium bromide (7.1 mL, 3M in ether) was added. The resulting mixture was allowed to stir at −10° C. for 1 h before it was diluted with aqueous ammonium chloride. The aqueous mixture was extracted with ethyl acetate (3×100 mL) and the combined organic extracts were dried over anhydrous sodium sulfate, before being concentrated under vacuum. The remaining residue was purified by column chromatography on silica, using ethyl acetate/petroleum ether (1:10 to 1:3) as the eluant, to afford 680 mg (42%) of racemic tert-butyl 2-hydroxy-2-methyl-7-azabicyclo[2.2.1]heptane-7-carboxylate as a white solid. Mass Spectrum (LCMS, ESI pos.): Calcd. for $C_{12}H_{21}NO_3$: 228 (M+H); found: 228. $^1$H NMR (300 MHz, $CDCl_3$): δ 4.15 (s, 1H), 3.81 (s, 1H), 2.22-2.19 (m, 1H), 1.87-1.51 (m, 3H), 1.50 (s, 9H), 1.48 (s, 3H), 1.39-1.29 (m, 1H).

B. (±)-(1R,2R,4S)-2-Methyl-7-azabicyclo[2.2.1]heptan-2-ol Hydrochloride

Into a 25 mL round-bottom flask was placed racemic tert-butyl 2-hydroxy-2-methyl-7-azabicyclo[2.2.1]heptane-7-carboxylate (300 mg, 1.32 mmol), which was then treated with a solution of hydrogen chloride in 1,4-dioxane (4M, 10 mL). The resulting mixture was allowed to stir at room temperature overnight. The reaction mixture was concentrated under vacuum to afford 300 mg of crude, racemic 2-methyl-7-azabicyclo[2.2.1]heptan-2-ol hydrogen chloride as a light brown solid. Mass Spectrum (LCMS, ESI pos.): Calcd. for $C_7H_{13}NO$: 128 (M+H); found: 128.

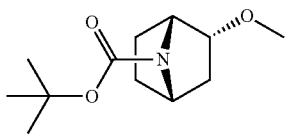

209

Preparation of Intermediate XIIIB: (±)-(1R,2S,4S)-2-(tert-Butyl)-7-azabicyclo[2.2.1]heptan-2-ol Hydrochloride

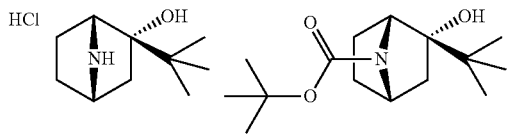

A. tert-Butyl (1R,2S,4S)-2-(tert-Butyl)-2-hydroxy-7-azabicyclo[2.2.1]heptane-7-carboxylate Into a 50 mL round-bottom flask, being maintained under an inert atmosphere of nitrogen, was placed a solution of racemic tert-butyl 2-oxo-7-azabicyclo[2.2.1]heptane-7-carboxylate (1.08 g, 5.11 mmol) in tetrahydrofuran (50 mL), followed by $LaCl_3(LiCl)_2$ (3.6 mL, 1.20 equiv). The resulting mixture was cooled to 0° C. and then treated with a solution of tert-butylmagnesium chloride (6 mL, 1.20 equiv). The reaction mixture was allowed to stir at 0° C. for 1 h and then warm to room temperature and stir for an additional 16 h. The reaction mixture was diluted with brine and then extracted with ethyl acetate. The combined organic extracts were dried over sodium sulfate and condensed in vacuo. The remaining residue was purified by column chromatography on silica, using ethyl acetate/petroleum ether (1:10) as the eluant, to afford 570 mg (41%) of racemic tert-butyl 2-tert-butyl-2-hydroxy-7-azabicyclo[2.2.1]heptane-7-carboxylate as an off-white solid. Mass Spectrum (LCMS, ESI pos.): Calcd. for $C_{15}H_{27}NO_3$: 270 (M+H); found: 270.

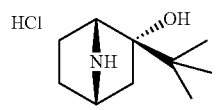

B. (±)-(1R,2S,4S)-2-(tert-Butyl)-7-azabicyclo[2.2.1]heptan-2-ol Hydrochloride Into a 50 mL round-bottom flask, being maintained under an inert atmosphere of nitrogen, was placed tert-butyl 2-tert-butyl-2-hydroxy-7-azabicyclo[2.2.1]heptane-7-carboxylate (570 mg, 2.12 mmol), which was then treated with a solution of hydrogen chloride in 1,4-dioxane (10 mL). The resulting mixture was allowed to stir at room temperature for 2 h. Concentrating the reaction mixture under vacuum afforded 358 mg of crude, racemic 2-tert-butyl-7-azabicyclo[2.2.1]heptan-2-ol as a white solid. Mass Spectrum (LCMS, ESI pos.): Calcd. for $C_{10}H_{19}NO$: 170 (M+H); found: 170.

210

Preparation of Intermediate XIVB: (±)-(1R,2R,4S)-2-(Trifluoromethyl)-7-azabicyclo[2.2.1]heptan-2-ol Hydrochloride

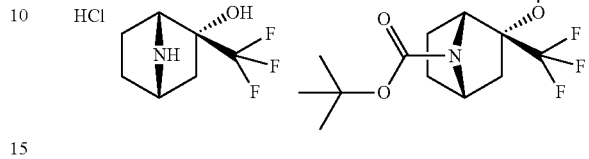

A. tert-Butyl (1R,2R,4S)-2-(Trifluoromethyl)-2-((trimethylsilyl)oxy)-7-azabicyclo[2.2.1]heptane-7-carboxylate Into a 50 mL round-bottom flask, being maintained under an inert atmosphere of nitrogen, was placed a mixture of racemic tert-butyl 2-oxo-7-azabicyclo[2.2.1]heptane-7-carboxylate (1.05 g, 4.97 mmol), trimethyl(trifluoromethyl)silane (860 mg, 6.05 mmol) and tetrabutylammonium fluoride (20 mg, 0.08 mmol) in tetrahydrofuran (25 mL). The reaction mixture was allowed to stir at room temperature for 2 h and then concentrated under vacuum. The remaining residue was purified by column chromatography on silica, using ethyl acetate/petroleum ether (1:6) as the eluant, to afford 1.5 g (85%) of racemic tert-butyl 2-(trifluoromethyl)-2-[(trimethylsilyl)oxy]-7-azabicyclo[2.2.1]heptane-7-carboxylate as colorless oil.

B. tert-Butyl (1R,2R,4S)-2-Hydroxy-2-(trifluoromethyl)-7-azabicyclo[2.2.1]heptane-7-carboxylate Into a 50 mL round-bottom flask, being maintained under an inert atmosphere of nitrogen, was placed a mixture of tert-butyl 2-oxo-7-azabicyclo[2.2.1]heptane-7-carboxylate (1.5 g, 7.10 mmol) and tetrabutylammonium fluoride (2.2 g, 8.41 mmol) in tetrahydrofuran (20 mL). The resulting mixture was allowed to stir at room temperature for 1 h and was then diluted with ethyl acetate (150 mL). The mixture was dried over anhydrous sodium sulfate and concentrated under vacuum. The remaining residue was purified by column chromatography on silica, using ethyl acetate/petroleum ether (1:4) as the eluant, to afford 500 mg (25%) of racemic tert-butyl 2-hydroxy-2-(trifluoromethyl)-7-azabicyclo[2.2.1]heptane-7-carboxylate as a white solid.

C. (±)-(1R,2R,4S)-2-(Trifluoromethyl)-7-azabicyclo[2.2.1]heptan-2-ol Hydrochloride Into a 25 mL round-bottom flask, being maintained under an inert atmosphere of nitrogen, was placed tert-butyl 2-hydroxy-2-(trifluoromethyl)-7-azabicyclo[2.2.1]heptane-7-carboxylate (560 mg, 1.99 mmol), which was then treated with a solution of hydrogen chloride in 1,4-dioxane (10 mL). The resulting mixture was allowed to stir at room temperature for 3 h, before being concentrated under vacuum. This process afforded 700 mg of racemic, crude 2-(trifluoromethyl)-7-azabicyclo[2.2.1]heptan-2-ol hydrochloride as a light brown crude solid.

Preparation of Intermediates XVB and XVIB: (1R,3s,5S)-3-(trifluoromethyl)-8-azabicyclo[3.2.1]octan-3-ol and (1R,3r,5S)-3-(Trifluoromethyl)-8-azabicyclo[3.2.1]octan-3-ol

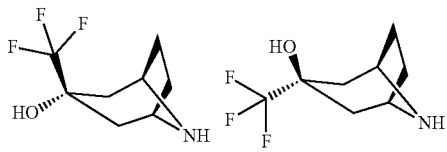

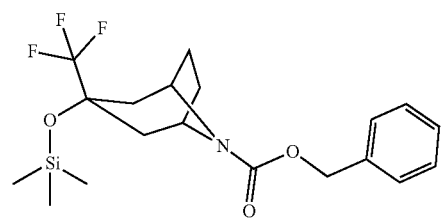

A. Benzyl 3-(Trifluoromethyl)-3-((trimethylsilyl)oxy)-8-azabicyclo[3.2.1]octane-8-carboxylate Into a 100 mL 3-necked round-bottom flask, being maintained under an inert atmosphere of nitrogen, was placed a solution of benzyl 3-oxo-8-azabicyclo[3.2.1]octane-8-carboxylate (5.2 g, 20.1 mmol) in tetrahydrofuran (50 mL). The solution was cooled to 0° C. and then trimethyl(trifluoromethyl)silane (3.4 g) and tetrabutylammonium fluoride (40 mg, 0.15 mmol) were added. The resulting mixture was allowed to warm to room temperature and stir for 1 h. The pH of the reaction mixture was neutralized by the addition of aqueous sodium bicarbonate and then extracted with ethyl acetate (3×100 mL). The combined organic extracts were dried over anhydrous sodium sulfate and concentrated under vacuum. The remaining residue was purified by column chromatography on silica, using ethyl acetate/petroleum ether (1:20) as the eluant, to afford 7.2 g (87%) of benzyl 3-(trifluoromethyl)-3-((trimethylsilyl)oxy)-8-azabicyclo[3.2.]octane-8-carboxylate as a yellow oil. Mass Spectrum (LCMS, ESI pos.): Calcd. for $C_{19}H_{26}F_3NO_3Si$: 402 (M+H); found: 402.

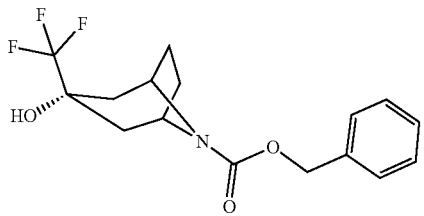

B. Benzyl 3-Hydroxy-3-(trifluoromethyl)-8-azabicyclo[3.2.1]octane-8-carboxylate Into a 50 mL round-bottom flask was placed a solution of benzyl 3-(trifluoromethyl)-3-((trimethylsilyl)oxy)-8-azabicyclo[3.2.1] octane-8-carboxylate (7.2 g, 17.9 mmol) in tetrahydrofuran (50 mL), which was then treated with a concentrated, aqueous solution of hydrogen chloride. The resulting mixture was allowed to stir at room temperature overnight before the pH was neutralized with an aqueous, saturated solution of sodium bicarbonate. The aqueous mixture was extracted with ethyl acetate and the combined organic extracts were dried over anhydrous sodium sulfate and concentrated under vacuum. The remaining residue was purified by column chromatography on silica, using ethyl acetate/hexane (1:8 to 1:2) as the eluant, to afford 2.5 g (42%) of benzyl 3-hydroxy-3-(trifluoromethyl)-8-azabicyclo[3.2.]octane-8-carboxylate as a white solid. Mass Spectrum (LCMS, ESI pos.): Calcd. for $C_{16}H_{18}F_3NO_3$: 330 (M+H); found: 330. $^1$H NMR (400 MHz, DMSO-$d_6$): δ 7.39-7.29 (m, 5H), 5.98-5.75 (m, 1H), 5.13-5.05 (m, 2H), 4.26 (s, 2H), 2.26-2.16 (m, 2H), 2.10-1.57 (m, 6H)

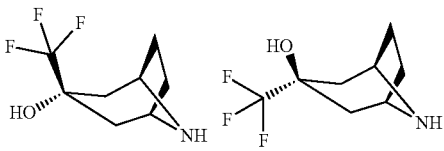

C. (1R,3s,5S)-3-(Trifluoromethyl)-8-azabicyclo[3.2.1]octan-3-ol and (1R,3r,5S)-3-(Trifluoromethyl)-8-azabicyclo[3.2.1]octan-3-ol Into a 50 mL round-bottom flask was placed a solution of benzyl (1R,3s,5S)-3-hydroxy-3-(trifluoromethyl)-8-azabicyclo[3.2.1]octane-8-carboxylate (1.5 g, 4.55 mmol) in methanol (25 mL), to which was then added palladium on carbon (225 mg). The resulting mixture was sparged with hydrogen gas and then allowed to stir at room temperature for 2 h. The solids were filtered from the reaction and the filtrate was concentrated under vacuum to afford 700 mg (79%) of a mixture of (1R,3s,5S)-3-(trifluoromethyl)-8-azabicyclo[3.2.1]octan-3-ol and (1R,3r,5S)-3-(trifluoromethyl)-8-azabicyclo[3.2.1]octan-3-ol as a white solid. Mass Spectrum (LCMS, ESI pos.): Calcd. for $C_8H_{12}F_3NO$: 196 (M+H); found: 196. $^1$H NMR (400 MHz, DMSO-$d_6$): δ 5.54 (s, 1H), 3.53 (s, 1H), 3.41 (s, 1H), 2.20-1.96 (m, 2H), 1.78-1.67 (m, 6H)

Preparation of Intermediates XVIIB and XVIIIB: (±)-(1S,2S,4R)-2-Methyl-7-azabicyclo[2.2.1]heptane Hydrochloride and (±)-(1S,2R,4R)-2-Methyl-7-azabicyclo[2.2.1]heptane Hydrochloride

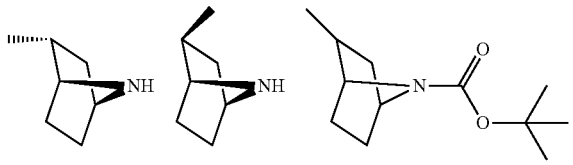

A. tert-Butyl (1S,4R)-2-Methyl-7-azabicyclo[2.2.1]heptane-7-carboxylate

Into a 100 mL round-bottom flask was placed a solution of tert-butyl 2-methylene-7-azabicyclo[2.2.1]heptane-7-carboxylate (800 mg, 3.83 mmol) in methanol (10 mL), to which palladium on carbon (200 mg) was added. The resulting mixture was sparged with hydrogen and then allowed to stir at room temperature for 2 h. The reaction mixture was diluted with methanol (20 mL) and then filtered. The filtrate was concentrated under vacuum to afford 770 mg (95%) of tert-butyl 2-methyl-7-azabicyclo[2.2.1]heptane-7-carboxylate as a crude oil. Mass Spectrum (LCMS, ESI pos.): Calcd. for $C_{12}H_{21}NO_2$: 213 (M+H); found: 213.

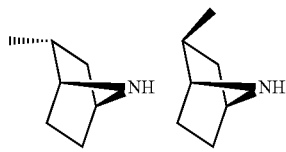

B. (±)-(1S,4R)-2-Methyl-7-azabicyclo[2.2.1]heptane Hydrochloride and (±)-(1S,2R,4R)-2-Methyl-7-azabicyclo[2.2.1]heptane Hydrochloride Into a 100 mL round-bottom flask was placed a solution of tert-butyl 2-methyl-7-azabicyclo[2.2.1]heptane-7-carboxylate (670 mg, 3.17 mmol) in 1,4-dioxane (3 mL), which was then treated with aqueous, concentrated hydrogen chloride (2 mL). The resulting mixture was allowed to stir at room temperature for 4 h. The reaction mixture was concentrated under vacuum to afford 620 mg of a mixture of crude (±)-(1S,2S,4R)-2-methyl-7-azabicyclo[2.2.1]heptane hydrochloride and (±)-(1S,2R,4R)-2-methyl-7-azabicyclo[2.2.1]heptane hydrochloride as a yellow oil.

Preparation of Intermediate XIXB: (±)-(3aR,4R,7S,7aS)-Octahydro-4,7-epiminoisobenzofuran Hydrochloride

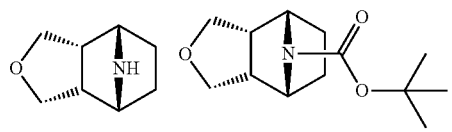

A. (±)-tert-Butyl (3aR,4R,7S,7aS)-Octahydro-4,7-epiminoisobenzofuran-8-carboxylate Into a 50 mL 3-necked round-bottom flask was placed a solution of racemic tert-butyl (2R,3S)-2,3-bis(hydroxymethyl)-7-azabicyclo[2.2.1]heptane-7-carboxylate (880 mg, 3.42 mmol) in dry tetrahydrofuran (20 mL). The solution was cooled to 0° C. and then n-butyllithium (1.4 mL, 2.45 M in hexanes) was added. The reaction mixture was allowed to stir at 0° C. for 30 min. Then a solution of tosyl chloride (650 mg, 3.41 mmol) in tetrahydrofuran (5 mL) was added to the flask, after which the reaction mixture was allowed to stir for 1 h at 0° C. Another portion of n-butyllithium (1.4 mL, 2.5 M in hexanes) was added to the flask and the reaction mixture was allowed to stir for 30 min at 0° C. before being diluted with water (15 mL). The mixture was extracted with ethyl acetate (3×20 mL) and the combined organic extracts were dried over anhydrous sodium sulfate and concentrated under vacuum. The remaining residue was purified by column chromatography on silica, using ethyl acetate/petroleum ether (1/5) as the eluant, to afford 560 mg (68%) of racemic tert-butyl (3aR,4R,7S,7aS)-octahydro-4,7-epiminoisobenzofuran-8-carboxylate as a yellow solid. Mass Spectrum (LCMS, ESI pos.): Calcd. for $C_{13}H_{21}NO_3$: 240 (M+H); found: 240.

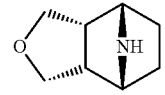

B. (±)-(3aR,4R,7S,7aS)-Octahydro-4,7-epiminoisobenzofuran Hydrochloride

Into a 50 mL round-bottom flask was placed a solution of racemic tert-butyl (3aR,4R,7S,7aS)-octahydro-4,7-epiminoisobenzofuran-8-carboxylate (560 mg, 2.34 mmol) in 1,4-dioxane (12 mL), which was then treated with concentrated, aqueous hydrogen chloride (1 mL). The resulting mixture was allowed to stir at room temperature for 1 h. The reaction mixture was concentrated under vacuum to afford 470 mg of crude, racemic (3aR,4R,7S,7aS)-octahydro-4,7-epiminoisobenzofuran hydrochloride as a yellow oil. Mass Spectrum (LCMS, ESI pos.): Calcd. for $C_8H_{13}NO$: 140 (M+H); found: 140.

Preparation of Intermediates XXB, XXIB, and XXIIB: (1R,2S,3S,4S)-2,3-Dimethyl-7-azabicyclo[2.2.1]heptane Hydrochloride and (1R,2S,3R,4S)-2,3-Dimethyl-7-azabicyclo[2.2.1]heptane Hydrochloride and (±)-(1R,2S,3R,4S)-2,3-Dimethyl-7-azabicyclo[2.2.1]heptane Hydrochloride

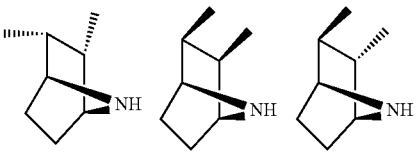

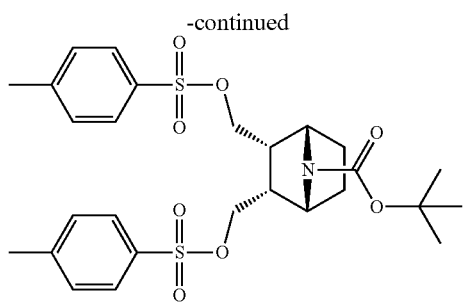

A. tert-Butyl (1R,2R,3S,4S)-2,3-Bis((tosyloxy) methyl)-7-azabicyclo[2.2.1]heptane-7-carboxylate Into a 100 mL round-bottom flask was placed a solution of tosyl chloride (10.4 g, 0.055 mol) in pyridine (30 mL). The solution as cooled to 0° C. and then treated with a solution of tert-butyl (1R,2R,3S,4S)-2,3-bis(hydroxymethyl)-7-azabicyclo[2.2.1]heptane-7-carboxylate (680 mg, 2.64 mmol) in pyridine (2 mL). The resulting mixture was allowed to warm to room temperature and stir overnight. The reaction mixture was diluted with water (30 mL) and then extracted with ethyl acetate (3×30 mL). The combined organic extracts were washed with brine (3×50 mL), dried over anhydrous sodium sulfate and then concentrated under vacuum. The remaining residue was purified by column chromatography on silica, using ethyl acetate/petroleum ether (1/1), as the eluant, to afford 719 mg (48%) of tert-butyl (1R,2R,3S,4S)-2,3-bis((tosyloxy)methyl)-7-azabicyclo[2.2.1]heptane-7-carboxylate as a yellow solid. Mass Spectrum (LCMS, ESI pos.): Calcd. for $C_{27}H_{35}NO_8S_2$: 566 (M+H); found: 566.

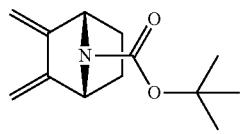 [SMILES: C=C1C(=C)[C@@H]2CC[C@H]1N2C(=O)OC(C)(C)C]

B. tert-Butyl (1R,4S)-2,3-Dimethylene-7-azabicyclo[2.2.1]heptane-7-carboxylate Into a 50 mL round-bottom flask was placed a solution of tert-butyl (1R,2R,3S,4S)-2,3-bis((tosyloxy)methyl)-7-azabicyclo[2.2.1]heptane-7-carboxylate (719 mg, 1.27 mmol) in dimethylsulfoxide (5 mL), which was then treated with potassium tert-butoxide (356 mg, 3.17 mmol). The resulting mixture was allowed to stir at room temperature overnight. The reaction mixture was then diluted with water (10 mL) and extracted with ethyl acetate (3×20 mL). The combined organic extracts were washed with brine (3×30 mL) and dried over anhydrous sodium sulfate. The organic phase was concentrated under vacuum to afford 280 mg (crude) of tert-butyl (1R,4S)-2,3-dimethylene-7-azabicyclo[2.2.1]heptane-7-carboxylate as a yellow oil. Mass Spectrum (LCMS, ESI pos.): Calcd. for $C_{13}H_{19}NO_2$: 222 (M+H); found: 222.

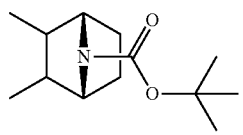 [SMILES: CC1C(C)[C@@H]2CC[C@H]1N2C(=O)OC(C)(C)C]

C. tert-Butyl (1R,4S)-2,3-Dimethyl-7-azabicyclo[2.2.1]heptane-7-carboxylate

Into a 50 mL round-bottom flask was placed a solution of crude tert-butyl (1R,4S)-2,3-dimethylene-7-azabicyclo[2.2.1]heptane-7-carboxylate (280 mg, 1.27 mmol) in ethyl acetate (20 mL), which was then treated with solid Pd/C (28 mg). The suspension was degassed under vacuum and back filled with hydrogen gas several times. The mixture was allowed to stir under an atmosphere of hydrogen at room temperature for 16 h. The solids were filtered from the reaction mixture and the filtrate was concentrated under vacuum. This process afforded 280 mg (98%) of tert-butyl (1R,4S)-2,3-dimethyl-7-azabicyclo[2.2.1]heptane-7-carboxylate as a colorless oil. Mass Spectrum (LCMS, ESI pos.): Calcd. for $C_{13}H_{23}NO_2$: 226 (M+H); found: 226.

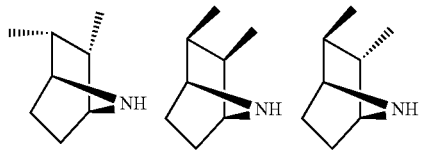

D. (1R,2S,3S,4S)-2,3-Dimethyl-7-azabicyclo[2.2.1]heptane Hydrochloride and (1R,2S,3R,4S)-2,3-Dimethyl-7-azabicyclo[2.2.1]heptane Hydrochloride and (±)-(1R,2S,3R,4S)-2,3-Dimethyl-7-azabicyclo[2.2.1]heptane Hydrochloride Into a 25 mL round-bottom flask was placed a solution of tert-butyl (1R,4S)-2,3-dimethyl-7-azabicyclo[2.2.1]heptane-7-carboxylate (270 mg, 1.20 mmol) in 1,4-dioxane (3 mL), which was then treated with aqueous, concentrated hydrogen chloride (1 mL). The resulting mixture was allowed to stir at room temperature for 2 h and then concentrated under vacuum to afford 220 mg (crude) of a mixture of (1R,2S,3S,4S)-2,3-dimethyl-7-azabicyclo[2.2.1] heptane hydrochloride, (1R,2S,3R,4S)-2,3-dimethyl-7-azabicyclo[2.2.1]heptane hydrochloride, and (1R,2S,3R,4S)-2,3-dimethyl-7-azabicyclo[2.2.1]heptane hydrochloride as a yellow solid.

Preparation of Intermediate XXIIIB: (±)-(E)-5,5-Dimethyl-3-(3-(4,4,5,5-tetramethyl-1,3,2-dioxaborolan-2-yl)allyl)dihydrofuran-2(3H)-one

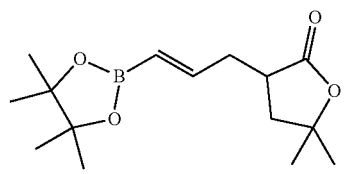

Into a 5-mL sealed tube, being maintained under an inert atmosphere of nitrogen, was placed a solution of 5,5-dimethyl-3-(prop-2-yn-1-yl)dihydrofuran-2(3H)-one (152 mg, 1.00 mmol) in ethanol (3 mL). To the solution were added 4,4,4',4',5,5,5',5'-octamethyl-2,2'-bi(1,3,2-dioxaborolane) (381 mg, 1.50 mmol), sodium methoxide (11 mg, 0.20 mmol) and copper powder (6.4 mg, 0.10 mmol). The resulting mixture was allowed to stir at room temperature overnight before being diluted with water (100 mL). The aqueous mixture was extracted with ethyl acetate (2×100 mL) and the combined organic extracts were washed with brine (3×100 mL). The organic phase was dried over anhydrous sodium sulfate and concentrated under vacuum. The remaining residue was purified by column chromatography on silica, using ethyl acetate/petroleum ether (1:5) as the eluant, to afford 240 mg (86%) of (±)-(E)-5,5-dimethyl-3-(3-(4,4,5,5-tetramethyl-1,3,2-dioxaborolan-2-yl)allyl)dihydrofuran-2(3H)-one as a yellow oil.

Preparation of Intermediates XXIVB and XXVB: (±)-(1S,4R)-2-(Trifluoromethyl)-7-azabicyclo[2.2.1]hept-2-ene Hydrochloride and (±)-(1,2S,4R)-2-(Trifluoromethyl)-7-azabicyclo[2.2.1]heptane Hydrochloride

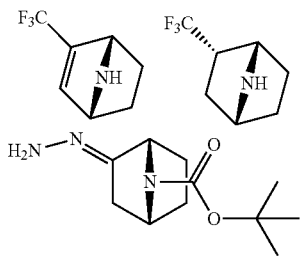

A. (±)-tert-Butyl (1S,4R)-2-Hydrazono-7-azabicyclo[2.2.1]heptane-7-carboxylate

Into a 250 mL round-bottom flask, being maintained under an inert atmosphere of nitrogen, was placed a solution of racemic tert-butyl 2-oxo-7-azabicyclo[2.2.1]heptane-7-carboxylate (2.11 g, 10.0 mmol) in methanol (50 mL). The solution was treated with $N_2H_4 \cdot H_2O$ (5.0 g, 100 mmol) and the resulting mixture was heated at 65° C. overnight. After cooling to room temperature, the reaction mixture was concentrated under vacuum and the remaining residue was purified by column chromatography on silica, using ethyl acetate/petroleum ether (1:1) as the eluant, to afford 3.0 g (crude) of (±)-tert-butyl (1S,4R)-2-hydrazono-7-azabicyclo[2.2.1]heptane-7-carboxylate as a yellow oil. Mass Spectrum (LCMS, ESI pos.): Calcd. for $C_{11}H_{19}N_3O_2$: 226 (M+H); found: 226.

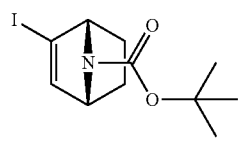

B. (±)-tert-Butyl (1S,4R)-2-Iodo-7-azabicyclo[2.2.1]hept-2-ene-7-carboxylate

Into a 100 mL round-bottom flask, being maintained under an inert atmosphere of nitrogen, was placed a mixture of iodine (6.76 g, 26.6 mmol), 1,1,3,3-tetramethylguanidine (7.59 g, 66.5 mmol), tetrahydrofuran (40 mL) and diethylether (20 mL). The mixture was cooled to 0° C. and allowed to stir for 30 min before it was treated with a solution of (±)-tert-butyl (1S,4R)-2-hydrazono-7-azabicyclo[2.2.1]heptane-7-carboxylate (2.99 g, 13.3 mmol). The reaction mixture was allowed to warm to room temperature and stir for an additional 20 h. The reaction was quenched through the addition of aqueous sodium thiosulfate and the resulting mixture was extracted with ethyl acetate (3×50 mL). The combined organic extracts were dried over anhydrous sodium sulfate and concentrated under vacuum. The remaining residue was purified by column chromatography on silica, using ethyl acetate/petroleum ether (1:15) as the eluant, to afford 340 mg (8%) of (±)-tert-butyl (1S,4R)-2-iodo-7-azabicyclo[2.2.1]hept-2-ene-7-carboxylate as a yellow solid. Mass Spectrum (LCMS, ESI pos.): Calcd. for $C_{11}H_{16}INO_2$: 322 (M+H); found: 322.

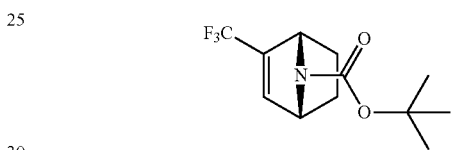

C. (±)-tert-Butyl (1S,4R)-2-(Trifluoromethyl)-7-azabicyclo[2.2.1]hept-2-ene-7-carboxylate Into a 50 mL round-bottom flask, being maintained under an inert atmosphere of nitrogen, was placed a mixture of (±)-tert-butyl (1S,4R)-2-iodo-7-azabicyclo[2.2.1]hept-2-ene-7-carboxylate (561 mg, 1.75 mmol), hexamethylphosphoramide (3.76 g, 21.0 mmol), copper(I) iodide (2.00 g, 10.5 mmol), and N,N-dimethylformamide (10 mL). The resulting mixture was treated with methyl 2,2-difluoro-2-(fluorosulfonyl)acetate (3.36 g, 17.5 mmol) and then heated at 70° C. for 24 h. After cooling to room temperature the reaction mixture was diluted with ethyl acetate (100 mL) and then washed with aqueous ammonium chloride (3×50 mL). The organic phase was dried over anhydrous sodium sulfate and concentrated under vacuum. The remaining residue was purified by column chromatography on silica, using ethyl acetate/petroleum ether (1:15) as the eluant, to afford 398 mg (87%) of (±)-tert-butyl (1S,4R)-2-(trifluoromethyl)-7-azabicyclo[2.2.1]hept-2-ene-7-carboxylate as a yellow oil. Mass Spectrum (LCMS, ESI pos.): Calcd. for $C_{12}H_{16}F_3NO_2$: 264 (M+H); found: 264.

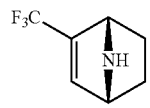 [SMILES: FC(F)(F)C1=C[C@H]2CC[C@@H]1N2]

D. (±)-(1S,4R)-2-(Trifluoromethyl)-7-azabicyclo[2.2.1]hept-2-ene Hydrochloride

Into a 50 mL round-bottom flask was placed a mixture of (±)-tert-butyl (1S,4R)-2-(trifluoromethyl)-7-azabicyclo

[2.2.1]hept-2-ene-7-carboxylate (398 mg, 1.51 mmol) and a solution of hydrogen chloride in 1,4-dioxane (4M, 10 mL). The reaction mixture was allowed to stir at room temperature overnight before it was concentrated under vacuum to afford 300 mg (crude) of (±)-(1S,4R)-2-(trifluoromethyl)-7-azabicyclo[2.2.1]hept-2-ene hydrochloride as a yellow oil. Mass Spectrum (LCMS, ESI pos.): Calcd. for $C_7H_8F_3N$: 164 (M+H); found: 164.

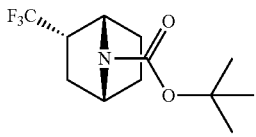 [SMILES: CC(C)(C)OC(=O)N1[C@@H]2CC[C@H]1[C@@H](C(F)(F)F)C2]

E. (±)-tert-Butyl (1S,2S,4R)-2-(Trifluoromethyl)-7-azabicyclo[2.2.1]heptane-7-carboxylate Into a 30 mL pressure tank reactor was placed a solution of (±)-tert-butyl (1S,4R)-2-(trifluoromethyl)-7-azabicyclo[2.2.1]hept-2-ene-7-carboxylate (428 mg, 1.63 mmol) in methanol (25 mL). To the solution was added palladium on carbon (86 mg) and the resulting mixture was sparged with hydrogen. The reactor was pressurized with hydrogen to 5 atm and then heated at 50° C. for 3 h. After cooling and venting the reactor, the reaction mixture was diluted with ethyl acetate (50 mL) and then filtered. The filtrate was concentrated under vacuum to afford 322 mg (75%) of (±)-tert-butyl (1S,2S,4R)-2-(trifluoromethyl)-7-azabicyclo[2.2.1]heptane-7-carboxylate as a yellow oil. Mass Spectrum (LCMS, ESI pos.): Calcd. for $C_{12}H_{18}F_3NO_2$: 266 (M+H); found: 266.

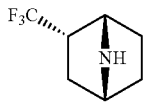

F. (±)-(1S,2S,4R)-2-(Trifluoromethyl)-7-azabicyclo[2.2.1]heptane Hydrochloride

Into a 50 mL round-bottom flask was placed a mixture of (±)-tert-butyl (1S,2S,4R)-2-(trifluoromethyl)-7-azabicyclo[2.2.1]heptane-7-carboxylate (322 mg, 1.22 mmol) and hydrogen chloride in 1,4-dioxane (8 mL, 4M). The reaction mixture was allowed to stir at room temperature overnight before it was concentrated under vacuum to afford 105 mg (43%) of (±)-2-(trifluoromethyl)-7-aza-bicyclo[2.2.1]heptane hydrochloride as a yellow oil.

Preparation of Intermediate XXVIB: (±)-(1S,4R)-2-(Trifluoromethoxy)-7-azabicyclo[2.2.1]heptane Hydrochloride

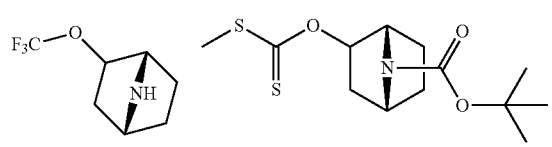

A. (±)-tert-Butyl (1S,4R)-2-(((Methylthio)carbonothioyl)oxy)-7-azabicyclo[2.2.1]heptane-7-carboxylate Into a 100 mL round-bottom flask, being maintained under an inert atmosphere of nitrogen, was placed a solution of racemic tert-butyl 2-hydroxy-7-azabicyclo[2.2.1]heptane-7-carboxylate (1.07 g, 5.00 mmol) in tetrahydrofuran (15 mL). The solution was cooled to 0° C. and then treated with sodium hydride (240 mg, 10.0 mmol). The resulting mixture was allowed to warm to room temperature and stir for 1.5 hours. The reaction mixture was again cooled to 0° C. and then carbon disulfide (1.9 g, 25.0 mmol, 5.00 equiv) was added to the flask in a dropwise manner over 5 min. The reaction mixture was allowed to warm to room temperature and stir for an additional 3 h. The reaction mixture was cooled to 0° C., followed by the addition of $CH_3I$ (1.42 g, 10.0 mmol). The reaction mixture as allowed to stir at the reduced temperature for 1 h and was then diluted with aqueous ammonium chloride. The aqueous mixture was extracted with ethyl acetate (3×30 mL) and the combined organic extracts were dried over sodium sulfate. The organic phase was concentrated under vacuum and the remaining residue was purified by column chromatography on silica, using ethyl acetate/petroleum ether (1:3) as the eluant, to afford 1.1 g (73%) of (±)-tert-butyl (1S,4R)-2-(((methylthio)carbonothioyl)oxy)-7-azabicyclo[2.2.1]heptane-7-carboxylate as yellow oil.

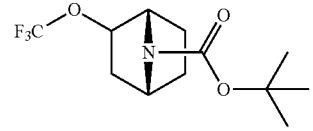

B. (±)-tert-Butyl (1S,4R)-2-(Trifluoromethoxy)-7-azabicyclo[2.2.1]heptane-7-carboxylate Into a 100 mL round-bottom flask, being maintained under an inert atmosphere of nitrogen, was placed a solution of N-bromosuccinimide (4.45 g, 25.0 mmol) in dichloromethane (30 mL). The solution was cooled to −40° C. and then hydrogen fluoride-pyridine (70%, 5 mL) and pyridine (2.3 mL) were added in a dropwise manner. The resulting mixture was allowed to warm to room temperature, stir for 5 min, and was then cooled to 0° C. The mixture was treated with tert-butyl 2-[[(methylsulfanyl)methanethioyl]oxy]-7-azabicyclo[2.2.1]heptane-7-carboxylate (1.52 g, 5.00 mmol) and was allowed to stir for 1 h. The pH of the reaction mixture was adjusted to 10 through the addition of aqueous sodium hydroxide and then extracted with dichloromethane (3×50 mL). The combined organic extracts were washed with brine (3×40 mL), dried over sodium sulfate, and then concentrated under vacuum. The remaining residue was purified by column chromatography on silica, using ethyl acetate/petroleum ether (1:10) as the eluant, to afford 200 mg (14%) of (±)-tert-butyl (1S,4R)-2-(trifluoromethoxy)-7-azabicyclo[2.2.1]heptane-7-carboxylate as a yellow oil. Mass Spectrum (LCMS, ESI pos.): Calcd. for $C_{12}H_{18}F_3NO_3$: 282 (M+H); found: 282.

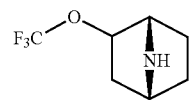

C. (±)-(1S,4R)-2-(Trifluoromethoxy)-7-azabicyclo[2.2.1]heptane Hydrochloride Into a 25 mL round-bottom flask was placed a mixture of (±)-tert-butyl (1S,4R)-2-(trifluoromethoxy)-7-azabicyclo[2.2.1]heptane-7-carboxylate (281 mg, 1.00 mmol) and a solution hydrogen chloride in 1,4-dioxane (8 mL, 4.0 M). The resulting mixture was allowed to stir for 2 h at room temperature before being concentrated under vacuum to afford 217 mg (crude) of (±)-(1S,4R)-2-(trifluoromethoxy)-7-azabicyclo[2.2.1]heptane hydrochloride as yellow oil.

Preparation of Intermediate XXVIIB: (1s,4s)-1-Methyl-7-azabicyclo[2.2.1]heptane Hydrochloride

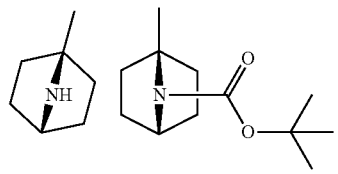

A. tert-Butyl (1s,4s)-1-Methyl-7-azabicyclo[2.2.1]heptane-7-carboxylate

Into a 100 mL round-bottom flask, being maintained under an atmosphere of nitrogen, was placed a mixture of tert-butyl 7-azabicyclo[2.2.1]heptane-7-carboxylate (1.0 g, 5.08 mmol) and N,N,N',N'-tetramethylethane-1,2-diamine (884 mg, 7.62 mmol) in diethyl ether (30 mL). The mixture was cooled to 0° C. and then treated with s-butyl lithium (1M, 7.62 mL, 7.62 mmol) in a dropwise fashion. The reaction mixture was allowed to stir at 0° C. for 3 h and then neat iodomethane (1.44 g, 10.2 mmol) was added to the flask. The resulting mixture was allowed to warm to room temperature and stir for 16 h before it was diluted with an aqueous solution of ammonium chloride. The mixture was extracted with ethyl acetate (2×50 mL) and the organic extracts were dried over sodium sulfate. The organic phase was concentrated under vacuum to afford 1.12 g (crude) of tert-butyl 1-methyl-7-azabicyclo[2.2.1]heptane-7-carboxylate as a yellow oil. Mass Spectrum (LCMS, ESI pos.): Calcd. for $C_{12}H_{21}NO_2$: 212 (M+H); found: 212.

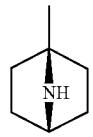

B. (1s,4s)-1-Methyl-7-azabicyclo[2.2.1]heptane Hydrochloride

Into a 100 mL round-bottom flask was placed a mixture of tert-butyl 1-methyl-7-azabicyclo[2.2.1]heptane-7-carboxylate (670 mg, 3.17 mmol) and a solution of hydrogen chloride in 1,4-dioxane (4M, 14 mL). The resulting mixture was allowed to stir at room temperature overnight before it was concentrated under vacuum to afford 572 mg (crude) of (1s,4s)-1-methyl-7-azabicyclo[2.2.1]heptane hydrochloride as a yellow oil.

Preparation of Intermediate XXVIIIB: (±)-(3aS,4R,7S,7aS)-Octahydro-4,7-epiminobenzofuran Hydro-4-methylbezenesulfonate

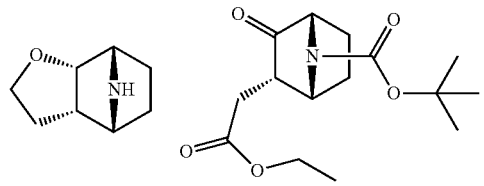

A. (±)-tert-Butyl (1R,2S,4S)-2-(2-Ethoxy-2-oxo-ethyl)-3-oxo-7-azabicyclo[2.2.1]heptane-7-carboxylate Into a 250 mL round-bottom flask, being maintained under an inert atmosphere of nitrogen, was placed a solution of n-butyl lithium (16 mL, 2.5M, 2.00 equiv) in tetrahydrofuran (100 mL). The solution was cooled to −78° C. and then racemic tert-butyl (1R,4S)-2-oxo-7-azabicyclo[2.2.1]heptane-7-carboxylate (4.22 g, 20.0 mmol) was added to the flask. The resulting mixture was allowed to stir at the reduced temperature for 30 min before it was treated with ethyl 2-bromoacetate (9 mL, 0.08 mmol). The reaction mixture was allowed to warm to room temperature and stir for an additional hour. The reaction mixture was diluted with an aqueous solution of ammonium chloride and then extracted with ethyl acetate (3×30 mL). The combined organic extracts were washed with brine (3×30 mL), dried over $Na_2SO_4$ and concentrated under vacuum. The remaining residue was purified by column chromatography on silica, using ethyl acetate/petroleum ether (1:1) as the eluant, to afford 4.23 g (71%) of (±)-tert-butyl (1R,2S,4S)-2-(2-ethoxy-2-oxoethyl)-3-oxo-7-azabicyclo[2.2.1]heptane-7-carboxylate as a light yellow oil. Mass Spectrum (LCMS, ESI pos.): Calcd. for $C_1H_{23}NO_5$: 298 (M+H); found: 298.

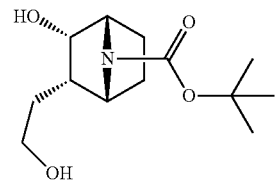 [SMILES: CC(C)(C)OC(=O)N1[C@@H]2CC[C@H]1[C@@H](O)[C@H]2CCO]

B. (±)-tert-Butyl (1S,2S,3S,4R)-2-Hydroxy-3-(2-hydroxyethyl)-7-azabicyclo[2.2.1]heptane-7-carboxylate Into a 25 mL round-bottom flask, being maintained under an inert atmosphere of nitrogen, was placed a solution of (±)-tert-butyl (1R,2S,4S)-2-(2-ethoxy-2-oxoethyl)-3-oxo-7-azabicyclo[2.2.1]heptane-7-carboxylate (297 mg, 1.00 mmol) in tetrahydrofuran (10 mL). The solution was cooled to 0° C. and then treated with lithium aluminum hydride (114 mg, 3.00 mmol) in a portionwise manner. The resulting mixture was allowed to stir at 0° C. for 3 h before it was treated with an aqueous saturated solution of ammonium chloride (10 mL). The mixture was extracted with ethyl acetate (3×15 mL) and the combined organic extracts were washed with brine (2×15 mL). The organic phase was dried over sodium sulfate and concentrated under vacuum to afford 115 mg (45%) of (±)-tert-butyl (1S,2S,3S,4R)-2-hydroxy-3-(2-hydroxyethyl)-7-azabicyclo[2.2.1]heptane-7-carboxylate as a light yellow oil. Mass Spectrum (LCMS, ESI pos.): Calcd. for $C_{13}H_{23}NO_4$: 258 (M+H); found: 258.

C. (±)-(3aS,4R,7S,7aS)-Octahydro-4,7-epiminobenzofuran Hydro-4-methylbezenesulfonate Into a 50 mL round-bottom flask, being maintained under an inert atmosphere of nitrogen, was placed a solution of (±)-tert-butyl (1S,2S,3S,4R)-2-hydroxy-3-(2-hydroxyethyl)-7-azabicyclo[2.2.1]heptane-7-carboxylate (464 mg, 1.80 mmol) in tetrahydrofuran (20 mL). The solution was then treated with n-butyllithium (0.74 mL, 1.00 equiv) in a dropwise manner. The resulting mixture was allowed to stir at room temperature for 30 min and was then treated with a solution of 4-methylbenzenesulfonyl chloride (343 mg, 1.80 mmol) in tetrahydrofuran (5 mL) in a dropwise manner. The reaction mixture was allowed to stir at room temperature for 3 h before being diluted with water (50 mL). The mixture was extracted with ethyl acetate (3×15 mL) and the combined organic extracts were concentrated under vacuum to afford 210 mg (37%) of (±)-(3aS,4R,7S,7aS)-octahydro-4,7-epiminobenzofuran hydro-4-methylbezenesulfonate as a white solid. Mass Spectrum (LCMS, ESI pos.): Calcd. for $C_8H_{13}NO$: 140 (M+H); found: 140.

Preparation of Intermediate XXIXB: (±)-1-((1s,4s)-7-Azabicyclo[2.2.1]heptan-1-yl)ethan-1-ol Hydrochloride

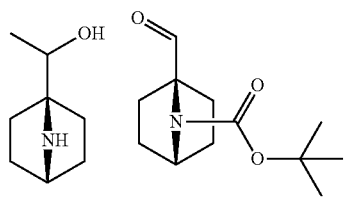

A. tert-Butyl (1s,4s)-1-Formyl-7-azabicyclo[2.2.1]heptane-7-carboxylate

Into a 100 mL round-bottom flask, being maintained under an inert atmosphere of nitrogen, was placed a mixture of tert-butyl 7-azabicyclo[2.2.1]heptane-7-carboxylate (1.18 g, 5.99 mmol), N,N,N',N'-tetramethylethane-1,2-diamine (1.04 g, 8.98 mmol) and diethyl ether (10 mL). The mixture was cooled to 0° C. and then treated with s-butyl lithium (576 mg, 1.50 equiv) in a dropwise manner. The mixture was allowed to stir at 0° C. for 1.5 h and was then treated with a solution of ethyl formate (1.33 g, 18.0 mmol) in diethyl ether (5 mL). The reaction mixture was allowed to warm to room temperature and stir for an additional 14 h before it was diluted with an aqueous saturated solution of ammonium chloride. The mixture was extracted with ethyl acetate (3×50 mL) and the combined organic extracts were dried over sodium sulfate and concentrated under vacuum. The remaining residue was purified by column chromatography on silica, using ethyl acetate/petroleum ether (1:10) as the eluant, to afford 352 mg (26%) of tert-butyl (1s,4s)-1-formyl-7-azabicyclo[2.2.1]heptane-7-carboxylate as yellow oil. Mass Spectrum (LCMS, ESI pos.): Calcd. for $C_{12}H_{19}NO_3$: 226 (M+H); found: 226.

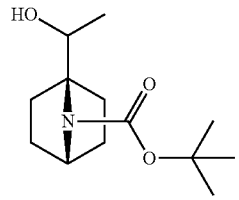 [SMILES: CC(O)[C@]12CC[C@H](CC1)N2C(=O)OC(C)(C)C]

B. (±)-tert-Butyl (1s,4s)-1-(1-Hydroxyethyl)-7-azabicyclo[2.2.1]heptane-7-carboxylate Into a 50 mL round-bottom flask, being maintained with an inert atmosphere of nitrogen, was placed a solution of tert-butyl (1s,4s)-1-formyl-7-azabicyclo[2.2.1]heptane-7-carboxylate (291 mg, 1.30 mmol) in tetrahydrofuran (8 mL). The solution was cooled to 0° C. and then treated with a solution of methylmagnesium bromide (M, 2.62 mL, 2.62 mmol) in a dropwise manner. The resulting mixture was allowed to warm to room temperature and stir for 2 h before it was diluted with brine. The aqueous mixture was extracted with ethyl acetate (3×20 mL) and the combined organic extracts were dried over sodium sulfate. The organic phase was concentrated under vacuum to afford 152 mg (49%) of (±)-tert-butyl (1s,4s)-1-(1-hydroxyethyl)-7-azabicyclo [2.2.1]heptane-7-carboxylate as a yellow oil. Mass Spectrum (LCMS, ESI pos.): Calcd. for $C_{13}H_{23}NO_3$: 242 (M+H); found: 242.

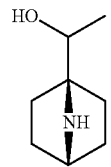

C. (±)-1-((1s,4s)-7-Azabicyclo[2.2.1]heptan-1-yl)ethan-1-ol Hydrochloride

Into a 50 mL round-bottom flask was placed a mixture of (±)-tert-butyl (1s,4s)-1-(1-hydroxyethyl)-7-azabicyclo [2.2.1]heptane-7-carboxylate (352 mg, 1.46 mmol) and a solution of hydrogen chloride in 1,4-dioxane (8 mL, 4M). The resulting mixture was allowed to stir at room temperature overnight. The reaction mixture was concentrated under vacuum to afford 312 mg (crude) of (±)-1-((1s,4s)-7-azabicyclo[2.2.1]heptan-1-yl)ethan-1-ol hydrochloride as a yellow oil.

Preparation of Intermediate XXXB: (±)-1-((1S,4R)-7-azabicyclo[2.2.1]heptan-2-yl)-2-methylpropan-2-ol Hydrochloride

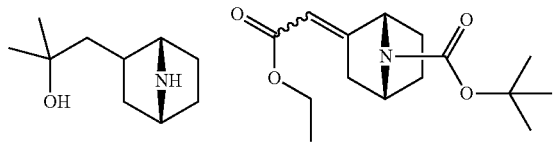 [SMILES: CC(C)(O)CC1C[C@H]2CC[C@@H]1N2 ; CCOC(=O)C=C1C[C@H]2CC[C@@H]1N2C(=O)OC(C)(C)C]

A. (±)-tert-Butyl (1S,4R)-2-(2-Ethoxy-2-oxoethylidene)-7-azabicyclo[2.2.1]heptane-7-carboxylate Into a 50 mL round-bottom flask, being maintained under an inert atmosphere of nitrogen, was placed a solution of ethyl 2-(diethoxyphosphoryl)acetate (2.7 g, 12.0 mmol) in tetrahydrofuran (5 mL). The solution was cooled to 0° C. and then treated with potassium tert-butoxide (1.34 g, 12.0 mmol). The resulting mixture was allowed to stir at 0° C. for 2 h, which was then treated with a solution of racemic tert-butyl 2-oxo-7-azabicyclo[2.2.1]heptane-7-carboxylate (848 mg, 4.01 mmol) in tetrahydrofuran (5 mL) in a dropwise manner. The reaction mixture was allowed to warm to room temperature and stir for 48 h, after which the mixture was diluted with water (50 mL). The aqueous mixture was extracted with ethyl acetate (3×50 mL) and the combined organic extracts were dried over anhydrous sodium sulfate and concentrated under vacuum. The remaining residue was purified by column chromatography on silica, using ethyl acetate/petroleum ether (1:20) as the eluant, to afford 1.02 g (90%) of (±)-tert-butyl (1S,4R)-2-(2-ethoxy-2-oxoethylidene)-7-azabicyclo[2.2.1]heptane-7-carboxylate as a light yellow solid. Mass Spectrum (LCMS, ESI pos.): Calcd. for $C_1H_{23}NO_4$: 282 (M+H); found: 282.

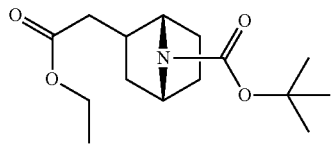 [SMILES: CCOC(=O)CC1C[C@H]2CC[C@@H]1N2C(=O)OC(C)(C)C]

B. (±)-tert-Butyl (1S,4R)-2-(2-Ethoxy-2-oxoethyl)-7-azabicyclo[2.2.1]heptane-7-carboxylate Into a 50 mL round-bottom flask was placed a solution of tert-butyl (1S,4R)-2-(2-ethoxy-2-oxoethylidene)-7-azabicyclo[2.2.1]heptane-7-carboxylate (500 mg, 1.78 mmol) in methanol (20 mL). To the solution was added palladium on carbon (0.1 g) and the resulting mixture was sparged by hydrogen gas. The reaction mixture was allowed to stir at room temperature for 1 h before the solids were filtered from the mixture. The filtrate was concentrated under vacuum to afford 0.46 g (91%) of (±)-tert-butyl (1S,4R)-2-(2-ethoxy-2-oxoethyl)-7-azabicyclo[2.2.1]heptane-7-carboxylate as a yellow oil. Mass Spectrum (LCMS, ESI pos.): Calcd. for $C_1H_{25}NO_4$: 284 (M+H); found: 284.

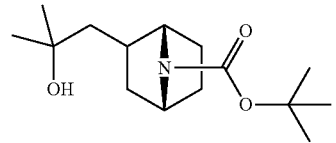 [SMILES: CC(C)(O)CC1C[C@H]2CC[C@@H]1N2C(=O)OC(C)(C)C]

C. (±)-tert-Butyl (1S,4R)-2-(2-Hydroxy-2-methylpropyl)-7-azabicyclo[2.2.1]heptane-7-carboxylate Into a 50 mL round-bottom flask, being maintained under an inert atmosphere of nitrogen, was placed a solution of (±)-tert-butyl (1S,4R)-2-(2-ethoxy-2-oxoethyl)-7-azabicyclo[2.2.1]heptane-7-carboxylate (500 mg, 1.76 mmol) in tetrahydrofuran (5 mL). The solution was cooled to 0° C. and then treated with a solution of methylmagnesium bromide in tetrahydrofuran (M, 17.6 mL, 17.6 mmol). The resulting mixture was allowed to stir at 0° C. for 1 h before it was diluted with water (15 mL). The aqueous mixture was extracted with ethyl acetate (3×15 mL) and the combined organic extracts were dried over anhydrous sodium sulfate. The organic phase was concentrated under vacuum to afford 343 mg (72%) of (±)-tert-butyl (1S,4R)-2-(2-hydroxy-2-methylpropyl)-7-azabicyclo[2.2.1]heptane-7-carboxylate as a yellow oil. Mass Spectrum (LCMS, ESI pos.): Calcd. for $C_1H_{27}NO_3$: 270 (M+H); found: 270.

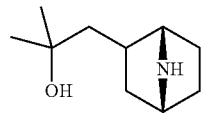

D. (±)-1-((1S,4R)-7-Azabicyclo[2.2.1]heptan-2-yl)-2-methylpropan-2-ol Hydrochloride Into a 25 mL round-bottom flask, being maintained under an inert atmosphere of nitrogen, was placed a solution of (±)-tert-butyl (1S,4R)-2-(2-hydroxy-2-methylpropyl)-7-azabicyclo[2.2.1]heptane-7-carboxylate (430 mg, 1.60 mmol) in 1,4-dioxane (5 mL), which was then treated with concentrated hydrochloric acid (3 mL) in a dropwise fashion. The reaction mixture was allowed to stir at room temperature for 2 h before it was concentrated under vacuum to afford 253 mg (94%) of (±)-1-((1S,4R)-7-azabicyclo[2.2.1]heptan-2-yl)-2-methylpropan-2-ol hydrochloride as a yellow oil. Mass Spectrum (LCMS, ESI pos.): Calcd. for $C_{10}H_{19}NO$: 170 (M+H); found: 170.

Preparation of Intermediate XXXIB: 2-Bromo-1-(3,3-difluorocyclobutyl)ethan-1-one

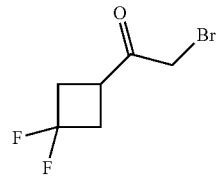

Into a 250 mL round-bottom flask was placed a mixture of 3,3-difluorocyclobutane-1-carboxylic acid (4.0 g, 29.4 mmol), tetrahydrofuran (60 mL), and N,N-dimethylformamide (1 mL). The mixture was treated with oxalyl chloride (5.6 g, 44.1 mmol) in a dropwise manner and then allowed to stir at room temperature for 1 h. The mixture was then treated with trimethylsilyl diazomethane (14.7 mL, 1.00 equiv). The resulting mixture was allowed to stir at room temperature for 1 h before hydrogen bromide (7.14 g, 88.2 mmol) was added dropwise. The reaction mixture was allowed to stir at room temperature for an additional 4 h before it was diluted with water (500 mL). The aqueous mixture was extracted with ethyl acetate (2×500 mL) and the combined organic extracts were washed with brine (3×500 mL). The organic phase was dried over anhydrous sodium sulfate and concentrated under vacuum to afford 6.4 g of 2-bromo-1-(3,3-difluorocyclobutyl)ethan-1-one as a yellow crude oil.

Example 1B. 2-(7-Azabicyclo[2.2.1]heptan-7-yl)-1-(1-(4-chlorophenyl)-5-((1,1-dioxidotetrahydro-2H-thiopyran-4-yl)methyl)-2-methyl-1H-pyrrol-3-yl)ethan-1-one (25B)

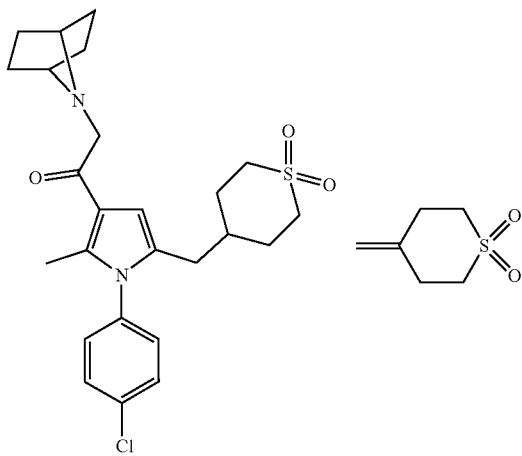

A. 4-Methylenetetrahydro-2H-thiopyran 1,1-dioxide

Into a 50 mL 3-necked round-bottom flask, purged and maintained under an inert atmosphere of nitrogen, was placed a mixture of zinc metal (0.79 g, 12.1 mmol) and diiodomethane (1.81 g, 6.76 mmol) in THF (20 mL). The resulting mixture was allowed to stir for 0.5 h at 0° C. A solution of titanium tetrachloride (256 mg, 1.35 mmol) in THF (1.35 mL) was then added to the reaction vessel and the resulting mixture was allowed to stir for 0.5 h at 0° C. A solution of tetrahydro-4H-thiopyran-4-one 1,1-dioxide (200 mg, 1.35 mmol) in oxalane (4 mL) was added to the reaction vessel and the resulting mixture was allowed to slowly warm to room temperature and stir for an additional 2 h. The reaction mixture was then diluted with 1 N aqueous hydrochloric acid (100 mL) and the mixture was extracted with dichloromethane (5×50 mL). The combined organic extracts were dried over anhydrous sodium sulfate, filtered, and then concentrated under vacuum. The remaining residue was purified by chromatography on silica, using ethyl acetate-hexane (1:5) as the eluant, to obtain 160 mg (81%) of 4-methylenetetrahydro-2H-thiopyran 1,1-dioxide as a white solid. $^1$H-NMR (300 MHz, CDCl$_3$) δ 4.95 (s, 2H), 3.08-3.04 (m, 2H), 2.75-2.72 (m, 2H).

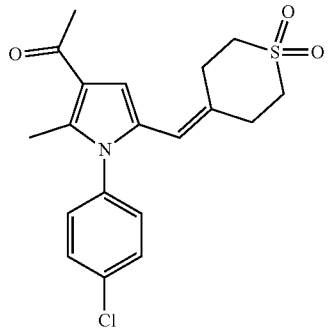 [SMILES: CC(=O)c1cc(C=C2CCS(=O)(=O)CC2)n(-c2ccc(Cl)cc2)c1C]

B. 1-(1-(4-Chlorophenyl)-5-((1,1-dioxidotetrahydro-4H-thiopyran-4-ylidene)methyl)-2-methyl-1H-pyrrol-3-yl)ethan-1-one Into a 25 mL sealed tube being maintained under a nitrogen atmosphere was placed a mixture of 1-(5-bromo-1-(4-chlorophenyl)-2-methyl-1H-pyrrol-3-yl)ethan-1-one (500 mg, 1.60 mmol), methylenetetrahydro-2H-thiopyran 1,1-dioxide (469 mg, 3.21 mmol,) and diisopropylethylamine (622 mg, 4.81 mmol) in N,N-dimethylformamide (15 mL). To the mixture were added P(o-Tol)$_3$ (195 mg, 0.64 mmol) and Pd(OAc)$_2$ (72 mg, 0.32 mmol). The resulting system was heated for 1 hour at 160° C. and then allowed to cool to room temperature. The reaction mixture was diluted with water and the resulting mixture was extracted with ethyl acetate. The combined organic extracts were washed with brine, dried over anhydrous sodium sulfate, and then concentrated under vacuum. The remaining residue was purified by column chromatography on silica gel using ethyl acetate/petroleum ether (1:3) as the eluant to afford 1-(1-(4-Chlorophenyl)-5-((1,1-dioxidotetrahydro-4H-thiopyran-4-ylidene)methyl)-2-methyl-1H-pyrrol-3-yl)ethan-1-one (225 mg, 37%) as a yellow oil. Mass Spectrum (LCMS, ESI pos.): Calcd. for C$_{19}$H$_{20}$ClNO$_3$S: 378 (M+H); found 378.

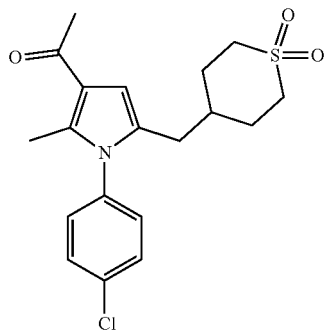 [SMILES: CC(=O)c1cc(CC2CCS(=O)(=O)CC2)n(-c2ccc(Cl)cc2)c1C]

C. 1-(1-(4-Chlorophenyl)-5-((1,1-dioxidotetrahydro-2H-thiopyran-4-yl)methyl)-2-methyl-1H-pyrrol-3-yl)ethan-1-one Into a 50 mL round-bottom flask, purged and maintained with under an atmosphere of nitrogen, were placed a mixture of 1-(1-(4-Chlorophenyl)-5-((1,1-dioxidotetrahydro-4H-thiopyran-4-ylidene)methyl)-2-methyl-1H-pyrrol-3-yl)ethan-1-one (280 mg, 0.74 mmol) and $PtO_2$ (30 mg) in ethyl acetate (5 mL). The resulting mixture was degassed and back filled with hydrogen gas. The system was allowed to stir at room temperature for 2 h. The reaction mixture was then filtered and the filtrate was concentrated under vacuum. The remaining residue was purified by column chromatography on silica gel using ethyl acetate/petroleum ether (1:3) as the eluant to afford 1-(1-(4-chlorophenyl)-5-((1,1-dioxidotetrahydro-2H-thiopyran-4-yl)methyl)-2-methyl-1H-pyrrol-3-yl)ethan-1-one (150 mg, 53%) as a light yellow oil. Mass Spectrum (LCMS, ESI pos.): Calcd. for $C_{19}H_{22}ClNO_3S$: 380 (M+H); found 380.

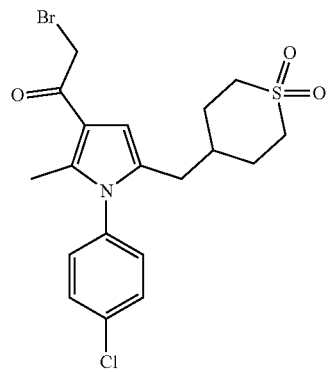 [SMILES: Cc1c(C(=O)CBr)cc(CC2CCS(=O)(=O)CC2)n1-c1ccc(Cl)cc1]

D. 2-Bromo-1-(1-(4-chlorophenyl)-5-((1,1-dioxidotetrahydro-2H-thiopyran-4-yl)methyl)-2-methyl-1H-pyrrol-3-yl)ethan-1-one Into a 50 mL, 3-necked round-bottom flask, purged and maintained under an atmosphere of nitrogen, was placed a solution of 1-(1-(4-chlorophenyl)-5-((1,1-dioxidotetrahydro-2H-thiopyran-4-yl)methyl)-2-methyl-1H-pyrrol-3-yl)ethan-1-one (120 mg, 0.32 mmol) in tetrahydrofuran (8 mL). To the flask was added diisopropylethylamine (163 mg, 1.26 mmol) and the resulting mixture was allowed to stir at 0° C. for 1 h. To the flask were then added TMSOTf (140 mg, 0.63 mmol) and a solution of NBS (56 mg, 0.31 mmol) in tetrahydrofuran (2 mL), in a dropwise manner. The resulting mixture was allowed to stir at 0° C. for 10 min and was then quenched through the addition of water. The reaction mixture was extracted with ethyl acetate and the combined organic extracts were washed with brine and dried over anhydrous sodium sulfate. Filtration and concentration of the filtrate under vacuum afforded crude 2-Bromo-1-(1-(4-chlorophenyl)-5-((1,1-dioxidotetrahydro-2H-thiopyran-4-yl)methyl)-2-methyl-1H-pyrrol-3-yl)ethan-1-one (120 mg, crude) as a yellow oil. Mass Spectrum (LCMS, ESI pos.): Calcd. for $C_{19}H_{21}BrClNO_3S$: 458 (M+H); found 458.

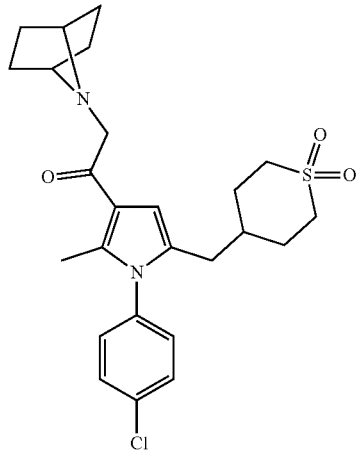 [SMILES: Cc1c(C(=O)CN2C3CCC2CC3)cc(CC2CCS(=O)(=O)CC2)n1-c1ccc(Cl)cc1]

E. 2-(7-Azabicyclo[2.2.1]heptan-7-yl)-1-(1-(4-chlorophenyl)-5-((1,1-dioxidotetrahydro-2H-thiopyran-4-yl)methyl)-2-methyl-1H-pyrrol-3-yl)ethan-1-one (25B)

Into a 50 mL round-bottom flask was placed a mixture of 2-Bromo-1-(1-(4-chlorophenyl)-5-((1,1-dioxidotetrahydro-2H-thiopyran-4-yl)methyl)-2-methyl-1H-pyrrol-3-yl)ethan-1-one (120 mg, 0.26 mmol), 7-azabicyclo[2.2.1]heptane hydrogen chloride (70 mg, 0.52 mmol) and potassium carbonate (144 mg, 1.04 mmol) in N,N-dimethylformamide (3 mL). The resulting mixture was allowed to stir at room temperature for 16 h and was then diluted with then diluted with water. The solid that formed was collected by filtration and then washed with water and methanol to afford 2-(7-azabicyclo[2.2.1]heptan-7-yl)-1-(1-(4-chlorophenyl)-5-((1,1-dioxidotetrahydro-2H-thiopyran-4-yl)methyl)-2-methyl-1H-pyrrol-3-yl)ethan-1-one (25B) (24 mg, 19%) as a white solid. Mass Spectrum (LCMS, ESI pos.): Calcd. for $C_{25}H_{31}ClN_2O_3S$: 475 (M+H); found 475. $^1H$ NMR (300 MHz, DMSO-$d_6$): δ 7.63-7.61 (d, 2H, J=8.4 Hz), 7.37-7.34 (d, 2H, J=8.4 Hz), 6.52 (s, 1H), 3.50 (s, 2H), 3.06-2.94 (m, 4H), 2.27-2.25 (d, 2H, J=6.6 Hz), 2.19 (s, 3H), 1.85-1.81 (m, 2H), 1.67-1.64 (m, 5H), 1.51-1.43 (m, 2H), 1.24-1.22 (m, 5H), 0.85-0.83 (m, 1H).

Example 2B. 4,4'-(4-(2-(7-Azabicyclo[2.2.1]heptan-7-yl)acetyl)-3,5-dimethyl-1H-pyrrole-1,2-diyl)dibenzonitrile (16B)

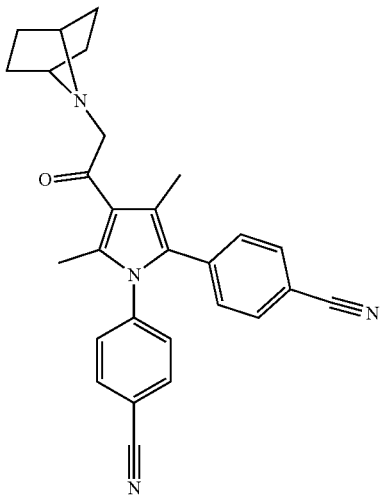 [SMILES: Cc1c(C(=O)CN2C3CCC2CC3)c(C)n(-c2ccc(C#N)cc2)c1-c1ccc(C#N)cc1]

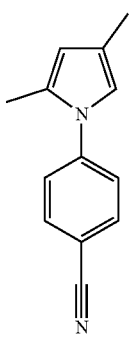

A. 4-(2,4-dimethyl-1H-pyrrol-1-yl)benzonitrile

Into a 250 mL round-bottom flask, being maintained under an inert atmosphere of nitrogen, was placed a solution of 2,4-dimethyl-1H-pyrrole (6.01 g, 63.2 mmol) in N,N-dimethylformamide (30 mL). To the solution were added 4-fluorobenzonitrile (11.5 g, 94.7 mmol) and $Cs_2CO_3$ (30.9 g, 94.7 mmol). The resulting mixture was heated at 130° C. overnight. After cooling to room temperature the reaction mixture was diluted with water (200 mL) and the resulting mixture was extracted with ethyl acetate (2×200 mL). The combined organic extracts were washed with brine (3×200 mL), dried over anhydrous sodium sulfate and then concentrated under vacuum. The remaining residue was purified by column chromatography on silica using ethyl acetate/petroleum ether (1:50) as the eluant to afford 9.05 g (73%) of 4-(2,4-dimethyl-1H-pyrrol-1-yl)benzonitrile as a yellow oil. Mass Spectrum (LCMS, ESI pos.): Calcd. for $C_{13}H_{12}N_2$: 197 (M+H); found 197.

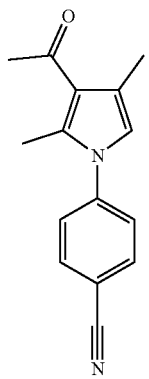 [SMILES: CC(=O)c1c(C)cn(-c2ccc(C#N)cc2)c1C]

B. 4-(3-Acetyl-2,4-dimethyl-1H-pyrrol-1-yl)benzonitrile

Into a 100 mL round-bottom flask, being maintained under an inert atmosphere of nitrogen, was placed a solution of 4-(2,4-dimethyl-1H-pyrrol-1-yl)benzonitrile (3.00 g, 15.3 mmol) in dichloromethane (25 mL). To the solution were added acetyl chloride (1.43 g, 18.2 mmol) and chlorodiethylaluminum (3.70 g, 30.7 mmol). The resulting mixture was allowed to stir at room temperature overnight. The reaction mixture was diluted with aqueous sodium bicarbonate (100 mL) and the resulting mixture was extracted with ethyl acetate (3×100 mL). The combined organic extracts were washed with brine (3×100 mL), dried over anhydrous sodium sulfate and concentrated under vacuum. The remaining residue was purified by column chromatography on silica gel using ethyl acetate/petroleum ether (1:4) as the eluant to afford 875 mg (24%) of 4-(3-acetyl-2,4-dimethyl-1H-pyrrol-1-yl)benzonitrile as a white solid. Mass Spectrum (LCMS, ESI pos.): Calcd. for $C_{15}H_{14}N_2O$: 239 (M+H); found 239. $^1$H NMR (400 MHz, $CDCl_3$): δ 7.78 (d, J=8.4 Hz, 2H), 7.39 (d, J=8.4 Hz, 2H), 6.52 (s, 1H), 2.48 (s, 3H), 2.44 (s, 3H), 2.30 (s, 3H).

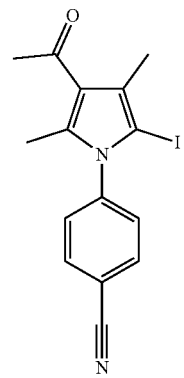 [SMILES: CC(=O)c1c(C)c(I)n(-c2ccc(C#N)cc2)c1C]

C. 4-(3-Acetyl-5-iodo-2,4-dimethyl-1H-pyrrol-1-yl)benzonitrile

Into a 100 mL round-bottom flask was placed a solution of 4-(3-acetyl-2,4-dimethyl-1H-pyrrol-1-yl)benzonitrile (600 mg, 2.52 mmol) in dichloromethane (7 mL). To this solution was added 1-iodopyrrolidine-2,5-dione (1.13 g, 5.04 mmol) and the resulting mixture was allowed to stir overnight at room temperature. The reaction mixture was diluted with aqueous sodium thiosulfate (100 mL) and the biphasic mixture was extracted with ethyl acetate (3×100 mL). The combined organic extracts were washed with brine (3×100 mL), dried over anhydrous sodium sulfate and then concentrated under vacuum. The remaining residue was purified by column chromatography on silica gel using ethyl acetate/petroleum ether (1:4) as the eluant to afford 860 mg (94%) of 4-(3-acetyl-5-iodo-2,4-dimethyl-1H-pyrrol-1-yl)benzonitrile as a white solid. Mass Spectrum (LCMS, ESI pos.): Calcd. for $C_{15}H_{13}IN_2O$: 365 (M+H); found 365. $^1$H NMR (400 MHz, $CDCl_3$): δ 7.85-7.83 (m, 2H), 7.34-7.32 (m, 2H), 2.49 (s, 3H), 2.35 (s, 3H), 2.33 (s, 3H).

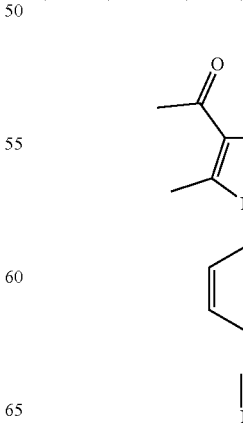

D. 4,4'-(4-Acetyl-3,5-dimethyl-1H-pyrrole-1,2-diyl)dibenzonitrile

Into a 25 mL sealed tube, being maintained under an inert atmosphere of nitrogen, was placed a solution of 4-(3-acetyl-5-iodo-2,4-dimethyl-1H-pyrrol-1-yl)benzonitrile (300 mg, 0.82 mmol) in 1,4-dioxane (4 mL). To the solution were added $Cs_2CO_3$ (538 mg, 1.65 mmol), (4-cyanophenyl)boronic acid (243 mg, 1.65 mmol) and $Pd(dppf)Cl_2$ (59 mg, 0.08 mmol). The resulting mixture was heated at 100° C. overnight. After cooling to room temperature the reaction mixture was diluted with water (100 mL) and the resulting mixture was extracted with ethyl acetate (3×100 mL). The combined organic extracts were washed with brine (3×100 mL), dried over anhydrous sodium sulfate and concentrated under vacuum. The remaining residue was purified by column chromatography on silica gel using ethyl acetate/petroleum ether (1:2) as the eluant to afford 150 mg (54%) of 4,4'-(4-acetyl-3,5-dimethyl-1H-pyrrole-1,2-diyl)dibenzonitrile as a yellow solid. Mass Spectrum (LCMS, ESI pos.): Calcd. for $C_{22}H_{17}N_3O$: 340 (M+H); found 340.

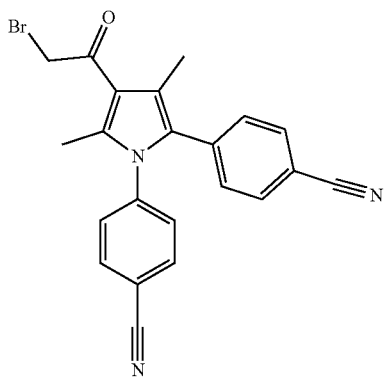 [SMILES: Cc1c(C(=O)CBr)c(C)n(-c2ccc(C#N)cc2)c1-c1ccc(C#N)cc1]

E. 4,4'-(4-(2-Bromoacetyl)-3,5-dimethyl-1H-pyrrole-1,2-diyl)dibenzonitrile

Into a 100 mL round-bottom flask, being maintained under an inert atmosphere of nitrogen, was placed a solution of 4,4'-(4-acetyl-3,5-dimethyl-1H-pyrrole-1,2-diyl)dibenzonitrile (264 mg, 0.78 mmol) in tetrahydrofuran (10 mL). To this solution were added diisopropylethylamine (403 mg, 3.12 mmol), TMSOTf (346 mg, 1.56 mmol) and 1-bromopyrrolidine-2,5-dione (139 mg, 0.78 mmol). The resulting mixture was allowed to stir at room temperature for 5 h and was then diluted with aqueous sodium thiosulfate (100 mL). The biphasic mixture was extracted with ethyl acetate (3×100 mL) and the combined organic extracts were washed with brine (3×100 mL), dried over anhydrous sodium sulfate and concentrated under vacuum. The remaining residue was purified by column chromatography on silica gel using ethyl acetate/petroleum ether (1:2) as the eluant to afford 80 mg (crude) of 4,4'-(4-(2-bromoacetyl)-3,5-dimethyl-1H-pyrrole-1,2-diyl)dibenzonitrile as a yellow solid. Mass Spectrum (LCMS, ESI pos.): Calcd. for $C_2H_{16}BrN_3$: 418 (M+H); found 418.

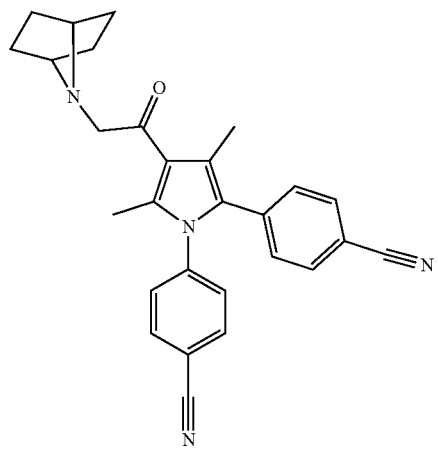 [SMILES: Cc1c(C(=O)CN2C3CCC2CC3)c(C)n(-c2ccc(C#N)cc2)c1-c1ccc(C#N)cc1]

F. 4,4'-(4-(2-(7-Azabicyclo[2.2.1]heptan-7-yl)acetyl)-3,5-dimethyl-1H-pyrrole-1,2-diyl)dibenzonitrile (16B)

Into a 50 mL round-bottom flask, being maintained under an inert atmosphere of nitrogen, was placed a solution of 4,4'-(4-(2-bromoacetyl)-3,5-dimethyl-1H-pyrrole-1,2-diyl)dibenzonitrile (30 mg, 0.07 mmol) in N,N-dimethylformamide (2 mL). To the solution were added $K_2CO_3$ (19 mg, 0.14 mmol) and 7-azabicyclo[2.2.1]heptane hydrochloride (19 mg, 0.14 mmol). The resulting mixture was allowed to stir overnight at room temperature before being diluted with water (50 mL). The biphasic mixture was extracted with ethyl acetate (3×50 mL) and the combined organic extracts were washed with brine (3×50 mL), dried over anhydrous sodium sulfate and concentrated under vacuum. The remaining residue was purified by column chromatography on silica gel using dichloromethane/methanol (10:1) as the eluant to afford 25 mg (79%) of 4,4'-(4-(2-(7-azabicyclo[2.2.1]heptan-7-yl)acetyl)-3,5-dimethyl-1H-pyrrole-1,2-diyl)dibenzonitrile (16B) as a white solid. Mass Spectrum (LCMS, ESI pos.): Calcd. for $C_{28}H_{26}N_4O$: 435 (M+H); found 435. $^1H$ NMR (400 MHz, methanol-$d_4$): δ 7.80-7.76 (m, 2H), 7.62-7.60 (m, 2H), 7.37-7.34 (m, 2H), 7.25-7.22 (m, 2H), 3.99 (brs, 2H), 2.46 (s, 3H), 2.30 (s, 3H), 2.14-2.07 (m, 4H), 1.72-1.70 (m, 4H).

Example 3B. 4-(3-(2-(7-Azabicyclo[2.2.1]heptan-7-yl)acetyl)-2,4-dimethyl-5-(4-(methylsulfonyl)butyl)-1H-pyrrol-1-yl)benzonitrile (1B)

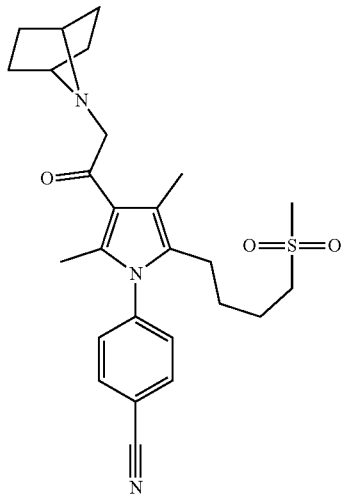 [SMILES: Cc1c(C(=O)CN2C3CCC2CC3)c(C)n(-c2ccc(C#N)cc2)c1CCCCS(C)(=O)=O]

A. 4-(3-(2-(7-Azabicyclo[2.2.1]heptan-7-yl)acetyl)-2,4-dimethyl-5-(4-(methylsulfonyl)butyl)-1H-pyrrol-1-yl)benzonitrile Into a 50 mL round-bottom flask was placed a solution of 4-[3-(2-[7-azabicyclo[2.2.1]heptan-7-yl]acetyl)-5-[(1E)-4-methanesulfonylbut-1-en-1-yl]-2,4-dimethyl-1H-pyrrol-1-yl]benzonitrile (Compound 36B) (21 mg, 0.05 mmol) in ethyl acetate (10 mL). To this solution was added solid palladium on carbon (5 mg). The mixture and reaction vessel were purged with hydrogen gas and the resulting system was allowed to stir overnight at room temperature. After removing the solvent, the crude product was purified by preparative HPLC under the following conditions: XBridge™ Prep C18 5 μm OBD™ 19*100 mm column; mobile phase—water with 0.05% $NH_4HCO_3$ and $CH_3CN$ (10.0% $CH_3CN$ up to 90.0% in 10 min, up to 95.0% in 1.5 mn, down to 10.0% in 1.5 min); Detector—254 nm. Purification afforded 4 mg (19%) of 4-(3-(2-(7-azabicyclo[2.2.1]heptan-7-yl)acetyl)-2,4-dimethyl-5-(4-(methylsulfonyl)butyl)-1H-pyrrol-1-yl)benzonitrile (1B) as a white solid. Mass Spectrum (LCMS, ESI pos.): Calcd. for $C_{26}H_{33}N_3O_3S$: 468 (M+H); found 468. $^1H$ NMR (400 MHz, methanol-$d_4$): δ 8.01-7.98 (d, J=8.4 Hz, 2H), 7.52-7.50 (d, J=8.4 Hz, 2H), 4.45-4.44 (m, 1H), 4.21 (s, 2H), 2.99-2.95 (m, 2H), 2.90 (s, 3H), 2.52-2.48 (t, J=7.6 Hz, 2H), 2.34 (s, 3H), 2.31 (s, 3H), 2.21-2.16 (m, 5H), 1.89-1.87 (m, 4H), 1.66-1.61 (m, 2H), 1.43-1.35 (m, 2H).

Example 4B. (E)-4-(3-(2-(7-Azabicyclo[2.2.1]heptan-7-yl)acetyl)-2,4-dimethyl-5-(4-(methylsulfonyl)but-1-en-1-yl)-1H-pyrrol-1-yl)benzonitrile (32) & (Z)-4-(3-(2-(7-Azabicyclo[2.2.1]heptan-7-yl)acetyl)-2,4-dimethyl-5-(4-(methylsulfonyl)but-1-en-1-yl)-1H-pyrrol-1-yl)benzonitrile (36B)

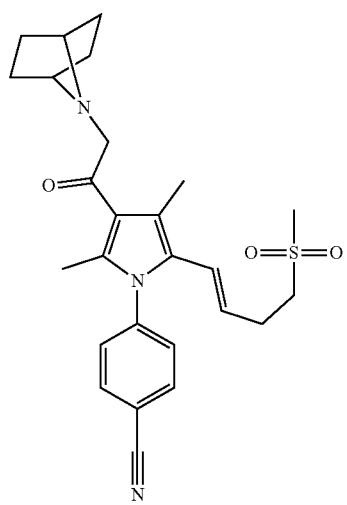

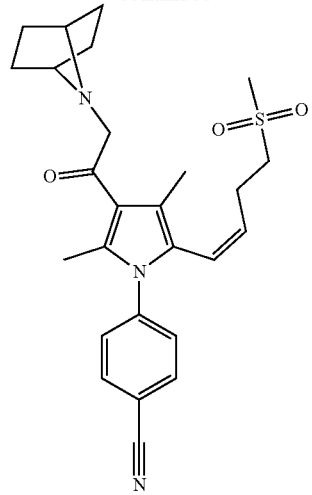

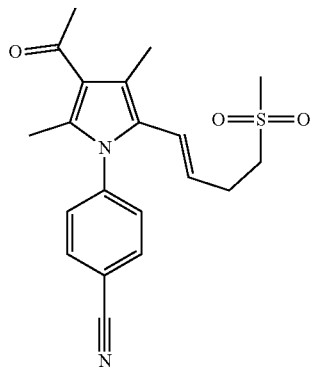

A. (E)-4-(3-Acetyl-2,4-dimethyl-5-(4-(methylsulfonyl)but-1-en-1-yl)-1H-pyrrol-1-yl)benzonitrile Into a 25 mL sealed tube, being maintained under an inert atmosphere of nitrogen, was placed a solution of 4-(3-acetyl-5-iodo-2,4-dimethyl-1H-pyrrol-1-yl)benzonitrile (600 mg, 1.65 mmol) in N,N-dimethylformamide (10 mL). To the solution were added diisopropylethylamine (426 mg, 3.30 mmol), 4-methanesulfonylbut-1-ene (442 mg, 3.29 mmol), P(o-Tol)$_3$ (148 mg, 0.49 mmol) and (acetyloxy)palladio acetate (100 mg, 0.33 mmol). The resulting mixture was heated at 120° C. overnight. After cooling to room temperature the reaction was diluted with water (100 mL) and the mixture was then extracted with ethyl acetate (3×100 mL). The combined organic extracts were washed with brine (3×100 mL), dried over anhydrous sodium sulfate and concentrated under vacuum. The remaining residue was purified by column chromatography on silica gel using ethyl acetate/petroleum ether (1:1) as the eluant to afford 200 mg (33%) of (E)-4-(3-acetyl-2,4-dimethyl-5-(4-(methylsulfonyl)but-1-en-1-yl)-1H-pyrrol-1-yl)benzonitrile as a yellow solid. Mass Spectrum (LCMS, ESI pos.): Calcd. for $C_{20}H_{22}N_2O_3S$: 371 (M+H); found 371.

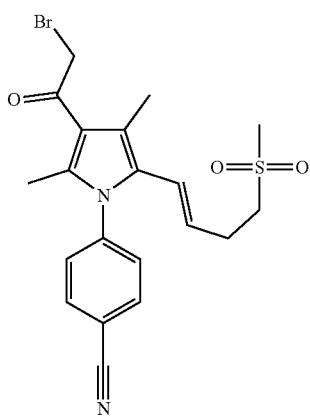 [SMILES: Cc1c(C(=O)CBr)c(C)n(-c2ccc(C#N)cc2)c1/C=C/CCS(C)(=O)=O]

B. (E)-4-(3-(2-Bromoacetyl)-2,4-dimethyl-5-(4-(methylsulfonyl)but-1-en-1-yl)-1H-pyrrol-1-yl)benzonitrile Into a 100 mL round-bottom flask, being maintained under an inert atmosphere of nitrogen, was placed a solution of (E)-4-(3-acetyl-2,4-dimethyl-5-(4-(methylsulfonyl)but-1-en-1-yl)-1H-pyrrol-1-yl)benzonitrile (256 mg, 0.69 mmol) in tetrahydrofuran (10 mL), diisopropylethylamine (357 mg, 2.76 mmol), trimethylsilyl trifluoromethanesulfonate (307 mg, 1.38 mmol), and 1-bromopyrrolidine-2,5-dione (123 mg, 0.69 mmol). The resulting mixture was allowed to stir at room temperature for 4 h. The reaction mixture was diluted with aqueous sodium thiosulfate (100 mL). The biphasic mixture was extracted with ethyl acetate (100 mL) and the combined organic extracts were washed with brine (3×100 mL), dried over anhydrous sodium sulfate, and then concentrated under vacuum. The remaining residue was purified by column chromatography on silica gel using ethyl acetate/petroleum ether (1:2) as the eluant to afford 60 mg (19%) of (E)-4-(3-(2-bromoacetyl)-2,4-dimethyl-5-(4-(methylsulfonyl)but-1-en-1-yl)-1H-pyrrol-1-yl)benzonitrile as a yellow solid. Mass Spectrum (LCMS, ESI pos.): Calcd. for $C_{20}H_{21}BrN_2O_3S$: 449 (M+H); found 449.

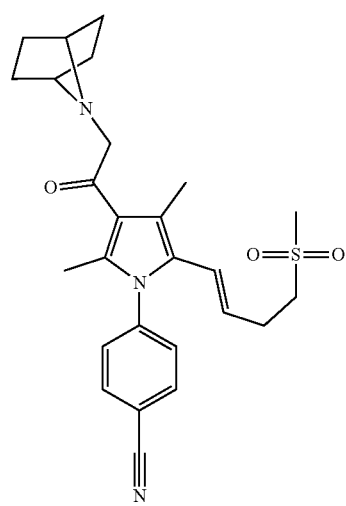 [SMILES: Cc1c(C(=O)CN2C3CCC2CC3)c(C)n(-c2ccc(C#N)cc2)c1/C=C/CCS(C)(=O)=O]

C. (E)-4-(3-(2-(7-Azabicyclo[2.2.1]heptan-7-yl)acetyl)-2,4-dimethyl-5-(4-(methylsulfonyl)but-1-en-1-yl)-1H-pyrrol-1-yl)benzonitrile (32B)

Into a 50 mL round-bottom, being maintained under an inert atmosphere of nitrogen, was placed a solution of (E)-4-(3-(2-bromoacetyl)-2,4-dimethyl-5-(4-(methylsulfonyl)but-1-en-1-yl)-1H-pyrrol-1-yl)benzonitrile (50 mg, 0.11 mmol) in N,N-dimethylformamide (3 mL). To the solution were added potassium carbonate (30 mg, 0.22 mmol) and 7-azabicyclo[2.2.1]heptane hydrochloride (30 mg, 0.22 mmol). The resulting mixture was allowed to stir at room temperature overnight. The crude product was purified by preparative HPLC using the following conditions: Column—XBridge™ Prep C18 5 µm OBD™ 19*100 mm; mobile phase—water with 0.05% $NH_4HCO_3$ and $CH_3CN$ (20.0% $CH_3CN$ up to 80.0% in 15 min, up to 95.0% in 5 min, down to 10.0% in 3 min); Detector—UV 254 nm. This process afforded 17 mg of (E)-4-(3-(2-(7-azabicyclo[2.2.1]heptan-7-yl)acetyl)-2,4-dimethyl-5-(4-(methylsulfonyl)but-1-en-1-yl)-1H-pyrrol-1-yl)benzonitrile (32B) as a white solid and 4 mg (7%) of (Z)-4-(3-(2-(7-azabicyclo[2.2.1]heptan-7-yl)acetyl)-2,4-dimethyl-5-(4-(methylsulfonyl)but-1-en-1-yl)-1H-pyrrol-1-yl)benzonitrile (36B). Mass Spectrum (LCMS, ESI pos.): Calcd. for $C_{26}H_{31}N_3O_3S$: 466 (M+H); found 466. $^1$H NMR (400 MHz, methanol-$d_4$): δ 7.95-7.93 (m, 2H), 7.45-7.43 (m, 2H), 6.01-5.97 (d, J=15.6 Hz, 1H), 5.60-5.56 (m, 1H), 3.95 (s, 2H), 3.12 (t, J=7.6 Hz, 2H), 2.92 (s, 3H), 2.57-2.52 (m, 2H), 2.39 (s, 3H), 2.30 (s, 3H), 2.07-2.05 (m, 4H), 1.70-1.68 (m, 4H), 1.29 (brs, 5H).

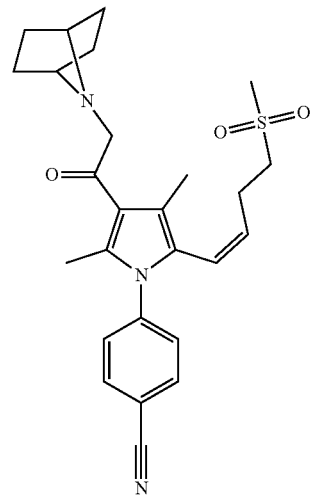 [SMILES: Cc1c(C(=O)CN2C3CCC2CC3)c(C)n(-c2ccc(C#N)cc2)c1/C=C\CCS(C)(=O)=O]

D. (Z)-4-(3-(2-(7-Azabicyclo[2.2.1]heptan-7-yl)acetyl)-2,4-dimethyl-5-(4-(methylsulfonyl)but-1-en-1-yl)-1H-pyrrol-1-yl)benzonitrile (36B)

See entry C (above) for the synthetic procedure. Mass Spectrum (LCMS, ESI pos.): Calcd. for $C_{26}H_{31}N_3O_3S$: 466 (M+H); found 466. $^1$H NMR (400 MHz, DMSO-$d_6$): δ 8.03-8.00 (m, 2H), 7.53-7.48 (m, 2H), 5.78-5.62 (m, 2H), 5.08-5.04 (m, 1H), 3.74-3.72 (d, J=7.6 Hz, 1H), 3.48-3.45 (d, J=11.6 Hz, 2H), 3.23-3.08 (m, 2H), 2.95 (s, 2H), 2.81 (s, 2H), 2.44-2.41 (m, 1H), 2.29 (s, 2H), 2.20-2.19 (d, J=2.8 Hz, 3H), 2.13 (s, 1H), 1.68-1.64 (m, 4H), 1.25-1.23 (m, 4H)

Example 5B. (4-(5-((E)-4-Cyanobut-1-en-1-yl)-3(2-((2R)-2-hydroxy-7-azabicyclo[2.2.1]heptan-7-yl)acetyl)-2-methyl-1H-pyrrol-1-yl)benzonitrile (20B)

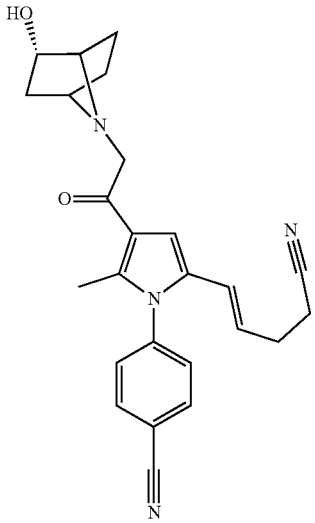

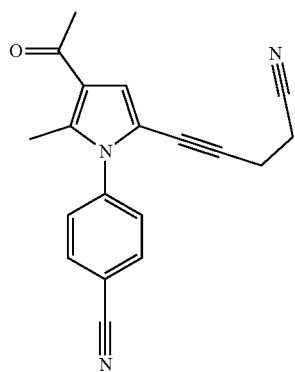

A. 4-(3-Acetyl-5-(4-cyanobut-1-yn-1-yl)-2-methyl-1H-pyrrol-1-yl)benzonitrile

Into a 250 mL, 3-necked round-bottom flask, being maintained under an inert atmosphere of nitrogen, was placed a solution of 4-(3-acetyl-5-iodo-2-methyl-1H-pyrrol-1-yl)benzonitrile (2.0 g, 5.71 mmol) in tetrahydrofuran (40 mL), followed by CuI (54 mg, 0.28 mmol) and Pd(PPh$_3$)$_2$Cl$_2$ (200 mg, 0.28 mmol). To this mixture were added pent-4-ynenitrile (686 mg, 8.67 mmol) and triethylamine (5.77 g, 57.02 mmol). The reaction mixture was heated at 60° C. overnight. After cooling to room temperature the reaction was diluted with water (50 mL) and then extracted with ethyl acetate (3×100 mL). The combined organic extracts were dried over anhydrous sodium sulfate and concentrated under vacuum. The remaining residue was purified by column chromatography on silica gel using ethyl acetate/petroleum ether (1:10 to 1:4) as the eluant to afford 1.3 g (76%) of 4-(3-Acetyl-5-(4-cyanobut-1-yn-1-yl)-2-methyl-1H-pyrrol-1-yl)benzonitrile as a brown foam. Mass Spectrum (LCMS, ESI pos.): Calcd. for C$_{19}$H$_{15}$N$_3$O: 302 (M+H); found 302.

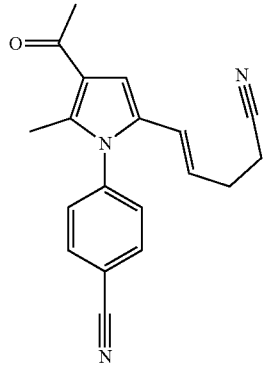 [SMILES: CC(=O)c1cc(/C=C/CCC#N)n(-c2ccc(C#N)cc2)c1C]

B. (E)-4-(3-Acetyl-5-(4-cyanobut-1-en-1-yl)-2-methyl-1H-pyrrol-1-yl)benzonitrile Into a 100 mL round-bottom flask, being maintained under an inert atmosphere of nitrogen, was placed a solution of 4-(3-acetyl-5-(4-cyanobut-1-yn-1-yl)-2-methyl-1H-pyrrol-1-yl)benzonitrile (2.0 g, 6.64 mmol) in toluene (35 mL), followed by Pd(dppf)C$_{12}$ (308 mg, 0.42 mmol), dppf (770 mg, 1.39 mmol), CuSO$_4$ (672 mg, 4.21 mmol), triethylsilane (2.44 g, 20.3 mmol) and water (3.5 mL). The resulting mixture was heated at 100° C. overnight. After cooling to room temperature the reaction mixture was diluted with water (50 mL) and then extracted with ethyl acetate (2×50 mL). The combined organic extracts were dried over anhydrous sodium sulfate and then concentrated under vacuum. The remaining residue was purified by column chromatography on silica gel using ethyl acetate/petroleum ether (1:6 to 1:2) as the eluant to afford 1.5 g of the title compound. This material was then purified by preparative-SFC under the following conditions: (prep SFC 350) Column—Phenomenex Lux 5u Cellulose-3, 5*25 cm, 5 μm; mobile phase—CO$_2$ (70%), 2-propanol (30%); Detector—UV 220 nm. This process afforded 520 mg (26%) of (E)-4-(3-acetyl-5-(4-cyanobut-1-en-1-yl)-2-methyl-1H-pyrrol-1-yl)benzonitrile as a yellow solid. Mass Spectrum (LCMS, ESI pos.): Calcd. for C$_{19}$H$_{17}$N$_3$O: 304 (M+H); found 304. $^1$H NMR (400 MHz, DMSO-d$_6$): δ 8.06-8.04 (d, J=8.4 Hz, 2H), 7.55-7.53 (d, J=8.4 Hz, 2H), 6.93 (s, 1H), 5.98-5.83 (m, 2H), 4.35-4.33 (m, 1H), 3.46-3.42 (m, 1H), 2.54-2.49 (m, 2H), 2.46 (s, 3H), 2.33-2.19 (m, 2H), 1.06-1.01 (m, 2H).

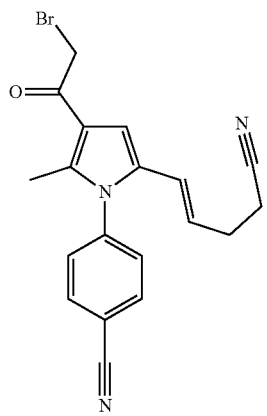 [SMILES: Cc1c(C(=O)CBr)cc(/C=C/CCC#N)n1-c1ccc(C#N)cc1]

C. (E)-4-(3-(2-Bromoacetyl)-5-(4-cyanobut-1-en-1-yl)-2-methyl-1H-pyrrol-1-yl)benzonitrile Into a 100 mL 3-necked, round-bottom flask was placed a solution of (E)-4-(3-acetyl-5-(4-cyanobut-1-en-1-yl)-2-methyl-1H-pyrrol-1-yl)benzonitrile (120 mg, 0.40 mmol) and diisopropylethylamine (205 mg, 1.59 mmol) in tetrahydrofuran (10 mL). The mixture was cooled to −30° C. and then then TMSOTf (132 mg, 0.59 mmol) was added. The reaction mixture was allowed to warm to room temperature and then stir for 1 h. The reaction mixture was cooled, again, to 0° C. and then 1-bromopyrrolidine-2,5-dione (78 mg, 0.44 mmol) was added. The resulting mixture was allowed to warm to room temperature and stir for 20 min. The reaction mixture was diluted with water and then extracted with ethyl acetate (2×10 mL). The combined organic extracts were dried over anhydrous sodium sulfate and concentrated under vacuum. The remaining residue was purified by column chromatography on silica gel using ethyl acetate/petroleum ether (1:3) as the eluant to afford 80 mg (53%) of (E)-4-(3-(2-bromoacetyl)-5-(4-cyanobut-1-en-1-yl)-2-methyl-1H-pyrrol-1-yl)benzonitrile as a light yellow solid. Mass Spectrum (LCMS, ESI pos.): Calcd. for $C_{19}H_{16}BrN_3O$: 382 (M+H); found 382.

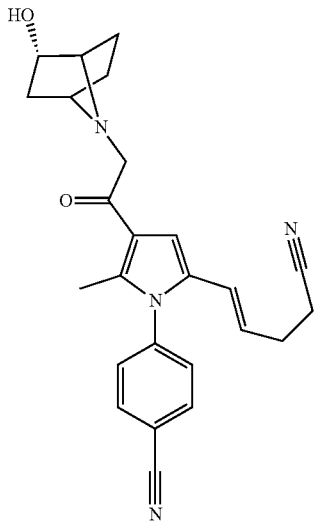 [SMILES: Cc1c(C(=O)CN2C3CCC2[C@@H](O)C3)cc(/C=C/CCC#N)n1-c1ccc(C#N)cc1]

D. (±)-4-(5-((E)-4-Cyanobut-1-en-1-yl)-3-(2-((2R)-2-hydroxy-7-azabicyclo[2.2.1]heptan-7-yl)acetyl)-2-methyl-1H-pyrrol-1-yl)benzonitrile (20B)

Into a 100 mL round-bottom flask, was placed a solution of 4-[3-(2-bromoacetyl)-5-[(1E)-4-cyanobut-1-en-1-yl]-2-methyl-1H-pyrrol-1-yl]benzonitrile (80 mg, 0.21 mmol, 1.00 equiv) in N,N-dimethylformamide (5 mL). To the solution were added (±)-(1R,2R,4S)-7-azabicyclo[2.2.1]heptan-2-ol hydrochloride (63 mg, 0.42 mmol, 2.01 equiv) and potassium carbonate (116 mg, 0.84 mmol, 4.01 equiv). The resulting solution was stirred overnight at room temperature. The resulting solution was diluted with H₂O. The resulting solution was extracted with ethyl acetate (3×10 mL) and the combined organic layers were dried over anhydrous sodium sulfate and concentrated under vacuum. The residue was applied onto a silica gel column with dichloromethane/methanol (10:1). The crude product was purified by Prep-HPLC with the following conditions (Waters): Column, XBridge BEH130 Prep C18 OBD Column, 19*150 mm 5 μm 13 nm; mobile phase, Water with 0.5% NH₄HCO₃ and ACN (30.0% ACN up to 70.0% in 8 min); Detector, UV 254/220 nm. This resulted in 23.4 mg (27%) of 4-[5-[(1E)-4-cyanobut-1-en-1-yl]-3-[2-[(1R,2R,4S)-2-hydroxy-7-azabicyclo[2.2.1]heptan-7-yl]acetyl]-2-methyl-1H-pyrrol-1-yl]benzonitrile (20B) as a white solid. Mass Spectrum (LCMS, ESI pos.): Calcd. for $C_{25}H_{26}N_4O_2$: 415 (M+H); found 415. ¹H NMR (300 MHz, DMSO-d₆): δ 8.06 (d, J=8.4 Hz, 2H), 7.55 (d, J=8.4 Hz, 2H), 6.99 (s, 1H), 5.98-5.88 (m, 2H), 4.66 (d, J=3.9 Hz, 1H), 4.06-4.03 (m, 1H), 3.66 (s, 2H), 3.28-3.25 (m, 2H), 2.55-2.53 (m, 2H), 2.32-2.28 (m, 5H), 2.08-1.96 (m, 2H), 1.79-1.75 (m, 1H), 1.55-1.52 (m, 1H), 1.35-1.28 (m, 1H), 0.85-0.72 (m, 1H).

Example 6B. (±)-4-(5-(((1R,2R)₂-(2-Cyanoethyl)cyclopropyl)-3-(2-((2R)-2-hydroxy-7-azabicyclo[2.2.1]heptan-7-yl)acetyl)-2-methyl-1H-pyrrol-1-yl)benzonitrile (17B)

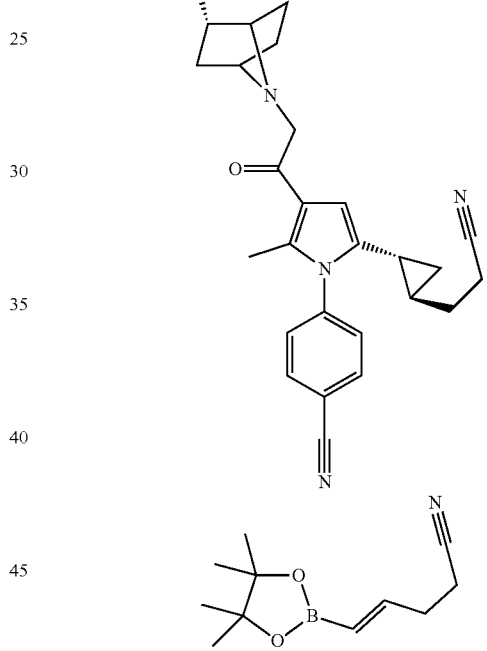

A. (E)-5-(4,4,5,5-Tetramethyl-1,3,2-dioxaborolan-2-yl)pent-4-enenitrile

Into a 250 mL, 3-necked round-bottom flask, being maintained under an inert atmosphere of nitrogen, were placed 4,4,4',4',5,5,5',5'-octamethyl-2,2'-bi(1,3,2-dioxaborolane) (11.6 g, 45.7 mmol), copper power (248 mg, 3.90 mmol), sodium methoxide (1.4 g, 25.9 mmol, 30% in methanol) and ethanol (50 mL). To the mixture was added pent-4-ynenitrile (3.0 g, 37.9 mmol) and the resulting mixture was allowed to stir at room temperature overnight. The reaction mixture was diluted with water (100 mL) and then extracted with dichloromethane (3×100 mL). The combined organic extracts were washed with brine (2×50 mL), dried over anhydrous sodium sulfate, and concentrated under vacuum. The remaining residue was purified by column chromatography on silica gel using ethyl acetate/petroleum ether (1:80 to 1:40) as the eluant to afford 1.5 g (19%) of (E)-5-(4,4,5,5-tetramethyl-1,3,2-dioxaborolan-2-yl)pent-4-enenitrile as a white solid. ¹H NMR (300 MHz, CDCl₃): δ 6.60-6.54 (m, 1H), 6.59-6.53 (d, J=18.0 Hz, 1H), 2.52-2.43 (m, 4H), 1.27 (s, 12H).

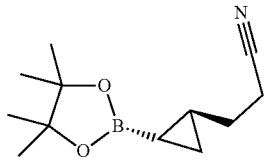

B. (±)-3-(1S,2S)-2-(4,4,5,5-Tetramethyl-1,3,2-dioxaborolan-2-yl)cyclopropyl)propanenitrile Into a 50 mL, 3-necked round-bottom flask, being maintained under an inert atmosphere of nitrogen, was placed dichloromethane (10 mL), followed by a solution of diethylzinc (5 mL, 1M in hexane). The solution was cooed to −78° C. and then CH₂I2 (2.60 g, 9.71 mmol) was added to the in a dropwise manner. The reaction mixture was allowed to stir at the reduced temperature for 30 min and then a solution of (E)-5-(4,4,5,5-tetramethyl-1,3,2-dioxaborolan-2-yl)pent-4-enenitrile (500 mg, 2.41 mmol) was added to the mixture. The resulting system was allowed to warm to room temperature and then stir for 3 h. The reaction was diluted with 1M aqueous HCl (5 mL) and the mixture was extracted with dichloromethane (3×50 mL). The combined organic extracts were washed with aqueous sodium carbonate (3×15 mL), brine (2×20 mL), dried over anhydrous sodium sulfate. Concentration of the organic filtrate afforded 600 mg of crude (±)-3-((1S,2S)-2-(4,4,5,5-tetramethyl-1,3,2-dioxaborolan-2-yl)cyclopropyl)propanenitrile as yellow oil. Mass Spectrum (LCMS, ESI pos.): Calcd. for C₁₂H₂₀BNO₂: 222 (M+H); found 222.

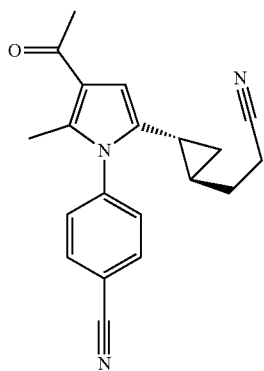 [SMILES: CC(=O)c1cc([C@@H]2C[C@H]2CCC#N)n(-c2ccc(C#N)cc2)c1C]

C. (±)-4-(3-Acetyl-5-((1R,2R)-2-(2-cyanoethyl)cyclopropyl)-2-methyl-1H-pyrrol-1-yl)benzonitrile Into a 20 mL sealed tube purged and maintained with an inert atmosphere of nitrogen, were placed 4-(3-acetyl-5-bromo-2-methyl-1H-pyrrol-1-yl)benzonitrile (300 mg, 0.99 mmol), (1)-3-((1S,2S)-2-(4,4,5,5-tetramethyl-1,3,2-dioxaborolan-2-yl)propanenitrile (350 mg, 1.58 mmol), Cs₂CO₃ (1.02 g, 3.13 mmol), and Pd(dppf)C₁₂ (75 mg, 0.10 mmol), dioxane (12 mL) and water (3 mL). The resulting mixture was heated at 100° C. for 2 hours inside of a microwave reactor. After cooling to room temperature the reaction mixture was filtered and the filtrate was diluted with water (10 mL). The mixture was extracted with ethyl acetate (2×30 mL) and the combined organic extracts were washed with brine (3×20 mL), dried over anhydrous sodium sulfate and concentrated under vacuum. The remaining residue was purified by preparative-TLC using ethyl acetate/petroleum ether (1:2) as the eluant to afford 100 mg (32%) of (±)-4-(3-acetyl-5-((1R,2R)-2-(2-cyanoethyl)cyclopropyl)-2-methyl-1H-pyrrol-1-yl)benzonitrile as a white solid. Mass Spectrum (LCMS, ESI pos.): Calcd. for C₂₀H₁₉N₃O: 318 (M+H); found 318.

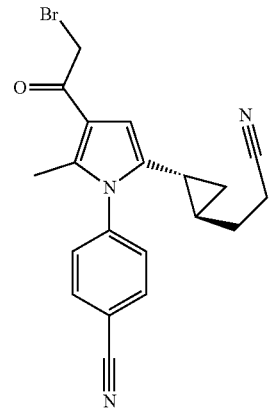 [SMILES: Cc1c(C(=O)CBr)cc([C@@H]2C[C@H]2CCC#N)n1-c1ccc(C#N)cc1]

D. (±)-4-(3-(2-Bromoacetyl)-5-((1R,2R)-2-(2-cyanoethyl)cyclopropyl)-2-methyl-1H-pyrrol-1-yl)benzonitrile Into a 100 mL 3-necked round-bottom flask, being maintained under an inert atmosphere of nitrogen, was placed a solution of (±)-4-(3-acetyl-5-((1R,2R)-2-(2-cyanoethyl)cyclopropyl)-2-methyl-1H-pyrrol-1-yl)benzonitrile (100 mg, 0.32 mmol) in THF (15 mL). To this solution was then added diisopropylethylamine (170 mg, 1.32 mmol) and TMSOTf (150 mg, 0.68 mmol). The reaction mixture was cooled to 0° C. and allowed to stir for 1 h before 1-bromopyrrolidine-2,5-dione (70 mg, 0.39 mmol) was added. The reaction mixture was allowed to stir for additional 10 min at 0° C. before it was diluted with water (10 mL). The mixture was extracted with ethyl acetate (3×30 mL) and the combined organic extracts were washed with brine (2×20 mL), dried over anhydrous sodium sulfate and concentrated under vacuum. The remaining residue was purified by preparative-TLC using ethyl acetate/petroleum ether (1:2) to afford 40 mg (32%) of (±)-4-(3-(2-bromoacetyl)-5-((1R,2R)-2-(2-cyanoethyl)cyclopropyl)-2-methyl-1H-pyrrol-1-yl)benzonitrile as a yellow solid. Mass Spectrum (LCMS, ESI pos.): Calcd. for C₂₀H₁₈BrN₃: 396 (M+H); found 396.

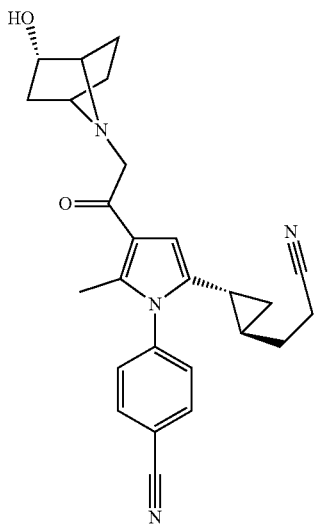 [SMILES: Cc1c(C(=O)CN2C3CCC2[C@@H](O)C3)cc([C@@H]2C[C@H]2CCC#N)n1-c1ccc(C#N)cc1]

E. (±)-4-(5-((1R,2R)-2-(2-Cyanoethyl)cyclopropyl)-3-(2-((2R)-2-hydroxy-7-azabicyclo[2.2.1]heptan-7-yl)acetyl)-2-methyl-1H-pyrrol-1-yl)benzonitrile (17B)

Into a 25 mL round-bottom flask, being maintained under an inert atmosphere of nitrogen, were placed (±)-4-(3-(2-bromoacetyl)-5-((1R,2R)-2-(2-cyanoethyl)cyclopropyl)-2-methyl-1H-pyrrol-1-yl)benzonitrile (35 mg, 0.09 mmol), (±)-(1R, 2R, 4S)-7-azabicyclo[2.2.1]heptan-2-ol (30 mg, 0.27 mmol), K$_2$CO$_3$ (68 mg, 0.49 mmol) and N,N-dimethylformamide (3 mL). The resulting mixture was allowed to stir at room temperature for 5 h before being diluted with water (30 mL). The mixture was extracted with ethyl acetate (3×50 mL) and the combined organic extracts were washed with brine (2×25 mL), dried over anhydrous sodium sulfate and concentrated under vacuum. The remaining residue was purified by preparative-TLC using dichloromethane/methanol (10:1) as the eluant to afford 8 mg (21%) of (±)-4-(5-((1R,2R)-2-(2-cyanoethyl)cyclopropyl)-3-(2-((2R)-2-hydroxy-7-azabicyclo[2.2.1]heptan-7-yl)acetyl)-2-methyl-1H-pyrrol-1-yl)benzonitrile (17B) as an off-white solid. Mass Spectrum (LCMS, ESI pos.): Calcd. for C$_{26}$H$_{28}$N$_4$O$_2$: 429 (M+H); found 429. $^1$H NMR (300 MHz, DMSO-d$_6$): δ 8.09 (d, J=8.7 Hz, 2H), 7.64 (d, J=8.4 Hz, 2H), 6.40 (s, 1H), 4.67 (brs, 1H), 4.06-4.00 (m, 1H), 3.54 (s, 2H), 3.30 (brs, 2H), 2.32-2.30 (m, 2H), 2.23 (s, 3H), 1.99-1.95 (m, 2H), 1.76-1.72 (m, 1H), 1.54-1.50 (m, 1H), 1.45-1.23 (m, 6H), 0.90-0.88 (m, 2H), 0.83-0.76 (m, 2H), 0.59-0.53 (m, 1H).

Example 7B. (±)-4-(3-Chloro-2-((E)-4-cyano-4-methylpent-1-en-1-yl)-4-(2-(2R)-2-hydroxy-7-azabicyclo[2.2.1]heptan-7-yl)acetyl)-5-methyl-1H-pyrrol-1-yl)benzonitrile (46B)

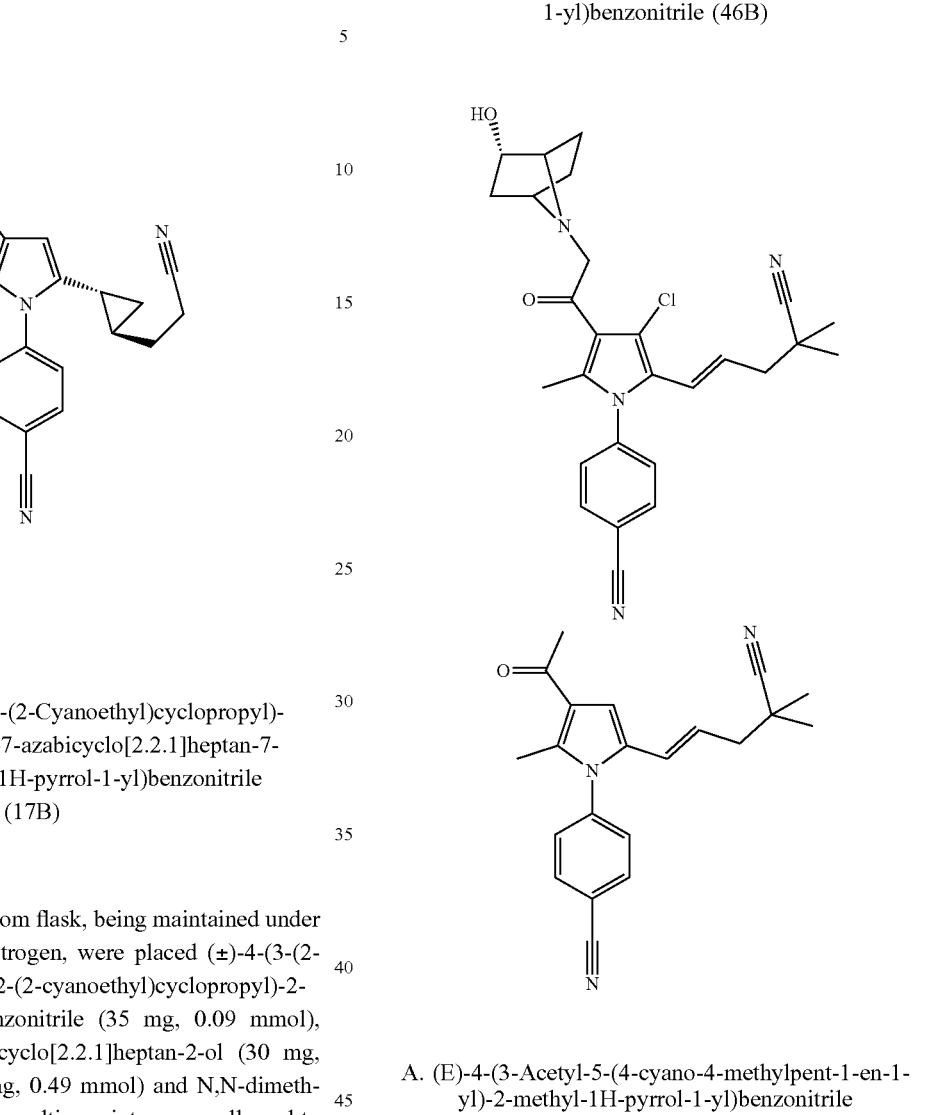

A. (E)-4-(3-Acetyl-5-(4-cyano-4-methylpent-1-en-1-yl)-2-methyl-1H-pyrrol-1-yl)benzonitrile Into a 50 mL round-bottom flask, being maintained under an inert atmosphere of nitrogen, was placed a mixture of 4-(3-acetyl-5-bromo-2-methyl-1H-pyrrol-1-yl)benzonitrile (900 mg, 2.97 mmol), (E)-2,2-dimethyl-5-(4,4,5,5-tetramethyl-1,3,2-dioxaborolan-2-yl)pent-4-enenitrile (860 mg, 3.66 mmol), cesium carbonate (2.95 g, 9.05 mmol), and Pd(dppf)C$_{12}$ (225 mg, 0.31 mmol), 1,4-dioxane (10 mL) and water (2.5 mL). The resulting mixture was heated at 100° C. for 6 h under an atmosphere of nitrogen. After cooling to room temperature the reaction mixture was diluted with water (20 mL) and then extracted with ethyl acetate (2×50 mL). The combined organic extracts were washed with brine (2×30 mL), dried over anhydrous sodium sulfate and then concentrated under vacuum. The remaining residue was purified by column chromatography on silica, using ethyl acetate/petroleum ether (1:6 to 1:2) as the eluant, to afford (E)-4-(3-acetyl-5-(4-cyano-4-methylpent-1-en-1-yl)-2-methyl-1H-pyrrol-1-yl)benzonitrile as a white solid. Mass Spectrum (LCMS, ESI pos.): Calcd. for C$_{21}$H$_{21}$N$_3$O: 332 (M+H); found 332. $^1$H NMR (300 MHz, CDCl$_3$): δ 7.85 (d, J=9.0 Hz, 2H), 7.38 (d, J=9.0 Hz, 2H), 6.79 (s, 1H), 6.03-5.93 (m, 1H), 5.87 (d, J=15.0 Hz, 2H), 2.48 (s, 3H), 2.35 (s, 3H), 2.25 (d, J=6.0 Hz, 2H), 1.32 (s, 6H).

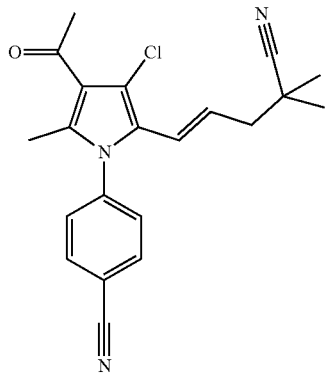 [SMILES: CC(=O)c1c(Cl)c(/C=C/CC(C)(C)C#N)n(-c2ccc(C#N)cc2)c1C]

B. (E)-4-(3-Acetyl-4-chloro-5-(4-cyano-4-methylpent-1-en-1-yl)-2-methyl-1H-pyrrol-1-yl)benzonitrile Into a 100 mL round-bottom flask, being maintained under an inert atmosphere of nitrogen, was placed a solution of (E)-4-(3-acetyl-5-(4-cyano-4-methylpent-1-en-1-yl)-2-methyl-1H-pyrrol-1-yl)benzonitrile (500 mg, 1.51 mmol) in acetonitrile (30 mL). To the solution was added N-chlorosuccinimide (300 mg, 2.25 mmol) and the resulting mixture was allowed to stir at room temperature for 3 days. The reaction mixture was concentrated under vacuum and the remaining residue was diluted with water (50 mL). The aqueous mixture was extracted with ethyl acetate (2×50 mL) and the combined organic extracts were washed with brine (2×20 mL), dried over anhydrous sodium sulfate and concentrated under vacuum. The remaining residue was purified by preparative-TLC on silica, using ethyl acetate/petroleum ether (1:5) as the developing solution, to afford 240 mg (43%) of (E)-4-(3-acetyl-4-chloro-5-(4-cyano-4-methylpent-1-en-1-yl)-2-methyl-1H-pyrrol-1-yl)benzonitrile as a white solid. Mass Spectrum (LCMS, ESI pos.): Calcd. for $C_{21}H_{20}ClN_3O$: 366 (M+H); found 366. $^1H$ NMR (400 MHz, CDCl$_3$): δ 7.84 (d, J=8.0 Hz, 2H), 7.37 (d, J=8.0 Hz, 2H), 5.97-5.85 (m, 2H), 2.63 (s, 3H), 2.26 (s, 3H), 2.23 (d, J=8.0 Hz, 2H), 1.27 (s, 6H).

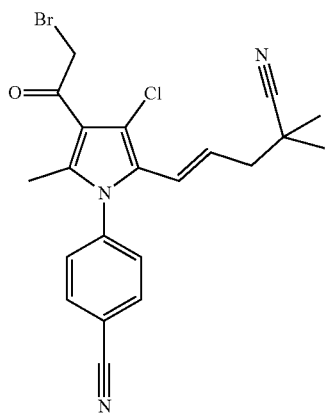 [SMILES: Cc1c(C(=O)CBr)c(Cl)c(/C=C/CC(C)(C)C#N)n1-c1ccc(C#N)cc1]

C. (E)-4-(3-(2-Bromoacetyl)-4-chloro-5-(4-cyano-4-methylpent-1-en-1-yl)-2-methyl-1H-pyrrol-1-yl)benzonitrile Into a 50 mL 3-necked round-bottom flask, being maintained under an inert atmosphere of nitrogen, was placed a solution of (E)-4-(3-acetyl-4-chloro-5-(4-cyano-4-methylpent-1-en-1-yl)-2-methyl-1H-pyrrol-1-yl)benzonitrile (200 mg, 0.55 mmol) in tetrahydrofuran (25 mL). The solution was cooled to 0° C. and then diisopropylethylamine (290 mg, 2.24 mmol) and trimethylsilyl trifluoromethylsulfonate (280 mg) were added in a dropwise fashion. The resulting mixture was allowed to stir at 0° C. 1.5 h and was then treated with N-bromosuccinimide (150 mg, 0.84 mmol). The reaction mixture was allowed to stir at 0° C. for an additional 10 min and was then diluted with water (20 mL). The mixture was extracted with ethyl acetate (2×50 mL) and the combined organic extracts were washed with brine (2×25 mL). The organic phase was dried over anhydrous sodium sulfate and then concentrated under vacuum to afford 150 mg (62%) of (E)-4-(3-(2-bromoacetyl)-4-chloro-5-(4-cyano-4-methylpent-1-en-1-yl)-2-methyl-1H-pyrrol-1-yl)benzonitrile as brown oil. Mass Spectrum (LCMS, ESI pos.): Calcd. for $C_{21}H_{19}BrClN_3O$: 444 (M+H); found 444.

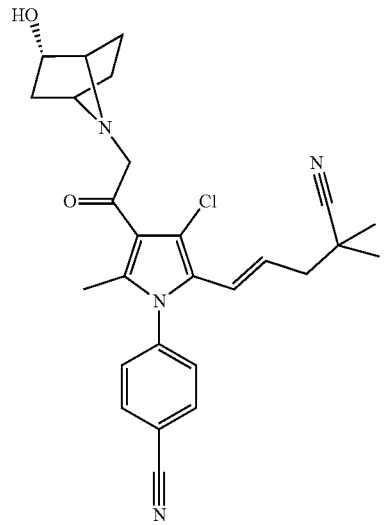 [SMILES: Cc1c(C(=O)CN2C3CCC2[C@@H](O)C3)c(Cl)c(/C=C/CC(C)(C)C#N)n1-c1ccc(C#N)cc1]

D. (±)-4-(3-Chloro-2-((E)-4-cyano-4-methylpent-1-en-1-yl)-4-(2-((2R)-2-hydroxy-7-azabicyclo[2.2.1]heptan-7-yl)acetyl)-5-methyl-1H-pyrrol-1-yl)benzonitrile (46B)

Into a 25 mL round-bottom flask, being maintained under an inert atmosphere of nitrogen, was placed a mixture of (E)-4-(3-(2-bromoacetyl)-4-chloro-5-(4-cyano-4-methylpent-1-en-1-yl)-2-methyl-1H-pyrrol-1-yl)benzonitrile (150 mg, 0.34 mmol), racemic (1R,2R,4S)-7-azabicyclo[2.2.1]heptan-2-ol (120 mg, 1.06 mmol), potassium carbonate (250 mg, 1.81 mmol), and N,N-dimethylformamide (5 mL). The resulting mixture was allowed to stir under an atmosphere of nitrogen at room temperature overnight. The reaction mixture was diluted with water (50 mL) and then extracted with ethyl acetate (2×50 mL). The combined organic extracts were washed with brine (2×25 mL), dried over anhydrous sodium sulfate and concentrated under vacuum. The crude product was purified by preparative-HPLC under the following conditions: Column-X Bridge C18 OBD Prep Column, 19 mm×250 mm; Mobile Phase A-water with 0.05% trifluoroacetic acid, Mobile Phase B-acetonitrile, Gradient: 20% B to 65% B in 7 min; Detector-UV 254/220 nm. This process afforded 34 mg (21%) of (±)-4-(3-Chloro-2-((E)-4-cyano-4-methylpent-1-en-1-yl)-4-(2-((2R)-2-hydroxy-7-azabicyclo[2.2.1]heptan-7-yl)acetyl)-5-methyl-1H-pyrrol-1-yl)benzonitrile (46B) as a white solid. Mass Spectrum (LCMS, ESI pos.): Calcd. for $C_{27}H_{29}ClN_4O_2$: 477 (M+H); found 477. $^1$H NMR (300 MHz, $CH_3OH$-$d_4$): δ 7.96 (d, J=8.7 Hz, 2H), 7.51 (d, J=8.4 Hz, 2H), 6.04 (d, J=16.2 Hz, 1H), 5.91-5.81 (m, 1H), 4.68 (s, 2H), 4.61-4.57 (m, 1H), 4.18-4.14 (m, 2H), 2.64-2.56 (m, 2H), 2.36 (s, 3H), 2.26-2.24 (d, J=7.8 Hz, 2H), 2.19-2.12 (m, 1H), 1.98-1.88 (m, 2H), 1.51-1.45 (m, 1H), 1.22 (s, 6H).

Example 8B. (±)-4-(3-Chloro-2-(4-cyanobutyl)-4-(2-((2R)-2-hydroxy-7-azabicyclo[2.2.1]heptan-7-yl)acetyl)-5-methyl-1H-pyrrol-1-yl)-2-fluorobenzonitrile (48B)

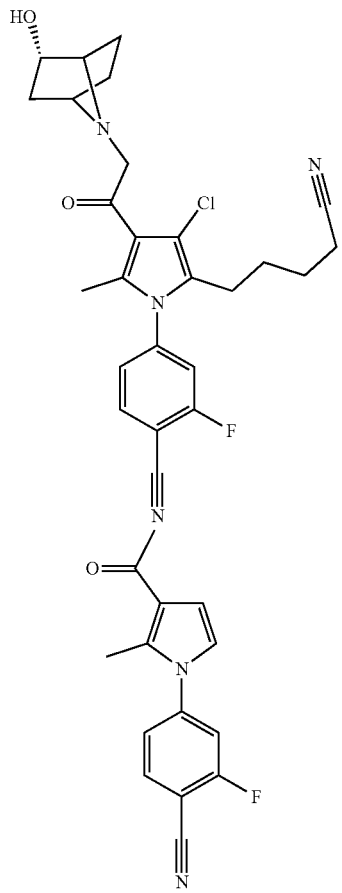

A. 4-(3-Acetyl-2-methyl-1H-pyrrol-1-yl)-2-fluorobenzonitrile

Into a 20 mL sealed tube, being maintained under an inert atmosphere of nitrogen, was placed a mixture of 1-(2-methyl-1H-pyrrol-3-yl)ethan-1-one (615 mg, 5.00 mmol), potassium phosphate (2.12 g, 10.0 mmol), 4-bromo-2-fluorobenzonitrile (1.99 g, 10.0 mmol), copper(I) iodide (190 mg, 1.00 mmol), racemic (1S,2S)-cyclohexane-1,2-diamine (228 mg, 2.00 mmol) and 1,4-dioxane (20 mL). The resulting mixture was heated at 110° C. overnight. After cooling to room temperature the reaction mixture was diluted with brine and extracted with ethyl acetate (3×40 mL). The combined organic extracts were washed with brine (3×30 mL), dried over anhydrous sodium sulfate and concentrated under vacuum. The remaining residue was purified by column chromatography on silica, using ethyl acetate/petroleum ether (1:5) as the eluant, to afford 320 mg (26%) of 4-(3-acetyl-2-methyl-1H-pyrrol-1-yl)-2-fluorobenzonitrile as a yellow solid. Mass Spectrum (LCMS, ESI pos.): Calcd. for $C_{14}H_1FN_2O$: 243 (M+H); found 243.

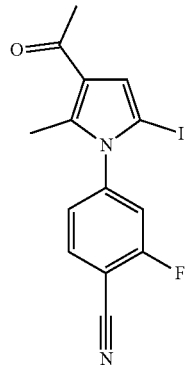 [SMILES: CC(=O)c1cc(I)n(-c2ccc(C#N)c(F)c2)c1C]

B. 4-(3-Acetyl-5-iodo-2-methyl-1H-pyrrol-1-yl)-2-fluorobenzonitrile

Into a 100 mL round-bottom flask, being maintained under an inert atmosphere of nitrogen, was placed a mixture of 4-(3-acetyl-2-methyl-1H-pyrrol-1-yl)-2-fluorobenzonitrile (1.37 g, 5.66 mmol), N-iodosuccinimide (1.40 g, 6.22 mmol), and dichloromethane (20 mL). The reaction mixture was allowed to stir at room temperature overnight before it was diluted with dichloromethane (50 mL). The mixture was washed with brine (3×15 mL), dried over sodium sulfate and concentrated under reduced pressure. The remaining residue was purified by column chromatography on silica, using ethyl acetate/petroleum ether (1:5), as the eluant to afford 760 mg (37%) of 4-(3-acetyl-5-iodo-2-methyl-1H-pyrrol-1-yl)-2-fluorobenzonitrile as a white solid. Mass Spectrum (LCMS, ESI pos.): Calcd. for $C_{14}H_{10}FIN_2O$: 368 (M+H); found 368.

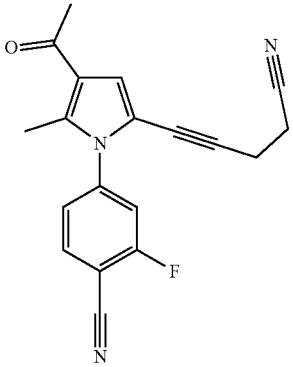 [SMILES: CC(=O)c1cc(C#CCCC#N)n(-c2ccc(C#N)c(F)c2)c1C]

C. 4-(3-Acetyl-5-(4-cyanobut-1-yn-1-yl)-2-methyl-1H-pyrrol-1-yl)-2-fluorobenzonitrile Into a 20 mL sealed tube purged and maintained with an inert atmosphere of nitrogen, was placed a mixture of 4-(3-acetyl-5-iodo-2-methyl-1H-pyrrol-1-yl)-2-fluorobenzonitrile (1.34 g, 5.00 mmol), triethylamine (5.05 g, 49.9 mmol), pent-4-ynenitrile (790 mg, 10.00 mmol), copper(I) iodide (190 mg, 1.00 mmol), Pd(PPh$_3$)$_2$Cl$_2$ (1.40 g, 2.00 mmol), and tetrahydrofuran (20 mL). The reaction mixture was heated at 60° C. overnight. After cooling to room temperature the reaction mixture was diluted with brine and then extracted with ethyl acetate (50 mL). The organic extract was washed with brine (3×15 mL), dried over sodium sulfate, and then concentrated under vacuum. The remaining residue was purified by column chromatography on silica, using ethyl acetate/petroleum ether (1:2) as the eluant, to afford 882 mg (76%) of 4-(3-acetyl-5-(4-cyanobut-1-yn-1-yl)-2-methyl-1H-pyrrol-1-yl)-2-fluorobenzonitrile as a yellow oil. Mass Spectrum (LCMS, ESI pos.): Calcd. for C$_{19}$H$_{14}$FN$_3$O: 320 (M+H); found 320.

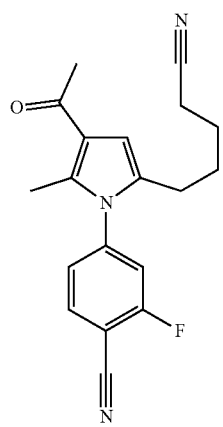 [SMILES: CC(=O)c1cc(CCCCC#N)n(-c2ccc(C#N)c(F)c2)c1C]

D. 4-(3-Acetyl-5-(4-cyanobutyl)-2-methyl-1H-pyrrol-1-yl)-2-fluorobenzonitrile Into a 50 mL round-bottom flask was placed a solution of 4-(3-acetyl-5-(4-cyanobut-1-yn-1-yl)-2-methyl-1H-pyrrol-1-yl)-2-fluorobenzonitrile (274 mg, 0.86 mmol) in ethyl acetate (20 mL). To the solution was added palladium on carbon (55 mg) and the resulting mixture was sparged with hydrogen. The reaction mixture was allowed to stir at room temperature overnight before it was diluted with ethyl acetate (50 mL). The solids were filtered from the reaction mixture and the filtrate was then concentrated under vacuum. The remaining residue was purified by column chromatography on silica, using ethyl acetate/petroleum ether (1:1) as the eluant, to afford 172 mg (62%) of 4-(3-acetyl-5-(4-cyanobutyl)-2-methyl-1H-pyrrol-1-yl)-2-fluorobenzonitrile as a yellow oil. Mass Spectrum (LCMS, ESI pos.): Calcd. for C$_{19}$H$_{18}$FN$_3$O: 324 (M+H); found 324.

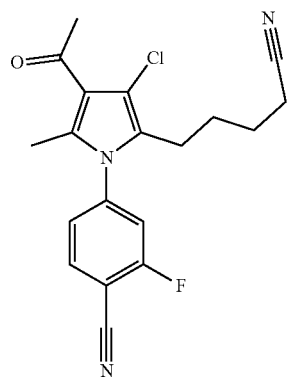 [SMILES: CC(=O)c1c(Cl)c(CCCCC#N)n(-c2ccc(C#N)c(F)c2)c1C]

E. 4-(3-Acetyl-4-chloro-5-(4-cyanobutyl)-2-methyl-1H-pyrrol-1-yl)-2-fluorobenzonitrile Into a 100 mL round-bottom flask was placed a solution of 4-(3-acetyl-5-(4-cyanobutyl)-2-methyl-1H-pyrrol-1-yl)-2-fluorobenzonitrile (323 mg, 1.00 mmol) in dichloromethane (30 mL). The solution was cooled to 0° C. and then treated with sulfuryl chloride in a dropwise fashion over 5 min. The reaction mixture was allowed to warm to room temperature and stir overnight before being diluted with brine. The mixture was extracted with dichloromethane (50 mL) and the organic extract was washed with brine (3×20 mL) and concentrated under vacuum. The remaining residue was purified by column chromatography on silica, using ethyl acetate/petroleum ether (1:2) as the eluant, to afford 183 mg (51%) of 4-(3-acetyl-4-chloro-5-(4-cyanobutyl)-2-methyl-1H-pyrrol-1-yl)-2-fluorobenzonitrile as a light yellow oil. Mass Spectrum (LCMS, ESI pos.): Calcd. for C$_{19}$H$_{17}$ClFN$_3$: 358 (M+H); found 358.

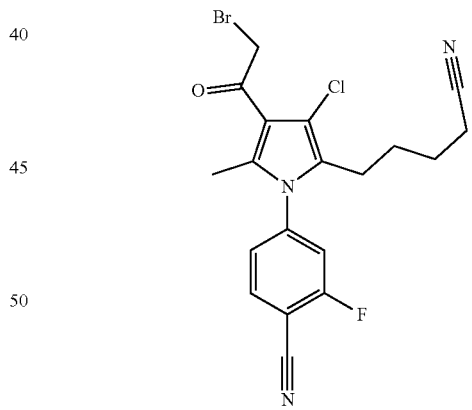

F. 4-(3-(2-Bromoacetyl)-4-chloro-5-(4-cyanobutyl)-2-methyl-1H-pyrrol-1-yl)-2-fluorobenzonitrile Into a 50 mL round-bottom flask, being maintained under an inert atmosphere of nitrogen, was placed a mixture of 4-(3-acetyl-4-chloro-5-(4-cyanobutyl)-2-methyl-1H-pyrrol-1-yl)-2-fluorobenzonitrile (183 mg, 0.51 mmol), diisopropylethylamine (199 mg, 1.54 mmol), and tetrahydrofuran (10 mL). The mixture was cooled to 0° C. and then treated with trimethylsilyl trifluoromethylsulfonate (217 mg). The resulting mixture was allowed to stir at 0° C. for 1 h and then N-bromosuccinimide (110 mg, 0.62 mmol) was added. The reaction mixture was allowed to warm to room temperature and stir for an additional 4 h before being diluted with ethyl acetate (50 mL). The mixture was washed with brine (3×20 mL), dried over sodium sulfate, and then concentrated under vacuum. The remaining residue was purified by column chromatography on silica, using ethyl acetate/petroleum ether (1:3) as the eluant, to afford 360 mg (semi-crude) of 4-(3-(2-bromoacetyl)-4-chloro-5-(4-cyanobutyl)-2-methyl-1H-pyrrol-1-yl)-2-fluorobenzonitrile as a yellow solid. Mass Spectrum (LCMS, ESI pos.): Calcd. for $C_{19}H_{16}BrClFN_3O$: 436 (M+H); found 436.

MHz, DMSO-$d_6$): δ 8.17-8.13 (m, 1H), 7.85-7.81 (m, 1H), 7.51 (s, 1H), 4.67 (d, J=3.6 Hz, 1H), 4.06-3.98 (m, 1H), 3.67 (s, 2H), 3.23-3.22 (m, 2H), 2.48-2.43 (m, 2H), 2.35-2.32 (m, 2H), 2.17 (s, 3H), 2.02-1.95 (m, 2H), 1.77-1.65 (m, 1H), 1.51-1.41 (m, 1H), 1.39-1.21 (m, 5H), 0.82-0.75 (m, 1H).

Example 9B. (±)-4-(3-(2-((2R)-2-Hydroxy-7-azabicyclo[2.2.1]heptan-7-yl)acetyl)-2-methyl-5-(2-(tetrahydro-2H-pyran-4-yl)ethyl)-1H-pyrrol-1-yl)benzonitrile (9B)

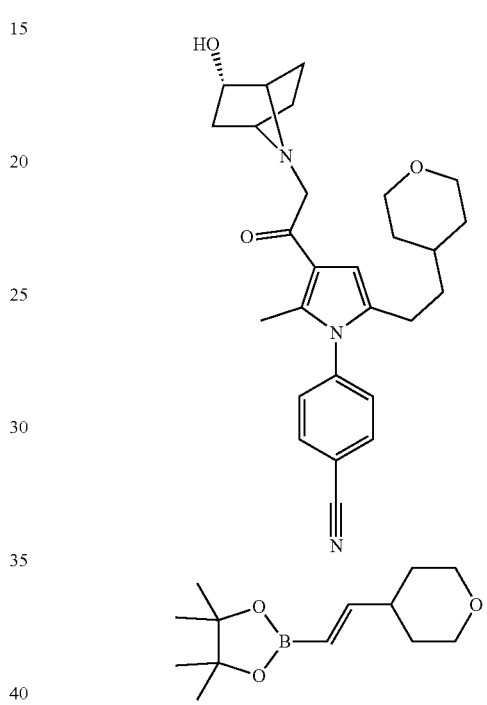

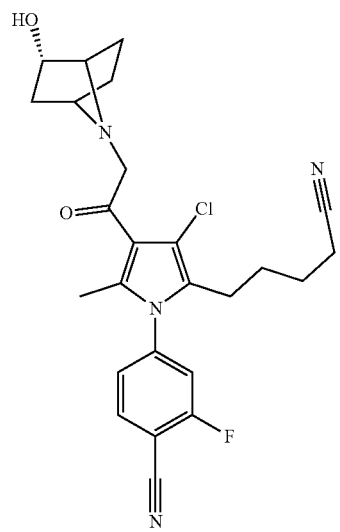 [SMILES: Cc1c(C(=O)CN2C3CCC2[C@@H](O)C3)c(Cl)c(CCCCC#N)n1-c1ccc(C#N)c(F)c1]

G. (±)-4-(3-Chloro-2-(4-cyanobutyl)-4-(2-((2R)-2-hydroxy-7-azabicyclo[2.2.1]heptan-7-yl)acetyl)-5-methyl-1H-pyrrol-1-yl)-2-fluorobenzonitrile (48B)

Into a 50 mL round-bottom flask, being maintained under an inert atmosphere of nitrogen, was placed a mixture of 4-(3-(2-bromoacetyl)-4-chloro-5-(4-cyanobutyl)-2-methyl-1H-pyrrol-1-yl)-2-fluorobenzonitrile (228 mg, 0.52 mmol), potassium carbonate (144 mg, 1.04 mmol), racemic (1R, 2R, 4S)-7-azabicyclo[2.2.1]heptan-2-ol hydrochloride (138 mg, 0.92 mmol), and in N,N-dimethylformamide (5 mL). The resulting mixture was allowed to stir at room temperature overnight. Solids were filtered from the reaction mixture and the filtrate was purified by preparative-HPLC under the following conditions: Column-X Bridge Prep C18 OBD Column, 5 μm, 19*150 nm; mobile phase-$H_2O$ (10 mmol/L $NH_4HCO_3$) and acetonitrile (30% acetonitrile up to 60% in 10 min); Detector-UV 254 nm. This process afforded 32 mg (13%) of (±)-4-(3-Chloro-2-(4-cyanobutyl)-4-(2-((2R)-2-hydroxy-7-azabicyclo[2.2.1]heptan-7-yl)acetyl)-5-methyl-1H-pyrrol-1-yl)-2-fluorobenzonitrile (48B) as a white solid. Mass Spectrum (LCMS, ESI pos.): Calcd. for $C_{25}H_{26}ClFN_4O_2$: 469 (M+H); found 469. $^1H$ NMR (400

A. (E)-4,4,5,5-Tetramethyl-2-(2-(tetrahydro-2H-pyran-4-yl)vinyl)-1,3,2-dioxaborolane Into a 100 mL round-bottom flask, being maintained under an inert atmosphere of nitrogen, was placed a solution of 4-ethynyltetrahydro-2H-pyran (2.0 g, 18.2 mmol) in ethanol (20 mL). To the solution were added 4,4,4',4',5,5,5',5'-octamethyl-2,2'-bi(1,3,2-dioxaborolane) (6.5 g, 25.6 mmol), copper powder (110 mg, 1.72 mmol) and sodium methoxide (899 mg, 16.7 mmol). The resulting mixture was allowed to stir at room temperature for 16 h before it was diluted with water (100 mL). The mixture was extracted with ethyl acetate (2×200 mL) and the combined organic extracts were washed with brine (2×100 mL). The organic phase was dried over anhydrous sodium sulfate and then concentrated under vacuum to afford 1.2 g (28%) of (E)-4,4,5,5-tetramethyl-2-(2-(tetrahydro-2H-pyran-4-yl)vinyl)-1,3,2-dioxaborolane as a yellow solid. $^1H$ NMR (300 MHz, CDCl$_3$): δ 6.57-6.49 (m, 1H), 5.43-5.36 (m, 1H), 3.96-3.90 (m, 2H), 3.42-3.34 (m, 2H), 2.29-2.22 (m, 1H), 1.52-1.38 (m, 4H), 1.24-1.19 (m, 12H).

255

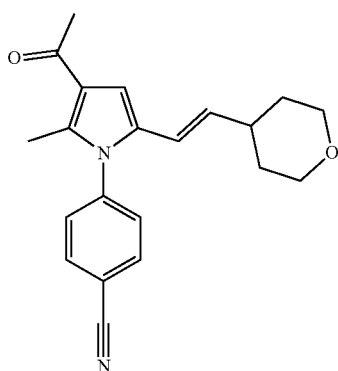 [SMILES: CC(=O)c1cc(/C=C/C2CCOCC2)n(-c2ccc(C#N)cc2)c1C]

B. (E)-4-(3-Acetyl-2-methyl-5-(2-(tetrahydro-2H-pyran-4-yl)vinyl)-1H-pyrrol-1-yl)benzonitrile Into a 25 mL sealed tube, being maintained under an inert atmosphere of nitrogen, was placed a solution of (E)-4,4,5,5-tetramethyl-2-(2-(tetrahydro-2H-pyran-4-yl)vinyl)-1,3,2-dioxaborolane (358 mg, 1.50 mmol) in 1,4-dioxane (6 mL). To the solution were added 4-(3-acetyl-5-iodo-2-methyl-1H-pyrrol-1-yl)benzonitrile (527 mg, 1.51 mmol), a solution of potassium carbonate (623 mg, 4.51 mmol) in water (2 mL) and Pd(dppf)C$_{12}$ (110 mg, 0.15 mmol). The resulting mixture was heated at 100° C. for 2 h. The reaction mixture was diluted with water (100 mL) and then extracted with ethyl acetate (2×100 mL). The combined organic extracts were washed with brine (2×100 mL), dried over anhydrous sodium sulfate, and then concentrated under vacuum to afford 150 mg (30%) of (E)-4-(3-acetyl-2-methyl-5-(2-(tetrahydro-2H-pyran-4-yl)vinyl)-1H-pyrrol-1-yl)benzonitrile as a yellow solid. Mass Spectrum (LCMS, ESI pos.): Calcd. for $C_{21}H_{22}N2O_2$: 335 (M+H); found 335.

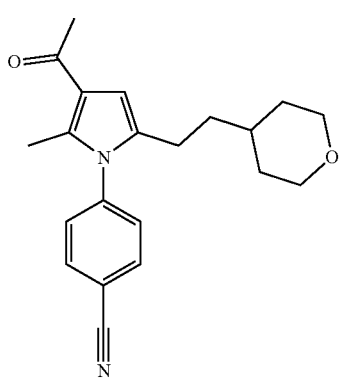 [SMILES: CC(=O)c1cc(CCC2CCOCC2)n(-c2ccc(C#N)cc2)c1C]

C. 4-(3-Acetyl-2-methyl-5-(2-(tetrahydro-2H-pyran-4-yl)ethyl)-1H-pyrrol-1-yl)benzonitrile Into a 50 mL round-bottom flask, being maintained under an inert atmosphere of nitrogen, was placed a solution of (E)-4-(3-acetyl-2-methyl-5-(2-(tetrahydro-2H-pyran-4-yl)vinyl)-1H-pyrrol-1-yl)benzonitrile (100 mg, 0.30 mmol) in ethyl acetate (10 mL). To the solution was added palladium on carbon (25 mg) and the resulting mixture was sparged with hydrogen gas. The reaction mixture was allowed to stir at room temperature for 16 h before being diluted with water (20 mL). The mixture was extracted with ethyl acetate (2×100 mL) and the combined organic extracts were washed with brine (2×50 mL). The organic phase was dried over anhydrous sodium sulfate and concentrated under vacuum to afford 90 mg (89%) of 4-(3-acetyl-2-methyl-5-(2-(tetrahydro-2H-pyran-4-yl)ethyl)-1H-pyrrol-1-yl)benzonitrile as a yellow solid. Mass Spectrum (LCMS, ESI pos.): Calcd. for $C_2H_{24}N_2O_2$: 337 (M+H); found 337.

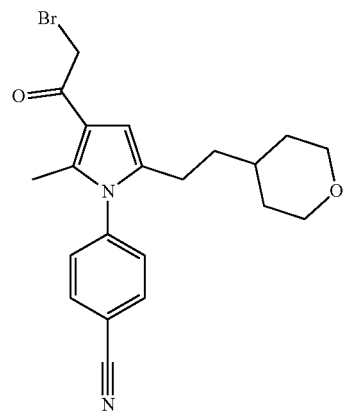 [SMILES: Cc1c(C(=O)CBr)cc(CCC2CCOCC2)n1-c1ccc(C#N)cc1]

D. 4-(3-(2-Bromoacetyl)-2-methyl-5-(2-(tetrahydro-2H-pyran-4-yl)ethyl)-1H-pyrrol-1-yl)benzonitrile Into a 50 mL 3-necked round-bottom flask, being maintained under an inert atmosphere of nitrogen, was placed a mixture of 4-(3-acetyl-2-methyl-5-(2-(tetrahydro-2H-pyran-4-yl)ethyl)-1H-pyrrol-1-yl)benzonitrile (100 mg, 0.30 mmol), diisopropylethylamine (153 mg, 1.18 mmol) and tetrahydrofuran (5 mL). The mixture was cooled to 0° C. and then treated with trimethylsilyl trifluoromethanesulfonate (132 mg, 0.59 mmol). The reaction mixture was allowed to stir at 0° C. for 0.5 and then solid N-bromosuccinimide (180 mg, 1.01 mmol) was added to the flask. The reaction mixture as allowed to warm to room temperature and stir for 1 h before it was diluted with water (50 mL). The aqueous mixture was extracted with ethyl acetate (2×100 mL) and the combined organic extracts were washed with brine (2×10 mL). The organic phase was dried over anhydrous sodium sulfate and then concentrated under vacuum to afford 120 mg (crude) of 4-(3-(2-bromoacetyl)-2-methyl-5-(2-(tetrahydro-2H-pyran-4-yl)ethyl)-1H-pyrrol-1-yl)benzonitrile as a yellow solid. Mass Spectrum (LCMS, ESI pos.): Calcd. for $C_{21}H_{23}BrN_2O_2$: 415 (M+H); found 415.

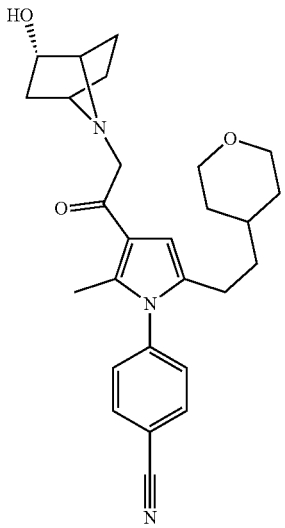 [SMILES: Cc1c(C(=O)CN2C3CCC2[C@@H](O)C3)cc(CCC2CCOCC2)n1-c1ccc(C#N)cc1]

E. (±)-4-(3-(2-((2R)-2-Hydroxy-7-azabicyclo[2.2.1]heptan-7-yl)acetyl)-2-methyl-5-(2-(tetrahydro-2H-pyran-4-yl)ethyl)-1H-pyrrol-1-yl)benzonitrile (9B)

Into a 50 mL round-bottom flask, being maintained under an inert atmosphere of nitrogen, was placed a solution of 4-(3-(2-bromoacetyl)-2-methyl-5-(2-(tetrahydro-2H-pyran-4-yl)ethyl)-1H-pyrrol-1-yl)benzonitrile (130 mg, 0.31 mmol) in N,N-dimethylformamide (5 mL). To the solution were added potassium carbonate (130 mg, 0.94 mmol) and racemic (1R, 2R, 4S)-7-azabicyclo[2.2.1]heptan-2-ol hydrochloride (37 mg, 0.25 mmol). The resulting mixture was allowed to stir at room temperature for 2 h. The crude product was purified by preparative-HPLC under the following conditions: column-Xbridge Jrep shield RP18, 5 nm, 19×150 mm; mobile phase-water with 0.05% $NH_4HCO_3$ and acetonitrile (20% acetonitrile up to 60% in 8 min); detector-UV 254/220 nm. This process afforded 40 mg (26%) of (±)-4-(3-(2-((2R)-2-hydroxy-7-azabicyclo[2.2.1]heptan-7-yl)acetyl)-2-methyl-5-(2-(tetrahydro-2H-pyran-4-yl)ethyl)-1H-pyrrol-1-yl)benzonitrile (9B) as a yellow solid. Mass Spectrum (LCMS, ESI pos.): Calcd. for $C_{27}H_{33}N_3O_3$: 448 (M+H); found 448. $^1$H NMR (300 MHz, DMSO-$d_6$): δ 8.06 (d, J=8.7 Hz, 2H), 7.60 (d, J=8.4 Hz, 2H), 6.51 (s, 1H), 4.66-4.65 (m, 1H), 4.03-4.02 (m, 1H), 3.76-3.72 (m, 2H), 3.54 (s, 2H), 2.26-3.14 (m, 4H), 2.32-2.27 (m, 2H), 2.18 (s, 3H), 1.98-1.96 (m, 2H), 1.75-1.74 (m, 1H), 1.55-1.34 (m, 7H), 1.10-0.95 (m, 2H), 0.81-0.73 (m, 1H).

Using the procedures described in Example 9B, reagents, starting materials, and conditions known to those skilled in the art, the following compounds representative of the present invention were prepared:

| Cpd | Data |
|---|---|
| 153B | (±)-4-(5-0E)-3-(1,3-Dioxoisoindolin-2-yl)prop-1-en-1-yl)-3-(2-((1R,2R,4S)-2-hydroxy-7-azabicyclo[2.2.1]heptan-7-yl)acetyl)-2-methyl-1H-pyrrol-1-yl)benzonitrile<br>Mass Spectrum (LCMS, ESI pos.): Calcd. for $C_{31}H_{28}N_4O_4$: 521 (M + H); found: 521. $^1$H NMR (400 MHz, $CH_3OH-d_4$): δ 7.83-7.81 (m, 6H), 7.40-7.37 (m, 2H), 6.92 (s, 1H), 5.99-5.94 (m, 1H), 5.85-5.81 (m, 1H), 4.86 (s, 2H), 4.32-4.30 (m, 1H), 4.25-4.23 (m, 2H), 3.84-3.78 (m, 1H), 3.48-3.43 (m, 2H), 2.31 (s, 3H), 2.22-2.13 (m, 2H), 1.91-1.90 (m, 1H), 1.72-1.67 (m, 1H), 1.51-1.48 (m, 1H), 1.00-0.97 (m, 1H). |
| 156B | (±)-4-(5-((E)-3-Aminoprop-1-en-1-yl)-3-(2-((1S,2R,4S)-2-hydroxy-7-azabicyclo[2.2.1]heptan-7-yl)acetyl)-2-methyl-1H-pyrrol-1-yl)benzonitrile<br>Mass Spectrum (LCMS, ESI pos.): Calcd. for $C_{23}H_{26}N_4O_2$: 391 (M + H); found: 391. $^1$H NMR (400 MHz, $CH_3OH-d_4$): δ 7.95 (d, J = 6.0 Hz, 2H), 7.47 (d, J = 6.0 Hz, 2H), 6.91 (s, 1H), 6.09-6.00 (m, 1H), 5.93 (d, J = 16 Hz, 1H), 4.33-4.30 (m, 1H), 4.86-4.75 (m, 1H), 3.48-3.45 (m, 1H), 3.43-3.40 (m, 1H), 3.24 (d, J = 4.8 Hz, 2H), 2.32 (s, 3H), 2.22-2.220 (m, 2H), 1.96-1.89 (m, 2H), 1.75-1.63 (m, 1H), 1.45-1.38 (m, 1H), 1.34-1.25 (m, 1H), 0.97-0.94 (m, 1H). |

Example 10B. (±)-4-(3-(2-((2R)-2-Hydroxy-7-azabicyclo[2.2.1]heptan-7-yl)acetyl)-2-methyl-5-(oxetan-3-ylethynyl)-1H-pyrrol-1-yl)benzonitrile (57B)

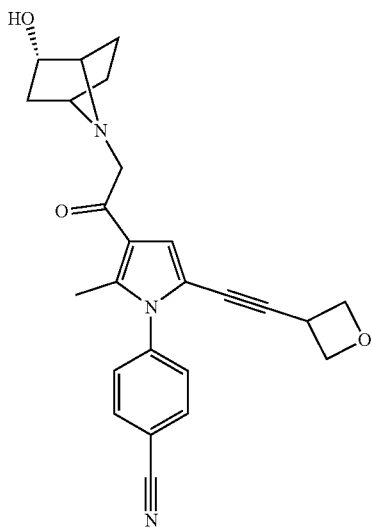

A. 4-(3-Acetyl-2-methyl-5-(oxetan-3-ylethynyl)-1H-pyrrol-1-yl)benzonitrile

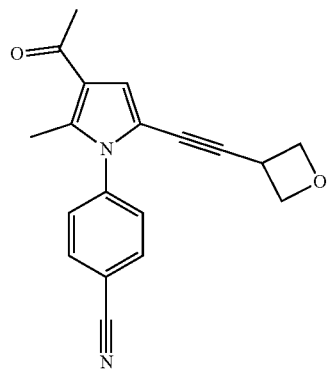

Into a 25 mL sealed tube, being maintained under an atmosphere of nitrogen, was placed a mixture of 4-(3-acetyl-5-iodo-2-methyl-1H-pyrrol-1-yl)benzonitrile (612 mg, 1.75 mmol), 3-ethynyloxetane (715 mg, 8.71 mmol), copper(I) iodide (66 mg, 0.35 mmol), Pd(dppf)$C_{12}$ (509 mg, 0.70 mmol) and triethylamine (5 mL). The resulting mixture was heated at 30° C. for 2 days at 30° C. before being diluted with dichloromethane (50 mL). The reaction mixture was washed with brine (2×20 mL) and then concentrated under vacuum. The remaining residue was purified by column chromatography on silica, using ethyl acetate/petroleum ether (1:10) as the eluant, to afford 315 mg (59%) of 4-(3-acetyl-2-methyl-5-(oxetan-3-ylethynyl)-1H-pyrrol-1-yl)benzonitrile as a yellow oil. Mass Spectrum (LCMS, ESI pos.): Calcd. for $C_{19}H_{16}N_2O_2$: 305 (M+H); found 305.

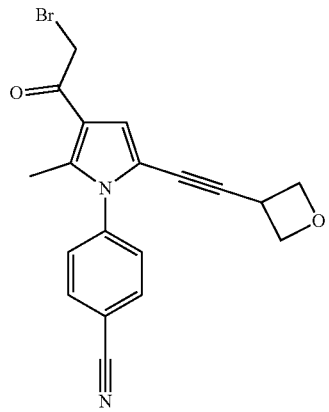 [SMILES: Cc1c(C(=O)CBr)cc(C#CC2COC2)n1-c1ccc(C#N)cc1]

B. 4-(3-(2-Bromoacetyl)-2-methyl-5-(oxetan-3-yl-ethynyl)-1H-pyrrol-1-yl)benzonitrile Into a 50 mL round-bottom flask was placed a solution of 4-(3-acetyl-2-methyl-5-(oxetan-3-ylethynyl)-1H-pyrrol-1-yl)benzonitrile (150 mg, 0.49 mmol) in anhydrous tetrahydrofuran (5 mL). The solution was cooled to 0° C. and then diisopropylethylamine (255 mg, 1.98 mmol) and trimethylsilyl trifluoromethylsulfonate (240 mg) were added to the flask. The mixture was allowed to stir at 0° C. for 1 h and then treated with a solution of N-bromosuccinimide (132 mg, 0.74 mmol) in tetrahydrofuran (1 mL). The reaction mixture was allowed to stir at 0° C. for 0.5 h and then warm to room temperature and stir for an additional 0.5 h. The reaction mixture was diluted with water (50 mL) and then extracted with ethyl acetate (5×50 mL). The combined organic extracts were concentrated under vacuum to afford 180 mg of crude 4-(3-(2-bromoacetyl)-2-methyl-5-(oxetan-3-ylethynyl)-1H-pyrrol-1-yl)benzonitrile as a light yellow solid. Mass Spectrum (LCMS, ESI pos.): Calcd. for $C_{19}H_{15}BrN_2O_2$: 383 (M+H); found 383.

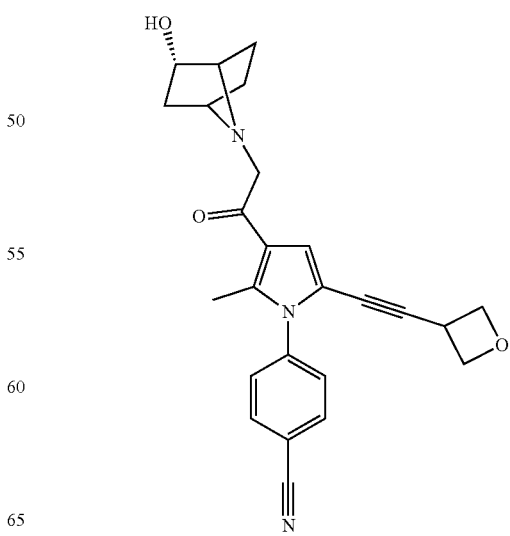

C. (±)-4-(3-(2-((2R)-2-Hydroxy-7-azabicyclo[2.2.1]heptan-7-yl)acetyl)-2-methyl-5-(oxetan-3-ylethynyl)-1H-pyrrol-1-yl)benzonitrile (57B)

Into a 50 mL round-bottom flask was placed a mixture of 4-(3-(2-bromoacetyl)-2-methyl-5-(oxetan-3-ylethynyl)-1H-pyrrol-1-yl)benzonitrile (176 mg, 0.46 mmol), potassium carbonate (329 mg, 2.38 mmol), racemic (1S,2S,4R)-7-azabicyclo[2.2.1]heptan-2-ol (159 mg, 1.07 mmol) in N,N-dimethylformamide (3 mL). The resulting mixture was allowed to stir at room temperature overnight. The solids were filtered from the reaction mixture and the crude product was purified by preparative-HPLC under the following conditions: Column-X Bridge Prep C18 OBD Column, 19*150 mm, 5 μm C-0013; mobile phase-Phase A: Water (10 mmol/L NH$_4$HCO$_3$), Phase B: acetonitrile (23% of B up to 42% in 8 min); Detector-UV 254/220 nm. This process afforded 21 mg (11%) of (±)-4-(3-(2-((2R)-2-Hydroxy-7-azabicyclo[2.2.1]heptan-7-yl)acetyl)-2-methyl-5-(oxetan-3-ylethynyl)-1H-pyrrol-1-yl)benzonitrile (57B) as a white solid. Mass Spectrum (LCMS, ESI pos.): Calcd. for C$_{25}$H$_{25}$N$_3$O$_3$: 416 (M+H); found 416. $^1$H NMR (400 MHz, CH$_3$OH-d$_4$): δ 7.98 (d, J=8.4 Hz, 2H), 7.60 (d, J=8.4 Hz, 2H), 7.03 (s, 1H), 4.90 (s, 2H), 4.79-4.76 (m, 2H), 4.46-4.43 (m, 2H), 4.35-4.31 (m, 1H), 3.96-3.92 (m, 1H), 3.51-3.43 (m, 2H), 2.43 (s, 3H), 2.23-2.13 (m, 2H), 1.94-1.91 (m, 1H), 1.73-1.69 (m, 1H), 1.55-1.49 (m, 1H), 1.02-0.98 (m, 1H).

Example 11B. (±)-4-(5-(2-Cyanoethoxy)methyl)-3-(2-((2R)-2-hydroxy-7-azabicyclo[2.2.1]heptan-7-yl)acetyl)-2-methyl-1H-pyrrol-1-yl)benzonitrile (5B)

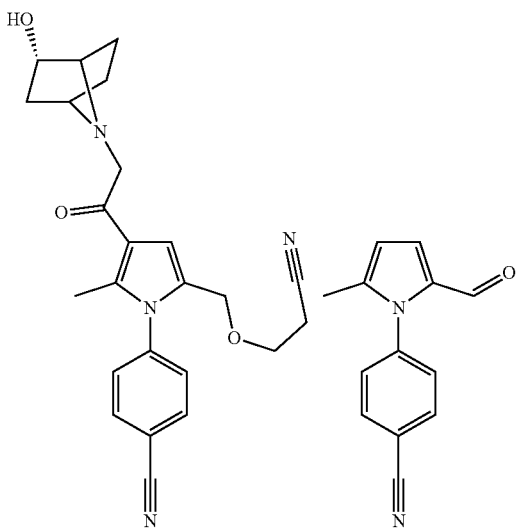

A.
4-(2-Formyl-5-methyl-1H-pyrrol-1-yl)benzonitrile

Into a 250 mL round-bottom flask was placed a solution of 5-methyl-1H-pyrrole-2-carbaldehyde (8 g, 73.4 mmol) in DMF (80 mL). To this solution was added 4-fluorobenzonitrile (17.8 g, 147 mmol) and Cs$_2$CO$_3$ (47.9 g, 147 mmol). The resulting mixture was heated at 120° C. overnight. After cooling to room temperature the reaction mixture was diluted with water (200 mL) and then extracted with ethyl acetate (3×200 mL). The combined organic extracts were washed with brine (3×200 mL), dried over anhydrous sodium sulfate and concentrated under vacuum. The remaining residue was purified by column chromatography on silica gel using ethyl acetate/petroleum ether (1:20) as the eluant to afford 7 g (45%) of 4-(2-formyl-5-methyl-1H-pyrrol-1-yl)benzonitrile as a yellow solid. Mass Spectrum (LCMS, ESI pos.): Calcd. for C$_{13}$H$_{10}$N$_2$O: 211 (M+H); found 211.

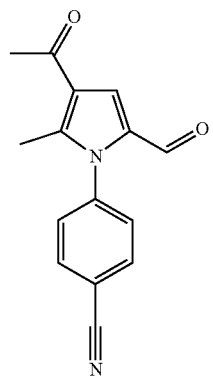 [SMILES: CC(=O)c1cc(C=O)n(-c2ccc(C#N)cc2)c1C]

B. 4-(3-Acetyl-5-formyl-2-methyl-1H-pyrrol-1-yl)benzonitrile

Into a 250 mL round-bottom flask was placed a solution of 4-(2-formyl-5-methyl-1H-pyrrol-1-yl)benzonitrile (7.7 g, 36.7 mmol) in dichloromethane (100 mL). To the solution were added acetic anhydride (5.61 g, 55 mmol) and SnCl$_4$ (20.1 g, 77 mmol). The resulting mixture was allowed to stir at room temperature overnight before being diluted with aqueous sodium carbonate (500 mL). The mixture was extracted with ethyl acetate (3×500 mL) and the combined organic extracts were washed with brine (3×500 mL), dried over Na$_2$SO$_4$ and concentrated. The remaining residue was purified by column chromatography on silica gel using ethyl acetate/petroleum ether (1:1) as the eluant afforded 4 g (43%) of 4-(3-acetyl-5-formyl-2-methyl-1H-pyrrol-1-yl)benzonitrile as a yellow solid. Mass Spectrum (LCMS, ESI pos.): Calcd. for C$_{15}$H$_{12}$N$_2$O$_2$: 253 (M+H); found 253.

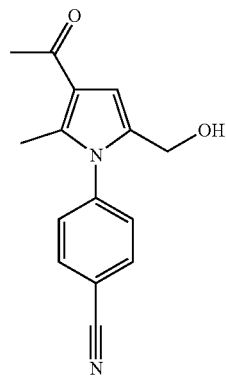 [SMILES: CC(=O)c1cc(CO)n(-c2ccc(C#N)cc2)c1C]

C. 4-(3-Acetyl-5-(hydroxymethyl)-2-methyl-1H-pyrrol-1-yl)benzonitrile

Into a 100 mL round-bottom flask, being maintained under an inert atmosphere of nitrogen, was placed a solution of 4-(3-acetyl-5-formyl-2-methyl-1H-pyrrol-1-yl)benzonitrile (110 mg, 0.4 mmol) in tetrahydrofuran (3 mL). To the solution was added ZnBH$_4$ (32 mg, 0.40 mmol) and the resulting mixture was allowed to stir at room temperature for 1 h. The reaction was diluted with water (100 mL) and then extracted with ethyl acetate (3×100 mL). The combined organic extracts were washed with brine (3×100 mL), dried over anhydrous sodium sulfate, and concentrated under vacuum. The remaining residue was purified by column chromatography on silica gel using ethyl acetate/petroleum ether (1:1) as the eluant to afford 100 mg (90%) of 4-[3-acetyl-5-(hydroxymethyl)-2-methyl-1H-pyrrol-1-yl]benzonitrile as a yellow solid. Mass Spectrum (LCMS, ESI pos.): Calcd. for $C_{15}H_{14}N_2O_2$: 255 (M+H); found 255. $^1$H NMR (300 MHz, CDCl$_3$) δ 7.78 (d, J=8.7 Hz, 2H), 7.31 (d, J=8.7 Hz, 2H), 6.51 (s, 1H), 4.00 (s, 2H), 2.45 (s, 3H), 2.33 (s, 3H).

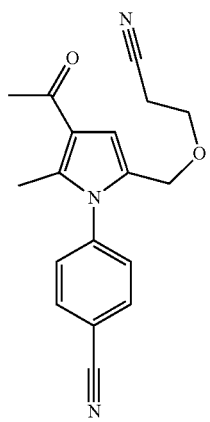 [SMILES: CC(=O)c1cc(COCCC#N)n(-c2ccc(C#N)cc2)c1C]

D. 4-(3-Acetyl-5-((2-cyanoethoxy)methyl)-2-methyl-1H-pyrrol-1-yl)benzonitrile Into a 100 mL round-bottom flask was placed a mixture of 4-[3-acetyl-5-(hydroxymethyl)-2-methyl-1H-pyrrol-1-yl]benzonitrile (300 mg, 1.18 mmol) and 3-bromopropanenitrile (1.58 g, 11.8 mmol) in tetrahydrofuran (20 mL). The mixture was cooled to 0° C. and then sodium hydride (566 mg, 23.58 mmol) was added. The resulting mixture was allowed to stir at room temperature for 5 h and was then diluted with water (100 mL). The mixture was extracted with ethyl acetate (3×100 mL) and the combined organic extracts were washed with brine (3×100 mL), dried over anhydrous sodium sulfate and concentrated under vacuum. The remaining residue was purified by column chromatography on silica gel using ethyl acetate/petroleum ether (1:2) as the eluant to afford 70 mg (19%) of 4-(3-acetyl-5-((2-cyanoethoxy)methyl)-2-methyl-1H-pyrrol-1-yl)benzonitrile as a yellow solid. Mass Spectrum (LCMS, ESI pos.): Calcd. for $C_{18}H_{17}N_3O_2$: 308 (M+H); found 308.

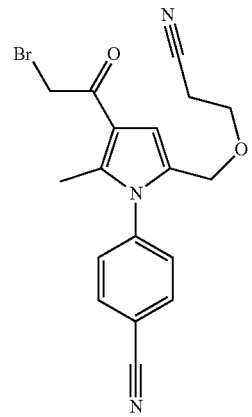 [SMILES: Cc1c(C(=O)CBr)cc(COCCC#N)n1-c1ccc(C#N)cc1]

E. 4-(3-(2-Bromoacetyl)-5-((2-cyanoethoxy)methyl)-2-methyl-1H-pyrrol-1-yl)benzonitrile Into a 100 mL round-bottom flask, being maintained under an inert atmosphere of nitrogen, was placed a solution of 4-(3-acetyl-5-((2-cyanoethoxy)methyl)-2-methyl-1H-pyrrol-1-yl)benzonitrile (70 mg, 0.23 mmol) in tetrahydrofuran (3 mL). To this solution were added diisopropylethylamine (118 mg, 0.91 mmol) and TMSOTf (101 mg, 0.45 mmol). The mixture cooled to 0° C. and allowed to stir for 30 min before 1-bromopyrrolidine-2,5-dione (41 mg, 0.23 mmol) was added. The reaction mixture was allowed to warm to room temperature and stir for 2 h before it was diluted with aqueous sodium thiosulfate (100 mL). The resulting mixture was extracted with ethyl acetate (3×100 mL) and the combined organic extracts were washed with brine (3×100 mL), dried over anhydrous sodium sulfate and concentrated under vacuum. The remaining residue was purified by column chromatography on silica gel using ethyl acetate/petroleum ether (1:4) as the eluant to afford 35 mg (40%) of 4-(3-(2-bromoacetyl)-5-((2-cyanoethoxy)methyl)-2-methyl-1H-pyrrol-1-yl)benzonitrile as a yellow solid. Mass Spectrum (LCMS, ESI pos.): Calcd. for $C_{18}H_{16}BrN_3O_2$: 386 (M+H); found 386.

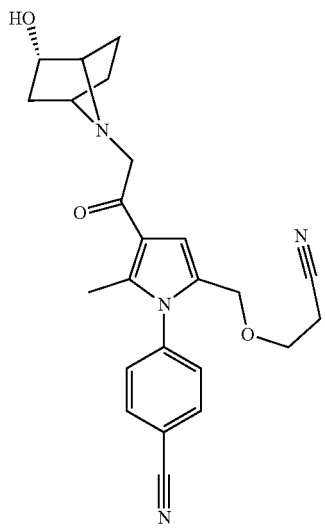 [SMILES: Cc1c(C(=O)CN2C3CCC2[C@@H](O)C3)cc(COCCC#N)n1-c1ccc(C#N)cc1]

F. (±)-4-(5-((2-Cyanoethoxy)methyl)-3-(2-((2R)-2-hydroxy-7-azabicyclo[2.2.1]heptan-7-yl)acetyl)-2-methyl-1H-pyrrol-1-yl)benzonitrile (5B)

Into a 100 mL round-bottom flask was placed a solution of 4-(3-(2-bromoacetyl)-5-((2-cyanoethoxy)methyl)-2-methyl-1H-pyrrol-1-yl)benzonitrile (35 mg, 0.09 mmol) in N,N-dimethylformamide (2 mL). To the solution were added potassium carbonate (62 mg, 0.45 mmol) and (±)-(1R,2S,4S)-7-azabicyclo[2.2.1]heptan-2-ol (41 mg, 0.36 mmol). The resulting mixture was allowed to stir at room temperature overnight. After removing the precipitate, the crude product was purified by preparative-HPLC under the following conditions: Column-XBridge Prep C18 OBD Column 19*100 mm 5 μm C-0013; mobile phase—water with 0.05% $NH_4HCO_3$ and $CH_3CN$ (33.0% $CH_3CN$ up to 67.0% in 10 min, up to 95.0% in 1.5 mn, down to 30.0% in 1.5 min); Detector-UV 254 nm. This process afforded 14 mg (37%) of (±)-4-(5-((2-cyanoethoxy)methyl)-3-(2-((2R)-2-hydroxy-7-azabicyclo[2.2.1]heptan-7-yl)acetyl)-2-methyl-1H-pyrrol-1-yl)benzonitrile (5B) as a white solid. Mass Spectrum (LCMS, ESI pos.): Calcd. for $C_{24}H_{26}N_4O_3$: 419 (M+H); found 419. $^1$H-NMR (400 MHz, methanol-$d_4$)δ 7.96-7.94 (m, 2H), 7.61-7.59 (m, 2H), 6.84 (s, 1H), 4.90 (s, 2H), 4.34-4.31 (m, 1H), 4.27 (s, 2H), 3.84-3.82 (m, 1H), 3.49-3.42 (m, 4H), 2.60 (t, J=6.0 Hz, 2H), 2.36 (s, 3H), 2.23-2.12 (m, 2H), 1.96-1.90 (m, 1H), 1.73-1.69 (m, 1H), 1.54-1.48 (m, 1H), 1.02-0.98 (m, 1H).

Example 12B. (±)-1-(4-Cyanophenyl)-4-(2-((2R)-2-hydroxy-7-azabicyclo[2.2.1]heptan-7-yl)acetyl)-2,5-dimethyl-1H-pyrrole-3-carbonitrile (33B)

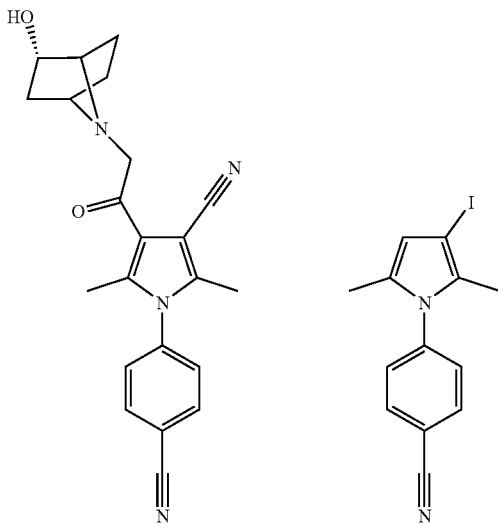

A. 4-(3-Iodo-2,5-dimethyl-1H-pyrrol-1-yl)benzonitrile

Into a 250 mL round-bottom flask was placed a solution of 4-(2,5-dimethyl-1H-pyrrol-1-yl)benzonitrile (4.0 g, 20.38 mmol) in acetonitrile (100 mL). The solution was cooled to 0° C. and then NIS (4.82 g, 21.42 mmol) was added in portions over 10 min. The resulting mixture was allowed to warm to room temperature and stir for 30 min before it was diluted with an aqueous solution of sodium sulfite (150 mL). The resulting mixture was extracted with ethyl acetate (2×200 mL) and the combined organic extracts were washed with brine (2×200 mL), dried over anhydrous sodium sulfate and concentrated under vacuum to afford 6.2 g (94%) of 4-(3-iodo-2,5-dimethyl-1H-pyrrol-1-yl)benzonitrile as a yellow solid. $^1$H NMR (300 MHz, DMSO-$d_6$) δ 8.05-7.98 (m, 2H), 7.56-7.53 (m, 2H), 6.06 (s, 1H), 1.99 (s, 3H), 1.97 (s, 3H).

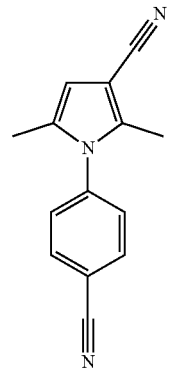

B. 1-(4-Cyanophenyl)-2,5-dimethyl-1H-pyrrole-3-carbonitrile

Into a 25 mL pressure tank, being maintained under an inert atmosphere of nitrogen, was placed a solution of 4-(3-iodo-2,5-dimethyl-1H-pyrrol-1-yl)benzonitrile (322 mg, 1.00 mmol) in dimethylacetamide (2 mL). Then sodium carbonate (106 mg, 1.00 mmol, $K_4[Fe(CN)_6]$ (74 mg, 0.20 mmol) and $Pd(OAc)_2$ (11 mg, 0.05 mmol) were added to the reaction vessel. The resulting mixture was heated at 120° C. overnight. After cooling to room temperature the reaction mixture was diluted with brine and extracted with ethyl acetate (3×50 mL). The combined organic extracts were dried over anhydrous sodium sulfate and concentrated under vacuum. The remaining residue was purified by column chromatography on silica gel, using ethyl acetate/petroleum ether (1:5) as the eluant, to afford 95 mg (43%) of 1-(4-cyanophenyl)-2,5-dimethyl-1H-pyrrole-3-carbonitrile as a yellow solid. Mass Spectrum (LCMS, ESI pos.): Calcd. for $C_{14}H_{11}N_3$: 222 (M+H); found 222. $^1$H NMR (400 MHz, DMSO-$d_6$) δ 8.10-8.07 (m, 2H), 7.67-7.64 (m, 2H), 6.33 (s, 1H), 2.12 (s, 3H), 1.97 (s, 3H).

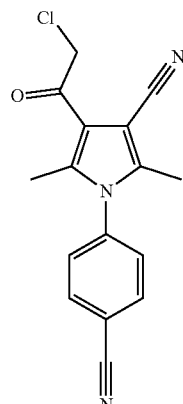

C. 4-(2-Chloroacetyl)-1-(4-cyanophenyl)-2,5-dimethyl-1H-pyrrole-3-carbonitrile Into a 50 mL round-bottom flask, being maintained under an inert atmosphere of nitrogen, was placed a solution of AlCl$_3$ (451 mg, 3.39 mmol) in dichloromethane (3 mL). This solution was cooled to 0° C. and then treated with 2-chloroacetyl chloride (383 mg, 3.39 mmol) in a dropwise manner. The resulting mixture was allowed to stir at 0° C. for 0.5 h and then a solution of 1-(4-cyanophenyl)-2,5-dimethyl-1H-pyrrole-3-carbonitrile (150 mg, 0.68 mmol) in dichloromethane (2 mL) was added to the reaction mixture in a dropwise fashion. The reaction mixture was allowed to stir 0.5 hour at 0° C. and then warm to room temperature and stir for an additional hour. The reaction mixture was diluted with brine and then extracted with dichloromethane (3×50 mL). The combined organic extracts were dried over sodium sulfate and concentrated under vacuum to afford 200 mg (99%) of 4-(2-chloroacetyl)-1-(4-cyanophenyl)-2,5-dimethyl-1H-pyrrole-3-carbonitrile as a yellow solid. Mass Spectrum (LCMS, ESI pos.): Calcd. for C$_{16}$H$_{12}$ClN$_3$O: 298 (M+H); found 298.

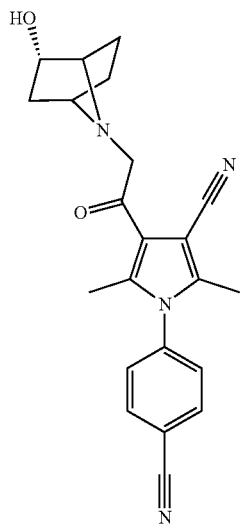 [SMILES: Cc1c(C#N)c(C(=O)CN2C3CCC2[C@@H](O)C3)c(C)n1-c1ccc(C#N)cc1]

D. (i)-1-(4-Cyanophenyl)-4-(2-((2R)-2-hydroxy-7-azabicyclo[2.2.1]heptan-7-yl)acetyl)-2,5-dimethyl-1H-pyrrole-3-carbonitrile (33B)

Into a 50 mL round-bottom flask, being maintained under an inert atmosphere of nitrogen, was placed a solution of 4-(2-chloroacetyl)-1-(4-cyanophenyl)-2,5-dimethyl-1H-pyrrole-3-carbonitrile (200 mg, 0.67 mmol) in N,N-dimethylformamide (2 mL). Then potassium carbonate (139 mg, 1.01 mmol) and (±)-(1R,2R,4S)-7-azabicyclo[2.2.1]heptan-2-ol (121 mg, 0.81 mmol) were added to the flask. The resulting mixture was allowed to stir at room temperature overnight. The precipitate was filtered from the reaction mixture and the filtrate was purified by preparative-HPLC under the following conditions: Column-SunFire C18 OBD Prep Column, 5 μm, 19 mm×250 mm; Mobile phase-Water with 0.05% NH$_4$HCO$_3$ and acetonitrile (30.0% acetonitrile up to 60.0% in 8 min); Detector-UV 254&220 nm. This process afforded 143 mg (57%) of (±)-1-(4-cyanophenyl)-4-(2-((2R)-2-hydroxy-7-azabicyclo[2.2.1]heptan-7-yl)acetyl)-2,5-dimethyl-1H-pyrrole-3-carbonitrile (33B) as a white solid. Mass Spectrum (LCMS, ESI pos.): Calcd. for C$_{22}$H$_{22}$N$_4$O$_2$: 375 (M+H); found 375. $^1$H NMR (400 MHz, DMSO-d$_6$) δ 8.13 (d, J=8.0 Hz, 2H), 7.70 (d, J=8.4 Hz, 2H), 4.70 (d, J=4.0 Hz, 1H), 4.09-4.02 (m, 1H), 3.65-3.55 (m, 2H), 3.23-3.16 (m, 2H), 2.24 (s, 3H), 2.11 (s, 3H), 2.04-1.93 (m, 2H), 1.75 (m, 1H), 1.54-1.48 (m, 1H), 1.38-1.35 (m, 1H), 0.88-0.72 (m, 1H).

Example 13B. (±)-4-(3-(2-((2R)-2-Hydroxy-7-azabicyclo[2.2.1]heptan-7-yl)acetyl)-2-methyl-5-(oxetan-3-ylmethyl)-1H-pyrrol-1-yl)benzonitrile (39B)

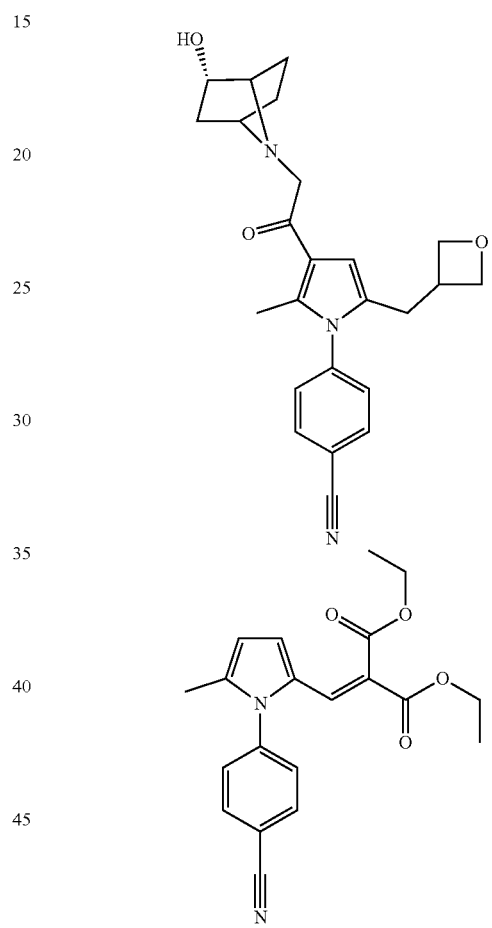

A. Diethyl 2-((1-(4-Cyanophenyl)-5-methyl-1H-pyrrol-2-yl)methylene)malonate Into a 500 mL round-bottom flask, was placed a solution of 4-(2-formyl-5-methyl-1H-pyrrol-1-yl)benzonitrile (2.0 g, 9.51 mmol; from Example 11B) in toluene (200 mL). To the solution were added benzoic acid (128 mg, 1.05 mmol), 1,3-diethyl propanedioate (3.28 g, 20.5 mmol) and piperidine (399 mg, 4.69 mmol). The resulting mixture was heated at 130° C. and then, after cooling to room temperature, was extracted with ethyl acetate (3×50 mL). The combined organic extracts were concentrated under vacuum and the remaining residue was purified by column chromatography on silica, using ethyl acetate/petroleum ether (1:6) as the eluant, to afford 3.83 g of diethyl 2-((1-(4-cyanophenyl)-5-methyl-1H-pyrrol-2-yl)methylene)malonate as a light yellow oil. Mass Spectrum (LCMS, ESI pos.): Calcd. for $C_{20}H_{22}N_2O_4$: 353 (M+H); found 353. $^1$H NMR (300 MHz, CDCl$_3$) δ 8.13-8.08 (m, 2H), 7.62-7.55 (m, 2H), 6.67 (d, J=3.0 Hz, 1H), 6.28 (d, J=3.0 Hz, 1H), 4.33-4.26 (m, 2H), 4.11-4.01 (m, 2H), 3.31 (s, 1H), 2.07 (s, 3H), 1.26 (t, J=6.0 Hz, 3H), 1.22 (t, J=6.0 Hz, 3H).

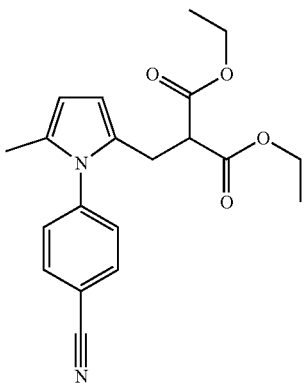 [SMILES: CCOC(=O)C(Cc1ccc(C)n1-c1ccc(C#N)cc1)C(=O)OCC]

B. Diethyl 2-((1-(4-Cyanophenyl)-5-methyl-1H-pyrrol-2-yl)methyl)malonate

Into a 250 mL round-bottom flask was placed a solution of diethyl 2-((1-(4-cyanophenyl)-5-methyl-1H-pyrrol-2-yl)methylene)malonate (3.83 g, 10.9 mmol) in ethyl acetate (200 mL). To the solution was added palladium on carbon (386 mg) and the resulting mixture was sparged with hydrogen. The system was maintained under an atmosphere of hydrogen and allowed to stir at room temperature for 6 h. The solids were then filtered from the reaction mixture and the filtrate was concentrated under vacuum. The remaining residue was purified by column chromatography, using ethyl acetate/petroleum ether (1:11) as the eluant, to afford 2.18 g (57%) of diethyl 2-((1-(4-cyanophenyl)-5-methyl-1H-pyrrol-2-yl)methyl)malonate as a yellow-green oil. Mass Spectrum (LCMS, ESI pos.): Calcd. for $C_{20}H_{22}N_2O_4$: 355 (M+H); found 355. $^1$H NMR (300 MHz, DMSO-d$_6$) δ 7.54-7.51 (m, 2H), 7.22-7.19 (m, 2H), 5.80 (s, 2H), 4.10-3.95 (m, 4H), 3.54-3.49 (m, 1H), 2.83-2.80 (m, 2H), 1.93 (s, 3H), 1.11-1.06 (m, 6H).

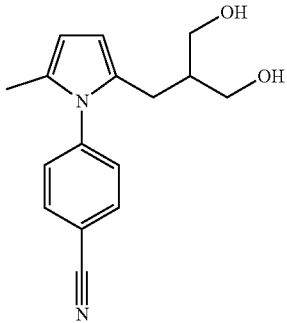 [SMILES: Cc1ccc(CC(CO)CO)n1-c1ccc(C#N)cc1]

C. 4-(2-(3-Hydroxy-2-(hydroxymethyl)propyl)-5-methyl-1H-pyrrol-1-yl)benzonitrile Into a 100 mL round-bottom flask was placed a solution of diethyl 2-((1-(4-cyanophenyl)-5-methyl-1H-pyrrol-2-yl)methyl)malonate (1.04 g, 2.93 mmol) in tetrahydrofuran (30 mL). To the solution was added lithium borohydride (165 mg). The resulting mixture was allowed to stir at room temperature overnight. The reaction mixture was diluted with brine (5 mL) and the aqueous mixture was extracted with ethyl acetate (3×50 mL). The combined organic extracts were concentrated under vacuum and the remaining residue was purified by column chromatography on silica, using ethyl acetate/petroleum ether (1:1) as the eluant, to afford 286 mg of 4-(2-(3-hydroxy-2-(hydroxymethyl)propyl)-5-methyl-1H-pyrrol-1-yl)benzonitrile. Mass Spectrum (LCMS, ESI pos.): Calcd. for $C_{16}H_{18}N_2O_2$: 271 (M+H); found 271.

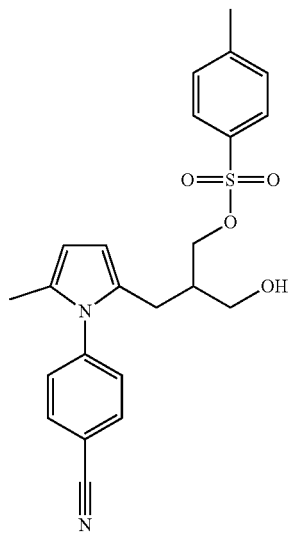 [SMILES: Cc1ccc(S(=O)(=O)OCC(CO)Cc2ccc(C)n2-c2ccc(C#N)cc2)cc1]

D. 3-(1-(4-Cyanophenyl)-5-methyl-1H-pyrrol-2-yl)-2-(hydroxymethyl)propyl-4-methylbenzenesulfonate Into a 250 mL round-bottom flask, being maintained under an atmosphere of nitrogen, was placed a solution of 4-(2-(3-hydroxy-2-(hydroxymethyl)propyl)-5-methyl-1H-pyrrol-1-yl)benzonitrile (1.56 g, 5.75 mmol) in tetrahydrofuran (80 mL). The solution was cooled to 0° C. and then n-BuLi (2.5 M in hexanes, 2.2 mL) was added. The mixture was allowed to stir at the reduced temperature for 0.5 h and was then treated with a solution of tosyl chloride (1.10 g, 5.74 mmol) in tetrahydrofuran (3 mL). The resulting mixture was allowed to stir for an additional 0.5 h at 0° C. before being diluted with a solution of aqueous saturated ammonium chloride. The aqueous mixture was extracted with ethyl acetate (3×50 mL) and the combined organic extracts were concentrated under vacuum. The remaining residue was purified by column chromatography on silica, using ethyl acetate/petroleum ether (1:8) as the eluant, to afford 995 mg (41%) of 3-(1-(4-cyanophenyl)-5-methyl-1H-pyrrol-2-yl)-2-(hydroxymethyl)propyl-4-methylbenzenesulfonate as a yellow oil. Mass Spectrum (LCMS, ESI pos.): Calcd. for $C_{23}H_{24}N_2O_4S$: 425 (M+H); found 425.

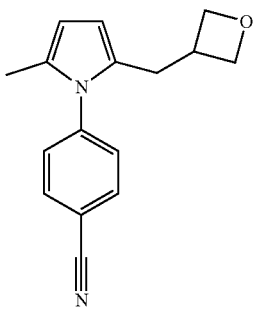 [SMILES: Cc1ccc(CC2COC2)n1-c1ccc(C#N)cc1]

E. 4-(2-Methyl-5-(oxetan-3-ylmethyl)-1H-pyrrol-1-yl)benzonitrile

Into a 100 mL round-bottom flask, was placed a solution of 3-(1-(4-cyanophenyl)-5-methyl-1H-pyrrol-2-yl)-2-(hydroxymethyl)propyl-4-methylbenzenesulfonate (995 mg, 2.34 mmol) in tetrahydrofuran (20 mL). The solution was treated with sodium hydride (160 mg, 6.67 mmol) and the resulting mixture was allowed to stir at room temperature overnight. The reaction mixture was diluted with brine (5 mL) and then extracted with ethyl acetate (3×50 mL). The combined organic extracts were concentrated under vacuum and the remaining residue was purified by column chromatography, using ethyl acetate/petroleum ether (1:8) as the eluant, to afford 420 mg (71%) of 4-(2-Methyl-5-(oxetan-3-ylmethyl)-1H-pyrrol-1-yl)benzonitrile as a yellow oil. Mass Spectrum (LCMS, ESI pos.): Calcd. for $C_{16}H_{16}N_2O$: 253 (M+H); found 253.

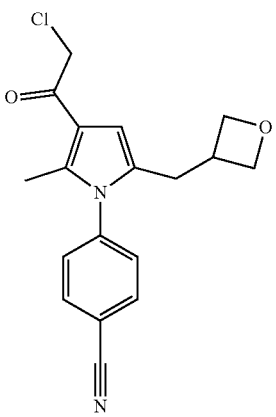 [SMILES: Cc1c(C(=O)CCl)cc(CC2COC2)n1-c1ccc(C#N)cc1]

F. 4-(3-(2-Chloroacetyl)-2-methyl-5-(oxetan-3-ylmethyl)-1H-pyrrol-1-yl)benzonitrile Into a 100 mL round-bottom flask was placed a solution of 3-(1-(4-cyanophenyl)-5-methyl-1H-pyrrol-2-yl)-2-(hydroxymethyl)propyl-4-methylbenzenesulfonate (277 mg, 1.10 mmol) in dichloromethane (30 mL). The solution was cooled to 0° C. and then 2-chloroacetyl chloride (0.25 mL) and diethylaluminum chloride (1M in toluene, 2.44 mL) were added. The resulting mixture was allowed to stir for 6 h at 0° C. before being diluted with brine (5 mL). The pH of the aqueous mixture was adjusted to 8 through the addition of an aqueous, saturated sodium bicarbonate solution, which was then extracted with dichloromethane (3×50 mL). The combined organic extracts were concentrated under vacuum to afford 376 mg crude of 4-(3-(2-chloroacetyl)-2-methyl-5-(oxetan-3-ylmethyl)-1H-pyrrol-1-yl)benzonitrile as a dark red solid. Mass Spectrum (LCMS, ESI pos.): Calcd. for $C_{18}H_{17}ClN_2O_2$: 329 (M+H); found 329.

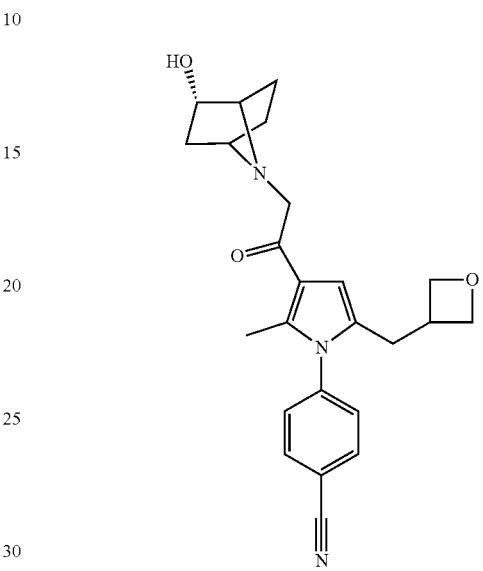

G. (±)-4-(3-(2-((2R)-2-Hydroxy-7-azabicyclo[2.2.1]heptan-7-yl)acetyl)-2-methyl-5-(oxetan-3-ylmethyl)-1H-pyrrol-1-yl)benzonitrile (39B)

Into a 50 mL round-bottom flask was placed a mixture of 4-(3-(2-chloroacetyl)-2-methyl-5-(oxetan-3-ylmethyl)-1H-pyrrol-1-yl)benzonitrile (162 mg, 0.49 mmol), potassium carbonate (369 mg, 2.67 mmol), racemic (1S,2S,4R)-7-azabicyclo[2.2.1]heptan-2-ol hydrochloride (160 mg, 1.07 mmol) and N,N-dimethylformamide (6 mL). The resulting mixture was allowed to stir at room temperature overnight. The precipitate was filtered from the reaction mixture and the filtrate was purified by preparative-HPLC under the following conditions: Column—X Bridge BEH130 Prep C18 OBD Column, 19*150 mm 5 μm C-0013; mobile phase-Phase A Water (10 mmol/L $NH_4HCO_3$), Phase B ACN (30% of B increasing to 40% within 10 min); Detector—UV 254/220 nm. This process afforded 28 mg of (±)-4-(3-(2-((2R)-2-Hydroxy-7-azabicyclo[2.2.1]heptan-7-yl)acetyl)-2-methyl-5-(oxetan-3-ylmethyl)-1H-pyrrol-1-yl)benzonitrile (39B) as a white solid. Mass Spectrum (LCMS, ESI pos.): Calcd. for $C_{24}H_{27}N_3O_3$: 406 (M+H); found 406. $^1$H NMR (300 MHz, DMSO-$d_6$) δ 8.08 (d, J=8.4 Hz, 2H), 7.62 (d, J=8.4 Hz, 2H), 6.42 (s, 1H), 4.69 (d, J=4.2 Hz, 1H), 4.64-4.60 (m, 2H), 4.18-4.14 (m, 2H), 4.06-4.04 (m, 1H), 3.54 (s, 2H), 3.28-3.25 (m, 2H), 3.14-3.06 (m, 1H), 2.63 (d, J=7.8 Hz, 2H), 2.21 (s, 3H), 2.02-1.93 (m, 2H), 1.76-1.71 (m, 1H), 1.59-1.43 (m, 1H), 1.39-1.28 (m, 1H), 0.85-0.75 (m, 1H).

Using the procedures described in Example 13B, reagents, starting materials, and conditions known to those skilled in the art, the following compounds representative of the present invention were prepared:

| Cpd | Data |
|---|---|
| 44B | (±)-4-(3-(2-((1R,2S,4R)-2-Hydroxy-7-azabicyclo[2.2.1]heptan-7-yl)acetyl)-2-methyl-5-((tetrahydro-2H-pyran-4-yl)methyl)-1H-pyrrol-1-yl)benzonitrile<br>Mass Spectrum (LCMS, ESI pos.): Calcd. for $C_{26}H_{31}N_3O_3$: 390 (M + H); found: 390. $^1$H NMR (300 MHz, DMSO-$d_6$): δ 8.07 (d, J = 8.1 Hz, 2H), 7.58 (d, J = 8.1 Hz, 2H), 6.55 (s, 1H), 4.80 (s, 1H), 4.11 (s, 1H), 4.11-3.68 (m, 4H), 3.36 (s, 2H), 3.14 (t, J = 11.4 Hz, 2H), 2.22 (brs, 5H), 2.03 (brs, 2H), 1.80 (brs, 1H), 1.56 (brs, 1H), 1.43-1.01 (m, 4H), 0.99-0.85 (m, 2H), 0.85 (d, J = 11.1 Hz, 1H). |
| 53B | (±)-4-(2-Methyl-3-(2-((1R,2R,4S)-2-methyl-7-azabicyclo[2.2.1]heptan-7-yl)acetyl)-5-(oxetan-3-ylmethyl)-1H-pyrrol-1-yl)benzonitrile<br>Mass Spectrum (LCMS, ESI pos.): Calcd. for $C_{25}H_{29}N_3O_2$: 404 (M + H); found: 404. $^1$H NMR (400 MHz, CDCl$_3$): δ 7.86 (d, J = 8.4 Hz, 2H), 7.35 (d, J = 8.4 Hz, 2H), 6.24 (s, 1H), 4.80 (m, 2H), 4.31-4.28 (m, 2H), 3.71 (s, 2H), 3.41-3.39 (m, 1H), 3.34-3.32 (m, 1H), 3.15-3.11 (m, 1H), 2.68 (d, J = 8.0 Hz, 2H), 2.35-2.30 (m, 4H), 2.14-2.08 (m, 2H), 1.85-1.80 (m, 1H), 1.74-1.64 (m, 2H), 1.33-1.27 (m, 1H), 1.00 (d, J = 6.8 Hz, 3H), 0.75-0.71 (m, 1H).<br>Compounds 53B and 56B were prepared as a mixture and then separated by HPLC under the following conditions. Column, XBridge Prep C18 OBD Column, 19*150 mm 5 μm C-0013; mobile phase, Phase A: Water (10 mmol/L NH$_4$HCO$_3$) Phase B: acetonitirile; Detector, UV 254/220. |
| 54B | 4-(3-(2-(7-Azabicyclo[2.2.1]heptan-7-yl)acetyl)-2-methyl-5-(oxetan-3-ylmethyl)-1H-pyrrol-1-yl)benzonitrile<br>Mass Spectrum (LCMS, ESI pos.): Calcd. for $C_{24}H_{27}N_3O_2$: 434 (M + H); found: 434. $^1$H NMR (400 MHz, DMSO-$d_6$): δ 8.09 (d, J = 8.4 Hz, 2H), 7.62 (d, J = 8.4 Hz, 2H), 6.43 (s, 1H), 4.64-4.60 (m, 2H), 4.18-4.15 (m, 2H), 3.53 (s, 2H), 3.50-3.36 (m, 2H), 3.13-3.06 (m, 1H), 2.68-2.62 (m, 2H), 2.22 (s, 3H), 1.77-1.66 (m, 4H), 1.26-1.24 (m, 4H). |
| 56B | (±)-4-(2-Methyl-3-(2-((1R,2S,4S)-2-methyl-7-azabicyclo[2.2.1]heptan-7-yl)acetyl)-5-(oxetan-3-ylmethyl)-1H-pyrrol-1-yl)benzonitrile<br>Mass Spectrum (LCMS, ESI pos.): Calcd. for $C_{25}H_{29}N_3O_2$: 404 (M + H); found: 404. $^1$H NMR (400 MHz, CDCl$_3$): δ 7.86 (d, J = 8.4 Hz, 2H), 7.36 (d, J = 8.4 Hz, 2H), 6.36 (s, 1H), 4.82-4.78 (m, 2H), 4.31-4.28 (m, 2H), 3.56 (s, 2H), 3.38 (brs, 1H), 3.17-3.10 (m, 1H), 3.07 (brs, 1H), 2.69-2.67 (d, J = 8.0 Hz, 2H), 2.31 (s, 3H), 1.82-1.80 (m, 2H), 1.66-1.61 (m, 1H), 1.53-1.50 (m, 1H), 1.33-1.25 (m, 3H), 1.07 (d, J = 6.8 Hz, 3H).<br>Compounds 53 and 56 were prepared as a mixture and then separated by HPLC under the following conditions. Column, XBridge Prep C18 OBD Column, 19*150 mm 5 μm C-0013; mobile phase, Phase A: Water (10 mmol/L NH$_4$HCO$_3$) Phase B: acetonitirile; Detector, UV 254/220. |

Example 14B. (±)-4-(3-Chloro-2-(4-cyanobutyl)-4-((2R)-2-hydroxy-7-azabicyclo[2.2.1]heptan-7-yl)acetyl)-5-methyl-1H-pyrrol-1-yl)-2-fluorobenzonitrile (40B)

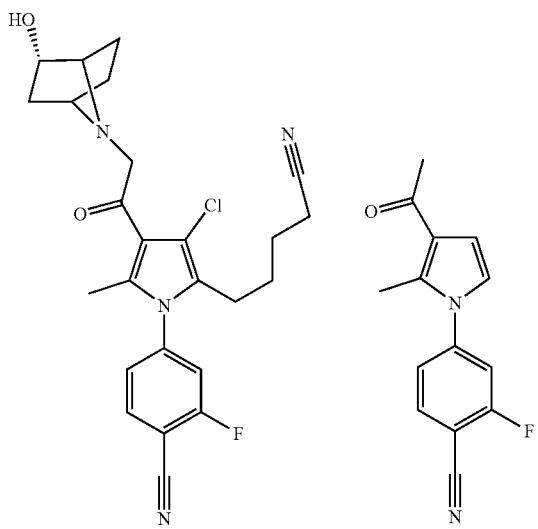 [SMILES: Cc1c(C(=O)CN2C3CCC2[C@@H](O)C3)c(Cl)c(CCCCC#N)n1-c1ccc(C#N)c(F)c1 ; CC(=O)c1ccn(-c2ccc(C#N)c(F)c2)c1C]

A. 4-(3-Acetyl-2-methyl-1H-pyrrol-1-yl)-2-fluorobenzonitrile

Into a 20 mL sealed tube, being maintained under an inert atmosphere of nitrogen, was placed a mixture of 1-(2-methyl-1H-pyrrol-3-yl)ethan-1-one (615 mg, 5.00 mmol), potassium phosphate (2.12 g, 10.0 mmol), 4-bromo-2-fluorobenzonitrile (1.99 g, 10.0 mmol), copper(I) iodide (190 mg, 1.00 mmol), racemic (1S,2S)-cyclohexane-1,2-diamine (228 mg, 2.00 mmol), and 1,4-dioxane (20 mL). The resulting mixture was heated at 110° C. overnight. After cooling to room temperature the reaction mixture was cooled with a water/ice bath and then diluted with brine. The resulting aqueous mixture was extracted with ethyl acetate (3×40 mL). The combined organic extracts were washed with brine (3×30 mL), dried over anhydrous sodium sulfate, and then concentrated under vacuum. The remaining residue was purified by column chromatography on silica, using ethyl acetate/petroleum ether (1:5) as the eluant, to afford 320 mg (26%) of 4-(3-acetyl-2-methyl-1H-pyrrol-1-yl)-2-fluorobenzonitrile as a yellow solid. Mass Spectrum (LCMS, ESI pos.): Calcd. for $C_{14}H_{11}FN_2O$: 243 (M+H); found 243.

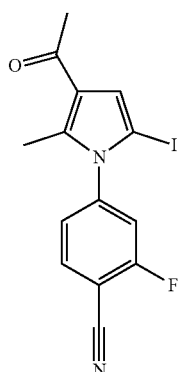 [SMILES: CC(=O)c1cc(I)n(-c2ccc(C#N)c(F)c2)c1C]

B. 4-(3-Acetyl-5-iodo-2-methyl-1H-pyrrol-1-yl)-2-fluorobenzonitrile

Into a 100 mL round-bottom flask, being maintained under an inert atmosphere of nitrogen, was placed a mixture of 4-(3-acetyl-2-methyl-1H-pyrrol-1-yl)-2-fluorobenzonitrile (1.37 g, 5.66 mmol) and N-iodosuccinimide (1.40 g, 6.22 mmol) in dichloromethane (20 mL). The resulting mixture was allowed to stir at room temperature overnight. The reaction mixture was then diluted with dichloromethane (50 mL) and washed with brine (3×15 mL). The organic phase was dried over sodium sulfate and concentrated under reduced pressure. The remaining residue was purified by column chromatography on silica, using ethyl acetate/petroleum ether (1:5) as the eluant, to afford 760 mg (37%) of 4-(3-acetyl-5-iodo-2-methyl-1H-pyrrol-1-yl)-2-fluorobenzonitrile as a white solid. Mass Spectrum (LCMS, ESI pos.): Calcd. for $C_{14}H_{10}FIN_2O$: 368 (M+H); found 368.

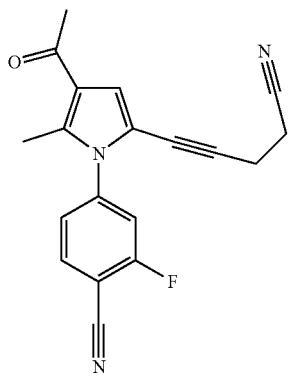 [SMILES: CC(=O)c1cc(C#CCCC#N)n(-c2ccc(C#N)c(F)c2)c1C]

C. 4-(3-Acetyl-5-(4-cyanobut-1-yn-1-yl)-2-methyl-1H-pyrrol-1-yl)-2-fluorobenzonitrile Into a 20 mL sealed tube, being maintained under an inert atmosphere of nitrogen, was placed a mixture of 4-(3-acetyl-5-iodo-2-methyl-1H-pyrrol-1-yl)-2-fluorobenzonitrile (1.34 g, 5.00 mmol), triethylamine (5.05 g, 49.9 mmol), pent-4-ynenitrile (790 mg, 10.0 mmol), copper(I) iodide (190 mg, 1.00 mmol), bis(triphenylphosphine)palladium(II) dichloride (1.40 g, 2.00 mmol), and tetrahydrofuran (20 mL). The resulting mixture was heated at 60° C. overnight. The reaction mixture was then diluted with brine and the resulting aqueous mixture was extracted with ethyl acetate (50 mL). The organic phase was washed with brine (3×15 mL), dried over $Na_2SO_4$ and then concentrated under vacuum. The remaining residue was purified by column chromatography on silica, using ethyl acetate/petroleum ether (1:2) as the eluant, to afford 882 mg (76%) of 4-(3-acetyl-5-(4-cyanobut-1-yn-1-yl)-2-methyl-1H-pyrrol-1-yl)-2-fluorobenzonitrile as yellow oil. Mass Spectrum (LCMS, ESI pos.): Calcd. for $C_{19}H_{14}FN_3O$: 320 (M+H); found 320.

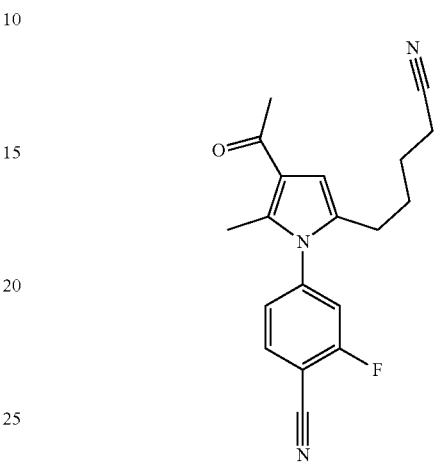

D. 4-(3-Acetyl-5-(4-cyanobutyl)-2-methyl-1H-pyrrol-1-yl)-2-fluorobenzonitrile Into a 50 mL round-bottom flask was placed a solution of 4-(3-acetyl-5-(4-cyanobut-1-yn-1-yl)-2-methyl-1H-pyrrol-1-yl)-2-fluorobenzonitrile (274 mg, 0.86 mmol) in ethyl acetate (20 mL). To the solution was added palladium on carbon (55 mg) and the resulting heterogeneous mixture was sparged with hydrogen. The reaction mixture was allowed to stir at room temperature, under an atmosphere of hydrogen, overnight. The reaction mixture was then diluted with ethyl acetate (50 mL) and filtered. The filtrate was concentrated under vacuum and the remaining residue was purified by column chromatography on silica, using ethyl acetate/petroleum ether (1:1) as the eluant, to afford 172 mg (62%) of 4-(3-acetyl-5-(4-cyanobutyl)-2-methyl-1H-pyrrol-1-yl)-2-fluorobenzonitrile as yellow oil. Mass Spectrum (LCMS, ESI pos.): Calcd. for $C_{19}H_{18}FN_3$: 324 (M+H); found 324.

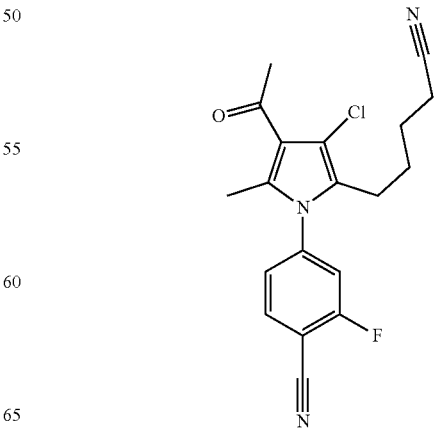

E. 4-(3-Acetyl-4-chloro-5-(4-cyanobutyl)-2-methyl-1H-pyrrol-1-yl)-2-fluorobenzonitrile Into a 100 mL round-bottom flask was placed a solution of 4-(3-acetyl-5-(4-cyanobutyl)-2-methyl-1H-pyrrol-1-yl)-2-fluorobenzonitrile (323 mg, 1.00 mmol) in dichloromethane (30 mL). The solution was cooled to 0° C. and then treated with neat sulfuryl chloride in a dropwise fashion over 5 min. After warming to room temperature, the reaction mixture was allowed to stir overnight. The reaction mixture was diluted with brine and the resulting solution was extracted with dichloromethane (50 mL). The organic phase was washed with brine (3×20 mL) and concentrated under vacuum. The remaining residue was purified by column chromatography on silica, using ethyl acetate/petroleum ether (1:2) as the eluant, to afford 183 mg (51%) of 4-(3-acetyl-4-chloro-5-(4-cyanobutyl)-2-methyl-1H-pyrrol-1-yl)-2-fluorobenzonitrile as a light yellow oil. Mass Spectrum (LCMS, ESI pos.): Calcd. for $C_{19}H_{17}ClFN_3O$: 358 (M+H); found 358.

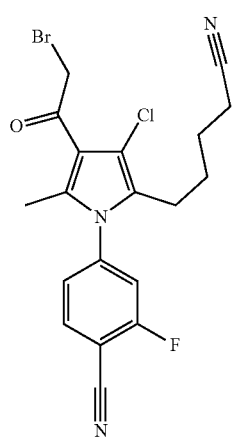 [SMILES: Cc1c(C(=O)CBr)c(Cl)c(CCCCC#N)n1-c1ccc(C#N)c(F)c1]

F. 4-(3-(2-Bromoacetyl)-4-chloro-5-(4-cyanobutyl)-2-methyl-1H-pyrrol-1-yl)-2-fluorobenzonitrile Into a 50 mL round-bottom flask, being maintained under an inert atmosphere of nitrogen, was placed a mixture of 4-(3-acetyl-4-chloro-5-(4-cyanobutyl)-2-methyl-1H-pyrrol-1-yl)-2-fluorobenzonitrile (183 mg, 0.51 mmol), diisopropylethylamine (199 mg, 1.54 mmol) and tetrahydrofuran (10 mL). The reaction vessel was cooled to 0° C. and then neat TMSOTf (218 mg) at 0° C. The reaction mixture was allowed to stir for 1 h at 0° C. and then solid N-bromosuccinimide (110 mg, 0.62 mmol) was added to the flask. The reaction mixture was allowed to warm to room temperature and stir for 4 h. The reaction mixture was diluted with ethyl acetate (50 mL) and then washed with brine (3×20 mL). The organic phase was dried over $Na_2SO_4$ and concentrated under vacuum. The remaining residue was purified by column chromatography on silica gel, using ethyl acetate/petroleum ether (1:3) as the eluant, to afford 360 mg of semi-crude 4-(3-(2-bromoacetyl)-4-chloro-5-(4-cyanobutyl)-2-methyl-1H-pyrrol-1-yl)-2-fluorobenzonitrile as a yellow solid. Mass Spectrum (LCMS, ESI pos.): Calcd. for $C_{19}H_{16}BrClFN_3$: 436 (M+H); found 436.

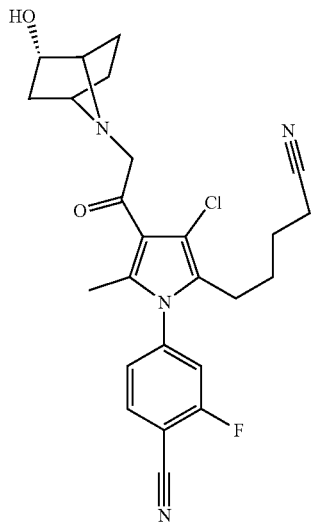 [SMILES: Cc1c(C(=O)CN2C3CCC2[C@@H](O)C3)c(Cl)c(CCCCC#N)n1-c1ccc(C#N)c(F)c1]

G. (±)-4-(3-Chloro-2-(4-cyanobutyl)-4-(2-((2R)-2-hydroxy-7-azabicyclo[2.2.1]heptan-7-yl)acetyl)-5-methyl-1H-pyrrol-1-yl)-2-fluorobenzonitrile (40B)

Into a 50 mL round-bottom flask, being maintained under an inert atmosphere of nitrogen, was placed a mixture of 4-(3-(2-bromoacetyl)-4-chloro-5-(4-cyanobutyl)-2-methyl-1H-pyrrol-1-yl)-2-fluorobenzonitrile (228 mg, 0.52 mmol), potassium carbonate (144 mg, 1.04 mmol), 5-amino-2-chlorocyclohexan-1-ol (138 mg, 0.92 mmol), and N,N-dimethylformamide (5 mL). The resulting mixture was allowed to stir at room temperature overnight, after which the solids were filtered from the mixture. The crude product was purified by preparative-HPLC under the following conditions: Column—X Bridge Prep C18 OBD Column, 5 μm, 19*150 nm; mobile phase—$H_2O$ (10 mmol/L $NH_4HCO_3$) and acetonitrile (30% acetonitrile up to 60% in 10 min); Detector—UV 254 nm. This process afforded in 32 mg (13%) of (±)-4-(3-chloro-2-(4-cyanobutyl)-4-(2-((2R)-2-hydroxy-7-azabicyclo[2.2.1]heptan-7-yl)acetyl)-5-methyl-1H-pyrrol-1-yl)-2-fluorobenzonitrile (40B) as a white solid. Mass Spectrum (LCMS, ESI pos.): Calcd. for $C_{25}H_{26}ClFN_4O_2$: 469 (M+H); found 469. $^1$H NMR (400 MHz, DMSO-$d_6$) δ 8.17-8.13 (m, 1H), 7.85-7.81 (m, 1H), 7.52-7.50 (m, 1H), 4.67 (d, J=3.6 Hz, 1H), 4.06-3.98 (m, 1H), 3.67 (s, 2H), 3.23-3.22 (m, 2H), 2.48-2.43 (m, 2H), 2.35-2.32 (m, 2H), 2.17 (s, 3H), 2.02-1.95 (m, 2H), 1.77-1.65 (m, 1H), 1.51-1.41 (m, 1H), 1.39-1.21 (m, 5H), 0.82-0.75 (m, 1H).

Example 15B. (±)-4-(3-(2-((2R)-2-Hydroxy-7-azabicyclo[2.2.1]heptan-7-yl)acetyl)-2-methyl-5-((2-methylthiazol-4-yl)methyl)-1H-pyrrol-1-yl)benzonitrile (41B)

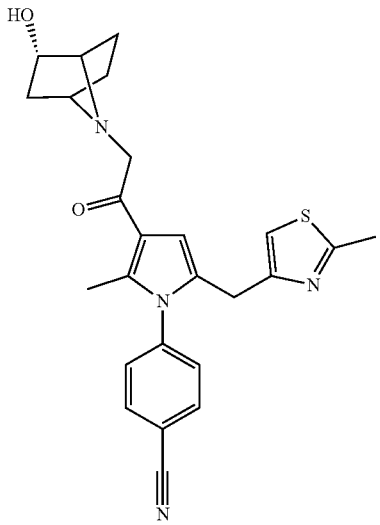

A. 4-(2-(1-Hydroxyprop-2-yn-1-yl)-5-methyl-1H-pyrrol-1-yl)benzonitrile

Into a 250 mL round-bottom flask, being maintained under an inert atmosphere of nitrogen, was placed a solution of 4-(2-formyl-5-methyl-1H-pyrrol-1-yl)benzonitrile (4.0 g, 19.0 mmol; from Example 11B) in tetrahydrofuran (30 mL). The solution was cooled to 0° C. and then treated with a solution of bromo(ethynyl)magnesium (2.6 g, 20.1 mmol) in tetrahydrofuran (20 mL). The resulting mixture was allowed to stir at 0° C. for 2 h, before being diluted with aqueous ammonium chloride (50 mL). The aqueous mixture was extracted with dichloromethane (3×100 mL) and the combined organic extracts were dried over sodium sulfate. The organic phase was concentrated under vacuum to afford 4.0 g (89%) of 4-(2-(1-hydroxyprop-2-yn-1-yl)-5-methyl-1H-pyrrol-1-yl)benzonitrile as a brown oil. Mass Spectrum (LCMS, ESI pos.): Calcd. for $C_{15}H_{12}N_2O$: 237 (M+H); found 237.

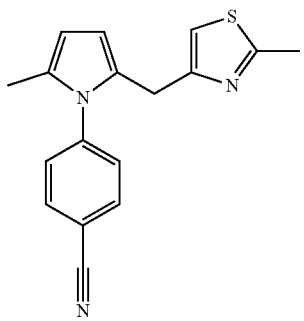

B. 4-(2-Methyl-5-((2-methylthiazol-4-yl)methyl)-1H-pyrrol-1-yl)benzonitrile

Into a 100 mL round-bottom flask was placed a solution of 4-(2-(1-hydroxyprop-2-yn-1-yl)-5-methyl-1H-pyrrol-1-yl)benzonitrile (4.0 g, 16.9 mmol) in chlorobenzene (50 mL). To the solution were added ethanethioamide (1.52 g, 20.2 mmol) and silver(I) trifluoromethanesulfonate (440 mg, 1.71 mmol). The resulting mixture was heated at 130° C. for 3 h. After being allowed to cool to room temperature the reaction mixture was concentrated under vacuum and the remaining material was dissolved in dichloromethane (100 mL). The resulting mixture was washed with water (2×100 mL) and then the organic phase was concentrated under vacuum. The remaining residue was purified by column chromatography on silica, using ethyl acetate/hexane (1:20 to 1:15) as the eluant, to afford 3.0 g (60%) of 4-(2-methyl-5-((2-methylthiazol-4-yl)methyl)-1H-pyrrol-1-yl)benzonitrile as a black oil. Mass Spectrum (LCMS, ESI pos.): Calcd. for $C_{17}H_{15}N_3S$: 294 (M+H); found 294. $^1$H NMR (300 MHz, CDCl$_3$): δ 7.69-7.65 (m, 2H), 7.25-7.21 (m, 2H), 6.44 (s, 1H), 6.03-6.01 (m, 1H), 5.97-5.96 (m, 1H), 3.83 (s, 2H), 2.59 (s, 3H), 2.00 (s, 3H).

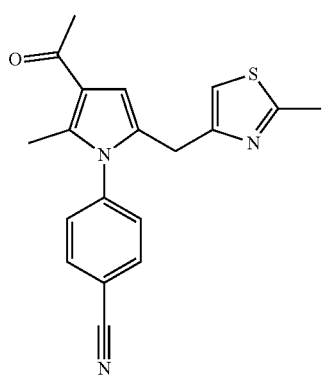 [SMILES: CC(=O)c1cc(Cc2csc(C)n2)n(-c2ccc(C#N)cc2)c1C]

C. 4-(3-Acetyl-2-methyl-5-((2-methylthiazol-4-yl)methyl)-1H-pyrrol-1-yl)benzonitrile Into a 100 mL, 3-necked, round-bottom flask, being maintained under an inert atmosphere of nitrogen, was placed a solution of 4-(2-methyl-5-((2-methylthiazol-4-yl)methyl)-1H-pyrrol-1-yl)benzonitrile (1.0 g, 3.41 mmol) in dichloromethane (10 mL). The solution was cooled to 0° C. and was then treated with a solution of diethylaluminum chloride in toluene (25% wt, 7.5 mL) in a dropwise fashion over 2 min. The mixture was allowed to stir for 30 min at 0° C. and then a solution of acetyl chloride (534 mg, 6.80 mmol) in dichloromethane (10 mL) was added dropwise over 2 min. The reaction mixture was allowed to warm to room temperature and stir for 12 h. The reaction mixture was ice-cold water (50 mL) and the resulting mixture was extracted with dichloromethane (2×50 mL). The combined organic extracts were dried over anhydrous sodium sulfate and then concentrated under vacuum. The remaining residue was purified by preparative-TLC (petroleum ether/ethyl acetate=2:1) to afford 0.7 g (61%) of 4-(3-acetyl-2-methyl-5-((2-methylthiazol-4-yl)methyl)-1H-pyrrol-1-yl)benzonitrile as a black oil. Mass Spectrum (LCMS, ESI pos.): Calcd. for $C_{19}H_{17}N_3OS$: 336 (M+H); found 336. $^1$H NMR (400 MHz, CDCl$_3$): δ 7.80-7.72 (m, 2H), 7.30-7.22 (m, 2H), 6.48 (dd, J=3.9, 1.0 Hz, 2H), 3.83 (s, 2H), 2.65 (d, J=1.4 Hz, 3H), 2.45 (s, 3H), 2.31 (s, 3H).

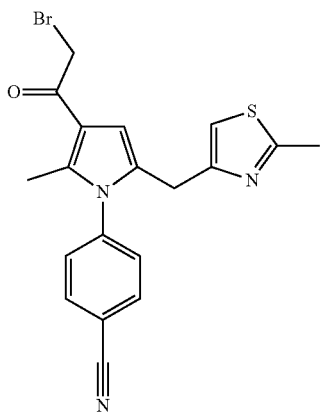 [SMILES: Cc1nc(Cc2cc(C(=O)CBr)c(C)n2-c2ccc(C#N)cc2)cs1]

D. 4-(3-(2-Bromoacetyl)-2-methyl-5-((2-methylthiazol-4-yl)methyl)-1H-pyrrol-1-yl)benzonitrile Into a 50 mL, 3-necked, round-bottom flask, being maintained under an inert atmosphere of nitrogen, was placed a mixture of 4-(3-Acetyl-2-methyl-5-((2-methylthiazol-4-yl)methyl)-1H-pyrrol-1-yl)benzonitrile (150 mg, 0.45 mmol), diisopropylethylamine (231 mg), and tetrahydrofuran (10 mL). The mixture was cooled to 0° C. a solution of TMSOTf (149 mg, 1.50 equiv) in tetrahydrofuran (2 mL). The resulting mixture was allowed to stir for 30 min at 0° C. and was then treated with a solution of N-bromosuccinimide (96 mg, 0.54 mmol) in tetrahydrofuran (2 mL). The reaction mixture was allowed to stir at 0° C. for 1 h before being diluted with ice water (50 mL). The aqueous mixture was extracted with dichloromethane (3×30 mL) and the combined organic extracts were dried over anhydrous sodium sulfate. Concentrating the organic phase under vacuum afford 150 mg (81%) of crude 4-(3-(2-Bromoacetyl)-2-methyl-5-((2-methylthiazol-4-yl)methyl)-1H-pyrrol-1-yl)benzonitrile as a brown oil, which was used in without further purification. Mass Spectrum (LCMS, ESI pos.): Calcd. for $C_{19}H_{16}BrN_3OS$: 414 (M+H); found 414.

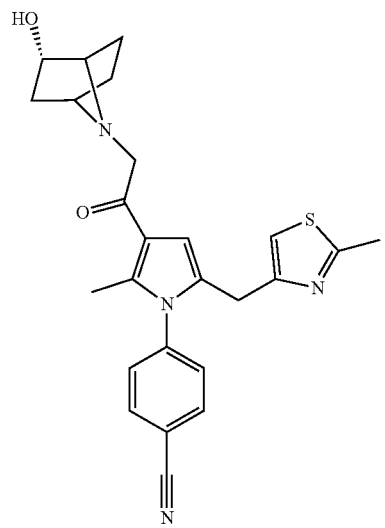 [SMILES: Cc1nc(Cc2cc(C(=O)CN3C4CCC3[C@@H](O)C4)c(C)n2-c2ccc(C#N)cc2)cs1]

E. (±)-4-(3-(2-((2R)-2-Hydroxy-7-azabicyclo[2.2.1]heptan-7-yl)acetyl)-2-methyl-5-((2-methylthiazol-4-yl)methyl)-1H-pyrrol-1-yl)benzonitrile (41B)

Into a 25 mL round-bottom flask was placed a solution of 4-(3-(2-bromoacetyl)-2-methyl-5-((2-methylthiazol-4-yl)methyl)-1H-pyrrol-1-yl)benzonitrile (150 mg, 0.36 mmol) in N,N-dimethylformamide (3 mL). To the solution were then added potassium carbonate (150 mg, 1.09 mmol) and racemic (1S,2S,4R)-7-azabicyclo[2.2.1]heptan-2-ol hydrochloride (65 mg, 0.43 mmol). The resulting mixture was allowed to stir for 13 h at room temperature before it was concentrated under vacuum. The remaining residue was purified by preparative-TLC (dichloromethane/methanol=9:1) to afford 90 mg (56%) of (±)-4-(3-(2-((2R)-2-hydroxy-7-azabicyclo[2.2.1]heptan-7-yl)acetyl)-2-methyl-5-((2-methylthiazol-4-yl)methyl)-1H-pyrrol-1-yl)benzonitrile (41B) as a light yellow solid. Mass Spectrum (LCMS, ESI pos.): Calcd. for $C_{25}H_{26}N_4O_2S$: 447 (M+H); found 447. $^1$H NMR (300 MHz, DMSO-d$_6$): δ 7.93 (d, J=8.3 Hz, 2H), 7.43 (d, J=8.3 Hz, 2H), 6.66 (s, 1H), 6.54 (s, 1H), 4.79 (s, 1H), 4.08 (d, J=9.6 Hz, 1H), 3.75 (s, 2H), 3.67 (s, 2H), 3.34 (s, 2H), 2.49 (s, 3H), 2.18 (s, 3H), 2.11-1.92 (m, 2H), 1.76 (s, 1H), 1.53 (s, 1H), 1.34 (s, 1H), 0.94-0.71 (m, 1H).

Example 16B. (±)-4-(3-Bromo-4-(2-((2R)-2-hydroxy-7-azabicyclo[2.2.1]heptan-7-yl)acetyl)-5-methyl-2-((2-methylthiazol-4-yl)methyl)-1H-pyrrol-1-yl)benzonitrile (129B)

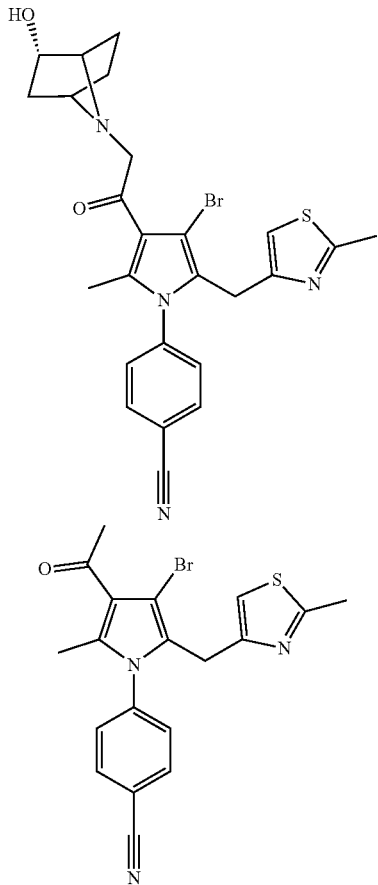

A. 4-(3-Acetyl-4-bromo-2-methyl-5-((2-methylthiazol-4-yl)methyl)-1H-pyrrol-1-yl)benzonitrile Into a 100 mL round-bottom flask was placed a solution of 4-(3-acetyl-2-methyl-5-((2-methylthiazol-4-yl)methyl)-1H-pyrrol-1-yl)benzonitrile (360 mg, 1.07 mmol, from Example 15B) in dichloromethane (10 mL). To this was added N-bromosuccinimide (192 mg, 1.08 mmol) and then resulting mixture was allowed to stir at room temperature for 3 h. The reaction mixture was diluted with water (10 mL) and then extracted with dichloromethane (3×10 mL). The combined organic extracts were dried over anhydrous sodium sulfate and then concentrated under vacuum. The remaining residue was purified by column chromatography on silica, using ethyl acetate/petroleum ether (1:1) as the eluant, to afford 270 mg (61%) of 4-(3-acetyl-4-bromo-2-methyl-5-((2-methylthiazol-4-yl)methyl)-1H-pyrrol-1-yl)benzonitrile as a light yellow solid. Mass Spectrum (LCMS, ESI pos.): Calcd. for $C_{19}H_{16}BrN_3OS$: 414 (M+H); found 414. $^1$H NMR (400 MHz, $CH_3OH-d_4$): δ 7.86-7.82 (m, 2H), 7.41-7.35 (m, 2H), 6.63 (s, 1H), 3.95 (s, 2H), 2.65 (s, 3H), 2.59 (s, 3H), 2.25 (s, 2H).

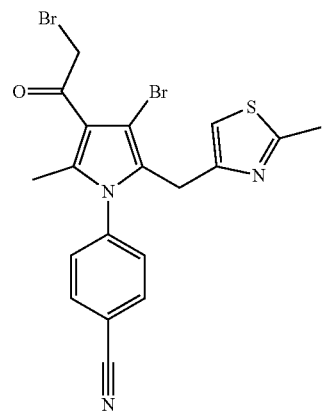 [SMILES: Cc1nc(Cc2c(Br)c(C(=O)CBr)c(C)n2-c2ccc(C#N)cc2)cs1]

B. 4-(3-Bromo-4-(2-bromoacetyl)-5-methyl-2-((2-methylthiazol-4-yl)methyl)-1H-pyrrol-1-yl)benzonitrile Into a 100 mL 3-necked round-bottom flask, being maintained under an inert atmosphere of nitrogen, was placed a mixture of 4-(3-acetyl-4-bromo-2-methyl-5-((2-methylthiazol-4-yl)methyl)-1H-pyrrol-1-yl)benzonitrile (272 mg, 0.66 mmol), diisopropylethylamine (339 mg, 2.62 mmol) and tetrahydrofuran (10 mL). The mixture was cooled to 0° C. and then treated with trimethylsilyl trifluoromethanesulfonate (292 mg, 1.31 mmol) in a dropwise manner. The resulting mixture was allowed to stir at 0° C. for 1 h and then solid N-bromosuccinimide (129 mg, 0.72 mmol) was added to the flask. The reaction mixture was allowed to warm to room temperature and stir for 20 min before it was diluted with water (10 mL). The aqueous mixture was extracted with ethyl acetate (3×15 mL) and the combined organic extracts were dried over anhydrous sodium sulfate. The organic phase was concentrated under vacuum to afford 200 mg (62%) of 4-(3-bromo-4-(2-bromoacetyl)-5-methyl-2-((2-methylthiazol-4-yl)methyl)-1H-pyrrol-1-yl)benzonitrile as a light yellow solid. Mass Spectrum (LCMS, ESI pos.): Calcd. for $C_{19}H_{15}Br_2N_3OS$: 493 (M+H); found 493.

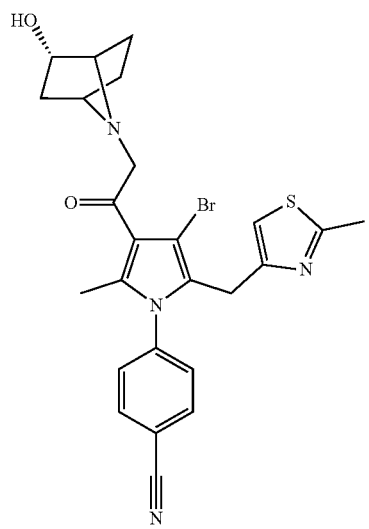 [SMILES: Cc1nc(Cc2c(Br)c(C(=O)CN3C4CCC3[C@@H](O)C4)c(C)n2-c2ccc(C#N)cc2)cs1]

C. (±)-4-(3-Bromo-4-(2-((2R)-2-hydroxy-7-azabicyclo[2.2.1]heptan-7-yl)acetyl)-5-methyl-2-((2-methylthiazol-4-yl)methyl)-1H-pyrrol-1-yl)benzonitrile (129B)

Into a 100 mL round-bottom flask was placed a solution of 4-(3-bromo-4-(2-bromoacetyl)-5-methyl-2-((2-methylthiazol-4-yl)methyl)-1H-pyrrol-1-yl)benzonitrile (200 mg, 0.41 mmol) in N,N-dimethylformamide (5 mL). To the solution were added potassium carbonate (224 mg, 1.62 mmol) and racemic (1S,2S,4R)-7-azabicyclo[2.2.1]heptan-2-ol hydrochloride (92 mg, 0.61 mmol). The resulting mixture was allowed to stir at room temperature overnight. The crude product was purified by preparative-HPLC under the following conditions: Column-X Bridge Shield RP18 OBD Column, 5 μm, 19*150 mm; mobile phase-Water (0.05% trifluoroacetic acid) and acetonitrile (15% acetonitrile up to 50% in 8 min); Detector-UV 254 nm. This process afforded 23 mg (11%) of (±)-4-(3-bromo-4-(2-((2R)-2-hydroxy-7-azabicyclo[2.2.1]heptan-7-yl)acetyl)-5-methyl-2-((2-methylthiazol-4-yl)methyl)-1H-pyrrol-1-yl)benzonitrile (129B) as a white solid. Mass Spectrum (LCMS, ESI pos.): Calcd. for $C_{25}H_{25}BrN_{42}S$: 525 (M+H); found 525. $^1H$ NMR (400 MHz, DMSO-$d_6$): δ 7.94 (d, J=8.4 Hz, 2H), 7.47 (d, J=8.4 Hz, 2H), 6.64 (s, 1H), 4.75-4.65 (m, 1H), 4.10-4.02 (m, 1H), 3.82 (s, 2H), 3.75-3.65 (m, 2H), 3.30-3.28 (m, 2H), 2.48 (s, 3H), 2.15 (s, 3H), 2.05-1.94 (m, 2H), 1.80-1.71 (m, 1H), 1.60-1.45 (m, 1H), 1.38-1.32 (m, 1H), 0.81-0.75 (m, 1H).

Using the procedures described in Example 16B, reagents, starting materials, and conditions known to those skilled in the art, the following compounds representative of the present invention were prepared:

| Cpd | Data |
|---|---|
| 128B | (±)-4-(3-Chloro-4-(2-((2R)-2-hydroxy-7-azabicyclo[2.2.1]heptan-7-yl)acetyl)-5-methyl-2-((2-methylthiazol-4-yl)methyl)-1H-pyrrol-1-yl)benzonitrile<br>Mass Spectrum (LCMS, ESI pos.): Calcd. for $C_{25}H_{25}ClN_4O_2S$: 481 (M + H); found: 481. $^1H$ NMR (400 MHz, $CH_3OH$-$d_4$): δ 7.87 (d, J = 8.4 Hz, 2H), 7.37 (d, J = 8.4 Hz, 2H), 6.63 (s, 1H), 4.80-4.71 (m, 2H), 4.68-4.63 (m, 1H), 4.25-4.19 (m, 2H), 3.96 (s, 2H), 2.69-2.54 (m, 2H), 2.62 (s, 3H), 2.34 (s, 3H), 2.24-2.14 (m, 1H), 2.07-1.97 (m, 2H), 1.60-1.54 (m, 1H). |

Example 17B. (±)-4-(5-(((1r,3R)-3-Cyanocyclobutyl)methyl)-3-(2-((2R)-2-hydroxy-7-azabicyclo[2.2.1]heptan-7-yl)acetyl)-2-methyl-1H-pyrrol-1-yl)benzonitrile (45B)

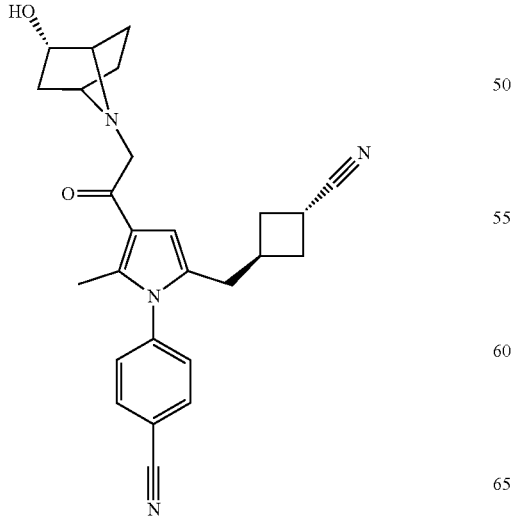

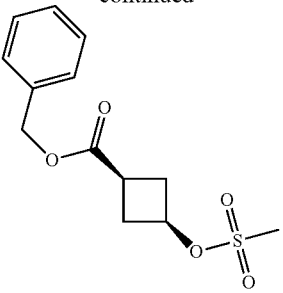

-continued

A. Benzyl (1s,3s)-3-((methylsulfonyl)oxy)cyclobutane-1-carboxylate

Into a 100 mL round-bottom flask was placed a mixture of (1s,3s)-benzyl 3-hydroxycyclobutanecarboxylate (5.0 g, 24.2 mmol), triethylamine (4.9 g, 48.5 mmol), and dichloromethane (50 mL). The mixture was cooled to 0° C. and then a solution of methanesulfonyl chloride (3.33 g, 29.1 mmol) in dichloromethane (10 mL) was added in a dropwise fashion. The resulting mixture was allowed to warm to room temperature and stir for 2 h. The reaction mixture was diluted with water (100 mL) and then extracted with dichloromethane (2×50 mL). The combined organic extracts were concentrated under vacuum to afford 6.0 g (87%) of benzyl (1s,3s)-3-((methylsulfonyl)oxy)cyclobutane-1-carboxylate as a colorless oil. ¹H NMR (300 MHz, CDCl₃): δ 7.26-7.24 (m, 5H), 5.01 (s, 2H), 4.83-4.80 (m, 1H), 3.05 (s, 3H), 2.84-2.62 (m, 1H), 2.64-2.48 (m, 2H), 2.34-2.18 (m, 2H).

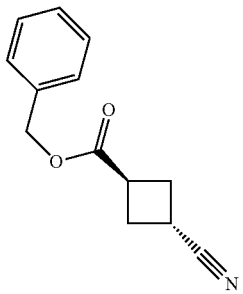 [SMILES: N#C[C@H]1C[C@H](C(=O)OCc2ccccc2)C1]

B. Benzyl (1r,3r)-3-cyanocyclobutane-1-carboxylate

Into a 100 ml round-bottom flask was placed a solution of benzyl (1s,3s)-3-((methylsulfonyl)oxy)cyclobutane-1-carboxylate (6.0 g, 21.1 mmol) in N,N-dimethylformamide (50 mL). To the solution were then added sodium cyanide (2.07 g, 42.2 mmol) and 15-crown-5 (464 mg). The reaction mixture was heated at 80° C. for 14 h and then allowed to cool to room temperature. The reaction mixture was diluted with an aqueous saturated solution of FeSO₄ and then extracted with dichloromethane (2×100 mL). The combined organic extracts were concentrated under vacuum and the remaining residue was purified by column chromatography on silica, using ethyl acetate/hexane (1:20 to 1:10) as the eluant, to afford 2.0 g (44%) of benzyl (1r,3r)-3-cyanocyclobutane-1-carboxylate as a light yellow liquid. ¹H NMR (400 MHz, CDCl₃): δ 7.46-7.27 (m, 5H), 5.14 (s, 2H), 3.48-3.15 (m, 2H), 2.83-2.53 (m, 4H).

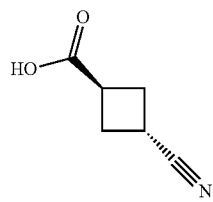

C. (1r,3r)-3-Cyanocyclobutane-1-carboxylic acid

Into a 100 mL round-bottom flask was placed a solution of benzyl (1r,3r)-3-cyanocyclobutane-1-carboxylate (2.0 g, 9.29 mmol) in ethyl acetate (30 mL). To the solution was added palladium on carbon (300 mg). The resulting mixture was sparged with hydrogen and then allowed to stir at room temperature for 12 h under an atmosphere of hydrogen. The solids were filtered from the reaction mixture and the filtrate was concentrated under vacuum to afford 1.0 g (86%) of (1r,3r)-3-cyanocyclobutane-1-carboxylic acid as a colorless liquid.

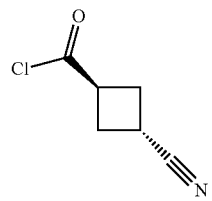

D. (1r,3r)-3-Cyanocyclobutane-1-carbonyl chloride

Into a 50 mL round-bottom flask was placed a solution of (1r,3r)-3-cyanocyclobutane-1-carboxylic acid (1.0 g, 7.99 mmol) in dichloromethane (10 mL). To the solution were added N,N-dimethylformamide (100 mg, 1.37 mmol) and oxalyl dichloride (2.03 g). The resulting mixture was allowed to stir at room temperature for 2 h before it was concentrated under vacuum to afford 1.0 g (87%) of (1r,3r)-3-cyanocyclobutane-1-carbonyl chloride as a brown oil

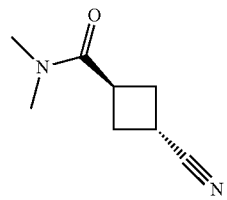

E. (1r,3r)-3-Cyano-N,N-dimethylcyclobutane-1-carboxamide

Into a 100 mL round-bottom flask was placed a solution of dimethylamine (70% in H₂O, 5 mL) in tetrahydrofuran (20 mL), which was then cooled to 0° C. The dimethylamine solution was then treated with a solution of (1r,3r)-3-cyanocyclobutane-1-carbonyl chloride (1.0 g, 6.97 mmol) in tetrahydrofuran (10 mL) in a dropwise manner. The resulting mixture was allowed to warm to room temperature and stir for 2 h, before being concentrated under vacuum. The remaining residue was purified by column chromatography on silica, using ethyl acetate/hexanes (1:5 to 1:2) as the eluant, to afford 0.7 g (66%) of (1r,3r)-3-cyano-N,N-dimethylcyclobutane-1-carboxamide as a light yellow liquid. ¹H NMR (400 MHz, DMSO-d₆): δ 3.45-3.34 (m, 1H), 3.34-3.23 (m, 1H), 2.86 (s, 3H), 2.81 (s, 3H), 2.57-2.46 (m, 2H), 2.45-2.34 (m, 2H).

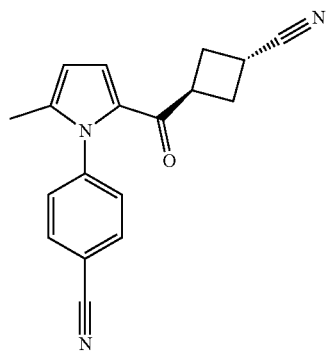 [SMILES: Cc1ccc(C(=O)[C@H]2C[C@H](C#N)C2)n1-c1ccc(C#N)cc1]

F. 4-(2(1r,3r)-3-Cyanocyclobutane-1-carbonyl)-5-methyl-1H-pyrrol-1-yl)benzonitrile Into a 50 mL round-bottom flask was placed a mixture of (1r,3r)-3-cyano-N,N-dimethylcyclobutane-1-carboxamide (700 mg, 4.60 mmol), phosphoryl trichloride (1.06 g, 6.91 mmol) and chloroform (10 mL). The was cooled to 0° C. and then neat 4-(2-methyl-1H-pyrrol-1-yl)benzonitrile (1.25 g, 6.86 mmol) was added to the mixture. The reaction mixture was allowed to warm to room temperature and was then heated at 70° C. for 14 h. After cooling to room temperature, the reaction mixture was diluted with an aqueous saturated solution of potassium carbonate (50 mL). The resulting mixture was heated at reflux for an additional 3 h and then extracted with dichloromethane (3×20 mL), after cooling to room temperature. The combined organic extracts were concentrated under vacuum and the remaining residue was purified by column chromatography on silica, using ethyl acetate/hexanes (1:10 to 1:5) as the eluant, to afford 1.0 g (75%) of 4-(2-((1r,3r)-3-cyanocyclobutane-1-carbonyl)-5-methyl-1H-pyrrol-1-yl)benzonitrile as a light yellow solid. $^1$H NMR (400 MHz, CDCl$_3$): δ 7.80-7.76 (m, 2H), 7.33-7.27 (m, 2H), 6.92 (d, J=4.0 Hz, 1H), 6.13 (d, J=4.0 Hz, 1H), 3.81-3.71 (m, 1H), 3.15-3.05 (m, 1H), 2.72-2.60 (m, 2H), 2.59-2.48 (m, 2H), 2.03 (s, 3H).

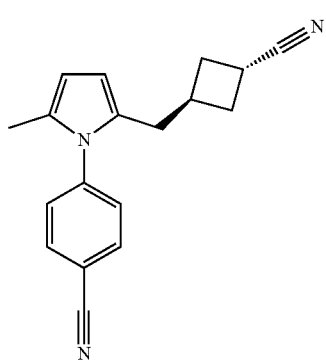 [SMILES: Cc1ccc(C[C@H]2C[C@H](C#N)C2)n1-c1ccc(C#N)cc1]

G. 4-(2-(((1r,3r)-3-Cyanocyclobutyl)methyl)-5-methyl-1H-pyrrol-1-yl)benzonitrile Into a 100 mL round-bottom flask was placed a solution of 4-(2-((1r,3r)-3-cyanocyclobutane-1-carbonyl)-5-methyl-1H-pyrrol-1-yl)benzonitrile (500 mg, 1.73 mmol) in acetonitrile (50 mL), which was then treated with a solution of BH$_3$ (1.0 M in THF, 14 mL). The resulting mixture was heated at 50° C. for 1 h. After cooling to room temperature the reaction was diluted with ice water (30 mL). The resulting mixture was concentrated under vacuum and the remaining residue was purified by preparative-TLC (petroleum ether:ethyl acetate=3:1) to afford 170 mg (36%) of 4-(2-(((1r,3r)-3-cyanocyclobutyl)methyl)-5-methyl-1H-pyrrol-1-yl)benzonitrile as light yellow oil. $^1$H NMR (400 MHz, CDCl$_3$): δ 7.82-7.78 (m, 2H), 7.34-7.29 (m, 2H), 5.95 (d, J=3.6 Hz, 1H), 5.88 (d, J=3.2 Hz, 1H), 3.04-2.96 (m, 1H), 2.74-2.64 (m, 1H), 2.51-2.40 m, 4H), 2.06-1.96 (m, 5H).

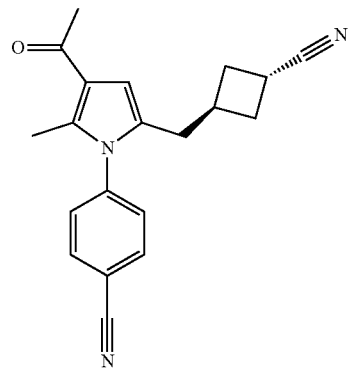 [SMILES: CC(=O)c1cc(C[C@H]2C[C@H](C#N)C2)n(-c2ccc(C#N)cc2)c1C]

H. 4-(3-Acetyl-5-(((1r,3r)-3-cyanocyclobutyl)methyl)-2-methyl-1H-pyrrol-1-yl)benzonitrile Into a 50 mL round-bottom flask was placed a solution of 4-(2-(((1r,3r)-3-cyanocyclobutyl)methyl)-5-methyl-1H-pyrrol-1-yl)benzonitrile (170 mg, 0.62 mmol) in dichloromethane (10 mL). The solution was cooled to 0° C. and then treated with acetyl chloride (145 mg, 1.85 mmol) in a dropwise manner. The resulting mixture was then treated with a solution of diethylaluminum chloride in toluene (1 M, 1.37 mL) in a dropwise fashion. The reaction mixture was allowed to warm to room temperature and stir for 13 h. The reaction mixture was diluted with ice water (10 mL) and then extracted with dichloromethane (2×20 mL). The combined organic extracts were concentrated under vacuum and the remaining residue was purified by preparative-TLC (petroleum ether:ethyl acetate=2:1) to afford 100 mg (51%) of 4-(3-acetyl-5-(((1r,3r)-3-cyanocyclobutyl)methyl)-2-methyl-1H-pyrrol-1-yl)benzonitrile as light yellow oil. $^1$H NMR (400 MHz, Methanol-d$_4$): δ 7.95-7.88 (m, 2H), 7.48-7.44 (m, 2H), 6.41 (s, 1H), 3.19-3.09 (m, 1H), 2.65-2.56 (m, 1H), 2.49-2.46 (d, J=12 Hz, 2H), 2.39-2.30 (m, 5H), 2.22 (s, 3H), 2.09-1.99 (m, 2H).

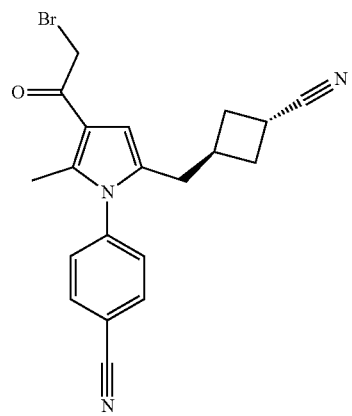 [SMILES: Cc1c(C(=O)CBr)cc(C[C@H]2C[C@H](C#N)C2)n1-c1ccc(C#N)cc1]

I. 4-(3-(2-Bromoacetyl)-5-(((1r,3r)-3-cyanocyclobutyl)methyl)-2-methyl-1H-pyrrol-1-yl)benzonitrile Into a 50 mL, 3-necked, round-bottom flask, being maintained under an inert atmosphere of nitrogen, was placed a mixture of 4-(3-acetyl-5-(((1r,3r)-3-cyanocyclobutyl)

methyl)-2-methyl-1H-pyrrol-1-yl)benzonitrile (140 mg, 0.44 mmol), diisopropylethylamine (230 mg, 1.78 mmol) and tetrahydrofuran (10 mL). The mixture was cooled to 0° C. and then treated portionwise with a solution of TMSOTf (195 mg, 0.88 mmol) in tetrahydrofuran (1 mL). The reaction mixture was allowed to stir at 0° C. for 2 h and then a solution of N-bromosuccinimide (94 mg, 0.53 mmol) in tetrahydrofuran (1 mL) was added in a dropwise fashion. The resulting mixture was allowed to stir at 0° C. for 1 h and was then diluted with ice water (20 mL). The aqueous mixture was extracted with dichloromethane (2×20 mL) and the combined organic extracts were dried over anhydrous sodium sulfate. The organic phase was concentrated under vacuum to afford 70 mg (40%) of 4-(3-(2-bromoacetyl)-5-(((1r,3r)-3-cyanocyclobutyl)methyl)-2-methyl-1H-pyrrol-1-yl)benzonitrile as yellow oil. Mass Spectrum (LCMS, ESI pos.): Calcd. for $C_{20}H_{18}BrN_3O_2$: 396 (M+H); found 396.

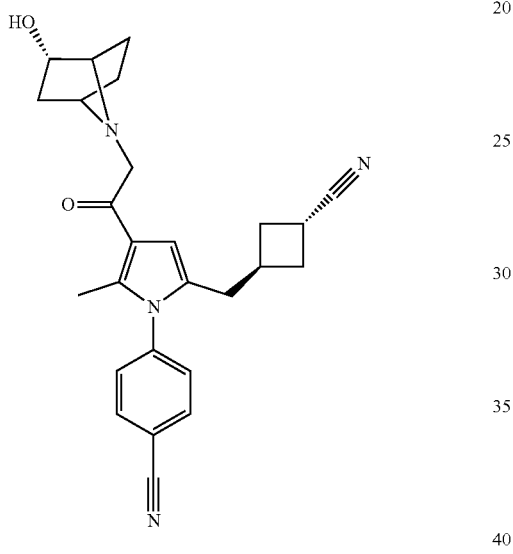

J. (±)-4-(5-(((1r,3R)-3-Cyanocyclobutyl)methyl)-3-(2-((2R)-2-hydroxy-7-azabicyclo[2.2.1]heptan-7-yl)acetyl)-2-methyl-1H-pyrrol-1-yl)benzonitrile (45B)

Into a 25 mL round-bottom flask was placed a solution of 4-(3-(2-bromoacetyl)-5-(((1r,3r)-3-cyanocyclobutyl)methyl)-2-methyl-1H-pyrrol-1-yl)benzonitrile (70 mg, 0.18 mmol) in N,N-dimethylformamide (3 mL). To the solution were added solid potassium carbonate (100 mg, 0.72 mmol) and racemic (1R,2R,4S)-7-azabicyclo[2.2.1]heptan-2-ol hydrochloride (47 mg, 0.31 mmol). The resulting mixture was allowed to stir at room temperature for 14 h, before it was concentrated under vacuum. The remaining residue was purified by preparative-TLC on silica (dichloromethane/methanol=10:1) to afford 57 mg (76%) of (±)-4-(5-(((1r,3R)-3-Cyanocyclobutyl)methyl)-3-(2-((2R)-2-hydroxy-7-azabicyclo[2.2.1]heptan-7-yl)acetyl)-2-methyl-1H-pyrrol-1-yl)benzonitrile (45B) as a light yellow solid. Mass Spectrum (LCMS, ESI pos.): Calcd. for $C_{26}H_{28}N_4O_2$: 492 (M+H); found 492. $^1$H NMR (300 MHz, DMSO-$d_6$): δ 8.05 (d, J=8.1 Hz, 2H), 7.58 (d, J=8.4 Hz, 2H), 6.47 (s, 1H), 4.68 (d, J=3.9 Hz, 1H), 4.05-4.03 (m, 1H), 3.54 (s, 2H), 3.35-3.32 (m, 1H), 3.26-3.25 (m, 2H), 2.50-2.41 (m, 2H), 2.38-2.29 (m, 2H), 2.19 (s, 3H), 2.01-1.93 (m, 4H), 1.80-1.75 (m, 1H), 1.51-1.46 (m, 1H), 1.34-1.28 (m, 2H), 0.80-0.75 (m, 1H).

Example 18B. (±)-4-(3-(2-((2R)-2-Hydroxy-7-azabicyclo[2.2.1]heptan-7-yl)acetyl)-2,5-dimethyl-4-(4-(methylsulfonyl)butyl)-1H-pyrrol-1-yl)benzonitrile (19B)

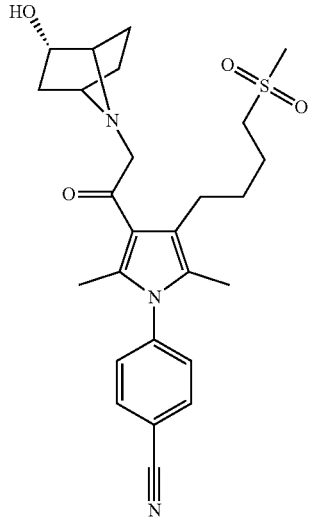

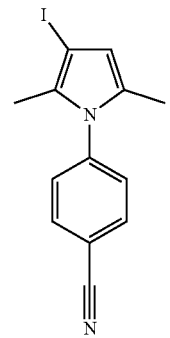

A.
4-(3-Iodo-2,5-dimethyl-1H-pyrrol-1-yl)benzonitrile

Into a 250 mL round-bottom flask was placed a solution of 4-(2,5-dimethyl-1H-pyrrol-1-yl)benzonitrile (4.0 g, 20.38 mmol) in acetonitrile (100 mL). The solution was cooled to 0° C. and then NIS (4.82 g, 21.42 mmol) was added in portions over 10 min. The resulting mixture was allowed to warm to room temperature and stir for 30 min before it was diluted with an aqueous solution of sodium sulfite (150 mL). The resulting mixture was extracted with ethyl acetate (2×200 mL) and the combined organic extracts were washed with brine (2×200 mL), dried over anhydrous sodium sulfate and concentrated under vacuum to afford 6.2 g (94%) of 4-(3-iodo-2,5-dimethyl-1H-pyrrol-1-yl)benzonitrile as a yellow solid. $^1$H NMR (300 MHz, DMSO-$d_6$) δ 8.05-7.98 (m, 2H), 7.56-7.53 (m, 2H), 6.06 (s, 1H), 1.99 (s, 3H), 1.97 (s, 3H).

293

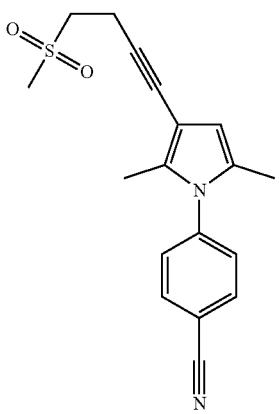 [SMILES: Cc1cc(C#CCCS(C)(=O)=O)c(C)n1-c1ccc(C#N)cc1]

B. 4-(2,5-Dimethyl-3-(4-(methylsulfonyl)but-1-yn-1-yl)-1H-pyrrol-1-yl)benzonitrile Into a 100 mL round-bottom flask was placed a solution of 4-(3-iodo-2,5-dimethyl-1H-pyrrol-1-yl)benzonitrile (2.0 g, 6.21 mmol) in acetonitrile (40 mL). To the solution were added tetrakis(triphenylphosphine)palladium (0) (693 mg, 0.60 mmol), copper(I) iodide (114 mg, 0.60 mmol), triethylamine (20 mL) and 4-(methylsulfonyl)but-1-yne (1.58 g, 12.0 mmol). The resulting mixture was heated at 80° C. for 3 h and then allowed to cool to room temperature. The reaction mixture was diluted with water (300 mL) and then extracted with ethyl acetate (3×200 mL). The combined organic extracts were washed with brine (2×300 mL), dried over sodium sulfate and concentrated under vacuum. The remaining residue was purified by column chromatography on silica gel, using petroleum ether/ethyl acetate (3:1) as the eluant, to afford 320 mg (16%) of 4-(2,5-dimethyl-3-(4-(methylsulfonyl)but-1-yn-1-yl)-1H-pyrrol-1-yl)benzonitrile as yellow oil. Mass Spectrum (LCMS, ESI pos.): Calcd. for $C_{18}H_{18}N_2O_2S$: 327 (M+H); found 327.

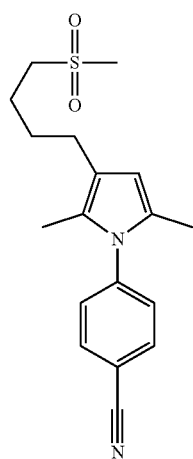 [SMILES: Cc1cc(CCCCS(C)(=O)=O)c(C)n1-c1ccc(C#N)cc1]

294

C. 4-(2,5-Dimethyl-3-(4-(methylsulfonyl)butyl)-1H-pyrrol-1-yl)benzonitrile

Into a 25 mL round-bottom flask was placed a solution of 4-(2,5-dimethyl-3-(4-(methylsulfonyl)but-1-yn-1-yl)-1H-pyrrol-1-yl)benzonitrile (315 mg, 0.97 mmol) in ethyl acetate (10 mL). To the solution was added palladium on carbon (32 mg). The reaction mixture was flushed with hydrogen and then allowed to stir at room temperature, under an atmosphere of hydrogen, for 6 h. Solids were then filtered from the reaction mixture and the filtrate was concentrated under vacuum to afford 280 mg (88%) of 4-(2,5-dimethyl-3-(4-(methylsulfonyl)butyl)-1H-pyrrol-1-yl)benzonitrile as yellow oil. Mass Spectrum (LCMS, ESI pos.): Calcd. for $C_{18}H_{18}N_2O_2S$: 331 (M+H); found 331.

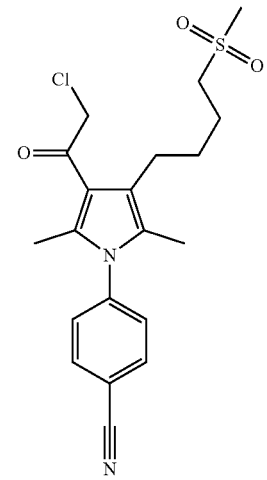 [SMILES: Cc1c(CCCCS(C)(=O)=O)c(C(=O)CCl)c(C)n1-c1ccc(C#N)cc1]

D. 4-(3-(2-Chloroacetyl)-2,5-dimethyl-4-(4-(methylsulfonyl)butyl)-1H-pyrrol-1-yl)benzonitrile Into a 50 mL round-bottom flask was placed a solution of 4-(2,5-dimethyl-3-(4-(methylsulfonyl)butyl)-1H-pyrrol-1-yl)benzonitrile (280 mg, 0.85 mmol) in dichloromethane (20 mL). To the solution were added a solution of diethylaluminum chloride (25% wt in toluene, 2.54 mL) and 2-chloroacetyl chloride (287 mg, 2.54 mmol). The resulting mixture was allowed to stir at room temperature for 3 h before being diluted with an aqueous solution of sodium bicarbonate (100 mL). The mixture was extracted with ethyl acetate (2×100 mL) and the combined organic extracts were washed with brine (2×100 mL), dried over anhydrous sodium sulfate and concentrated under vacuum to afford 350 mg (crude) of 4-(3-(2-chloroacetyl)-2,5-dimethyl-4-(4-(methylsulfonyl) butyl)-1H-pyrrol-1-yl)benzonitrile as yellow oil. Mass Spectrum (LCMS, ESI pos.): Calcd. for $C_{20}H_{23}ClN_{23}S$: 407 (M+H); found 407.

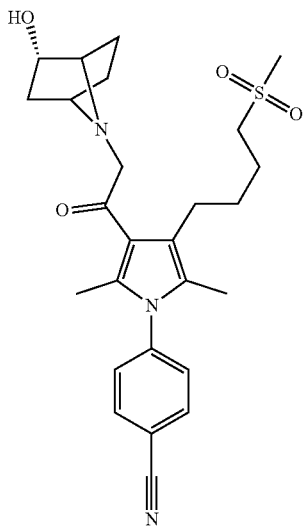 [SMILES: Cc1c(CCCCS(C)(=O)=O)c(C(=O)CN2C3CCC2[C@@H](O)C3)c(C)n1-c1ccc(C#N)cc1]

E. (±)-4-(3-(2-((2R)-2-Hydroxy-7-azabicyclo[2.2.1]heptan-7-yl)acetyl)-2,5-dimethyl-4-(4-(methylsulfonyl)butyl)-1H-pyrrol-1-yl)benzonitrile (19B)

Into a 25 mL round-bottom flask was placed a solution of 4-(3-(2-chloroacetyl)-2,5-dimethyl-4-(4-(methylsulfonyl)butyl)-1H-pyrrol-1-yl)benzonitrile (150 mg, 0.37 mmol) in N,N-dimethylformamide (5 mL). To the solution were added potassium carbonate (153 mg, 1.11 mmol) and (±)-(1R,2R,4S)-7-azabicyclo[2.2.1]heptan-2-ol hydrochloride (55 mg, 0.37 mmol). The resulting mixture was allowed to stir at room temperature for 16 h before it was filtered. The filtrate was purified by preparative-HPLC under the following conditions: Column-Xbridge Phenyl OBD Column, 5 μm, 19*150 mm; Mobile Phase-Water with 0.5% NH$_4$HCO$_3$ and acetonitrile (40.0% acetonitrile up to 60.0% in 8 min); Detector-UV 254/220 nm. This process afforded 25 mg (14%) of (±)-4-(3-(2-((2R)-2-hydroxy-7-azabicyclo[2.2.1]heptan-7-yl)acetyl)-2,5-dimethyl-4-(4-(methylsulfonyl)butyl)-1H-pyrrol-1-yl)benzonitrile (19B) as a light yellow solid. Mass Spectrum (LCMS, ESI pos.): Calcd. for C$_{26}$H$_{33}$N$_3$O$_4$S: 484 (M+H); found 484. $^1$H NMR (300 MHz, DMSO-d$_6$) δ 8.06 (d, J=8.7 Hz, 2H), 7.54 (d, J=8.7 Hz, 2H), 4.67 (d, J=3.6 Hz, 1H), 4.03-4.00 (m, 1H), 3.45 (s, 2H), 3.28 (brs, 2H), 3.14-3.12 (m, 2H), 2.95 (s, 3H), 2.64 (t, J=7.5 Hz, 2H), 2.22 (s, 3H), 2.02-1.95 (m, 2H), 1.86 (s, 3H), 1.75-1.67 (m, 3H), 1.55-1.45 (m, 3H), 1.38-1.24 (m, 1H), 0.75-0.71 (m, 1H).

Example 19B. (±)-4-(3-(2-((2R)-2-Hydroxy-7-azabicyclo[2.2.1]heptan-7-yl)acetyl)-2-methyl-5-(4-(methylsulfonyl)butan-2-yl)-1H-pyrrol-1-yl)benzonitrile (11B)

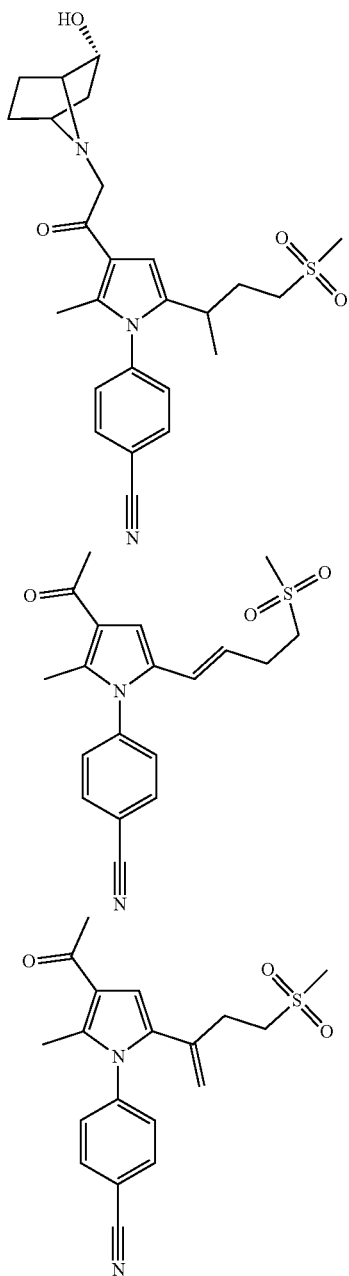

A. (E)-4-(3-Acetyl-2-methyl-5-(4-(methylsulfonyl)but-1-en-1-yl)-1H-pyrrol-1-yl)benzonitrile and 4-(3-Acetyl-2-methyl-5-(4-(methylsulfonyl)but-1-en-2-yl)-1H-pyrrol-1-yl)benzonitrile Into a 20 mL sealed tube was placed a mixture of 4-(3-acetyl-5-iodo-2-methyl-1H-pyrrol-1-yl)benzonitrile (1.18 g, 3.37 mmol), 4-methanesulfonylbut-1-ene (905 mg, 6.74 mmol, diisopropylethylamine (1.31 g, 10.1 mmol), palladium(II) acetate (76 mg, 0.34 mmol, tri-o-tolylphosphine (205 mg, 0.67 mmol), and N,N-dimethylformamide (10 mL). The reaction mixture was heated at 80° C. for 1 h before it was allowed to cool to room temperature. The mixture was diluted with ethyl acetate (50 mL) and the solids were filtered from the mixture. The filtrate was washed with water (3×50 mL), dried over sodium sulfate, and concentrated under vacuum. The remaining residue was purified by column chromatography on silica, using ethyl acetate:petroleum ether (3:1) as the eluant, to afford 885 mg (74%) of mixture of (E)-4-(3-acetyl-2-methyl-5-(4-(methylsulfonyl)but-1-en-1-yl)-1H-pyrrol-1-yl)benzonitrile and 4-(3-acetyl-2-methyl-5-(4-(methylsulfonyl)but-1-en-2-yl)-1H-pyrrol-1-yl)benzonitrile as a colorless oil. Mass Spectrum (LCMS, ESI pos.): Calcd. for $C_{19}H_{20}N_2O_3S$: 357 (M+H); found 357.

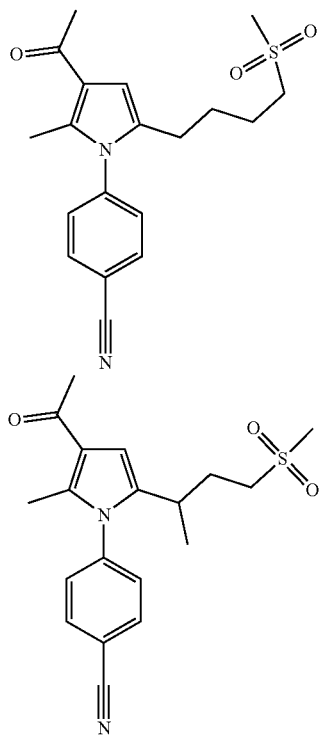

B. 4-(3-Acetyl-2-methyl-5-(4-(methylsulfonyl) butyl)-1H-pyrrol-1-yl)benzonitrile and 4-(3-Acetyl-2-methyl-5-(4-(methylsulfonyl)butan-2-yl)-1H-pyrrol-1-yl)benzonitrile Into a 100 mL round-bottom flask was placed a mixture of (E)-4-(3-acetyl-2-methyl-5-(4-(methylsulfonyl)but-1-en-1-yl)-1H-pyrrol-1-yl)benzonitrile and 4-(3-acetyl-2-methyl-5-(4-(methylsulfonyl)but-1-en-2-yl)-1H-pyrrol-1-yl)benzonitrile (1.25 g, 3.51 mmol) in ethyl acetate (20 mL). Palladium on carbon (400 mg) was added to the flask and the resulting mixture was sparged with hydrogen. The reaction mixture was allowed to stir at room temperature, under an atmosphere of hydrogen, overnight. The reaction mixture was diluted with ethyl acetate (50 mL) and the solids were filtered from the mixture. The filtrate was concentrated under vacuum and the remaining residue was purified by column chromatography on silica, using ethyl acetate/petroleum ether (2:3) as the eluant, to afford 83 mg (7%) of 4-(3-acetyl-2-methyl-5-(4-(methylsulfonyl)butan-2-yl)-1H-pyrrol-1-yl)benzonitrile as an off-white solid and 110 mg of 4-(3-acetyl-2-methyl-5-(4-(methylsulfonyl)butyl)-1H-pyrrol-1-yl)benzonitrile as an off-white solid.

Analytical data for 4-(3-acetyl-2-methyl-5-(4-(methylsulfonyl)butan-2-yl)-1H-pyrrol-1-yl)benzonitrile: Mass Spectrum (LCMS, ESI pos.): Calcd. for $C_{19}H_{22}N_2O_3S$: 359 (M+H); found 359. $^1$H NMR (300 MHz, CDCl$_3$) δ δ 7.85 (d, J=8.4 Hz, 2H), 7.34 (d, J=8.4 Hz, 2H)), 6.38 (s, 1H), 4.18-4.09 (m, 1H), 2.97-2.92 (m, 2H), 2.88 (s, 3H), 2.43 (s, 3H), 2.38-2.34 (m, 2H), 2.29 (s, 3H), 1.87-1.77 (m, 2H), 1.68-1.58 (m, 3H).

Analytical data for 4-(3-acetyl-2-methyl-5-(4-(methylsulfonyl)butyl)-1H-pyrrol-1-yl)benzonitrile: Mass Spectrum (LCMS, ESI pos.): Calcd. for $C_{19}H_{22}N_2O_3S$: 359 (M+H); found 359. $^1$H NMR (300 MHz, DMSO-d$_6$) δ 8.07 (d, J=8.4 Hz, 2H), 7.60 (d, J=8.4 Hz, 2H), 6.55 (s, 1H), 3.04-2.96 (m, 2H), 2.90 (s, 3H), 2.38-2.30 (m, 5H), 2.21 (s, 3H), 1.66-1.44 (m, 4H).

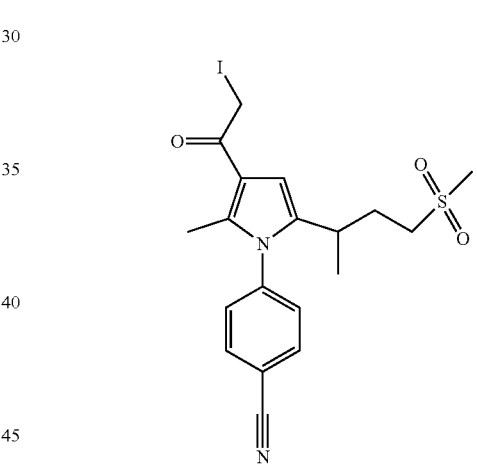

C. 4-(3-(2-Iodoacetyl)-2-methyl-5-(4-(methylsulfonyl)butan-2-yl)-1H-pyrrol-1-yl)benzonitrile Into a 50 mL round-bottom flask was placed a solution of 4-(3-acetyl-2-methyl-5-(4-(methylsulfonyl)butan-2-yl)-1H-pyrrol-1-yl)benzonitrile (106 mg, 0.30 mmol) in tetrahydrofuran (5 mL). The solution was cooled to −20° C. and then treated with both diisopropylethylamine (152 mg, 1.18 mmol) and trimethylsilyl trifluoromethanesulfonate (132 mg, 1.00 mmol). The resulting mixture as allowed to stir at −20° C. for 1 h and then solid N-iodosuccinimide (71 mg, 0.32 mmol) was added to the flask. The reaction mixture was allowed to stir for an 10 min at −20° C. before it was diluted with water (10 mL). The reaction mixture was extracted with ethyl acetate (3×30 mL) and the combined organic extracts were dried over sodium sulfate. The organic phase was concentrated under vacuum and the remaining residue was purified by column chromatography on silica, using ethyl acetate/petroleum ether (1:3) as the eluant, to afford 79 mg (55%) of 4-(3-(2-iodoacetyl)-2-methyl-5-(4-(methylsulfonyl)butan-2-yl)-1H-pyrrol-1-yl)benzonitrile as a light yellow solid. Mass Spectrum (LCMS, ESI pos.): Calcd. for $C_{19}H_{21}IN_2O_3S$: 485 (M+H); found 485.

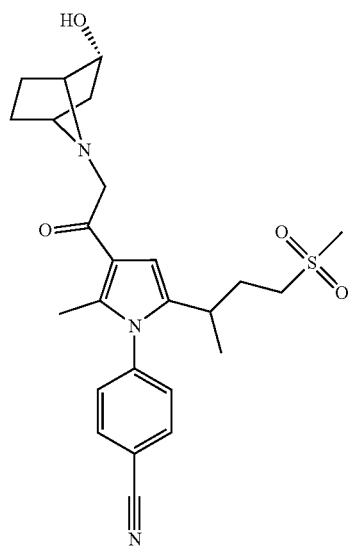 [SMILES: Cc1c(C(=O)CN2C3CCC2[C@H](O)C3)cc(C(C)CCS(C)(=O)=O)n1-c1ccc(C#N)cc1]

D. (±)-4-(3-(2-((2R)-2-Hydroxy-7-azabicyclo[2.2.1]heptan-7-yl)acetyl)-2-methyl-5-(4-(methylsulfonyl)butan-2-yl)-1H-pyrrol-1-yl)benzonitrile (11B)

Into a 100 mL round-bottom flask was placed a solution of 4-(3-(2-iodoacetyl)-2-methyl-5-(4-(methylsulfonyl)butan-2-yl)-1H-pyrrol-1-yl)benzonitrile (80 mg, 0.22 mmol) in N,N-dimethylformamide (5 mL). To the solution were added racemic (1R,2R,4S)-7-azabicyclo[2.2.1]heptan-2-ol (50 mg, 0.44 mmol) and potassium carbonate (118 mg, 0.86 mmol). The resulting mixture was allowed to stir at room temperature overnight. The solids were filtered from the reaction mixture and the crude product was purified by preparative-HPLC under the following conditions: Column-XBridge Prep C18 OBD Column, 5 μm, 19*150 mm; mobile phase-Water with 0.05% NH$_4$HCO$_3$ and acetonitrile (20% acetonitrile up to 70% in 8 min); Detector-UV 254/220 nm. This process afforded 20 mg (19%) of a diastereomeric mixture of (±)-4-(3-(2-((2R)-2-hydroxy-7-azabicyclo[2.2.1]heptan-7-yl)acetyl)-2-methyl-5-(4-(methylsulfonyl)butan-2-yl)-1H-pyrrol-1-yl)benzonitrile (11B) as an off-white solid. Mass Spectrum (LCMS, ESI pos.): Calcd. for $C_{25}H_{31}N_3O_4S$: 470 (M+H); found 470. $^1$H NMR (300 MHz, DMSO-d$_6$) δ 8.07 (d, J=8.4 Hz, 2H), 7.63-7.60 (m, 2H), 6.60 (s, 1H), 4.67 (s, 1H), 4.06-4.04 (m, 1H), 3.59-3.57 (m, 2H), 3.32-3.28 (m, 2H), 2.99-2.90 (m, 6H), 2.59-2.50 (m, 1H), 2.18 (s, 3H), 1.98-1.93 (m, 2H), 1.89-1.84 (m, 1H), 1.74-1.69 (m, 2H), 1.54-1.48 (m, 2H), 1.35-1.28 (m, 1H), 1.04 (d, J=6.8 Hz, 2H), 0.80-0.76 (m, 1H).

Example 20B. (±>4-(3-(2-((2R)-2-Hydroxy-7-azabicyclo[2.2.1]heptan-7-yl)acetyl)-2-methyl-5-(4-(methylthio)butyl-1H-pyrrol-1-yl)benzonitrile (37B)

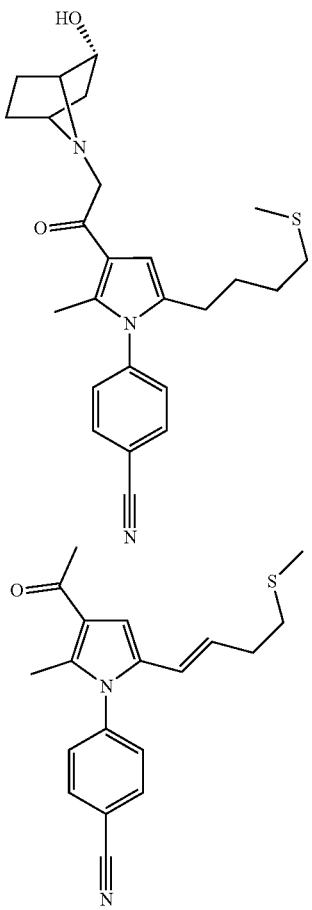

A. (E)-4-(3-Acetyl-2-methyl-5-(4-(methylthio)but-1-en-1-yl)-1H-pyrrol-1-yl)benzonitrile Into a 20 mL sealed tube, being maintained under an atmosphere of nitrogen, was placed a mixture of 4-(3-acetyl-5-bromo-2-methyl-1H-pyrrol-1-yl)benzonitrile (2.00 g, 6.60 mmol) and but-3-en-1-yl(methyl)sulfane (1.34 g, 13.1 mmol) in N,N-dimethylformamide (10 mL). To the mixture were added P(o-Tol)$_3$ (800 mg, 2.63 mol), diisopropylethylamine (2.50 g, 19.38 mmol) and Pd(OAc)$_2$ (300 mg, 1.34 mol). The system was heated in a microwave reactor at 160° C. for 2 h. After cooling to room temperature the reaction mixture was concentrated under vacuum and the remaining residue was purified by column chromatography on silica gel using ethyl acetate/hexanes (1:15) as the eluant. The material obtained after column chromatography was further purified by preparative-HPLC under the following conditions: IntelFlash-1 Column-C18; mobile phase—CH$_3$CN/H$_2$O=0/100 increasing to CH$_3$CN/H$_2$O=90/10 within 30 min; Detector—UV 254 nm. This process afforded 600 mg (28%) of (E)-4-(3-acetyl-2-methyl-5-(4-(methylthio)but-1-en-1-yl)-1H-pyrrol-1-yl)benzonitrile as a light yellow oil. Mass Spectrum (LCMS, ESI pos.): Calcd. for $C_{19}H_{20}N_2OS$: 325 (M+H); found 325.

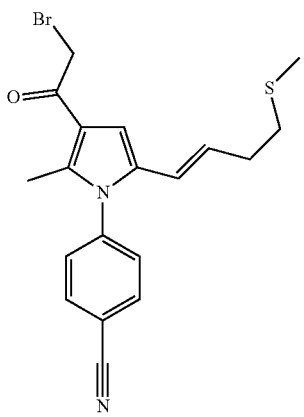 [SMILES: CSCC/C=C/c1cc(C(=O)CBr)c(C)n1-c1ccc(C#N)cc1]

B. (E)-4-(3-(2-Bromoacetyl)-2-methyl-5-(4-(methylthio)but-1-en-1-yl)-1H-pyrrol-1-yl)benzonitrile Into a 50 mL, 3-necked round-bottom flask, being maintained under an atmosphere of nitrogen, was placed a solution of (E)-4-(3-acetyl-2-methyl-5-(4-(methylthio)but-1-en-1-yl)-1H-pyrrol-1-yl)benzonitrile (150 mg, 0.46 mmol) in THF (20 mL). To the solution was cooled to 0° C. and then diisopropylethylamine (179 mg, 1.39 mmol) and TMSOTf (154 mg, 0.693 mmol) were added. The resulting mixture was allowed to stir at 0° C. for 1 h. Then a solution of NBS (90 mg, 0.51 mmol) in THF (2 mL) was added to the reaction mixture. The resulting mixture was allowed to stir 0° C. for 5 min before it was diluted with ice cold water (50 mL). The mixture was extracted with dichloromethane (2×30 mL) and the combined organic extracts were dried over anhydrous sodium sulfate and concentrated to dryness. The remaining residue was purified by preparative-TLC (petroleum ether/ethyl acetate=2:1) to afford 70 mg (38%) of (E)-4-(3-(2-bromoacetyl)-2-methyl-5-(4-(methylthio)but-1-en-1-yl)-1H-pyrrol-1-yl)benzonitrile as yellow oil. Mass Spectrum (LCMS, ESI pos.): Calcd. for $C_{19}H_{19}N_2OS$: 403 (M+H); found 403.

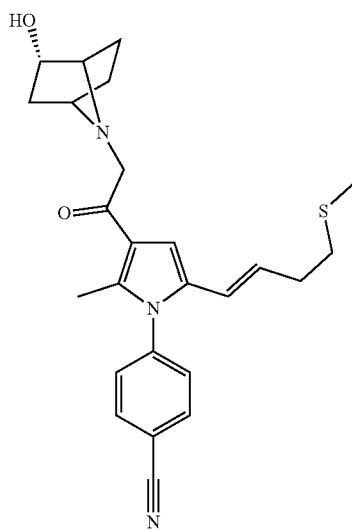 [SMILES: CSCC/C=C/c1cc(C(=O)CN2C3CCC2[C@@H](O)C3)c(C)n1-c1ccc(C#N)cc1]

C. (±)-4-(3-(2-((2R)-2-hydroxy-7-azabicyclo[2.2.1]heptan-7-yl)acetyl)-2-methyl-5-((E)-4-(methylthio)but-1-en-1-yl)-1H-pyrrol-1-yl)benzonitrile Into a 25 mL round-bottom flask was placed a mixture of (E)-4-(3-(2-bromoacetyl)-2-methyl-5-(4-(methylthio)but-1-en-1-yl)-1H-pyrrol-1-yl)benzonitrile (120 mg, 0.30 mmol) and (±)-(2R)-7-azabicyclo[2.2.1]heptan-2-ol (68 mg, 0.60 mmol) in N,N-dimethylformamide (3 mL). To the mixture was added potassium carbonate (124 mg, 0.90 mmol) and the resulting heterogeneous mixture was allowed to stir overnight at room temperature. The crude product was purified by preparative-HPLC under the following conditions: IntelFlash-2 Column C18; mobile phase—$CH_3CN$:$H_2O$=0:100 increasing to $CH_3CN$:$H_2O$=90:10 within 30 min; Detector-UV 254 nm. This process afforded 100 mg (77%) of (±)-4-(3-(2-((2R)-2-hydroxy-7-azabicyclo[2.2.1]heptan-7-yl)acetyl)-2-methyl-5-((E)-4-(methylthio)but-1-en-1-yl)-1H-pyrrol-1-yl)benzonitrile as colorless oil. Mass Spectrum (LCMS, ESI pos.): Calcd. for $C_{25}H_{29}N_3O_2S$: 436 (M+H); found 436.

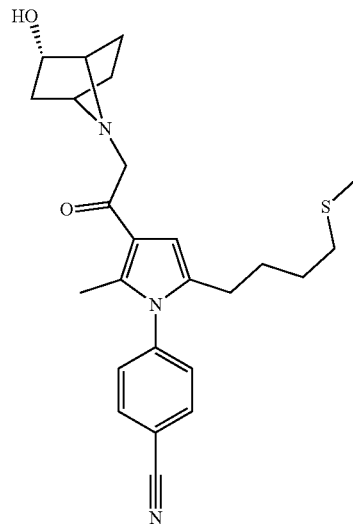 [SMILES: CSCCCCc1cc(C(=O)CN2C3CCC2[C@@H](O)C3)c(C)n1-c1ccc(C#N)cc1]

D. (±)-4-(3-(2-((2R)-2-Hydroxy-7-azabicyclo[2.2.1]heptan-7-yl)acetyl)-2-methyl-5-(4-(methylthio)butyl)-1H-pyrrol-1-yl)benzonitrile (37B)

Into a 100 mL round-bottom flask was placed a solution of (±)-4-(3-(2-((2R)-2-hydroxy-7-azabicyclo[2.2.1]heptan-7-yl)acetyl)-2-methyl-5-((E)-4-(methylthio)but-1-en-1-yl)-1H-pyrrol-1-yl)benzonitrile (100 mg, 0.23 mmol) in ethyl acetate (20 mL). To the solution was added palladium on carbon (100 mg). The mixture was purged with hydrogen and the resulting mixture was allowed to stir for 3 days at room temperature. The reaction mixture was filtered and the filtrate was concentrated under vacuum. The remaining residue was purified by preparative-TLC (DCM:MeOH=10:1) and then further purified by preparative-HPLC under the following conditions: Column—C18; mobile phase, water with 0.05% $NH_4HCO_3$, 0.1% $NH_4OH$ and $CH_3CN$ (10% $CH_3CN$ up to 90% in 30 min); Detector—UV 254 nm. This process afforded 16 mg (16%) of (±)-4-(3-(2-((2R)-2-Hydroxy-7-azabicyclo[2.2.1]heptan-7-yl)acetyl)-2-methyl-5-(4-(methylthio)butyl)-1H-pyrrol-1-yl)benzonitrile (37B) as a white solid. Mass Spectrum (LCMS, ESI pos.): Calcd. for

303

$C_{25}H_{31}N_3O_2S$: 438 (M+H); found 438. $^1$H-NMR (400 MHz, DMSO-d$_6$) δ 7.97 (d, J=6.8 Hz, 2H), 7.51 (d, J=6.8 Hz, 2H), 6.50 (s, 1H), 4.33-4.42 (m, 1H), 3.75-3.92 (m, 1H), 3.42-3.63 (m, 2H), 3.31 (s, 2H), 2.35-2.45 (m, 4H), 2.30 (s, 4H), 2.15-2.32 (m, 2H), 2.01 (s, 3H), 1.82-2.01 (m, 1H), 1.62-1.71 (m, 1H), 1.42-1.59 (m, 5H), 0.91-1.13 (m, 1H).

Examples 21B and 22B. 2-(7-Azabicyclo[2.2.1]heptan-7-yl)-1-(1-(4-chlorophenyl)-2-methyl-5-(4-(methylsulfonyl)butyl)-1H-pyrrol-3-yl)ethan-1-one (18B) and (E)-2-(7-Azabicyclo[2.2.1]heptan-7-yl)-1-(1-(4-chlorophenyl)-2-methyl-5-(4-(methylsulfonyl)but-1-en-1-yl)-1H-pyrrol-3-yl)ethan-1-one (34B)

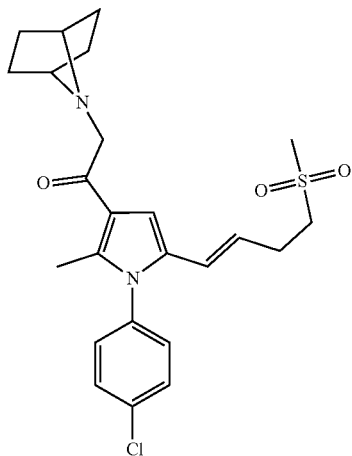

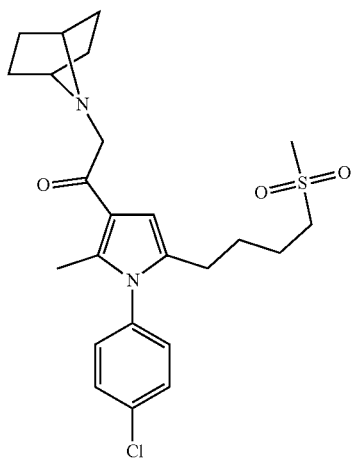

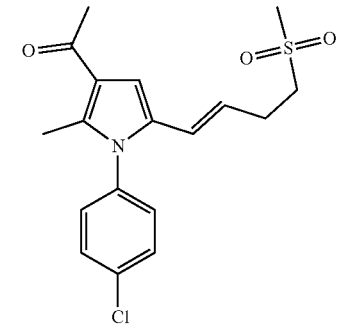

304

A. (E)-1-(1-(4-Chlorophenyl)-2-methyl-5-(4-(methylsulfonyl)but-1-en-1-yl)-1H-pyrrol-3-yl)ethan-1-one Into a 5 mL sealed tube, being maintained under an inert atmosphere of nitrogen, was placed a mixture of 1-(5-bromo-1-(4-chlorophenyl)-2-methyl-1H-pyrrol-3-yl)ethan-1-one (400 mg, 1.28 mmol), 4-methanesulfonylbut-1-ene (343 mg, 2.56 mmol), diisopropylethylamine (0.5 mL) and palladium(II) acetate (60 mg, 0.27 mmol) in N,N-dimethylformamide (3.5 mL). To the flask was added P(o-Tol)$_3$ (160 mg, 0.53 mmol) and the resulting mixture was at 160° C. for 2 h. After cooling to room temperature the reaction mixture was concentrated under vacuum and the remaining residue was purified by preparative-TLC (petroleum ether: ethyl acetate=1:2) to afford 190 mg (41%) of (E)-1-(1-(4-chlorophenyl)-2-methyl-5-(4-(methylsulfonyl)but-1-en-1-yl)-1H-pyrrol-3-yl)ethan-1-one as yellow oil. Mass Spectrum (LCMS, ESI pos.): Calcd. for $C_{18}H_{20}ClNO_3S$: 366 (M+H); found 366.

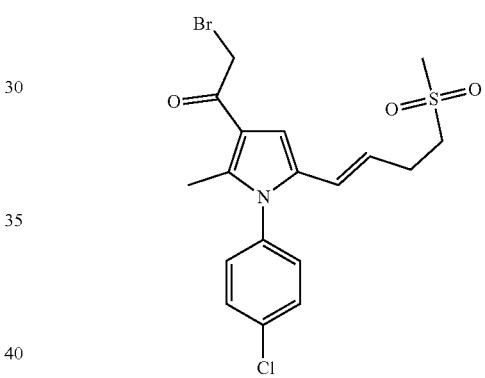

B. (E)-2-Bromo-1-(1-(4-chlorophenyl)-2-methyl-5-(4-(methylsulfonyl)but-1-en-1-yl)-1H-pyrrol-3-yl)ethan-1-one Into a 50 mL 3-necked, round-bottom flask were placed (E)-1-(1-(4-chlorophenyl)-2-methyl-5-(4-(methylsulfonyl)but-1-en-1-yl)-1H-pyrrol-3-yl)ethan-1-one (200 mg, 0.55 mmol), diisopropylethylamine (1 mL, 5.74 mmol), trimethylsilyl trifluoromethanesulfonate (0.5 mL, 2.76 mmol) and tetrahydrofuran (15 mL). The resulting mixture was cooled to 0° C. and allowed to stir for 0.5 h. The reaction mixture was then treated with a solution of NBS (195 mg, 1.10 mmol) in tetrahydrofuran (5 mL). The mixture was allowed to stir at 0° C. for 1 h before it was diluted with cold water (50 mL). The mixture was extracted with dichloromethane (3×50 mL) and the combined organic extracts were dried over anhydrous sodium sulfate. Concentrating the organic phase under vacuum afforded 200 mg of crude (E)-2-bromo-1-(1-(4-chlorophenyl)-2-methyl-5-(4-(methylsulfonyl)but-1-en-1-yl)-1H-pyrrol-3-yl)ethan-1-one as brown oil. The crude residue was used in the next step without further purification. Mass Spectrum (LCMS, ESI pos.): Calcd. for $C_{18}H_{19}BrClNO_3S$: 444 (M+H); found 444.

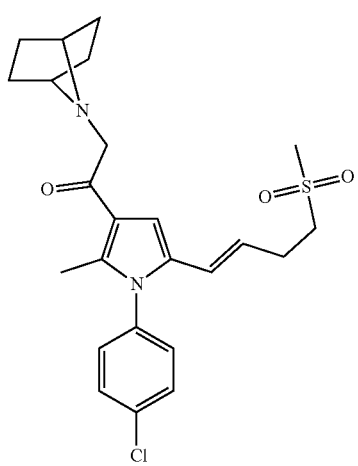 [SMILES: Cc1c(C(=O)CN2C3CCC2CC3)cc(/C=C/CCS(C)(=O)=O)n1-c1ccc(Cl)cc1]

C. (E)-2-(7-Azabicyclo[2.2.1]heptan-7-yl)-1-(1-(4-chlorophenyl)-2-methyl-5-(4-(methylsulfonyl)but-1-en-1-yl)-1H-pyrrol-3-yl)ethan-1-one (34B)

Into a 25 mL round-bottom flask were placed (E)-2-bromo-1-(1-(4-chlorophenyl)-2-methyl-5-(4-(methylsulfonyl)but-1-en-1-yl)-1H-pyrrol-3-yl)ethan-1-one (100 mg, 0.22 mmol), 7-azabicyclo[2.2.1]heptane (60 mg, 0.62 mmol), $K_2CO_3$ (120 mg, 0.86 mmol) and N,N-dimethylformamide (4 mL). The resulting mixture was allowed to stir overnight at room temperature before the solids were filtered from the mixture. The crude product was purified by preparative-HPLC under the following conditions: Column-C18; Mobile Phase, methanol/$H_2O$=0:100 increasing to methanol/$H_2O$=90:10 within 20 min; Detector—UV 254 nm. This process afforded 100 mg of (E)-2-(7-azabicyclo[2.2.1]heptan-7-yl)-1-(1-(4-chlorophenyl)-2-methyl-5-(4-(methylsulfonyl)but-1-en-1-yl)-1H-pyrrol-3-yl)ethan-1-one (34B). Mass Spectrum (LCMS, ESI pos.): Calcd. for $CH_2ClN_2O_3S$: 461 (M+H); found 461. $^1$H-NMR (300 MHz, DMSO-$d_6$) δ 7.62-7.65 (m, 2H), 7.35 (d, J=8.7 Hz, 2H), 6.92 (s, 1H), 5.72-5.75 (m, 1H), 5.48-5.54 (m, 2H), 3.56 (s, 2H), 3.30-3.32 (m, 2H), 3.25-3.27 (m, 2H), 3.01 (s, 3H), 2.73-2.80 (m, 2H), 2.26 (s, 3H), 1.67-1.69 (m, 4H), 1.23-1.25 (m, 4H).

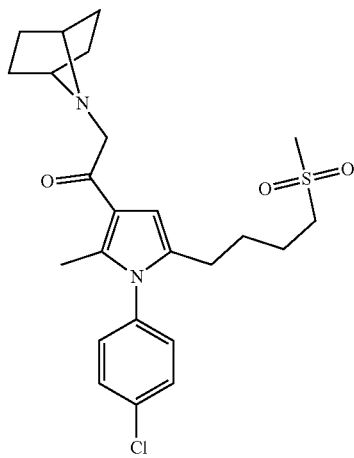 [SMILES: Cc1c(C(=O)CN2C3CCC2CC3)cc(CCCCS(C)(=O)=O)n1-c1ccc(Cl)cc1]

D. 2-(7-Azabicyclo[2.2.1]heptan-7-yl)-1-(1-(4-chlorophenyl)-2-methyl-5-(4-(methylsulfonyl)butyl)-1H-pyrrol-3-yl)ethan-1-one (18B)

Into a 50 mL round-bottom flask was placed a solution of (E)-2-(7-azabicyclo[2.2.1]heptan-7-yl)-1-(1-(4-chlorophenyl)-2-methyl-5-(4-(methylsulfonyl)but-1-en-1-yl)-1H-pyrrol-3-yl)ethan-1-one (34B) (200 mg, 0.43 mmol) in ethyl acetate (20 mL), to which was then added palladium on carbon (50 mg). The mixture was purged with hydrogen gas and the mixture was allowed to stir for at room temperature for 12 h. The solids were filtered from the reaction mixture and the filtrate was concentrated under vacuum. The crude product was purified by preparative-HPLC under the following conditions: Column (Waters)-X Bridge C18, 19*150 mm, 5 μm; Mobile Phase A-Water with 0.5% $NH_4HCO_3$, Mobile Phase B-ACN; Flow rate-20 mL/min; Gradient-35% B to 65% B in 10 min; Detector-UV 254 nm. This process afforded 12 mg (6%) of 2-(7-azabicyclo[2.2.1]heptan-7-yl)-1-(1-(4-chlorophenyl)-2-methyl-5-(4-(methylsulfonyl)butyl)-1H-pyrrol-3-yl)ethan-1-one (18B) as an off-white solid. Mass Spectrum (LCMS, ESI pos.): Calcd. for $CH_{31}ClN_2O_3S$: 463 (M+H); found: 463. $^1$H NMR (300 MHz, DMSO-$d_6$): δ 7.62-7.64 (m, 2H), 7.31-7.39 (m, 2H), 6.77 (s, 0.3H), 6.49 (s, 0.7H), 3.51 (s, 2H), 3.33-3.34 (m, 4H), 3.00-3.02 (m, 2H), 2.90 (s, 3H), 2.28-2.32 (m, 2H), 2.21 (s, 3H), 1.49-1.67 (m, 8H), 1.23-1.25 (m, 4H).

Example 23B. 4-(3-(2-(7-Azabicyclo[2.2.1]heptan-7-yl)acetyl)-2-methyl-5-(4-(methylsulfonyl)butyl)-1H-pyrrol-1-yl)benzonitrile (30B)

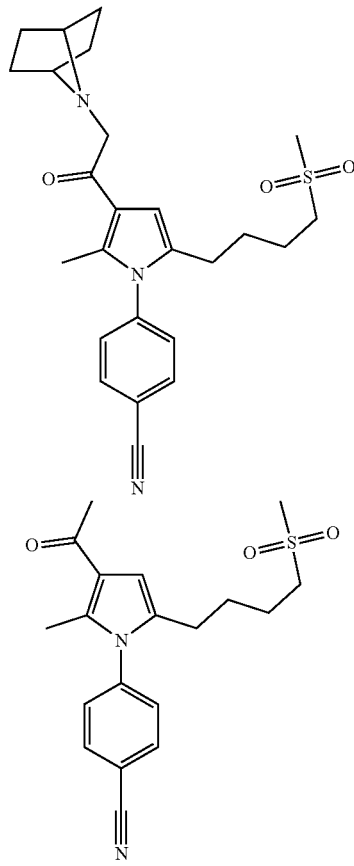

A. 4-(3-Acetyl-2-methyl-5-(4-(methylsulfonyl) butyl)-1H-pyrrol-1-yl)benzonitrile Into a 100 mL round-bottom flask was placed a mixture of (E)-4-(3-acetyl-2-methyl-5-(4-(methylsulfonyl)but-1-en-1-yl)-1H-pyrrol-1-yl)benzonitrile (1.25 g, 3.51 mmol; prepared via methods analogous to those described in Example 19B), ethyl acetate (20 mL) and palladium on carbon (400 mg). The purged with hydrogen and the resulting mixture was allowed to stir overnight at room temperature. The reaction mixture was then diluted with ethyl acetate (50 mL) and filtered to remove the solids. The filtrate was concentrated under vacuum and the remaining residue was purified by column chromatography on silica gel using ethyl acetate/petroleum ether (2:3) as the eluant to afford 83 mg (7%) of 4-(3-Acetyl-2-methyl-5-(4-(methylsulfonyl)butyl)-1H-pyrrol-1-yl)benzonitrile as an off-white solid. Mass Spectrum (LCMS, ESI pos.): Calcd. for $C_{19}H_{22}N_2O_3S$: 359 (M+H); found 359. $^1$H-NMR (300 MHz, DMSO-$d_6$)δ 8.07 (d, 2H, J=8.4 Hz), 7.60 (d, 2H, J=8.4 Hz), 6.55 (s, 1H), 3.04-2.96 (m, 2H), 2.90 (s, 3H), 2.38-2.30 (m, 5H), 2.21 (s, 3H), 1.66-1.44 (m, 4H).

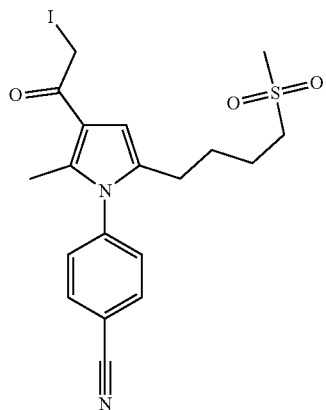 [SMILES: Cc1c(C(=O)CI)cc(CCCCS(C)(=O)=O)n1-c1ccc(C#N)cc1]

B. 4-(3-(2-Iodoacetyl)-2-methyl-5-(4-(methylsulfonyl)butyl)-1H-pyrrol-1-yl)benzonitrile Into a 25 mL round-bottom flask was placed a solution of 4-(3-acetyl-2-methyl-5-(4-(methylsulfonyl)butyl)-1H-pyrrol-1-yl)benzonitrile (83 mg, 0.23 mmol) in tetrahydrofuran (4 mL). To the solution was added TMSOTf (103 mg, 0.46 mmol) and diisopropylethylamine (120 mg, 0.93 mmol). The resulting mixture was allowed to stir at −16° C. for 1 h and then N-iodosuccinimide (66 mg, 0.30 mmol) was added. The resulting mixture was allowed to stir at −16° C. for 1 h before it was diluted with water (10 mL). The aqueous mixture was extracted with ethyl acetate (3×30 mL) and the combined organic extracts were dried over anhydrous sodium sulfate and concentrated under vacuum. The remaining residue was purified by column chromatography on silica gel using ethyl acetate/petroleum ether (3:1) as the eluant to afford 80 mg (71%) of 4-(3-(2-iodoacetyl)-2-methyl-5-(4-(methylsulfonyl)butyl)-1H-pyrrol-1-yl)benzonitrile as a light yellow solid. Mass Spectrum (LCMS, ESI pos.): Calcd. for $C_{19}H_{21}IN_2O_3S$: 485 (M+H); found 485.

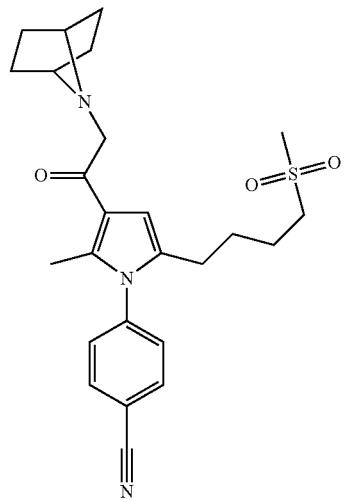 [SMILES: Cc1c(C(=O)CN2C3CCC2CC3)cc(CCCCS(C)(=O)=O)n1-c1ccc(C#N)cc1]

C. 4-(3-(2-(7-Azabicyclo[2.2.1]heptan-7-yl)acetyl)-2-methyl-5-(4-(methylsulfonyl)butyl)-1H-pyrrol-1-yl)benzonitrile (30B)

Into a 100 mL round-bottom flask was placed a solution of 4-(3-(2-iodoacetyl)-2-methyl-5-(4-(methylsulfonyl)butyl)-1H-pyrrol-1-yl)benzonitrile (83 mg, 0.17 mmol) in N,N-dimethylformamide (5 mL). To the solution were added potassium carbonate (118 mg, 0.86 mmol) and 7-azabicyclo[2.2.1]heptane (50 mg, 0.51 mmol). The resulting mixture was allowed to stir at room temperature overnight. The insoluble material was filtered from the reaction mixture and the filtrate was concentrated under vacuum. The remaining residue was purified by preparative HPLC under the following conditions: Column—XBridge C18 OBD Prep Column, 5 μm, 19 mm×150 mm; mobile phase—Water with 0.5% NH$_4$HCO$_3$ and ACN (15.0% ACN up to 45.0% in 6 min); Detector—UV 254 nm. This process afforded 49 mg (62%) of 4-(3-(2-(7-azabicyclo[2.2.1]heptan-7-yl)acetyl)-2-methyl-5-(4-(methylsulfonyl)butyl)-1H-pyrrol-1-yl)benzonitrile (30B) as an off-white solid. Mass Spectrum (LCMS, ESI pos.): Calcd. for $C_{25}H_{31}N_3O_3S$: 454 (M+H); found 454. $^1$H-NMR (400 MHz, DMSO-$d_6$) δ 8.07 (d, 2H, J=8.4 Hz), 7.60 (d, 2H, J=8.4 Hz), 6.54 (s, 1H), 3.53 (s, 2H), 3.35-3.33 (m, 2H), 3.02-3.00 (m, 2H), 2.90 (s, 3H), 2.34-2.31 (m, 2H), 2.23 (s, 3H), 1.63-1.57 (m, 6H), 1.52-1.48 (m, 2H), 1.27-1.25 (m, 4H).

Using the procedures described in Examples 19B through 23B, reagents, starting materials, and conditions known to those skilled in the art, the following compounds representative of the present invention were prepared:

| Cpd | Data |
|---|---|
| 4B | (±)-4-(5-4(1s,3S)-3-cyanocyclobutyl)methyl)-3-(2-((1R,2R,4S)-2-hydroxy-7-azabicyclo[2.2.1]heptan-7-yl)acetyl)-2-methyl-1H-pyrrol-1-yl)benzonitrile<br>Mass Spectrum (LCMS, ESI pos.): Calcd. for $C_{26}H_{28}N_4O_2$: 429 (M + H); found: 429. $^1$H NMR (300 MHz, DMSO-$d_6$): δ 8.07 (d, J = 8.0 Hz, 2H), 7.59 (d, J = 8.0 Hz, 2H), 6.48 (s, 1H), 4.68-4.67 (m, 1H), 4.05 (brs, 1H), 3.54 (s, 2H), 2.28-2.25 (m, 2H), 3.18-3.09 (m, 1H), 2.51-2.41 (m, 5H), 2.20 (s, 3H), 1.99-97 (m, 2H), |

| Cpd | Data |
|---|---|
| | 1.88-1.86 (m, 2H), 1.75-1.73 (m, 1H), 1.54-1.51 (m, 1H), 1.30-1.24 (m, 1H), 0.80-0.77 (m, 1H). |
| 7B | 4-(3-(2-((1R,3r,5S)-3-Hydroxy-8-azabicyclo[3.2.1]octan-8-yl)acetyl)-2-methyl-5-(4-(methylsulfonyl)butyl)-1H-pyrrol-1-yl)benzonitrile<br>Mass Spectrum (LCMS, ESI pos.): Calcd. for $C_{26}H_{33}N_3O_4S$: 484 (M + H); found: 484. $^1$H NMR (400 MHz, DMSO-$d_6$): δ 8.06 (d, 2H, J = 8.4 Hz), 7.59 (d, 2H, J = 8.4 Hz), 6.57 (s, 1H), 4.27 (s, 1H), 3.82 (brs, 1H), 3.49 (s, 2H), 3.13 (brs, 2H), 3.03-3.01 (m, 2H), 2.99 (s, 3H), 2.34-2.31 (m, 2H), 2.22 (s, 3H), 2.07-2.02 (m, 2H), 1.92-1.91 (m, 2H), 1.82-1.81 (m, 2H), 1.64-4.56 (m, 6H). |
| 8B | (±)-4-(3-(2-((1R,2R,4S)-2-Hydroxy-7-azabicyclo[2.2.1]heptan-7-yl)acetyl-2-methyl-5-(4-(methylsulfonyl)butyl)-1H-pyrrol-1-yl)benzonitrile<br>Mass Spectrum (LCMS, ESI pos.): Calcd. for $C_{25}H_{31}N_3O_4S$: 470 (M + H); found: 470. $^1$H NMR (400 MHz, DMSO-$d_6$): δ 8.06 (d, 2H, J = 8.4 Hz), 7.59 (d, 2H, J = 8.4 Hz), 6.52 (s, 1H), 4.67 (d, 1H, J = 4.0 Hz), 4.05 (m, 1H), 3.55 (s, 2H), 3.30-3.27 (m, 2H), 3.03-3.02 (m, 2H), 2.90 (s, 3H), 2.34-2.32 (m, 2H), 2.21 (s, 3H), 2.01-1.95 (m, 2H), 1.75-1.64 (m, 1H), 1.60-1.58 (m, 2H), 1.56-1.46 (m, 3H), 1.34-1.28 (m, 1H), 0.79-0.76 (m, 1H). |
| 26B | (Z)-4-(3-(2-(7-Azabicyclo[2.2.1]heptan-7-yl)acetyl-2-methyl-5-(4-(methylsulfonyl)but-1-en-1-yl)-1H-pyrrol-1-yl)benzonitrile<br>Mass Spectrum (LCMS, ESI pos.): Calcd. for $C_{25}H_{29}N_3O_3S$: 452 (M + H); found: 452. $^1$H NMR (400 MHz, DMSO-$d_6$): δ 8.05 (d, 2H, J = 8.4 Hz), 7.55 (d, 2H, J = 8.4 Hz), 6.96 (s, 1H), 5.72-5.69 (m, 1H), 5.52-5.49 (m, 1H), 3.56 (s, 2H), 3.28-3.24 (m, 4H), 3.00 (s, 3H), 2.76-2.74 (m, 2H), 2.26 (s, 3H), 1.67-1.66 (m, 4H), 1.23-1.22 (m, 4H). |
| 29B | (±)-5-(1-(4-Chlorophenyl)-4-(2-((1R,2R,4S)-2-hydroxy-7-azabicyclo[2.2.1]heptan-7-yl)acetyl)-5-methyl-1H-pyrrol-2-yl)pentanenitrile<br>Mass Spectrum (LCMS, ESI pos.): Calcd. for $C_{24}H_{28}ClN_3O_2$: 426 (M + H); found: 426. $^1$H NMR (300 MHz, DMSO-$d_6$): δ 7.63 (d, J = 8.7 Hz, 2H), 7.38 (d, J = 8.7 Hz, 2H), 6.77 (s, 1H), 4.87-4.63 (m, 1H), 4.20-4.09 (m, 1H), 3.65-3.55 (m, 2H), 3.30-3.23 (m, 2H), 2.44-2.40 (m, 2H), 2.38-2.34 (m, 2H), 2.30 (s, 3H), 2.10-1.97 (m, 2H), 1.87-1.77 (m, 1H), 1.61-1.47 (m, 5H), 1.39-1.36 (m, 1H), 0.90-0.81 (m, 1H). |
| 31B | 5-(4-(2-(7-Azabicyclo[2.2.1]heptan-7-yl)acetyl)-1-(4-chlorophenyl)-5-methyl-1H-pyrrol-2-yl)pentanenitrile<br>Mass Spectrum (LCMS, ESI pos.): Calcd. for $C_{26}H_{28}N_4O_2$: 410 (M + H); found: 410. $^1$H NMR (300 MHz, DMSO-$d_6$): δ 7.65-7.60 (m, 2H), 7.40-7.35 (m, 2H), 6.50 (s, 1H), 3.54 (s, 2H), 3.34-3.22 (m, 2H), 2.44-2.40 (m, 2H), 2.32-2.27 (m, 2H), 2.21 (s, 3H), 1.68-1.65 (m, 4H), 1.48-1.46 (m, 4H), 1.24-1.18 (m, 4H). |
| 35B | (E)-4-(3-(2-(7-Azabicyclo[2.2.1]heptan-7-yl)acetyl)-2-methyl-5-(4-(methylsulfonyl)but-1-en-1-yl)-1H-pyrrol-1-yl)benzonitrile<br>Mass Spectrum (LCMS, ESI pos.): Calcd. for $C_{25}H_{29}N_3O_3S$: 452 (M + H); found: 452. $^1$H NMR (400 MHz, DMSO-$d_6$): δ 8.06 (d, 2H, J = 8.4 Hz), 7.54 (d, 2H, J = 8.4 Hz), 6.96 (s, 1H), 6.00-5.93 (m, 1H), 5.84 (d, 1H, J = 16.0 Hz), 3.57 (s, 2H), 3.34-3.31 (m, 2H), 3.13-3.11 (m, 2H), 2.92 (s, 3H), 2.49-2.48 (m, 2H), 2.24 (s, 3H), 1.67-1.66 (m, 4H), 1.25-1.23 (m, 4H). |
| 38B | (±)-4-(3-(2-((1R,2R,4S)-2-Hydroxy-7-azabicyclo[2.2.1]heptan-7-yl)acetyl)-2-methyl-5-(5-(methylthio)pentyl)-1H-pyrrol-1-yl)benzonitrile<br>Mass Spectrum (LCMS, ESI pos.): Calcd. for $C_{26}H_{33}N_3O_2S$: 452 (M + H); found: 452. $^1$H NMR (300 MHz, DMSO-$d_6$): δ 8.06 (d, J = 8.4 Hz, 2H), δ 7.59 (d, J = 8.4 Hz, 2H), 6.51 (s, 1H), 4.66 (d, J = 3.9 Hz, 1H), 4.03-4.05 (m, 1H), 3.55 (s, 2H), 3.23-3.26 (m, 2H), 2.25-2.38 (m, 4H), 2.21 (s, 3H), 1.99-2.03 (m, 5H), 1.76-1.94 (m, 1H), 1.49-1.54 (m, 1H), 1.15-1.49 (m, 7H), 0.75-0.81 (m, 1H). |

Example 24B. (±)-4-(5-(4-Cyanobut-1-yn-1-yl)-3-(2-((2R)-2-hydroxy-7-azabicyclo[2.2.1]heptan-7-yl)acetyl)-2-methyl-1H-pyrrol-1-yl)benzonitrile (10B)

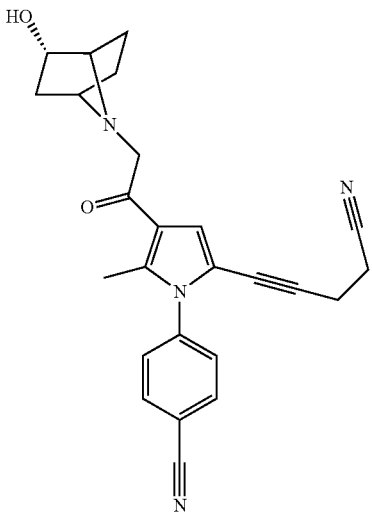 [SMILES: Cc1c(C(=O)CN2C3CCC2[C@@H](O)C3)cc(C#CCCC#N)n1-c1ccc(C#N)cc1]

A. 4-(3-Acetyl-5-(4-cyanobut-1-yn-1-yl)-2-methyl-1H-pyrrol-1-yl)benzonitrile

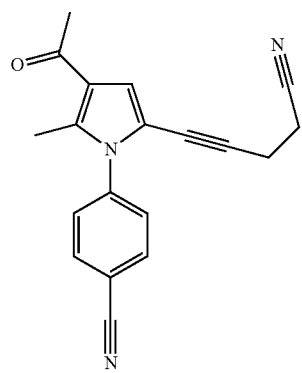

Into a 250 mL, 3-necked round-bottom flask, being maintained under an atmosphere of nitrogen, was placed a mixture of 4-(3-acetyl-5-iodo-2-methyl-1H-pyrrol-1-yl)benzonitrile (5.00 g, 14.3 mmol), pent-4-ynenitrile (1.7 g, 21.5 mmol), copper(I) iodide (135 mg, 0.71 mmol), Pd(PPh$_3$)$_2$Cl$_2$ (500 mg, 0.71 mmol) and tetrahydrofuran (100 mL). To this mixture was added triethylamine (14.2 g, 140 mmol) and the resulting mixture was heated at 60° C. overnight. After cooling to room temperature, the reaction mixture was diluted with water (300 mL) and then extracted with ethyl acetate (2×300 mL). The combined organic extracts were washed with brine (2×50 mL), dried over anhydrous sodium sulfate and then concentrated under vacuum. The remaining residue was purified by column chromatography on silica gel using ethyl acetate/petroleum ether (1:4) as the eluent to afford 3.78 g (88%) of 4-(3-acetyl-5-(4-cyanobut-1-yn-1-yl)-2-methyl-1H-pyrrol-1-yl)benzonitrile as a brown solid. Mass Spectrum (LCMS, ESI pos.): Calcd. for C$_{19}$H$_{15}$N$_3$O: 302 (M+H); found: 302. $^1$H NMR (400 MHz, CDCl$_3$): δ 7.85-7.82 (m, 2H), 7.45-7.43 (m, 2H), 6.88 (s, 1H), 2.63-2.60 (m, 2H), 2.48-2.45 (m, 2H), 2.44 (s, 3H), 2.40 (s, 3H).

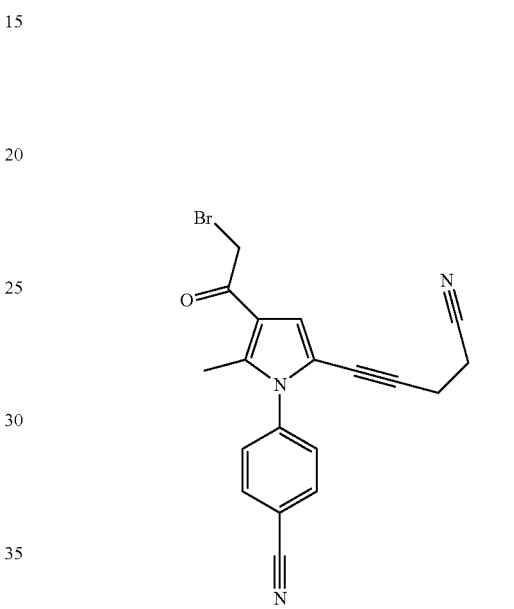

B. 4-(3-(2-Bromoacetyl)-5-(4-cyanobut-1-yn-1-yl)-2-methyl-1H-pyrrol-1-yl)benzonitrile Into a 50 mL, 3-necked round-bottom, being maintained under an atmosphere of nitrogen, was placed a mixture of 4-(3-acetyl-5-(4-cyanobut-1-yn-1-yl)-2-methyl-1H-pyrrol-1-yl)benzonitrile (300 mg, 1.00 mmol), diisopropylethylamine (516 mg, 3.99 mmol) and tetrahydrofuran (25 mL). The mixture was then cooled to 0° C. and treated with TMSOTf (450 mg, 2.02 mmol) in a dropwise manner. The resulting mixture was allowed to stir at 0° C. for 1 h and then NBS (190 mg, 1.07 mmol) was added. The reaction mixture was allowed to stir for 10 min before it was diluted with water (10 mL). The aqueous mixture was extracted with ethyl acetate (2×30 mL) and the combined organic extracts were dried over anhydrous sodium sulfate and concentrated under vacuum. The remaining residue was purified by preparative-TLC using ethyl acetate/petroleum ether (1:2) to afford 50 mg (13%) of 4-(3-(2-bromoacetyl)-5-(4-cyanobut-1-yn-1-yl)-2-methyl-1H-pyrrol-1-yl)benzonitrile as a yellow solid. Mass Spectrum (LCMS, ESI pos.): Calcd. for C$_{19}$H$_{14}$BrN$_3$O: 380 (M+H); found: 380.

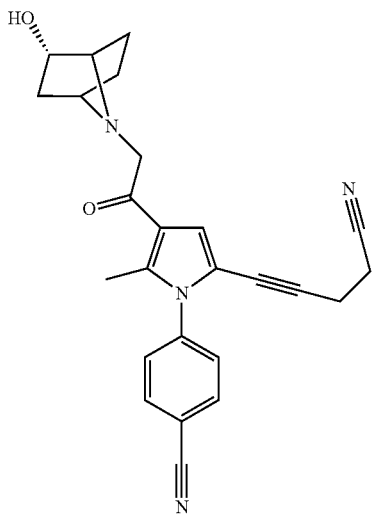

C. (±)-4-(5-(4-Cyanobut-1-yn-1-yl)-3-(2-((2R)-2-hydroxy-7-azabicyclo[2.2.1]heptan-7-yl)acetyl)-2-methyl-1H-pyrrol-1-yl)benzonitrile (10B)

Into a 50 mL, 3-necked round-bottom flask, being maintained under an atmosphere of nitrogen, was placed a mixture of 4-(3-(2-bromoacetyl)-5-(4-cyanobut-1-yn-1-yl)-2-methyl-1H-pyrrol-1-yl)benzonitrile (200 mg, 0.53 mmol), (±)-(1R,2R,4S)-7-azabicyclo[2.2.1]heptan-2-ol hydrochloride (298 mg, 1.99 mmol), potassium carbonate (460 mg, 3.33 mmol) and tetrahydrofuran (25 mL). The resulting mixture was allowed to stir overnight at room temperature before it was diluted with water (30 mL). The aqueous mixture was extracted with ethyl acetate (2×50 mL) and the combined organic layers were washed with brine (2×25 mL), dried over $Na_2SO_4$ and concentrated under reduced pressure. The remaining residue was purified by preparative-HPLC under the following conditions: Column—XBridge BEH130 Prep C18 OBD Column, 19*150 mm 5 μm; Mobile Phase A: water with 0.05% $NH_4HCO_3$, Mobile Phase B: ACN, Gradient—30% B increasing to 65% B in 7 min; Detector—UV 254 nm. This process afforded 29 mg (13%) of (±)-4-(5-(4-cyanobut-1-yn-1-yl)-3-(2-((2R)-2-hydroxy-7-azabicyclo[2.2.1]heptan-7-yl)acetyl)-2-methyl-1H-pyrrol-1-yl)benzonitrile (10B) as a white solid. Mass Spectrum (LCMS, ESI pos.): Calcd. for $C_{25}H_{24}N_4O_2$: 413 (M+H); found: 413. $^1$H NMR (400 MHz, DMSO-$d_6$): δ 8.02-8.01 (m, 2H), 7.63-7.61 (m, 2H), 7.11 (s, 1H), 4.66 (s, 1H), 4.03-4.00 (m, 1H), 3.55 (s, 2H), 3.23-3.20 (m, 2H), 2.61-2.56 (m, 4H), 2.31 (s, 3H), 1.98-1.95 (m, 2H), 1.73-1.71 (m, 1H), 1.52-1.48 (m, 1H), 1.32-1.27 (m, 1H), 0.78-0.74 (m, 1H).

Using the procedures described in Example 24B, reagents, starting materials, and conditions known to those skilled in the art, the following compounds representative of the present invention were prepared:

| Cpd | Data |
|---|---|
| 3B | 4-(3-(2-(7-Azabicyclo[2.2.1]heptan-7-yl)acetyl)-5-(4-cyanobut-1-yn-1-yl)-2-methyl-1H-pyrrol-1-yl)benzonitrile<br>Mass Spectrum (LCMS, ESI pos.): Calcd. for $C_{25}H_{24}N_4O$: 397 (M + H); found: 397. $^1$H NMR (400 MHz, DMSO-$d_6$): δ 8.03-8.00 (m, 2H), 7.64-7.61 (m, 2H), 7.12 (s, 1H), 3.52 (s, 2H), 2.65-2.60 (m, 4H), 2.32 (s, 3H), 1.66-1.64 (m, 4H), 1.28-1.23 (m, 4H). |
| 21B | 4-(3-(2-((1r,3r,5r,7r)-2-Oxa-6-azaadamantan-6-yl)acetyl)-5-(4-cyanobut-1-yn-1-yl)-2-methyl-1H-pyrrol-1-yl)benzonitrile<br>Mass Spectrum (LCMS, ESI pos.): Calcd. for $C_{27}H_{26}N_4O_2$: 439 (M + H); found: 439. $^1$H NMR (300 MHz, DMSO-$d_6$): δ 8.03 (d, J = 8.4 Hz, 2H), 7.64 (d, J = 8.4 Hz, 2H), 7.20 (s, 1H), 4.16-3.93 (m, 2H), 3.85 (s, 2H), 3.01 (s, 2H), 2.59 (s, 4H), 2.32 (s, 3H), 2.01-1.85 (m, 4H), 1.80-1.68 (m, 4H). |

Example 25B. (±)-4-(5-(3-(1H-Pyrazol-1-yl)propyl)-3-(2-((2R)-2-hydroxy-7-azabicyclo[2.2.1]heptan-7-yl)acetyl)-2-methyl-1H-pyrrol-1-yl)benzonitrile (24B)

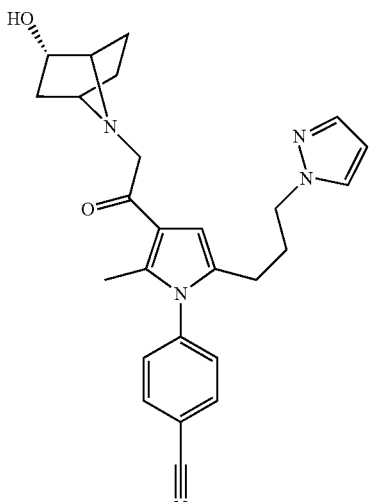

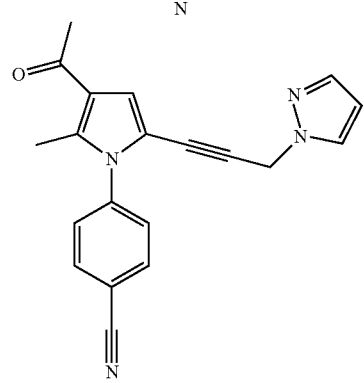

A. 4-(5-(3-(1H-Pyrazol-1-yl)prop-1-yn-1-yl)-3-acetyl-2-methyl-1H-pyrrol-1-yl)benzonitrile Into a 100 mL round-bottom flask, being maintained under an inert atmosphere of nitrogen, was placed a mixture of 4-(3-acetyl-5-iodo-2-methyl-1H-pyrrol-1-yl)benzonitrile (350 mg, 1.00 mmol) and 1-(prop-2-yn-1-yl)-1H-pyrazole (159 mg, 1.50 mmol) in tetrahydrofuran (5 mL). To this mixture were added triethylamine (1.01 g, 9.98 mmol), CuI (10 mg, 0.05 mmol) and Pd(PPh$_3$)$_2$Cl$_2$ (35 mg, 0.05 mmol). The resulting was heated at 60° C. overnight. After cooling to room temperature the mixture was diluted with ethyl acetate (100 mL) and the mixture was washed with brine (3×50 mL). The organic phase was then dried over anhydrous sodium sulfate and concentrated under vacuum. The remaining residue was purified by column chromatography on silica gel using ethyl acetate/petroleum ether (1:5-1:4) as the eluant to afford 140 mg (43%) of 4-(5-(3-(1H-pyrazol-1-yl)prop-1-yn-1-yl)-3-acetyl-2-methyl-1H-pyrrol-1-yl)benzonitrile. Mass Spectrum (LCMS, ESI pos.): Calcd. for C$_{20}$H$_{16}$N$_4$O: 329 (M+H); found: 329. $^1$H NMR (400 MHz, DMSO-d$_6$): δ 8.02 (d, J=8.4 Hz, 2H), 7.62 (d, J=8.4 Hz, 2H), 7.57 (d, J=2.0 Hz, 1H), 7.45 (d, J=1.2 Hz, 1H), 7.16 (s, 1H), 6.25-6.24 (m, 1H), 5.12 (s, 2H), 2.44 (s, 3H), 2.42 (s, 3H).

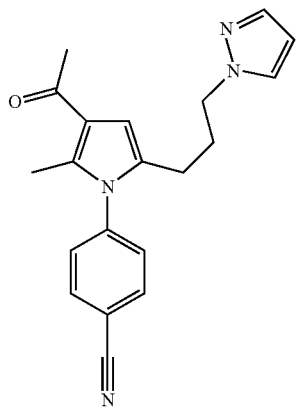 [SMILES: CC(=O)c1cc(CCCn2cccn2)n(-c2ccc(C#N)cc2)c1C]

B. 4-(5-(3-(1H-pyrazol-1-yl)propyl)-3-acetyl-2-methyl-1H-pyrrol-1-yl)benzonitrile Into a 100 mL round-bottom flask, being maintained under an inert atmosphere of nitrogen, was placed a solution of 4-(5-(3-(1H-pyrazol-1-yl)prop-1-yn-1-yl)-3-acetyl-2-methyl-1H-pyrrol-1-yl)benzonitrile (300 mg, 0.91 mmol) in ethyl acetate (40 mL). Then solid palladium on carbon (60 mg) was added to the flask. The resulting mixture was purged with hydrogen and then maintained under a stable atmosphere of hydrogen. The reaction mixture was allowed to stir overnight at room temperature before it was filtered. The filtrate was concentrated under vacuum to afford 290 mg (95%) of 4-(5-(3-(1H-pyrazol-1-yl)propyl)-3-acetyl-2-methyl-1H-pyrrol-1-yl)benzonitrile as a yellow solid. Mass Spectrum (LCMS, ESI pos.): Calcd. for C$_{20}$H$_{20}$N$_4$O: 333 (M+H); found: 333.

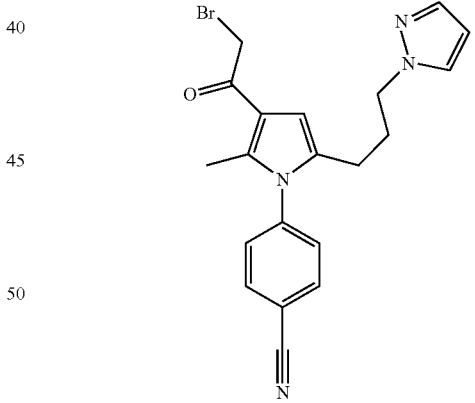

C. 4-(5-(3-(1H-Pyrazol-1-yl)propyl)-3-(2-bromoacetyl)-2-methyl-1H-pyrrol-1-yl)benzonitrile Into a 50 mL round-bottom flask, being maintained under an inert atmosphere of nitrogen, was placed a mixture of 4-(5-(3-(1H-pyrazol-1-yl)propyl)-3-acetyl-2-methyl-1H-pyrrol-1-yl)benzonitrile (310 mg, 0.93 mmol) and diisopropylethylamine (361 mg, 2.79 mmol) in tetrahydrofuran (10 mL). The mixture was cooled to 0° C. and then treated with TMSOTf (415 mg, 1.87 mmol) in a dropwise fashion. The solution was allowed to stir at 0° C. for 1 h and then a solution of NBS (199 mg, 1.12 mmol) in THF was added in a dropwise fashion. The resulting mixture was allowed to warm to room temperature and stir for 1 hour before being diluted with brine (50 mL). The biphasic mixture was extracted with ethyl acetate (2×150 mL) and the combined organic extracts were washed with brine (3×100 mL), dried over sodium sulfate and concentrated under vacuum. The remaining residue was purified by column chromatography on silica gel using petroleum ether/ethyl acetate (1:1) as the eluant to afford 250 mg (65%) of 4-(5-(3-(1H-pyrazol-1-yl)propyl)-3-(2-bromoacetyl)-2-methyl-1H-pyrrol-1-yl)benzonitrile as a yellow solid. Mass Spectrum (LCMS, ESI pos.): Calcd. for $C_{20}H_{19}BrN_4O$: 411 (M+H); found: 411.

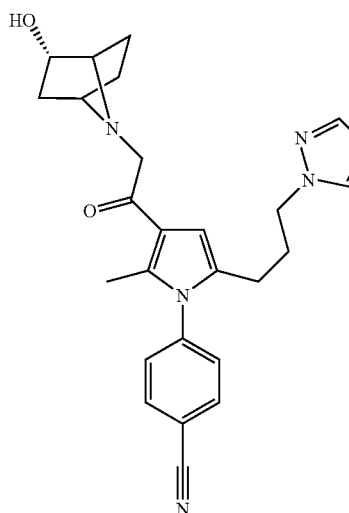

D. (±)-4-(5-(3-(1H-pyrazol-1-yl)propyl)-3-(2-((2R)-2-hydroxy-7-azabicyclo[2.2.1]heptan-7-yl)acetyl)-2-methyl-1H-pyrrol-1-yl)benzonitrile (24B)

Into a 25 mL round-bottom flask, being maintained under an inert atmosphere of nitrogen, was placed a solution of 4-(5-(3-(1H-pyrazol-1-yl)propyl)-3-(2-bromoacetyl)-2-methyl-1H-pyrrol-1-yl)benzonitrile (250 mg, 0.61 mmol) in N,N-dimethylformamide (3 mL). To this was added solid potassium carbonate (252 mg, 1.82 mmol) and (±)-(1S,2S,4R)-7-azabicyclo[2.2.1]heptan-2-ol (137 mg, 0.91 mmol). The resulting mixture was allowed to stir overnight at room temperature before it was filtered. The filtrate was condensed in vacuo and the remaining crude product was purified by preparative-HPLC under the following conditions: Column-XBridge C18 OBD Prep Column, 19 mm×250 mm; mobile phase-Mobile Phase A: water with 0.05% $NH_4HCO_3$, Mobile Phase B: acetonitrile; Flow rate- 25 mL/min; Gradient-35% B to 40% B in 8 min; Detector— 254 nm. This process afforded 148 mg (55%) of (±)-4-(5-(3-(1H-pyrazol-1-yl)propyl)-3-(2-((2R)-2-hydroxy-7-azabicyclo[2.2.1]heptan-7-yl)acetyl)-2-methyl-1H-pyrrol-1-yl)benzonitrile (24B) as a light yellow solid. Mass Spectrum (LCMS, ESI pos.): Calcd. for $C_{26}H_{29}N_5O_2$: 444 (M+H); found: 444. $^1$H NMR (400 MHz, DMSO-$d_6$): δ 8.02 (d, J=8.4 Hz, 2H), 7.57 (d, J=2.1 Hz, 1H), 7.53 (d, J=8.4 Hz, 2H), 7.35 (d, J=1.8 Hz, 1H), 6.53 (s, 1H), 6.16-6.15 (m, 1H), 4.65 (d, J=4.2 Hz, 1H), 4.09-3.99 (m, 3H), 3.55 (s, 2H), 3.25-3.22 (m, 2H), 2.27-2.19 (m, 5H), 2.00-1.70 (m, 5H), 1.58-1.42 (m, 1H), 1.37-1.24 (m, 1H), 0.82-0.70 (m, 1H).

Example 26B. (±)-4-(3-(2-((2R)-2-Hydroxy-7-azabicyclo[2.2.1]heptan-7-yl)acetyl)-2-methyl-5-(2-(trimethylsilyl)ethyl)-1H-pyrrol-1-yl)benzonitrile (50B)

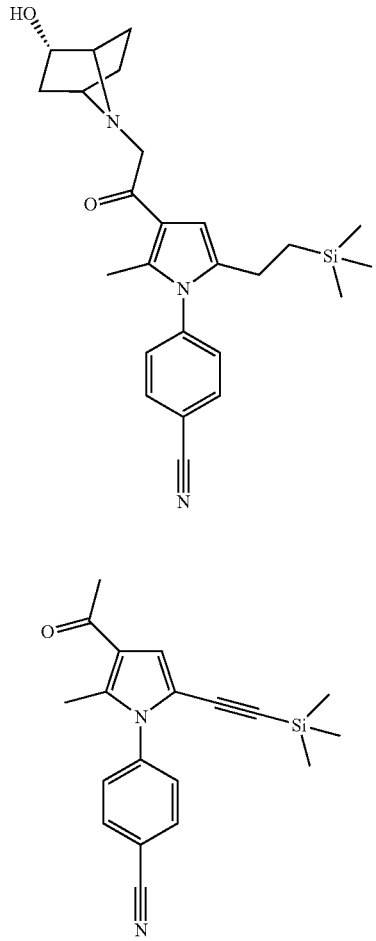 [SMILES: Cc1c(C(=O)CN2C3CCC2[C@@H](O)C3)cc(CC[Si](C)(C)C)n1-c1ccc(C#N)cc1 ; CC(=O)c1cc(C#C[Si](C)(C)C)n(-c2ccc(C#N)cc2)c1C]

A. 4-(3-Acetyl-2-methyl-5-((trimethylsilyl)ethynyl)-1H-pyrrol-1-yl)benzonitrile

Into a 20 mL sealed tube, being maintained under an inert atmosphere of nitrogen, was placed a mixture of 4-(3-acetyl-5-iodo-2-methyl-1H-pyrrol-1-yl)benzonitrile (1.05 g, 3.00 mmol), triethylamine (3.03 g, 30.0 mmol), ethynyltrimethylsilane (588 mg, 6.00 mmol), copper(I) iodide (114 mg, 0.60 mmol), $Pd(PPh_3)_2Cl_2$ (843 mg, 1.20 mmol), and tetrahydrofuran (10 mL). The resulting mixture was heated at 60° C. overnight. After cooling to room temperature the reaction mixture was diluted with brine and then extracted with ethyl acetate (3×30 mL). The combined organic extracts were washed with brine (2×40 mL), dried over anhydrous sodium sulfate and concentrated under vacuum. The remaining residue was purified by column chromatography on silica, using ethyl acetate/petroleum ether (1:10) as the eluant, to afford 945 mg (99%) of 4-(3-acetyl-2-methyl-5-((trimethylsilyl)ethynyl)-1H-pyrrol-1-yl)benzonitrile as a yellow solid. Mass Spectrum (LCMS, ESI pos.): Calcd. for $C_{19}H_{20}N_2OSi$: 321 (M+H); found 321.

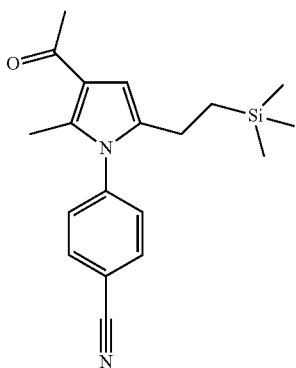 [SMILES: CC(=O)c1cc(CC[Si](C)(C)C)n(-c2ccc(C#N)cc2)c1C]

B. 4-(3-Acetyl-2-methyl-5-(2-(trimethylsilyl)ethyl)-1H-pyrrol-1-yl)benzonitrile Into a 30 mL pressure-tank reactor was placed a solution of 4-(3-acetyl-2-methyl-5-((trimethylsilyl)ethynyl)-1H-pyrrol-1-yl)benzonitrile (302 mg, 0.94 mmol) in ethyl acetate (20 mL). To the solution was added palladium on carbon (60 mg) and the resulting mixture was sparged with hydrogen. The reactor was pressurized with hydrogen to 5 atm and allowed to stir at room temperature for 5 h. After venting the reactor, the reaction mixture was diluted with ethyl acetate (30 mL) and then filtered. The filtrate was concentrated under vacuum and the remaining residue was purified by column chromatography on silica, using ethyl acetate/petroleum ether (1:4) as the eluant, to afford 280 mg (92%) of 4-(3-acetyl-2-methyl-5-(2-(trimethylsilyl)ethyl)-1H-pyrrol-1-yl)benzonitrile as a yellow oil. Mass Spectrum (LCMS, ESI pos.): Calcd. for $C_{19}H_{24}N_2OSi$: 325 (M+H); found 325. $^1$H-NMR (400 MHz, CDCl$_3$) δ 7.85-7.82 (m, 2H), 7.35-7.32 (m, 2H), 6.37 (s, 1H), 2.44 (s, 3H), 2.30 (s, 3H), 2.29-2.26 (m, 2H), 0.68-0.64 (m, 2H), 0.01 (s, 9H).

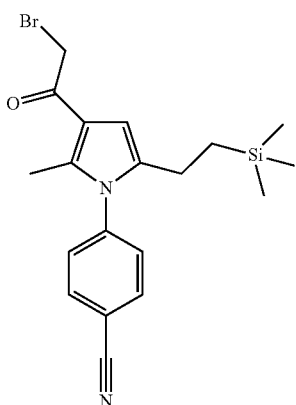 [SMILES: Cc1c(C(=O)CBr)cc(CC[Si](C)(C)C)n1-c1ccc(C#N)cc1]

C. 4-(3-(2-Bromoacetyl)-2-methyl-5-(2-(trimethylsilyl)ethyl)-1H-pyrrol-1-yl)benzonitrile Into a 50 mL round-bottom flask, being maintained under an inert atmosphere of nitrogen, was placed a mixture of 4-(3-acetyl-2-methyl-5-(2-(trimethylsilyl)ethyl)-1H-pyrrol-1-yl)benzonitrile (172 mg, 0.53 mmol), diisopropylethylamine (206 mg, 1.59 mmol), and tetrahydrofuran (8 mL). The mixture was cooled to 0° C. and then treated with trimethylsilyl trifluoromethylsulfonate (236 mg, 1.06 mmol). The resulting mixture was allowed to stir for 1.5 h at 0° C. and then a solution of N-bromosuccinimide (142 mg, 0.80 mmol) was added in a dropwise fashion. The reaction mixture was allowed to stir at 0° C. for 2 h before it was diluted with brine. The aqueous mixture was extracted with ethyl acetate (3×30 mL) and the combined organic extracts were dried over sodium sulfate. The organic layer was concentrated under vacuum and the remaining residue was purified by column chromatography on silica, using ethyl acetate/petroleum ether (1:3) as the eluant, to afford 340 mg (semi-crude) of 4-(3-(2-bromoacetyl)-2-methyl-5-(2-(trimethylsilyl)ethyl)-1H-pyrrol-1-yl)benzonitrile as a yellow oil. Mass Spectrum (LCMS, ESI pos.): Calcd. for $C_{19}H_{23}BrN_2OSi$: 403 (M+H); found 403.

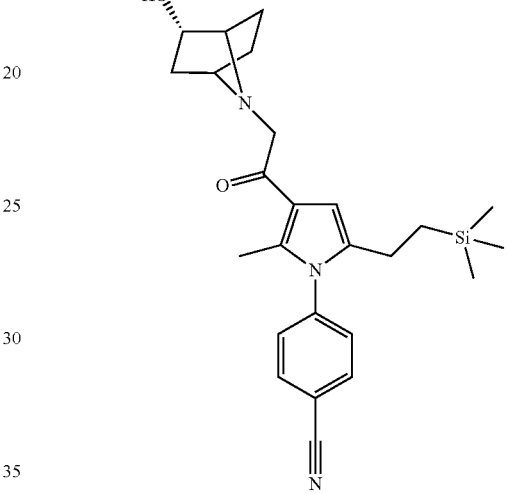

D. (±)-4-(3-(2-((2R)-2-Hydroxy-7-azabicyclo[2.2.1]heptan-7-yl)acetyl)-2-methyl-5-(2-(trimethylsilyl)ethyl)-1H-pyrrol-1-yl)benzonitrile (50B)

Into a 50 mL round-bottom flask was placed a mixture of 4-(3-(2-bromoacetyl)-2-methyl-5-(2-(trimethylsilyl)ethyl)-1H-pyrrol-1-yl)benzonitrile (340 mg, 0.84 mmol), racemic (1R,2R,5S)-5-amino-2-chlorocyclohexan-1-ol (189 mg, 1.26 mmol), potassium carbonate (232 mg, 1.68 mmol) and N,N-dimethylformamide (8 mL). The reaction mixture was allowed to stir overnight at room temperature. The crude product was purified by preparative-HPLC under the following conditions: Column-X Bridge C18 OBD Prep Column, 19 mm×250 mm; mobile phase-Water (10 mmol/L NH$_4$HCO$_3$) and acetonitrile (55% acetonitrile up to 70% in 8 min); Detector-UV 254/220 nm. This process afforded 130 mg (35%) of (±)-4-(3-(2-((2R)-2-hydroxy-7-azabicyclo[2.2.1]heptan-7-yl)acetyl)-2-methyl-5-(2-(trimethylsilyl)ethyl)-1H-pyrrol-1-yl)benzonitrile (50B) as a white solid. Mass Spectrum (LCMS, ESI pos.): Calcd. for $C_{25}H_{33}N_3O_2Si$: 436 (M+H); found 436. $^1$H-NMR (400 MHz, DMSO-d$_6$) δ 8.25 (d, J=8.4 Hz, 2H), 7.75 (d, J=8.4 Hz, 2H), 6.67 (s, 1H), 4.83 (d, J=4.0 Hz, 1H), 4.22-4.18 (m, 1H), 3.71 (s, 2H), 3.45-3.41 (m, 2H), 2.47-2.43 (m, 2H), 2.37 (s, 3H), 2.16-2.11 (m, 2H), 1.91-1.90 (m, 1H), 1.50-1.47 (m, 1H), 1.35-1.27 (m, 1H), 0.95-0.92 (m, 1H), 0.61-0.50 (m, 2H), 0.00 (s, 9H).

Using the procedures described in Examples 25B and 26B, reagents, starting materials, and conditions known to those skilled in the art, the following compounds representative of the present invention were prepared:

| Cpd | Data |
|---|---|
| 2B | (±)-4-(3-(2-((1S,2S,4R)-2-Hydroxy-7-azabicyclo[2.2.1]heptan-7-yl)acetyl)-2-methyl-5-(3-(tetrahydro-2H-pyran-4-yl)propyl)-1H-pyrrol-1-yl)benzonitrile<br>Mass Spectrum (LCMS, ESI pos.): Calcd. for $C_{28}H_{35}N_3O_3$: 462 (M + H); found: 462. $^1$H NMR (300 MHz, DMSO-$d_6$): δ 8.07 (d, J = 8.4 Hz, 2H), 7.58 (d, J = 8.4 Hz, 2H), 6.52 (s, 1H), 4.71-4.69 (m, 1H), 4.11-4.06 (m, 1H), 3.79-3.74 (m, 2H), 3.61 (brs, 2H), 3.19-3.15 (m, 2H), 2.27-2.22 (m, 5H), 2.01-1.99 (m, 3H), 1.78 (brs, 1H), 1.54-1.49 (m, 1H), 1.36-1.24 (m, 10H), 1.14-1.13 (m, 5H), 0.89-0.80 (m, 2H). |
| 12B | (rel)-4-(3-(2-((1R,2R,4S)-2-Hydroxy-7-azabicyclo[2.2.1]heptan-7-yl)acetyl)-5-(4-methoxybutyl)-2-methyl-1H-pyrrol-1-yl)benzonitrile<br>Mass Spectrum (LCMS, ESI pos.): Calcd. for $C_{25}H_{31}N_3O_3$: 422 (M + H); found: 422. $^1$H NMR (300 MHz, DMSO-$d_6$): δ 8.04 (d, J = 8.4 Hz, 2H), 7.57 (d, J = 8.4 Hz, 2H), 6.49 (s, 1H), 4.66-4.65 (m, 1H), 4.03-4.02 (m, 2H), 3.31 (s, 3H), 3.25-3.13 (m, 4H), 2.26.-2.22 (m, 2H), 2.19 (s, 3H), 2.00-1.91 (m, 2H), 1.74-1.70 (m, 1H), 1.52-1.31 (m, 7H), 0.80-0.75 (m, 1H). Retention time on a Phenomenex Lux 5 u Cellulose-3, 5 × 25 cm, 5 μm column with a hexanes and 0.1% diethylamine/ethanol (1:1) mobile phase: 1.6 min (first peak). |
| 13B | (rel)-4-(3-(2-((1S,2S,4R)-2-Hydroxy-7-azabicyclo[2.2.1]heptan-7-yl)acetyl)-5-(4-methoxybutyl)-2-methyl-1H-pyrrol-1-yl)benzonitrile<br>Mass Spectrum (LCMS, ESI pos.): Calcd. for $C_{25}H_{31}N_3O_3$: 422 (M + H); found: 422. $^1$H NMR (300 MHz, DMSO-$d_6$): δ 7.96-7.93 (m, 2H), 7.49-7.47 (m, 2H), 6.47 (s, 1H), 4.33-4.30 (m, 1H), 3.81-3.79 (m, 2H), 3.49-3.42 (m, 3H), 3.32-3.27 (m, 2H), 3.25 (s, 3H), 2.38-2.34 (m, 2H), 2.29 (s, 3H), 2.24-2.13 (m, 2H), 1.93-1.90 (m, 1H), 1.68-1.61 (m, 2H), 1.52-1.46 (m, 5H), 1.03-0.95 (m, 1H). Retention time on a Phenomenex Lux 5 u Cellulose-3, 5 × 25 cm, 5 μm column with a hexanes and 0.1% diethylamine/ethanol (1:1) mobile phase: 2.4 min (second peak). |
| 14B | (±)-4-(3-(2-((1S,2S,4R)-2-Hydroxy-7-azabicyclo[2.2.1]heptan-7-yl)acetyl)-2-methyl-5-(4-(tetrahydro-2H-pyran-4-yl)butyl)-1H-pyrrol-1-yl)benzonitrile<br>Mass Spectrum (LCMS, ESI pos.): Calcd. for $C_{29}H_{37}N_3O_3$: 476 (M + H); found: 476. $^1$H NMR (300 MHz, DMSO-$d_6$): δ 8.06 (d, J = 8.7 Hz, 2H), 7.58 (d, J = 8.4 Hz, 2H), 6.50 (s, 1H), 4.65 (d, J = 4.2 Hz, 1H), 4.03-4.00 (m, 1H), 3.79-3.77 (m, 2H), 3.54 (s, 2H), 3.25-3.18 (m, 4H), 2.30-2.25 (m, 2H), 2.21 (s, 3H), 1.97-1.96 (m, 2H), 1.80-1.71 (m, 1H), 1.54-1.42 (m, 3H), 1.31-1.29 (m, 4H), 1.17-1.15 (m, 2H), 1.09-1.05 (m, 4H), 0.80-0.75 (m, 1H). |
| 22B | (±)-4-(3-(2-((1R,2R,4S)-2-Hydroxy-7-azabicyclo[2.2.1]heptan-7-yl)acetyl)-2-methyl-5-(3-(oxetan-3-yl)propyl)-1H-pyrrol-1-yl)benzonitrile<br>Mass Spectrum (LCMS, ESI pos.): Calcd. for $C_{26}H_{31}N_3O_3$: 434 (M + H); found: 434. $^1$H NMR (300 MHz, DMSO-$d_6$): δ 8.06 (d, J = 8.4 Hz, 2H), 7.58 (d, J = 8.4 Hz, 2H), 6.50 (s, 1H), 4.67 (brs, 1H), 4.56-4.52 (m, 2H), 4.11 (t, J = 6.0 Hz, 2H), 4.09-4.05 (m, 1H), 3.55 (s, 2H), 3.27 (brs, 2H), 2.84-2.73 (m, 1H), 2.28-2.23 (m, 2H), 2.21 (s, 3H), 2.02-1.98 (m, 2H), 1.79-1.74 (m, 1H), 1.55-1.52 (m, 3H), 1.30-1.23 (m, 3H), 080-0.76 (m, 1H). |
| 23B | (±)-4-(3-(2-((1S,2S,4R)-2-Hydroxy-7-azabicyclo[2.2.1]heptan-7-yl)acetyl)-2-methyl-5-(4-(oxetan-3-yl)butyl)-1H-pyrrol-1-yl)benzonitrile<br>Mass Spectrum (LCMS, ESI pos.): Calcd. for $C_{27}H_{33}N_3O_3$: 448 (M + H); found: 448. $^1$H NMR (400 MHz, DMSO-$d_6$): δ 8.05 (d, 2H, J = 8.1 Hz), 7.58 (d, 2H, J = 8.1 Hz), 6.50 (s, 1H), 4.67 (d, 1H, J = 3.9 Hz), 4.57 (t, 2H, J = 6.3 Hz), 4.14 (t, 2H, J = 6.3 Hz), 4.03-4.05 (m, 1H), 3.54 (s, 2H), 3.24-3.26 (m, 2H), 2.77-2.82 (m, 1H), 2.22-2.29 (m, 5H), 1.96-1.98 (m, 2H), 1.68-1.81 (m, 1H), 1.42-1.57 (m, 3H), 1.25-1.47 (m, 3H), 1.01-1.15 (m, 2H), 0.75-0.85 (m, 1H). |
| 28B | 4-(3-(2-((1r,3r,5r,7r)-2-Oxa-6-azaadamantan-6-yl)acetyl)-5-(4-cyanobutyl)-2-methyl-1H-pyrrol-1-yl)benzonitrile<br>Mass Spectrum (LCMS, ESI pos.): Calcd. for $C_{27}H_{30}N_4O_2$: 443 (M + H); found: 443. $^1$H NMR (400 MHz, DMSO-$d_6$): δ 8.04 (d, J = 8.4 Hz, 2H), 7.58 (d, J = 8.4 Hz, 2H), 6.62 (s, 1H), 3.97 (brs, 2H), 3.82 (s, 2H), 3.01 (brs, 1H), 2.48-2.49 (m, 2H), 2.35-2.41 (m, 2H), 2.29-2.32 (m, 2H), 2.19 (s, 3H), 1.89-1.92 (m, 4H), 1.71-1.74 (m, 4H), 1.44-1.45 (m, 4H). |
| 42B | (±)-4-(3-(2-((2R)-2-Hydroxy-7-azabicyclo[2.2.1]heptan-7-yl)acetyl)-2-methyl-5-(3-(3-methyloxetan-3-yl)propyl)-1H-pyrrol-1-yl)benzonitrile<br>Mass Spectrum (LCMS, ESI pos.): Calcd. for $C_{27}H_{33}N_3O_3$: 448 (M + H); found: 448. $^1$H NMR (400 MHz, DMSO-$d_6$): δ 8.06 (d, J = 8.4 Hz, 2H), 7.59 (d, J = 8.4 Hz, 2H), 6.52 (s, 1H), 4.76 (brs, 1H), 4.16-4.10 (m, 4H), 3.67-3.59 (m, 2H), 3.20 (brs, 2H), 2.28 (t, J = 7.5 Hz, 2H), 2.21 (s, 3H), 2.06-2.02 (m, 2H), 1.81-1.77 (m, 1H), 1.57-1.55 (m, 1H), 1.46-1.25 (m, 5H), 1.10 (s, 3H), 0.88-0.82 (m, 1H). |
| 43B | (±)-4-(3-(2-((2R)-2-Hydroxy-7-azabicyclo[2.2.1]heptan-7-yl)acetyl)-2-methyl-5-(2-(oxetan-3-yl)ethyl)-1H-pyrrol-1-yl)benzonitrile<br>Mass Spectrum (LCMS, ESI pos.): Calcd. for $C_{25}H_{29}N_3O_3$: 420 (M + H); found: 420. $^1$H NMR (400 MHz, Methanol-$d_4$): δ 7.98 (d, J = 8.4 Hz, 2H), 7.53 (d, J = 8.4 Hz, 2H), 6.51 (s, 1H), 4.90 (s, 2H), 4.70-4.69 (m, 2H), 4.35-4.33 (m, 1H), 4.21-4.18 (m, 2H), 3.51-3.44 (m, 2H), 2.95-2.90 (m, 1H), 2.35-2.31 (m, 5H), 2.26-2.15 (m, 2H), 1.94-1.90 (m, 1H), 1.83-1.79 (m, 2H), 1.77-1.67 (m, 1H), 1.55-1.49 (m, 1H), 1.30 (d, J = 6.8 Hz, 1H), 1.03-0.99 (m, 1H). |
| 51B | (±)-4-(5-(3-(5,5-Dimethyl-2-oxotetrahydrofuran-3-yl)propyl)-3-(2-((1R,2R,4S)-2-hydroxy-7-azabicyclo[2.2.1]heptan-7-yl)acetyl)-2-methyl-1H-pyrrol-1-yl)benzonitrile<br>Mass Spectrum (LCMS, ESI pos.): Calcd. for $C_{29}H_{35}N_3O_4$: 490 (M + H); found: 490. $^1$H NMR (300 MHz, DMSO-$d_6$): δ 8.07 (d, J = 8.4 Hz, 2H), 7.60 (d, J = 8.1 |

-continued

| Cpd | Data |
|---|---|
| | Hz, 2H), 6.52 (s, 1H), 4.67 (d, J = 3.9 Hz, 1H), 4.06-4.04 (m, 1H), 3.55 (s, 2H), 3.28-3.24 (m, 2H), 2.79-2.73 (m, 1H), 2.51 (s, 2H), 2.35-2.31 (m, 2H), 2.22 (s, 3H), 2.10-1.95 (m, 3H), 1.76-1.73 (m, 1H), 1.62-1.50 (m, 3H), 1.42-1.21 (m, 10H), 0.81-0.75 (m, 1H).<br>Material is a mixture of diastereomers based on the configuration of the lactone ring stereocenter. |
| 55B | (±)-4-(3-(2-((1R,2R,4S)-2-Hydroxy-7-azabicyclo[2.2.1]heptan-7-yl)acetyl)-2-methyl-5-(2-(3-methyloxetan-3-yl)ethyl)-1H-pyrrol-1-yl)benzonitrile<br>Mass Spectrum (LCMS, ESI pos.): Calcd. for $C_{26}H_{31}N_3O_3$: 434 (M + H); found: 434. $^1$H NMR (400 MHz, DMSO-$d_6$): δ 8.06-8.05 (m, 2H), 7.62-7.60 (m, 2H), 6.55 (s, 1H), 4.66 (d, J = 4.0 Hz, 1H), 4.08-4.02 (m, 5H), 3.54 (s, 2H), 3.26-3.22 (m, 2H), 2.27-2.22 (m, 2H), 2.21 (s, 3H), 1.99-1.94 (m, 2H), 1.74-1.73 (m, 1H), 1.65-1.61 (m, 2H), 1.55-1.48 (m, 1H), 1.33-1.28 (m, 1H), 1.05 (s, 3H), 0.78-0.75 (m, 1H). |
| 155B | (±)-4-(3-(2-((1R,2R,4R)-2-Hydroxy-7-azabicyclo[2.2.1]heptan-7-yl(acetyl)-2-methyl-5-(3-(trifluoromethoxy)propyl)-1H-pyrrol-1-yl)benzonitrile<br>Mass Spectrum (LCMS, ESI pos.): Calcd. for $C_{24}H_{26}F_3N_3O_3$: 462 (M + H); found: 462. $^1$H NMR (400 MHz, CH$_3$OH-$d_4$): δ 7.96 (dd, J = 2, 6.8 Hz, 2H), 7.49 (dd, J = 2, 6.8 Hz, 2H), 6.52 (s, 1H), 4.87 (s, 2H), 4.36-4.24 (m, 1H), 3.95 (t, J = 6 Hz, 2H), 3.82-3.71 (m, 1H), 3.48-3.40 (m, 2H), 2.47 (dd, J = 0.8, 7.2 Hz, 2H), 2.30 (s, 3H), 2.25-2.16 (m, 2H), 1.97-1.77 (m, 3H), 1.75-1.61 (m, 1H), 1.53-1.42 (m, 1H), 0.99-0.92 (m, 1H). |

Example 27B. (±)-4-(3-(2-((2R)-2-Hydroxy-7-azabicyclo[2.2.1]heptan-7-yl)acetyl)-2-methyl-5-((E)-3-(2-methyl-1H-imidazol-1-yl)prop-1-en-1-yl)-1H-pyrrol-1-yl)benzonitrile (6B)

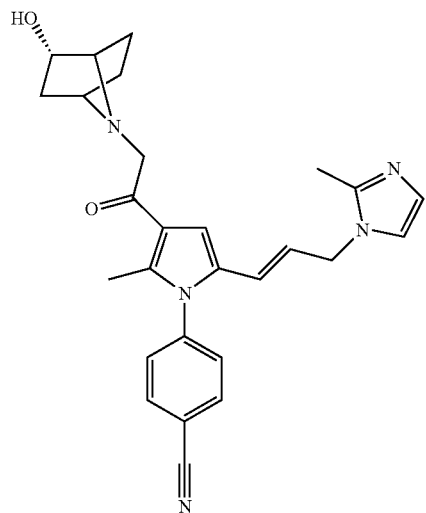

A. (E)-2-Methyl-1-(3-(4,4,5,5-tetramethyl-1,3,2-dioxaborolan-2-yl)allyl)-1H-imidazole Into a 50 mL round-bottom flask, being maintained under an inert atmosphere of nitrogen, was placed a mixture of 2-methyl-1-(prop-2-yn-1-yl)-1H-imidazole (120 mg, 1.00 mmol) and 4,4,4',4',5,5,5',5'-octamethyl-2,2'-bi(1,3,2-dioxaborolane) (381 mg, 1.50 mmol) in ethanol (3 mL). Then copper sand (6 mg, 0.09 mmol) and sodium methoxide (11 mg, 0.20 mmol) were added to the flask. The resulting mixture was allowed to stir at room temperature overnight. The reaction mixture was then diluted with ethyl acetate (100 mL) and washed with brine (3×50 mL). The organic phase was then dried over anhydrous sodium sulfate and concentrated under vacuum to afford 340 mg of (E)-2-methyl-1-(3-(4,4,5,5-tetramethyl-1,3,2-dioxaborolan-2-yl)allyl)-1H-imidazole as green, crude oil. Mass Spectrum (LCMS, ESI pos.): Calcd. for $C_{13}H_{21}BN_2O_2$: 249 (M+H); found: 249.

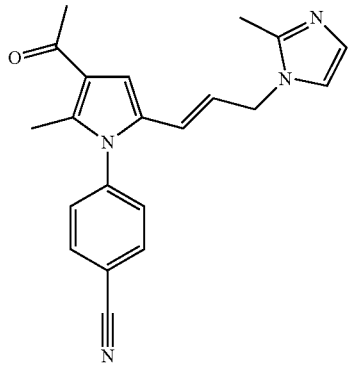 [SMILES: CC(=O)c1cc(/C=C/Cn2ccnc2C)n(-c2ccc(C#N)cc2)c1C]

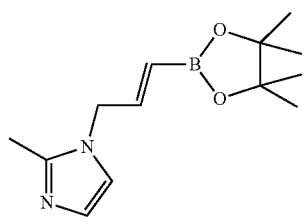

B. (E)-4-(3-Acetyl-2-methyl-5-(3-(2-methyl-1H-imidazol-1-yl)prop-1-en-1-yl)-1H-pyrrol-1-yl)benzonitrile Into a 100 mL round-bottom flask, being maintained under an inert atmosphere of nitrogen, was placed a mixture of 4-(3-acetyl-2-methyl-1H-pyrrol-1-yl)benzonitrile (1.40 g, 4.00 mmol), (E)-2-methyl-1-(3-(4,4,5,5-tetramethyl-1,3,2-dioxaborolan-2-yl)allyl)-1H-imidazole (1.98 g, 8.00 mmol) and potassium carbonate (1.65 g, 11.94 mmol) in 1,4-dioxane (18 mL) and water (6 mL). Then Pd(dppf)Cl$_2$ (293 mg, 0.40 mmol) was added to the flask. The resulting mixture was heated at 100° C. overnight. After cooling to room temperature the reaction mixture was diluted with brine (100 mL) and then extracted with ethyl acetate (3×150 mL). The combined organic extracts were dried over anhydrous sodium sulfate and concentrated under vacuum. The remaining residue was purified by column chromatography on silica gel, using a gradient of ethyl acetate/petroleum ether (1:1-10:1), to afford 870 mg (63%) of (E)-4-(3-acetyl-2-methyl-5-(3-(2-methyl-1H-imidazol-1-yl)prop-1-en-1-yl)-1H-pyrrol-1-yl)benzonitrile as a yellow solid. Mass Spectrum (LCMS, ESI pos.): Calcd. for C$_{21}$H$_{20}$N$_4$O: 345 (M+H); found: 345.

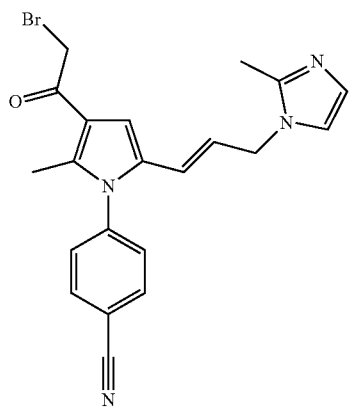 [SMILES: Cc1nccn1C/C=C/c1cc(C(=O)CBr)c(C)n1-c1ccc(C#N)cc1]

C. (E)-4-(3-(2-Bromoacetyl)-2-methyl-5-(3-(2-methyl-1H-imidazol-1-yl)prop-1-en-1-yl)-1H-pyrrol-1-yl)benzonitrile Into a 50 mL round-bottom flask, being maintained under an inert atmosphere of nitrogen, was placed a solution of (E)-2-methyl-1-(3-(4,4,5,5-tetramethyl-1,3,2-dioxaborolan-2-yl)allyl)-1H-imidazole (250 mg, 0.73 mmol) and diisopropylethylamine (281 mg, 2.17 mmol) in tetrahydrofuran (5 mL). The flask was cooled to 0° C. and then TMSOTf (323 mg, 1.45 mmol) was added in a dropwise fashion. The reaction mixture was allowed to stir at 0° C. for 1 h and then a solution of NBS (155 mg, 0.87 mmol) in tetrahydrofuran (3 mL) was added in a dropwise fashion. The resulting mixture was allowed to stir for 0.5 hour at 0° C. and then warm to room temperature and stir for an additional 1 h. The reaction mixture was diluted with ethyl acetate (100 mL) and then washed with brine (3×100 mL). The organic phase was dried over anhydrous sodium sulfate and concentrated under vacuum. The remaining residue was purified by column chromatography on silica gel, using dichloromethane/methanol (15:1) as the eluant, to afford 50 mg (16%) of (E)-4-(3-(2-bromoacetyl)-2-methyl-5-(3-(2-methyl-1H-imidazol-1-yl)prop-1-en-1-yl)-1H-pyrrol-1-yl)benzonitrile as a yellow solid. Mass Spectrum (LCMS, ESI pos.): Calcd. for C$_{21}$H$_{19}$BrN$_4$O: 423 (M+H); found: 423.

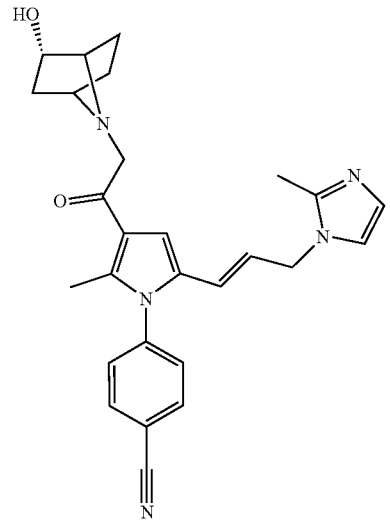 [SMILES: Cc1nccn1C/C=C/c1cc(C(=O)CN2C3CCC2[C@@H](O)C3)c(C)n1-c1ccc(C#N)cc1]

D. (±)-4-(3-(2-((2R)-2-Hydroxy-7-azabicyclo[2.2.1]heptan-7-yl)acetyl)-2-methyl-5-((E)-3-(2-methyl-1H-imidazol-1-yl)prop-1-en-1-yl)-1H-pyrrol-1-yl)benzonitrile (6B)

Into a 50 mL round-bottom flask, being maintained under an inert atmosphere of nitrogen, was placed a solution of (E)-4-(3-(2-bromoacetyl)-2-methyl-5-(3-(2-methyl-1H-imidazol-1-yl)prop-1-en-1-yl)-1H-pyrrol-1-yl)benzonitrile (50 mg, 0.12 mmol) in N,N-dimethylformamide (1 mL). Then solid potassium carbonate (24 mg, 0.17 mmol) and (±)-(1S,2S,4R)-7-azabicyclo[2.2.1]heptan-2-ol (21 mg, 0.14 mmol) were added to the flask. The resulting mixture was allowed to stir overnight at room temperature. The reaction mixture was then filtered and the filtrate was purified by preparative-HPLC by the following conditions: Column-XBridge C18 OBD Prep Column, 19 mm×250 mm, 5 μm 13 nm; Mobile Phase A-Water with 0.05% NH$_4$HCO$_3$, Mobile Phase B-acetonitrile; Flow rate-20 mL/min; Gradient-25% B to 40% B in 8 min; Detector-UV 254 nm. This process afforded 5 mg (9%) of (±)-4-(3-(2-((2R)-2-hydroxy-7-azabicyclo[2.2.1]heptan-7-yl)acetyl)-2-methyl-5-((E)-3-(2-methyl-1H-imidazol-1-yl)prop-1-en-1-yl)-1H-pyrrol-1-yl)benzonitrile (6B) as a yellow solid. Mass Spectrum (LCMS, ESI pos.): Calcd. for C$_{27}$H$_{29}$N$_5$O$_2$: 456 (M+H); found: 456. $^1$H NMR (300 MHz, CH$_3$OH-d$_4$): δ 7.89 (d, J=8.4 Hz, 2H), 7.39 (d, J=8.4 Hz, 2H), 6.93 (s, 1H), 6.84 (s, 1H), 6.71 (s, 1H), 6.06-5.97 (m, 1H), 5.61 (d, J=15.6 Hz, 1H), 4.53 (d, J=5.7 Hz, 2H), 4.31-4.27 (m, 1H), 3.82-3.80 (m, 1H), 3.46-3.40 (m, 2H), 2.29 (s, 3H), 2.20 (s, 3H), 2.16-2.07 (m, 2H), 1.93-1.69 (m, 1H), 1.65-1.51 (m, 1H), 1.50-1.43 (m, 1H), 1.27-1.25 (m, 1H), 0.99-0.93 (m, 1H).

Using the procedures described in Example 27B, reagents, starting materials, and conditions known to those skilled in the art, the following compounds representative of the present invention were prepared:

| Cpd | Data |
|---|---|
| 15B | (±)-4-(5-((E)-4-Cyano-4-methylpent-1-en-1-yl)-3-(2-((1R,2R,4S)-2-hydroxy-7-azabicyclo[2.2.1]heptan-7-yl)acetyl)-2-methyl-1H-pyrrol-1-yl)benzonitrile<br>Mass Spectrum (LCMS, ESI pos.): Calcd. for $C_{27}H_{30}N_4O_2$: 443 (M + H); found: 443. $^1$H NMR (400 MHz, DMSO-$d_6$): δ 8.07 (d, J = 8.4 Hz, 2H), 7.57 (d, J = 8.4 Hz, 2H), 7.05 (s, 1H), 5.90 (d, J = 4.8 Hz, 2H), 4.69 (brs, 1H), 4.07-4.05 (m, 1H), 3.66 (s, 2H), 3.30-3.28 (m, 2H), 2.27-2.25 (m, 5H), 1.99 (brs, 2H), 1.81-1.77 (m, 1H), 1.56-1.53 (m, 1H), 1.35-1.31 (m, 2H), 1.23 (s, 5H), 0.80 (d, J = 11.6 Hz, 1H). |
| 27B | (±)-4-(5-((E)-3-(1H-Pyrazol-1-yl)prop-1-en-1-yl)-3-(2-((1S,2S,4R)-2-hydroxy-7-azabicyclo[2.2.1]heptan-7-yl)acetyl)-2-methyl-1H-pyrrol-1-yl)benzonitrile<br>Mass Spectrum (LCMS, ESI pos.): Calcd. for $C_{26}H_{27}N_5O_2$: 442 (M + H); found: 442. $^1$H NMR (400 MHz, DMSO-$d_6$): δ 8.08 (d, J = 8.8 Hz, 2H), 7.63 (d, J = 2.0 Hz, 1H), 7.55 (d, J = 8.4 Hz, 2H), 7.40 (d, J = 1.6 Hz, 1H), 7.11 (s, 1H), 6.22-6.21 (m, 1H), 6.16-6.10 (m, 1H), 5.87 (d, J = 15.6 Hz, 1H), 4.74 (d, J = 5.6 Hz, 2H), 4.67 (s, 1H), 4.05 (brs, 1H), 3.61 (s, 2H), 3.26 (brs, 2H), 2.25 (s, 3H), 1.98 (brs, 2H), 1.78-1.76 (m, 1H), 1.55-1.51 (m, 1H), 1.36-1.32 (m, 1H), 0.83-0.72 (m, 1H). |
| 52B | (±)-4-(5-((E)-3-(5,5-Dimethyl-2-oxotetrahydrofuran-3-yl)prop-1-en-1-yl)-3-(2-((1S,2S,4R)-2-hydroxy-7-azabicyclo[2.2.1]heptan-7-yl)acetyl)-2-methyl-1H-pyrrol-1-yl)benzonitrile<br>Mass Spectrum (LCMS, ESI pos.): Calcd. for $C_{29}H_{33}N_3O_4$: 488 (M + H); found: 488. $^1$H NMR (300 MHz, $CH_3OH$-$d_4$): δ 7.93 (d, J = 8.4 Hz, 2H), 7.44 (d, J = 8.4 Hz, 2H), 6.84 (s, 1H), 5.89-5.80 (m, 2H), 4.80 (s, 2H), 4.32-4.28 (m, 1H), 3.83-3.80 (m, 1H), 3.48-3.41 (m, 2H), 2.94-2.90 (m, 1H), 2.48-2.41 (m, 1H), 2.30 (s, 3H), 2.26-2.10 (m, 4H), 1.90-1.86 (m, 1H), 1.73-1.65 (m, 2H), 1.52-1.48 (m, 1H), 1.38 (s, 3H), 1.33 (s, 3H), 1.00-0.95 (m, 1H).<br>Material is a mixture of diastereomers based on the configuration of the lactone ring stereocenter. |

Example 28B. (±)-4-(3-(2-((2R)-2-Hydroxy-7-azabicyclo[2.2.1]heptan-7-yl)acetyl)-2,5-dimethyl-1H-pyrrol-1-yl)benzonitrile (64B)

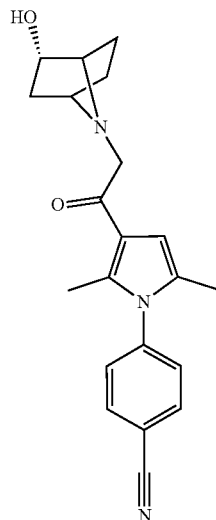

Into a 25 mL round-bottom flask was placed a solution of 4-(3-(2-chloroacetyl)-2,5-dimethyl-1H-pyrrol-1-yl)benzonitrile (100 mg, 0.37 mmol) in N,N-dimethylformamide (5 mL). To the solution were added (±)-(1S,2S,4R)-7-azabicyclo[2.2.1]heptan-2-ol (62 mg, 0.55 mmol) and potassium carbonate (152 mg). The resulting mixture was allowed to stir at room temperature for 2 h. The solids were filtered from the reaction mixture and the filtrate was purified by preparative-HPLC under the following conditions: Intel-Flash-1 Column-C18; mobile phase—$H_2O:CH_3CN$=75:25 increasing to $H_2O:CH_3CN$=25:75 within 20 min; Detector-UV 254 nm. This process afforded 71 mg (56%) of (±)-4-(3-(2-((2R)-2-Hydroxy-7-azabicyclo[2.2.1]heptan-7-yl)acetyl)-2,5-dimethyl-1H-pyrrol-1-yl)benzonitrile (64B) as a yellow solid. Mass Spectrum (LCMS, ESI pos.): Calcd. for $C_{21}H_{23}N_3O_2$: 350 (M+H); found: 350. $^1$H NMR (400 MHz, $CDCl_3$): δ 7.83 (d, J=8.4 Hz, 2H), 7.33 (d, J=8.0 Hz, 2H), 6.35 (s, 1H), 4.56-4.55 (m, 2H), 3.77 (d, J=6.8 Hz, 2H), 3.66 (brs, 1H), 3.57 (brs, 1H), 2.44-2.41 (m, 1H), 2.32 (s, 3H), 2.22-2.19 (m, 1H), 1.99 (s, 3H), 1.92-1.89 (m, 2H), 1.74-1.68 (m, 1H), 1.61-1.55 (m, 1H), 1.06-1.03 (m, 1H).

Using the procedures described in Example 28B, reagents, starting materials, and conditions known to those skilled in the art, the following compounds representative of the present invention were prepared:

| Cpd | Data |
|---|---|
| 63B | 4-(3-(2-(7-Azabicyclo[2.2.1]heptan-7-yl)acetyl)-2,5-dimethyl-1H-pyrrol-1-yl)benzonitrile<br>Mass Spectrum (LCMS, ESI pos.): Calcd. for $C_{21}H_{23}N_3O$: 334 (M + H); found: 334. $^1$H NMR (400 MHz, DMSO-$d_6$): δ 8.06 (d, J = 8.4 Hz, 2H), 7.58 (d, J = 8.0 Hz, 2H), 6.50 (s, 1H), 3.50 (s, 2H), 3.33-3.29 (m, 2H), 2.24 (s, 3H), 1.95 (s, 3H), 1.67-1.65 (m, 4H), 1.30-1.22 (m, 4H). |
| 66B | 4-(3-(2-((1R,3r,5S)-3-Hydroxy-8-azabicyclo[3.2.1]octan-8-yl)acetyl)-2,5-dimethyl-1H-pyrrol-1-yl)benzonitrile<br>Mass Spectrum (LCMS, ESI pos.): Calcd. for $C_{22}H_{25}N_3O_2$: 364 (M + H); found: 364. $^1$H |

| Cpd | Data |
|---|---|
| | NMR (400 MHz, DMSO-$d_6$): δ 8.05 (d, J = 8.4 Hz, 2H), 7.59 (d, J = 8.4 Hz, 2H), 6.53 (s, 1H), 4.27 (s, 1H), 3.83 (brs, 1H), 3.48 (s, 2H), 3.14 (brs, 2H), 2.24 (s, 3H), 2.07-2.04 (m, 2H), 1.96 (s, 3H), 1.95-1.91 (m, 2H), 1.83-1.82 (m, 2H), 1.56-1.52 (m, 2H). |
| 67B | 4-(3-(2-((1R,3s,5S)-3-hydroxy-8-azabicyclo[3.2.1]octan-8-yl)acetyl)-2,5-dimethyl-1H-pyrrol-1-yl)benzonitrile<br>Mass Spectrum (LCMS, ESI pos.): Calcd. for $C_{22}H_{25}N_3O_2$: 364 (M + H); found: 364. $^1$H NMR (300 MHz, DMSO-$d_6$): δ 8.05 (d, J = 8.4 Hz, 2H), 7.59 (d, J = 8.4 Hz, 2H), 6.54 (s, 1H), 4.34 (d, J = 5.7 Hz, 1H), 3.73-3.64 (m, 1H), 3.55 (s, 2H), 3.27-3.18 (m, 2H), 2.23 (s, 3H), 1.96 (s, 3H), 1.86-1.83 (m, 2H), 1.64-1.59 (m, 2H), 1.53-1.47 (m, 4H). |
| 68B | 4-(3-(2-((1R,3r,5S)-3-Hydroxy-3-methyl-8-azabicyclo[3.2.1]octan-8-yl)acetyl)-2,5-dimethyl-1H-pyrrol-1-yl)benzonitrile<br>Mass Spectrum (LCMS, ESI pos.): Calcd. for $C_{23}H_{27}N_3O_2$: 378 (M + H); found: 378. $^1$H NMR (400 MHz, DMSO-$d_6$): δ 8.05 (d, J = 8.4 Hz, 2H), 7.59 (d, J = 8.4 Hz, 2H), 6.52 (s, 1H), 3.91 (s, 1H), 3.50 (s, 2H), 3.16 (brs, 2H), 2.23 (s, 3H), 2.08-2.03 (m, 2H), 1.96 (s, 3H), 1.78-1.72 (m, 4H), 1.54-1.50 (m, 2H), 1.03 (s, 3H). |
| 69B | 4-(3-(2-(8-Azabicyclo[3.2.1]octan-8-yl)acetyl)-2,5-dimethyl-1H-pyrrol-1-yl)benzonitrile<br>Mass Spectrum (LCMS, ESI pos.): Calcd. for $C_{22}H_{25}N_3O$: 348 (M + H); found: 348. $^1$H NMR (400 MHz, DMSO-$d_6$): δ 8.07 (d, J = 8.4 Hz, 2H), 7.60 (d, J = 8.8 Hz, 2H), 6.55 (s, 1H), 3.48 (s, 2H), 3.19 (s, 2H), 2.24 (s, 3H), 1.96 (s, 3H), 1.92-1.89 (m, 2H), 1.68-1.65 (m, 2H), 1.54-1.37 (m, 4H), 1.29-1.27 (m, 2H). |
| 70B | (±)-4-(3-(2-((1R,2R,4S)-2-Methoxy-7-azabicyclo[2.2.1]heptan-7-yl)acetyl)-2,5-dimethyl-1H-pyrrol-1-yl)benzonitrile<br>Mass Spectrum (LCMS, ESI pos.): Calcd. for $C_{22}H_{25}N_3O_2$: 364 (M + H); found: 364. $^1$H NMR (400 MHz, DMSO-$d_6$): δ 8.06 (d, J = 8.4 Hz, 2H), 7.59 (d, J = 8.4 Hz, 2H), 6.50 (s, 1H), 3.72-3.71 (m, 1H), 3.55 (s, 2H), 3.52 (t, J = 4.4 Hz, 1H), 3.29 (t, J = 4.4 Hz, 1H), 3.15 (s, 3H), 2.24 (s, 3H), 2.00-1.96 (m, 4H), 1.77-1.74 (m, 2H), 1.59-1.55 (m, 1H), 1.32-1.30 (m, 1H), 0.92-0.79 (m, 1H). |
| 71B | (±)-4-(3-(2-((1R,2R,4S)-2-Hydroxy-2-methyl-7-azabicyclo[2.2.1]heptan-7-yl)acetyl)-2,5-dimethyl-1H-pyrrol-1-yl)benzonitrile<br>Mass Spectrum (LCMS, ESI pos.): Calcd. for $C_{22}H_{25}N_3O_2$: 364 (M + H); found: 364. $^1$H NMR (300 MHz, DMSO-$d_6$): δ 7.83 (d, J = 8.4 Hz, 1H), 7.34 (d, J = 8.4 Hz, 1H), 6.43 (s, 1H), 3.63 (s, 2H), 3.49 (s, 1H), 3.39 (s, 1H), 2.34 (s, 3H), 2.23-2.18 (m, 1H), 2.01 (s, 3H), 1.88-1.81 (m, 2H), 1.71-1.64 (m, 1H), 1.62-1.53 (m, 4H), 1.47-1.26 (m, 2H). |
| 72B | (±)-4-(3-(2-((1R,2S,4S)-2-(tert-Butyl)-2-hydroxy-7-azabicyclo[2.2.1]heptan-7-yl)acetyl)-2,5-dimethyl-1H-pyrrol-1-yl)benzonitrile<br>Mass Spectrum (LCMS, ESI pos.): Calcd. for $C_{25}H_{31}N_3O_2$: 406 (M + H); found: 406. $^1$H NMR (400 MHz, DMSO-$d_6$): δ 8.04 (d, J = 8.4 Hz, 2H), 7.57 (d, J = 8.4 Hz, 2H), 6.44 (s, 1H), 3.95 (s, 1H), 3.48-3.40 (m, 3H), 3.21 (brs, 1H), 2.32 (s, 3H), 2.08-2.06 (m, 1H), 1.94 (s, 3H), 1.84-1.82 (m, 1H), 1.70 (brs, 1H), 1.52 (brs, 1H), 1.41 (m, 1H), 0.88 (s, 9H). |
| 73B | (±)-4-(3-(2-((1R,2R,4S)-2-Hydroxy-2-(trifluoromethyl)-7-azabicyclo[2.2.1]heptan-7-yl)acetyl)-2,5-dimethyl-1H-pyrrol-1-yl)benzonitrile<br>Mass Spectrum (LCMS, ESI pos.): Calcd. for $C_{22}H_{22}F_3N_3O_2$: 418 (M + H); found: 418. $^1$H NMR (400 MHz, DMSO-$d_6$): δ 8.04 (d, J = 8.4 Hz, 2H), 7.56 (d, J = 8.4 Hz, 2H), 6.48-6.52 (m, 1H), 6.02 (s, 1H), 3.41-3.60 (m, 2H), 3.31-3.38 (m, 2H), 2.28 (s, 3H), 2.06-2.09 (m, 1H), 2.01-2.04 (m, 4H), 1.91-1.93 (m, 1H), 1.78-1.85 (m, 1H), 1.67-1.75 (m, 1H). |
| 74B | 4-(3-(2-((1R,3r,5S)-3-Hydroxy-3-(trifluoromethyl)-8-azabicyclo[3.2.1]octan-8-yl)acetyl)-2,5-dimethyl-1H-pyrrol-1-yl)benzonitrile<br>Mass Spectrum (LCMS, ESI pos.): Calcd. for $C_{23}H_{24}F_3N_3O_2$: 432 (M + H); found: 432. $^1$H NMR (400 MHz, DMSO-$d_6$): δ 8.07-8.04 (m, 2H), 7.58-7.56 (m, 2H), 6.92 (s, 1H), 6.46 (s, 1H), 3.62 (s, 2H), 3.33-3.31 (m, 2H), 2.26-2.20 (m, 5H), 2.08-2.01 (m, 2H), 1.97 (s, 3H), 1.52-1.48 (m, 4H).<br>Compound 74B was prepared as a mixture from Intermediates 15B and 16B.<br>Compounds 74B and 75B were then separated. |
| 75B | 4-(3-(2-((1R,3s,5S)-3-Hydroxy-3-(trifluoromethyl)-8-azabicyclo[3.2.1]octan-8-yl)acetyl)-2,5-dimethyl-1H-pyrrol-1-yl)benzonitrile<br>Mass Spectrum (LCMS, ESI pos.): Calcd. for $C_{23}H_{24}F_3N_3O_2$: 432 (M + H); found: 432. $^1$H NMR (400 MHz, DMSO-$d_6$): δ 8.05-8.03 (m, 2H), 7.58-7.56 (m, 2H), 6.50 (s, 1H), 5.59 (s, 1H), 3.54 (s, 2H), 3.31-3.29 (m, 2H), 2.22 (s, 3H), 2.01-1.92 (m, 7H), 1.85-1.83 (m, 2H), 1.62-1.58 (m, 2H).<br>Compound 75B was prepared as a mixture from Intermediates 15B and 16B.<br>Compounds 74B and 75B were then separated. |
| 80B | 4-(3-(2-((5r,7r)-2-Azaadamantan-2-yl)acetyl)-2,5-dimethyl-1H-pyrrol-1-yl)benzonitrile<br>Mass Spectrum (LCMS, ESI pos.): Calcd. for $C_{24}H_{27}N_3O$: 374 (M + H); found: 374. $^1$H NMR (300 MHz, CH$_3$OH-$d_4$): δ 7.94 (d, J = 8.4 Hz, 2H), 7.47 (d, J = 8.4 Hz, 2H), 6.54 (s, 1H), 4.85 (s, 2H), 2.97 (s, 2H), 2.29 (s, 3H), 2.23-2.17 (m, 4H), 2.07-1.99 (m, 5H), 1.87 (s, 2H), 1.69-1.60 (m, 4H). |
| 81B | 4-(3-(2-((5s,7s)-5-Hydroxy-2-azaadamantan-2-yl)acetyl)-2,5-dimethyl-1H-pyrrol-1-yl)benzonitrile<br>Mass Spectrum (LCMS, ESI pos.): Calcd. for $C_{24}H_{27}N_3O_2$: 390 (M + H); found: 390. $^1$H NMR (300 MHz, DMSO-$d_6$): δ 8.06 (d, J = 8.4 Hz, 2H), 7.59 (d, J = 8.4 Hz, 2H), 6.61 (s, 1H), 4.58 (brs, 1H), 4.01 (brs, 2H), 3.17 (brs, 2H), 2.24 (s, 3H), 2.12 (s, 1H), 1.97 (s, 3H), 1.91 (brs, 4H), 1.64 (s, 2H), 1.54-1.33 (m, 4H). |

-continued

| Cpd | Data |
|---|---|
| 82B | (±)-4-(3-(2-((1S,5R,6R)-6-Hydroxy-8-azabicyclo[3.2.1]octan-8-yl)acetyl)-2,5-dimethyl-1H-pyrrol-1-yl)benzonitrile<br>Mass Spectrum (LCMS, ESI pos.): Calcd. for $C_{22}H_{25}N_3O_2$: 364 (M + H); found: 364. $^1$H NMR (300 MHz, DMSO-$d_6$): δ 8.06 (d, J = 8.1 Hz, 2H), 7.59 (d, J = 8.4 Hz, 2H), 6.53 (s, 1H), 4.76 (d, J = 3.6 Hz, 1H), 4.40-4.36 (m, 1H), 3.78 (s, 2H), 3.18-3.11 (m, 1H), 3.00-2.98 (m, 1H), 2.44-2.41 (m, 1H), 2.23 (s, 3H), 1.96 (s, 3H), 1.88-1.85 (m, 2H), 1.70-1.63 (m, 1H), 1.60-1.31 (m, 3H), 1.15-1.12 (m, 1H). |
| 83B | (±)-4-(3-(2-((1S,5R,6S)-6-Hydroxy-8-azabicyclo[3.2.1]octan-8-yl)acetyl)-2,5-dimethyl-1H-pyrrol-1-yl)benzonitrile<br>Mass Spectrum (LCMS, ESI pos.): Calcd. for $C_{22}H_{25}N_3O_2$: 364 (M + H); found: 364. $^1$H NMR (400 MHz, DMSO-$d_6$): δ 8.08-8.05 (m, 2H), 7.61-7.59 (m, 2H), 6.49 (d, J = 1.2 Hz, 1H), 4.68 (d, J = 3.2 Hz, 1H), 4.18-4.17 (m, 1H), 3.97 (d, J = 16.8 Hz, 1H), 3.78 (d, J = 16.6 Hz, 1H), 3.36-3.34 (m, 1H), 3.05 (s, 1H), 2.25 (s, 3H), 1.97-1.84 (m, 5H), 1.64-1.57 (m, 2H), 1.45-1.29 (m, 1H), 1.20-1.17 (m, 1H). |
| 84B | 4-(3-(2-((1r,3r)-2-Oxa-6-azaadamantan-6-yl)acetyl)-2,5-dimethyl-1H-pyrrol-1-yl)benzonitrile<br>Mass Spectrum (LCMS, ESI pos.): Calcd. for $C_{23}H_{25}N_3O_2$: 376 (M + H); found: 376. $^1$H NMR (300 MHz, DMSO-$d_6$): δ 8.05 (d, J = 8.7 Hz, 2H), 7.59 (d, J = 8.7 Hz, 2H), 6.60 (s, 1H), 3.99 (s, 2H), 3.82 (s, 2H), 3.02 (s, 2H), 2.23 (s, 3H), 1.97 (s, 3H), 1.95-1.89 (m, 4H), 1.76-1.71 (m, 4H). |
| 85B | 4-(3-(2-((1R,3s,5S)-3-Hydroxy-9-azabicyclo[3.3.1]nonan-9-yl)acetyl)-2,5-dimethyl-1H-pyrrol-1-yl)benzonitrile<br>Mass Spectrum (LCMS, ESI pos.): Calcd. for $C_{23}H_{27}N_3O_2$: 378 (M + H); found: 378. $^1$H NMR (300 MHz, DMSO-$d_6$): δ 8.06 (d, J = 8.4 Hz, 2H), 7.60 (d, J = 8.4 Hz, 2H), 6.59 (1H, s), 4.49 (d, J = 5.4 Hz, 1H), 4.20-4.18 (m, 1H), 3.72 (s, 2H), 2.98-2.94 (m, 2H), 2.27 (s, 3H), 1.97 (3H, s), 1.85-1.81 (m, 2H), 1.75-1.56 (m, 6H), 1.43-1.38 (m, 2H). |
| 86B | 4-(3-(2-((1R,3r,5S)-3-Hydroxy-9-azabicyclo[3.3.1]nonan-9-yl)acetyl)-2,5-dimethyl-1H-pyrrol-1-yl)benzonitrile<br>Mass Spectrum (LCMS, ESI pos.): Calcd. for $C_{23}H_{27}N_3O_2$: 378 (M + H); found: 378. $^1$H NMR (300 MHz, DMSO-$d_6$): δ 8.06 (d, J = 8.4 Hz, 2H), 7.59 (d, J = 8.4 Hz, 2H), 6.54 (1H, s), 4.40 (d, J = 4.5 Hz, 1H), 3.96-3.90 (1H, m), 3.67 (s, 2H), 3.18-3.16 (m, 1H), 3.00-2.97 (m, 2H), 2.22-2.15 (m, 6H), 1.96 (s, 3H), 1.88-1.82 (m, 2H), 1.40-1.35 (m, 1H), 1.27-1.23 (m, 2H), 1.11-1.05 (m, 2H). |
| 87B | 4-(3-(2-((1s,5s)-9-Azabicyclo[3.3.1]nonan-9-yl)acetyl)-2,5-dimethyl-1H-pyrrol-1-yl)benzonitrile<br>Mass Spectrum (LCMS, ESI pos.): Calcd. for $C_{23}H_{27}N_3O$: 362 (M + H); found: 362. $^1$H NMR (300 MHz, DMSO-$d_6$): δ 8.06 (d, J = 8.4 Hz, 2H), 7.60 (d, J = 8.4 Hz, 2H), 6.60 (s, 1H), 3.76 (s, 2H), 2.80 (brs, 2H), 2.23 (s, 3H), 1.97-1.92 (m, 9H), 1.57-1.53 (m, 2H), 1.44-1.42 (m, 4H). |
| 88B | 4-(3-(2-((1R,3r,5S)-3-Methoxy-8-azabicyclo[3.2.1]octan-8-yl)acetyl)-2,5-dimethyl-1H-pyrrol-1-yl)benzonitrile<br>Mass Spectrum (LCMS, ESI pos.): Calcd. for $C_{23}H_{27}N_3O_2$: 378 (M + H); found: 378. $^1$H NMR (400 MHz, CDCl$_3$): δ 8.05 (d, J = 8.4 Hz, 2H), 7.59 (d, J = 8.4 Hz, 2H), 6.53 (s, 1H), 3.48 (s, 2H), 3.36-3.32 (m, 1H), 3.16-3.14 (m, 5H), 2.23 (s, 3H), 1.95 (s, 3H), 1.88-1.80 (m, 6H), 1.73-1.69 (m, 2H). |
| 89B | 4-(3-(2-((1R,3s,5S)-3-Methoxy-8-azabicyclo[3.2.1]octan-8-yl)acetyl)-2,5-dimethyl-1H-pyrrol-1-yl)benzonitrile<br>Mass Spectrum (LCMS, ESI pos.): Calcd. for $C_{23}H_{27}N_3O_2$: 378 (M + H); found: 378. $^1$H NMR (400 MHz, DMSO-$d_6$): δ 8.04 (d, J = 8.8 Hz, 2H), 7.58 (d, J = 8.8 Hz, 2H), 6.53 (s, 1H), 3.54 (s, 2H), 3.45-3.41 (m, 1H), 3.31-3.27 (m, 2H), 3.16 (s, 3H), 2.22 (s, 3H), 1.94 (s, 3H), 1.86-1.84 (m, 2H), 1.79-1.74 (m, 2H), 1.52-1.47 (m, 4H). |
| 92B | (±)-4-(3-(2-((2R,3aS,5R,6aS)-Hexahydro-4H-2,5-methanofuro[3,2-b]pyrrol-4-yl)acetyl)-2,5-dimethyl-1H-pyrrol-1-yl)benzonitrile<br>Mass Spectrum (LCMS, ESI pos.): Calcd. for $C_{22}H_{23}N_3O_2$: 362 (M + H); found: 362. $^1$H NMR (400 MHz, DMSO-$d_6$): δ 8.05 (d, J = 8.8 Hz, 2H), 7.59 (d, J = 8.4 Hz, 2H), 6.52 (s, 1H), 4.57 (s, 1H), 4.20 (s, 1H), 3.73-3.64 (m, 3H), 3.28 (s, 1H), 2.24-2.19 (m, 4H), 1.96 (s, 3H), 1.87 (d, J = 11.2 Hz, 1H), 1.82-1.77 (m, 1H), 1.59 (d, J = 12.4 Hz, 1H), 1.50 (d, J = 13.2 Hz, 1H), 1.45-1.42 (m, 1H). |
| 100B | (±)-4-(2,5-Dimethyl-3-(2-((1S,2S,4R)-2-methyl-7-azabicyclo[2.2.1]heptan-7-yl)acetyl)-1H-pyrrol-1-yl)benzonitrile<br>Mass Spectrum (LCMS, ESI pos.): Calcd. for $C_{22}H_{25}N_3O$: 348 (M + H); found: 348. $^1$H NMR (400 MHz, DMSO-$d_6$): δ 8.06 (d, J = 8.4 Hz, 2H), 7.59 (d, J = 8.4 Hz, 2H), 6.51 (s, 1H), 3.56 (s, 2H), 3.25 (t, J = 4.4 Hz, 1H), 3.17 (t, J = 4.4 Hz, 1H), 2.24 (s, 3H), 2.13-2.08 (m, 1H), 1.96 (s, 3H), 1.93-1.88 (m, 1H), 1.75-1.71 (m, 1H), 1.69-1.54 (m, 2H), 1.22-1.14 (m, 1H), 0.94 (d, J = 7.2 Hz, 3H), 0.66-0.62 (m, 1H).<br>Compound 100B was prepared as a mixture from Intermediates 17B and 18B.<br>Compounds 100B and 122B were then separated. |
| 102B | (±)-4-(2,5-Dimethyl-3-(2-((1R,2R,4S)-2-(trifluoromethyl)-7-azabicyclo[2.2.1]heptan-7-yl)acetyl)-1H-pyrrol-1-yl)benzonitrile<br>Mass Spectrum (LCMS, ESI pos.): Calcd. for $C_{22}H_{22}F_3N_3O$: 376 (M + H); found: 376. $^1$H NMR (400 MHz, CH$_3$OH-$d_4$): δ 7.96-7.93 (m, 2H), 7.49-7.45 (m, 2H), 6.47 (s, 1H), 3.80 (s, 2H), 3.67 (t, J = 4.4 Hz, 1H), 3.56 (t, J = 4.4 Hz, 1H), 2.97-2.94 (m, 1H), 2.31 (s, 3H), 2.15-2.09 (m, 1H), 2.00 (s, 3H), 1.94-1.79 (m, 3H), 1.47-1.39 (m, 2H). |
| 105B | (±)-4-(2,5-Dimethyl-3-(2-((1R,2R,4S)-2-(trifluoromethoxy)-7-azabicyclo[2.2.1]heptan-7-yl)acetyl)-1H-pyrrol-1-yl)benzonitrile<br>Mass Spectrum (LCMS, ESI pos.): Calcd. for $C_{22}H_{22}F_3N_3O_2$: 418 (M + H); found: 418. $^1$H NMR (400 MHz, CDCl$_3$): δ 7.76 (d, J = 8.4 Hz, 2H), 7.26 (d, J = 8.4 Hz, 2H), 6.28 |

| Cpd | Data |
|---|---|
| | (s, 1H), 4.67-4.64 (m, 1H), 3.65-3.62 (m, 3H), 3.42 (d, J = 4.8 Hz, 1H), 2.32-2.28 (m, 1H), 2.25 (s, 3H), 1.99-1.94 (m, 1H), 1.93 (s, 3H), 1.87-1.80 (m, 1H), 1.72-1.67 (m, 1H), 1.49-1.40 (m, 1H), 1.21-1.11 (m, 1H). |
| 106B | (±)-4-(2,5-Dimethyl-3-(2-((3aR,4R,7S,7aS)-octahydro-4,7-epiminoisobenzofuran-8-yl)acetyl)-1H-pyrrol-1-yl)benzonitrile<br>Mass Spectrum (LCMS, ESI pos.): Calcd. for $C_{23}H_{25}N_3O_2$: 402 (M + H); found: 402. $^1$H NMR (300 MHz, DMSO-$d_6$): δ 8.02 (d, J = 8.4 Hz, 2H), 7.55 (d, J = 8.7 Hz, 2H), 6.48 (s, 1H), 3.68-3.61 (m, 4H), 3.28 (s, 2H), 3.21-3.16 (m, 2H), 2.73-2.64 (m, 2H), 2.20 (s, 3H), 1.92 (s, 3H), 1.45 (brs, 4H). |
| 122B | (±)-4-(2,5-Dimethyl-3-(2-((1S,2R,4R)-2-methyl-7-azabicyclo[2.2.1]heptan-7-yl)acetyl)-1H-pyrrol-1-yl)benzonitrile<br>Mass Spectrum (LCMS, ESI pos.): Calcd. for $C_{22}H_{25}N_3O$: 348 (M + H); found: 348. $^1$H NMR (400 MHz, DMSO-$d_6$): δ 8.06 (d, J = 8.4 Hz, 2H), 7.59 (d, J = 8.4 Hz, 2H), 6.54 (s, 1H), 3.53-3.43 (m, 2H), 3.30 (s, 1H), 2.98 (s, 1H), 2.25 (s, 3H), 1.96 (s, 3H), 1.74-1.72 (m, 2H), 1.58-1.51 (m, 1H), 1.46-1.41 (m, 1H), 1.26-1.20 (m, 2H), 1.08-1.06 (m, 1H), 0.95 (d, J = 6.4 Hz, 3H).<br>Compound 122B was prepared as a mixture from Intermediates 17B and 18B.<br>Compounds 100B and 122B were then separated. |
| 124B | 4-(3-(2-((1R,2R,3S,4S)-2,3-Dimethyl-7-azabicyclo[2.2.1]heptan-7-yl)acetyl)-2,5-dimethyl-1H-pyrrol-1-yl)benzonitrile<br>Mass Spectrum (LCMS, ESI pos.): Calcd. for $C_{23}H_{27}N_3O$: 362 (M + H); found: 362. $^1$H NMR (300 MHz, CDCl$_3$): δ 7.83 (d, J = 7.8 Hz, 2H), 7.33 (d, J = 8.1 Hz, 2H), 6.40 (s, 1H), 3.79 (s, 2H), 3.31 (brs, 2H), 2.33 (brs, 5H), 2.00 (s, 3H), 1.64-1.61 (m, 4H), 0.83-0.80 (m, 6H).<br>Compound 124B was prepared as a mixture from Intermediates 19B, 20B, and 21B.<br>Compounds 124B, 138b, and 140B were then separated. |
| 125B | 4-(2,5-Dimethyl-3-(2-(1-methyl-7-azabicyclo[2.2.1]heptan-7-yl)acetyl)-1H-pyrrol-1-yl)benzonitrile<br>Mass Spectrum (LCMS, ESI pos.): Calcd. for $C_{22}H_{25}N_3O$: 348 (M + H); found: 348. $^1$H NMR (400 MHz, CDCl$_3$): δ 7.8-7.81 (m, 2H), 7.34-7.31 (m, 2H), 6.42 (s, 1H), 3.64-3.62 (m, 1H), 3.58 (s, 2H), 2.29 (s, 3H), 2.00 (s, 3H), 1.94-1.87 (m, 2H), 1.65-1.56 (m, 2H), 1.49-1.45 (m, 2H), 1.41-1.33 (m, 2H), 1.30 (s, 3H). |
| 126B | 4-(3-(2-(1-(Hydroxymethyl)-7-azabicyclo[2.2.1]heptan-7-yl)acetyl)-2,5-dimethyl-1H-pyrrol-1-yl)benzonitrile<br>Mass Spectrum (LCMS, ESI pos.): Calcd. for $C_{22}H_{25}N_3O_2$: 364 (M + H); found: 364. $^1$H NMR (400 MHz, DMSO-$d_6$): δ 8.06 (d, J = 8.4 Hz, 2H), 7.60 (d, J = 8.4 Hz, 2H), 6.56 (s, 1H), 4.58 (brs, 1H), 3.55-3.51 (m, 3H), 3.33 (s, 2H), 2.24 (s, 3H), 1.96 (s, 3H), 1.76-1.59 (m, 4H), 1.33-1.24 (m, 4H). |
| 127B | 7-(2-(1-(4-Cyanophenyl)-2,5-dimethyl-1H-pyrrol-3-yl)-2-oxoethyl)-7-azabicyclo[2.2.1]heptane-1-carboxylic Acid<br>Mass Spectrum (LCMS, ESI pos.): Calcd. for $C_{22}H_{23}N_3O_2$: 378 (M + H); found: 378. $^1$H NMR (400 MHz, CH$_3$OH-$d_4$): δ 7.97 (d, J = 8.8 Hz, 2H), 7.49 (d, J = 8.4 Hz, 2H), 6.52 (s, 1H), 5.03 (brs, 1H), 4.59 (s, 1H), 4.28 (s, 2H), 2.34 (s, 3H), 2.34-2.12 (m, 6H), 2.02 (s, 3H), 1.91-1.85 (m, 2H). |
| 130B | (±)-4-(3-(2-((2R)-2-(Hydroxymethyl)-7-azabicyclo[2.2.1]heptan-7-yl)acetyl)-2,5-dimethyl-1H-pyrrol-1-yl)benzonitrile<br>Mass Spectrum (LCMS, ESI pos.): Calcd. for $C_{22}H_{25}N_3O_2$: 364 (M + H); found: 364. $^1$H NMR (300 MHz, CH$_3$OH-$d_4$): δ 7.92 (d, J = 8.7 Hz, 2H), 7.45 (d, J = 8.7 Hz, 2H), 6.43 (s, 1H), 4.82 (s, 2H, occluded by solvent), 3.50-3.47 (m, 2H), 3.40-3.38 (m, 2H), 2.27 (s, 3H), 1.97 (s, 3H), 1.91-1.85 (m, 2H), 1.79-1.71 (m, 1H), 1.47-1.40 (m, 4H). |
| 138B | 4-(3-(2-((1R,2S,3R,4S)-2,3-Dimethyl-7-azabicyclo[2.2.1]heptan-7-yl)acetyl)-2,5-dimethyl-1H-pyrrol-1-yl)benzonitrile<br>Mass Spectrum (LCMS, ESI pos.): Calcd. for $C_{23}H_{27}N_3O$: 362 (M + H); found: 362. $^1$H NMR (300 MHz, CDCl$_3$): δ 7.82 (d, J = 8.4 Hz, 2H), 7.34 (d, J = 8.4 Hz, 2H), 6.55 (s, 1H), 3.53 (s, 2H), 2.97 (brs, 2H), 2.34 (s, 3H), 2.00 (s, 3H), 1.83-1.80 (m, 2H), 1.69 (brs, 2H), 1.37-1.34 (m, 2H), 0.95 (d, J = 5.7 Hz, 6H).<br>Compound 138B was prepared as a mixture from Intermediates 19B, 20B, and 21B.<br>Compounds 124B, 138B, and 140B were then separated. |
| 139B | (±)-4-(2,5-Dimethyl-3-(2-((3aR,4S,7R,7aR)-octahydro-4,7-epiminobenzofuran-8-yl)acetyl)-1H-pyrrol-1-yl)benzonitrile<br>Mass Spectrum (LCMS, ESI pos.): Calcd. for $C_{23}H_{25}N_3O_2$: 376 (M + H); found: 376. $^1$H NMR (400 MHz, CDCl$_3$): δ 7.86-7.83 (m, 2H), 7.34-7.26 (m, 2H), 6.55 (s, 0.5H), 6.40 (s, 0.5H), 4.92-4.89 (m, 0.5H), 4.71 (brs, 0.5H), 4.46-4.42 (m, 0.5H), 4.20 (brs, 0.5H), 3.81 (brs, 0.5H), 3.66-3.51 (m, 0.5H), 2.98-2.57 (m, 2H), 2.36 (s, 3H), 2.31-2.14 (m, 2H), 2.00 (s, 3H), 1.98-1.72 (m, 4H), 1.70-1.59 (m, 1H). |
| 140B | (±)-4-(3-(2-((1R,2R,3R,4S)-2,3-Dimethyl-7-azabicyclo[2.2.1]heptan-7-yl)acetyl)-2,5-dimethyl-1H-pyrrol-1-yl)benzonitrile<br>Mass Spectrum (LCMS, ESI pos.): Calcd. for $C_{23}H_{27}N_3O$: 362 (M + H); found: 362. $^1$H NMR (300 MHz, CDCl$_3$): δ 7.83 (d, J = 8.4 Hz, 2H), 7.34 (d, J = 8.4 Hz, 2H), 6.48 (s, 1H), 3.65 (d, J = 3.3 Hz, 2H), 3.26 (brs, 1H), 3.05-3.04 (m, 1H), 2.33 (s, 3H), 2.00 (d, J = 3.3 Hz, 4H), 1.87-1.57 (m, 4H), 1.28-1.23 (m, 1H), 1.08 (d, J = 1.5 Hz, 3H), 1.00-0.94 (m, 1H), 0.92 (d, J = 1.5 Hz, 3H).<br>Compound 140B was prepared as a mixture from Intermediates 19B, 20B, and 21B.<br>Compounds 124B, 138B, and 140B were then separated. |
| 141B | (±)-4-(2,5-Dimethyl-3-(2-((1R,4S)-2-(trifluoromethyl)-7-azabicyclo[2.2.1]hept-2-en-7-yl)acetyl)-1H-pyrrol-1-yl)benzonitrile<br>Mass Spectrum (LCMS, ESI pos.): Calcd. for $C_{22}H_{20}F_3N_3O$: 400 (M + H); found: 400. |

-continued

| Cpd | Data |
|---|---|
|  | ¹H NMR (400 MHz, DMSO-d₆): δ 8.04 (d, J = 8.8 Hz, 2H), 7.57 (d, J = 8.4 Hz, 2H), 6.76 (s, 1H), 6.39 (s, 1H), 4.19 (s, 1H), 4.11 (s, 1H), 3.45-3.34 (m, 2H), 2.22 (s, 3H), 1.93 (s, 3H), 1.88-1.86 (m, 2H), 1.09-1.03 (m, 2H). |
| 143B | (±)-4-(3-(2-(1-((R)-1-Hydroxyethyl)-7-azabicyclo[2.2.1]heptan-7-yl)acetyl)-2,5-dimethyl-1H-pyrrol-1-yl)benzonitrile<br>Mass Spectrum (LCMS, ESI pos.): Calcd. for $C_{23}H_{27}N_3O_2$: 378 (M + H); found: 378. ¹H NMR (400 MHz, DMSO-d₆): δ 8.07 (d, J = 6.8 Hz, 2H), 7.60 (d, J = 6.8 Hz, 2H), 6.58 (s, 1H), 4.68 (s, 1H), 3.68-3.64 (m, 2H), 3.55-3.51 (m, 1H), 3.33-3.30 (m, 1H), 2.24 (s, 3H), 1.96 (s, 3H), 1.84-1.80 (m, 2H), 1.64-1.61 (m, 1H), 1.44-1.36 (m, 2H), 1.32-1.22 (m, 3H), 1.02-0.98 (m, 3H). |
| 148B | (±)-4-(3-(2-((2S)-2-(2-Hydroxy-2-methylpropyl)-7-azabicyclo[2.2.1]heptan-7-yl)acetyl)-2,5-dimethyl-1H-pyrrol-1-yl)benzonitrile<br>Mass Spectrum (LCMS, ESI pos.): Calcd. for $C_{25}H_{31}N_3O_2$: 406 (M + H); found: 406. ¹H NMR (400 MHz, DMSO-d₆): δ 8.06 (d, J = 8.4 Hz, 2H), 7.59 (d, J = 8.4 Hz, 2H), 6.53 (s, 1H), 4.04 (s, 1H), 3.51-3.44 (m, 2H), 3.30-3.17 (m, 2H), 2.25 (s, 3H), 1.96 (s, 3H), 1.72-1.65 (m, 4H), 1.52-1.48 (m, 1H), 1.32-1.26 (m, 4H), 1.06 (s, 6H). |

Example 29B. (±)-1-(4-Cyanophenyl)-4-(2-((2R)-2-hydroxy-7-azabicyclo[2.2.1]heptan-7-yl)acetyl)-5-methyl-1H-pyrrole-2-carbonitrile (47B)

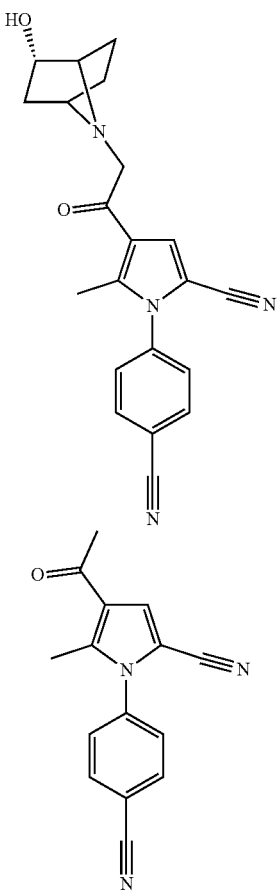

A. 4-Acetyl-1-(4-cyanophenyl)-5-methyl-1H-pyrrole-2-carbonitrile

Into a 30 mL sealed tube, being maintained under an inert atmosphere of nitrogen, was placed a mixture of 4-(3-acetyl-5-iodo-2-methyl-1H-pyrrol-1-yl)benzonitrile (2.10 g, 6.01 mmol), copper(I) cyanide (815 mg), and potassium tert-butoxide (141 mg, 1.26 mmol) in N,N-dimethylacetamide (20 mL). To the mixture was then added Pd(dppf)Cl₂.CH₂Cl₁₂ (470 mg). The reaction mixture was heated at 120° C. for 5 h and then diluted with a solution of ammonium hydroxide (1 mL) after cooling to room temperature. The resulting mixture was extracted with ethyl acetate (3×100 mL) and the combined organic extracts were concentrated under vacuum. The remaining residue was purified by column chromatography on silica, using ethyl acetate/petroleum ether (1:8) as the eluant, to afford 368 mg 4-acetyl-1-(4-cyanophenyl)-5-methyl-1H-pyrrole-2-carbonitrile as a light yellow solid. Mass Spectrum (LCMS, ESI pos.): Calcd. for $C_{15}H_{11}N_3O$: 250 (M+H); found: 250. ¹H NMR (400 MHz, CDCl₃): δ 7.94-7.91 (m, 2H), 7.51-7.48 (m, 2H), 7.36 (s, 1H), 2.51 (s, 3H), 2.48 (s, 3H).

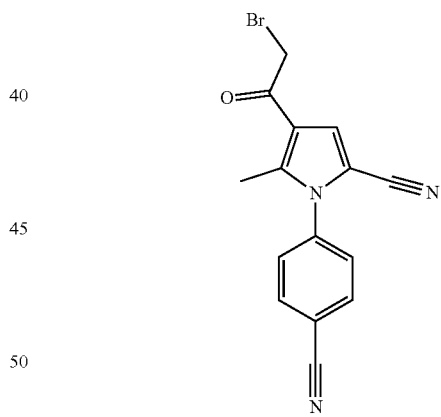

B. 4-(2-Bromoacetyl)-1-(4-cyanophenyl)-5-methyl-1H-pyrrole-2-carbonitrile

Into a 50-mL 3-necked round-bottom flask purged and maintained with an inert atmosphere of nitrogen, was placed a solution of 4-acetyl-1-(4-cyanophenyl)-5-methyl-1H-pyrrole-2-carbonitrile (227 mg, 0.91 mmol, 1.00 equiv) and DIEA (475 mg, 3.68 mmol, 4.04 equiv) in tetrahydrofuran (20 mL). To the solution was added TMSOTf (613 mg) at 0° C. in ice/water and the solution was stirred for 2 hours. Then NBS (230 mg, 1.29 mmol, 1.42 equiv) was also added at 0° C. and the mixture was stirred for additional 0.5 hour. The reaction mixture was diluted with 50 mL of water and the resulting solution was extracted with ethyl acetate (3×50 mL). The combined organic layers were concentrated under vacuum. This resulted in 257 mg (crude) of 4-(2-bromoacetyl)-1-(4-cyanophenyl)-5-methyl-1H-pyrrole-2-carbonitrile as a reddish solid. Mass Spectrum (LCMS, ESI pos.): Calcd. for $C_{15}H_{10}BrN_3O$: 328 (M+H); found: 328.

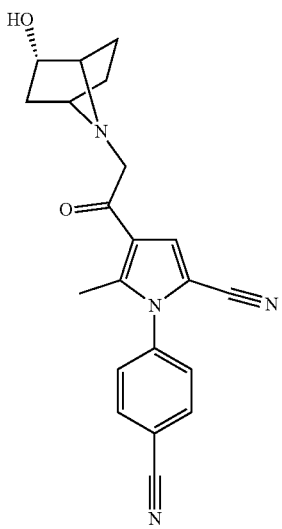 [SMILES: Cc1c(C(=O)CN2C3CCC2[C@@H](O)C3)cc(C#N)n1-c1ccc(C#N)cc1]

C. (±)-1-(4-Cyanophenyl)-4-(2-((2R)-2-hydroxy-7-azabicyclo[2.2.1]heptan-7-yl)acetyl)-5-methyl-1H-pyrrole-2-carbonitrile (47B)

Into a 50 mL round-bottom flask, being maintained under an atmosphere of nitrogen, was placed a solution of 4-(2-bromoacetyl)-1-(4-cyanophenyl)-5-methyl-1H-pyrrole-2-carbonitrile (257 mg, 0.78 mmol) in N,N-dimethylformamide (10 mL). The solution was treated with potassium carbonate (542 mg, 3.92 mmol) and racemic (1S,2S,4R)-7-azabicyclo[2.2.1]heptan-2-ol (154 mg, 1.36 mmol). The reaction mixture was allowed to stir at room temperature overnight before it was diluted with water (50 mL). The aqueous mixture was extracted with ethyl acetate (5×50 mL) and the combined organic extracts were concentrated under vacuum. The crude product was purified by preparative-HPLC under the following conditions: Column-X Bridge BEH130 Prep C18 OBD Column, 19*150 mm 5 μm C-0013; mobile phase-Phase A: water (10 mmol/L $NH_4HCO_3$), Phase B: acetonitrile (25% B up to 45% in 10 min, up to 95% in 1.5 min, down to 25% in 1.5 min); Detector-UV 254. This process afforded 108 mg (38%) of (±)-1-(4-cyanophenyl)-4-(2-((2R)-2-hydroxy-7-azabicyclo[2.2.1]heptan-7-yl) acetyl)-5-methyl-1H-pyrrole-2-carbonitrile (47B) as a light yellow solid. Mass Spectrum (LCMS, ESI pos.): Calcd. for $C_{21}H_{20}N_4O_2$: 361 (M+H); found: 361. $^1$H NMR (400 MHz, DMSO-$d_6$): δ 8.16-8.14 (m, 2H), 7.88 (s, 1H), 7.82-7.80 (m, 2H), 4.70 (d, J=4.4 Hz, 1H), 4.08-4.03 (m, 1H), 3.62 (s, 2H), 3.24-3.22 (m, 2H), 2.36 (s, 3H), 2.00-1.96 (m, 2H), 1.79-1.75 (m, 1H), 1.58-1.48 (m, 1H), 1.36-1.28 (m, 1H), 0.81-0.77 (m, 1H).

Using the procedures described in Example 29B, reagents, starting materials, and conditions known to those skilled in the art, the following compounds representative of the present invention were prepared:

| Cpd | Data |
| --- | --- |
| 136B | (±)-1-(4-Cyanophenyl)-5-methyl-4-(2-((1R,2R,4S)-2-methyl-7-azabicyclo[2.2.1]heptan-7-yl)acetyl)-1H-pyrrole-2-carbonitrile<br>Mass Spectrum (LCMS, ESI pos.): Calcd. for $C_{22}H_{22}N_4O$: 359 (M + H); found: 359. $^1$H NMR (400 MHz, CDCl$_3$): δ 7.88 (d, J = 8.4 Hz, 2H), 7.66 (s, 1H), 7.48 (d, J = 8.8 Hz, 2H), 3.60-3.52 (m, 2H), 3.33 (brs, 1H), 3.01 (brs, 1H), 2.46 (s, 3H), 1.84-1.76 (m, 3H), 1.68-1.60 (m, 1H), 1.54-1.49 (m, 1H), 1.36-1.31 (m, 2H), 1.30-1.29 (m, 1H), 1.05-1.03 (d, J = 6.8 Hz, 3H). |
| 137B | 4-(2-(7-Azabicyclo[2.2.1]heptan-7-yl)acetyl)-1-(4-cyanophenyl)-5-methyl-1H-pyrrole-2-carbonitrile<br>Mass Spectrum (LCMS, ESI pos.): Calcd. for $C_{21}H_{20}N_4O$: 345 (M + H); found: 345. $^1$H NMR (400 MHz, CDCl$_3$): δ 8.03-8.00 (m, 2H), 7.68-7.64 (m, 3H), 3.50-3.49 (m, 2H), 3.32-3.30 (m, 2H), 2.45 (s, 3H), 1.85-1.83 (m, 4H), 1.40-1.39 (m, 4H). |

Example 30B. (±)-4-(3-Fluoro-4-(2-((2R)-2-hydroxy-7-azabicyclo[2.2.1]heptan-7-yl)acetyl)-2,5-dimethyl-1H-pyrrol-1-yl)benzonitrile (78B)

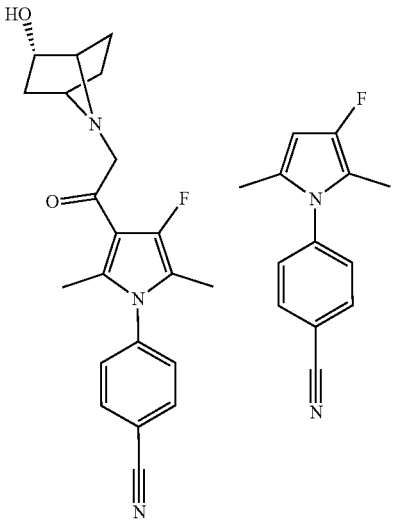

A. 4-(3-fluoro-2,5-dimethyl-1H-pyrrol-1-yl)benzonitrile

Into a 250 mL round-bottom flask was placed a solution of 4-(2,5-dimethyl-1H-pyrrol-1-yl)benzonitrile (5.0 g, 25.5 mmol, from preparation of Intermediate XB) in acetonitrile (100 mL). The solution was cooled to 0° C. and then treated with Selectfluor (1.23 g, 51.3 mmol) in a portionwise manner. The resulting mixture was allowed to warm to room temperature and stir overnight. The reaction mixture was concentrated under vacuum and the remaining residue was purified by column chromatography on silica, using ethyl acetate/petroleum ether (1:3) as the eluant, to afford 280 mg (5%) of 4-(3-fluoro-2,5-dimethyl-1H-pyrrol-1-yl)benzonitrile as a white solid. Mass Spectrum (LCMS, ESI pos.): Calcd. for $C_3H_{11}FN_2$: 215 (M+H); found: 215. $^1$H NMR (300 MHz, DMSO-$d_6$): δ 8.03-7.98 (m, 2H), 7.57-7.53 (m, 2H), 5.89 (s, 1H), 1.99 (s, 3H), 1.92 (s, 3H).

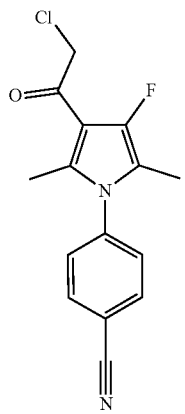 [SMILES: Cc1c(F)c(C(=O)CCl)c(C)n1-c1ccc(C#N)cc1]

B. 4-(3-(2-Chloroacetyl)-4-fluoro-2,5-dimethyl-1H-pyrrol-1-yl)benzonitrile

Into a 100 mL 3-necked round-bottom flask was placed a solution of 4-(3-fluoro-2,5-dimethyl-1H-pyrrol-1-yl)benzonitrile (100 mg, 0.47 mmol) in dichloromethane (5 mL). The solution was cooled to 0° C. and then treated with 2-chloroacetyl chloride (0.05 mL) and diethylaluminum chloride (0.78 mL). The resulting mixture was allowed to warm to room temperature and stir overnight. The reaction was diluted with water and the pH of the mixture as adjusted to a value of 8 through the addition of an aqueous sodium carbonate solution. The mixture was extracted with dichloromethane (3×10 mL) and the combined organic extracts were dried over anhydrous sodium sulfate. The organic phase was concentrated under vacuum and the remaining residue was purified by column chromatography on silica, using ethyl acetate/petroleum ether (1:3) as the eluant, to afford 60 mg (44%) of 4-(3-(2-chloroacetyl)-4-fluoro-2,5-dimethyl-1H-pyrrol-1-yl)benzonitrile as a yellow solid. Mass Spectrum (LCMS, ESI pos.): Calcd. for $C_{13}H_{12}ClFN_2O$: 291 (M+H); found: 291.

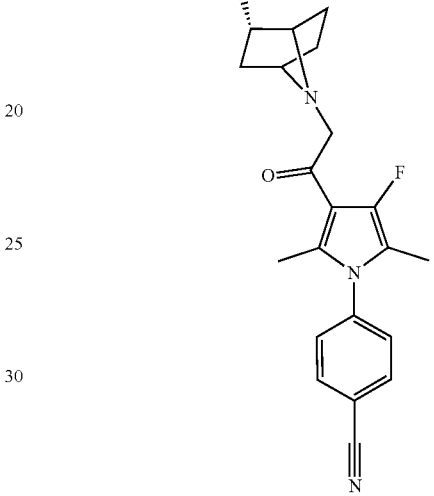

C. (±)-4-(3-Fluoro-4-(2-((2R)-2-hydroxy-7-azabicyclo[2.2.1]heptan-7-yl)acetyl)-2,5-dimethyl-1H-pyrrol-1-yl)benzonitrile (78B)

Into a 100 mL round-bottom flask was placed a solution of 4-(3-(2-chloroacetyl)-4-fluoro-2,5-dimethyl-1H-pyrrol-1-yl)benzonitrile (180 mg, 0.62 mmol) in N,N-dimethylformamide (5 mL). To the solution were then added racemic (1R,2R,4S)-7-azabicyclo[2.2.1]heptan-2-ol hydrochloride (112 mg, 0.75 mmol) and potassium carbonate (340 mg, 2.46 mmol). The resulting mixture was allowed to stir at room temperature overnight before it was diluted with water. The aqueous mixture was extracted with ethyl acetate (2×5 mL) and the combined organic extracts were dried over anhydrous sodium sulfate. The organic phase was concentrated under vacuum and the remaining crude product was purified by preparative-HPLC under the following conditions: Column-Xbridge C18 OBD Prep Column, 5 μm, 19 mm×250 mm; mobile phase-water with 0.05% $NH_4HCO_3$ and acetonitrile (26% acetonitrile up to 62% in 8 min); Detector-UV 254 nm. This process afforded 31 mg (14%) of (±)-4-(3-fluoro-4-(2-((2R)-2-hydroxy-7-azabicyclo[2.2.1]heptan-7-yl)acetyl)-2,5-dimethyl-1H-pyrrol-1-yl)benzonitrile (78B) as a white solid. Mass Spectrum (LCMS, ESI pos.): Calcd. for $C_{21}H_{22}FN_3O_2$: 368 (M+H); found: 368. $^1$H NMR (400 MHz, DMSO-$d_6$): δ 8.08 (d, J=8.8 Hz, 2H), 7.63 (d, J=8.4 Hz, 2H), 4.69 (brs, 2H), 4.10-4.08 (m, 2H), 3.57-3.54 (m, 2H), 2.23 (s, 3H), 2.03-1.94 (m, 2H), 1.91 (s, 3H), 1.74 (brs, 1H), 1.53-1.35 (m, 2H), 0.85-0.82 (m, 1H)

Using the procedures described in Example 30B, reagents, starting materials, and conditions known to those skilled in the art, the following compounds representative of the present invention were prepared:

| Cpd | Data |
|---|---|
| 101B | (±)-4-(3-Fluoro-2,5-dimethyl-4-(2-((1S,2S,4R)-2-methyl-7-azabicyclo[2.2.1]heptan-7-yl)acetyl)-1H-pyrrol-1-yl)benzonitrile<br>Mass Spectrum (LCMS, ESI pos.): Calcd. for $C_{22}H_{24}FN_3O$: 366 (M + H); found: 366. $^1$H NMR (300 MHz, DMSO-$d_6$): δ 8.10-8.05 (m, 2H), 7.67-7.61 (m, 2H), 3.56 (s, 2H), 3.27-3.16 (m, 2H), 2.23 (s, 3H), 2.13-2.06 (m, 1H), 1.98-1.94 (m, 1H), 1.94 (s, 3H), 1.71-1.47 (m, 3H), 1.25-1.20 (m, 1H), 0.92 (d, J = 6.9 Hz, 3H), 0.65-0.61 (m, 1H). |
| 103B | (±)-4-(3-Fluoro-2,5-dimethyl-4-(2-((1R,2R,4S)-2-(trifluoromethyl)-7-azabicyclo[2.2.1]heptan-7-yl)acetyl)-1H-pyrrol-1-yl)benzonitrile<br>Mass Spectrum (LCMS, ESI pos.): Calcd. for $C_{22}H_{21}F_4N_3O$: 420 (M + H); found: 420. $^1$H NMR (400 MHz, $CH_3OH$-$d_4$): δ 7.96-7.94 (m, 2H), 7.51-7.48 (m, 2H), 3.79 (s, 2H), 3.68 (t, J = 4.4 Hz, 1H), 3.56 (t, J = 4.4 Hz, 1H), 2.97-2.93 (m, 1H), 2.28 (s, 3H), 2.15-2.08 (m, 1H), 1.94 (s, 3H), 1.93-1.78 (m, 3H), 1.48-1.41 (m, 2H). |
| 104B | 4-(3-(2-((1s,4s)-7-Azabicyclo[2.2.1]heptan-7-yl)acetyl)-4-fluoro-2,5-dimethyl-1H-pyrrol-1-yl)benzonitrile<br>Mass Spectrum (LCMS, ESI pos.): Calcd. for $C_{22}H_{21}FN_3O$: 352 (M + H); found: 352. $^1$H NMR (300 MHz, DMSO-$d_6$): δ 8.07 (d, J = 8.4 Hz, 2H), 7.63 (d, J = 8.4 Hz, 2H), 3.48 (s, 2H), 3.32-3.31 (m, 2H), 2.22 (s, 3H), 1.90 (s, 3H), 1.66-1.64 (m, 4H), 1.25-1.23 (m, 4H). |
| 121B | (±)-4-(3-Fluoro-2,5-dimethyl-4-(2-((1S,2R,4R)-2-methyl-7-azabicyclo[2.2.1]heptan-7-yl)acetyl)-1H-pyrrol-1-yl)benzonitrile<br>Mass Spectrum (LCMS, ESI pos.): Calcd. for $C_{22}H_{24}FN_3O$: 366 (M + H); found: 366. $^1$H NMR (300 MHz, DMSO-$d_6$): δ 8.06 (d, J = 8.4 Hz, 2H), 7.62 (d, J = 8.7 Hz, 2H), 3.48 (s, 2H), 3.31 (brs, 1H), 2.97 (brs, 1H), 2.22 (s, 3H), 1.90 (s, 3H), 1.71-1.68 (m, 2H), 1.59-1.53 (m, 1H), 1.47-1.40 (m, 1H), 1.25-1.20 (m, 2H), 1.09-1.07 (m, 1H), 0.92 (d, J = 6.6 Hz, 3H). |
| 149B | (±)-4-(3-Fluoro-2,5-dimethyl-4-(2-((1R,4S)-2-(trifluoromethyl)-7-azabicyclo[2.2.1]hept-2-en-7-yl)acetyl)-1H-pyrrol-1-yl)benzonitrile<br>Mass Spectrum (LCMS, ESI pos.): Calcd. for $C_{22}H_{19}F_4N_3O$: 418 (M + H); found: 418. $^1$H NMR (300 MHz, DMSO-$d_6$): δ 8.03 (d, J = 8.4 Hz, 2H), 7.58 (d, J = 8.4 Hz, 2H), 6.74 (s, 1H), 4.14-4.08 (m, 2H), 3.38-3.36 (m, 2H), 2.16 (s, 3H), 1.84 (brs, 5H), 1.06-1.03 (m, 2H). |

Example 31B. (±)-4-(3-(2-((2R)-2-Hydroxy-7-azabicyclo[2.2.1]heptan-7-yl)acetyl)-2,4,5-trimethyl-1H-pyrrol-1-yl)benzonitrile (76B)

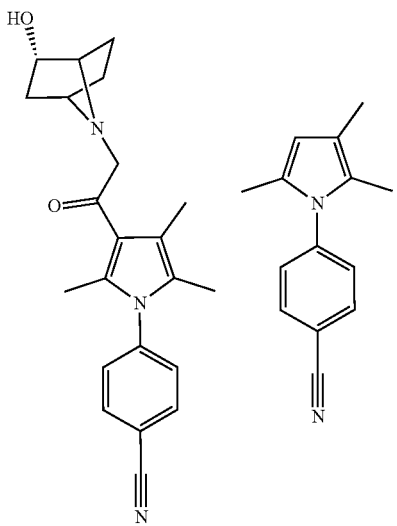

A. 4-(2,3,5-Trimethyl-1H-pyrrol-1-yl)benzonitrile

Into a 20 mL sealed tube, being maintained under an inert atmosphere of nitrogen, was placed a solution of 4-(3-iodo-2,5-dimethyl-1H-pyrrol-1-yl)benzonitrile (1.0 g, 3.10 mmol, from Example 12B) in 1,4-dioxane (15 mL). To the solution were added methylboronic acid (373 mg, 6.23 mmol), cesium carbonate (2.02 g, 6.21 mmol) and Pd(dppf)$C_{l2}$ (454 mg, 0.62 mmol). The resulting mixture was heated at 80° C. for 16 h. After cooling to room temperature, the reaction mixture was diluted with brine and then extracted with ethyl acetate. The combined organic extracts were dried over sodium sulfate and concentrated under vacuum. The remaining crude product was purified by preparative-HPLC under the following conditions: Column-C18; mobile phase-$CH_3CN/H_2O$=0:50 increasing to $CH_3CN/H_2O$=95:5 within 20 min; Detector-UV 254 nm. This process afforded 95 mg (15%) of 4-(2,3,5-trimethyl-1H-pyrrol-1-yl)benzonitrile as a yellow solid. $^1$H NMR (400 MHz, DMSO-$d_6$): δ 7.97-7.95 (m, 2H), 7.47-7.45 (m, 2H), 5.74 (s, 1H), 1.95 (s, 3H), 1.93 (s, 3H), 1.89 (s, 3H).

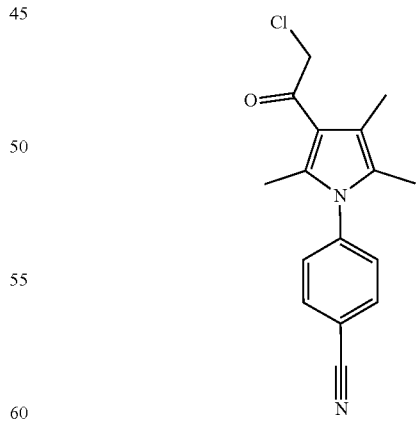

B. 4-(3-(2-Chloroacetyl)-2,4,5-trimethyl-1H-pyrrol-1-yl)benzonitrile

Into a 50 mL round-bottom flask, being maintained under an inert atmosphere of nitrogen, was placed a solution of 4-(2,3,5-trimethyl-1H-pyrrol-1-yl)benzonitrile (95 mg, 0.45 mmol) in dichloromethane (5 mL). The solution was cooled to 0° C. and then 2-chloroacetyl chloride (0.11 mL) and diethylaluminum chloride (1.0 mL) were added to the flask. The resulting mixture was allowed to stir at 0° C. for 1 h before being diluted with brine. The pH of the mixture was adjusted to a value of 8 through the addition of an aqueous sodium bicarbonate solution. The mixture was then extracted with dichloromethane and the combined organic extracts were dried over anhydrous sodium sulfate. The organic phase was concentrated under vacuum to afford 129 mg (crude) of 4-(3-(2-chloroacetyl)-2,4,5-trimethyl-1H-pyrrol-1-yl)benzonitrile as a light yellow solid. Mass Spectrum (LCMS, ESI pos.): Calcd. for $C_{16}H_{15}ClN_2O$: 287 (M+H); found: 287.

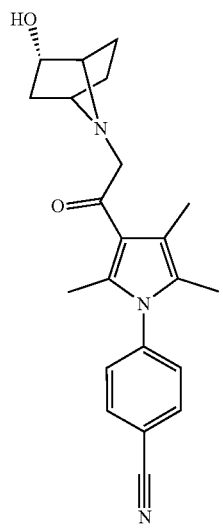

C. (±)-4-(3-(2-((2R)-2-Hydroxy-7-azabicyclo[2.2.1]heptan-7-yl)acetyl)-2,4,5-trimethyl-1H-pyrrol-1-yl)benzonitrile (76B)

Into a 50 mL round-bottom flask, being maintained under an inert atmosphere of nitrogen, was placed a solution of 4-(3-(2-chloroacetyl)-2,4,5-trimethyl-1H-pyrrol-1-yl)benzonitrile (129 mg, 0.45 mmol) in N,N-dimethylformamide (4 mL). To the solution were added racemic (1R,2R,4S)-7-azabicyclo[2.2.1]heptan-2-ol hydrochloride (136 mg, 0.91 mmol) and potassium carbonate (125 mg, 0.91 mmol). The resulting mixture was allowed to stir at room temperature for 20 h, before the precipitate was filtered from the mixture. The crude product was purified by preparative-HPLC under the following conditions: column-XBridge C18 OBD Prep Column, 19×150 mm; mobile phase-water (0.05% $NH_4HCO_3$):$CH_3CN$ (25% $CH_3CN$ up to 85% in 10 min, up to 95% in 1.5 min, down to 25% in 1.5 min); detector—UV 254 nm. This process afforded 65 mg (39%) of (±)-4-(3-(2-((2R)-2-hydroxy-7-azabicyclo[2.2.1]heptan-7-yl)acetyl)-2,4,5-trimethyl-1H-pyrrol-1-yl)benzonitrile (76B) as an off-white solid. Mass Spectrum (LCMS, ESI pos.): Calcd. for $C_{21}H_{25}N_3O_2$: 364 (M+H); found: 364. $^1$H NMR (400 MHz, DMSO-$d_6$): δ 8.03 (d, J=8.4 Hz, 2H), 7.52 (d, J=8.4 Hz, 2H), 4.65-4.64 (m, 1H), 4.02-3.99 (m, 1H), 3.48-3.40 (m, 2H), 3.20 (brs, 2H), 2.18-2.16 (m, 6H), 2.00-1.94 (m, 2H), 1.84 (s, 3H), 1.73-1.69 (m, 1H), 1.51-1.46 (m, 1H), 1.33-1.32 (m, 1H), 0.80-0.75 (m, 1H).

Example 32B. (±)-4-(3-Chloro-4-(2-((2R)-2-hydroxy-7-azabicyclo[2.2.1]heptan-7-yl)acetyl)-2,5-dimethyl-1H-pyrrol-1-yl)benzonitrile (77B)

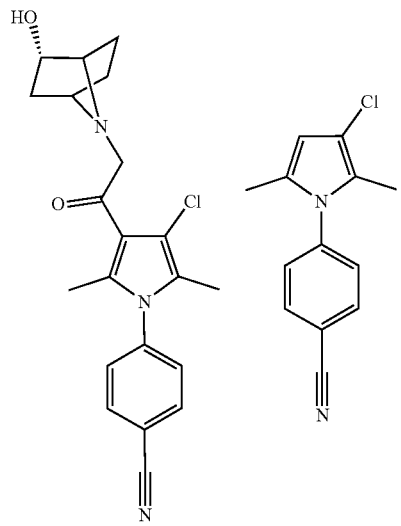

A. 4-(3-Chloro-2,5-dimethyl-1H-pyrrol-1-yl)benzonitrile

Into a 100 mL round-bottom flask was placed a solution of 4-(2,5-dimethyl-1H-pyrrol-1-yl)benzonitrile (1.0 g, 5.10 mmol) in acetonitrile (30 mL), which was then treated with N-chlorosuccinimide (749 mg, 5.61 mmol). The resulting mixture was allowed to stir at room temperature for 5 min before it was diluted with water (100 mL). The aqueous mixture was extracted with ethyl acetate (2×100 mL) and the combined organic extracts were washed with brine (2×100 mL), dried over anhydrous sodium sulfate and concentrated under vacuum. The crude product was purified by preparative-HPLC under the following conditions: column-C18; mobile phase-$H_2O$ (0.5% $NH_4HCO_3$)/acetonitrile=80/20 increasing to $H_2O$ (0.5% $NH_4HCO_3$)/acetonitrile=40/60 within 35 min; detector-UV 254 nm. This process afforded 400 mg (34%) of 4-(3-chloro-2,5-dimethyl-1H-pyrrol-1-yl)benzonitrile as a light yellow solid. $^1$H NMR (400 MHz, DMSO-$d_6$): δ 8.04-8.01 (m, 2H), 7.59-7.56 (m, 2H), 6.00 (s, 1H), 1.98 (s, 3H), 1.96 (s, 3H).

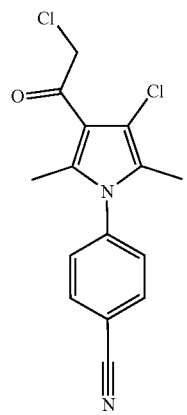

B. 4-(3-Chloro-4-(2-chloroacetyl)-2,5-dimethyl-1H-pyrrol-1-yl)benzonitrile

Into a 100 mL round-bottom flask was placed a solution of 4-(3-chloro-2,5-dimethyl-1H-pyrrol-1-yl)benzonitrile (300 mg, 1.30 mmol) in dichloromethane (30 mL). To the solution were added diethylaluminum chloride (3.9 mL) and 2-chloroacetyl chloride (441 mg, 3.90 mmol). The resulting mixture was allowed to stir at room temperature for 1 h before it was diluted with a solution of aqueous sodium bicarbonate (100 mL). The mixture was extracted with ethyl acetate (2×100 mL) and the combined organic extracts were washed with brine (2×100 mL). Drying the organic phase over anhydrous sodium sulfate, followed by concentrating under vacuum, afforded 370 mg (93%) of 4-(3-chloro-4-(2-chloroacetyl)-2,5-dimethyl-1H-pyrrol-1-yl)benzonitrile as a yellow solid. Mass Spectrum (LCMS, ESI pos.): Calcd. for $C_{15}H_{12}C_{12}N_2O$: 307 (M+H); found: 307.

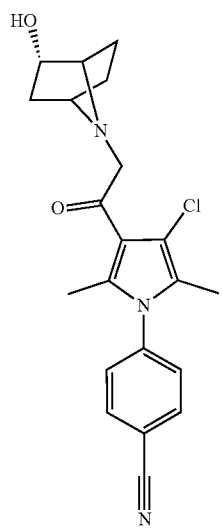 [SMILES: Cc1c(Cl)c(C(=O)CN2C3CCC2[C@@H](O)C3)c(C)n1-c1ccc(C#N)cc1]

C. (±)-4-(3-Chloro-4-(2-((2R)-2-hydroxy-7-azabicyclo[2.2.1]heptan-7-yl)acetyl)-2,5-dimethyl-1H-pyrrol-1-yl)benzonitrile (77B)

Into a 25 mL round-bottom flask was placed a solution of 4-(3-chloro-4-(2-chloroacetyl)-2,5-dimethyl-1H-pyrrol-1-yl)benzonitrile (460 mg, 1.50 mmol) in N,N-dimethylformamide (10 mL). To the solution were added potassium carbonate (621 mg, 4.49 mmol) and racemic (1R,2R,4S)-7-azabicyclo[2.2.1]heptan-2-ol hydrochloride (269 mg, 1.80 mmol). The resulting mixture was allowed to stir at room temperature for 16 h. The crude product was purified by preparative-HPLC under the following conditions: column-C18; mobile phase-H₂O (0.5% NH₄HCO₃)/acetonitrile=95/5 increasing to H₂O (0.5% NH₄HCO₃)/acetonitrile=5/95 within 35 min; detector-UV 254 nm. This process afforded 112 mg (19%) of (±)-4-(3-chloro-4-(2-((2R)-2-hydroxy-7-azabicyclo[2.2.1]heptan-7-yl)acetyl)-2,5-dimethyl-1H-pyrrol-1-yl)benzonitrile (77B) as a light yellow solid. Mass Spectrum (LCMS, ESI pos.): Calcd. for $C_{21}H_{22}ClN_3O_2$: 384 (M+H); found: 384. ¹H NMR (300 MHz, DMSO-d₆): δ 8.09 (d, J=8.4 Hz, 2H), 7.63 (d, J=8.4 Hz, 2H), 4.69 (d, J=4.2 Hz, 1H), 4.06-4.02 (m, 1H), 3.68 (s, 2H), 3.25-3.22 (m, 2H), 2.19 (s, 3H), 2.04-1.94 (m, 5H), 1.74-1.72 (m, 1H), 1.55-1.31 (m, 2H), 0.81-0.78 (m, 1H).

Example 33B. (±)-4-(3-(2-((2R)-2-Hydroxy-7-azabicyclo[2.2.1]heptan-7-yl)acetyl)-2,5-dimethyl-4-(trifluoromethyl)-1H-pyrrol-1-yl)benzonitrile (79B)

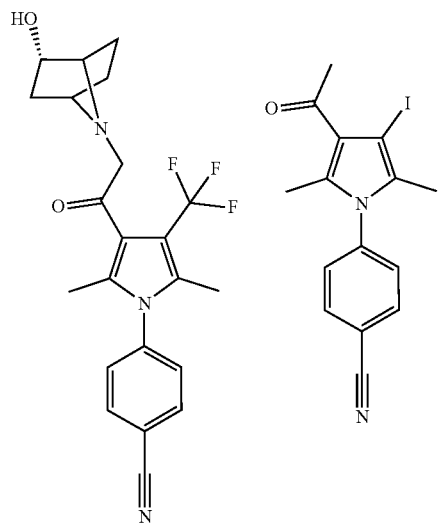

A. 4-(3-Acetyl-4-iodo-2,5-dimethyl-1H-pyrrol-1-yl)benzonitrile

Into a 250 mL 3-necked round-bottom flask, being maintained under an inert atmosphere of nitrogen, was placed a solution of 4-(3-iodo-2,5-dimethyl-1H-pyrrol-1-yl)benzonitrile (4.0 g, 12.4 mmol, from Example 12B) in dichloromethane (20 mL). The solution was cooled to 0° C. and then treated with diethylaluminum chloride (50 mL) and acetyl chloride (1.46 g, 18.6 mmol). The resulting mixture was allowed to stir at 0° C. for 2 h before it was diluted with water (100 mL). The mixture was extracted with dichloromethane (2×50 mL) and the combined organic extracts were washed with an aqueous solution of sodium bicarbonate (2×100 mL). The organic phase was dried over sodium sulfate, followed by concentrating under vacuum, to afford 5 g (crude) 4-(3-acetyl-4-iodo-2,5-dimethyl-1H-pyrrol-1-yl)benzonitrile as a yellow solid. Mass Spectrum (LCMS, ESI pos.): Calcd. for $C_{15}H_{13}IN_2O$: 365 (M+H); found: 365.

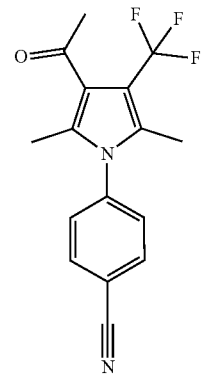 [SMILES: CC(=O)c1c(C(F)(F)F)c(C)n(-c2ccc(C#N)cc2)c1C]

B. 4-(3-Acetyl-2,5-dimethyl-4-(trifluoromethyl)-1H-pyrrol-1-yl)benzonitrile

Into a 100 mL round-bottom flask, being maintained under an inert atmosphere of nitrogen, was placed a mixture of 4-(3-acetyl-4-iodo-2,5-dimethyl-1H-pyrrol-1-yl)benzonitrile (2.0 g, 5.49 mmol), methyl 2,2-difluoro-2-(fluorosulfonyl)acetate (4.22 g, 22.0 mmol), copper(I) iodide (1.05 g, 5.51 mmol) and N,N-dimethylformamide (20 mL). The reaction mixture was heated at 100° C. overnight and then allowed to cool to room temperature. The reaction mixture was concentrated under vacuum and the remaining residue was purified by column chromatography on silica, using ethyl acetate/hexane (1:15-1:5) as the eluant, to afford 1.4 g (83%) of 4-(3-acetyl-2,5-dimethyl-4-(trifluoromethyl)-1H-pyrrol-1-yl)benzonitrile as a light yellow solid. Mass Spectrum (LCMS, ESI pos.): Calcd. for $C_6H_{13}F_3N_2O$: 307 (M+H); found: 307.

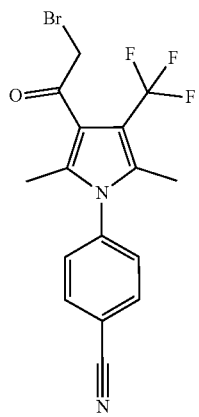 [SMILES: Cc1c(C(=O)CBr)c(C(F)(F)F)c(C)n1-c1ccc(C#N)cc1]

C. 4-(3-(2-Bromoacetyl)-2,5-dimethyl-4-(trifluoromethyl)-1H-pyrrol-1-yl)benzonitrile Into a 50 mL 3-necked round-bottom flask, being maintained under an inert atmosphere of nitrogen, was placed a mixture of 4-(3-acetyl-2,5-dimethyl-4-(trifluoromethyl)-1H-pyrrol-1-yl)benzonitrile (200 mg, 0.65 mmol), diisopropylethylamine (250 mg, 1.94 mmol), trimethylsilyl trifluoromethanesulfonate (216 mg, 0.97 mmol) and tetrahydrofuran (10 mL). The resulting mixture was allowed to stir at 0° C. for 1 h and then a solution of N-bromosuccinimide (127 mg, 0.71 mmol) in tetrahydrofuran (1 mL) was added. The reaction mixture was allowed to stir for additional 10 min before being diluted with water (10 mL). The aqueous mixture was extracted with dichloromethane (3×20 mL) and the combined organic extracts were dried over sodium sulfate. The organic phase was concentrated under vacuum to afford 200 mg (crude) of 4-(3-(2-bromoacetyl)-2,5-dimethyl-4-(trifluoromethyl)-1H-pyrrol-1-yl)benzonitrile as yellow solid, which was used without any further purification.

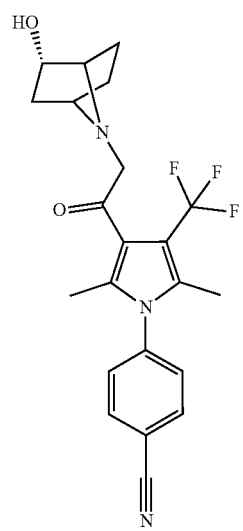 [SMILES: Cc1c(C(=O)CN2C3CCC2[C@@H](O)C3)c(C(F)(F)F)c(C)n1-c1ccc(C#N)cc1]

D. (±)-4-(3-(2-((2R)-2-Hydroxy-7-azabicyclo[2.2.1]heptan-7-yl)acetyl)-2,5-dimethyl-4-(trifluoromethyl)-1H-pyrrol-1-yl)benzonitrile (79B)

Into a 25 mL round-bottom flask, being maintained under an inert atmosphere of nitrogen, was placed a mixture of 4-(3-(2-bromoacetyl)-2,5-dimethyl-4-(trifluoromethyl)-1H-pyrrol-1-yl)benzonitrile (200 mg, 0.52 mmol), racemic (1R, 2R,4S)-7-azabicyclo[2.2.1]heptan-2-ol (88 mg, 0.78 mmol), potassium carbonate (143 mg, 1.03 mmol) and N,N-dimethylformamide (2 mL). The reaction mixture was allowed to stir at room temperature for 12 h before it was concentrated under vacuum. The remaining residue was purified by preparative TLC (dichloromethane:methanol=10:1) afforded 60 mg (28%) of (±)-4-(3-(2-((2R)-2-hydroxy-7-azabicyclo[2.2.1]heptan-7-yl)acetyl)-2,5-dimethyl-4-(trifluoromethyl)-1H-pyrrol-1-yl)benzonitrile (79B) as a white solid. Mass Spectrum (LCMS, ESI pos.): Calcd. for $C_{22}H_{22}F_3N_3O_2$: 418 (M+H); found: 418. $^1$H NMR (300 MHz, DMSO-$d_6$): δ 8.10 (d, 2H, J=8.4 Hz), 7.65 (d, 2H, J=8.4 Hz), 4.72 (s, 1H), 4.00 (brs, 1H), 3.51 (brs, 2H), 3.18 (brs, 2H), 2.09 (s, 3H), 2.02 (s, 3H), 1.99-1.95 (m, 2H), 1.71-1.63 (m, 1H), 1.36-1.32 (m, 1H), 0.79-0.76 (m, 1H).

Example 34B. (±)-1-(4-Cyanophenyl)₄-(2-((2R)-2-hydroxy-7-azabicyclo[2.2.1]heptan-7-yl)acetyl)-2,5-dimethyl-1H-pyrrole-3-carbonitrile (95B)

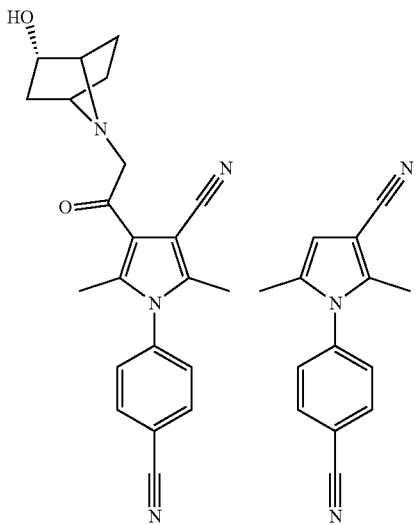

A. 1-(4-Cyanophenyl)-2,5-dimethyl-1H-pyrrole-3-carbonitrile

Into a 5 mL pressure tank reactor, being maintained under an inert atmosphere of nitrogen, was placed a solution of 4-(3-iodo-2,5-dimethyl-1H-pyrrol-1-yl)benzonitrile (322 mg, 1.00 mmol) in N,N-dimethylacetamide (2 mL). Then sodium carbonate (106 mg, 1.00 mmol), K₄[Fe(CN)₆] (74 mg, 0.20 mmol) and palladium(II) acetate (11 mg, 0.05 mmol) were added to the reactor. The resulting mixture was heated at 120° C. overnight before it was allowed to cool to room temperature. The reaction mixture was diluted with brine and then extracted with ethyl acetate (3×50 mL). The combined organic extracts were dried over anhydrous sodium sulfate and concentrated under vacuum. The remaining residue was purified by column chromatography on silica, using ethyl acetate/petroleum ether (1:5) as the eluant, to afford 95 mg (43%) of 1-(4-cyanophenyl)-2,5-dimethyl-1H-pyrrole-3-carbonitrile as a yellow solid. Mass Spectrum (LCMS, ESI pos.): Calcd. for $C_{14}H_{11}N_3$: 222 (M+H); found: 222. ¹H NMR (400 MHz, DMSO-d₆): δ 8.10-8.07 (m, 2H), 7.67-7.64 (m, 2H), 6.33 (s, 1H), 2.12 (s, 3H), 1.97 (s, 3H).

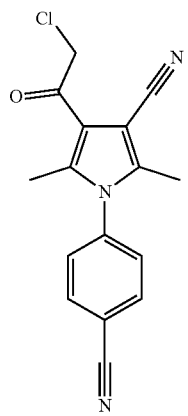 [SMILES: Cc1c(C#N)c(C(=O)CCl)c(C)n1-c1ccc(C#N)cc1]

B. 4-(2-Chloroacetyl)-1-(4-cyanophenyl)-2,5-dimethyl-1H-pyrrole-3-carbonitrile Into a 50 mL round-bottom flask, being maintained under an inert atmosphere of nitrogen, was placed a solution of aluminum chloride (451 mg, 3.39 mmol) in dichloromethane (3 mL). The solution was cooled to 0° C. and then treated with 2-chloroacetyl chloride (383 mg, 3.39 mmol) in a dropwise fashion. The mixture was allowed to stir at 0° C. for 0.5 h before a solution of 1-(4-cyanophenyl)-2,5-dimethyl-1H-pyrrole-3-carbonitrile (150 mg, 0.68 mmol) in dichloromethane (2 mL) was added in a dropwise fashion. The reaction mixture was allowed to stir at 0° C. for 0.5 h and then warm to room temperature and stir for an additional hour. The reaction mixture was diluted with brine and then extracted with dichloromethane (3×50 mL). The combined organic extracts were dried over sodium sulfate and concentrated under vacuum to afford 200 mg (99%) of 4-(2-chloroacetyl)-1-(4-cyanophenyl)-2,5-dimethyl-1H-pyrrole-3-carbonitrile as a yellow solid. Mass Spectrum (LCMS, ESI pos.): Calcd. for $C_{16}H_{12}ClN_3O$: 298 (M+H); found: 298.

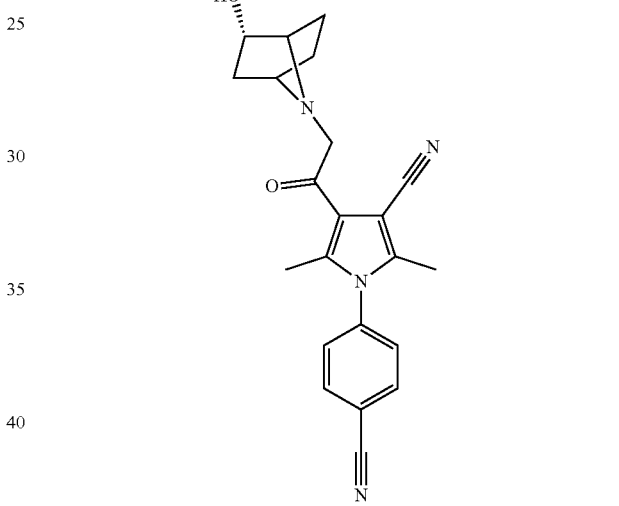

C. (±)-1-(4-Cyanophenyl)-4-(2-((2R)-2-hydroxy-7-azabicyclo[2.2.1]heptan-7-yl)acetyl)-2,5-dimethyl-1H-pyrrole-3-carbonitrile (95B)

Into a 50 mL round-bottom flask, being maintained under an inert atmosphere of nitrogen, was placed a solution of 4-(2-chloroacetyl)-1-(4-cyanophenyl)-2,5-dimethyl-1H-pyrrole-3-carbonitrile (200 mg, 0.67 mmol) in N,N-dimethylformamide (2 mL). Then potassium carbonate (139 mg, 1.01 mmol) and racemic (1R,2R,4S)-7-azabicyclo[2.2.1]heptan-2-ol (121 mg, 0.81 mmol) were added. The resulting mixture was allowed to stir at room temperature overnight before the solids were filtered rom the mixture. The crude product was purified by preparative-HPLC under the following conditions: column-SunFire C18 OBD Prep Column, 5 μm, 19 mm×250 mm; mobile phase-Water with 0.05% NH₄HCO₃ and acetonitrile (30% acetonitrile up to 60% in 8 min); Detector-UV 254 & 220 nm. This process afforded 143 mg (57%) of (±)-1-(4-cyanophenyl)-4-(2-((2R)-2-hydroxy-7-azabicyclo[2.2.1]heptan-7-yl)acetyl)-2,5-dimethyl-1H-pyrrole-3-carbonitrile (95B) as a white solid. Mass Spectrum (LCMS, ESI pos.): Calcd. for $C_{22}H_{22}N_3O_2$: 375

(M+H); found: 375. ¹H NMR (400 MHz, DMSO-d₆): δ 8.13 (d, J=8.0 Hz, 2H), 7.70 (d, J=8.4 Hz, 2H), 4.70 (d, J=4.0 Hz, 1H), 4.09-4.02 (m, 1H), 3.65-3.55 (m, 2H), 3.23-3.16 (m, 2H), 2.24 (s, 3H), 2.11 (s, 3H), 2.04-1.93 (m, 2H), 1.75 (m, 1H), 1.54-1.48 (m, 1H), 1.38-1.35 (m, 1H), 0.88-0.72 (m, 1H).

Example 35B. (±)-4-(5-Chloro-3(2-((2R)-2-hydroxy-7-azabicyclo[2.2.1]heptan-7-yl)acetyl)-2-methyl-1H-pyrrol-1-yl)benzonitrile (96B)

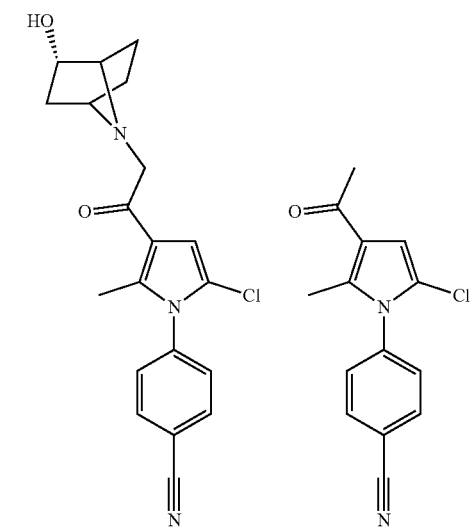

A. 4-(3-Acetyl-5-chloro-2-methyl-1H-pyrrol-1-yl)benzonitrile

Into a 50 mL 3-necked round-bottom flask, being maintained under an inert atmosphere of nitrogen, was placed a solution of 4-(3-acetyl-2-methyl-1H-pyrrol-1-yl)benzonitrile (1.0 g, 4.46 mmol, from Intermediate IB) in dichloromethane (10 mL). The solution was cooled to 0° C. and then treated in a dropwise manner with SO₂Cl₂ (4.6 mL). The resulting mixture was allowed to stir at 0° C. for 1 h before it was diluted with water (20 mL). The mixture was extracted with dichloromethane (2×50 mL) and the combined organic extracts were washed with an aqueous sodium bicarbonate solution (1×20 mL). The organic phase was washed with brine (2×30 mL), dried over anhydrous sodium sulfate and concentrated under vacuum. The remaining residue was purified by preparative TLC on silica, using ethyl acetate/petroleum ether (1:8) as the developing solution, to afford 600 mg (52%) of 4-(3-acetyl-5-chloro-2-methyl-1H-pyrrol-1-yl)benzonitrile as a white solid. Mass Spectrum (LCMS, ESI pos.): Calcd. for $C_4H_{11}ClN_2O$: 259 (M+H); found: 259. ¹H NMR (300 MHz, CDCl₃): δ 7.81 (d, J=9.0 Hz, 2H), 7.35 (d, J=6.0 Hz, 2H), 6.53 (s, 1H), 2.39 (s, 3H), 2.32 (s, 3H).

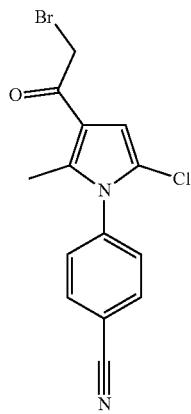 [SMILES: Cc1c(C(=O)CBr)cc(Cl)n1-c1ccc(C#N)cc1]

B. 4-(3-(2-Bromoacetyl)-5-chloro-2-methyl-1H-pyrrol-1-yl)benzonitrile

Into a 50 mL 3-necked round-bottom flask, being maintained under an inert atmosphere of nitrogen, was placed a solution of 4-(3-acetyl-5-chloro-2-methyl-1H-pyrrol-1-yl) benzonitrile (300 mg, 1.16 mmol) in tetrahydrofuran (20 mL). The solution was cooled to 0° C. and then diisopropylethylamine (620 mg, 4.80 mmol) and trimethylsilyl trifluoromethanesulfonate (580 mg) were added to the flask. The resulting mixture was allowed to stir at 0° C. for 1.5 h and then solid N-bromosuccinimide (320 mg, 1.80 mmol) was added. The reaction mixture was allowed to stir at 0° C. for 1.5 h before it was diluted with water (20 mL). The aqueous mixture was extracted with ethyl acetate (2×50 mL) and the combined organic extracts were washed with brine (2×20 mL). The organic phase was dried over anhydrous sodium sulfate and concentrated under vacuum. The remaining residue was purified by preparative TLC on silica, using ethyl acetate/petroleum ether (1:5) as the developing solution, to afford 180 mg (46%) of 4-(3-(2-bromoacetyl)-5-chloro-2-methyl-1H-pyrrol-1-yl)benzonitrile as a white solid. Mass Spectrum (LCMS, ESI pos.): Calcd. for $C_{14}H_{10}BrClN_2O$: 337 (M+H); found: 337.

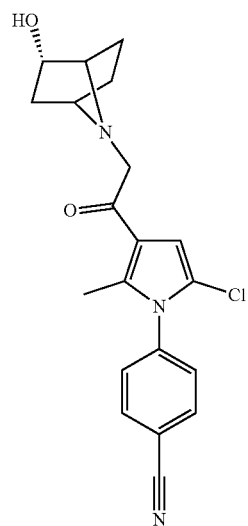

C. (±)-4-(5-Chloro-3-(2-((2R)-2-hydroxy-7-azabicyclo[2.2.1]heptan-7-yl)acetyl)-2-methyl-1H-pyrrol-1-yl)benzonitrile (96B)

Into a 25 mL round-bottom flask, being maintained under an inert atmosphere of nitrogen, was placed a mixture of 4-(3-(2-bromoacetyl)-5-chloro-2-methyl-1H-pyrrol-1-yl)benzonitrile (150 mg, 0.44 mmol), racemic (1R,2R,4S)-7-azabicyclo[2.2.1]heptan-2-ol (138 mg, 1.22 mmol), potassium carbonate (320 mg, 2.32 mmol) in N,N-dimethylformamide (5 mL). The mixture was allowed to stir at room temperature for overnight before being diluted with water (50 mL). The mixture was extracted with ethyl acetate (2×50 mL) and the combined organic extracts were washed with brine (3×30 mL). The organic phase was dried over anhydrous sodium sulfate and concentrated under vacuum. The remaining residue was purified by preparative TLC on silica, using dichloromethane/methanol (10:1) as the developing agent, to afford 49 mg (30%) of (±)-4-(5-chloro-3-(2-((2R)-2-hydroxy-7-azabicyclo[2.2.1]heptan-7-yl)acetyl)-2-methyl-1H-pyrrol-1-yl)benzonitrile (96B) as a white solid. Mass Spectrum (LCMS, ESI pos.): Calcd. for $C_{20}H_{20}ClN_3O_2$: 370 (M+H); found: 370. $^1$H NMR (400 MHz, DMSO-$d_6$): δ 8.10 (d, J=8.4 Hz, 2H), 7.66 (d, J=8.7 Hz, 2H), 6.91 (s, 1H), 4.67 (d, J=3.9 Hz, 1H), 4.06-4.03 (m, 1H), 3.56 (s, 2H), 3.24 (brs, 2H), 2.27 (s, 3H), 2.01-1.94 (m, 2H), 1.75-1.74 (m, 1H), 1.52-1.50 (m, 1H), 1.36-1.32 (m, 1H), 0.81-0.76 (m, 1H).

Example 36B. (±)-4-(2,3-Dichloro-4-(2-((2R)-2-hydroxy-7-azabicyclo[2.2.1]heptan-7-yl)acetyl)-5-methyl-1H-pyrrol-1-yl)benzonitrile (97B)

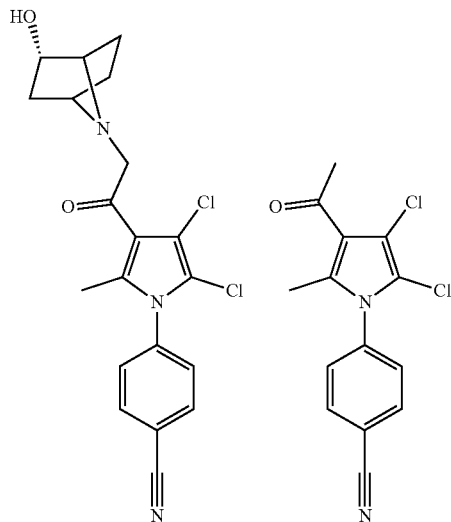

A. 4-(3-Acetyl-4,5-dichloro-2-methyl-1H-pyrrol-1-yl)benzonitrile

Into a 50 mL 3-necked round-bottom flask, being maintained under an inert atmosphere of nitrogen, was placed a solution of 4-(3-acetyl-2-methyl-1H-pyrrol-1-yl)benzonitrile (700 mg, 3.12 mmol, from Intermediate IB) in dichloromethane (25 mL). The solution was cooled to 0° C. and then treated with $SO_2Cl_2$ (6.2 mL) in a dropwise manner. The reaction mixture was allowed to stir at 0° C. for 30 min before being diluted with water (30 mL). The mixture was extracted with dichloromethane (2×50 mL) and the combined organic extracts were washed with an aqueous solution of sodium bicarbonate (20 mL). The organic phase was washed further with brine (3×30 mL), dried over anhydrous sodium sulfate and then concentrated under vacuum. The remaining residue was purified by preparative TLC on silica, using ethyl acetate/petroleum ether (1:9) as the eluant, to afford 240 mg (26%) of 4-(3-acetyl-4,5-dichloro-2-methyl-1H-pyrrol-1-yl)benzonitrile as a light yellow solid. Mass Spectrum (LCMS, ESI pos.): Calcd. for $C_{14}H_{10}Cl_2N_2O$: 293 (M+H); found: 293. $^1$H NMR (400 MHz, CDCl$_3$): δ 7.87 (d, J=12.0 Hz, 2H), 7.38 (d, J=12.0 Hz, 2H), 2.61 (s, 3H), 2.31 (s, 3H).

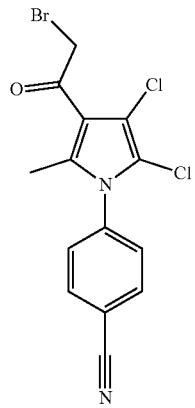 [SMILES: Cc1c(C(=O)CBr)c(Cl)c(Cl)n1-c1ccc(C#N)cc1]

B. 4-(3-(2-Bromoacetyl)-4,5-dichloro-2-methyl-1H-pyrrol-1-yl)benzonitrile

Into a 50 mL 3-necked round-bottom flask, being maintained under an inert atmosphere of nitrogen, was placed a solution of 4-(3-acetyl-4,5-dichloro-2-methyl-1H-pyrrol-1-yl)benzonitrile (200 mg, 0.68 mmol) in tetrahydrofuran (25 mL). The solution was cooled to 0° C. and then treated with diisopropylethylamine (360 mg, 2.79 mmol) and trimethylsilyl trifluoromethylsulfonate (300 mg). The resulting mixture was allowed to stir at 0° C. for 2 h before it was treated with N-bromosuccinimide (180 mg, 1.01 mmol). The reaction mixture was allowed to stir for an additional 10 min at the reduced temperature and was then diluted with water (20 mL). The mixture was extracted with ethyl acetate (2×50 mL) and the combined organic extracts were washed with brine (2×25 mL). The organic phase was dried over anhydrous sodium sulfate and concentrated under vacuum to afford 200 mg (79%) of 4-(3-(2-bromoacetyl)-4,5-dichloro-2-methyl-1H-pyrrol-1-yl)benzonitrile as a brown oil. Mass Spectrum (LCMS, ESI pos.): Calcd. for $C_{14}H_9BrCl_2N_2O$: 371 (M+H); found: 371.

355

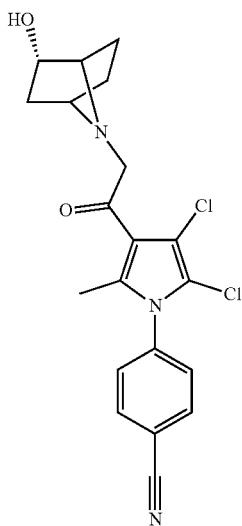 [SMILES: Cc1c(C(=O)CN2C3CCC2[C@@H](O)C3)cc(Br)n1-c1ccc(C#N)cc1]

C. (±)-4-(2,3-Dichloro-4-(2-((2R)-2-hydroxy-7-azabicyclo[2.2.1]heptan-7-yl)acetyl)-5-methyl-1H-pyrrol-1-yl)benzonitrile (97B)

Into a 25 mL round-bottom flask, being maintained under an inert atmosphere of nitrogen, was placed a mixture of 4-(3-(2-bromoacetyl)-4,5-dichloro-2-methyl-1H-pyrrol-1-yl)benzonitrile (200 mg, 0.54 mmol), racemic (1R,2R,4S)-7-azabicyclo[2.2.1]heptan-2-ol (168 mg, 1.48 mmol), potassium carbonate (380 mg, 2.75 mmol), and N,N-dimethylformamide (5 mL). The reaction mixture was allowed to stir at room temperature for 8 h before it was diluted with water (50 mL). The aqueous mixture was extracted with ethyl acetate (2×50 mL) and the combined organic extracts were washed with brine (2×25 mL). The organic phase was dried over anhydrous sodium sulfate and concentrated under vacuum. The remaining residue was purified by preparative TLC on silica, using dichloromethane/methanol (10:1) as the developing solution, to afford 28 mg (13%) of (±)-4-(2,3-dichloro-4-(2-((2R)-2-hydroxy-7-azabicyclo[2.2.1]heptan-7-yl)acetyl)-5-methyl-1H-pyrrol-1-yl)benzonitrile (97B) as an off-white solid. Mass Spectrum (LCMS, ESI pos.): Calcd. for $C_{20}H_{19}C_{12}N_3O_2$: 404 (M+H); found: 404. $^1$H NMR (400 MHz, CDCl$_3$): δ 8.11 (d, J=8.8 Hz, 2H), 7.71 (d, J=8.4 Hz, 2H), 4.69 (s, 1H), 4.04-4.03 (m, 1H), 3.67 (brs, 2H), 3.31 (brs, 2H), 2.23 (s, 3H), 2.03-1.97 (m, 2H), 1.73-1.69 (m, 1H), 1.49-1.46 (m, 1H), 1.37-1.32 (m, 1H), 0.80-0.78 (m, 1H).

356

Example 37B. (±)-4-(5-Bromo-3-(2-((2R)-2-hydroxy-7-azabicyclo[2.2.1]heptan-7-yl)acetyl)-2-methyl-1H-pyrrol-1-yl)benzonitrile (119B)

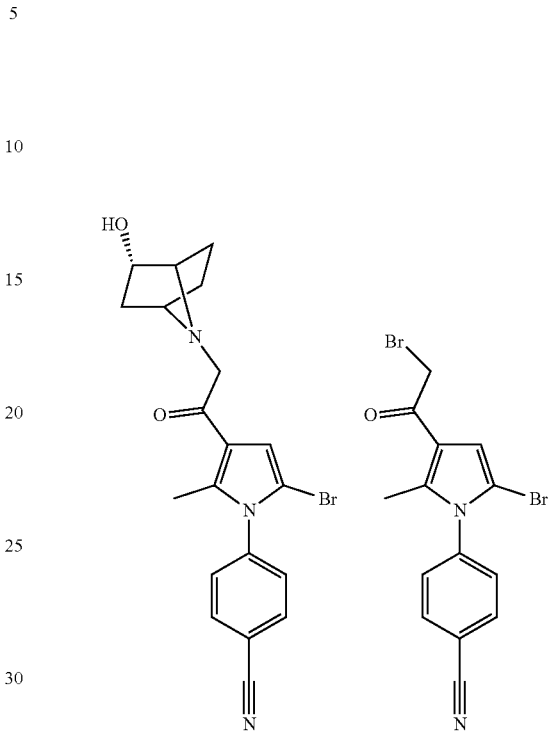

A. 4-(5-Bromo-3-(2-bromoacetyl)-2-methyl-1H-pyrrol-1-yl)benzonitrile

Into a 50-mL 3-necked round-bottom flask, being maintained under an inert atmosphere of nitrogen, was placed a solution of 4-(3-acetyl-5-bromo-2-methyl-1H-pyrrol-1-yl)benzonitrile (250 mg, 0.82 mmol, prepared in a manner analogous to Intermediate IB using N-bromosuccinimide) in tetrahydrofuran (5 mL). The solution was cooled to 0° C. and then treated with trimethylsilyl trifluoromethylsulfonate (0.368 g) and diisopropylethylamine (428 mg, 3.31 mmol). The resulting mixture was allowed to stir at 0° C. for 0.5 h and then a solution of N-bromosuccinimide (163 mg, 0.92 mmol) was added to the flask. The reaction mixture was allowed to stir for an addition hour at the reduced temperature before it was diluted with water (5 mL). The aqueous mixture was extracted with ethyl acetate (3×20 mL) and the combined organic extracts were dried over anhydrous sodium sulfate. Concentrating the organic phase under vacuum afforded 0.25 g (79%) of 4-(5-bromo-3-(2-bromoacetyl)-2-methyl-1H-pyrrol-1-yl)benzonitrile as a yellow oil. Mass Spectrum (LCMS, ESI pos.): Calcd. for $C_{14}H_{10}Br_2N_2O$: 381 (M+H); found: 381.

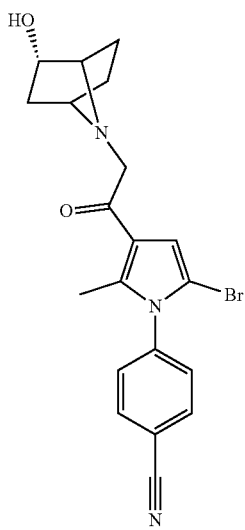

B. (±)-4-(5-Bromo-3-(2-((2R)-2-hydroxy-7-azabicyclo[2.2.1]heptan-7-yl)acetyl)-2-methyl-1H-pyrrol-1-yl)benzonitrile (119B)

Into a 100 mL round-bottom flask, being maintained under an inert atmosphere of nitrogen, was placed a mixture of 4-(5-bromo-3-(2-bromoacetyl)-2-methyl-1H-pyrrol-1-yl)benzonitrile (180 mg, 0.47 mmol), racemic (1R,2R,4S)-7-azabicyclo[2.2.1]heptan-2-ol (82 mg, 0.72 mmol), potassium carbonate (0.20 g) and N,N-dimethylformamide (3 mL). The reaction mixture was allowed to stir at room temperature overnight before being diluted with water (5 mL). The aqueous mixture was extracted with ethyl acetate (3×20 mL) and the combined organic extracts were dried over anhydrous sodium sulfate, followed by concentration under vacuum. The crude product was purified by preparative-HPLC under the following conditions: column-XBridge C18 OBD Prep Column 100 Å, 10 μm, 19 mm×250 mm; mobile phase A—Water (10 mmol/L $NH_4HCO_3$), mobile phase B—acetonitrile, flow rate: 20 mL/min, gradient: 15% B to 70% B in 8 min; detector-UV 254 nm. This process afforded 60 mg (31%) of (±)-4-(5-bromo-3-(2-((2R)-2-hydroxy-7-azabicyclo[2.2.1]heptan-7-yl)acetyl)-2-methyl-1H-pyrrol-1-yl)benzonitrile (119B) as a white solid. Mass Spectrum (LCMS, ESI pos.): Calcd. for $C_{20}H_{20}BrN_3O_2$: 416 (M+H); found: 416. $^1$H NMR (400 MHz, DMSO-$d_6$): δ 8.08 (m, 2H), 7.62-7.60 (m, 2H), 6.97 (s, 1H), 4.66 (brs, 1H), 4.04 (brs, 1H), 3.55 (s, 2H), 3.23-3.21 (m, 2H), 2.25 (s, 3H), 1.97-1.95 (m, 2H), 1.74 (brs, 1H), 1.50 (brs, 1H), 1.31 (brs, 1H), 0.78-0.76 (m, 1H).

Example 38B. (±)-2-Fluoro-4-(3-(2-((2R)-2-hydroxy-7-azabicyclo[2.2.1]heptan-7-yl)acetyl)-2,5-dimethyl-1H-pyrrol-1-yl)benzonitrile (90B)

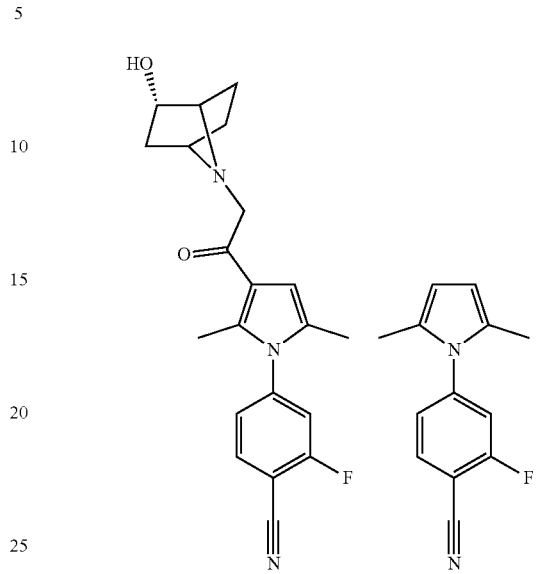

A. 4-(2,5-Dimethyl-1H-pyrrol-1-yl)-2-fluorobenzonitrile

Into a 250 mL round-bottom flask was placed a solution of 4-amino-2-fluorobenzonitrile (5.0 g, 36.7 mmol) in toluene (40 mL). To the solution were added hexane-2,5-dione (6.3 g, 55.2 mmol) and acetic acid (10 mL). The resulting mixture was heated at 90° C. overnight and then allowed to cool to room temperature. The reaction mixture was concentrated under vacuum and the remaining residue was treated with water. The aqueous mixture was extracted with ethyl acetate (3×40 mL) and the combined organic extracts were dried over anhydrous sodium sulfate. The organic phase was concentrated under vacuum and the remaining residue was purified by column chromatography on silica, using ethyl acetate/petroleum ether (1:20) as the eluant, to afford 5.32 g (68%) of 4-(2,5-dimethyl-1H-pyrrol-1-yl)-2-fluorobenzonitrile as a yellow solid. Mass Spectrum (LCMS, ESI pos.): Calcd. for $C_{13}H_{11}FN_2$: 215 (M+H); found: 215.

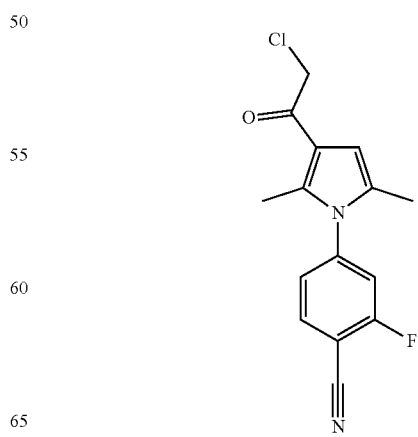

B. 4-(3-(2-Chloroacetyl)-2,5-dimethyl-1H-pyrrol-1-yl)-2-fluorobenzonitrile

Into a 100 mL 3-necked round-bottom flask was placed a solution of 4-(2,5-dimethyl-1H-pyrrol-1-yl)-2-fluorobenzonitrile (500 mg, 2.33 mmol) in dichloromethane (15 mL). The solution was cooled to 0° C. and then treated with 2-chloroacetyl chloride (0.264 mL) in a dropwise fashion. To this was added diethyl aluminum chloride (3.9 mL) and the resulting mixture was allowed to warm to room temperature and stir for 3 h. The reaction mixture was diluted with water and the pH of the system was adjusted to a value of 8 through the addition of an aqueous sodium carbonate solution. The mixture was extracted with dichloromethane (3×10 mL) and the combined organic extracts were dried over anhydrous sodium sulfate and concentrated under vacuum. The remaining residue was purified by column chromatography on silica, using ethyl acetate/petroleum ether (1:3) as the eluant, to afford 560 mg (83%) of 4-(3-(2-chloroacetyl)-2,5-dimethyl-1H-pyrrol-1-yl)-2-fluorobenzonitrile as a yellow solid. Mass Spectrum (LCMS, ESI pos.): Calcd. for $C_{1}H_{12}ClFN_2O$: 291 (M+H); found: 291.

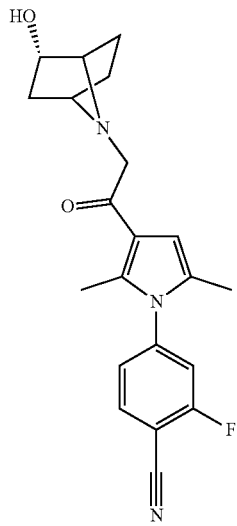 [SMILES: Cc1cc(C(=O)CN2C3CCC2[C@@H](O)C3)c(C)n1-c1ccc(C#N)c(F)c1]

C. (±)-2-Fluoro-4-(3-(2-((2R)-2-hydroxy-7-azabicyclo[2.2.1]heptan-7-yl)acetyl)-2,5-dimethyl-1H-pyrrol-1-yl)benzonitrile (90B)

Into a 100 mL round-bottom flask was placed a solution of 4-(3-(2-chloroacetyl)-2,5-dimethyl-1H-pyrrol-1-yl)-2-fluorobenzonitrile (240 mg, 0.83 mmol) in N,N-dimethylformamide (10 mL). To the solution were added racemic (1R,2R,4S)-7-azabicyclo[2.2.1]heptan-2-ol hydrochloride (148 mg, 0.99 mmol) and potassium carbonate (456 mg, 3.30 mmol). The resulting mixture was allowed to stir at room temperature overnight. The reaction mixture was diluted with water and then extracted with ethyl acetate (2×10 mL). The combined organic extracts were dried over anhydrous sodium sulfate and concentrated under vacuum. The remaining residue was purified by column chromatography on silica, using dichloromethane/methanol (10:1) as the eluant to afford 48 mg (16%) of (±)-2-fluoro-4-(3-(2-((2R)-2-hydroxy-7-azabicyclo[2.2.1]heptan-7-yl)acetyl)-2,5-dimethyl-1H-pyrrol-1-yl)benzonitrile (90B) as a light yellow solid. Mass Spectrum (LCMS, ESI pos.): Calcd. for $C_{21}H_{22}FN_3O_2$: 368 (M+H); found: 368. $^1$H NMR (300 MHz, DMSO-$d_6$): δ 8.17-8.13 (m, 1H), 7.79-7.76 (m, 1H), 7.48-7.45 (m, 1H), 6.50 (s, 1H), 4.67 (d, J=3.0 Hz, 1H), 4.05-4.02 (m, 1H), 3.52 (s, 2H), 3.26-3.22 (m, 2H), 2.27 (s, 3H), 1.99 (s, 3H), 1.96-1.95 (m, 2H), 1.74-1.71 (m, 1H), 1.53-1.47 (m, 1H), 1.34-1.28 (m, 1H), 0.80-0.75 (m, 1H).

Example 39B. (±)-3-Fluoro-4-(3-(2-((2R)-2-hydroxy-7-azabicyclo[2.2.1]heptan-7-yl)acetyl)-2,5-dimethyl-1H-pyrrol-1-yl)benzonitrile (91B)

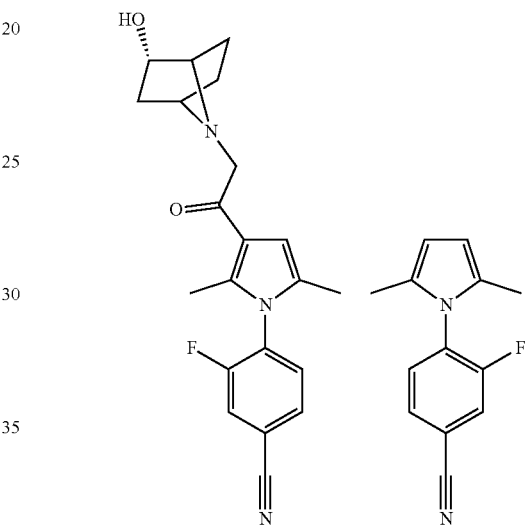

A. 4-(2,5-Dimethyl-1H-pyrrol-1-yl)-3-fluorobenzonitrile

Into a 250 mL round-bottom flask was placed a solution of 4-amino-3-fluorobenzonitrile (5.5 g, 40.4 mmol) in toluene (50 mL). To the solution were added hexane-2,5-dione (6.8 g, 59.6 mmol) and acetic acid (10 mL). The resulting mixture was heated at 100° C. overnight and then allowed to cool to room temperature. The reaction mixture was concentrated under vacuum and the remaining residue was diluted with water. The aqueous mixture was extracted with ethyl acetate (3×30 mL) and the combined organic extracts were dried over anhydrous sodium sulfate. The organic phase was concentrated under vacuum and the remaining residue was purified by column chromatography on silica, using ethyl acetate/petroleum ether (1:5) the eluant, to afford 3.83 g (44%) of 4-(2,5-dimethyl-1H-pyrrol-1-yl)-3-fluorobenzonitrile as a white solid. Mass Spectrum (LCMS, ESI pos.): Calcd. for $C_{13}H_{11}FN_3$: 215 (M+H); found: 215. $^1$H NMR (300 MHz, DMSO-$d_6$): δ 8.17-8.13 (m, 1H), 7.89-7.86 (m, 1H), 7.69-7.63 (m, 1H), 6.87 (s, 1H), 1.93 (s, 6H).

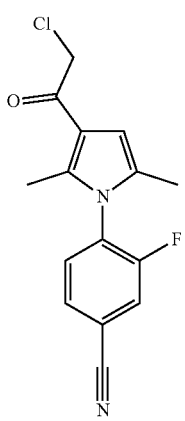 [SMILES: Cc1cc(C(=O)CCl)c(C)n1-c1ccc(C#N)cc1F]

B. 4-(3-(2-Chloroacetyl)-2,5-dimethyl-1H-pyrrol-1-yl)-3-fluorobenzonitrile

Into a 100 mL 3-necked round-bottom flask was placed a solution of 4-(2,5-dimethyl-1H-pyrrol-1-yl)-3-fluorobenzonitrile (500 mg, 2.33 mmol) in dichloromethane (15 mL). The solution was cooled to 0° C. and then treated with 2-chloroacetyl chloride (0.264 mL) and then diethyl aluminum chloride (3.9 mL). The resulting mixture was allowed to warm to room temperature and stir for 2 h. The reaction mixture was diluted with water and then the pH of the mixture was adjusted to a value of 8 through the addition of an aqueous sodium bicarbonate solution. The aqueous mixture was extracted with dichloromethane (3×10 mL) and the combined organic extracts were dried over anhydrous sodium sulfate and concentrated under vacuum to afford 470 mg (69%) of 4-(3-(2-chloroacetyl)-2,5-dimethyl-1H-pyrrol-1-yl)-3-fluorobenzonitrile as a light yellow solid. Mass Spectrum (LCMS, ESI pos.): Calcd. for $C_{15}H_{12}ClFN_2O$: 291 (M+H); found: 291.

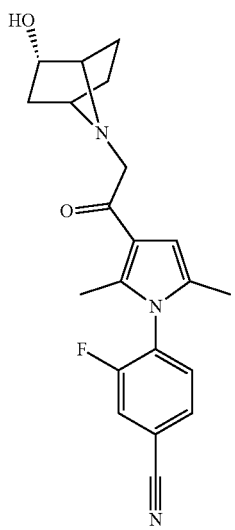 [SMILES: Cc1cc(C(=O)CN2C3CCC2[C@@H](O)C3)c(C)n1-c1ccc(C#N)cc1F]

C. (±)-3-Fluoro-4-(3-(2-((2R)-2-hydroxy-7-azabicyclo[2.2.1]heptan-7-yl)acetyl)-2,5-dimethyl-1H-pyrrol-1-yl)benzonitrile (91B)

Into a 100 mL round-bottom flask was placed a solution of 4-(3-(2-chloroacetyl)-2,5-dimethyl-1H-pyrrol-1-yl)-3-fluorobenzonitrile (470 mg, 1.62 mmol) in N,N-dimethylformamide (8 mL). To the solution were added racemic (1R,2R,4S)-7-azabicyclo[2.2.1]heptan-2-ol hydrochloride (290 mg, 1.94 mmol) and potassium carbonate (892 mg, 6.45 mmol). The resulting mixture was allowed to stir at room temperature overnight before it was diluted with water. The aqueous mixture was extracted with ethyl acetate (2×8 mL) and the combined organic extracts were dried over anhydrous sodium sulfate. The organic phase was concentrated under vacuum and the remaining residue was purified by column chromatography on silica, using dichloromethane/methanol (10:1) as the eluant, to afford 124 mg (21%) of (±)-3-fluoro-4-(3-(2-((2R)-2-hydroxy-7-azabicyclo[2.2.1]heptan-7-yl)acetyl)-2,5-dimethyl-1H-pyrrol-1-yl)benzonitrile (91B) as an off-white solid. Mass Spectrum (LCMS, ESI pos.): Calcd. for $C_{21}H_{22}FN_3O_2$: 368 (M+H); found: 368. $^1$H-NMR (300 MHz, DMSO-d$_6$): δ 8.22 (dd, J=9.6 Hz, 1.5 Hz, 1H), 7.96-7.93 (m, 1H), 7.79-7.74 (m, 1H), 6.52 (s, 1H), 4.67 (d, J=4.2 Hz, 1H), 4.08-4.02 (m, 1H), 3.54 (s, 2H), 3.25-3.24 (m, 2H), 2.20 (s, 3H), 2.01-1.97 (m, 2H), 1.94 (s, 3H), 1.75-1.72 (m, 1H), 1.54-1.47 (m, 1H), 1.35-1.31 (m, 1H), 0.82-0.75 (m, 1H).

Example 40B. (±)-2,6-Difluoro-4-(3-(2-((2R)-2-hydroxy-7-azabicyclo[2.2.1]heptan-7-yl)acetyl)-2,5-dimethyl-1H-pyrrol-1-yl)benzonitrile (94B)

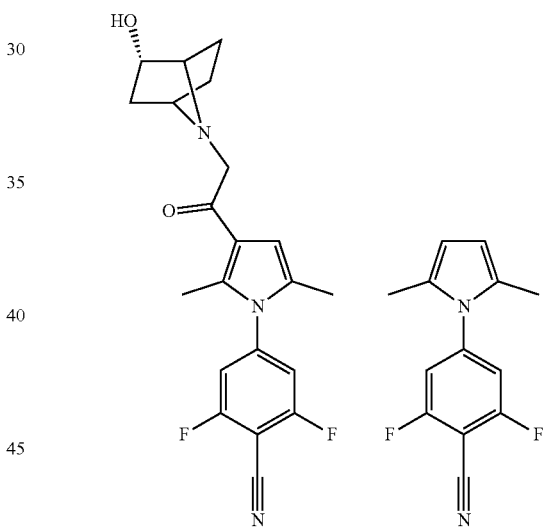

A. 4-(2,5-Dimethyl-1H-pyrrol-1-yl)-2,6-difluorobenzonitrile

Into a 100 mL 3-necked round-bottom flask was placed a solution of hexane-2,5-dione (2.2 g, 19.3 mmol) in toluene (20 mL). To the solution were added 4-amino-2,6-difluorobenzonitrile (2.0 g, 13.0 mmol) and acetic acid (15 mL). The resulting mixture was heated at 110° C. for 16 h and then allowed to cool to room temperature. The reaction mixture was concentrated under vacuum and the remaining residue was purified by column chromatography on silica, using ethyl acetate/petroleum ether (1:20) as the eluant, to afford 2.2 g (73%) of 4-(2,5-dimethyl-1H-pyrrol-1-yl)-2,6-difluorobenzonitrile as an off-white solid. Mass Spectrum (LCMS, ESI pos.): Calcd. for $C_{13}H_{10}F_2N_2$: 233 (M+H); found: 233. $^1$H NMR (300 MHz, CDCl$_3$): δ 6.94-6.90 (m, 2H), 5.93 (s, 2H).

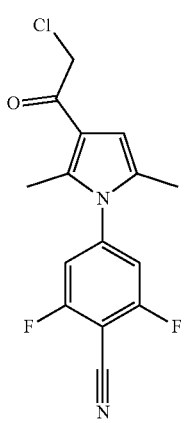 [SMILES: Cc1cc(C(=O)CCl)c(C)n1-c1cc(F)c(C#N)c(F)c1]

B. 4-(3-(2-Chloroacetyl)-2,5-dimethyl-1H-pyrrol-1-yl)-2,6-difluorobenzonitrile Into a 50 mL round-bottom flask, being maintained under an inert atmosphere of nitrogen, was placed a solution of 4-(2,5-dimethyl-1H-pyrrol-1-yl)-2,6-difluorobenzonitrile (500 mg, 2.15 mmol) in dichloromethane (10 mL). The solution as cooled to 0° C. and then treated with diethyl aluminum chloride (390 mg, 3.25 mmol) in dropwise manner. The resulting mixture was allowed to stir at 0° C. for 30 min and was then treated with 2-chloroacetyl chloride (360 mg, 3.19 mmol) at 0° C. The reaction mixture was allowed to warm to room temperature and stir for 1 h before it was diluted with brine (10 mL). The pH value of the mixture was adjusted to 7 with an aqueous sodium bicarbonate solution and then extracted with dichloromethane (4×50 mL). The combined organic extracts were dried over anhydrous sodium sulfate and concentrated under vacuum to afford 503 mg (76%) of 4-(3-(2-chloroacetyl)-2,5-dimethyl-1H-pyrrol-1-yl)-2,6-difluorobenzonitrile as an off-white solid. Mass Spectrum (LCMS, ESI pos.): Calcd. for $C_{15}H_{11}ClF_2N_2O$: 309 (M+H); found: 309.

C. (±)-2,6-Difluoro-4-(3-(2-((2R)-2-hydroxy-7-azabicyclo[2.2.1]heptan-7-yl)acetyl)-2,5-dimethyl-1H-pyrrol-1-yl)benzonitrile (94B)

Into a 25 mL round-bottom flask, being maintained under an inert atmosphere of nitrogen, was placed a solution of 4-(3-(2-chloroacetyl)-2,5-dimethyl-1H-pyrrol-1-yl)-2,6-difluorobenzonitrile (200 mg, 0.65 mmol) in N,N-dimethylformamide (4 mL). To the solution were added potassium carbonate (134 mg, 0.97 mmol) and racemic (1R,2R,4S)-7-azabicyclo[2.2.1]heptan-2-ol hydrochloride (97 mg, 0.65 mmol). The resulting mixture was allowed to stir at room temperature for 16 h before it was diluted with water (10 mL). The aqueous mixture was extracted with dichloromethane (3×10 mL) and then the combined organic extracts were concentrated under vacuum. The remaining crude product was purified by column chromatography on silica, using petroleum ether/ethyl acetate (1:1) as the eluant to afford 70 mg (28%) of (±)-2,6-difluoro-4-(3-(2-((2R)-2-hydroxy-7-azabicyclo[2.2.1]heptan-7-yl)acetyl)-2,5-dimethyl-1H-pyrrol-1-yl)benzonitrile (94B) as a light yellow solid. Mass Spectrum (LCMS, ESI pos.): Calcd. for $C_{21}H_{21}F_2N_3O_2$: 386 (M+H); found: 386. $^1$H NMR (400 MHz, DMSO-$d_6$): δ 7.74-7.62 (m, 2H), 6.49 (s, 1H), 4.66 (d, J=4.4 Hz, 1H), 4.03-4.00 (m, 1H), 3.55 (s, 2H), 3.23-3.20 (m, 2H), 2.28 (s, 3H), 2.01 (s, 3H), 1.99-1.91 (m, 2H), 1.73-1.69 (m, 1H), 1.51-1.47 (m, 1H), 1.33-1.26 (m, 1H), 0.78-0.74 (m, 1H).

Example 41B. (±)-2,3-Difluoro-4-(3-(2-((2R)-2-hydroxy-7-azabicyclo[2.2.1]heptan-7-yl)acetyl)-2,5-dimethyl-1H-pyrrol-1-yl)benzonitrile (99B)

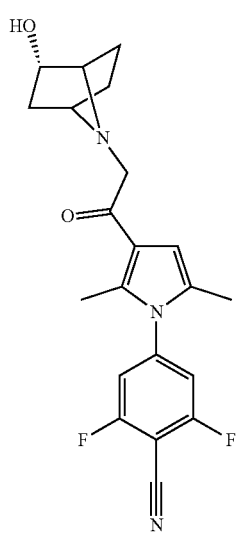 [SMILES: Cc1cc(C(=O)CN2C3CCC2[C@@H](O)C3)c(C)n1-c1cc(F)c(C#N)c(F)c1]
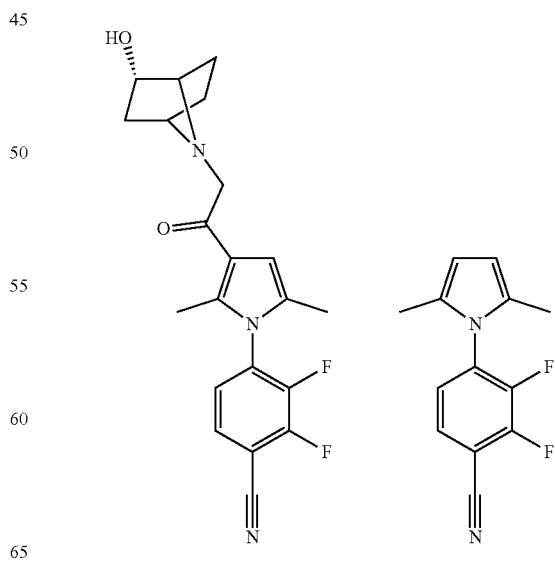

A. 4-(2,5-Dimethyl-1H-pyrrol-1-yl)-2,3-difluorobenzonitrile

Into a 100 mL round-bottom flask, being maintained under an inert atmosphere of nitrogen, was placed a solution of 4-amino-2,3-difluorobenzonitrile (1.54 g, 9.99 mmol) in toluene (12 mL). To the solution were added hexane-2,5-dione (3.42 g, 30.0 mmol) and acetic acid (10 mL). The resulting mixture was heated at 80° C. overnight and then allowed to cool to room temperature. The reaction mixture was diluted with an aqueous solution of sodium carbonate (100 mL) and then extracted with ethyl acetate (3×100 mL). The combined organic extracts were washed with brine (3×100 mL), dried over anhydrous sodium sulfate and then concentrated under vacuum. The remaining residue was purified by column chromatography on silica, using ethyl acetate/petroleum ether (1:10) as the eluant, to afford 2.15 g (93%) of 4-(2,5-dimethyl-1H-pyrrol-1-yl)-2,3-difluorobenzonitrile as a yellow solid. Mass Spectrum (LCMS, ESI pos.): Calcd. for $C_{13}H_{10}F_2N_2$: 233 (M+H); found: 233.

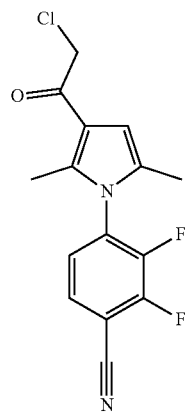 [SMILES: Cc1cc(C(=O)CCl)c(C)n1-c1ccc(C#N)c(F)c1F]

B. 4-(3-(2-Chloroacetyl)-2,5-dimethyl-1H-pyrrol-1-yl)-2,3-difluorobenzonitrile Into a 100 mL round-bottom flask, being maintained under an inert atmosphere of nitrogen, was placed a solution of 4-(2,5-dimethyl-1H-pyrrol-1-yl)-2,3-difluorobenzonitrile (942 mg, 4.06 mmol) in dichloromethane (10 mL). The solution was cooled to 0° C. and then treated with 2-chloroacetyl chloride (1.36 g, 12.0 mmol) and diethyl aluminum chloride (1.45 g, 12.0 mmol). The resulting mixture was allowed to warm to room temperature and stir for 4 h. The reaction mixture was diluted with an aqueous solution of sodium carbonate (100 mL) and then extracted with ethyl acetate (3×100 mL). The combined organic extracts were washed with brine (3×100 mL), dried over anhydrous sodium sulfate and then concentrated under vacuum. The remaining residue was purified by column chromatography on silica, using ethyl acetate/petroleum ether (1:5) as the eluant, to afford 1.03 g (82%) of 4-(3-(2-chloroacetyl)-2,5-dimethyl-1H-pyrrol-1-yl)-2,3-difluorobenzonitrile as a yellow solid. Mass Spectrum (LCMS, ESI pos.): Calcd. for $C_{15}H_{11}ClF_2N_2O$: 309 (M+H); found: 309.

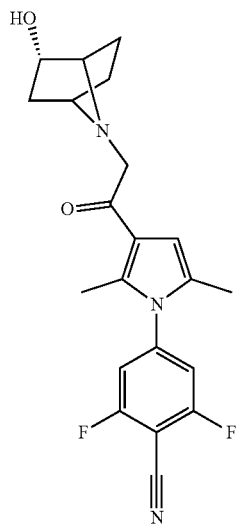

C. (±)-2,3-Difluoro-4-(3-(2-((2R)-2-hydroxy-7-azabicyclo[2.2.1]heptan-7-yl)acetyl)-2,5-dimethyl-1H-pyrrol-1-yl)benzonitrile (99B)

Into a 100 mL round-bottom flask was placed a solution of 4-(3-(2-chloroacetyl)-2,5-dimethyl-1H-pyrrol-1-yl)-2,3-difluorobenzonitrile (100 mg, 0.32 mmol) in N,N-dimethylformamide (3 mL). To the solution were added racemic (1R,2S,4S)-7-azabicyclo[2.2.1]heptan-2-ol hydrochloride (94 mg, 0.63 mmol) and $K_2CO_3$ (224 mg, 1.62 mmol). The resulting mixture was allowed to stir for at room temperature for 4 h before being concentrated. The crude product was purified by preparative HPLC under the following conditions: Column-XBridge Prep C18 OBD Column 19*100 mm 5 µmC-0013; mobile phase-water with 0.05% $NH_4HCO_3$ and $CH_3CN$ (30.0% $CH_3CN$ up to 75.0% in 10 min, up to 95.0% in 1.5 min, down to 30.0% in 1.5 min); Detector, 254 nm. This process afforded 28 mg (22%) of (±)-2,3-difluoro-4-(3-(2-((2R)-2-hydroxy-7-azabicyclo[2.2.1]heptan-7-yl)acetyl)-2,5-dimethyl-1H-pyrrol-1-yl)benzonitrile (99B) as a white solid. Mass Spectrum (LCMS, ESI pos.): Calcd. for $C_{21}H_{21}F_2N_3O_2$: 386 (M+H); found: 386. $^1$H NMR (400 MHz, DMSO-$d_6$): δ 8.03-7.99 (m, 1H), 7.63-7.59 (m, 1H), 6.54 (s, 1H), 4.68 (d, J=4.0 Hz, 1H), 4.06-4.02 (m, 1H), 3.55-3.53 (m, 2H), 3.26-3.23 (m, 2H), 2.24 (s, 3H), 2.01-1.97 (m, 5H), 1.76-1.72 (m, 1H), 1.54-1.47 (m, 1H), 1.38-1.33 (m, 1H), 0.80-0.75 (m, 1H).

Example 42B. (±)-2,5-Difluoro-4-(3-(2-((2R)-2-hydroxy-7-azabicyclo[2.2.1]heptan-7-yl)acetyl)-2,5-dimethyl-1H-pyrrol-1-yl)benzonitrile (107B)

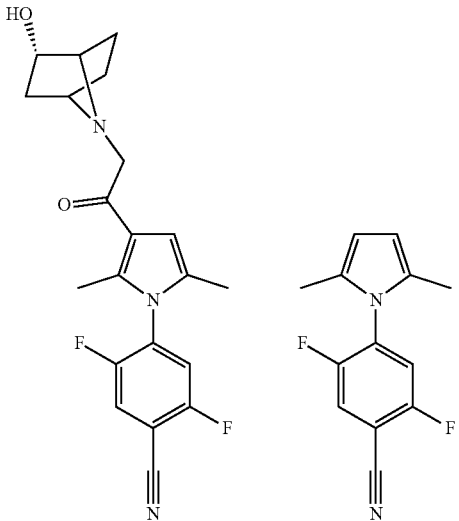

A. 4-(2,5-Dimethyl-1H-pyrrol-1-yl)-2,5-difluorobenzonitrile

Into a 100 mL round-bottom flask was placed a solution of 4-amino-2,5-difluorobenzonitrile (1.54 g, 10 mmol) in toluene (13 mL). To the solution were added hexane-2,5-dione (3.42 g, 30 mmol) and acetic acid (10 mL). The resulting mixture was heated at 80° C. overnight and then allowed to cool to room temperature. The reaction mixture was diluted with a solution of aqueous sodium carbonate (100 mL) and then extracted with ethyl acetate (3×100 mL). The combined organic extracts were washed with brine (3×100 mL), dried over anhydrous sodium sulfate and then concentrated under vacuum. The remaining residue was purified by column chromatography on silica, using ethyl acetate/petroleum ether (1:10) as the eluant, to afford 1.34 g (58%) of 4-(2,5-dimethyl-1H-pyrrol-1-yl)-2,5-difluorobenzonitrile as a yellow solid. Mass Spectrum (LCMS, ESI pos.): Calcd. for $C_{13}H_{10}F_2N_2$: 233 (M+H); found: 233.

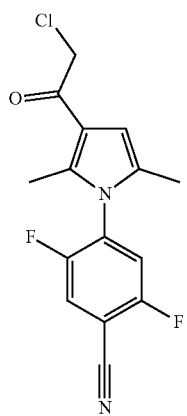 [SMILES: Cc1cc(C(=O)CCl)c(C)n1-c1cc(F)c(C#N)cc1F]

B. 4-(3-(2-Chloroacetyl)-2,5-dimethyl-1H-pyrrol-1-yl)-2,5-difluorobenzonitrile Into a 100 mL round-bottom flask was placed a solution of 4-(2,5-dimethyl-1H-pyrrol-1-yl)-2,5-difluorobenzonitrile (800 mg, 3.44 mmol) in dichloromethane (15 mL). To the solution were added 2-chloroacetyl chloride (1.17 g, 10.4 mmol) and diethyl aluminum chloride (835 mg, 6.93 mmol). The resulting mixture was allowed to stir at room temperature for 4 h before it was diluted with an aqueous solution of sodium bicarbonate (100 mL). The biphasic mixture was extracted with ethyl acetate (3×100 mL) and the combined organic extracts were washed with brine (3×100 mL), dried over anhydrous sodium sulfate and concentrated under vacuum. The remaining residue was purified by column chromatography on silica, using ethyl acetate/petroleum ether (1:6) as the eluant, to afford 1.14 g of 4-(3-(2-chloroacetyl)-2,5-dimethyl-1H-pyrrol-1-yl)-2,5-difluorobenzonitrile as a yellow solid. Mass Spectrum (LCMS, ESI pos.): Calcd. for $C_{15}H_{11}ClF_2N_2O$: 309 (M+H); found: 309.

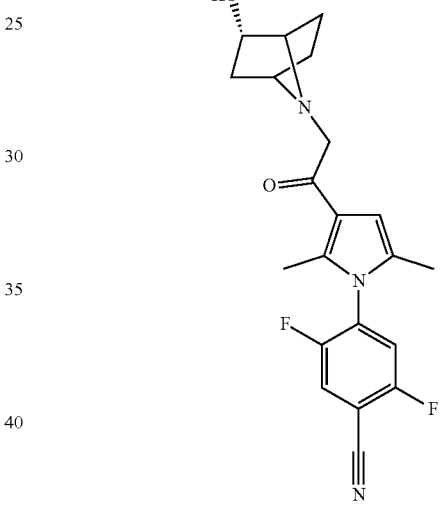

C. (1)-2,5-Difluoro-4-(3-(2-((2R)-2-hydroxy-7-azabicyclo[2.2.1]heptan-7-yl)acetyl)-2,5-dimethyl-1H-pyrrol-1-yl)benzonitrile (107B)

Into a 100 mL round-bottom flask was placed a solution of 4-(3-(2-chloroacetyl)-2,5-dimethyl-1H-pyrrol-1-yl)-2,5-difluorobenzonitrile (200 mg, 0.65 mmol) in N,N-dimethylformamide (3 mL). To the solution were added racemic (1R,2S,4S)-7-azabicyclo[2.2.1]heptan-2-ol (146 mg, 0.98 mmol) and potassium carbonate (270 mg, 1.94 mmol). The resulting mixture was allowed to stir overnight at room temperature before it was concentrated. The crude product was purified by preparative HPLC under the following conditions: Column-XBridge Prep C18 OBD Column 19*100 mm 5 μmC-0013; mobile phase-water with 0.05% $NH_4HCO_3$ and $CH_3CN$ (10.0% $CH_3CN$ up to 90.0% in 10 min, up to 95.0% in 1.5 mn, down to 10.0% in 1.5 min); Detector-254 nm. This process afforded 136 mg (54%) of (±)-2,5-difluoro-4-(3-(2-((2R)-2-hydroxy-7-azabicyclo[2.2.1]heptan-7-yl)acetyl)-2,5-dimethyl-1H-pyrrol-1-yl)benzonitrile (107B) as a white solid. Mass Spectrum (LCMS, ESI pos.): Calcd. for $C_{21}H_{21}F_2N_3O_2$: 386 (M+H);

found: 386. ¹H NMR (300 MHz, DMSO-d₆): δ 8.38-9.33 (m, 1H), 8.01-7.96 (m, 1H), 6.53 (s, 1H), 4.67 (d, J=3.9 Hz, 1H), 4.07-4.03 (m, 1H), 3.54 (s, 2H), 3.25-3.24 (m, 2H), 2.24 (s, 3H), 2.01-1.95 (m, 5H), 1.82-1.75 (m, 1H), 1.54-1.47 (m, 1H), 1.36-1.29 (m, 1H), 0.81-0.76 (m, 1H).

Example 43B. (±)-4-(3-(2-((1r,3r)-2-Oxa-6-azaadamantan-6-yl)acetyl)-4-fluoro-2,5-dimethyl-1H-pyrrol-1-yl)-2-fluorobenzonitrile (116B)

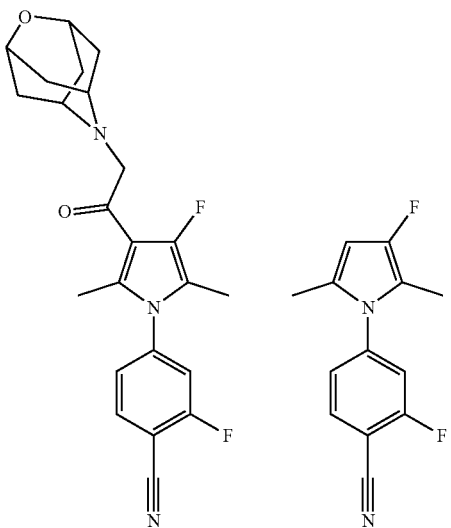

A. 2-Fluoro-4-(3-fluoro-2,5-dimethyl-1H-pyrrol-1-yl)benzonitrile

Into a 1000 mL round-bottom flask, was placed a solution of 4-(2,5-dimethyl-1H-pyrrol-1-yl)-2-fluorobenzonitrile (2.5 g, 11.7 mmol; from Example 38B) in acetonitrile (500 mL). The solution was cooled to 0° C. and then treated with Selectfluor® (4.56 g, 12.9 mmol) in a portionwise manner. The resulting mixture was allowed to warm to room temperature and then stir overnight before being concentrated under vacuum. The remaining residue was purified by column chromatography on silica, using ethyl acetate/petroleum ether (1:30), afforded 170 mg (6%) of 2-fluoro-4-(3-fluoro-2,5-dimethyl-1H-pyrrol-1-yl)benzonitrile as a white solid. Mass Spectrum (LCMS, ESI pos.): Calcd. for $C_{13}H_{10}F_2N_2$: 233 (M+H); found: 233.

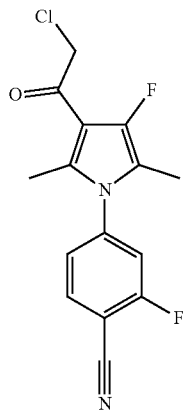 [SMILES: Cc1c(F)c(C(=O)CCl)c(C)n1-c1ccc(C#N)c(F)c1]

B. 4-(3-(2-Chloroacetyl)-4-fluoro-2,5-dimethyl-1H-pyrrol-1-yl)-2-fluorobenzonitrile Into a 250 mL 3-necked round-bottom flask, being maintained under an inert atmosphere of nitrogen, was placed a solution of 2-fluoro-4-(3-fluoro-2,5-dimethyl-1H-pyrrol-1-yl)benzonitrile (2.4 g, 10.3 mmol) in dichloromethane (100 mL). The solution was cooled to 0° C. and then treated with diethyl aluminum chloride (17.2 mL, 1.50 equiv) in a dropwise manner. The resulting mixture was then treated with 2-chloroacetyl chloride (1.16 mL) in a dropwise fashion. The reaction mixture was allowed to warm to room temperature and stir overnight before being diluted with water (50 mL). The biphasic mixture was extracted with dichloromethane (3×50 mL) and the combined organic extracts were dried over anhydrous sodium sulfate. The organic phase was then concentrated under vacuum to afford 3 g (94%) of 4-(3-(2-chloroacetyl)-4-fluoro-2,5-dimethyl-1H-pyrrol-1-yl)-2-fluorobenzonitrile as a brown solid. Mass Spectrum (LCMS, ESI pos.): Calcd. for $C_{15}H_{11}ClF_2N_2O$: 309 (M+H); found: 309.

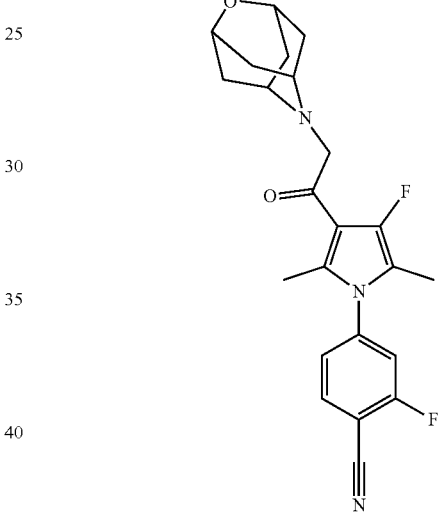

C. (±)-4-(3-(2-((1r,3r)-2-Oxa-6-azaadamantan-6-yl)acetyl)-4-fluoro-2,5-dimethyl-1H-pyrrol-1-yl)-2-fluorobenzonitrile (116B)

Into a 100 mL round-bottom flask was placed a mixture of 4-(3-(2-chloroacetyl)-4-fluoro-2,5-dimethyl-1H-pyrrol-1-yl)-2-fluorobenzonitrile (265 mg, 0.85 mmol), potassium carbonate (469 mg, 3.39 mmol) and (1r,3r,5r,7r)-2-oxa-6-azaadamantane hydrochloride (150 mg, 0.85 mmol) in N,N-dimethylformamide (5 mL). The reaction mixture was allowed to stir at room temperature overnight before being concentrated under vacuum. The remaining residue was diluted with water (10 mL) and then extracted with ethyl acetate (3×10 mL). The combined organic extracts were dried over anhydrous sodium sulfate and concentrated under vacuum. The remaining residue was purified by column chromatography on silica, using dichloromethane/methanol (10:1) as the eluant, afforded 11 mg (3%) of (±)-4-(3-(2-((1r,3r)-2-Oxa-6-azaadamantan-6-yl)acetyl)-4-fluoro-2,5-dimethyl-1H-pyrrol-1-yl)-2-fluorobenzonitrile (116B) as a white solid. Mass Spectrum (LCMS, ESI pos.): Calcd. for $C_{23}H_{23}F_2N_3O_2$: 412 (M+H); found: 412. ¹H NMR (400

MHz, DMSO-d$_6$): δ 8.20-8.15 (m, 1H), 7.81-7.78 (m, 1H), 7.50-7.48 (m, 1H), 3.97 (brs, 2H), 3.78 (s, 2H), 2.99 (s, 2H), 2.22 (s, 3H), 1.93 (s, 3H), 1.88-1.86 (m, 4H), 1.75-1.73 (m, 4H).

Example 44B. (±)-2-Fluoro-4-(3-fluoro-4-(2-((2R)-2-hydroxy-7-azabicyclo[2.2.1]heptan-7-yl)acetyl)-2,5-dimethyl-1H-pyrrol-1-yl)benzonitrile (120B)

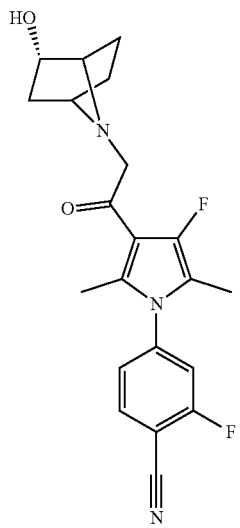 [SMILES: Cc1c(F)c(C(=O)CN2C3CCC2[C@@H](O)C3)c(C)n1-c1ccc(C#N)c(F)c1]

Into a 250 mL round-bottom flask was placed a solution of 4-(3-(2-chloroacetyl)-4-fluoro-2,5-dimethyl-1H-pyrrol-1-yl)-2-fluorobenzonitrile (3 g, 9.72 mmol, from Example 38B) in N,N-dimethylformamide (20 mL). To this was added potassium carbonate (5.36 g, 38.8 mmol) and racemic (1R,2R,4S)-7-azabicyclo[2.2.1]heptan-2-ol hydrochloride (1.75 g, 11.7 mmol). The resulting mixture was allowed to stir at room temperature overnight before being concentrated under vacuum. The remaining residue was diluted with water (20 mL) and then extracted with ethyl acetate (3×20 mL). The combined organic extracts were dried over anhydrous sodium sulfate and concentrated under vacuum. The residue was purified by column chromatography on silica, using dichloromethane/methanol (10:1) as the eluant. The semi-crude product was further purified by preparative HPLC under the following conditions: Column-C18; mobile phase—acetonitrile:water (10 mmol/L NH$_4$HCO$_3$)=5:95 increasing to acetonitrile:water (10 mmol/L NH$_4$HCO$_3$)=80:20 within 30 min; Detector-UV 254 nm. This process afforded 2.02 g (54%) of (±)-2-fluoro-4-(3-fluoro-4-(2-((2R)-2-hydroxy-7-azabicyclo[2.2.1]heptan-7-yl)acetyl)-2,5-dimethyl-1H-pyrrol-1-yl)benzonitrile (120B) as an off-white solid Mass Spectrum (LCMS, ESI pos.): Calcd. for C$_{21}$H$_{21}$F$_2$N$_3$O$_2$: 386 (M+H); found: 386. $^1$H NMR (400 MHz, DMSO-d$_6$): δ 8.17 (t, J=8.0 Hz, 1H), 7.82-7.80 (m, 1H), 7.51-7.49 (m, 1H), 4.69 (d, J=4.4 Hz, 1H), 4.05-4.02 (m, 1H), 3.52 (s, 2H), 3.25-3.22 (m, 2H), 2.24 (s, 3H), 2.02-1.96 (m, 2H), 1.93 (s, 3H), 1.73-1.65 (m, 1H), 1.51-1.44 (m, 1H), 1.35-1.28 (m, 1H), 0.80-0.72 (m, 1H).

Example 45B. (±)-1-(1-(4-Chloro-3-fluorophenyl)-2,5-dimethyl-1H-pyrrol-3-yl)-2-((2R)-2-hydroxy-7-azabicyclo[2.2.1]heptan-7-yl)ethan-1-one (117B)

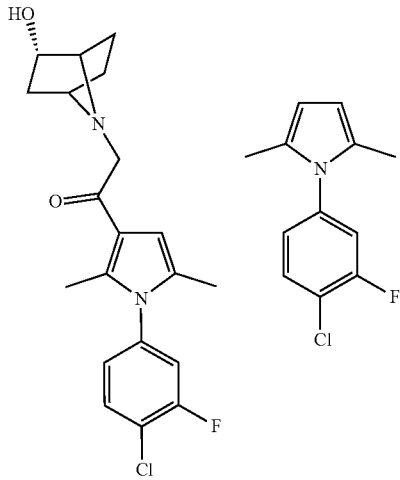

A. 1-(4-Chloro-3-fluorophenyl)-2,5-dimethyl-1H-pyrrole

Into a 250 mL round-bottom flask, being maintained under an inert atmosphere of nitrogen, was placed a mixture of 4-chloro-3-fluoroaniline (10 g, 68.7 mmol) and hexane-2,5-dione (11.8 g, 103 mmol), acetic acid (50 mL) and toluene (50 mL). The reaction mixture was heated at 110° C. overnight. After cooling to room temperature, the reaction mixture was condensed in vacuo and the remaining residue was purified by column chromatography, using ethyl acetate/petroleum ether (1:4) as the eluant, to afford 7 g of 1-(4-chloro-3-fluorophenyl)-2,5-dimethyl-1H-pyrrole as a light yellow solid. Mass Spectrum (LCMS, ESI pos.): Calcd. for C$_{12}$H$_{11}$ClFN: 224 (M+H); found: 224.

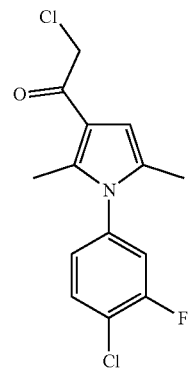 [SMILES: Cc1cc(C(=O)CCl)c(C)n1-c1ccc(Cl)c(F)c1]

B. 2-Chloro-1-(1-(4-chloro-3-fluorophenyl)-2,5-dimethyl-1H-pyrrol-3-yl)ethan-1-one Into a 50 mL round-bottom flask, being maintained under an inert atmosphere of nitrogen, was placed a solution of 1-(4-chloro-3-fluorophenyl)-2,5-dimethyl-1H-pyrrole (223 mg, 1.00 mmol) in dichloromethane (5 mL). The solution was cooled to 0° C. and then treated with diethylaluminum chloride (1.7 mL, 1.50 equiv). The resulting mixture was allowed to stir for 20 min at 0° C. and was then treated with 2-chloroacetyl chloride (0.113 mL) in one portion. The reaction mixture was allowed to warm to room temperature and stir overnight before it was diluted with water. The biphasic mixture was extracted with dichloromethane and the combined organic extracts were concentrated under vacuum to afford 349 mg of crude 2-chloro-1-(1-(4-chloro-3-fluorophenyl)-2,5-dimethyl-1H-pyrrol-3-yl)ethan-1-one as a brown liquid. Mass Spectrum (LCMS, ESI pos.): Calcd. for $C_4H_{12}C_{12}FNO$: 300 (M+H); found: 300.

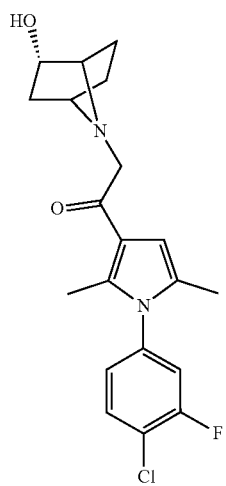 [SMILES: Cc1cc(C(=O)CN2C3CCC2[C@@H](O)C3)c(C)n1-c1ccc(Cl)c(F)c1]

C. (±)-1-(1-(4-Chloro-3-fluorophenyl)-2,5-dimethyl-1H-pyrrol-3-yl)-2-((2R)-2-hydroxy-7-azabicyclo[2.2.1]heptan-7-yl)ethan-1-one (117B)

Into a 100 mL round-bottom flask, being maintained under an inert atmosphere of nitrogen, was placed a solution of 2-chloro-1-(1-(4-chloro-3-fluorophenyl)-2,5-dimethyl-1H-pyrrol-3-yl)ethan-1-one (349 mg, 1.16 mmol) in N,N-dimethylformamide (5 mL). To the solution were added potassium carbonate (414 mg, 3.00 mmol) and racemic (2R)-bicyclo[2.2.1]heptan-2-ol hydrochloric acid (165 mg, 1.10 mmol). The resulting mixture was allowed to stir overnight at room temperature. The solids were filtered from the reaction mixture and then the crude product was purified by preparative-HPLC under the following conditions: Column—XBridge Prep C18 OBD Column 19*250 mm, 10 μm; Mobile Phase A: Water (10 mmol/L $NH_4HCO_3$), Mobile Phase B: acetonitrile, Flow rate—25 mL/min, Gradient: 15% B to 60% B in 8 min; Detector—254/220 nm. This process afforded 749 mg (17%) of (±)-1-(1-(4-Chloro-3-fluorophenyl)-2,5-dimethyl-1H-pyrrol-3-yl)-2-((2R)-2-hydroxy-7-azabicyclo[2.2.1]heptan-7-yl)ethan-1-one (117B) as a white solid. Mass Spectrum (LCMS, ESI pos.): Calcd. for $C_{20}H_{22}ClFN_2O_2$: 377 (M+H); found: 377. $^1$H NMR (300 MHz, DMSO-$d_6$): δ 7.81-7.76 (m, 1H), 7.63-7.59 (m, 1H), 7.27-7.24 (m, 1H), 6.46 (s, 1H), 4.66 (d, J=3.9 Hz, 1H), 4.06-4.02 (m, 1H), 3.52 (s, 2H), 3.31-3.22 (m, 2H), 2.24 (s, 3H), 2.03-1.94 (m, 2H), 1.97 (s, 3H), 1.75-1.71 (m, 1H), 1.54-1.45 (m, 1H), 1.35-1.34 (m, 1H), 0.80-076 (m, 1H).

Example 46B. (±)-1-(1-(4-Chloro-3,5-difluorophenyl)-2,5-dimethyl-1H-pyrrol-3-yl)-2-((2R)-2-hydroxy-7-azabicyclo[2.2.1]heptan-7-yl)ethan-1-one (118B)

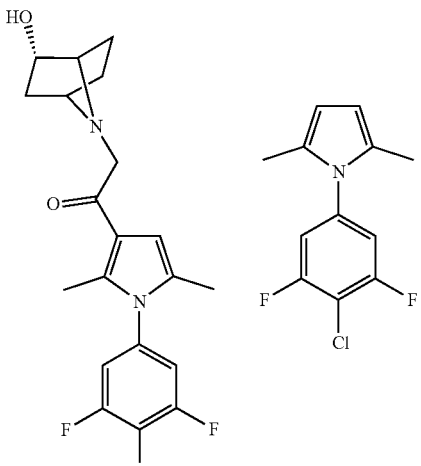

A. 1-(4-Chloro-3,5-difluorophenyl)-2,5-dimethyl-1H-pyrrole

Into a 250 mL round-bottom flask, being maintained under an inert atmosphere of nitrogen, was placed a mixture of 4-chloro-3,5-difluoroaniline (10 g, 61.1 mmol) hexane-2,5-dione (11.8 g, 103 mmol), acetic acid (50 mL) and toluene (50 mL). The reaction mixture was heated at 110° C. overnight before being allowed to cool to room temperature. The reaction mixture was concentrated in vacuo and the remaining residue purified by column chromatography on silica, using ethyl acetate/petroleum ether (1:4) as the eluant, to afford 8 g of 1-(4-chloro-3,5-difluorophenyl)-2,5-dimethyl-1H-pyrrole as a light yellow solid. Mass Spectrum (LCMS, ESI pos.): Calcd. for $C_{12}H_{10}ClF_2N$: 242 (M+H); found: 242.

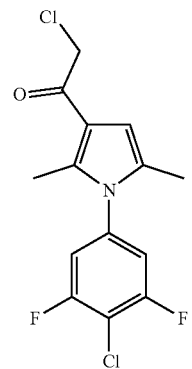 [SMILES: Cc1cc(C(=O)CCl)c(C)n1-c1cc(F)c(Cl)c(F)c1]

B. 2-Chloro-1-(1-(4-chloro-3,5-difluorophenyl)-2,5-dimethyl-1H-pyrrol-3-yl)ethan-1-one Into a 50 mL round-bottom flask, being maintained under an inert atmosphere of nitrogen, was placed a mixture of 1-(4-chloro-3,5-difluorophenyl)-2,5-dimethyl-1H-pyrrole (240 mg, 0.99 mmol), diethyl aluminum chloride (1.7 mL, 1.50 equiv), and dichloromethane (5 mL). The mixture was cooled to 0° C. and allowed to stir for 20 min before being treated with 2-chloroacetyl chloride (167 mg, 1.48 mmol). The resulting mixture was allowed to stir overnight at 0° C. and then diluted with water. The biphasic mixture was extracted with dichloromethane and the combined organic extracts were concentrated under vacuum to afford 331 mg of crude 2-chloro-1-(1-(4-chloro-3,5-difluorophenyl)-2,5-dimethyl-1H-pyrrol-3-yl)ethan-1-one as a brown liquid. Mass Spectrum (LCMS, ESI pos.): Calcd. for $C_4H_{11}Cl_2F_2NO$: 318 (M+H); found: 318.

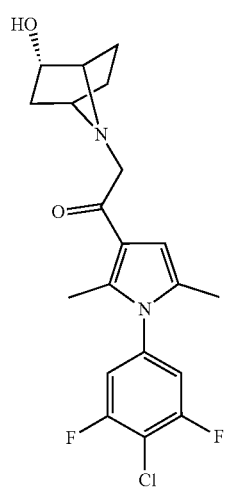 [SMILES: Cc1cc(C(=O)CN2C3CCC2[C@@H](O)C3)c(C)n1-c1cc(F)c(Cl)c(F)c1]

C. (±)-1-(1-(4-Chloro-3,5-difluorophenyl)-2,5-dimethyl-1H-pyrrol-3-yl)-2-((2R)-2-hydroxy-7-azabicyclo[2.2.1]heptan-7-yl)ethan-1-one (118B)

Into a 100 mL round-bottom flask, being maintained under an atmosphere of nitrogen, was placed a solution of 2-chloro-1-(1-(4-chloro-3,5-difluorophenyl)-2,5-dimethyl-1H-pyrrol-3-yl)ethan-1-one (331 mg, 1.04 mmol) in N,N-dimethylformamide (5 mL). To the solution were added potassium carbonate (414 mg, 3.00 mmol) and racemic (2R)-bicyclo[2.2.1]heptan-2-ol hydrochloric acid (165 mg, 1.10 mmol). The resulting mixture was allowed to stir overnight at room temperature. The solids were filtered from the reaction mixture and then the crude product was purified by preparative-HPLC under the following conditions: Column—XBridge C18 OBD 19*250 mm, 10 μm; Mobile Phase A—Water (10 mmol/L $NH_4HCO_3$), Mobile Phase B: acetonitrile; Flow rate: 20 mL/min; Gradient: 40% B to 70% B in 8 min; Detector—254/220 nm. This process afforded 72 mg (17%) of (±)-1-(1-(4-Chloro-3,5-difluorophenyl)-2,5-dimethyl-1H-pyrrol-3-yl)-2-((2R)-2-hydroxy-7-azabicyclo[2.2.1]heptan-7-yl)ethan-1-one (118B) as a white solid. Mass Spectrum (LCMS, ESI pos.): Calcd. for $C_{20}H_{21}ClF_2N_2O_2$: 395 (M+H); found: 395. $^1$H NMR (300 MHz, DMSO-$d_6$): δ 7.57-7.54 (m, 2H), 6.47 (s, 1H), 4.66 (d, J=3.9 Hz, 1H), 4.06-4.02 (m, 1H), 3.46 (s, 2H), 3.25-3.23 (m, 2H), 2.27 (s, 3H), 2.03 (s, 3H), 2.00-1.94 (m, 2H), 1.78-1.72 (m, 1H), 1.54-1.46 (m, 1H), 1.34-1.27 (m, 1H), 0.80-0.75 (m, 1H).

Example 47B. (±)-4-(5-Cyclopropyl-3-(2-((2R)-2-hydroxy-7-azabicyclo[2.2.1]heptan-7-yl)acetyl)-2-methyl-1H-pyrrol-1-yl)-benzonitrile (98B)

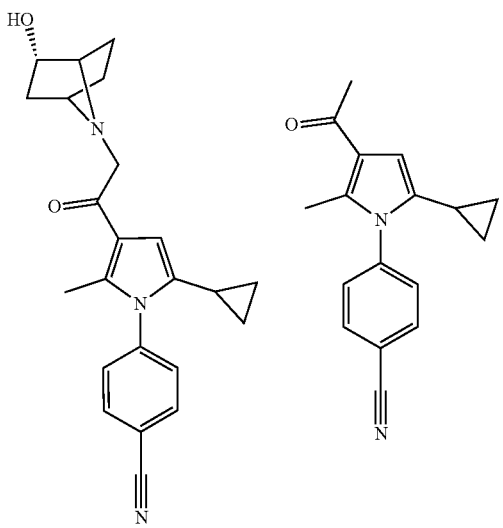 [SMILES: Cc1c(C(=O)CN2C3CCC2[C@@H](O)C3)cc(C2CC2)n1-c1ccc(C#N)cc1 ; CC(=O)c1cc(C2CC2)n(-c2ccc(C#N)cc2)c1C]

A. 4-(3-Acetyl-5-cyclopropyl-2-methyl-1H-pyrrol-1-yl)benzonitrile

Into a 100 mL round-bottom flask, being maintained under an inert atmosphere of nitrogen, was placed a mixture of 4-(3-acetyl-5-iodo-2-methyl-1H-pyrrol-1-yl)benzonitrile (1.0 g, 2.86 mmol, Intermediate IB), cyclopropylboronic acid (300 mg, 3.49 mmol), cesium carbonate (2.74 g, 8.41 mmol), Pd(dppf)Cl$_2$·CH$_2$Cl$_2$ (180 mg, 0.22 mmol), 1,4-dioxane (10 mL) and water (2 mL). The reaction mixture was heated at 80° C. for 5 h and then allowed to cool before being diluted with ethyl acetate (50 mL). The mixture was washed with brine (2×30 mL), dried over anhydrous sodium sulfate and concentrated under vacuum. The remaining residue was purified by preparative-TLC, using ethyl acetate/petroleum ether (1:3) as the developing solution, to afford 500 mg (66%) of 4-(3-acetyl-5-cyclopropyl-2-methyl-1H-pyrrol-1-yl)benzonitrile as a white solid. Mass Spectrum (LCMS, ESI pos.): Calcd. for $C_{17}H_6N_2O$: 265 (M+H); found: 265. $^1$H NMR (300 MHz, CDCl$_3$): δ 7.88-7.82 (m, 2H), 7.45-7.41 (m, 2H), 6.21 (s, 1H), 2.41 (s, 3H), 2.33 (s, 3H), 1.37-1.28 (m, 1H), 0.76-0.68 (m, 2H), 0.65-0.54 (m, 2H).

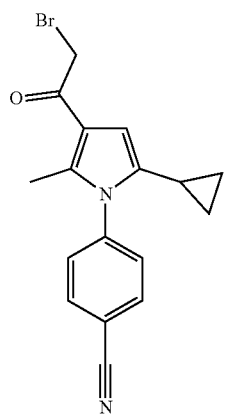 [SMILES: Cc1c(C(=O)CBr)cc(C2CC2)n1-c1ccc(C#N)cc1]

B. 4-(3-(2-Bromoacetyl)-5-cyclopropyl-2-methyl-1H-pyrrol-1-yl)benzonitrile

Into a 50 mL 3-necked round-bottom flask, being maintained under an inert atmosphere of nitrogen, was placed a solution of 4-(3-acetyl-5-cyclopropyl-2-methyl-1H-pyrrol-1-yl)benzonitrile (500 mg, 1.89 mmol) in tetrahydrofuran (25 mL). The solution was cooled to 0° C. and then treated with diisopropylethylamine (980 mg, 7.58 mmol) and trimethylsilyl trifluoromethylsulfonate (850 mg). The mixture was allowed to stir at 0° C. for 1 h and then N-bromosuccinimide (350 mg, 1.97 mmol) was added. The reaction mixture was allowed to stir at 0° C. for 0.5 h and was then diluted with water (20 mL). The mixture was extracted with ethyl acetate (2×50 mL) and the combined organic extracts were washed with brine (2×20 mL). The organic phase was dried over anhydrous sodium sulfate and concentrated under vacuum to afford 300 mg (46%) of 4-(3-(2-bromoacetyl)-5-cyclopropyl-2-methyl-1H-pyrrol-1-yl)benzonitrile as a brown solid. Mass Spectrum (LCMS, ESI pos.): Calcd. for $C_{17}H_{15}BrN_2O$: 343 (M+H); found: 343.

C. (±)-4-(5-Cyclopropyl-3-(2-((2R)-2-hydroxy-7-azabicyclo[2.2.1]heptan-7-yl)acetyl)-2-methyl-1H-pyrrol-1-yl)benzonitrile (98B)

Into a 25 mL round-bottom flask, being maintained under an inert atmosphere of nitrogen, was placed a mixture of 4-(3-(2-bromoacetyl)-5-cyclopropyl-2-methyl-1H-pyrrol-1-yl)benzonitrile (300 mg, 0.87 mmol), racemic (1R,2R,4S)-7-azabicyclo[2.2.1]heptan-2-ol (150 mg, 1.33 mmol), potassium carbonate (620 mg, 4.49 mmol) and N,N-dimethylformamide (5 mL). The reaction mixture was allowed to stir overnight at room temperature before it was diluted with water (50 mL). The mixture was extracted with ethyl acetate (2×50 mL) and the combined organic extracts were washed with brine (2×25 mL), dried over anhydrous sodium sulfate and concentrated under vacuum. The crude product was purified by preparative-HPLC under the following conditions: Mobile Phase A-water with 0.05% trifluoroacetic acid, Mobile Phase B-acetonitrile; Flow rate-20 μL/min; Gradient-20% B to 70% B in 8 min; Detector—UV 254 nm. This process afforded 87 mg (27%) of (±)-4-(5-cyclopropyl-3-(2-((2R)-2-hydroxy-7-azabicyclo[2.2.1]heptan-7-yl)acetyl)-2-methyl-1H-pyrrol-1-yl)benzonitrile (98B) as a white solid. Mass Spectrum (LCMS, ESI pos.): Calcd. for $C_{23}H_{25}N_3O_2$: 376 (M+H); found: 376. $^1$H NMR (400 MHz, $CH_3OH$-$d_4$): δ 7.98-7.96 (m, 2H), 7.57-7.55 (m, 2H), 6.41 (s, 1H), 4.60-4.56 (m, 1H), 4.52-4.51 (m, 1H), 4.16-4.11 (m, 2H), 2.61-2.55 (m, 2H), 2.36 (s, 3H), 2.25-1.18 (m, 1H), 1.93-1.90 (m, 2H), 1.51-1.47 (m, 1H), 1.42-1.38 (m, 1H), 0.73-0.69 (m, 2H), 0.62-0.59 (m, 2H).

Example 48B. (±)-4-(5-Cyclobutyl-3-(2-((2R)-2-hydroxy-7-azabicyclo[2.2.1]heptan-7-yl)acetyl)-2-methyl-1H-pyrrol-1-yl)benzonitrile (108B)

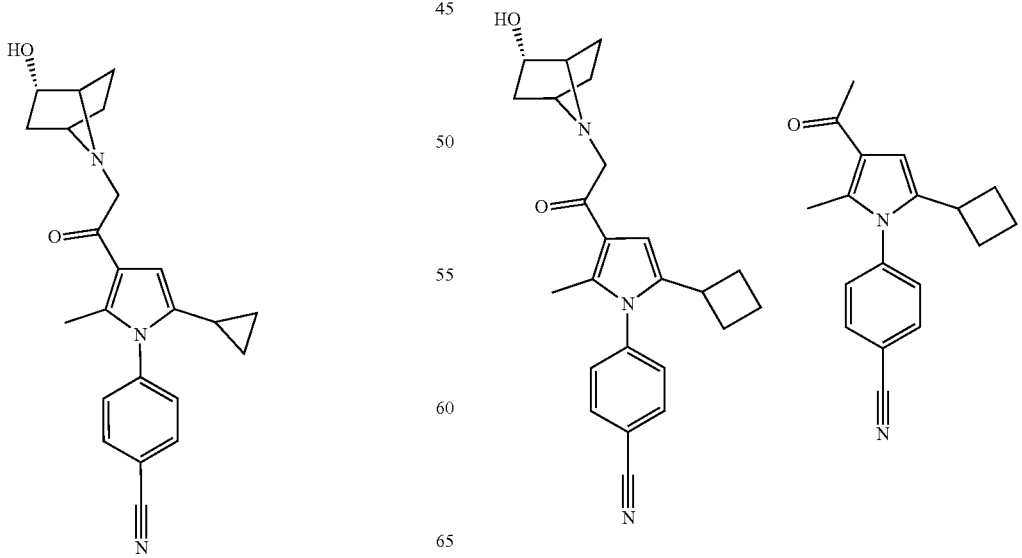

A. 4-(3-Acetyl-5-cyclobutyl-2-methyl-1H-pyrrol-1-yl)benzonitrile

Into a 100 mL round-bottom flask, being maintained under an inert atmosphere of nitrogen, was placed a mixture of 4-(3-acetyl-5-iodo-2-methyl-1H-pyrrol-1-yl)benzonitrile (530 mg, 1.51 mmol, Intermediate IB), copper(I) iodide (67 mg, 0.35 mmol), Pd(dppf)C$_{12}$CH$_2$C$_{12}$ (132 mg, 0.16 mmol), and tetrahydrofuran (20 mL). The mixture was then treated with a solution of bromo(cyclobutyl)zinc (3.6 mL, 0.70 equiv) in tetrahydrofuran in dropwise manner. The resulting mixture was heated at 60° C. for 16 h and then allowed to cool to room temperature. The reaction mixture was diluted with water (20 mL) and then extracted with ethyl acetate (2×100 mL). The combined organic extracts were washed with brine (2×20 mL), dried over anhydrous sodium sulfate and concentrated under vacuum to afford 95 mg (23%) of 4-(3-acetyl-5-cyclobutyl-2-methyl-1H-pyrrol-1-yl)benzonitrile as a yellow solid. Mass Spectrum (LCMS, ESI pos.): Calcd. for C$_{18}$H$_{18}$N$_2$O: 279 (M+H); found: 279.

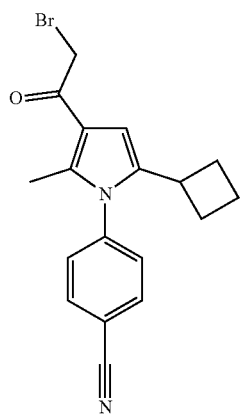 [SMILES: Cc1c(C(=O)CBr)cc(C2CCC2)n1-c1ccc(C#N)cc1]

B. 4-(3-(2-Bromoacetyl)-5-cyclobutyl-2-methyl-1H-pyrrol-1-yl)benzonitrile

Into a 50 mL 3-necked round-bottom flask, being maintained under an inert atmosphere of nitrogen, was placed a mixture of 4-(3-acetyl-5-cyclobutyl-2-methyl-1H-pyrrol-1-yl)benzonitrile (200 mg, 0.72 mmol), diisopropylethylamine (370 mg, 2.87 mmol) and tetrahydrofuran (20 mL). The mixture was cooled to 0° C. and then treated with trimethylsilyl trifluoromethanesulfonate (318 mg, 1.43 mmol). After the reaction mixture was allowed to stir at 0° C. for 1 h, solid N-bromosuccinimide (382 mg, 2.15 mmol) was added over 30 min. The resulting mixture was allowed to stir at 0° C. for 1 h before it was diluted with water (50 mL). The aqueous mixture was extracted with ethyl acetate (2×100 mL) and the combined organic extracts were washed with brine (2×20 mL). The organic phase was dried over anhydrous sodium sulfate and then concentrated under vacuum to afford 120 mg (47%) of 4-(3-(2-bromoacetyl)-5-cyclobutyl-2-methyl-1H-pyrrol-1-yl)benzonitrile as a yellow oil. Mass Spectrum (LCMS, ESI pos.): Calcd. for C$_{18}$H$_{17}$BrN$_2$O: 357 (M+H); found: 357.

C. (±)-4-(5-Cyclobutyl-3-(2-((2R)-2-hydroxy-7-azabicyclo[2.2.1]heptan-7-yl)acetyl)-2-methyl-1H-pyrrol-1-yl)benzonitrile (108B)

Into a 50 mL round-bottom flask, being maintained under an inert atmosphere of nitrogen, was placed a solution of 4-(3-(2-bromoacetyl)-5-cyclobutyl-2-methyl-1H-pyrrol-1-yl)benzonitrile (120 mg, 0.34 mmol) in N,N-dimethylformamide (5 mL). To the solution were added potassium carbonate (139 mg, 1.01 mmol) and racemic (1R,2R,4S)-7-azabicyclo[2.2.1]heptan-2-ol (75 mg, 0.50 mmol). The resulting mixture was allowed to stir at room temperature for 2 h before the solids were filtered from the mixture. The crude product was purified by preparative-HPLC under the following conditions: Column-XBridge C18 OBD Prep Column 100 Å, 10 μm, 19 mm×250 mm; mobile phase-Water with 10 mM NH$_4$HCO$_3$ and acetonitrile (20% acetonitrile up to 67% in 8 min); Detector-UV 254 nm. This process afforded 61 mg (47%) of (±)-4-(5-cyclobutyl-3-(2-((2R)-2-hydroxy-7-azabicyclo[2.2.1]heptan-7-yl)acetyl)-2-methyl-1H-pyrrol-1-yl)benzonitrile (108B) as a yellow solid. Mass Spectrum (LCMS, ESI pos.): Calcd. for C$_{24}$H$_{27}$N$_3$O$_2$: 390 (M+H); found: 390. $^1$H NMR (300 MHz, DMSO-d$_6$): δ 8.05 (d, J=8.4 Hz, 2H), 7.53 (d, J=8.4 Hz, 2H), 6.59 (s, 1H), 4.68 (d, J=3.0 Hz, 1H), 4.07 (brs, 1H), 3.60 (s, 2H), 3.28-3.23 (m, 1H), 3.08-3.03 (m, 1H), 2.20 (s, 3H), 2.02-1.88 (m, 6H), 1.78-1.71 (m, 3H), 1.55-1.48 (m, 1H), 1.36-1.31 (m, 1H), 0.82-0.77 (m, 1H).

Example 49B. (±)-4-(3-(2-((2R)-2-Hydroxy-7-azabicyclo[2.2.1]heptan-7-yl)acetyl)-2-methyl-5-(trifluoromethyl)-1H-pyrrol-1-yl)benzonitrile (109B)

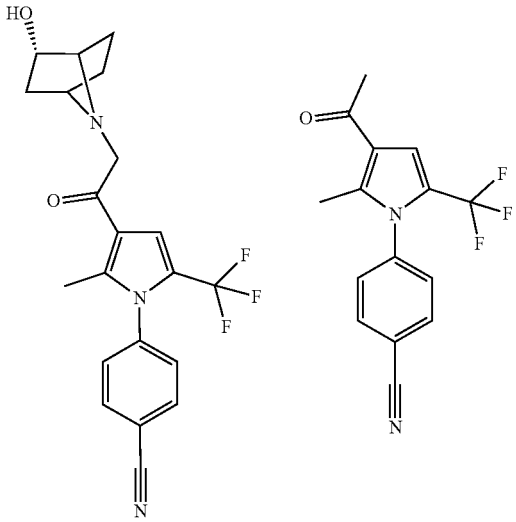 [SMILES: Cc1c(C(=O)CN2C3CCC2[C@@H](O)C3)cc(C(F)(F)F)n1-c1ccc(C#N)cc1 ; CC(=O)c1cc(C(F)(F)F)n(-c2ccc(C#N)cc2)c1C]

A. 4-(3-Acetyl-2-methyl-5-(trifluoromethyl)-1H-pyrrol-1-yl)benzonitrile

Into a 100 mL round-bottom flask, being maintained under an inert atmosphere of nitrogen, was placed a solution of 4-(3-acetyl-5-iodo-2-methyl-1H-pyrrol-1-yl)benzonitrile (525 mg, 1.50 mmol, Intermediate IB) in N,N-dimethylformamide (10 mL). The solution was then treated with copper (I) iodide (285 mg, 1.50 mmol) and methyl 2,2-difluoro-2-(fluorosulfonyl)acetate (1.15 g, 5.99 mmol). The resulting mixture was heated at 100° C. for 16 h before being allowed to cool to room temperature. The reaction mixture was diluted with water and then concentrated under vacuum. The remaining residue was purified by column chromatography on silica, using ethyl acetate/petroleum ether (1:3) as the eluant, to afford 305 mg (70%) of 4-(3-acetyl-2-methyl-5-(trifluoromethyl)-1H-pyrrol-1-yl)benzonitrile as a yellow oil. Mass Spectrum (LCMS, ESI pos.): Calcd. for $C_{15}H_{13}F_3N_2O$: 293 (M+H); found: 293.

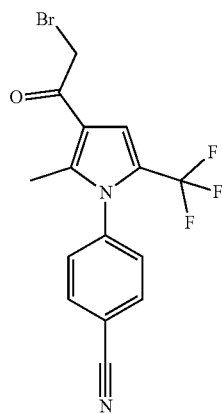 [SMILES: Cc1c(C(=O)CBr)cc(C(F)(F)F)n1-c1ccc(C#N)cc1]

B. 4-(3-(2-Bromoacetyl)-2-methyl-5-(trifluoromethyl)-1H-pyrrol-1-yl)benzonitrile Into a 50 mL round-bottom flask, being maintained under an inert atmosphere of nitrogen, was placed a solution of 4-(3-acetyl-2-methyl-5-(trifluoromethyl)-1H-pyrrol-1-yl)benzonitrile (305 mg, 1.04 mmol) in tetrahydrofuran (10 mL). The solution was cooled to 0° C. and then treated with trimethylsilyl trifluoromethylsulfonate (0.38 mL) and diisopropylethylamine (0.52 mL). The mixture was allowed to stir at 0° C. for 30 min and then solid N-bromosuccinimide (223 mg, 1.25 mmol) was added. The resulting mixture was allowed to stir at 0° C. for 1 h before it was diluted with brine. The aqueous mixture was extracted with ethyl acetate and the combined organic extracts were concentrated to afford 500 mg of crude 4-(3-(2-bromoacetyl)-2-methyl-5-(trifluoromethyl)-1H-pyrrol-1-yl)benzonitrile as a brown oil. Mass Spectrum (LCMS, ESI pos.): Calcd. for $C_{15}H_{10}BrF_3N_2O$: 371 (M+H); found: 371.

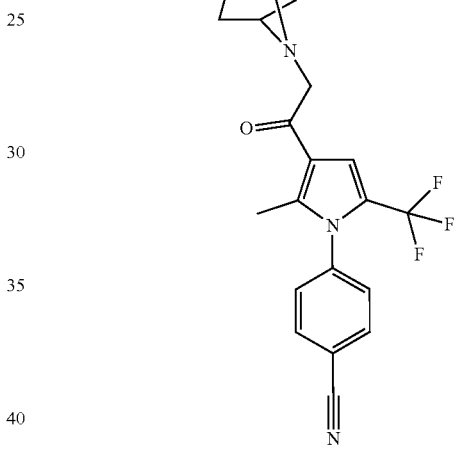

C. (±)-4-(3-(2-((2R)-2-Hydroxy-7-azabicyclo[2.2.1]heptan-7-yl)acetyl)-2-methyl-5-(trifluoromethyl)-1H-pyrrol-1-yl)benzonitrile (109B)

Into a 50 mL round-bottom flask, being maintained under an inert atmosphere of nitrogen, was placed a solution of 4-(3-(2-bromoacetyl)-2-methyl-5-(trifluoromethyl)-1H-pyrrol-1-yl)benzonitrile (385 mg, 1.04 mmol) in N,N-dimethylformamide (4 mL). To the solution were added potassium carbonate (432 mg, 3.13 mmol) and racemic (2R)-bicyclo[2.2.1]heptan-2-ol hydrochloride (235 mg, 1.57 mmol). The resulting mixture was allowed to stir at room temperature overnight before the solids were filtered from the mixture. The reaction mixture was concentrated under vacuum and the remaining residue was purified by preparative-HPLC under the following conditions: Column-X Bridge BEH130 Prep C18 OBD Column, 19×250 mm, 10 µm; Mobile Phase A: Water with 10 mM $NH_4HCO_3$, Mobile Phase B-acetonitrile; Flow rate: 20 mL/min; Gradient: 37% B to 47% B in 7 min; Detector-254 nm. This process afforded 159 mg (38%) of (±)-4-(3-(2-((2R)-2-Hydroxy-7-azabicyclo[2.2.1]heptan-7-yl)acetyl)-2-methyl-5-(trifluoromethyl)-1H-pyrrol-1-yl)benzonitrile (109B) as a white solid. Mass Spectrum (LCMS, ESI pos.): Calcd. for $C_{21}H_{20}F_3N_3O_2$: 404

(M+H); found: 404. ¹H NMR (300 MHz, DMSO-d₆): δ 8.10 (d, J=8.7 Hz, 2H), 7.71 (d, J=8.4 Hz, 2H), 7.50 (s, 1H), 4.69 (d, J=3.9 Hz, 1H), 4.07-4.04 (m, 1H), 3.72 (brs, 2H), 3.26-3.16 (m, 2H), 2.22 (s, 3H), 2.13-1.96 (m, 2H), 1.77-1.73 (m, 1H), 1.56-1.48 (m, 1H), 1.37-1.29 (m, 1H), 0.85-0.79 (m, 1H).

Example 50B. (±)-4-(5-Cyclopentyl-3-(2-((2R)-2-hydroxy-7-azabicyclo[2.2.1]heptan-7-yl)acetyl)-2-methyl-1H-pyrrol-1-yl)benzonitrile (110B)

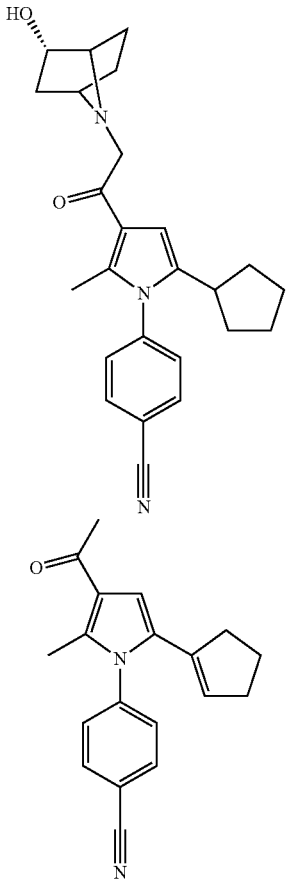

A. 4-(3-Acetyl-5-(cyclopent-1-en-1-yl)-2-methyl-1H-pyrrol-1-yl)benzonitrile

Into a 10 mL sealed tube, being maintained under an inert atmosphere of nitrogen, was placed a mixture of 4-(3-acetyl-5-iodo-2-methyl-1H-pyrrol-1-yl)benzonitrile (500 mg, 1.65 mmol; Intermediate IB), (cyclopent-1-en-1-yl)boronic acid (280 mg, 2.50 mmol), cesium carbonate (1.6 g, 5.00 mmol), 1,4-dioxane (5 mL) and water (1 mL). To the mixture was added tetrakis(triphenylphosphine)palladium(0) (190 mg, 0.16 mmol) and the resulting system was heated in a microwave for 1 h at 100° C. After cooling to room temperature, the reaction mixture was concentrated under vacuum and the remaining residue was purified by preparative-TLC (petroleum ether/ethyl acetate=2:1 developing solution) to afford 450 mg (94%) of 4-(3-acetyl-5-(cyclopent-1-en-1-yl)-2-methyl-1H-pyrrol-1-yl)benzonitrile as a brown solid. Mass Spectrum (LCMS, ESI pos.): Calcd. for $C_{19}H_{18}N_2O$: 291 (M+H); found: 291.

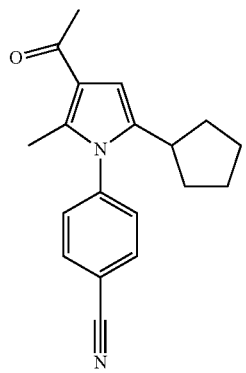 [SMILES: CC(=O)c1cc(C2CCCC2)n(-c2ccc(C#N)cc2)c1C]

B. 4-(3-Acetyl-5-cyclopentyl-2-methyl-1H-pyrrol-1-yl)benzonitrile

Into a 100 mL round-bottom flask was placed a solution of 4-(3-acetyl-5-(cyclopent-1-en-1-yl)-2-methyl-1H-pyrrol-1-yl)benzonitrile (450 mg, 1.55 mmol) in ethyl acetate (20 mL). To the solution was added palladium on carbon (100 mg, 1.13 mmol) and the resulting mixture was sparged with hydrogen. The reaction mixture was allowed to stir at room temperature for 10 h under an atmosphere of hydrogen. The solids were filtered from the reaction mixture and then the filtrate was concentrated under vacuum. The remaining residue was purified by preparative-TLC (petroleum ether/ethyl acetate=2:1 developing solution) to afford 300 mg (66%) of 4-(3-acetyl-5-cyclopentyl-2-methyl-1H-pyrrol-1-yl)benzonitrile as a light yellow solid. Mass Spectrum (LCMS, ESI pos.): Calcd. for $C_{19}H_{20}N_2O$: 293 (M+H); found: 293. ¹H NMR (300 MHz, DMSO-d₆): δ 8.10-8.02 (m, 2H), 7.59-7.54 (m, 2H), 6.89 (s, 1H), 4.61-4.58 (m, 1H), 2.53-2.47 (m, 4H) 2.37 (s, 2H), 2.25-2.17 (m, 2H), 2.20 (s, 3H), 1.79-1.69 (m, 2H).

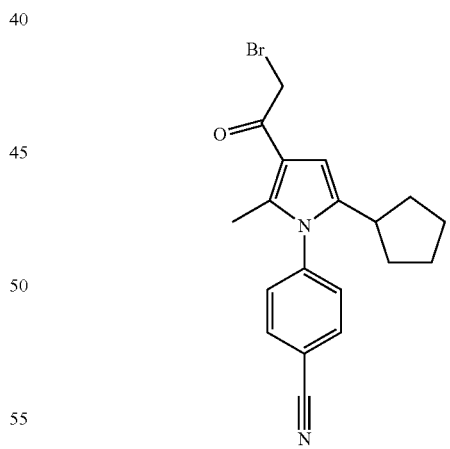

C. 4-(3-(2-Bromoacetyl)-5-cyclopentyl-2-methyl-1H-pyrrol-1-yl)benzonitrile

Into a 50 mL 3-necked round-bottom flask, being maintained under an inert atmosphere of nitrogen, was placed a mixture of 4-(3-acetyl-5-cyclopentyl-2-methyl-1H-pyrrol-1-yl)benzonitrile (170 mg, 0.58 mmol), diisopropylethylamine (225 mg, 1.74 mmol), and tetrahydrofuran (20 mL). The mixture was cooled to 0° C. and was then treated with trimethylsilyl trifluoromethanesulfonate (194 mg). The resulting mixture was allowed to stir at 0° C. for 30 min and then a solution of N-bromosuccinimide (124 mg, 0.70 mmol) in tetrahydrofuran (2 mL) was added. The reaction mixture was allowed to stir at 0° C. for an additional 2 h before being diluted with water (50 mL). The aqueous mixture was extracted with dichloromethane (3×20 mL) and the combined organic extracts were dried over anhydrous sodium sulfate. The organic phase was concentrated under vacuum to afford 170 mg (79%) of 4-(3-(2-Bromoacetyl)-5-cyclopentyl-2-methyl-1H-pyrrol-1-yl)benzonitrile as a light yellow oil. Mass Spectrum (LCMS, ESI pos.): Calcd. for $C_{19}H_{19}BrN_2O$: 371 (M+H); found: 371.

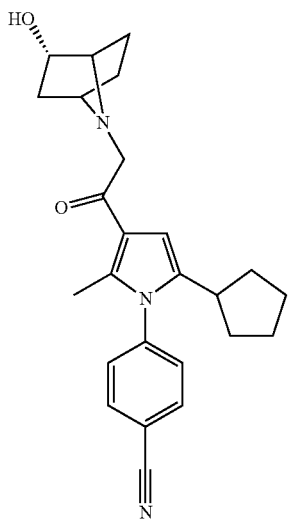 [SMILES: Cc1c(C(=O)CN2C3CCC2[C@@H](O)C3)cc(C2CCCC2)n1-c1ccc(C#N)cc1]

D. (±)-4-(5-Cyclopentyl-3-(2-((2R)-2-hydroxy-7-azabicyclo[2.2.1]heptan-7-yl)acetyl)-2-methyl-1H-pyrrol-1-yl)benzonitrile (110B)

Into a 25 mL round-bottom flask was placed a mixture of 4-(3-(2-bromoacetyl)-5-cyclopentyl-2-methyl-1H-pyrrol-1-yl)benzonitrile (170 mg, 0.46 mmol), racemic (2R)-bicyclo[2.2.1]heptan-2-ol hydrochloride (140 mg, 1.05 mmol), potassium carbonate (194 mg, 1.40 mmol), and N,N-dimethylformamide (3 mL). The reaction mixture was allowed to stir at room temperature for 13 h before it was concentrated under vacuum. The remaining residue was purified by preparative-TLC (dichloromethane/methanol=10:1 developing solution) to afford 164 mg (89%) of (±)-4-(5-Cyclopentyl-3-(2-((2R)-2-hydroxy-7-azabicyclo[2.2.1]heptan-7-yl)acetyl)-2-methyl-1H-pyrrol-1-yl)benzonitrile (110B) as a light yellow solid. Mass Spectrum (LCMS, ESI pos.): Calcd. for $C_{25}H_{29}N_3O_2$: 404 (M+H); found: 404. $^1$H NMR (400 MHz, DMSO-$d_6$): δ 8.05 (d, J=8.4 Hz, 2H), 7.59 (d, J=8.0 Hz, 2H), 6.53 (s, 1H), 4.67 (d, J=4.0 Hz, 1H), 4.08-4.03 (m, 1H), 3.57 (s, 2H), 3.27-3.26 (m, 2H), 2.65-2.61 (m, 1H), 2.19 (s, 3H), 2.02-1.95 (m, 2H), 1.76-1.73 (m, 1H), 1.62-1.28 (m, 11H), 0.81-0.76 (m, 1H).

Using the procedures described in Example 47B through 50B, reagents, starting materials, and conditions known to those skilled in the art, the following compounds representative of the present invention were prepared:

| Cpd | Data |
|---|---|
| 111B | (±)-4-(5-Cyclohexyl-3-(2-((1R,2R,4S)-2-hydroxy-7-azabicyclo[2.2.1]heptan-7-yl)acetyl)-2-methyl-1H-pyrrol-1-yl)benzonitrile<br>Mass Spectrum (LCMS, ESI pos.): Calcd. for $C_{26}H_{31}N_3O_2$: 418 (M + H); found: 418.<br>$^1$H NMR (300 MHz, DMSO-$d_6$): δ 8.06 (d, J = 8.4 Hz, 2H), 7.58 (d, J = 8.4 Hz, 2H), 6.51 (s, 1H), 4.77-4.67 (m, 1H), 4.09-4.06 (m, 1H), 3.63 (s, 2H), 3.36-3.31 (m, 2H), 2.22-2.11 (m, 4H), 2.03-1.96 (m, 2H), 1.78-1.75 (m, 1H), 1.67-1.50 (m, 6H), 1.38-1.22 (m, 3H), 1.18-1.01 (m, 3H), 0.84-0.79 (m, 1H). |
| 112B | (±)-4-(3-(2-((1R,2R,4S)-2-Hydroxy-7-azabicyclo[2.2.1]heptan-7-yl)acetyl)-5-isopropyl-2-methyl-1H-pyrrol-1-yl)benzonitrile<br>Mass Spectrum (LCMS, ESI pos.): Calcd. for $C_{23}H_{27}N_3O_2$: 378 (M + H); found: 378.<br>$^1$H NMR (400 MHz, DMSO-$d_6$): δ 8.06 (d, J = 8.4 Hz, 2H), 7.61 (d, J = 8.4 Hz, 2H), 6.52 (s, 1H), 4.68 (d, J = 4.0 Hz, 1H), 4.07-4.01 (m, 1H), 3.57 (s, 2H), 3.27-3.26 (m, 2H), 2.55-2.52 (m, 1H), 2.19 (s, 3H), 2.04-1.97 (m, 2H), 1.81-1.70 (m, 1H), 1.55-1.51 (m, 1H), 1.35-1.25 (m, 1H), 1.00 (d, J = 6.8 Hz, 6H), 0.79-0.73 (m, 1H). |
| 114B | (±)-4-(5-(sec-Butyl)-3-(2-((1R,2R,4S)-2-hydroxy-7-azabicyclo[2.2.1]heptan-7-yl)acetyl)-2-methyl-1H-pyrrol-1-yl)benzonitrile<br>Mass Spectrum (LCMS, ESI pos.): Calcd. for $C_{24}H_{29}N_3O_2$: 392 (M + H); found: 392.<br>$^1$H NMR (300 MHz, CH$_3$OH-$d_4$): δ 7.92 (d, J = 8.7 Hz, 2H), 7.44 (d, J = 8.4 Hz, 2H), 6.43 (s, 1H), 4.85 (s, 2H), 4.29-4.27 (m, 1H), 3.80-3.78 (m, 1H), 3.48-3.42 (m, 1H), 3.29-3.27 (m, 1H), 2.35-2.29 (m, 1H), 2.24 (s, 3H), 2.20-2.08 (m, 2H), 1.90-1.85 (m, 1H), 1.70-1.66 (m, 1H), 1.53-1.43 (m, 2H), 1.40-1.33 (m, 1H), 1.07 (d, J = 6.9 Hz, 3H), 0.99-0.94 (m, 1H), 0.75-0.70 (m, 3H). Mixture of diastereomers. |
| 131B | (±)-4-(5-(3,3-Difluorocyclobutyl)-3-(2-((1R,2R,4S)-2-hydroxy-7-azabicyclo[2.2.1]heptan-7-yl)acetyl)-2-methyl-1H-pyrrol-1-yl)benzonitrile<br>Mass Spectrum (LCMS, ESI pos.): Calcd. for $C_{24}H_{25}F_2N_3O_2$: 426 (M + H); found: 426.<br>$^1$H NMR (300 MHz, CH$_3$OH-$d_4$): δ 7.94 (d, J = 8.4 Hz, 2H), 7.46 (d, J = 8.4 Hz, 2H), 6.66 (s, 1H), 4.82 (s, 2H), 4.45-4.42 (m, 1H), 4.14 (s, 1H), 3.79-3.74 (m, 2H), 3.03-2.95 (m, 1H), 2.63-2.55 (m, 4H), 2.34-2.32 (m, 2H), 2.28 (s, 3H), 2.08-1.99 (m, 1H), 1.85-1.81 (m, 1H), 1.77-1.70 (m, 1H), 1.21-1.14 (m, 1H). |

387

Example 51B. (±)-4-(5-(tert-Butyl)-3-(2-(2R)-2-hydroxy-7-azabicyclo[2.2.1]heptan-7-yl)acetyl)-2-methyl-1H-pyrrol-1-yl)benzonitrile (113B)

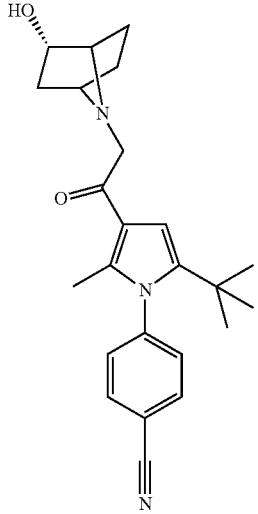

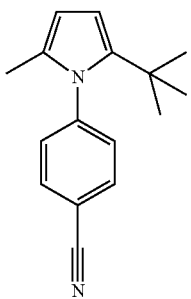

A. 4-(2-(tert-Butyl)-5-methyl-1H-pyrrol-1-yl)benzonitrile

Into a 100 mL round-bottom flask was placed a solution of 6,6-dimethylheptane-2,5-dione (200 mg, 1.28 mmol) in toluene (8 mL). To the solution were added 4-aminobenzonitrile (302 mg, 2.56 mmol) and acetic acid (5 mL). The resulting mixture was heated overnight at 110° C., after which it was allowed to cool to room temperature. The reaction mixture was diluted with water (100 mL) and then extracted with ethyl acetate (2×100 mL). The combined organic extracts were washed with brine (3×100 mL), dried over anhydrous sodium sulfate, and concentrated under vacuum. The remaining residue was purified by column chromatography, using ethyl acetate/petroleum ether (1:10) as the eluant, to afford 170 mg (56%) of 4-(2-(tert-butyl)-5-methyl-1H-pyrrol-1-yl)benzonitrile as a white solid. $^1$H NMR (400 MHz, CDCl$_3$): δ 7.81-7.76 (m, 2H), 7.46-7.43 (m, 2H), 6.02-6.01 (m, 1H), 5.94-5.92 (m, 1H), 1.84 (s, 3H), 1.13 (s, 9H

388

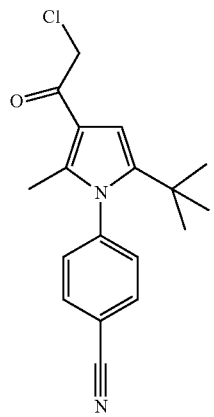 [SMILES: Cc1c(C(=O)CCl)cc(C(C)(C)C)n1-c1ccc(C#N)cc1]

B. 4-(5-(tert-Butyl)-3-(2-chloroacetyl)-2-methyl-1H-pyrrol-1-yl)benzonitrile

Into a 100 mL round-bottom flask, being maintained under an inert atmosphere of nitrogen, was placed a solution of 4-(2-(tert-butyl)-5-methyl-1H-pyrrol-1-yl)benzonitrile (170 mg, 0.71 mmol) in dichloromethane (5 mL). To the solution were added diethylaluminum chloride (170 mg, 1.40 mmol) and 2-chloroacetyl chloride (158 mg, 1.40 mmol). The resulting mixture was allowed to stir at room temperature for 4 h before it was diluted with an aqueous solution of sodium bicarbonate (100 mL). The biphasic mixture was extracted with ethyl acetate (2×100 mL) and the combined organic extracts were washed with brine (3×100 mL). The organic phase was dried over anhydrous sodium sulfate and concentrated under vacuum. The remaining residue was purified by column chromatography on silica, using ethyl acetate/petroleum ether (1:5) as the eluant, to afford 270 mg of 4-(5-(tert-butyl)-3-(2-chloroacetyl)-2-methyl-1H-pyrrol-1-yl)benzonitrile as a yellow solid. Mass Spectrum (LCMS, ESI pos.): Calcd. for C$_{18}$H$_{19}$ClN$_2$O: 315 (M+H); found: 315.

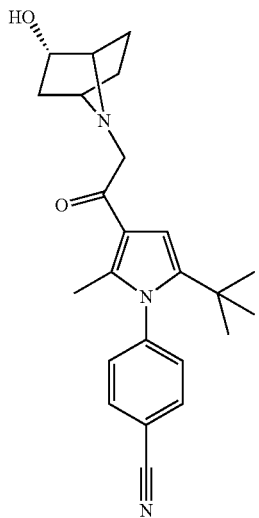 [SMILES: Cc1c(C(=O)CN2C3CCC2[C@@H](O)C3)cc(C(C)(C)C)n1-c1ccc(C#N)cc1]

C. (±)-4-(5-(tert-Butyl)-3-(2-((2R)-2-hydroxy-7-azabicyclo[2.2.1]heptan-7-yl)acetyl)-2-methyl-1H-pyrrol-1-yl)benzonitrile (113B)

Into a 100 mL round-bottom flask was placed a solution of 4-(5-(tert-butyl)-3-(2-chloroacetyl)-2-methyl-1H-pyrrol-1-yl)benzonitrile (270 mg, 0.86 mmol) in N,N-dimethylformamide (3 mL). To the solution were added racemic (1R,2S,4S)-7-azabicyclo[2.2.1]heptan-2-ol hydrochloride (258 mg, 1.72 mmol) and potassium carbonate (594 mg, 4.30 mmol). The resulting mixture was allowed to stir overnight at room temperature. The crude product was purified by preparative-HPLC under the following conditions: Column-SunFire Prep C18, 19*150 mm 5 μm; mobile phase-water with 0.05% $NH_4HCO_3$ and $CH_3CN$ (10% $CH_3CN$ up to 90% in 10 min, up to 95% in 1.5 min, down to 10% in 1.5 min); Detector-254 nm. This process afforded 102 mg (30%) of (±) 4-(5-(tert-butyl)-3-(2-((2R)-2-hydroxy-7-azabicyclo[2.2.1]heptan-7-yl)acetyl)-2-methyl-1H-pyrrol-1-yl)benzonitrile (113B) as a light yellow solid. Mass Spectrum (LCMS, ESI pos.): Calcd. for $C_{24}H_{29}N_3O_2$: 392 (M+H); found: 392. $^1$H NMR (300 MHz, DMSO-$d_6$): δ 8.05 (d, J=8.7 Hz, 2H), 7.62 (d, J=8.7 Hz, 2H), 6.53 (s, 1H), 4.66 (d, J=4.2 Hz, 1H), 4.07-4.03 (m, 1H), 3.56 (s, 2H), 3.28-3.24 (m, 2H), 2.03 (s, 3H), 2.00-1.94 (m, 2H), 1.82-1.73 (m, 1H), 1.55-1.50 (m, 1H), 1.35-1.32 (m, 1H), 1.01 (s, 9H), 0.80-0.75 (m, 1H).

Example 52B. (±)-4-(5-(3-Fluorocyclobutyl)-3-(2-((2R)-2-hydroxy-7-azabicyclo[2.2.1]heptan-7-yl)acetyl)-2-methyl-1H-pyrrol-1-yl)benzonitrile (132B)

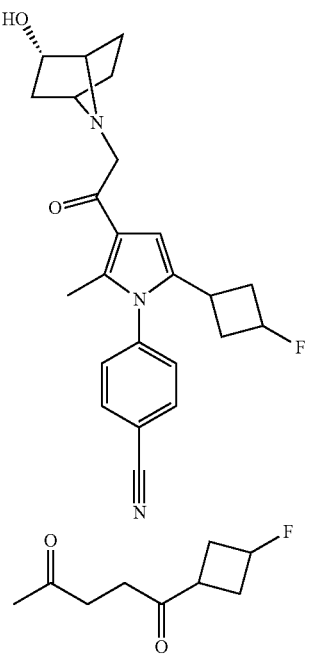

A. 1-(3-Fluorocyclobutyl)pentane-1,4-dione

Into a 250 mL round-bottom flask was placed a solution of 3-fluorocyclobutane-1-carbaldehyde (3.46 g, 34.0 mmol) in ethanol (50 mL). To the solution were added but-3-en-2-one (4.76 g, 68.0 mmol), triethylamine (10.3 g, 102 mmol) and 3-benzyl-5-(2-hydroxyethyl)-4-methyl-1,3-thiazol-3-ium chloride (1.84 g, 6.80 mmol). The resulting mixture was heated at 80° C. overnight before it was allowed to cool to room temperature. The reaction mixture was concentrated under vacuum and the remaining residue was redissolved in ethyl acetate (100 mL). The mixture was washed with brine (3×100 mL), dried over anhydrous sodium sulfate and concentrated under vacuum. The remaining residue was purified by column chromatography on silica, using ethyl acetate/petroleum ether (1:5) as the eluant, to afford 1 g (17%) of 1-(3-fluorocyclobutyl)pentane-1,4-dione as yellow oil. $^1$H NMR (300 MHz, CDCl$_3$): δ 5.04-4.91 (m, 0.5H), 4.85-4.78 (m, 0.5H), 2.80-2.66 (m, 5H), 2.63-2.30 (m, 4H), 2.15 (s, 3H).

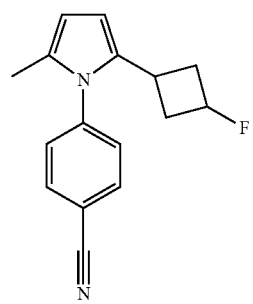 [SMILES: Cc1ccc(C2CC(F)C2)n1-c1ccc(C#N)cc1]

B. 4-(2-(3-Fluorocyclobutyl)-5-methyl-1H-pyrrol-1-yl)benzonitrile

Into a 100 mL round-bottom flask was placed a solution of 1-(3-fluorocyclobutyl)pentane-1,4-dione (660 mg, 3.83 mmol) in toluene (6 mL). To the solution were added 4-aminobenzonitrile (906 mg, 7.67 mmol) and acetic acid (5 mL). The resulting mixture was heated at 100° C. overnight before cooling to room temperature. The reaction mixture was diluted with an aqueous solution of sodium carbonate (100 mL) and then extracted with ethyl acetate (2×100 mL). The combined organic extracts were washed with brine (3×100 mL), dried over anhydrous sodium sulfate and concentrated under vacuum. The remaining residue was purified by column chromatography on silica, using ethyl acetate/petroleum ether (1:10) as the eluant, to afford 700 mg (72%) of 4-(2-(3-fluorocyclobutyl)-5-methyl-1H-pyrrol-1-yl)benzonitrile as a yellow solid. $^1$H NMR (300 MHz, CDCl$_3$) δ 7.77-7.74 (m, 2H), 7.30-7.25 (m, 2H), 6.04-6.01 (m, 1H), 5.99-5.95 (m, 1H), 2.52-2.39 (m, 3H), 2.35-2.16 (m, 3H), 1.99 (s, 3H).

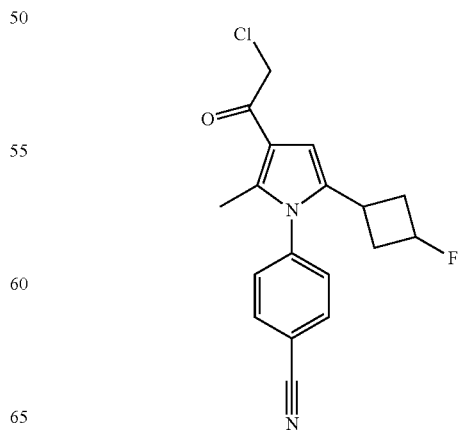

C. 4-(3-(2-Chloroacetyl)-5-(3-fluorocyclobutyl)-2-methyl-1H-pyrrol-1-yl)benzonitrile Into a 100 mL round-bottom flask was placed a solution of 4-(2-(3-fluorocyclobutyl)-5-methyl-1H-pyrrol-1-yl)benzonitrile (230 mg, 0.90 mmol) in dichloromethane (5 mL). To the solution were added 2-chloroacetyl chloride (203 mg, 1.80 mmol) and diethylaluminum chloride (1.5 mL, 0.9M). The reaction mixture was allowed to stir at room temperature for 3 h before it was diluted with water (100 mL). The biphasic mixture was extracted with ethyl acetate (3×100 mL) and the combined organic extracts were washed with brine (3×100 mL), dried over anhydrous sodium sulfate and concentrated under vacuum to afford 290 mg (97%) of crude 4-(3-(2-chloroacetyl)-5-(3-fluorocyclobutyl)-2-methyl-1H-pyrrol-1-yl)benzonitrile as a yellow solid. Mass Spectrum (LCMS, ESI pos.): Calcd. for $C_{18}H_{16}ClFN_2O$: 331 (M+H); found: 331.

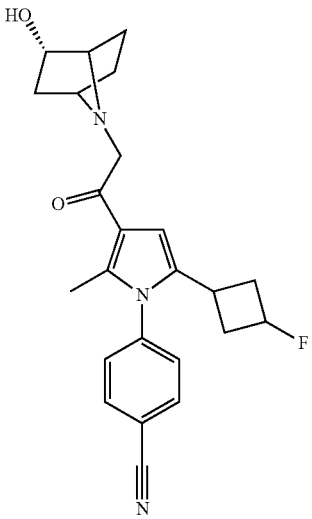 [SMILES: Cc1c(C(=O)CN2C3CCC2[C@@H](O)C3)cc(C2CC(F)C2)n1-c1ccc(C#N)cc1]

D. (±)-4-(5-(3-Fluorocyclobutyl)-3-(2-((2R)-2-hydroxy-7-azabicyclo[2.2.1]heptan-7-yl)acetyl)-2-methyl-1H-pyrrol-1-yl)benzonitrile (132B)

Into a 100 mL round-bottom flask was placed a solution of 4-(3-(2-chloroacetyl)-5-(3-fluorocyclobutyl)-2-methyl-1H-pyrrol-1-yl)benzonitrile (290 mg, 0.88 mmol) in N,N-dimethylformamide (3 mL). To the solution were added racemic (1R,2R,4S)-7-azabicyclo[2.2.1]heptan-2-ol (264 mg, 1.76 mol) and potassium carbonate (607 mg, 4.40 mmol). The resulting mixture was allowed to stir at room temperature overnight. The crude product was purified by preparative-HPLC with the following conditions: Column-SunFire Prep C18, 19*150 mm 5 μm; mobile phase-water with 0.05% trifluoroacetic acid and $CH_3CN$ (10% $CH_3CN$ up to 30% in 10 min, up to 100% in 2 min, down to 10% in 1 min); Detector-254 nm. This process afforded 17 mg (5%) of (±)-4-(5-(3-fluorocyclobutyl)-3-(2-((2R)-2-hydroxy-7-azabicyclo[2.2.1]heptan-7-yl)acetyl)-2-methyl-1H-pyrrol-1-yl)benzonitrile (132B) as a white solid and mixture of diastereomers. Mass Spectrum (LCMS, ESI pos.): Calcd. for $C_{24}H_{26}FN_3O_2$: 408 (M+H); found: 408. $^1$H NMR (300 MHz, $CH_3OH-d_4$) δ 7.92 (d, J=8.4 Hz, 2H), 7.42 (d, J=8.4 Hz, 2H), 6.54 (s, 1H), 4.87-4.84 (m, 1H) 4.82 (s, 2H), 4.68-4.63 (m, 0.5H), 4.31-4.28 (m, 1H), 3.79-3.77 (m, 1H), 3.47-3.40 (m, 2H), 2.54-2.52 (m, 1H), 2.41-2.36 (m, 2H), 2.25 (s, 3H), 2.23-2.07 (m, 4H), 1.93-1.89 (m, 1H), 1.70-1.65 (m, 1H), 1.51-1.45 (m, 1H), 0.98-0.93 (m, 1H).

Using the procedures described in Examples 51B and 52B, reagents, starting materials, and conditions known to those skilled in the art, the following compounds representative of the present invention were prepared:

| Cpd | Data |
|---|---|
| 142B | (±)-4-(3-(2-((1S,2R,4R)-2-Hydroxy-7-azabicyclo[2.2.1]heptan-7-yl)acetyl)-2-methyl-5-(2-methylcyclopropyl)-1H-pyrrol-1-yl)benzonitrile<br>Mass Spectrum (LCMS, ESI pos.): Calcd. for $C_{24}H_{27}N_3O_2$: 390 (M + H); found: 390. $^1$H NMR (400 MHz, DMSO-$d_6$): δ 8.08 (d, J = 8.8 Hz, 2H), 7.64 (d, J = 8.4 Hz, 1H), 6.37 (s, 1H), 4.67 (d, J = 4.0 Hz, 1H), 4.05-4.02 (m, 1H), 3.53 (t, J = 6.0 Hz, 2H), 3.26-3.22 (m, 2H), 2.24 (s, 3H), 1.99-1.95 (m, 2H), 1.78-1.69 (m, 1H), 1.52-1.48 (m, 1H), 1.33-1.25 (m, 1H), 1.07-1.01 (m, 1H), 0.86-0.72 (m, 5H), 0.52-0.46 (m, 1H). Mixture of diastereomers. |
| 144B | (±)-4-(3-(2-((1R,2R,4S)-2-Hydroxy-7-azabicyclo[2.2.1]heptan-7-yl)acetyl)-2-methyl-5-(2-methylthiazol-4-yl)-1H-pyrrol-1-yl)benzonitrile<br>Mass Spectrum (LCMS, ESI pos.): Calcd. for $C_{24}H_{24}N_4O_2S$: 433 (M + H); found: 433. $^1$H NMR (400 MHz, DMSO-$d_6$): δ 8.04 (d, J = 8.4 Hz, 2H), 7.57 (d, J = 8.4 Hz, 2H), 7.16 (s, 1H), 6.40 (s, 1H), 4.70 (d, J = 4 Hz, 1H), 4.09-4.05 (m, 1H), 3.66 (s, 2H), 3.31-3.27 (m, 2H), 2.52 (s, 3H), 2.29 (s, 3H), 2.04-1.95 (m, 2H), 1.85-1.75 (m, 1H), 1.61-1.50 (m, 1H), 1.40-1.30 (m, 1H), 0.85-0.74 (m, 1H). |
| 145B | (±)-4-(3-(2-((1R,2R,4S)-2-Hydroxy-7-azabicyclo[2.2.1]heptan-7-yl)acetyl)-2-methyl-5-(2-(trifluoromethyl)thiazol-4-yl)-1H-pyrrol-1-yl)benzonitrile<br>Mass Spectrum (LCMS, ESI pos.): Calcd. for $C_{24}H_{21}F_3N_4O_2S$: 487 (M + H); found: 487. $^1$H NMR (400 MHz, DMSO-$d_6$): δ 8.05 (d, J = 8.4 Hz, 2H), 7.60 (d, J = 8.4 Hz, 2H), 7.32 (s, 1H), 7.19 (s, 1H), 4.70 (s, 1H), 4.08-4.07 (m, 1H), 3.70 (s, 2H), 3.33-3.31 (m, 2H), 2.31 (s, 3H), 2.03-1.97 (m 2H), 1.80-1.78 (m, 1H), 1.60-1.55 (m, 1H), 1.37-1.33 (m, 1H), 0.82-0.78 (m, 1H). |
| 146B | (±)-4-(3-(2-((1R,2R,4S)-2-Hydroxy-7-azabicyclo[2.2.1]heptan-7-yl)acetyl)-2-methyl-5-(thiazol-2-yl)-1H-pyrrol-1-yl)benzonitrile<br>Mass Spectrum (LCMS, ESI pos.): Calcd. for $C_{24}H_{22}N_4O_2S$: 419 (M + H); found: 419. $^1$H NMR (400 MHz, DMSO-$d_6$): δ 8.04 (d, J = 8.4 Hz, 2H), 7.64-7.61 (m, 3H), 7.52 (d, J = 3.2 Hz, 1H), 7.44 (s, 1H), 4.69 (d, J = 4 Hz, 1H), 4.11-4.05 (m, |

| Cpd | Data |
|---|---|
| | 1H), 3.67 (s, 2H), 3.29-3.26 (m, 2H), 2.28 (s, 3H), 2.00-1.98 (m, 2H), 1.85-1.72 (m, 1H), 1.60-1.48 (m, 1H), 1.36-1.28 (m, 1H), 0.81-0.78 (m, 1H). |
| 147B | (±)-4-(3-(2-(((1R,2R,4S)-2-Hydroxy-7-azabicyclo[2.2.1]heptan-7-yl)acetyl)-2-methyl-5-(2-methylthiazol-5-yl)-1H-pyrrol-1-yl)benzonitrile<br>Mass Spectrum (LCMS, ESI pos.): Calcd. for $C_{24}H_{24}N_4O_2S$: 433 (M + H); found: 433. $^1$H NMR (400 MHz, $CH_3OH$-$d_4$): δ 7.94 (d, J = 8.4 Hz, 2H), 7.52 (d, J = 8.4 Hz 2H), 7.26 (s, 1H), 7.03 (s, 1H), 4.89 (s, 2H), 4.36-4.32 (m, 1H), 3.51 (t, J = 4.4 Hz, 1H), 3.46 (t, J = 4.8 Hz, 1H), 2.61(s, 3H), 2.39 (s, 3H), 2.19-2.13 (m, 2H), 2.05-1.91 (m, 1H), 1.74-1.70 (m, 1H), 1.55-1.49 (m, 1H), 1.03-0.99 (m 1H). |

Example 53B. (±)-4-(5-((3,3-Difluorocyclobutyl)methyl)-3-(2-((2R)-2-hydroxy-7-azabicyclo[2.2.1]heptan-7-yl)acetyl)-2-methyl-1H-pyrrol-1-yl)benzonitrile (135B)

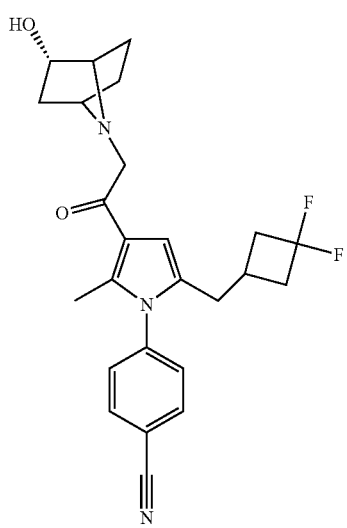

A. 4-(2-(3,3-Difluorocyclobutane-1-carbonyl)-5-methyl-1H-pyrrol-1-yl)benzonitrile

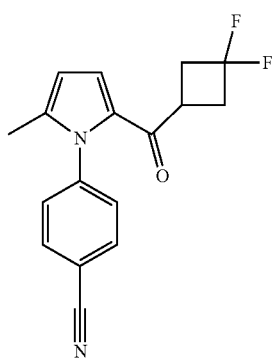

Into a 100 mL round-bottom flask, being maintained under an inert atmosphere of nitrogen, was placed a mixture of 3,3-difluoro-N,N-dimethylcyclobutane-1-carboxamide (2.15 g, 13.2 mmol) and phosphorous oxychloride (2.03 g, 13.2 mmol). The mixture was kept at 0° C. for 1 h and allowed to stir. Then a solution of 4-(2-methyl-1H-pyrrol-1-yl)benzonitrile (2.0 g, 11.0 mmol) in chloroform (30 mL) was added to the flask. The resulting mixture was allowed to warm to room temperature and was then heated at 80° C. for 14 h. The reaction mixture was allowed to cool to room temperature and was diluted with water (50 mL). The resulting mixture was extracted with dichloromethane (2×50 mL) and the combined organic extracts were concentrated under vacuum. The remaining residue was purified by column chromatography on silica, using ethyl acetate/hexane (1:30 to 1:20) as the eluant, to afford 3 g (91%) of 4-(2-(3,3-difluorocyclobutane-1-carbonyl)-5-methyl-1H-pyrrol-1-yl)benzonitrile as a light yellow solid. Mass Spectrum (LCMS, ESI pos.): Calcd. for $C_{17}H_{14}F_2N_2O$: 301 (M+H); found: 301. $^1$H NMR (300 MHz, $CDCl_3$): δ 7.82-7.77 (m, 2H), 7.33-7.29 (m, 2H), 7.01 (d, J=4.0 Hz, 1H), 6.18-6.16 (m, 1H), 3.66-3.51 (m, 1H), 2.93-2.67 (m, 4H), 2.05 (s, 3H).

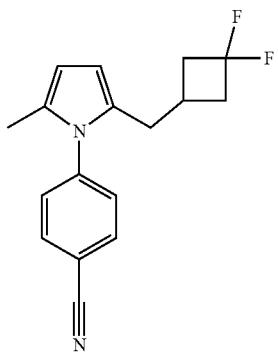 [SMILES: Cc1ccc(CC2CC(F)(F)C2)n1-c1ccc(C#N)cc1]

B. 4-(2-((3,3-Difluorocyclobutyl)methyl)-5-methyl-1H-pyrrol-1-yl)benzonitrile

Into a 250 mL round-bottom flask, being maintained under an inert atmosphere of nitrogen, was placed a solution of 4-(2-(3,3-difluorocyclobutane-1-carbonyl)-5-methyl-1H-pyrrol-1-yl)benzonitrile (1.50 g, 4.99 mmol) in acetonitrile (100 mL). The solution was cooled to 0° C. and then treated with a borane/tetrahydrofuran solution (30 mL, 6.00 equiv) in a dropwise fashion. The resulting mixture was allowed to warm to room temperature and was then heated at 50° C. for 1 h. After cooling, the reaction mixture was diluted with methanol (20 mL) and then concentrated under vacuum. The remaining residue was purified by column chromatography on silica, using ethyl acetate/hexane (1:50 to 1:30) as the eluant, to afford 200 mg (14%) of 4-(2-((3,3-difluorocyclobutyl)methyl)-5-methyl-1H-pyrrol-1-yl)benzonitrile as a colorless crystal. Mass Spectrum (LCMS, ESI pos.): Calcd. for $C_{17}H_6F_2N_2$: 287 (M+H); found: 287. $^1$H NMR (400 MHz, CDCl$_3$): δ 7.82-7.78 (m, 2H), 7.35-7.32 (m, 2H), 5.96-5.90 (m, 2H), 222.57 (1H) 2.53 (d, J=7.5 Hz, 2H), 2.26-2.08 (m, 4H), 2.02 (s, 3H).

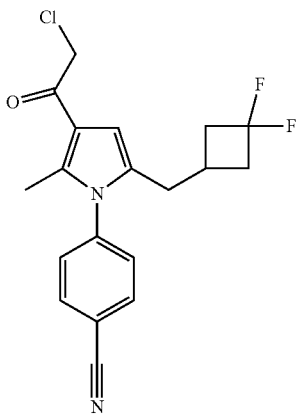 [SMILES: Cc1c(C(=O)CCl)cc(CC2CC(F)(F)C2)n1-c1ccc(C#N)cc1]

C. 4-(3-(2-Chloroacetyl)-5-((3,3-difluorocyclobutyl)methyl)-2-methyl-1H-pyrrol-1-yl)benzonitrile Into a 50 mL 3-necked round-bottom flask, being maintained under an inert atmosphere of nitrogen, was placed a solution of 4-(2-((3,3-difluorocyclobutyl)methyl)-5-methyl-1H-pyrrol-1-yl)benzonitrile (200 mg, 0.70 mmol) in dichloromethane (10 mL). The solution was cooled to 0° C. and then treated with diethylaluminum chloride (1.17 mL, 1.50 equiv), followed by 2-chloroacetyl chloride (118 mg, 1.04 mmol). The resulting mixture was allowed to stir at 0° C. for 2 h before it was diluted with ice water (30 mL). The pH value of the aqueous phase was adjusted to 9 through the addition of an aqueous sodium carbonate solution. The biphasic mixture was extracted with dichloromethane (3×10 mL) and the combined organic extracts were concentrated under vacuum. The remaining residue was purified by preparative-TLC (petroleum ether/ethyl acetate=3:1, developing solution) to afford 150 mg (59%) of 4-(3-(2-chloroacetyl)-5-((3,3-difluorocyclobutyl)methyl)-2-methyl-1H-pyrrol-1-yl)benzonitrile as a brown oil. Mass Spectrum (LCMS, ESI pos.): Calcd. for $C_{19}H_{17}ClF_2N_2O$: 363 (M+H); found: 363.

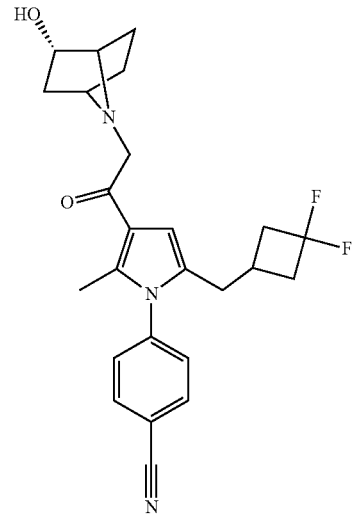

D. (±)-4-(5-((3,3-Difluorocyclobutyl)methyl)-3-(2-((2R)-2-hydroxy-7-azabicyclo[2.2.1]heptan-7-yl)acetyl)-2-methyl-1H-pyrrol-1-yl)benzonitrile (135B)

Into a 25 mL round-bottom flask was placed a solution of 4-(3-(2-chloroacetyl)-5-((3,3-difluorocyclobutyl)methyl)-2-methyl-1H-pyrrol-1-yl)benzonitrile (150 mg, 0.41 mmol) in N,N-dimethylformamide (4.0 g, 54.7 mmol). To the solution were added potassium carbonate (304 mg, 2.20 mmol) and racemic (1R,2R,4S)-7-azabicyclo[2.2.1]heptan-2-ol hydrochloride (164 mg, 1.10 mmol). The resulting mixture was allowed to stir at room temperature for 14 h. The reaction mixture was concentrated under vacuum and the remaining residue was purified by preparative-HPLC under the following conditions: Column-X Bridge C18 OBD Prep Column 100 Å, 10 μm, 19 mm×250 mm; Mobile Phase A-Water (10 mmol/L NH$_4$HCO$_3$), Mobile Phase B-acetonitrile; Flow rate-20 mL/min; Gradient—45% B to 75% B in 8 min; 254/220 nm. This process afforded 50 mg (28%) of (±)-4-(5-((3,3-difluorocyclobutyl)methyl)-3-(2-((2R)-2-hydroxy-7-azabicyclo[2.2.1]heptan-7-yl)acetyl)-2-methyl-1H-pyrrol-1-yl)benzonitrile (135) as a white solid. Mass Spectrum (LCMS, ESI pos.): Calcd. for $C_{25}H_{27}F_2N_3O_2$: 440 (M+H); found: 440. $^1$H NMR (400 MHz, CH$_3$OH-d$_4$): δ 8.01-7.97 (m, 2H), 7.54-7.50 (m, 2H), 6.50 (s, 1H), 4.90 (s, 2H), 4.35-4.32 (m, 1H), 3.52-3.44 (m, 2H), 2.67-2.60 (m, 2H), 2.55 (d, J=7.5 Hz, 2H), 2.31 (s, 3H), 2.27-2.10 (m, 5H), 1.96-1.93 (m, 1H), 1.73-1.68 (m, 1H), 1.55-1.51 (m, 1H), 1.03-0.99 (m, 1H).

Using the procedures described in Example 53B, reagents, starting materials, and conditions known to those skilled in the art, the following compounds representative of the present invention were prepared:

| Cpd | Data |
|---|---|
| 133B | (±)-4-(5-(Cyclobutylmethyl)-3-(2-((1R,2R,4S)-2-hydroxy-7-azabicyclo[2.2.1]heptan-7-yl)acetyl)-2-methyl-1H-pyrrol-1-yl)benzonitrile<br>Mass Spectrum (LCMS, ESI pos.): Calcd. for $C_{25}H_{29}N_3O_2$: 404 (M + H); found: 404. $^1$H NMR (400 MHz, CH$_3$OH-d$_4$): δ 7.97 (d, J = 8.0 Hz, 2H), 7.49 (d, J = 8.0 Hz, 2H), 6.43 (s, 1H), 4.91 (s, 2H), 4.35-4.32 (m, 1H), 3.85-3.77 (m, 1H), 3.50 (t, J = 4.2 Hz, 1H), 3.44 (t, J = 4.9 Hz, 1H), 2.43-2.39 (m, 3H), 2.30 (s, 3H), 2.27-2.12 (m, 2H), 2.04-2.02 (m, 2H), 1.92-1.79 (m, 3H), 1.76-1.72 (m, 1H), 1.69-1.59 (m, 3H), 1.03-0.98 (m, 1H). |

| Cpd | Data |
|---|---|
| 134B | (±)-4-(5-((3,3-Dimethylcyclobutyl)methyl)-3-(2-((1R,2R,4S)-2-hydroxy-7-azabicyclo[2.2.1]heptan-7-yl)acetyl)-2-methyl-1H-pyrrol-1-yl)benzonitrile<br>Mass Spectrum (LCMS, ESI pos.): Calcd. for $C_{27}H_{33}N_3O_2$: 432 (M + H); found: 432. $^1$H NMR (400 MHz, DMSO-$d_6$): δ 8.08 (d, J = 7.6 Hz, 2H), 7.59 (d, J = 7.9 Hz, 2H), 6.47 (s, 1H), 4.75 (s, 1H), 4.07 (brs, 1H), 3.56 (brs, 2H), 3.29 (brs, 2H), 2.35-2.22 (m, 6H), 2.10-1.97 (m, 2H), 1.90-1.74 (m, 3H), 1.57-1.54 (m, 1H), 1.35 (brs, 3H), 1.09 (s, 3H), 0.99 (s, 3H), 0.82-0.80 (m, 1H). |
| 157B | (±)-4-(5-((1-Chlorocyclobutyl)methyl)-3-(2-((1S,2R,4R)-2-hydroxy-7-azabicyclo[2.2.1]heptan-7-yl)acetyl)-2-methyl-1H-pyrrol-1-yl)benzonitrile<br>Mass Spectrum (LCMS, ESI pos.): Calcd. for $C_{25}H_{28}ClN_3O_2$: 438 (M + H); found: 438. $^1$H NMR (400 MHz, CDCl$_3$): δ 7.96 (brs, 2H), 7.48 (brs, 2H), 6.72 (s, 1H), 4.61 (brs, 1H), 4.54 (brs, 1H), 4.13 (brs, 2H), 3.75 (brs, 2H), 2.98 (s, 1H), 2.62 (s, 1H), 2.38-2.26 (m, 8H), 2.16-1.96 (m, 4H), 1.84 (brs, 1H), 1.67 (brs, 2H), 1.39-1.28 (m, 1H), 1.27-1.13 (m, 1H). |
| 158B | (±)-4-(5-(Bicyclo[1.1.1]pentan-1-ylmethyl)-3-(2-((1R,2S,4S)-2-hydroxy-7-azabicyclo[2.2.1]heptan-7-yl)acetyl)-2-methyl-1H-pyrrol-1-yl)benzonitrile<br>Mass Spectrum (LCMS, ESI pos.): Calcd. for $C_{26}H_{29}N_3O_2$: 416 (M + H); found: 416. $^1$H NMR (400 MHz, CDCl$_3$): δ 7.81 (d, J = 8.4 Hz, 2H), 7.29 (d, J = 8.4 Hz, 2H), 6.37 (s, 1H), 4.53-4.49 (m, 1H), 3.81-3.69 (m, 2H), 3.59-3.55 (m, 1H), 3.51-3.47 (m, 1H), 2.48 (s, 2H), 2.42 (s, 1H), 2.37-2.26 (m, 4H), 2.19-2.12 (m, 1H), 2.07-1.85 (m, 3H), 1.74-1.61 (m, 1H), 1.55-1.47 (m, 7H), 1.00 (dd, J = 3.2, 12.4 Hz, 1H). |

Examples 54B and 55B. (±)-4-(5-((S)-1-Cyclobutylethyl)-3-(2-((2R)-2-hydroxy-7-azabicyclo[2.2.1]heptan-7-yl)acetyl)-2-methyl-1H-pyrrol-1-yl)benzonitrile (150) and 4-(5-((R)-1-Cyclobutylethyl)-3-(2-((2R)-2-hydroxy-7-azabicyclo[2.2.1]heptan-7-yl)acetyl)-2-methyl-1H-pyrrol-1-yl)benzonitrile (151B)

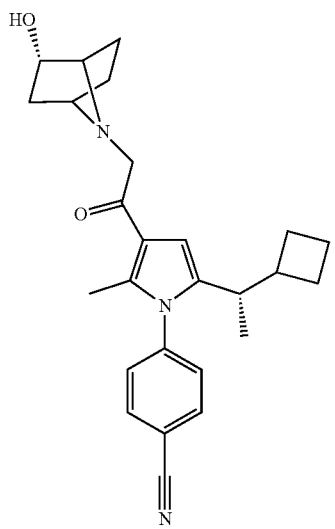

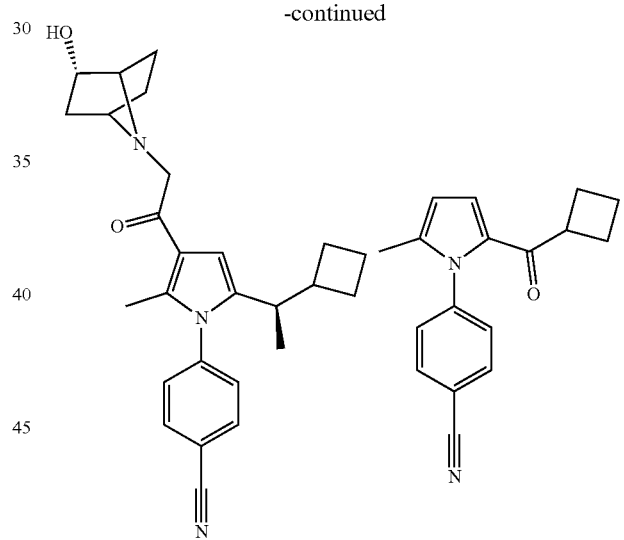

A. 4-(2-(Cyclobutanecarbonyl)-5-methyl-1H-pyrrol-1-yl)benzonitrile

Into a 500 mL round-bottom flask, being maintained under an inert atmosphere of nitrogen, was placed a solution of phosphorus oxychloride (8.13 g, 53.0 mmol) and N,N-dimethylcyclobutanecarboxamide (4.5 g, 35.4 mmol). The solution was cooled to 0° C. and allowed to stir for 30 min. Then the solution was treated with a solution of 4-(2-methyl-1H-pyrrol-1-yl)benzonitrile (7.74 g, 42.5 mmol) in 1,2-dichloroethane (40 mL). The resulting mixture was allowed to warm to room temperature and was then heated at 80° C. overnight. After cooling to room temperature the pH value of the mixture was adjusted to 10 through the addition of an aqueous solution of potassium hydroxide aqueous. The resulting mixture was extracted with ethyl acetate (2×200 mL) and the combined organic extracts were washed with brine (3×200 mL). The organic phase was dried over anhydrous sodium sulfate and concentrated under vacuum. The remaining residue was purified by column chromatography on silica, using ethyl acetate/petroleum ether (1:4) as the eluant, to afford 4.2 g (37%) of 4-(2-(cyclobutanecarbonyl)-5-methyl-1H-pyrrol-1-yl)benzonitrile as a yellow solid. Mass Spectrum (LCMS, ESI pos.): Calcd. for $C_{17}H_{16}N_2O$: 265 (M+H); found: 265. $^1$H-NMR (400 MHz, DMSO-$d_6$) δ 7.99-7.94 (m, 2H), 7.46-7.42 (m, 2H), 7.10 (d, J=4.0 Hz, 1H), 6.18 (d, J=4.0 Hz, 1H), 3.92-3.84 (m, 1H), 2.18-2.07 (m, 4H), 2.02-1.92 (m, 4H), 1.75-1.66 (m, 1H).

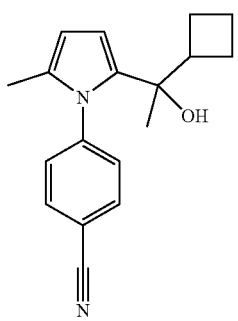 [SMILES: Cc1ccc(C(C)(O)C2CCC2)n1-c1ccc(C#N)cc1]

B. 4-(2-(1-Cyclobutyl-1-hydroxyethyl)-5-methyl-1H-pyrrol-1-yl)benzonitrile

Into a 250 mL round-bottom flask, being maintained under an inert atmosphere of nitrogen, was placed a solution of 4-(2-(cyclobutanecarbonyl)-5-methyl-1H-pyrrol-1-yl) benzonitrile (1.0 g, 3.78 mmol) in tetrahydrofuran (20 mL). The solution was treated with a solution of methylmagnesium bromide in ether (1.52 mL, 3M). The resulting mixture was allowed to stir at room temperature for 5 h before it was diluted with water (100 mL). The aqueous mixture was extracted with ethyl acetate (2×100 mL) and the combined organic extracts were washed with brine (3×100 mL). The organic phase was dried over anhydrous sodium sulfate and concentrated under vacuum. The remaining residue was purified by column chromatography on silica, using ethyl acetate/petroleum ether (1:1) as the eluant, to afford 600 mg (57%) of 4-(2-(1-cyclobutyl-1-hydroxyethyl)-5-methyl-1H-pyrrol-1-yl)benzonitrile as a yellow solid. Mass Spectrum (LCMS, ESI pos.): Calcd. for $C_{18}H_{20}N_2O$: 281 (M+H); found: 281.

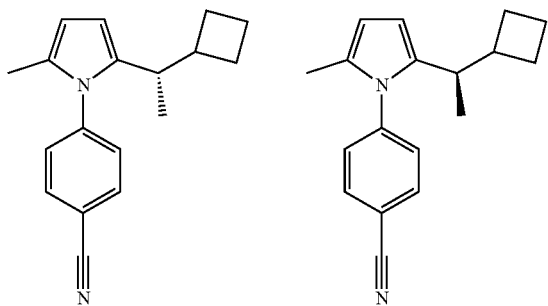 [SMILES: Cc1ccc([C@@H](C)C2CCC2)n1-c1ccc(C#N)cc1 ; Cc1ccc([C@H](C)C2CCC2)n1-c1ccc(C#N)cc1]

C. (S)-4-(2-(1-Cyclobutylethyl)-5-methyl-1H-pyrrol-1-yl)benzonitrile and (R)-4-(2-(1-Cyclobutylethyl)-5-methyl-1H-pyrrol-1-yl)benzonitrile Into a 100 mL round-bottom flask, being maintained under an inert atmosphere of nitrogen, was placed a mixture of 4-(2-(1-cyclobutyl-1-hydroxyethyl)-5-methyl-1H-pyrrol-1-yl)benzonitrile (600 mg, 2.14 mmol), dichloromethane (20 mL), and trifluoroacetic acid (4 mL). The mixture was cooled to 0° C. and then treated with triethylsilane (4 mL). The resulting mixture was allowed to stir at 0° C. for 3 h and was then diluted with an aqueous solution of sodium carbonate (100 mL). The biphasic mixture was extracted with dichloromethane (2×100 mL) and the combined organic extracts were washed with brine (3×100 mL). The organic phase was dried over anhydrous sodium sulfate and concentrated under vacuum. The remaining residue was purified by column chromatography on silica, using ethyl acetate/petroleum ether (1:4) as the eluant to provide the product as a mixture of enantiomers. The enantiomers were separated by preparative-SFC under the following conditions: Column-Phenomenex Lux Cellulose-3; Mobile phase: Hexanes (0.1% diethylamine)/ethanol=99:1; Detector-UV 220 nm. This process afforded 150 mg of (R)-4-(2-(1-cyclobutylethyl)-5-methyl-1H-pyrrol-1-yl)benzonitrile (first peak) as a white solid and 135 mg of (S)-4-(2-(1-cyclobutylethyl)-5-methyl-1H-pyrrol-1-yl)benzonitrile (second peak) as a white solid. The absolute stereochemistry of the chiral centers was not determined for each enantiomer and an arbitrary assignment was made for naming purposes.

(S)-4-(2-(1-cyclobutylethyl)-5-methyl-1H-pyrrol-1-yl) benzonitrile Analytical Data: Mass Spectrum (LCMS, ESI pos.): Calcd. for $C_{18}H_{20}N_2$: 265 (M+H); found: 265.

(R)-4-(2-(1-cyclobutylethyl)-5-methyl-1H-pyrrol-1-yl) benzonitrile Analytical Data: Mass Spectrum (LCMS, ESI pos.): Calcd. for $C_{18}H_{20}N_2$: 265 (M+H); found: 265.

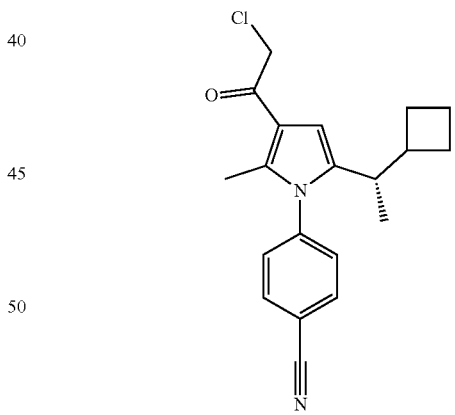

D. (S)-4-(3-(2-Chloroacetyl)-5-(1-cyclobutylethyl)-2-methyl-1H-pyrrol-1-yl)benzonitrile Into a 50 mL sealed tube, being maintained under an inert atmosphere of nitrogen, was placed a solution of (S)-4-(2-(1-cyclobutylethyl)-5-methyl-1H-pyrrol-1-yl)benzonitrile (150 mg, 0.57 mmol) in dichloromethane (5 mL). The solution was cooled to 0° C. and then diethyl aluminum chloride (1 mL) and 2-chloroacetyl chloride (110 mg, 0.97 mmol) were added. The resulting mixture was allowed to stir at 0° C. for 2 h before it was diluted with water (100 mL).

The reaction mixture was extracted with dichloromethane (1×100 mL) and the organic phase was washed with an aqueous solution of sodium carbonate (1×100 mL). The organic phase was further was with brine (1×100 mL) and then concentrated under vacuum to afford 178 mg (92%) of (S)-4-(3-(2-chloroacetyl)-5-(1-cyclobutylethyl)-2-methyl-1H-pyrrol-1-yl)benzonitrile as a brown oil. Mass Spectrum (LCMS, ESI pos.): Calcd. for $C_{20}H_{21}ClN_2O$: 341 (M+H); found: 341.

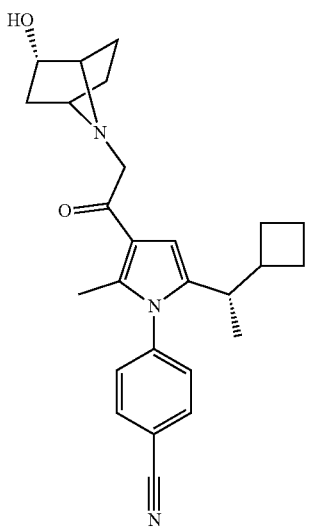 [SMILES: Cc1c(C(=O)CN2C3CCC2[C@@H](O)C3)cc([C@@H](C)C2CCC2)n1-c1ccc(C#N)cc1]

E. (±)-4-(5-((S)-1-Cyclobutylethyl)-3-(2-((2R)-2-hydroxy-7-azabicyclo[2.2.1]heptan-7-yl)acetyl)-2-methyl-1H-pyrrol-1-yl)benzonitrile (150B)

Into a 50 mL round-bottom flask, being maintained under an inert atmosphere of nitrogen, was placed a mixture of (S)-4-(3-(2-chloroacetyl)-5-(1-cyclobutylethyl)-2-methyl-1H-pyrrol-1-yl)benzonitrile (178 mg, 0.52 mmol), racemic (1R,2S,4S)-7-azabicyclo[2.2.1]heptan-2-ol hydrochloride (156 mg, 1.04 mmol), potassium carbonate (359 mg, 2.58 mmol) and N,N-dimethylformamide (3 mL). The mixture was allowed to stir at room temperature overnight. The crude product was purified by preparative-HPLC under the following conditions (Waters): Column-SunFire Prep C18, 19*150 mm 5 μm; mobile phase-water with 0.05% trifluoroacetic acid and $CH_3CN$ (10% $CH_3CN$ up to 30% in 10 min, up to 100% in 2 min, down to 10% in 1 min); Detector-UV 220/254 nm. This process afforded 65 mg (31%) of (±)-4-(5-((S)-1-cyclobutylethyl)-3-(2-((2R)-2-hydroxy-7-azabicyclo[2.2.1]heptan-7-yl)acetyl)-2-methyl-1H-pyrrol-1-yl)benzonitrile (150B) as a white solid. Mass Spectrum (LCMS, ESI pos.): Calcd. for $C_{26}H_{31}N_3O_2$: 418 (M+H); found: 418. $^1$H-NMR (400 MHz, DMSO-$d_6$): δ 8.09-8.06 (m, 2H), 7.60-7.56 (m, 2H), 6.47 (s, 1H), 4.67 (s, 1H), 4.05-4.03 (m, 1H), 3.56-3.52 (m, 2H), 3.28-3.24 (m, 2H), 2.42-2.37 (m, 1H), 2.32-2.28 (m, 1H), 2.18 (s, 3H), 1.98-1.87 (m, 4H), 1.75-1.71 (m, 2H), 1.60-1.41 (m, 4H), 1.35-1.28 (m, 1H), 0.83 (d, J=6.8 Hz, 3H), 0.80-0.76 (m, 1H). The absolute stereochemistry of the benzylic chiral center was not determined for each enantiomer and an arbitrary assignment was made for naming purposes.

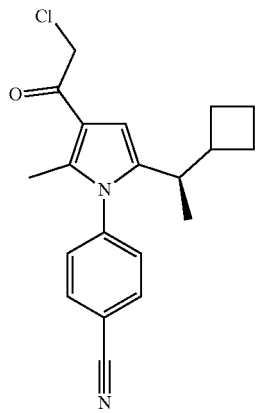 [SMILES: Cc1c(C(=O)CCl)cc([C@H](C)C2CCC2)n1-c1ccc(C#N)cc1]

F. (R)-4-(3-(2-Chloroacetyl)-5-(1-cyclobutylethyl)-2-methyl-1H-pyrrol-1-yl)benzonitrile Into a 50 mL sealed tube, being maintained under an inert atmosphere of nitrogen, was placed a solution of (R)-4-(2-(1-cyclobutylethyl)-5-methyl-1H-pyrrol-1-yl)benzonitrile (150 mg, 0.57 mmol) in dichloromethane (5 mL). The solution was cooled to 0° C. and then diethylaluminum chloride (1 mL) and 2-chloroacetyl chloride (110 mg, 0.97 mmol) were added. The resulting mixture was allowed to stir at 0° C. for 2 h before it was diluted with water (100 mL). The mixture was extracted with dichloromethane (2×100 mL) and the combined organic extracts were washed with an aqueous solution of sodium carbonate (1×100 mL). The organic phase was further washed with brine (1×100 mL) and then concentrated under vacuum to afford 178 mg (92%) of (R)-4-(3-(2-chloroacetyl)-5-(1-cyclobutylethyl)-2-methyl-1H-pyrrol-1-yl)benzonitrile as a brown oil. Mass Spectrum (LCMS, ESI pos.): Calcd. for $C_{20}H_{21}ClN_2O$: 341 (M+H); found: 341.

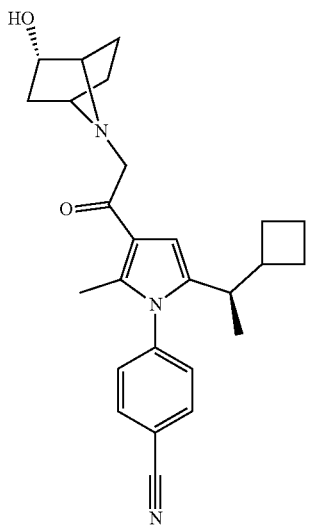 [SMILES: Cc1c(C(=O)CN2C3CCC2[C@@H](O)C3)cc([C@H](C)C2CCC2)n1-c1ccc(C#N)cc1]

G. 4-(5-((R)-1-Cyclobutylethyl)-3-(2-((2R)-2-hydroxy-7-azabicyclo[2.2.1]heptan-7-yl)acetyl)-2-methyl-1H-pyrrol-1-yl)benzonitrile (151B)

Into a 50 mL round-bottom flask, being maintained under an inert atmosphere of nitrogen, was placed a solution of (R)-4-(3-(2-chloroacetyl)-5-(1-cyclobutylethyl)-2-methyl-1H-pyrrol-1-yl)benzonitrile (167 mg, 0.49 mmol) in N,N-dimethylformamide (5 mL). The solution was treated with racemic (1R,2S,4S)-7-azabicyclo[2.2.1]heptan-2-ol hydrochloride (147 mg, 0.98 mmol) and potassium carbonate (338 mg, 2.43 mmol). The resulting mixture was allowed to stir at room temperature overnight. The crude product was purified by preparative-HPLC under the following conditions: Column-SunFire Prep C18, 19*150 mm, 5 µm; mobile phase-water with 0.05% trifluoroacetic acid and $CH_3CN$ (10% $CH_3CN$ up to 30% in 10 min, up to 100% in 2 min, down to 10% in 1 min); Detector-254 nm. This process afforded 72 mg (35%) of 4-(5-((R)-1-cyclobutylethyl)-3-(2-((2R)-2-hydroxy-7-azabicyclo[2.2.1]heptan-7-yl)acetyl)-2-methyl-1H-pyrrol-1-yl)benzonitrile (151) as a white solid. Mass Spectrum (LCMS, ESI pos.): Calcd. for $C_{26}H_{31}N_3O_2$: 418 (M+H); found: 418. $^1$H-NMR (400 MHz, DMSO-$d_6$): δ 8.09-8.06 (m, 2H), 7.59-7.56 (m, 2H), 6.47 (s, 1H), 4.67 (d, J=3.2 Hz, 1H), 4.05-4.03 (m, 1H), 3.56-3.52 (m, 2H), 3.28-3.24 (m, 2H), 2.42-2.37 (m, 1H), 2.32-2.28 (m, 1H), 2.18 (s, 3H), 1.98-1.87 (m, 4H), 1.75-1.71 (m, 2H), 1.60-1.41 (m, 4H), 1.35-1.25 (m, 1H), 0.84-0.82 (d, J=6.8 Hz, 1H), 0.80-0.76 (m, 1H).

Examples 56B. (±4-(3-(2-((2R)-2-Hydroxy-7-azabicyclo[2.2.1]heptan-7-yl)acetyl)-2-methyl-5-(2,2,2-trifluoroethyl)-1H-pyrrol-1-yl)benzonitrile (115B)

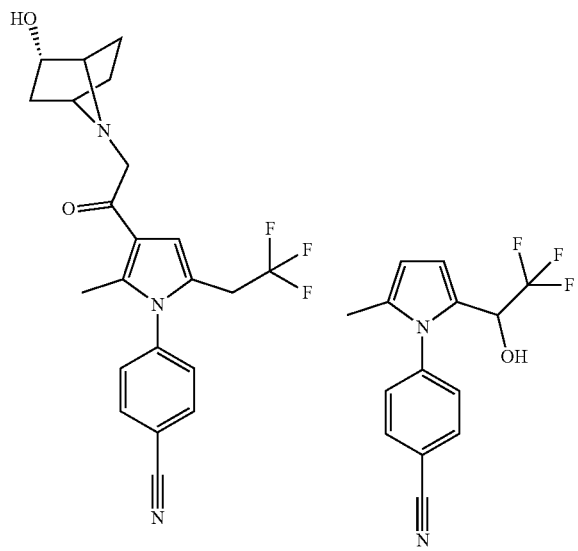

A. 4-(2-Methyl-5-(2,2,2-trifluoro-1-hydroxyethyl)-1H-pyrrol-1-yl)benzonitrile

Into a 100 mL round-bottom flask, being maintained under an inert atmosphere of nitrogen, was placed a mixture of 4-(2-formyl-5-methyl-1H-pyrrol-1-yl)benzonitrile (1.08 g, 5.14 mmol, from Example 11B), trimethyl(trifluoromethyl)silane (1.09 g, 7.69 mmol) and tetrahydrofuran (30 mL). The mixture was cooled to 0° C. and then treated with TBAF (13 mg, 0.05 mmol). The resulting mixture was allowed to warm to room temperature and stir for 2 h before it was diluted with an aqueous solution of 1 M hydrogen chloride (30 mL). The reaction mixture was allowed to stir at room temperature overnight and was then diluted with brine. The aqueous mixture was extracted with ethyl acetate (3×30 mL) and the combined organic extracts were dried over anhydrous sodium sulfate. The organic phase was concentrated under vacuum and the remaining residue was purified by column chromatography on silica, using ethyl acetate/petroleum ether (1:6) as the eluant, to afford 1.62 g of semi-crude 4-(2-methyl-5-(2,2,2-trifluoro-1-hydroxyethyl)-1H-pyrrol-1-yl)benzonitrile as a white solid. $^1$H-NMR (400 MHz, $CDCl_3$): δ 7.89-7.83 (m, 2H), 7.55-7.46 (m, 2H), 6.53-6.52 (m, 1H), 6.11-6.10 (m, 1H), 4.57-4.52 (m, 1H), 2.24 (s, 1H), 2.08 (s, 3H).

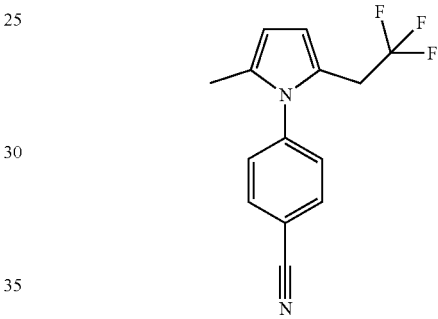

B. 4-(2-Methyl-5-(2,2,2-trifluoroethyl)-1H-pyrrol-1-yl)benzonitrile

Into a 100 mL round-bottom flask, being maintained under an inert atmosphere of nitrogen, was placed a mixture of 4-(2-methyl-5-(2,2,2-trifluoro-1-hydroxyethyl)-1H-pyrrol-1-yl)benzonitrile (1.4 g, 5.00 mmol), trifluoroacetic acid (1.14 g, 10.0 mmol) and dichloromethane (50 mL). The mixture was cooled to 0° C. and then treated with triethylsilane (5.8 g, 50.0 mmol). The resulting was allowed to warm to room temperature and stir for 1 h before it was diluted with an aqueous solution of sodium bicarbonate. The biphasic mixture was extracted with dichloromethane (3×30 mL) and the combined organic extracts were dried over anhydrous sodium sulfate. The organic phase was concentrated under vacuum and the remaining residue was purified by column chromatography on silica, using ethyl acetate/petroleum ether (1:8) as the eluant, to afford 132 mg (10%) of 4-(2-methyl-5-(2,2,2-trifluoroethyl)-1H-pyrrol-1-yl)benzonitrile as a yellow oil. Mass Spectrum (LCMS, ESI pos.): Calcd. for $C_{14}H_{11}F_3N_2$: 265 (M+H); found: 265. $^1$H-NMR (300 MHz, $CDCl_3$): δ 7.83-7.78 (m, 2H), 7.35-7.32 (m, 2H), 6.27 (d, J=3.0 Hz, 1H), 6.04 (d, J=3.0 Hz, 1H), 3.18 (q, J=9.0 Hz, 1H), 2.02 (s, 3H).

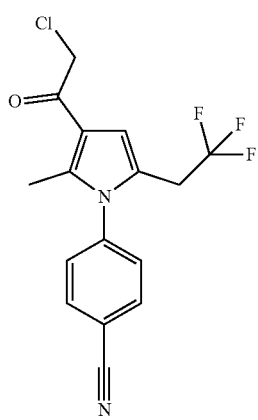 [SMILES: Cc1c(C(=O)CCl)cc(CC(F)(F)F)n1-c1ccc(C#N)cc1]

C. 4-(3-(2-Chloroacetyl)-2-methyl-5-(2,2,2-trifluoroethyl)-1H-pyrrol-1-yl)benzonitrile Into a 50 mL round-bottom flask, being maintained under an inert atmosphere of nitrogen, was placed a mixture of 4-(2-methyl-5-(2,2,2-trifluoroethyl)-1H-pyrrol-1-yl)benzonitrile (210 mg, 0.795 mmol), 2-chloroacetyl chloride (134 mg, 1.20 mmol), and dichloromethane (10 mL). The mixture was cooled to 0° C. and then treated with diethylaluminum chloride (144 mg, 1.20 mmol). The resulting mixture was allowed to warm to room temperature and stir for 2 h before it was diluted with brine. The biphasic mixture was extracted with dichloromethane (3×30 mL) and the combined organic extracts were dried over anhydrous sodium sulfate. The organic phase was concentrated under vacuum and the remaining residue was purified by column chromatography, using ethyl acetate/petroleum ether (1:5) as the eluant, to afford 172 mg (64%) of 4-(3-(2-chloroacetyl)-2-methyl-5-(2,2,2-trifluoroethyl)-1H-pyrrol-1-yl)benzonitrile as a yellow oil. Mass Spectrum (LCMS, ESI pos.): Calcd. for $C_{16}H_{12}Cl_1F_3N_2O$: 341 (M+H); found: 341.

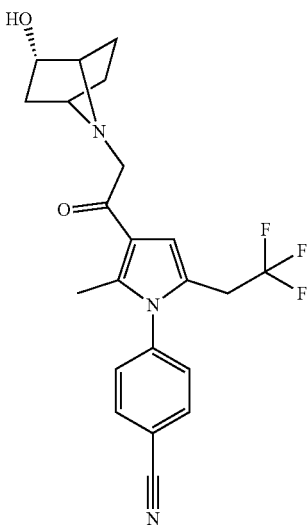 [SMILES: Cc1c(C(=O)CN2C3CCC2[C@@H](O)C3)cc(CC(F)(F)F)n1-c1ccc(C#N)cc1]

D. (±)-4-(3-(2-((2R)-2-Hydroxy-7-azabicyclo[2.2.1]heptan-7-yl)acetyl)-2-methyl-5-(2,2,2-trifluoroethyl)-1H-pyrrol-1-yl)benzonitrile (115B)

Into a 25 mL round-bottom flask, being maintained under an inert atmosphere of nitrogen, was placed a solution of 4-(3-(2-chloroacetyl)-2-methyl-5-(2,2,2-trifluoroethyl)-1H-pyrrol-1-yl)benzonitrile (180 mg, 0.53 mmol) in N,N-dimethylformamide (5 mL). The solution was then treated with potassium carbonate (146 mg, 1.05 mmol) and racemic (1R,2S,4S)-7-azabicyclo[2.2.1]heptan-2-ol hydrochloride (119 mg, 0.80 mmol). The resulting mixture was allowed to stir at room temperature overnight. The crude product was purified by preparative-HPLC under the following conditions: Column-X Bridge Prep C18 OBD column 19*150 nm; mobile phase-water (10 mmol/L NH$_4$HCO$_3$) and acetonitrile (30% acetonitrile up to 60% in 10 min); Detector-UV 254 nm. This process afforded 115 mg (52%) of (±)-4-(3-(2-((2R)-2-hydroxy-7-azabicyclo[2.2.1]heptan-7-yl)acetyl)-2-methyl-5-(2,2,2-trifluoroethyl)-1H-pyrrol-1-yl)benzonitrile (115B) as a white solid. Mass Spectrum (LCMS, ESI pos.): Calcd. for $C_{22}H_{22}F_3N_3O_2$: 418 (M+H); found: 418. $^1$H-NMR (400 MHz, DMSO-d$_6$): δ 8.05 (d, J=8.4 Hz, 2H), 7.57 (d, J=8.4 Hz, 2H), 6.83 (s, 1H), 4.67 (d, J=4.0 Hz, 1H), 4.04 (m, 1H), 3.60 (s, 2H), 3.48-3.43 (m, 2H), 3.25-3.22 (m, 2H), 2.22 (s, 3H), 2.00-1.92 (m, 2H), 1.75-1.70 (m, 1H), 1.53-1.49 (m, 1H), 1.34-1.27 (m, 1H), 0.79-0.75 (m, 1H).

Example 57B: Usp14 Inhibition Assay

Using previously described methodology [B. H. Lee et al. Nature 2010, 467 (9), 179, the contents of which are expressly incorporated by reference herein], select compounds described herein were found to inhibit USP14 as delineated in Table 5. "I" in the table below designates an IC$_{50}$ of >0.5 μM, "II" in the Table below designates and IC$_{50}$ between 0.05 and 0.5 μM, and "III" designates an IC$_{50}$<0.05 μM. The IC$_{50}$ values in the Table below represent the average value from a minimum of two experimental determinations.

TABLE 5

| Compound No. | Usp14 Activity |
| --- | --- |
| 1B | I |
| 2B | III |
| 3B | III |
| 4B | III |
| 5B | I |
| 6B | III |
| 7B | III |
| 8B | III |
| 9B | III |
| 10B | III |
| 11B | I |
| 12B | III |
| 13B | III |
| 14B | III |
| 15B | III |
| 16B | I |
| 17B | II |
| 18B | II |
| 19B | I |
| 20B | III |
| 21B | II |
| 22B | III |
| 23B | III |
| 24B | II |
| 25B | II |
| 26B | III |
| 27B | III |

TABLE 5-continued

| Compound No. | Usp14 Activity |
|---|---|
| 28B | III |
| 29B | III |
| 30B | III |
| 31B | II |
| 32B | II |
| 33B | I |
| 34B | III |
| 35B | III |
| 36B | |
| 37B | III |
| 38B | III |
| 39B | III |
| 40B | III |
| 41B | III |
| 42B | III |
| 43B | III |
| 44B | III |
| 45B | III |
| 46B | II |
| 47B | III |
| 50B | II |
| 51B | III |
| 52B | III |
| 53B | III |
| 54B | III |
| 55B | III |
| 56B | II |
| 57B | II |
| 63B | I |
| 64B | II |
| 66B | II |
| 67B | II |
| 68B | II |
| 69B | II |
| 70B | II |
| 71B | I |
| 72B | I |
| 73B | I |
| 74B | I |
| 75B | II |
| 76B | II |
| 77B | II |
| 78B | II |
| 79B | I |
| 80B | III |
| 81B | II |
| 82B | II |
| 83B | II |
| 84B | II |
| 85B | II |
| 86B | II |
| 87B | II |
| 88B | II |
| 89B | II |
| 90B | III |
| 91B | II |
| 92B | |
| 94B | II |
| 95B | I |
| 96B | II |
| 97B | II |
| 98B | II |
| 99B | I |
| 100B | I |
| 101B | II |
| 102B | I |
| 103B | I |
| 104B | II |
| 105B | I |
| 106B | II |
| 107B | II |
| 108B | III |
| 109B | II |
| 110B | II |
| 111B | II |
| 112B | II |
| 113B | II |
| 114B | II |

TABLE 5-continued

| Compound No. | Usp14 Activity |
|---|---|
| 115B | II |
| 116B | II |
| 117B | II |
| 118B | I |
| 119B | II |
| 120B | III |
| 121B | II |
| 122B | II |
| 124B | II |
| 125B | II |
| 126B | II |
| 127B | I |
| 128B | III |
| 129B | II |
| 130B | II |
| 131B | II |
| 132B | III |
| 133B | III |
| 134B | III |
| 135B | III |
| 136B | III |
| 137B | III |
| 138B | I |
| 139B | I |
| 140B | II |
| 141B | I |
| 142B | II |
| 143B | II |
| 144B | II |
| 145B | I |
| 146B | I |
| 147B | II |
| 148B | I |
| 149B | II |
| 150B | II |
| 151B | I |
| 153B | III |
| 155B | II |
| 156B | III |
| 157B | II |
| 158B | I |

While this invention has been particularly shown and described with references to preferred embodiments thereof, it will be understood by those skilled in the art that various changes in form and details may be made therein without departing from the scope of the invention encompassed by the appended claims.

What is claimed is:

1. A compound having the Formula (Ib):

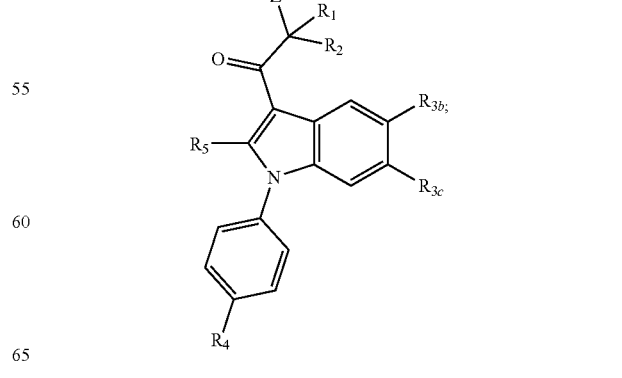

(Ib)

or a pharmaceutically acceptable salt, solvate, or clathrate thereof; wherein:

each of $R_1$ and $R_2$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl;

each of $R_{3b}$ and $R_{3c}$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C=NR_d)R_c$, $OC(O)R_c$, optionally substituted heterocyclic and optionally substituted heteroaryl;

$R_4$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C=NR_d)R_c$, $OC(O)R_c$, optionally substituted heterocyclic and optionally substituted heteroaryl;

$R_5$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C=NR_d)R_c$, $OC(O)R_c$, optionally substituted heterocyclic, and optionally substituted heteroaryl;

wherein substituents of optionally substituted Z, $R_1$, $R_2$, $R_{3b}$, $R_{3c}$, $R_4$, and $R_5$ are each independently selected from the group consisting of $C_1$-$C_{10}$ alkyl, $C_2$-$C_{10}$ alkenyl, $C_2$-$C_{10}$ alkynyl, $C_3$-$C_{12}$ cycloalkyl, $C_3$-$C_{12}$ cycloalkenyl, aryl, halo, $N_3$, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C=NR_d)R_c$, $OC(O)R_c$, heterocyclic, and heteroaryl;

Z is:

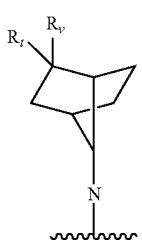 or 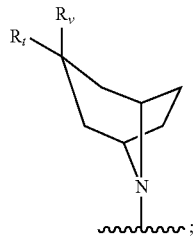;

wherein $R_t$ is selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C=NR_d)R_c$, $OC(O)R_c$, optionally substituted heterocyclic and optionally substituted heteroaryl;

$R_y$ is selected from the group consisting of hydrogen and optionally substituted $C_1$-$C_{10}$ alkyl;

each n is independently 0, 1 or 2;

each $R_c$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl; and each $R_d$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl; or two geminal $R_d$ groups are taken together with the nitrogen atom to which they are attached to form an optionally substituted heterocyclic or an optionally substituted heteroaryl.

2. The compound of claim 1, or a pharmaceutically acceptable salt, solvate, or clathrate thereof, wherein substituents of optionally substituted Z, $R_1$, $R_2$, $R_{3b}$, $R_{3c}$, $R_4$ and $R_5$ are each independently selected from the group consisting of $C_1$-$C_4$ alkyl, halo, $OR_c$, CN, $S(O)_nR_c$, heterocyclyl, and heteroaryl.

3. The compound of claim 1, or a pharmaceutically acceptable salt, solvate, or clathrate thereof, wherein each of $R_1$ and $R_2$ is hydrogen.

4. The compound of claim 1, or a pharmaceutically acceptable salt, solvate, or clathrate thereof, wherein $R_4$ is halo.

5. The compound of claim 4, or a pharmaceutically acceptable salt, solvate, or clathrate thereof, wherein $R_4$ is Cl.

6. The compound of claim 1, or a pharmaceutically acceptable salt, solvate, or clathrate thereof, wherein $R_5$ is hydrogen or $C_1$-$C_{10}$ alkyl.

7. The compound of claim 6, or a pharmaceutically acceptable salt, solvate, or clathrate thereof, wherein $R_5$ is methyl.

8. The compound of claim 1, or a pharmaceutically acceptable salt, solvate, or clathrate thereof, wherein $R_{3b}$ is hydrogen.

9. The compound of claim 1, or a pharmaceutically acceptable salt, solvate, or clathrate thereof, wherein
each of $R_1$ and $R_2$ is hydrogen;
$R_4$ is Cl;
$R_5$ is methyl; and
$R_{3b}$ is hydrogen.

10. The compound of claim 1, or a pharmaceutically acceptable salt, solvate, or clathrate thereof, wherein $R_{3c}$ is independently selected from the group consisting of optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted aryl, halo, $N_3$, $OR_c$, $NR_dR_d$, $C(O)OR_c$, $NO_2$, CN, $C(O)R_c$, $C(O)C(O)R_c$, $C(O)NR_dR_d$, $NR_dC(O)R_c$, $NR_dS(O)_nR_c$, $N(R_d)(COOR_c)$, $NR_dC(O)C(O)R_c$, $NR_dC(O)NR_dR_d$, $NR_dS(O)_nNR_dR_d$, $NR_dS(O)_nR_c$, $S(O)_nR_c$, $S(O)_nNR_dR_d$, $OC(O)OR_c$, $(C=NR_d)R_c$, $OC(O)R_c$, optionally substituted heterocyclic and optionally substituted heteroaryl, wherein each $R_c$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl;

each $R_d$ is independently selected from the group consisting of hydrogen, optionally substituted $C_1$-$C_{10}$ alkyl, optionally substituted $C_2$-$C_{10}$ alkenyl, optionally substituted $C_2$-$C_{10}$ alkynyl, optionally substituted $C_1$-$C_{10}$ alkoxy, optionally substituted $C_3$-$C_{12}$ cycloalkyl, optionally substituted $C_3$-$C_{12}$ cycloalkenyl, optionally substituted heterocyclic, optionally substituted aryl, and optionally substituted heteroaryl; or two geminal $R_d$ groups are taken together with the nitrogen atom to which they are attached to form an optionally substituted heterocyclic or an optionally substituted heteroaryl; and each n is independently 0, 1 or 2.

11. The compound of claim 1, or a pharmaceutically acceptable salt, solvate, or clathrate thereof, wherein $R_{3c}$ is independently selected from the group consisting of $C_1$-$C_{10}$ alkyl substituted with CN; $S(O)_nR_c$, wherein $R_c$ is $C_1$-$C_{10}$ alkyl or $C_3$-$C_{12}$ cycloalkyl, and n is 2; optionally substituted heterocyclic; or and optionally substituted heteroaryl.

12. The compound of claim 1, or a pharmaceutically acceptable salt, solvate, or clathrate thereof, wherein $R_t$ is selected from the group consisting of hydrogen, $C_1$-$C_{10}$ alkyl, and $OR_c$, wherein $R_c$ is hydrogen or $C_1$-$C_{10}$ alkyl; and $R_v$ is hydrogen or $C_1$-$C_4$ alkyl.

13. The compound of claim 1, said compound selected from the group consisting of:

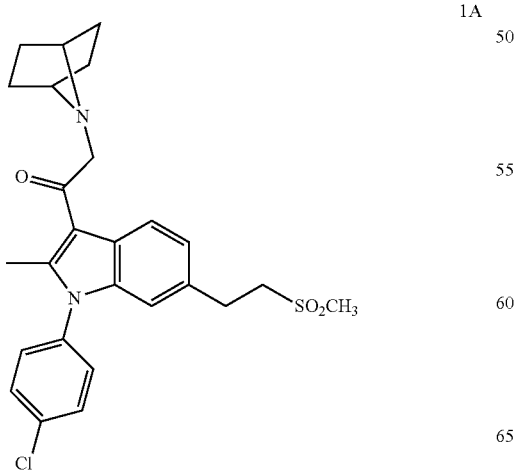

1A

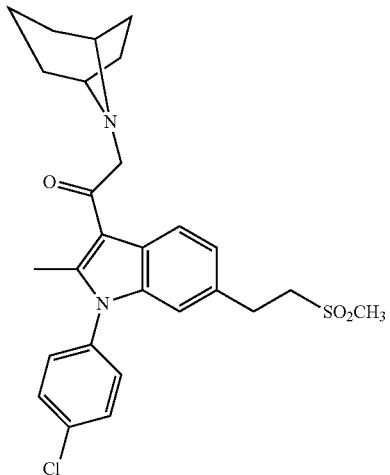

2A

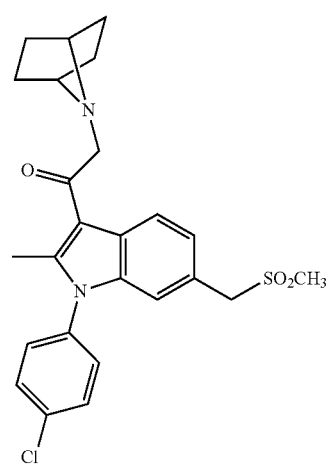

3A

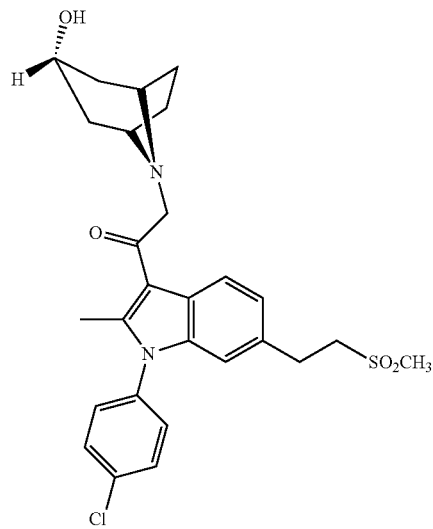

4A

413
-continued
5A
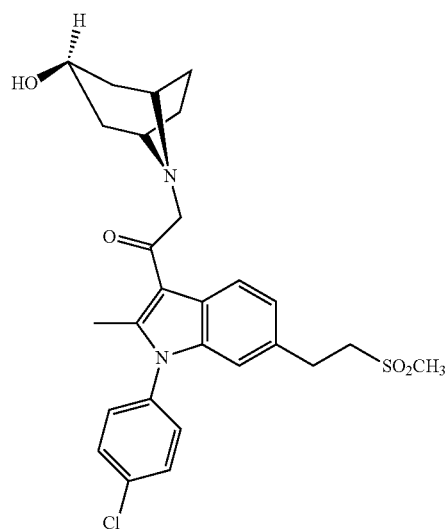
6A
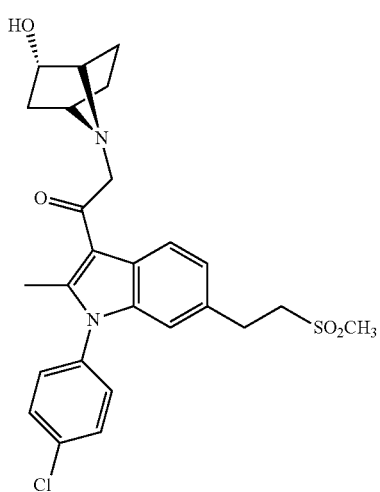
8A
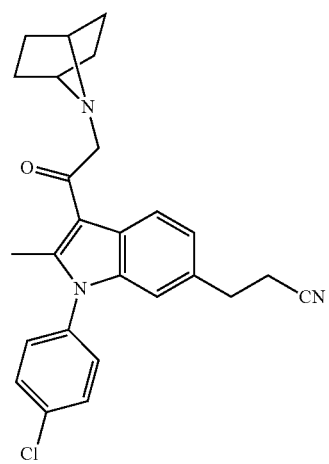
414
-continued
10A
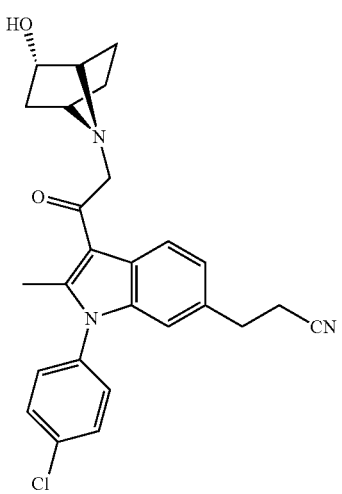
11A
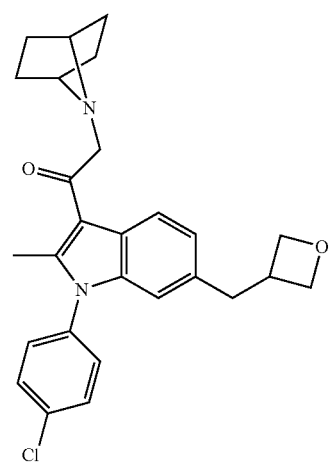
12A
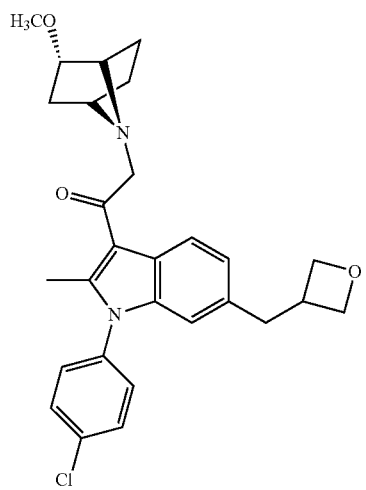

415
-continued
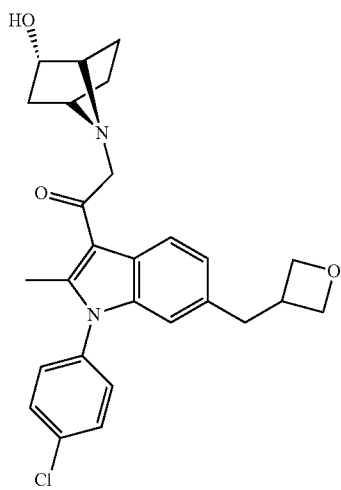
13A
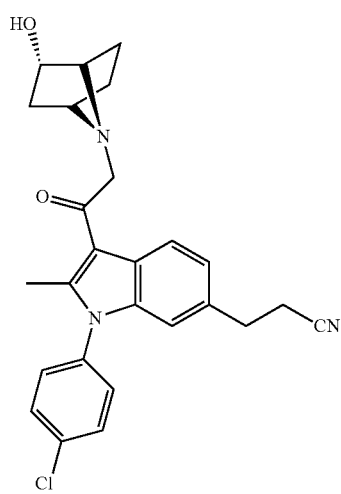
15A
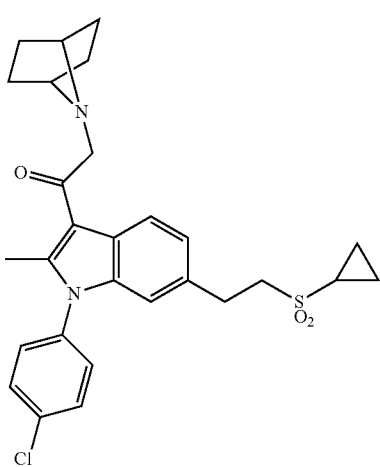
16A
416
-continued
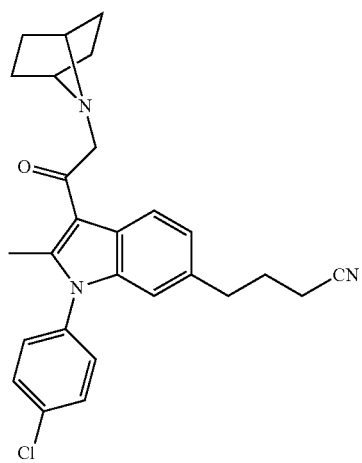
17A
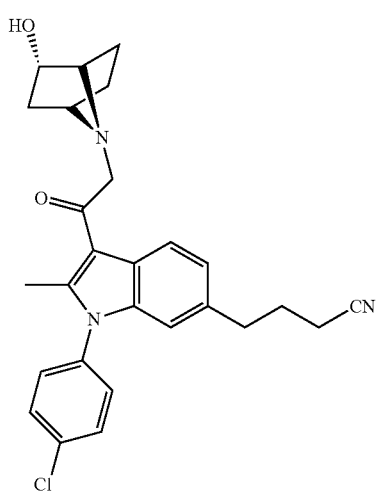
18A
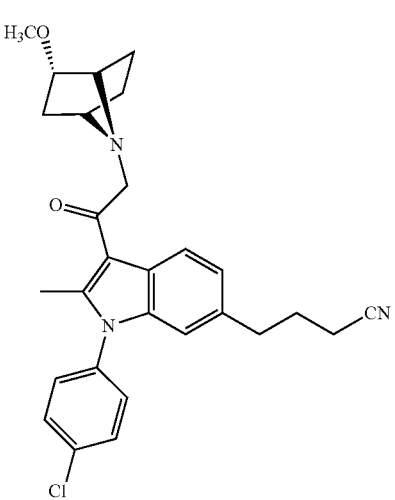
19A

| 417 -continued | | 418 -continued | |
|---|---|---|---|
| 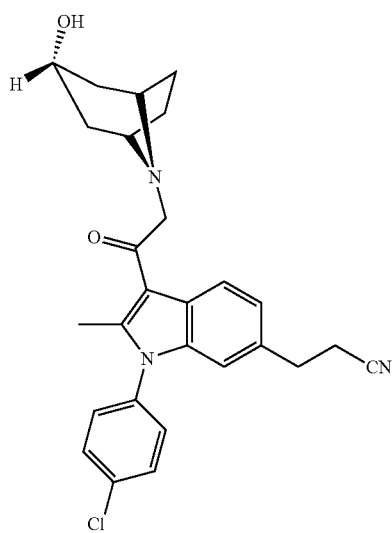 | 20A | 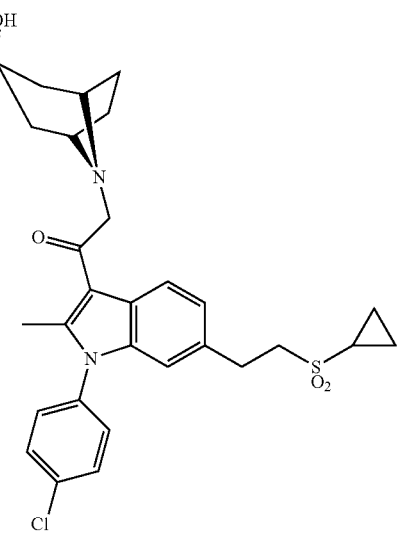 | 23A |
| 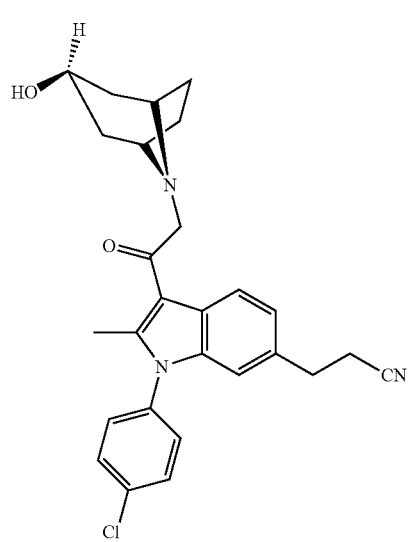 | 21A | 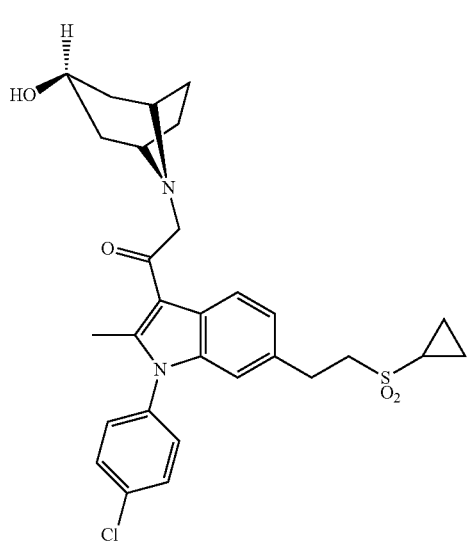 | 24A |
| 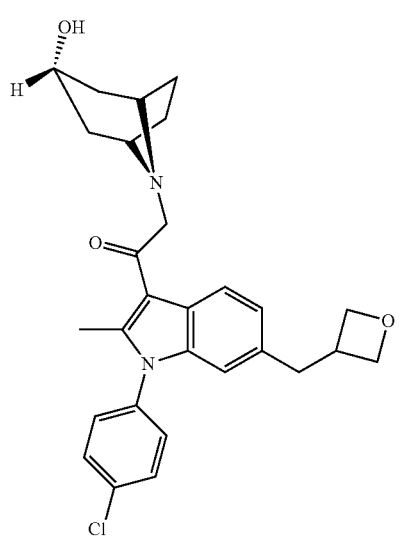 | 22A | 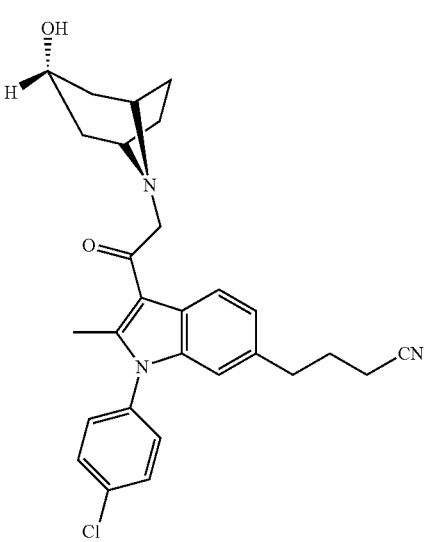 | 25A |

419
-continued

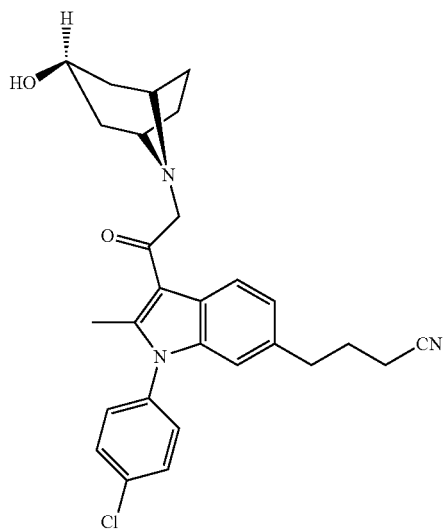
26A

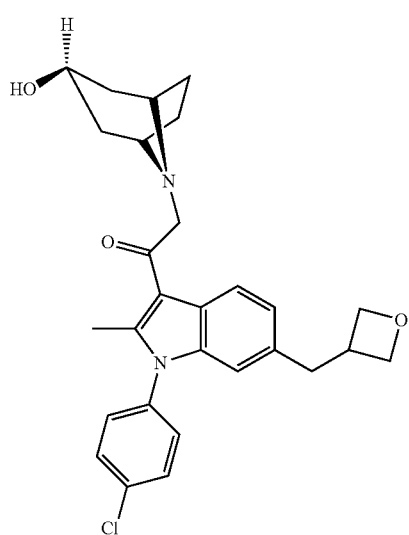
27A

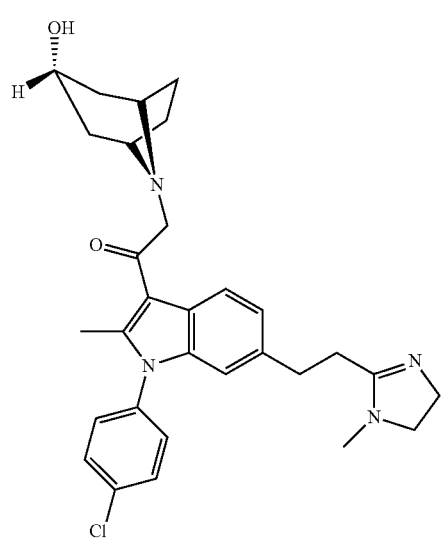
28A

420
-continued

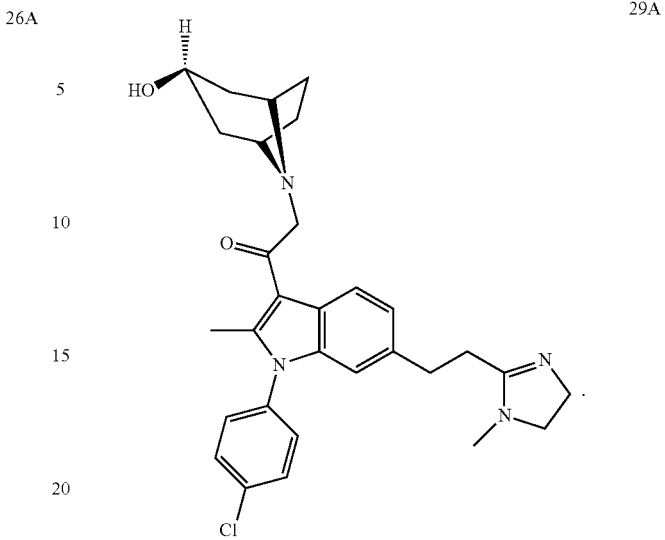
29A

14. A pharmaceutical composition comprising the compound of claim 1 or a pharmaceutically acceptable salt, solvate, or clathrate thereof, and a pharmaceutically acceptable excipient.

15. The compound of claim 1, or a pharmaceutically acceptable salt, solvate, or clathrate thereof, wherein:
each of $R_1$, $R_2$, and $R_{3b}$ is hydrogen;
$R_3$ is optionally substituted $C_1$-$C_3$ alkyl;
$R_4$ is halo or CN;
$R_5$ is methyl;
Z is

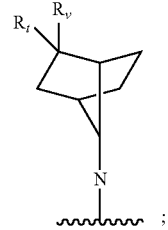

$R_y$ is hydrogen;
$R_t$ is hydrogen or $OR_c$; and
$R_c$ is hydrogen or optionally substituted $C_1$-$C_{10}$ alkyl.

16. The compound of claim 15, or a pharmaceutically acceptable salt, solvate, or clathrate thereof, wherein $R_{3c}$ is substituted methyl.

17. The compound of claim 15, or a pharmaceutically acceptable salt, solvate, or clathrate thereof, wherein $R_{3c}$ is $C_1$-$C_3$ alkyl substituted with CN.

18. The compound of claim 15, or a pharmaceutically acceptable salt, solvate, or clathrate thereof, wherein $R_{3c}$ is methyl substituted with CN.

19. The compound of claim 15, or a pharmaceutically acceptable salt, solvate, or clathrate thereof, wherein $R_{3c}$ is $C_1$-$C_3$ alkyl substituted with $S(O)_nR_c$, wherein n is 2 and $R_c$ is selected from the group consisting of $C_1$-$C_{10}$ alkyl, $C_3$-$C_{12}$ cycloalkyl, and oxetanyl.

20. The compound of claim 15, or a pharmaceutically acceptable salt, solvate, or clathrate thereof, wherein $R_{3c}$ is $C_1$-$C_3$ alkyl substituted with optionally substituted imidazolyl.

21. The compound of claim 15, or a pharmaceutically acceptable salt, solvate, or clathrate thereof, wherein:

$R_t$ is $OR_c$; and $R_c$ is hydrogen or methyl.

* * * * *

UNITED STATES PATENT AND TRADEMARK OFFICE
CERTIFICATE OF CORRECTION

PATENT NO. : 11,560,385 B2  
APPLICATION NO. : 17/133372  
DATED : January 24, 2023  
INVENTOR(S) : Matthew Cullen et al.

Page 1 of 2

It is certified that error appears in the above-identified patent and that said Letters Patent is hereby corrected as shown below:

In the Claims

In Claim 1, Column 410, Line 13, delete "$R_y$" and insert therefor -- $R_v$ --.

In Claim 13, Column 415, Lines 25-45, please delete the existing Structure 15A and insert therefor the following structure:

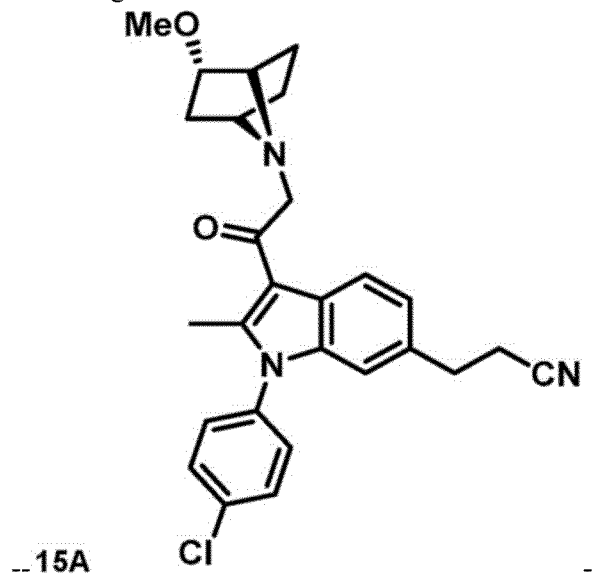

-- 15A                               --.

Signed and Sealed this  
Twenty-third Day of July, 2024

*Katherine Kelly Vidal*

Katherine Kelly Vidal  
*Director of the United States Patent and Trademark Office*

CERTIFICATE OF CORRECTION (continued)
U.S. Pat. No. 11,560,385 B2

In Claim 13, Column 420, Line 22, insert the following rows and columns:

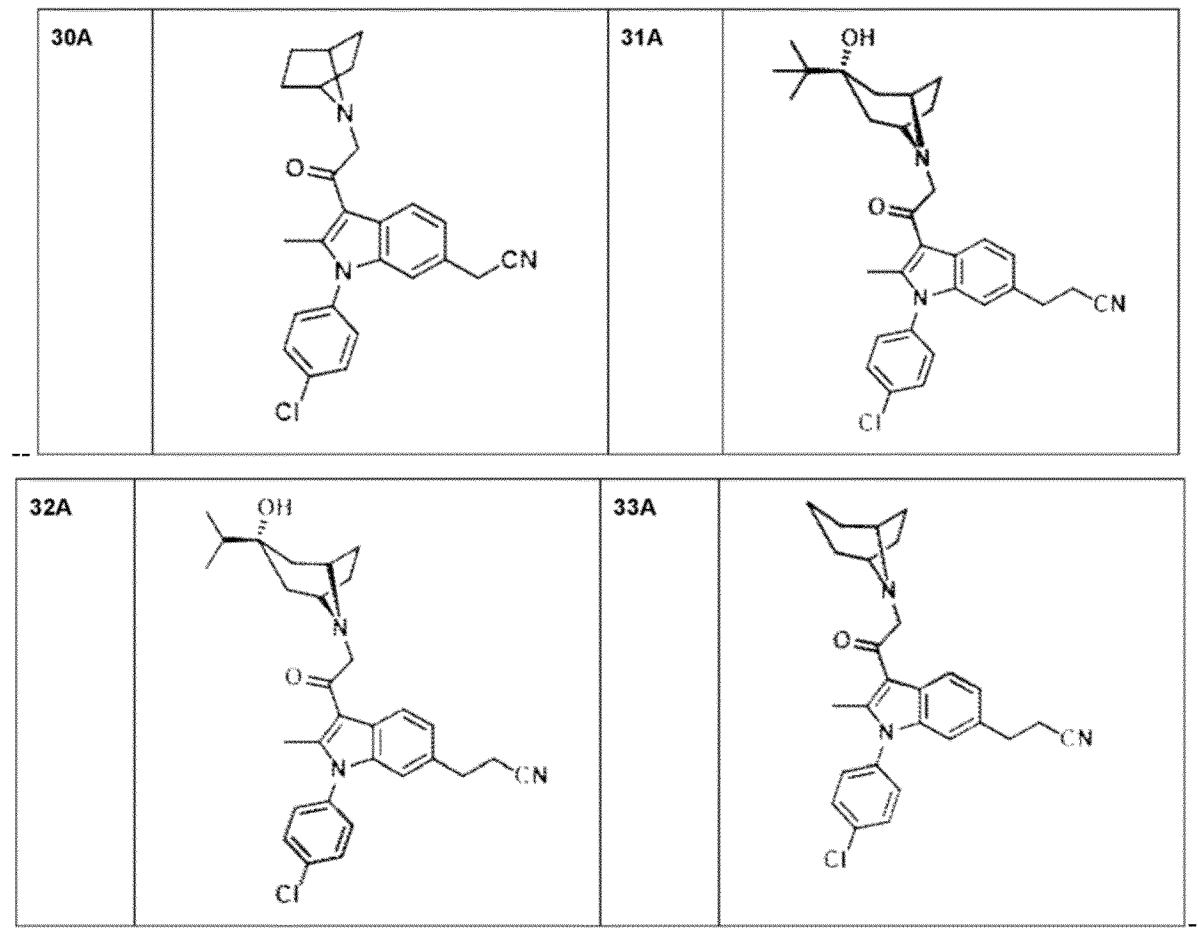

--.

In Claim 13, Column 420, Line 23, insert -- or a pharmaceutically acceptable salt, solvate, or clathrate thereof. --.

In Claim 15, Column 420, Line 31, delete "$R_3$ is optionally substituted $C_1$-$C_3$ alkyl;" and insert therefor -- $R_{3c}$ is optionally substituted $C_1$-$C_3$ alkyl; --.